United States Patent
Chu et al.

(10) Patent No.: US 12,202,842 B2
(45) Date of Patent: *Jan. 21, 2025

(54) MCL1 INHIBITORS

(71) Applicant: Gilead Sciences, Inc., Foster City, CA (US)

(72) Inventors: Hang Chu, San Mateo, CA (US); Juan A. Guerrero, Clayton, CA (US); Anna E. Hurtley, San Mateo, CA (US); Lan Jiang, Foster City, CA (US); Darryl Kato, San Francisco, CA (US); Tetsuya Kobayashi, Pleasanton, CA (US); David W. Lin, Berkeley, CA (US); Jonathan William Medley, San Bruno, CA (US); Devan Naduthambi, San Bruno, CA (US); Vickie H. Tsui, Burlingame, CA (US); Chandrasekar Venkataramani, San Carlos, CA (US); William J. Watkins, Saratoga, CA (US); Hong Yang, Fremont, CA (US); Qingming Zhu, Walnut Creek, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/181,116

(22) Filed: Mar. 9, 2023

(65) Prior Publication Data
US 2023/0348494 A1   Nov. 2, 2023

Related U.S. Application Data

(63) Continuation of application No. 17/094,447, filed on Nov. 10, 2020, now Pat. No. 11,667,652.

(60) Provisional application No. 62/934,400, filed on Nov. 12, 2019.

(51) Int. Cl.
| | |
|---|---|
| *C07D 413/08* | (2006.01) |
| *A61K 31/553* | (2006.01) |
| *A61K 45/06* | (2006.01) |
| *A61P 35/00* | (2006.01) |
| *C07D 513/08* | (2006.01) |
| *C07D 513/10* | (2006.01) |
| *C07D 513/18* | (2006.01) |
| *C07D 513/20* | (2006.01) |
| *C07D 513/22* | (2006.01) |
| *C07D 519/00* | (2006.01) |
| *C07K 16/28* | (2006.01) |

(52) U.S. Cl.
CPC .......... *C07D 513/18* (2013.01); *A61K 45/06* (2013.01); *C07D 513/08* (2013.01); *C07D 513/20* (2013.01); *C07D 513/22* (2013.01); *C07D 519/00* (2013.01); *C07K 16/2818* (2013.01); *C07K 16/2827* (2013.01)

(58) Field of Classification Search
CPC .. C07D 513/08; C07D 513/10; C07D 513/20; C07D 513/22; A61K 31/553; A61P 35/00
See application file for complete search history.

(56) References Cited

U.S. PATENT DOCUMENTS

| | | | |
|---|---|---|---|
| 10,703,733 B2 | 7/2020 | Chu et al. | |
| 10,988,451 B2 | 4/2021 | Chu et al. | |
| 11,325,891 B2 | 5/2022 | Brak et al. | |
| 11,643,400 B2 | 5/2023 | Chu et al. | |
| 11,667,652 B2 | 6/2023 | Chu et al. | |
| 2016/0068545 A1 | 3/2016 | Brown et al. | |
| 2017/0088560 A1 | 3/2017 | Brown et al. | |
| 2018/0289720 A1 | 10/2018 | Harrington et al. | |
| 2019/0352271 A1 | 11/2019 | Chu et al. | |
| 2020/0331870 A1 | 10/2020 | Chu et al. | |
| 2021/0171543 A1 | 6/2021 | Chu et al. | |
| 2021/0179570 A1 | 6/2021 | Brak et al. | |
| 2022/0177409 A1 | 6/2022 | Dixon et al. | |

(Continued)

FOREIGN PATENT DOCUMENTS

| WO | WO-2016/033486 A1 | 3/2016 |
|---|---|---|
| WO | WO-2017/147410 A1 | 8/2017 |
| WO | WO-2018/183418 A1 | 10/2018 |

(Continued)

OTHER PUBLICATIONS

U.S. Appl. No. 18/181,336, filed Mar. 9, 2023, Hang Chu et al.

(Continued)

*Primary Examiner* — Bruck Kifle

(57) ABSTRACT

The present disclosure generally relates to compounds of Formula (1) and pharmaceutical compositions that may be used in methods of treating cancer.

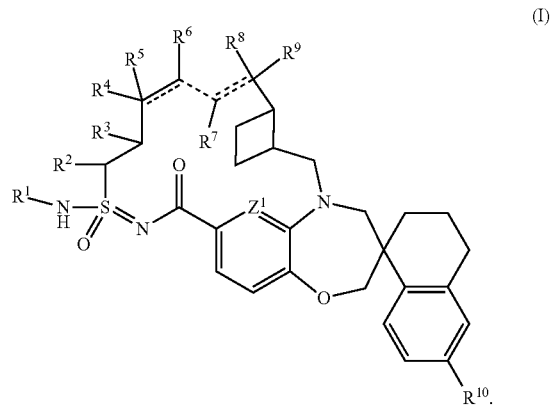

(I)

8 Claims, No Drawings

(56) References Cited

U.S. PATENT DOCUMENTS

2022/0340535 A1  10/2022  Chu et al.
2023/0312490 A1  10/2023  Chu et al.

FOREIGN PATENT DOCUMENTS

| WO | WO-2019/036575 A1 | 2/2019 |
| WO | WO-2019/046150 A1 | 3/2019 |
| WO | WO-2019/079578 A1 | 4/2019 |
| WO | WO-2019/173181 A1 | 9/2019 |
| WO | WO-2019/222112 A1 | 11/2019 |
| WO | WO-2019/222266 A1 | 11/2019 |
| WO | WO-2019/222269 A1 | 11/2019 |
| WO | WO-2020/023657 A1 | 1/2020 |
| WO | WO-2020/097577 A1 | 5/2020 |
| WO | WO-2020/147802 A1 | 7/2020 |
| WO | WO-2021/005043 A1 | 1/2021 |
| WO | WO-2021/108254 A1 | 6/2021 |
| WO | WO-2021/202452 A1 | 10/2021 |
| WO | WO-2021/225823 A1 | 11/2021 |
| WO | WO-2021/226168 A1 | 11/2021 |
| WO | WO-2021/250102 A1 | 12/2021 |
| WO | WO-2022/008674 A1 | 1/2022 |
| WO | WO-2022/108984 A1 | 5/2022 |

OTHER PUBLICATIONS

Izzo, F. et al. (2018) "Exploration of Novel Chemical Space: Synthesis and in vitro Evaluation of N-Functionalized Tertiary Sulfonimidamides", Chem Eur J, 24(37):9295-9304.

Luecking, U. (2013) "Sulfoximines: A Neglected Opportunity in Medicinal Chemistry", Angew Chem Int Ed, 52(36):9399-9408.

Luecking, U. (2019) "Neglected sulfur(VI) pharmacophores in drug discovery: exploration of novel chemical space by the interplay of drug design and method development", Org Chem Front, 6(8): 1319-1324.

Non-Final Office Action dated Jun. 7, 2022 for U.S. Appl. No. 17/094,447.

Office Action dated May 24, 2023 for Chinese Appl. No. 202080085147.9.

Examination Report dated Jun. 19, 2023 for Canadian Appl. No. 3,158,771.

Office Action dated Jun. 20, 2023 for Japanese Appl. No. 2022-527119.

Office Action dated Oct. 18, 2023 for Chinese Appl. No. 202080085147.9.

Office Action dated Nov. 22, 2023 for Japanese Appl. No. 2022-527119.

Examination Report dated Jan. 19, 2024 for Australian Appl. No. 2020384216.

Intl. Search Report—Written Opinion dated Jan. 21, 2028 for Intl. Appl. No. PCT/US2020/059837.

Office Action dated Dec. 22, 2021 for Taiwanese Appl. No. 109138370.

Intl. Preliminary Report on Patentability dated May 27, 2022 for Intl. Appl. No. PCT/US2020/059837.

Notice of Allowance dated Jun. 27, 2022 for Taiwanese Appl. No. 109138370.

Examination Report dated Oct. 6, 2022 for Indian Appl. No. 202217024369.

Notice of Allowance and Fees Due dated Dec. 19, 2022 for U.S. Appl. No. 17/094,447.

Corrected Notice of Allowability dated Dec. 28, 2022 for U.S. Appl. No. 17/094,447.

Examination Report dated May 9, 2023 for Australian Appl. No. 2020384216.

Pre-Appeal Examination Report dated Jun. 24, 2024 for Japanese Appl. No. 2022-527119.

MCL1 INHIBITORS

CROSS REFERENCE TO RELATED APPLICATIONS

This application is a continuation of U.S. patent application Ser. No. 17/094,447 filed on Nov. 10, 2020, which claims priority to U.S. Provisional Application No. 62/934,400, filed Nov. 12, 2019. The entire contents of these applications are incorporated herein in their entirety for all purposes.

FIELD

This application generally relates to certain compounds that inhibit MCL1, pharmaceutical compositions comprising the compounds, use of the compounds to treat cancers, and methods of making the compounds.

BACKGROUND

Apoptosis (programmed cell death) is a process for elimination of unwanted or potentially dangerous cells from an organism. Avoidance of apoptosis is critical for the development and sustained growth of tumors. Myeloid cell leukemia 1 protein (MCL1) is an antiapoptotic member of the Bcl-2 family of proteins. MCL1 is overexpressed in many cancers. Overexpression of MCL1 prevents cancer cells from undergoing apoptosis. Research has shown that MCL1 inhibitors can be used to treat cancers. Thus, a need exists for new compounds that inhibit MCL1.

BRIEF SUMMARY

The foregoing need is addressed by the present disclosure. In particular, inhibitors of MCL1 are provided herein.

In one embodiment, the present disclosure provides a compound according to Formula (I):

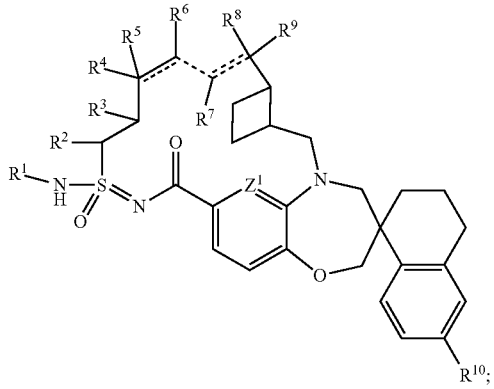

(I)

or a pharmaceutically acceptable salt thereof, wherein:
═════ is a single or double bond; when ═════ is a double bond, $R^5$ is absent;
------- is a single, double bond or triple bond; when ------- is a triple bond, $R^6$ and $R^7$ are absent;
══════ is a single or double bond; when ══════ is a double bond, $R^9$ is absent;
$Z^1$ is $CR^{1a}$ or N; wherein $R^{1a}$ is selected from hydrogen, halo, $C_{1-6}$alkyl, $C_{1-6}$alkoxyl, $C_{1-6}$haloalkyl, and $C_{1-6}$haloalkoxyl;

$R^1$ is —C(O)$R^{15}$, or $R^{16}$;
wherein $R^{15}$ is selected from $C_{1-6}$alkyl, $C_{1-6}$haloalkyl, $C_{3-10}$cycloalkyl, 3-12 membered heterocyclyl, $C_{6-10}$aryl, 5-10 membered heteroaryl, $C_{1-6}$alkylene-O-$C_{3-10}$cycloalkyl, —$C_{1-6}$alkylene-O-3-12 membered heterocyclyl, $C_{1-6}$alkylene-O—$C_{6-10}$aryl, —$C_{1-6}$alkylene-5-10 membered heteroaryl, and —NR$^{15a}$R$^{15b}$; wherein $R^{15}$ is optionally substituted with 1-5 $R^4$;
wherein each $R^{15a}$ and $R^{15b}$ is independently selected from hydrogen, $C_{1-6}$alkyl, $C_{3-10}$cycloalkyl, 3-12 membered heterocyclyl, $C_{6-10}$aryl, 5-10 membered heteroaryl, —$C_{1-6}$alkylene-$C_{3-10}$cycloalkyl, —$C_{1-6}$alkylene-3-12 membered heterocyclyl, —$C_{1-6}$alkylene-$C_{6-10}$aryl, and —$C_{1-6}$alkylene-5-10 membered heteroaryl;
wherein each $C_{1-6}$alkyl, $C_{3-10}$cycloalkyl, 3-12 membered heterocyclyl, $C_{6-10}$aryl, 5-10 membered heteroaryl, —$C_{1-6}$alkylene-$C_{3-10}$cycloalkyl, —$C_{1-6}$alkylene-3-12 membered heterocyclyl, —$C_{1-6}$alkylene-$C_{6-10}$aryl, and —$C_{1-6}$alkylene-5-10 membered heteroaryl of $R^{15a}$ and $R^{15b}$ is independently optionally substituted with one to four groups independently selected from halo, hydroxyl, oxo, —CN, $C_{1-6}$alkyl, $C_{2-6}$alkenyl, $C_{2-6}$alkynyl, $C_{1-6}$alkoxyl, $C_{1-6}$haloalkyl, and $C_{1-6}$haloalkoxyl;
wherein $R^{16}$ is 3-12 membered heterocyclyl or 5-12 membered heteroaryl; wherein $R^{16}$ is optionally substituted with 1-5 $R^4$;
$R^2$ is selected from hydrogen, halo, $C_{1-6}$alkyl, $C_{1-6}$haloalkyl, $C_{1-6}$alkoxyl, and —$C_{1-4}$alkylene-O—$C_{1-6}$-alkyl;
$R^3$ is selected from hydrogen, halo, $C_{1-6}$alkyl, $C_{1-6}$haloalkyl, $C_{1-6}$alkoxyl, $C_{3-10}$cycloalkyl, 3-12 membered heterocyclyl, and —$C_{1-4}$alkylene-O-5-10 membered heteroaryl; wherein each $C_{1-6}$alkyl, $C_{1-6}$haloalkyl, $C_{1-6}$alkoxyl, $C_{3-10}$cycloalkyl, 3-12 membered heterocyclyl, and —$C_{1-4}$alkylene-O-5-10 membered heteroaryl of $R^3$ is optionally substituted with one to four groups independently selected from halo, $C_{1-6}$alkyl, $C_{1-6}$haloalkyl, and $C_{1-6}$alkoxyl;
each $R^4$ and $R^5$ is independently selected from hydrogen, halo, hydroxyl, $C_{1-6}$alkyl, $C_{2-6}$alkenyl, $C_{2-6}$alkynyl, $C_{1-6}$haloalkyl, $C_{1-6}$alkoxyl, $C_{1-6}$haloalkoxyl, —NR$^{aa}$R$^{bb}$, —NHC(O)—$C_{1-6}$alkyl, —C(O)NH—$C_{1-6}$alkyl, —O—$C_{2-6}$alkynyl, —OC(O)—$C_{1-6}$alkyl, —O—(CH$_2$CH$_2$O)n-$C_{1-6}$alkyl, $C_{3-10}$cycloalkyl, 3-12 membered heterocyclyl, —O—$C_{3-10}$cycloalkyl, —O-3-12 membered heterocyclyl, —O—$C_{1-4}$alkylene-$C_{3-10}$cycloalkyl, 5-10 membered heteroaryl, —O—$C_{1-4}$alkylene-3-12 membered heterocyclyl, —O-5-10 membered heteroaryl, and —O—$C_{1-4}$alkylene-5-10 membered heteroaryl;
wherein each $C_{1-6}$alkyl, $C_{2-6}$alkenyl, $C_{2-6}$alkynyl, $C_1$-haloalkyl, $C_{1-6}$alkoxyl, $C_{1-6}$haloalkoxyl, —NHC(O)—$C_{1-6}$alkyl, —C(O)NH—$C_{1-6}$alkyl, —O—$C_{2-6}$alkynyl, —OC(O)—$C_{1-6}$alkyl, —O—(CH$_2$CH$_2$O)n-$C_{1-6}$alkyl, $C_{3-10}$cycloalkyl, 3-12 membered heterocyclyl, —O—$C_{3-10}$cycloalkyl, —O-3-12 membered heterocyclyl, —O—$C_{1-4}$alkylene-$C_{3-10}$cycloalkyl, 5-10 membered heteroaryl, —O—$C_{1-4}$alkylene-3-12 membered heterocyclyl, —O-5-10 membered heteroaryl, and —O—$C_{1-4}$alkylene-5-10 membered heteroaryl of $R^4$ and $R^5$ is optionally substituted with one to four groups independently selected from halo, hydroxyl, oxo, $C_{1-6}$alkyl, $C_{1-6}$alkoxyl, $C_{1-6}$haloalkoxyl, —$NR^{aa}R^{bb}$, $C_{3-10}$cycloalkyl, and 3-12 membered heterocyclyl;
each $R^6$ and $R^7$ is independently selected from hydrogen, halo, hydroxyl, $C_{1-6}$alkyl, $C_{1-6}$alkoxyl, $C_{1-6}$haloalkyl, and $C_{1-6}$haloalkoxyl;
$R^8$ is selected from hydrogen, halo, hydroxyl, oxo, $C_{1-6}$alkyl, $C_{2-6}$alkenyl, $C_{2-6}$alkynyl, $C_{1-6}$alkoxyl, —O—$C_{2-6}$alkenyl, —O—$C_{2-6}$alkynyl, $C_{3-10}$cycloalkyl, 3-12 membered heterocyclyl, $C_{6-10}$aryl, 5-10 membered heteroaryl, —O—$C_{3-10}$cycloalkyl, —O-3-12 membered heterocyclyl, —O—$C_{6-10}$aryl, —O-5-10 membered heteroaryl, —O—$C_{1-4}$alkylene-$C_{3-10}$cycloalkyl, —O—$C_{1-4}$alkylene-3-12 membered heterocyclyl, —O—$C_{1-4}$alkylene-$C_{6-10}$aryl, and —O—$C_{1-4}$alkylene-5-10 membered heteroaryl;
$R^9$ is absent or selected from hydrogen, halo, hydroxyl, $C_{1-6}$alkyl, $C_{2-6}$alkenyl, $C_{2-6}$alkynyl, $C_{1-6}$alkoxyl, —O—$C_{2-6}$alkenyl, —O—$C_{2-6}$alkynyl, $C_{3-10}$cycloalkyl, 3-12 membered heterocyclyl, $C_{6-10}$aryl, 5-10 membered heteroaryl, —O—$C_{3-10}$cycloalkyl, —O-3-12 membered heterocyclyl, —O—$C_{6-10}$aryl, —O-5-10 membered heteroaryl, —O—$C_{1-4}$alkylene-$C_{3-10}$cycloalkyl, —O—$C_{1-4}$alkylene-3-12 membered heterocyclyl, —O—$C_{1-4}$alkylene-$C_{6-10}$aryl, and —O—$C_{1-4}$alkylene-5-10 membered heteroaryl;
  wherein each $C_{1-6}$alkyl, $C_{2-6}$alkenyl, $C_{2-6}$alkynyl, $C_{1-6}$alkoxyl, —O—$C_{2-6}$alkenyl, —O—$C_{2-6}$alkynyl, $C_{3-10}$cycloalkyl, 3-12 membered heterocyclyl, $C_{6-10}$aryl, 5-10 membered heteroaryl, —O—$C_{3-10}$cycloalkyl, —O-3-12 membered heterocyclyl, —O—$C_{6-10}$aryl, —O-5-10 membered heteroaryl, —O—$C_{1-4}$alkylene-$C_{3-10}$cycloalkyl, —O—$C_{1-4}$alkylene-3-12 membered heterocyclyl, —O—$C_{1-4}$alkylene-$C_{6-10}$aryl, and —O—$C_{1-4}$alkylene-5-10 membered heteroaryl of $R^8$ and $R^9$ is independently optionally substituted with 1-5 $R^A$; or
$R^2$ and $R^4$, $R^4$ and $R^6$, $R^6$ and $R^7$, or $R^7$ and $R^8$, together with the atoms to which they are attached form a 3-7 membered heterocyclyl or 5-6 membered heteroaryl; wherein each 3-7 membered heterocyclyl and 5-6 membered heteroaryl contains one to three heteroatoms; and wherein each 3-7 membered heterocyclyl and 5-6 membered heteroaryl is optionally substituted with one to four groups independently selected from halo, oxo, hydroxyl, $C_{1-6}$alkyl, $C_{1-6}$haloalkyl, $C_{1-6}$alkoxyl, $C_{1-6}$haloalkoxyl, $C_{2-6}$alkenyl, $C_{2-6}$alkynyl, —$NR^{aa}R^{bb}$, and —$C_{1-6}$alkylene-$NR^{aa}R^{bb}$; or
$R^4$, $R^6$, and $R^7$ together with the atoms to which they are attached form an 8-12 membered fused heterocyclyl; wherein the 8-12 membered fused heterocyclyl contains one to four heteroatoms; and wherein the 8-12 membered fused heterocyclyl is optionally substituted with one to four groups independently selected from halo, oxo, hydroxyl, $C_{1-6}$alkyl, $C_{1-6}$haloalkyl, $C_{1-6}$alkoxyl, $C_{1-6}$haloalkoxyl, $C_{2-6}$alkenyl, $C_{2-6}$alkynyl, —$NR^{aa}R^{bb}$, and —$C_{1-6}$alkylene-$NR^{aa}R^{bb}$; or
$R^4$ and $R^8$ together with the atoms to which they are attached form an 8-16 membered heterocyclyl; wherein the 8-16 membered heterocyclyl contains one to four heteroatoms; and wherein the 8-16 membered heterocyclyl is optionally substituted with one to three groups independently selected from halo, oxo, hydroxyl, $C_{1-6}$alkyl, $C_{1-6}$haloalkyl, $C_{1-6}$alkoxyl, $C_{1-6}$haloalkoxyl, $C_{2-6}$alkenyl, $C_{2-6}$alkynyl, —$NR^{aa}R^{bb}$, and —$C_{1-6}$alkylene-$NR^{aa}R^{bb}$;

$R^{10}$ is selected from hydrogen, halo, hydroxyl, —CN, $C_{1-6}$alkyl, $C_{1-6}$alkoxyl, $C_{1-6}$haloalkyl, and $C_{1-6}$haloalkoxyl;
each $R^{11}$, $R^{12}$, $R^{13}$, and $R^{14}$ is independently selected from hydrogen, halo, hydroxyl, —CN, $C_{1-6}$alkyl, $C_{1-6}$alkoxy, and $C_{1-6}$haloalkyl; or
$R^{11}$ and $R^{13}$ together with the atoms to which they are attached form a $C_{3-6}$ cycloalkyl or 3-6 membered heterocyclyl; wherein the 3-6 membered heterocyclyl contains one to three heteroatoms; and wherein each $C_{3-6}$ cycloalkyl and 3-6 membered heterocyclyl is optionally substituted with one to three groups independently selected from halo, hydroxyl, —CN, $C_{1-6}$alkyl, $C_{1-6}$alkoxy, $C_{1-6}$haloalkyl, and $C_{1-6}$haloalkoxyl;
each $R^A$ is independently selected from halo, hydroxyl, oxo, —CN, $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, —$C_{1-4}$alkylene-O—$C_{1-4}$alkyl, $C_{3-10}$cycloalkyl, 3-12 membered heterocyclyl, $C_{6-10}$aryl, 5-10 membered heteroaryl, and —$NR^{aa}R^{bb}$;
  wherein each $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, —$C_{1-4}$alkylene-O—$C_{1-4}$alkyl, $C_{3-10}$cycloalkyl, 3-12 membered heterocyclyl, $C_{6-10}$aryl, 5-10 membered heteroaryl of $R^A$ is independently substituted with one to three groups independently selected from halo, hydroxyl, —CN, $C_{1-6}$alkyl, $C_{1-6}$alkoxy, $C_{1-6}$haloalkyl, $C_1$-haloalkoxyl, $C_{3-10}$cycloalkyl, 3-12 membered heterocyclyl, $C_{6-10}$aryl, 5-10 membered heteroaryl, and —$NR^{aa}R^{bb}$; and
each $R^{aa}$ and $R^{bb}$ is independently selected from hydrogen, $C_{1-6}$alkyl, $C_{3-10}$cycloalkyl, 3-12 membered heterocyclyl, $C_{6-10}$aryl, 5-10 membered heteroaryl, —$C_{1-6}$alkylene-$C_{3-10}$cycloalkyl, —$C_{1-6}$alkylene-3-12 membered heterocyclyl, —$C_{1-6}$alkylene-$C_{6-10}$aryl, and —$C_{1-6}$alkylene-5-10 membered heteroaryl;
  wherein each $C_{1-6}$alkyl, $C_{3-10}$cycloalkyl, 3-12 membered heterocyclyl, $C_{6-10}$aryl, 5-10 membered heteroaryl, —$C_{1-6}$alkylene-$C_{3-10}$cycloalkyl, —$C_{1-6}$alkylene-3-12 membered heterocyclyl, —$C_{1-6}$alkylene-$C_{6-10}$aryl, and —$C_{1-6}$alkylene-5-10 membered heteroaryl of $R^{aa}$ and $R^{bb}$ is independently optionally substituted with one to four groups independently selected from halo, $C_{1-6}$alkyl, —CN, $C_{1-6}$alkoxyl, and $C_1$-haloalkyl;
wherein the 3-12 membered heterocyclyl is a single ring or multiple rings having one to four heteroatoms independently selected from nitrogen, sulfur, phosphorus, —N(O)—, —S(O)—, and —S(O)$_2$—; and wherein the multiple rings may be fused, bridged, or spiro;
wherein the 5-10 membered heteroaryl is an aromatic group having a single ring or multiple rings; wherein the 5-10 membered heteroaryl contains one to four heteroatoms independently selected from nitrogen, oxygen, sulfur, —N(O)—, —S(O)—, and —S(O)$_2$; and
provided:
when ------- is a single bond, at least one of ====== and ====== is a double bond; and
when ------- is a double bond,
(a) $R^1$ is $R^{16}$;
(b) $Z^1$ is N;
(c) $Z^1$ is $CR^{1a}$, wherein $R^{1a}$ is selected from halo, $C_{1-6}$alkyl, $C_{1-6}$alkoxyl, $C_1$-haloalkyl, and $C_1$-haloalkoxyl;
(d) each $R^4$ and $R^5$ is not hydrogen;
(e) each $R^8$ and $R^9$ is not hydrogen;

(f) $R^5$ is hydrogen, $R^4$ is selected from $C_{2-6}$alkenyl, $C_{2-6}$alkynyl, and —O—$C_{2-6}$alkynyl, each of which is optionally substituted with one to four groups independently selected from halo, hydroxyl, oxo, $C_{1-6}$alkyl, $C_{1-6}$alkoxyl, $C_1$-haloalkoxyl, —$NR^{aa}R^{bb}$, $C_{3-10}$cycloalkyl, and 3-12 membered heterocyclyl;

(g) $R^9$ is hydrogen, $R^8$ is selected from hydrogen, halo, $C_{2-6}$alkenyl, $C_{2-6}$alkynyl, —O—$C_{2-6}$alkenyl, —O—$C_{2-6}$alkynyl, $C_{3-10}$cycloalkyl, 3-12 membered heterocyclyl, $C_{6-10}$aryl, and 5-10 membered heteroaryl; wherein each $C_{2-6}$alkynyl, O—$C_{2-6}$alkenyl, —O—$C_{2-6}$alkynyl, $C_{3-10}$cycloalkyl, 3-12 membered heterocyclyl, $C_{6-10}$aryl, and 5-10 membered heteroaryl of $R^8$ is independently optionally substituted with 1-5 $R^A$;

(h) $R^2$ and $R^4$, $R^4$ and $R^6$, $R^6$ and $R^7$, or $R^7$ and $R^8$, together with the atoms to which they are attached form a 3-7 membered heterocyclyl or 5-6 membered heteroaryl; wherein each 3-7 membered heterocyclyl and 5-6 membered heteroaryl contains one to three heteroatoms; and each 3-7 membered heterocyclyl and 5-6 membered heteroaryl is optionally substituted with one to four groups independently selected from halo, oxo, hydroxyl, $C_{1-6}$alkyl, $C_1$-haloalkyl, $C_{1-6}$alkoxyl, $C_1$-haloalkoxyl, $C_{2-6}$alkenyl, $C_{2-6}$alkynyl, —$NR^{aa}R^{bb}$, and —$C_{1-6}$alkylene-$NR^{aa}R^{bb}$;

(i) $R^4$, $R^6$, and $R^7$ together with the atoms to which they are attached form an 8-12 membered fused heterocyclyl; wherein the 8-12 membered fused heterocyclyl contains one to three heteroatoms; wherein the 8-12 membered fused heterocyclyl is optionally substituted with one to four groups independently selected from halo, oxo, hydroxyl, $C_{1-6}$alkyl, $C_1$-haloalkyl, $C_{1-6}$alkoxyl, $C_1$-haloalkoxyl, $C_{2-6}$alkenyl, $C_{2-6}$alkynyl, —$NR^{aa}R^{bb}$, and —$C_{1-6}$alkylene-$NR^{aa}R^{bb}$; or (j) $R^4$ and $R^8$ together with the atoms to which they are attached form an 8-16 membered heterocyclyl; wherein the 8-16 membered fused heterocyclyl contains one to three heteroatoms; wherein the 8-16 membered heterocyclyl is optionally substituted with one to three groups independently selected from halo, oxo, hydroxyl, $C_{1-6}$alkyl, $C_1$-haloalkyl, $C_{1-6}$alkoxyl, $C_1$-haloalkoxyl, $C_{2-6}$alkenyl, $C_{2-6}$alkynyl, —$NR^{aa}R^{bb}$, and —$C_{1-6}$alkylene-$NR^{aa}R^{bb}$.

In some embodiments, a pharmaceutical composition comprising a compound according to Formula (I), or pharmaceutically acceptable salt thereof, and a pharmaceutically acceptable excipient is provided herein.

In some embodiments, a method of inhibiting MCL1 in a patient comprising administering a compound according to Formula (I), or a pharmaceutically acceptable salt thereof, to the patient is provided herein.

In some embodiments, a method of treating cancer in a patient, comprising administering a compound according to Formula (I), or a pharmaceutically acceptable salt thereof, to the patient is provided herein.

DETAILED DESCRIPTION

Unless the context requires otherwise, throughout the present specification and claims, the word "comprise" and variations thereof, such as, "comprises" and "comprising" are to be construed in an open, inclusive sense, that is as "including, but not limited to".

A prefix such as "$C_{u-v}$" or ($C_u$-$C_v$) indicates that the following group has from u to v carbon atoms, where u and v are integers. For example, "$C_{1-6}$alkyl" indicates that the alkyl group has from 1 to 6 carbon atoms.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. Unless chemically or structurally required, no directionality is indicated or implied by the order in which a chemical group is written or named.

A squiggly line on a chemical group as shown below, for example,

indicates a point of attachment, i.e., it shows the broken bond by which the group is connected to another described group.

The term "substituted" means that one or more hydrogen atoms on a hydrocarbon is replaced with one or more atoms or groups other than hydrogen, provided that the designated carbon atom's or atoms' normal valence is not exceeded. A "substituent" is an atom or group that replaces a hydrogen atom on a hydrocarbon when it is "substituted." Unless specified otherwise, where a group is described as optionally substituted, any substituents of the group are themselves unsubstituted.

The term "about" refers to a value or parameter±10% the indicated amount.

As used herein, "alkyl" is a linear or branched saturated monovalent hydrocarbon. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), and 2,3-dimethyl-2-butyl (—C(CH$_3$)$_2$CH(CH$_3$)$_2$), 3,3-dimethyl-2-butyl (—CH(CH$_3$)C(CH$_3$)$_3$.

"Alkylene" (including those which are part of other groups) refers to branched and unbranched divalent "alkyl" groups. As used herein, alkylene has 1 to 20 carbon atoms (i.e., $C_{1-20}$alkylene), 1 to 8 carbon atoms (i.e., $C_{1-8}$ alkylene), 1 to 6 carbon atoms (i.e., $C_{1-6}$ alkylene), or 1 to 4 carbon atoms (i.e., $C_{1-4}$ alkylene). Examples include: methylene, ethylene, propylene, 1-methylethylene, butylene, 1-methylpropylene, 1,1-dimethylethylene or 1,2-dimethylethylene. Unless stated otherwise, the definitions propylene and butylene include all the possible isomeric forms of the groups in question with the same number of carbons. Thus, for example, propylene also includes 1-methylethylene and butylene includes 1-methylpropylene, 1,1-dimethylethylene, and 1,2-dimethylethylene.

"Alkenyl" refers to an aliphatic group containing at least one carbon-carbon double bond. Examples of alkenyl groups include ethenyl, propenyl, butadienyl (including 1,2-butadienyl, and 1,3-butadienyl).

"Alkoxy" as used herein refers to a radical of the formula —OR$_A$ where R$_A$ is an alkyl radical as defined above. Non-limiting examples of alkoxy include methoxy, ethoxy, propoxy, and butoxy.

"Alkynyl" refers to an aliphatic group containing at least one carbon-carbon triple bond.

"Aryl" refers to a monoradical or diradical aromatic carbocyclic group having a single ring (e.g., monocyclic) or multiple rings (e.g., bicyclic or tricyclic) including fused ring systems wherein one or more fused rings is/are fully or partially unsaturated. Non-limiting examples of aryl groups as used herein include phenyl, naphthyl, fluorenyl, indanyl, tetrahydroindanuyl, and anthryl. Aryl, however, does not encompass or overlap in any way with heteroaryl defined below. If one or more aryl groups are fused with a heteroaryl ring, the resulting ring system is heteroaryl. The classification of mono or diradical indicates whether the aryl group terminates the chain (monoradical) or is within a chain (diradical). The above definition does not preclude additional substituents on the aryl group. For example, as used herein, the aryl group in "A-aryl-B" is a diradical whereas the aryl group in "A-B-aryl" is monoradical, though additional substituents may be present on each aryl group.

"Cycloalkyl" refers to a saturated or partially saturated cyclic alkyl group having a single ring or multiple rings including fused, bridged, and spiro ring systems. Examples of cycloalkyl groups include cyclopropyl, cyclobutyl, cyclopentyl, and cyclohexyl.

"Halo" and "halogen" are used herein to refer to fluoro (—F), chloro (—Cl), bromo (—Br) and iodo (—I).

The term "haloalkyl" as used herein refers to an alkyl as defined herein, wherein one or more hydrogen atoms of the alkyl are independently replaced by a halogen substituent, which may be the same or different. For example, $C_{1-6}$haloalkyl is a $C_{1-6}$alkyl wherein one or more of the hydrogen atoms of the $C_{1-6}$alkyl have been replaced by a halo substituent. Examples of haloalkyl groups include, but are not limited to, fluoromethyl, fluorochloromethyl, difluoromethyl, difluorochloromethyl, trifluoromethyl, 1,1,1-trifluoroethyl, and pentafluoroethyl.

"Heteroaryl" refers to a monoradical or diradical aromatic group having a single ring, multiple rings, or multiple fused rings, with one or more ring heteroatoms independently selected from nitrogen, oxygen, and sulfur. The heteroatoms within the "heteroaryl" may be oxidized, e.g., —N(O)—, —S(O)—, —S(O)$_2$—. The term includes fused ring systems wherein one or more fused rings is/are fully or partially unsaturated. The classification of mono or diradical indicates whether the heteroaryl group terminates the chain (monoradical) or is within a chain (diradical). The above definition does not preclude additional substituents on the heteroaryl group. For example, the heteroaryl group in "A-heteroaryl-B" is a diradical whereas the heteroaryl group in "A-B-heteroaryl" is monoradical, though additional substituents may be present on each heteroaryl group. Heteroaryl does not encompass or overlap with aryl as defined above. Non-limiting examples of heteroaryl groups include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-IH-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl.

The term "heterocyclyl," "heterocycle," or "heterocyclic" refers to a monoradical or diradical saturated or unsaturated group having a single ring or multiple condensed rings having one or more heteroatoms selected from nitrogen, sulfur, phosphorus, and/or oxygen within the ring. The heteroatoms within the "heterocyclyl" may be oxidized, e.g., —N(O)—, —S(O)—, —S(O)$_2$—. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Exemplary heterocyclic groups include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxothiomorpholinyl.

The term "cyano" refers to the group —CN.

The term "oxo" refers to a group =O.

The term "carboxy" refers to a group —C(O)—OH.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The symbol "(±)" is used to designate a racemic mixture where appropriate.

"Diastereoisomers" are stereoisomers that have at least two asymmetric atoms, but which are not mirror-images of each other.

As used herein, "treatment" or "treating" is an approach for obtaining beneficial or desired results. For purposes of the present disclosure, beneficial or desired results include, but are not limited to, alleviation of a symptom and/or diminishment of the extent of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

As used herein, "prevention" or "preventing" refers to a regimen that protects against the onset of a disease or disorder such that the clinical symptoms of the disease or disorder do not develop. Thus, "prevention" relates to administration of a therapy to a subject before signs of the disease are detectable in the subject. The subject may be an individual at risk of developing the disease or disorder, such as an individual who has one or more risk factors known to be associated with development or onset of the disease or disorder.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease. The effective amount will vary depending on the particular compound, and characteristics of the subject to be treated, such as age, weight, etc. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

As used herein, "co-administration" includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure.

Also provided herein are pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are suitable for veterinary or human pharmaceutical use.

Compounds described herein may be prepared and/or formulated as pharmaceutically acceptable salts. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Williams and Wilkins, Philadelphia, Pa., 2006.

Non-limiting examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4$+(wherein X is $C_1$-$C_4$ alkyl). Also included are base addition salts, such as sodium or potassium salts.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

A "tautomer" refers to a proton shift from one atom of a molecule to another atom of the same molecule. The present disclosure includes tautomers of any said compounds.

A "solvate" is formed by the interaction of a solvent and a compound. Solvates of salts of the compounds described herein are also provided. Hydrates of the compounds described herein are also provided.

The term "prodrug" as used herein is a biologically inactive derivative of a drug that upon administration to the human body is converted to the biologically active parent drug according to some chemical or enzymatic pathway.

LIST OF ABBREVIATIONS AND ACRONYMS

Abbreviation Meaning

ACN or MeCN Acetonitrile
MeTHF 2-methyl tetrahydrofuran
AcOH Acetic acid
Ar Argon
Bn Benzyl
Boc t-Butyloxycarbonyl
BSA Bovine Serum Albumin
calcd or calc'd Calculated
DCE 1,2-Dichloroethane
DCM Dichloromethane
DIPEA N,N-Diisopropylethylamine
DMAP 4-Dimethylaminopyridine
DMF Dimethylformamide
DMSO Dimethylsulfoxide Et Ethyl
EDCl 1-Ethyl-3-(3-dirmethylaminopropyl)carbodiimide hydrochloride
EDTA Ethylenediaminetetraacetic acid
ESI Electrospray Ionization
EtOAc Ethyl acetate
EtOH Ethanol
h or hr(s) Hour(s)
HPLC High performance liquid chromatography
i-Pr Isopropyl
KHMDS Potassium bis(trimethylsilyl)amide
LAH Lithium aluminum hydride
LCMS or Liquid Chromatography Mass Spectrometry LC/MS
LDA Lithium diisopropylamide
Me Methyl
MeOH Methanol
min Minute(s)
MS Mass Spectrometry
m/z Mass-to-charge ratio
NMR Nuclear Magnetic Resonance spectroscopy
n-BuLi n-Butyllithium
Ph Phenyl
PPh$_3$ Triphenylphosphine
PPh$_3$Cl$_2$ Triphenylphosphine Dichloride
RT or rt Room temperature
STAB Sodium triacetoxyborohydride
SFC Supercritical Fluid Chromatography
TBAF Tetra-n-butylammonium fluoride
TBDMS t-Butyldimethylsilyl
TBDMSCl t-Butyldimethylsilyl chloride
TBSOTf t-Butyldimethylsilyl triflate
tBu or t-Bu tert-butyl
TEA Triethylamine
TFA Trifluoroacetic acid
THF Tetrahydrofuran
TLC Thin Layer Chromatography Compounds In some embodiments, the present disclosure provides a compound according to Formula (I):

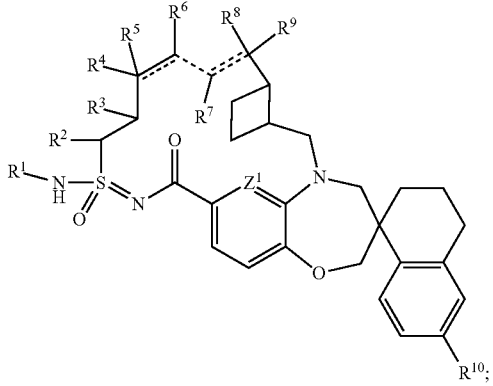

or a pharmaceutically acceptable salt thereof, wherein:
====== is a single or double bond; when ====== is a double bond, $R^5$ is absent;
------- is a single, double bond or triple bond; when ------- is a triple bond, $R^6$ and $R^7$ are absent;
====== is a single or double bond; when ====== is a double bond, $R^9$ is absent;

$Z^1$ is $CR^{1a}$ or N; wherein $R^{1a}$ is selected from hydrogen, halo, $C_{1-6}$alkyl, $C_{1-6}$alkoxyl, $C_{1-6}$haloalkyl, and $C_{1-6}$haloalkoxyl;

$R^1$ is $-C(O)R^{15}$, or $R^{16}$;
  wherein $R^{15}$ is selected from $C_{1-6}$alkyl, $C_{1-6}$haloalkyl, $C_{3-10}$cycloalkyl, 3-12 membered heterocyclyl, $C_{6-10}$aryl, 5-10 membered heteroaryl, $C_{1-6}$alkylene-O-$C_{3-10}$cycloalkyl, $-C_{1-6}$alkylene-O-3-12 membered heterocyclyl, $C_{1-6}$alkylene-O-$C_{6-10}$aryl, $-C_{1-6}$alkylene-5-10 membered heteroaryl, and $-NR^{15a}R^{15b}$; wherein $R^{15}$ is optionally substituted with 1-5 $R^A$;
    wherein each $R^{15a}$ and $R^{15b}$ is independently selected from hydrogen, $C_{1-6}$alkyl, $C_{3-10}$cycloalkyl, 3-12 membered heterocyclyl, $C_{6-10}$aryl, 5-10 membered heteroaryl, $-C_{1-6}$alkylene-$C_{3-10}$cycloalkyl, $-C_{1-6}$alkylene-3-12 membered heterocyclyl, $-C_{1-6}$alkylene-$C_{6-10}$aryl, and $-C_{1-6}$alkylene-5-10 membered heteroaryl;
      wherein each $C_{1-6}$alkyl, $C_{3-10}$cycloalkyl, 3-12 membered heterocyclyl, $C_{6-10}$aryl, 5-10 membered heteroaryl, $-C_{1-6}$alkylene-$C_{3-10}$cycloalkyl, $-C_{1-6}$alkylene-3-12 membered heterocyclyl, $-C_{1-6}$alkylene-$C_{6-10}$aryl, and $-C_{1-6}$alkylene-5-10 membered heteroaryl of $R^{15a}$ and $R^{15b}$ is independently optionally substituted with one to four groups independently selected from halo, hydroxyl, oxo, $-CN$, $C_{1-6}$alkyl, $C_{2-6}$alkenyl, $C_{2-6}$alkynyl, $C_{1-6}$alkoxyl, $C_{1-6}$haloalkyl, and $C_{1-6}$haloalkoxyl;
  wherein $R^{16}$ is 3-12 membered heterocyclyl, or 5-12 membered heteroaryl; wherein $R^{16}$ is optionally substituted with 1-5 $R^A$;

$R^2$ is selected from hydrogen, halo, $C_{1-6}$alkyl, $C_{1-6}$haloalkyl, $C_{1-6}$alkoxyl, and $-C_{1-4}$alkylene-O-$C_{1-6}$alkyl;

$R^3$ is selected from hydrogen, halo, $C_{1-6}$alkyl, $C_{1-6}$haloalkyl, $C_{1-6}$alkoxyl, $C_{3-10}$cycloalkyl, 3-12 membered heterocyclyl, and $-C_{1-4}$alkylene-O-5-10 membered heteroaryl; wherein each $C_1$-6alkyl, $C_{1-6}$haloalkyl, $C_{1-6}$alkoxyl, $C_{3-10}$cycloalkyl, 3-12 membered heterocyclyl, and $-C_{1-4}$alkylene-O-5-10 membered heteroaryl of $R^3$ is optionally substituted with one to four groups independently selected from halo, $C_{1-6}$alkyl, $C_{1-6}$haloalkyl, and $C_{1-6}$alkoxyl;

each $R^4$ and $R^5$ is independently selected from hydrogen, halo, hydroxyl, $C_{1-6}$alkyl, $C_{2-6}$alkenyl, $C_{2-6}$alkynyl, $C_{1-6}$haloalkyl, $C_{1-6}$alkoxyl, $C_{1-6}$haloalkoxyl, $-NR^{aa}R^{bb}$, $-NHC(O)-C_{1-6}$alkyl, $-C(O)NH-C_{1-6}$alkyl, $-O-C_{2-6}$alkynyl, $-OC(O)-C_{1-6}$alkyl, $-O-(CH_2CH_2O)n-C_{1-6}$alkyl, $C_{3-10}$cycloalkyl, 3-12 membered heterocyclyl, $-O-C_{3-10}$cycloalkyl, $-O$-3-12 membered heterocyclyl, $-O-C_{1-4}$alkylene-$C_{3-10}$cycloalkyl, 5-10 membered heteroaryl, $-O-C_{1-4}$alkylene-3-12 membered heterocyclyl, $-O$-5-10 membered heteroaryl, and $-O-C_{1-4}$alkylene-5-10 membered heteroaryl;
  wherein each $C_{1-6}$alkyl, $C_{2-6}$alkenyl, $C_{2-6}$alkynyl, $C_1$-haloalkyl, $C_{1-6}$alkoxyl, $C_{1-6}$haloalkoxyl, $-NHC(O)-C_{1-6}$alkyl, $-C(O)NH-C_{1-6}$alkyl, $-O-C_{2-6}$alkynyl, $-OC(O)-C_{1-6}$alkyl, $-O-(CH_2CH_2O)n-C_{1-6}$alkyl, $C_{3-10}$cycloalkyl, 3-12 membered heterocyclyl, $-O-C_{3-10}$cycloalkyl, $-O$-3-12 membered heterocyclyl, $-O-C_{1-4}$alkylene-$C_{3-10}$cycloalkyl, 5-10 membered heteroaryl, $-O-C_{1-4}$alkylene-3-12 membered heterocyclyl, $-O$-5-10 membered heteroaryl, and $-O-C_{1-4}$alkylene-5-10 membered heteroaryl of $R^4$ and $R^5$ is optionally substituted with one to four groups independently selected from halo, hydroxyl, oxo, $C_{1-6}$alkyl, $C_{1-6}$alkoxyl, $C_{1-6}$haloalkoxyl, —$NR^{aa}R^{bb}$, $C_{3-10}$cycloalkyl, and 3-12 membered heterocyclyl;

each $R^6$ and $R^7$ is independently selected from hydrogen, halo, hydroxyl, $C_{1-6}$alkyl, $C_{1-6}$alkoxyl, $C_{1-6}$haloalkyl, and $C_{1-6}$haloalkoxyl;

$R^8$ is selected from hydrogen, halo, hydroxyl, oxo, $C_{1-6}$alkyl, $C_{2-6}$alkenyl, $C_{2-6}$alkynyl, $C_{1-6}$alkoxyl, —O—$C_{2-6}$alkenyl, —O—$C_{2-6}$alkynyl, $C_{3-10}$cycloalkyl, 3-12 membered heterocyclyl, $C_{6-10}$aryl, 5-10 membered heteroaryl, —O—$C_{3-10}$cycloalkyl, —O-3-12 membered heterocyclyl, —O—$C_{6}$-oaryl, —O-5-10 membered heteroaryl, —O—$C_{1-4}$alkylene-$C_{3-10}$cycloalkyl, —O—$C_{1-4}$alkylene-3-12 membered heterocyclyl, —O—$C_{1-4}$alkylene-$C_{6-10}$aryl, and —O—$C_{1-4}$alkylene-5-10 membered heteroaryl;

$R^9$ is absent or selected from hydrogen, halo, hydroxyl, $C_{1-6}$alkyl, $C_{2-6}$alkenyl, $C_{2-6}$alkynyl, $C_{1-6}$alkoxyl, —O—$C_{2-6}$alkenyl, —O—$C_{2-6}$alkynyl, $C_{3-10}$cycloalkyl, 3-12 membered heterocyclyl, $C_{6-10}$aryl, 5-10 membered heteroaryl, —O—$C_{3-10}$cycloalkyl, —O-3-12 membered heterocyclyl, —O—$C_{6-10}$aryl, —O-5-10 membered heteroaryl, —O—$C_{1-4}$alkylene-$C_{3-10}$cycloalkyl, —O—$C_{1-4}$alkylene-3-12 membered heterocyclyl, —O—$C_{1-4}$alkylene-$C_{6-10}$aryl, and —O—$C_{1-4}$alkylene-5-10 membered heteroaryl;

wherein each $C_{1-6}$alkyl, $C_{2-6}$alkenyl, $C_{2-6}$alkynyl, $C_{1-6}$alkoxyl, —O—$C_{2-6}$alkenyl, —O—$C_{2-6}$alkynyl, $C_{3-10}$cycloalkyl, 3-12 membered heterocyclyl, $C_{6-10}$aryl, 5-10 membered heteroaryl, —O—$C_{3-10}$cycloalkyl, —O-3-12 membered heterocyclyl, —O—$C_{6-10}$aryl, —O-5-10 membered heteroaryl, —O—$C_{1-4}$alkylene-$C_{3-10}$cycloalkyl, —O—$C_{1-4}$alkylene-3-12 membered heterocyclyl, —O—$C_{1-4}$alkylene-$C_{6-10}$aryl, and —O—$C_{1-4}$alkylene-5-10 membered heteroaryl of $R^8$ and $R^9$ is independently optionally substituted with 1-5 $R^A$; or $R^2$ and $R^4$, $R^4$ and $R^6$, $R^6$ and $R^7$, or $R^7$ and $R^1$, together with the atoms to which they are attached form a 3-7 membered heterocyclyl or 5-6 membered heteroaryl; wherein each 3-7 membered heterocyclyl and 5-6 membered heteroaryl contains one to three heteroatoms; and wherein each 3-7 membered heterocyclyl and 5-6 membered heteroaryl is optionally substituted with one to four groups independently selected from halo, oxo, hydroxyl, $C_{1-6}$alkyl, $C_{1-6}$haloalkyl, $C_{1-6}$alkoxyl, $C_{1-6}$haloalkoxyl, $C_{2-6}$alkenyl, $C_{2-6}$alkynyl, —$NR^{aa}R^{bb}$, and —$C_{1-6}$alkylene-$NR^{aa}R^{bb}$; or $R^4$, $R^6$, and $R^7$ together with the atoms to which they are attached form an 8-12 membered fused heterocyclyl; wherein the 8-12 membered fused heterocyclyl contains one to four heteroatoms; and wherein the 8-12 membered fused heterocyclyl is optionally substituted with one to four groups independently selected from halo, oxo, hydroxyl, $C_{1-6}$alkyl, $C_{1-6}$haloalkyl, $C_{1-6}$alkoxyl, $C_{1-6}$haloalkoxyl, $C_{2-6}$alkenyl, $C_{2-6}$alkynyl, —$NR^{aa}R^{bb}$, and —$C_{1-6}$alkylene-$NR^{aa}R^{bb}$; or $R^4$ and $R^8$ together with the atoms to which they are attached form an 8-16 membered heterocyclyl; wherein the 8-16 membered heterocyclyl contains one to four heteroatoms; and wherein the 8-16 membered heterocyclyl is optionally substituted with one to three groups independently selected from halo, oxo, hydroxyl, $C_{1-6}$alkyl, $C_{1-6}$haloalkyl, $C_{1-6}$alkoxyl, $C_{1-6}$haloalkoxyl, $C_{2-6}$alkenyl, $C_{2-6}$alkynyl, —$NR^{aa}R^{bb}$, and —$C_{1-6}$alkylene-$NR^{aa}R^{bb}$;

$R^{10}$ is selected from hydrogen, halo, hydroxyl, —CN, $C_{1-6}$alkyl, $C_{1-6}$alkoxyl, $C_{1-6}$haloalkyl, and $C_{1-6}$haloalkoxyl;

each $R^{11}$, $R^{12}$, $R^{13}$, and $R^{14}$ is independently selected from hydrogen, halo, hydroxyl, —CN, $C_{1-6}$alkyl, $C_{1-6}$alkoxy, and $C_{1-6}$haloalkyl; or $R^{11}$ and $R^{13}$ together with the atoms to which they are attached form a $C_{3-6}$ cycloalkyl or 3-6 membered heterocyclyl; wherein the 3-6 membered heterocyclyl contains one to three heteroatoms; and wherein each $C_{3-6}$ cycloalkyl and 3-6 membered heterocyclyl is optionally substituted with one to three groups independently selected from halo, hydroxyl, —CN, $C_{1-6}$alkyl, $C_{1-6}$alkoxy, $C_{1-6}$haloalkyl, and $C_{1-6}$haloalkoxyl;

each $R^A$ is independently selected from halo, hydroxyl, oxo, —CN, $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, —$C_{1-4}$alkylene-O—$C_{1-4}$alkyl, $C_{3-10}$cycloalkyl, 3-12 membered heterocyclyl, $C_{6-10}$aryl, 5-10 membered heteroaryl, and —$NR^{aa}R^{bb}$;

wherein each $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, —$C_{1-4}$alkylene-O—$C_{1-4}$alkyl, $C_{3-10}$cycloalkyl, 3-12 membered heterocyclyl, $C_{6-10}$aryl, 5-10 membered heteroaryl of $R^A$ is independently substituted with one to three groups independently selected from halo, hydroxyl, —CN, $C_{1-6}$alkyl, $C_{1-6}$alkoxy, $C_{1-6}$haloalkyl, $C_1$-haloalkoxyl, $C_{3-10}$cycloalkyl, 3-12 membered heterocyclyl, $C_{6-10}$aryl, 5-10 membered heteroaryl, and —$NR^{aa}R^{bb}$; and each $R^{aa}$ and $R^{bb}$ is independently selected from hydrogen, $C_{1-6}$alkyl, $C_{3-10}$cycloalkyl, 3-12 membered heterocyclyl, $C_{6-10}$aryl, 5-10 membered heteroaryl, —$C_{1-6}$alkylene-$C_{3-10}$cycloalkyl, —$C_{1-6}$alkylene-3-12 membered heterocyclyl, —$C_{1-6}$alkylene-$C_{6-10}$aryl, and —$C_{1-6}$alkylene-5-10 membered heteroaryl;

wherein each $C_{1-6}$alkyl, $C_{3-10}$cycloalkyl, 3-12 membered heterocyclyl, $C_{6-10}$aryl, 5-10 membered heteroaryl, —$C_{1-6}$alkylene-$C_{3-10}$cycloalkyl, —$C_{1-6}$alkylene-3-12 membered heterocyclyl, —$C_{1-6}$alkylene-$C_{6-10}$aryl, and —$C_{1-6}$alkylene-5-10 membered heteroaryl of $R^{aa}$ and $R^{bb}$ is independently optionally substituted with one to four groups independently selected from halo, $C_{1-6}$alkyl, —CN, $C_{1-6}$alkoxyl, and $C_1$-haloalkyl;

wherein the 3-12 membered heterocyclyl is a single ring or multiple rings having one to four heteroatoms independently selected from nitrogen, sulfur, phosphorus, —N(O)—, —S(O)—, and —S(O)$_2$—; and wherein the multiple rings may be fused, bridged, or spiro;

wherein the 5-10 membered heteroaryl is an aromatic group having a single ring or multiple rings; and wherein the 5-10 membered heteroaryl contains one to four heteroatoms independently selected from nitrogen, oxygen, sulfur, —N(O)—, —S(O)—, and —S(O)$_2$; and provided:

when ------- is a single bond, at least one of ===== and ====== is a double bond; and when ------- is a double bond,
(a) $R^1$ is $R^{16}$;
(b) $Z^1$ is N;
(c) $Z^1$ is $CR^{1a}$, wherein $R^{1a}$ is selected from halo, $C_{1-6}$alkyl, $C_{1-6}$alkoxyl, $C_1$-haloalkyl, and $C_1$-haloalkoxyl;
(d) each $R^4$ and $R^5$ is not hydrogen;

(e) each $R^8$ and $R^9$ is not hydrogen;
(f) $R^5$ is hydrogen, $R^4$ is selected from $C_{2-6}$alkenyl, $C_{2-6}$alkynyl, and —O—$C_{2-6}$alkynyl, each of which is optionally substituted with one to four groups independently selected from halo, hydroxyl, oxo, $C_{1-6}$alkyl, $C_{1-6}$alkoxyl, $C_1$-haloalkoxyl, —$NR^{aa}R^{bb}$, $C_{3-10}$cycloalkyl, and 3-12 membered heterocyclyl;
(g) $R^9$ is hydrogen, $R^8$ is selected from hydrogen, halo, $C_{2-6}$alkenyl, $C_{2-6}$alkynyl, —O—$C_{2-6}$alkenyl, —O—$C_{2-6}$alkynyl, $C_{3-10}$cycloalkyl, 3-12 membered heterocyclyl, $C_{6-10}$aryl, and 5-10 membered heteroaryl; wherein each $C_{2-6}$alkynyl, O—$C_{2-6}$alkenyl, —O—$C_{2-6}$alkynyl, $C_{3-10}$cycloalkyl, 3-12 membered heterocyclyl, $C_{6-10}$aryl, and 5-10 membered heteroaryl of $R^8$ is independently optionally substituted with 1-5 $R^A$;
(h) $R^2$ and $R^4$, $R^4$ and $R^6$, $R^6$ and $R^7$, or $R^7$ and $R^8$, together with the atoms to which they are attached form a 3-7 membered heterocyclyl or 5-6 membered heteroaryl; wherein each 3-7 membered heterocyclyl and 5-6 membered heteroaryl contains one to three heteroatoms; and each 3-7 membered heterocyclyl and 5-6 membered heteroaryl is optionally substituted with one to four groups independently selected from halo, oxo, hydroxyl, $C_{1-6}$alkyl, $C_1$-haloalkyl, $C_{1-6}$alkoxyl, $C_1$-haloalkoxyl, $C_{2-6}$alkenyl, $C_{2-6}$alkynyl, —$NR^{aa}R^{bb}$, and —$C_{1-6}$alkylene-$NR^{aa}R^{bb}$;
(i) $R^4$, $R^6$, and $R^7$ together with the atoms to which they are attached form an 8-12 membered fused heterocyclyl; wherein the 8-12 membered fused heterocyclyl contains one to three heteroatoms; wherein the 8-12 membered fused heterocyclyl is optionally substituted with one to four groups independently selected from halo, oxo, hydroxyl, $C_{1-6}$alkyl, $C_1$-haloalkyl, $C_{1-6}$alkoxyl, $C_1$-haloalkoxyl, $C_{2-6}$alkenyl, $C_{2-6}$alkynyl, —$NR^{aa}R^{bb}$, and —$C_{1-6}$alkylene-$NR^{aa}R^{bb}$; or
(j) $R^4$ and $R^8$ together with the atoms to which they are attached form an 8-16 membered heterocyclyl; wherein the 8-16 membered fused heterocyclyl contains one to three heteroatoms; and wherein the 8-16 membered heterocyclyl is optionally substituted with one to three groups independently selected from halo, oxo, hydroxyl, $C_{1-6}$alkyl, $C_1$-haloalkyl, $C_{1-6}$alkoxyl, $C_1$-haloalkoxyl, $C_{2-6}$alkenyl, $C_{2-6}$alkynyl, —$NR^{aa}R^{bb}$, and —$C_{1-6}$alkylene-$NR^{aa}R^{bb}$.

In some embodiments of Formula (I), the present disclosure provides a compound of Formula (Ia):

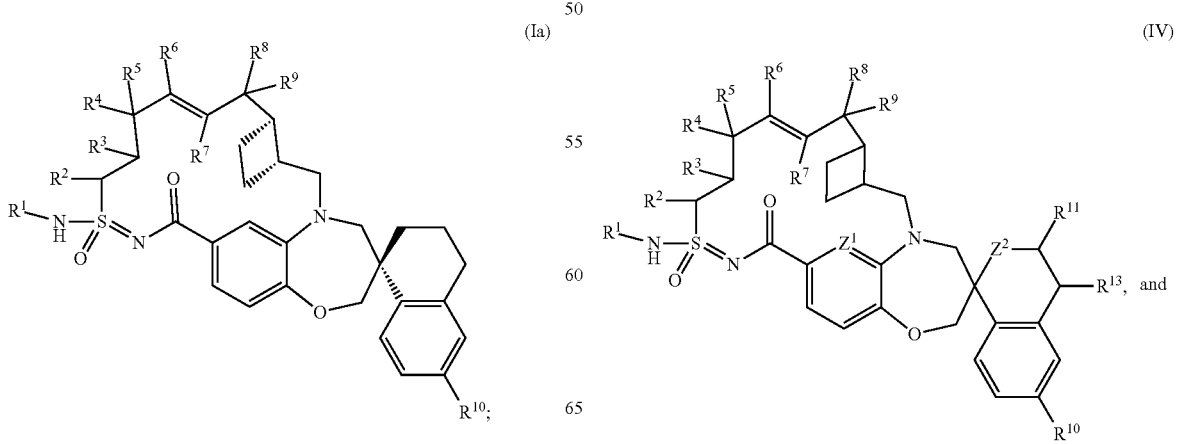

or a pharmaceutically acceptable salt thereof. Each $R^1$, $R^2$, $R^3$, $R^4$, $R^5$, $R^6$, $R^7$, $R^8$, $R^9$, and $R^{10}$ is defined as above, or elsewhere in this disclosure.

In some embodiments, the present disclosure provides a compound according to a formula selected from (II), (III), (IV), and (V):

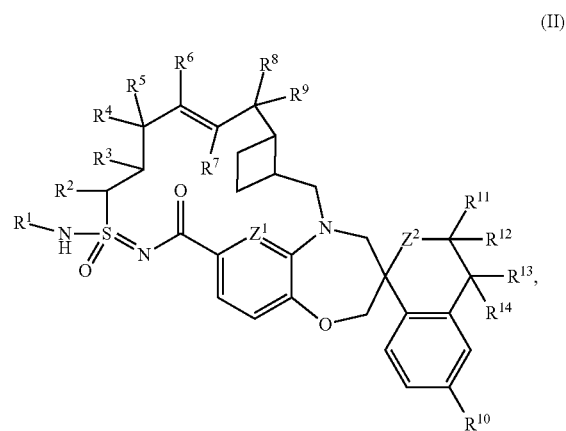

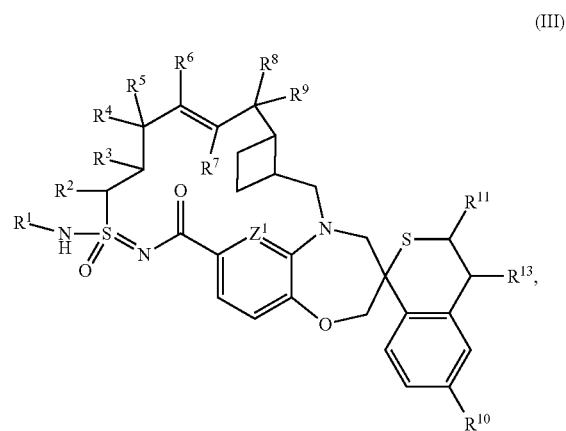

(V)

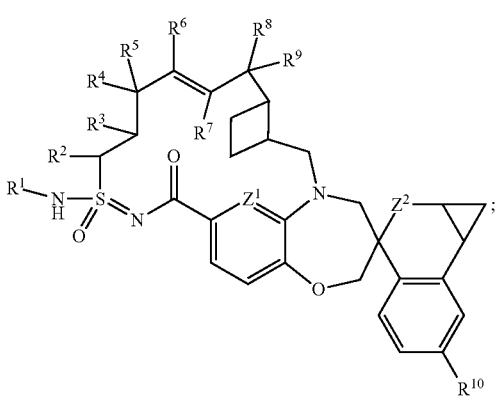

or a pharmaceutically acceptable salt thereof, wherein:

$Z^1$ is $CR^{1a}$ or N;

$Z^2$ is selected from $CR^{2a}R^{2b}$, S, $NR^{2c}$, and O;
 wherein each $R^{1a}$, $R^{2a}$, and $R^{2b}$ is independently selected from hydrogen, halo, $C_{1-6}$alkyl, $C_{1-6}$alkoxyl, $C_{1-6}$haloalkyl, and $C_{1-6}$haloalkoxyl; and
 wherein $R^{2c}$ is selected from hydrogen, $C_{1-6}$alkyl, and $C_{1-6}$haloalkyl; $R^1$ is $-C(O)R^{15}$, or $R^{16}$;
 wherein $R^{15}$ is selected from $C_{1-6}$alkyl, $C_{1-6}$haloalkyl, $C_{3-10}$cycloalkyl, 3-12 membered heterocyclyl, $C_{6-10}$aryl, 5-10 membered heteroaryl, $C_{1-6}$alkylene-O-$C_{3-10}$cycloalkyl, $-C_{1-6}$alkylene-O-3-12 membered heterocyclyl, $C_{1-6}$alkylene-O-$C_{6-10}$aryl, $-C_{1-6}$alkylene-5-10 membered heteroaryl, and $-NR^{15a}R^{15b}$; wherein $R^{15}$ is optionally substituted with 1-5 $R^A$;
  wherein each $R^{15a}$ and $R^{15b}$ is independently selected from hydrogen, $C_{1-6}$alkyl, $C_{3-10}$cycloalkyl, 3-12 membered heterocyclyl, $C_{6-10}$aryl, 5-10 membered heteroaryl, $-C_{1-6}$alkylene-$C_{3-10}$cycloalkyl, $-C_{1-6}$alkylene-3-12 membered heterocyclyl, $-C_{1-6}$alkylene-$C_{6-10}$aryl, and $-C_{1-6}$alkylene-5-10 membered heteroaryl;
   wherein each $C_{1-6}$alkyl, $C_{3-10}$cycloalkyl, 3-12 membered heterocyclyl, $C_{6-10}$aryl, 5-10 membered heteroaryl, $-C_{1-6}$alkylene-$C_{3-10}$cycloalkyl, $-C_{1-6}$alkylene-3-12 membered heterocyclyl, $-C_{1-6}$alkylene-$C_{6-10}$aryl, and $-C_{1-6}$alkylene-5-10 membered heteroaryl of $R^{15a}$ and $R^{15b}$ is independently optionally substituted with one to four groups independently selected from halo, hydroxyl, oxo, $-CN$, $C_{1-6}$alkyl, $C_{2-6}$alkenyl, $C_{2-6}$alkynyl, $C_{1-6}$alkoxyl, $C_{1-6}$haloalkyl, and $C_{1-6}$haloalkoxyl;
 wherein $R^{16}$ is 3-12 membered heterocyclyl, or 5-12 membered heteroaryl; wherein $R^{16}$ is optionally substituted with 1-5 $R^A$;

$R^2$ is selected from hydrogen, halo, $C_{1-6}$alkyl, $C_{1-6}$haloalkyl, $C_{1-6}$alkoxyl, and $-C_{1-4}$alkylene-O-$C_{1-6}$alkyl;

$R^3$ is selected from hydrogen, halo, $C_{1-6}$alkyl, $C_{1-6}$haloalkyl, $C_{1-6}$alkoxyl, $C_{3-10}$cycloalkyl, 3-12 membered heterocyclyl, and $-C_{1-4}$alkylene-O-5-10 membered heteroaryl; wherein each $C_{1-6}$alkyl, $C_{1-6}$haloalkyl, $C_{1-6}$alkoxyl, $C_{3-10}$cycloalkyl, 3-12 membered heterocyclyl, and $-C_{1-4}$alkylene-O-5-10 membered heteroaryl of $R^3$ is optionally substituted with one to four groups independently selected from halo, $C_{1-6}$alkyl, $C_{1-6}$haloalkyl, and $C_{1-6}$alkoxyl;

each $R^4$ and $R^5$ is independently selected from hydrogen, halo, hydroxyl, $C_{1-6}$alkyl, $C_{2-6}$alkenyl, $C_{2-6}$alkynyl, $C_{1-6}$haloalkyl, $C_{1-6}$alkoxyl, $C_{1-6}$haloalkoxyl, $-NR^{aa}R^{bb}$, $-NHC(O)-C_{1-6}$alkyl, $-C(O)NH-C_{1-6}$alkyl, $-O-C_{2-6}$alkynyl, $-OC(O)-C_{1-6}$alkyl, $-O-(CH_2CH_2O)n-C_{1-6}$alkyl, $C_{3-10}$cycloalkyl, 3-12 membered heterocyclyl, $-O-C_{3-10}$cycloalkyl, $-O$-3-12 membered heterocyclyl, $-O-C_{1-4}$alkylene-$C_{3-10}$cycloalkyl, 5-10 membered heteroaryl, $-O-C_{1-4}$alkylene-3-12 membered heterocyclyl, $-O$-5-10 membered heteroaryl, and $-O-C_{1-4}$alkylene-5-10 membered heteroaryl;
 wherein each $C_{1-6}$alkyl, $C_{2-6}$alkenyl, $C_{2-6}$alkynyl, $C_{1-6}$haloalkyl, $C_{1-6}$alkoxyl, $C_{1-6}$haloalkoxyl, $-NHC(O)-C_{1-6}$alkyl, $-C(O)NH-C_{1-6}$alkyl, $-O-C_{2-6}$alkynyl, $-OC(O)-C_{1-6}$alkyl, $-O-(CH_2CH_2O)_n-C_1$-alkyl, $C_{3-10}$cycloalkyl, 3-12 membered heterocyclyl, $-O-C_{3-10}$cycloalkyl, $-O$-3-12 membered heterocyclyl, $-O-C_{1-4}$alkylene-$C_{3-10}$cycloalkyl, 5-10 membered heteroaryl, $-O-C_{1-4}$alkylene-3-12 membered heterocyclyl, $-O$-5-10 membered heteroaryl, and $-O-C_{1-4}$alkylene-5-10 membered heteroaryl of $R^4$ and $R^5$ is optionally substituted with one to four groups independently selected from halo, hydroxyl, oxo, $C_{1-6}$alkyl, $C_{1-6}$alkoxyl, $C_{1-6}$haloalkoxyl, $-NR^{aa}R^{bb}$, $C_{3-10}$cycloalkyl, and 3-12 membered heterocyclyl;

each $R^6$ and $R^7$ is independently selected from hydrogen, halo, hydroxyl, $C_{1-6}$alkyl, $C_{1-6}$alkoxyl, $C_{1-6}$haloalkyl, and $C_{1-6}$haloalkoxyl;

$R^8$ is selected from hydrogen, halo, hydroxyl, oxo, $C_{1-6}$alkyl, $C_{2-6}$alkenyl, $C_{2-6}$alkynyl, $C_{1-6}$alkoxyl, $-O-C_{2-6}$alkenyl, $-O-C_{2-6}$alkynyl, $C_{3-10}$cycloalkyl, 3-12 membered heterocyclyl, $C_{6-10}$aryl, 5-10 membered heteroaryl, $-O-C_{3-10}$cycloalkyl, $-O$-3-12 membered heterocyclyl, $-O-C_{6-10}$aryl, $-O$-5-10 membered heteroaryl, $-O-C_{1-4}$alkylene-$C_{3-10}$cycloalkyl, $-O-C_{1-4}$alkylene-3-12 membered heterocyclyl, $-O-C_{1-4}$alkylene-$C_{6-10}$aryl, and $-O-C_{1-4}$alkylene-5-10 membered heteroaryl;

$R^9$ is absent or selected from hydrogen, halo, hydroxyl, $C_{1-6}$alkyl, $C_{2-6}$alkenyl, $C_{2-6}$alkynyl, $C_{1-6}$alkoxyl, $-O-C_{2-6}$alkenyl, $-O-C_{2-6}$alkynyl, $C_{3-10}$cycloalkyl, 3-12 membered heterocyclyl, $C_{6-10}$aryl, 5-10 membered heteroaryl, $-O-C_{3-10}$cycloalkyl, $-O$-3-12 membered heterocyclyl, $-O-C_{6-10}$aryl, $-O$-5-10 membered heteroaryl, $-O-C_{1-4}$alkylene-$C_{3-10}$cycloalkyl, $-O-C_{1-4}$alkylene-3-12 membered heterocyclyl, $-O-C_{1-4}$alkylene-$C_{6-10}$aryl, and $-O-C_{1-4}$alkylene-5-10 membered heteroaryl;
 wherein each $C_{1-6}$alkyl, $C_{2-6}$alkenyl, $C_{2-6}$alkynyl, $C_{1-6}$alkoxyl, $-O-C_{2-6}$alkenyl, $-O-C_{2-6}$alkynyl, $C_{3-10}$cycloalkyl, 3-12 membered heterocyclyl, $C_{6-10}$aryl, 5-10 membered heteroaryl, $-O-C_{3-10}$cycloalkyl, $-O$-3-12 membered heterocyclyl, —O—C$_{6-10}$aryl, —O-5-10 membered heteroaryl, —O—C$_{1-4}$alkylene-C$_{3-10}$cycloalkyl, —O—C$_{1-4}$alkylene-3-12 membered heterocyclyl, —O—C$_{1-4}$alkylene-C$_{6-10}$aryl, and —O—C$_{1-4}$alkylene-5-10 membered heteroaryl of R$^8$ and R$^9$ is independently optionally substituted with 1-5 R$^A$;

R$^{10}$ is selected from hydrogen, halo, hydroxyl, —CN, C$_{1-6}$alkyl, C$_{1-6}$alkoxyl, C$_{1-6}$haloalkyl, and C$_{1-6}$haloalkoxyl;

each R$^{11}$, R$^{12}$, R$^{13}$, and R$^{14}$ is independently selected from hydrogen, halo, hydroxyl, —CN, C$_{1-6}$alkyl, C$_{1-6}$alkoxy, and C$_{1-6}$haloalkyl; or R$^{11}$ and R$^{13}$ together with the atoms to which they are attached form a C$_{3-6}$ cycloalkyl or 3-6 membered heterocyclyl; wherein each C$_{1-6}$ cycloalkyl and 3-6 membered heterocyclyl is optionally substituted with one to three groups independently selected from halo, hydroxyl, —CN, C$_{1-6}$alkyl, C$_{1-6}$alkoxy, C$_{1-6}$haloalkyl, and C$_{1-6}$haloalkoxyl;

each R$^A$ is independently selected from halo, hydroxyl, oxo, —CN, C$_{1-6}$alkyl, C$_{2-6}$alkenyl, C$_{2-6}$alkynyl, C$_{1-6}$alkoxyl, C$_{1-6}$haloalkyl, C$_{1-6}$haloalkoxyl, —C$_{1-4}$alkylene-O—C$_{1-4}$alkyl, C$_{3-10}$cycloalkyl, 3-12 membered heterocyclyl, C$_{6-10}$aryl, 5-10 membered heteroaryl, and —NR$^{aa}$R$^{bb}$;

wherein each C$_{1-6}$alkyl, C$_{2-6}$alkenyl, C$_{2-6}$alkynyl, C$_{1-6}$alkoxyl, C$_{1-6}$haloalkyl, C$_{1-6}$haloalkoxyl, —C$_{1-4}$alkylene-O—C$_{1-4}$alkyl, C$_{3-10}$cycloalkyl, 3-12 membered heterocyclyl, C$_{6-10}$aryl, 5-10 membered heteroaryl of R$^A$ is independently substituted with one to three groups independently selected from halo, hydroxyl, —CN, C$_{1-6}$alkyl, C$_{1-6}$alkoxy, C$_{1-6}$haloalkyl, C$_{1-6}$haloalkoxyl, C$_{3-10}$cycloalkyl, 3-12 membered heterocyclyl, C$_{6-10}$aryl, 5-10 membered heteroaryl, and —NR$^{aa}$R$^{bb}$;

each R$^{aa}$ and R$^{bb}$ is independently selected from hydrogen, C$_{1-6}$alkyl, C$_{3-10}$cycloalkyl, 3-12 membered heterocyclyl, C$_{6-10}$aryl, 5-10 membered heteroaryl, —C$_{1-6}$alkylene-C$_{3-10}$cycloalkyl, —C$_{1-6}$alkylene-3-12 membered heterocyclyl, —C$_{1-6}$alkylene-C$_{6-10}$aryl, and —C$_{1-6}$alkylene-5-10 membered heteroaryl;

wherein each C$_{1-6}$alkyl, C$_{3-10}$cycloalkyl, 3-12 membered heterocyclyl, C$_{6-10}$aryl, 5-10 membered heteroaryl, —C$_{1-6}$alkylene-C$_{3-10}$cycloalkyl, —C$_{1-6}$alkylene-3-12 membered heterocyclyl, —C$_{1-6}$alkylene-C$_{6-10}$aryl, and —C$_{1-6}$alkylene-5-10 membered heteroaryl of R$^{aa}$ and R$^{bb}$ is independently optionally substituted with one to four groups independently selected from halo, C$_{1-6}$alkyl, —CN, C$_{1-6}$alkoxyl, and C$_{1-6}$haloalkyl;

wherein the 3-12 membered heterocyclyl is a single ring or multiple rings having one to four heteroatoms independently selected from nitrogen, sulfur, phosphorus, —N(O)—, —S(O)—, and —S(O)$_2$—; and wherein the multiple rings may be fused, bridged, or spiro; and wherein the 5-10 membered heteroaryl is an aromatic group having a single ring or multiple rings; and wherein the 5-10 membered heteroaryl contains one to four heteroatoms independently selected from nitrogen, oxygen, sulfur, —N(O)—, —S(O)—, and —S(O)$_2$.

In some embodiments, the present disclosure provides a compound of Formula (II):

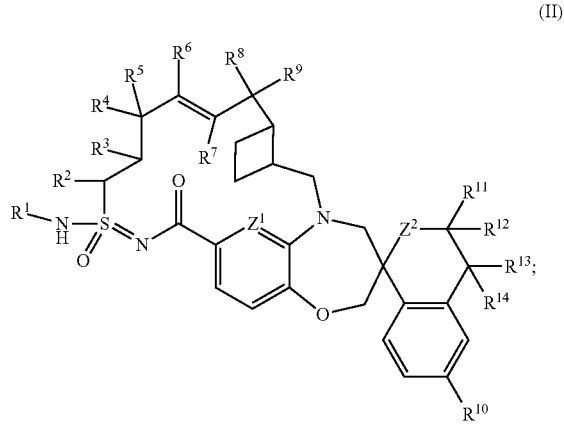

(II)

or a pharmaceutically acceptable salt thereof. Each Z$^1$, Z$^2$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, and R$^{16}$ is defined as above, or elsewhere in this disclosure.

In some embodiments of Formula (II), the present disclosure provides compounds of Formula (IIa):

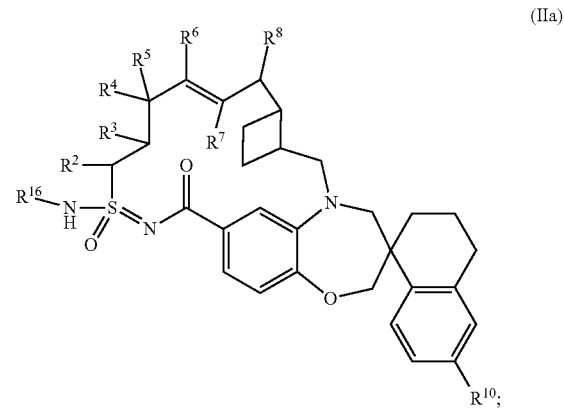

(IIa)

or a pharmaceutically acceptable salt thereof. Each R$^2$, R$^3$, R$^4$, R$^6$, R$^7$, R$^8$, R$^{10}$, and R$^{16}$ is defined as above, or elsewhere in this disclosure.

In some embodiments of Formula (II), the present disclosure provides compounds of Formula (IIb):

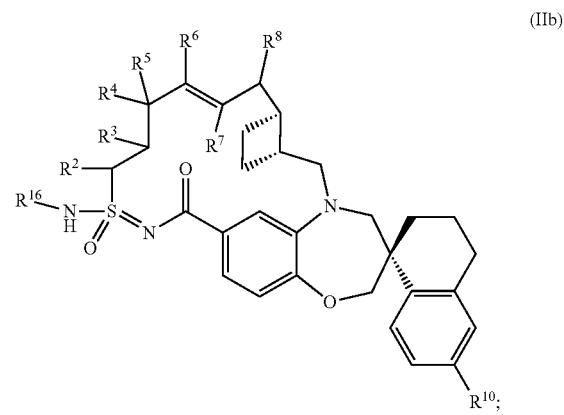

(IIb)

or a pharmaceutically acceptable salt thereof. Each $R^2$, $R^3$, $R^4$, $R^6$, $R^7$, $R^8$, $R^{10}$, and $R^{16}$ is defined as above, or elsewhere in this disclosure.

In some embodiments, the present disclosure provides a compound of Formula (III):

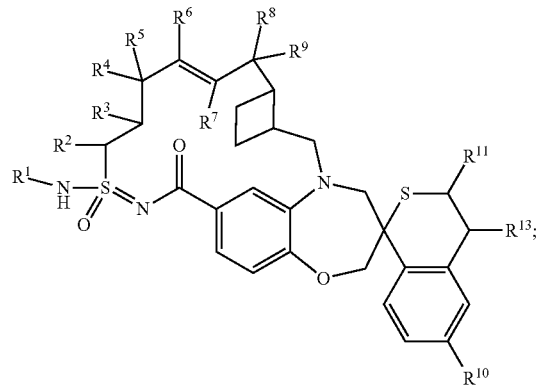

(III)

or a pharmaceutically acceptable salt thereof. Each $Z^1$, $R^1$, $R^2$, $R^3$, $R^4$, $R^5$, $R^6$, $R^7$, $R^8$, $R^9$, $R^{10}$, $R^{11}$, and $R^{13}$ is defined as above, or elsewhere in this disclosure.

In some embodiments of Formula (III), the present disclosure provides compounds of Formula (IIIa):

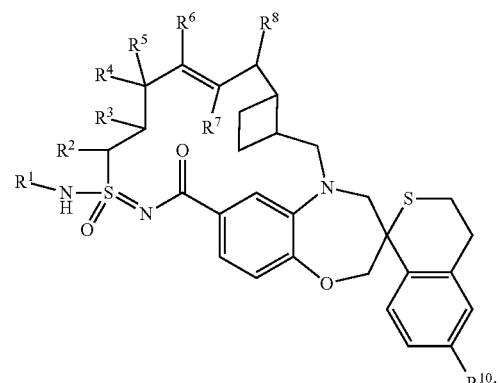

(IIIa)

or a pharmaceutically acceptable salt thereof. Each $R^1$, $R^2$, $R^3$, $R^4$, $R^6$, $R^7$, $R^8$, and $R^{10}$ is defined as above, or elsewhere in this disclosure.

In some embodiments of Formula (III), the present disclosure provides compounds of Formula (IIIb):

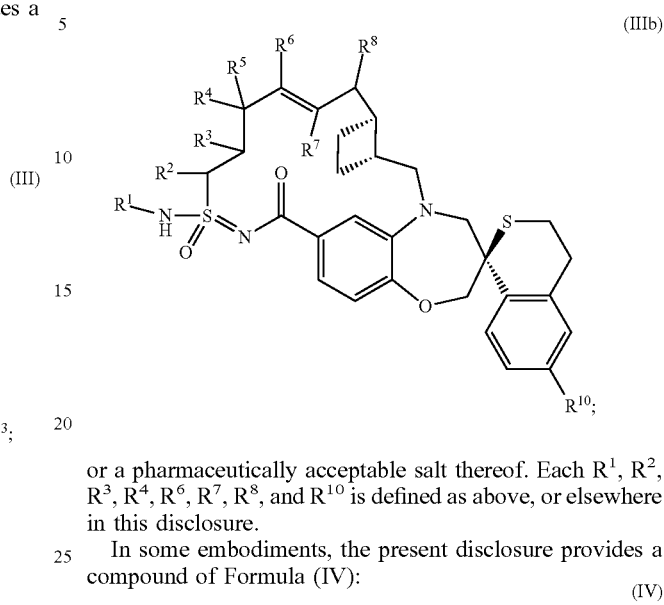

(IIIb)

or a pharmaceutically acceptable salt thereof. Each $R^1$, $R^2$, $R^3$, $R^4$, $R^6$, $R^7$, $R^8$, and $R^{10}$ is defined as above, or elsewhere in this disclosure.

In some embodiments, the present disclosure provides a compound of Formula (IV):

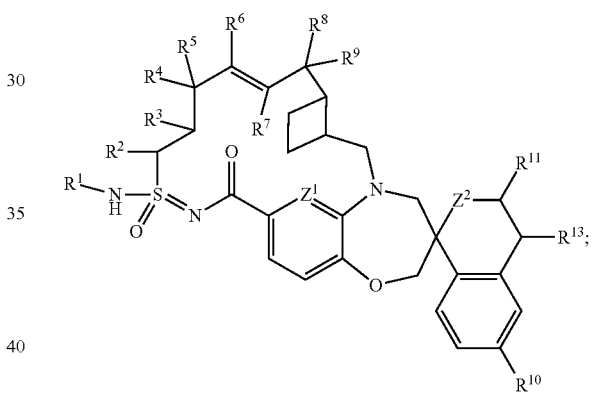

(IV)

or a pharmaceutically acceptable salt thereof. Each $Z^2$, $R^1$, $R^2$, $R^3$, $R^4$, $R^5$, $R^6$, $R^7$, $R^8$, $R^9$, $R^{10}$, $R^{11}$, and $R^{13}$ is defined as above, or elsewhere in this disclosure.

In some embodiments of Formula (IV), the present disclosure provides compounds of Formula (IVa):

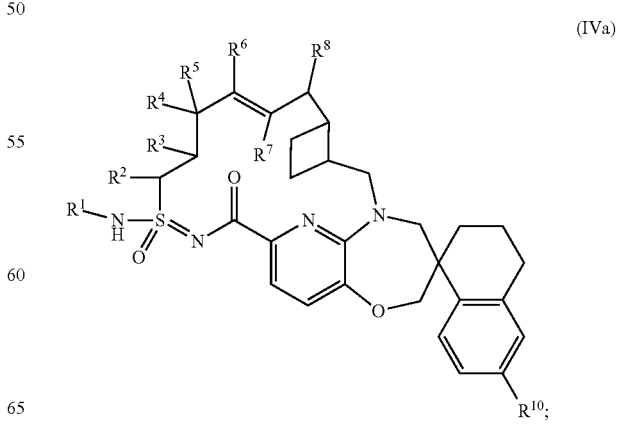

(IVa)

or a pharmaceutically acceptable salt thereof. Each $R^1$, $R^2$, $R^3$, $R^4$, $R^6$, $R^7$, $R^8$, and $R^{10}$ is defined as above, or elsewhere in this disclosure.

In some embodiments of Formula (IV), the present disclosure provides compounds of Formula (IVb):

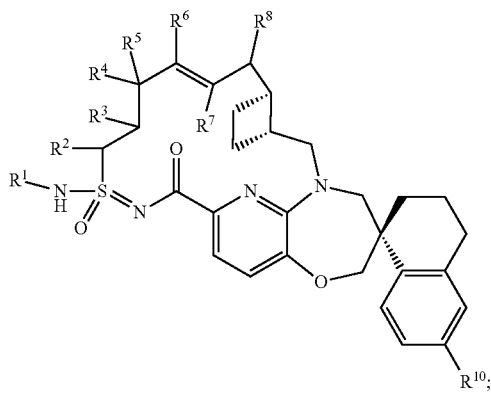

(IVb)

or a pharmaceutically acceptable salt thereof. Each $R^1$, $R^2$, $R^3$, $R^4$, $R^6$, $R^7$, $R^8$, and $R^{10}$ is defined as above, or elsewhere in this disclosure.

In some embodiments, the present disclosure provides a compound of Formula (V):

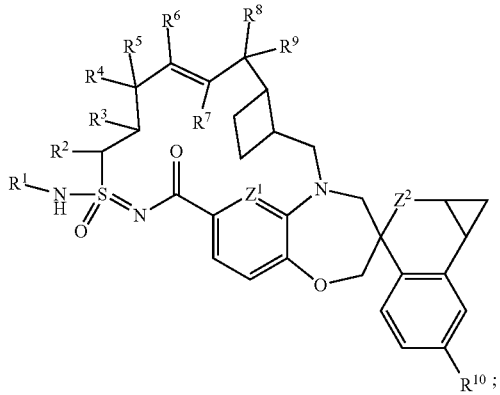

(V)

or a pharmaceutically acceptable salt thereof. Each $Z^1$, $Z^2$, $R^1$, $R^2$, $R^3$, $R^4$, $R^5$, $R^6$, $R^7$, $R^8$, $R^9$, $R^{10}$, $R^{11}$, and $R^{13}$ is defined as above, or elsewhere in this disclosure.

In some embodiments of Formula (V), the present disclosure provides compounds of Formula (Va):

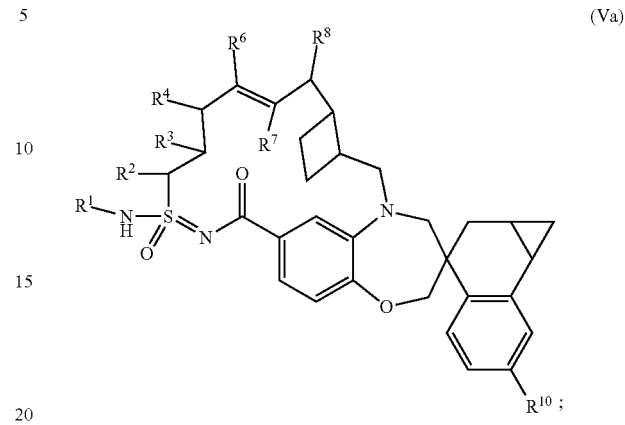

(Va)

or a pharmaceutically acceptable salt thereof. Each $R^1$, $R^2$, $R^3$, $R^4$, $R^6$, $R^7$, $R^8$, and $R^{10}$ is defined as above, or elsewhere in this disclosure.

In some embodiments of Formula (V), the present disclosure provides compounds of Formula (Vb):

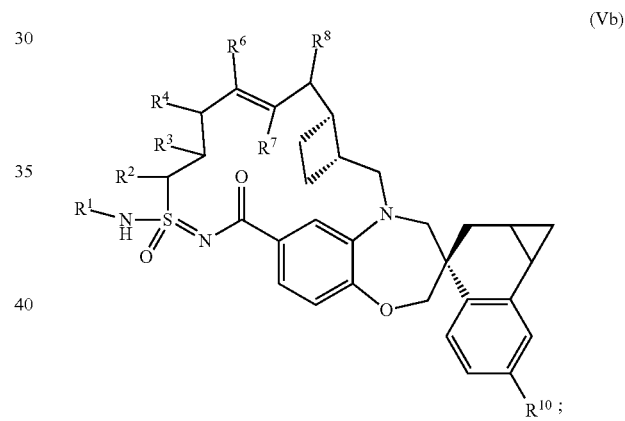

(Vb)

or a pharmaceutically acceptable salt thereof. Each $R^1$, $R^2$, $R^3$, $R^4$, $R^6$, $R^7$, $R^8$, and $R^{10}$ is defined as above, or elsewhere in this disclosure.

In some embodiments of Formula (I), (II), (III), or (V), $Z^1$ is CH. In some embodiments, $Z^1$ is N. In some embodiments, $Z^1$ is $CR^{1a}$, and $C^{1a}$ is halo. In some embodiments, $Z^1$ is CF.

In some embodiments of Formula (II), (IV), or (V), $Z^2$ is $CH_2$. In some embodiments, $Z^2$ is S.

In some embodiments of Formula (II), or (V), $Z^1$ is CH, and $Z^2$ is S. In some embodiments, $Z^1$ is CH, and $Z^2$ is $CH_2$. In some embodiments, $Z^1$ is N, and $Z^2$ is $CH_2$.

In some embodiments of Formula (II), (III), or (IV), $R^{11}$ and $R^{13}$ form a $C_{3-6}$ cycloalkyl. In some embodiments, $R^{11}$ and $R^{13}$ form cyclopropyl.

In some embodiments of Formula (II), or (III), $Z^1$ is CH, and $R^{11}$ and $R^{13}$ form a $C_{3-6}$ cycloalkyl. In some embodiments, $R^{11}$ and $R^{13}$ form cyclopropyl.

In some embodiments of Formula (II), or (IV), $Z^2$ is $CH_2$, and $R^{11}$ and $R^{13}$ form a $C_{3-6}$ cycloalkyl. In some embodiments, $R^{11}$ and $R^{13}$ form cyclopropyl.

In some embodiments of Formula (II), $Z^1$ is CH, $Z^2$ is $CH_2$, and $R^{11}$ and $R^{13}$ form a $C_{3-6}$ cycloalkyl. In some embodiments, $R^{11}$ and $R^{13}$ form cyclopropyl.

In some embodiments of Formula (I), (Ia), (III), (IIIa), (IIIb), (IV), (IVa), (IVb), (V), (Va), or (Vb), $R^1$ is —C(O)$R^{15}$; wherein $R^{15}$ is selected from —$CH_3$, —$CH_2CH_3$, cyclopropyl, cyclobutyl, —NH-cyclopropyl, —NH-cyclobutyl, pyrrolyl, imidazolyl, pyrazolyl, pyridinyl, pyrazinyl, pyrimidinyl, and pyridazinyl; and wherein each $R^{15}$ is optionally substituted with 1-3 $R^A$ independently selected from F, C, —OH, —CN, —$CH_3$, —$CH_2CH_3$, —$CH_2CH_2CH_3$, —$CH(CH_3)_2$, —$C(CH_3)_3$, —$CH_2F$, —$CHF_2$, —$CF_3$, —$CH_2OCH_3$, —$OCH_3$, —$OCH_2CH_3$, —O—$CH_2CH_2CH_3$, —$OCH(CH_3)_2$, —$OC(CH_3)_3$, —$NH_2$, —$NHCH_3$, —$N(CH_3)_2$,

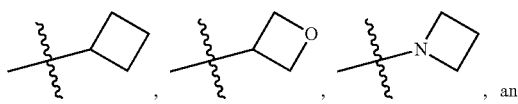

, and

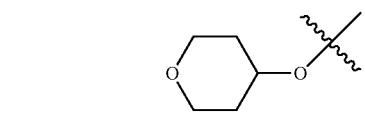

.

In some embodiments, $R^{15}$ is selected from

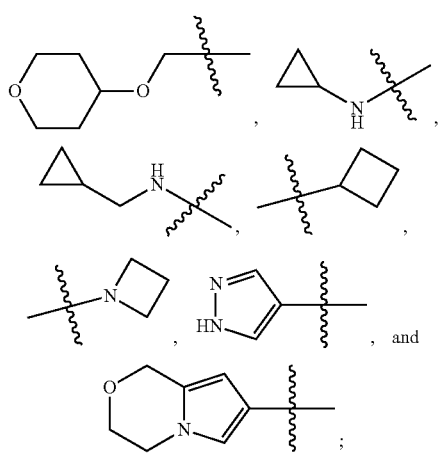

, and

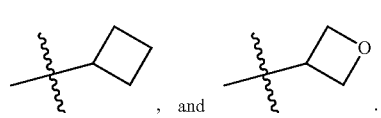 [SMILES: *C1CCC1 ; *C1COC1]

;

each $R^{15}$ is optionally substituted with one to three $R^A$ independently selected from F, C, —OH, —CN, —$CH_3$, —$CH_2CH_3$, —$CH_2CH_2CH_3$, —$CH(CH_3)_2$, —$C(CH_3)_3$, —$CH_2F$, —$CHF_2$, —$CF_3$, —$CH_2OCH_3$, —$OCH_3$, —$OCH_2CH_3$, —O—$CH_2CH_2CH_3$, —$OCH(CH_3)_2$, —$OC(CH_3)_3$,

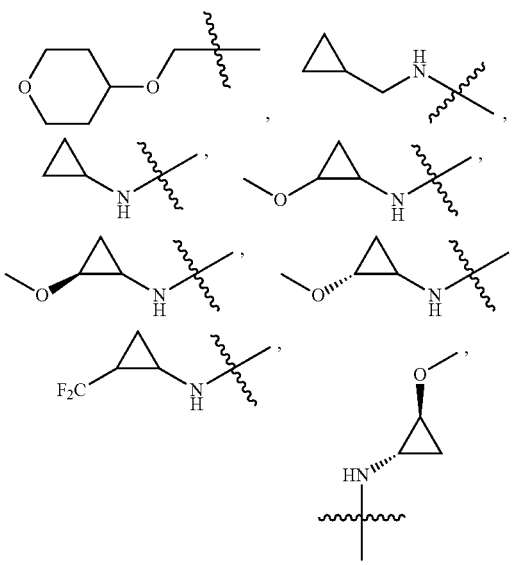

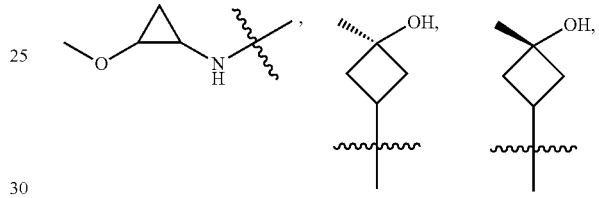

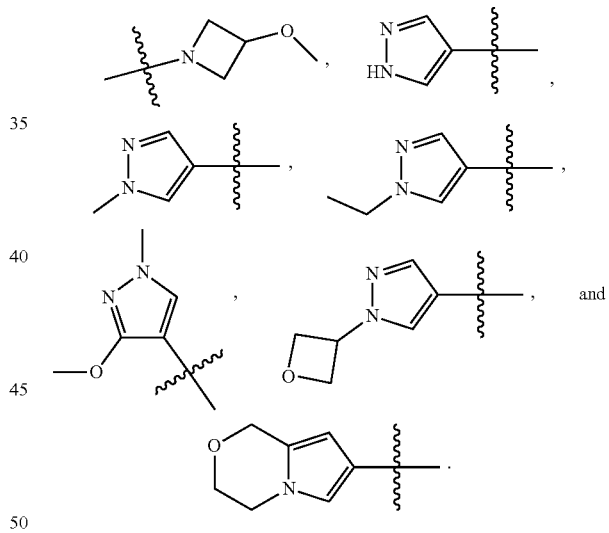

, and

In some embodiments of Formula (I), (Ia), (III), (IIIa), (IIIb), (IV), (IVa), (IVb), (V), (Va), or (Vb), $R^1$ is —C(O)$R^{15}$; wherein $R^{15}$ is 5-10 membered heteroaryl optionally substituted with 1-3 $R^A$. In some embodiments, $R^{15}$ is

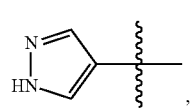

, optionally substituted with 1-3 $R^A$.

In some embodiments of Formula (I), (Ia), (III), (IIIa), (IIIb), (IV), (IVa), (IVb), (V), (Va), or (Vb), $R^1$ is —C(O)$R^{15}$; wherein $R^{15}$ is In some embodiments of Formula (I), (Ia), (III), (IIIa), (IIIb), (IV), (IVa), (IVb), (V), (Va), or (Vb), $R^1$ is —C(O)$R^{15}$; wherein $R^{15}$ is selected from

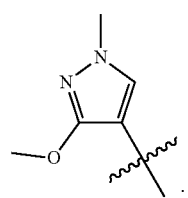 [SMILES: *c1cn(C)nc1OC]

In some embodiments of Formula (I), (Ia), (III), (IIIa), (IIIb), (IV), (IVa), (IVb), (V), (Va), or (Vb), $R^1$ is —C(O)$R^{15}$; wherein $R^{15}$ is selected from

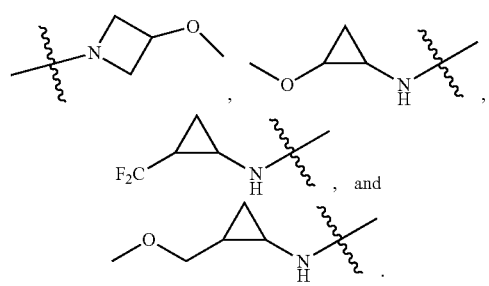

In some embodiments of Formula (I), (Ia), (III), (IIIa), (IIIb), (IV), (IVa), (IVb), (V), (Va), or (Vb), $R^1$ is selected from

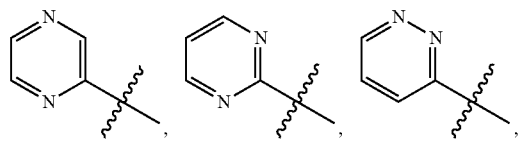

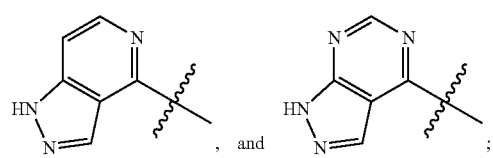

and wherein each $R^1$ is optionally substituted with 1-3 $R^A$ independently selected from F, Cl, —OH, —CN, —CH$_3$, —CH$_2$CH$_3$, —OCH$_3$, —OCH$_2$CH$_3$, —NHCH$_3$, and —N(CH$_3$)$_2$, and

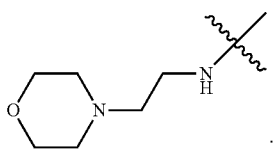 [SMILES: *NCCN1CCOCC1]

In some embodiments of Formula (I), (Ia), (III), (IIIa), (IIIb), (IV), (IVa), (IVb), (V), (Va), or (Vb), $R^1$ is selected from

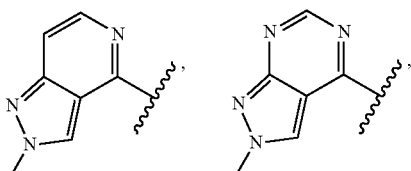

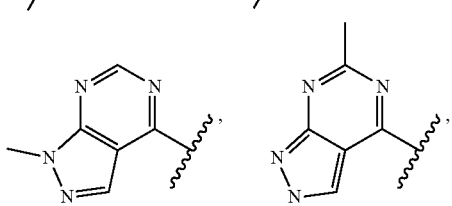

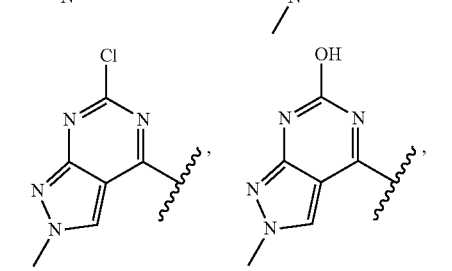

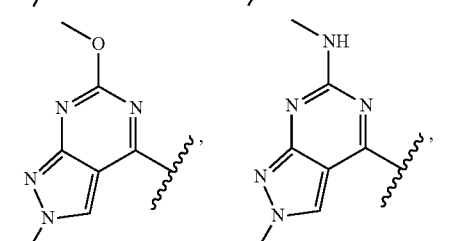

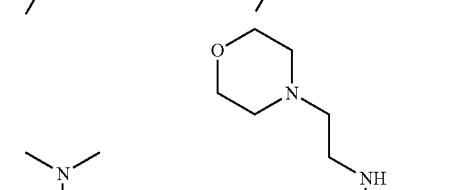

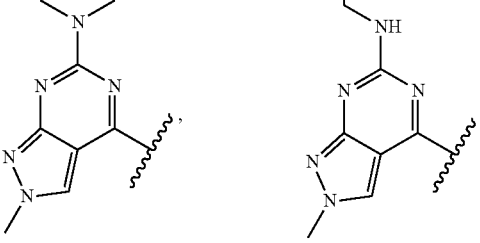

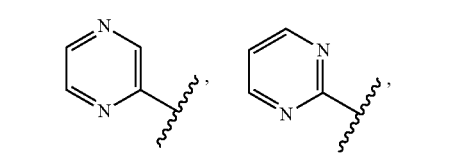

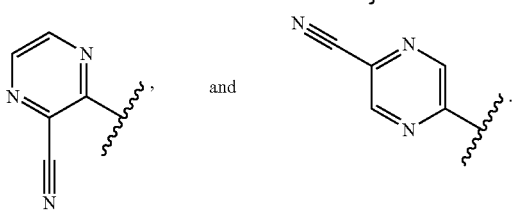

In some embodiments, $R^1$ is

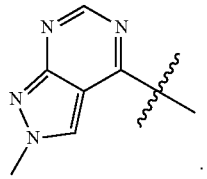 [SMILES: *c1ncnc2nn(C)cc12]

In some embodiments of Formula (I), (Ia), (III), (IIIa), (IIIb), (IV), (IVa), (IVb), (V), (Va), or (Vb), $R^1$ is selected from

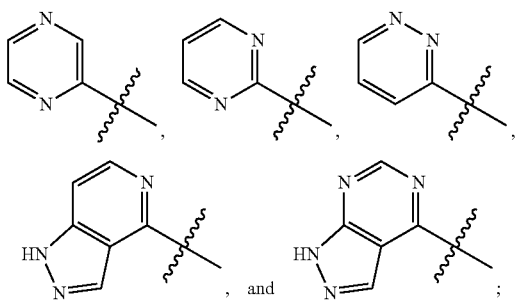

and wherein each $R^1$ is optionally substituted with 1-3 $R^A$ independently selected from F, Cl, —OH, —CN, —$CH_3$, —$CH_2CH_3$, —$OCH_3$, —$OCH_2CH_3$, —$NHCH_3$, and —$N(CH_3)_2$, and

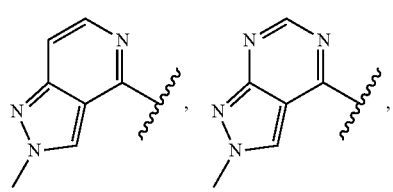

In some embodiments of Formula (II), (IIa), or (IIb), $R^{16}$ is selected from N

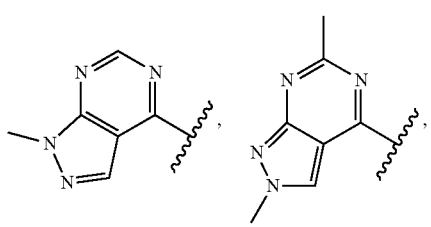

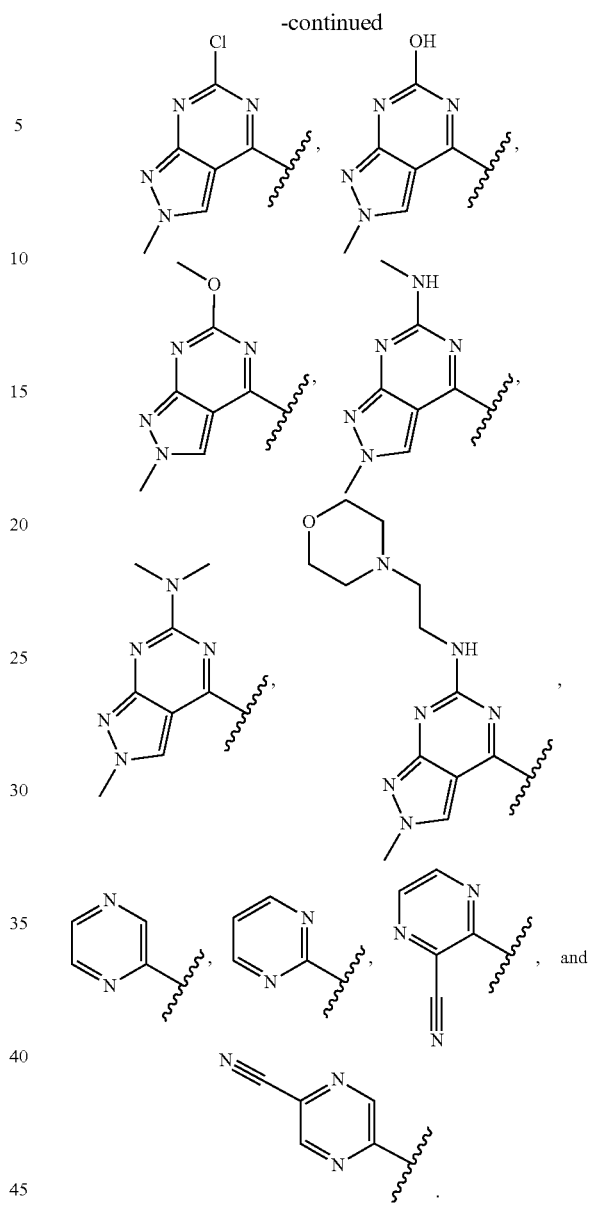

In some embodiments of Formula (I), (Ia), (II), (IIa), (IIb), (III), (IIIa), (IIIb), (IV), (IVa), (IVb), (V), (Va), or (Vb), $R^2$ is hydrogen or $C_{1-3}$alkyl. In some embodiments, $R^2$ is hydrogen.

In some embodiments of Formula (I), (Ia), (II), (IIa), (IIb), (III), (IIIa), (IIIb), (IV), (IVa), (IVb), (V), (Va), or (Vb), $R^3$ is hydrogen or $C_{1-3}$alkyl. In some embodiments, $R^3$ is —$CH_3$.

In some embodiments of Formula (I), (Ia), (II), (IIa), (IIb), (III), (IIIa), (IIIb), (IV), (IVa), (IVb), (V), (Va), or (Vb), $R^4$ is selected from hydrogen, hydroxyl, halo, $C_{1-6}$alkoxyl, —NHC(O)—$C_{1-6}$alkyl, —O—$C_{2-6}$alkynyl, —OC(O)—$C_{1-6}$alkyl, —O—$(CH_2CH_2O)_n$—$C_{1-6}$alkyl, —O—$C_{1-4}$alkylene-$C_{3-10}$cycloalkyl, —O—$C_{1-4}$alkylene-3-12 membered heterocyclyl, —O-5-10 membered heteroaryl, and —O—$C_{1-4}$alkylene-5-10 membered heteroaryl. In some embodiments, $R^4$ is selected from hydrogen, hydroxyl, F, —$CH_3$, —$CH_2CH_3$, —$CH_2CH_2CH_3$, —$OCH_3$, —$OCH_2CH_3$, —$OCH_2CH_2CH_3$,

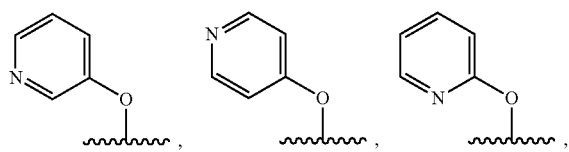
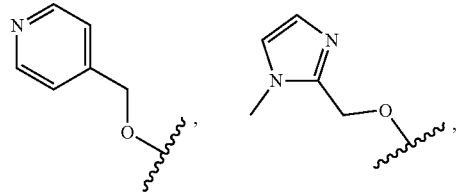
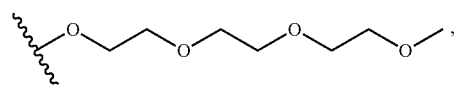
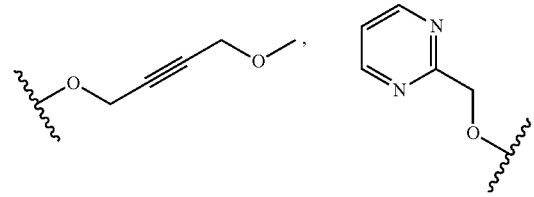
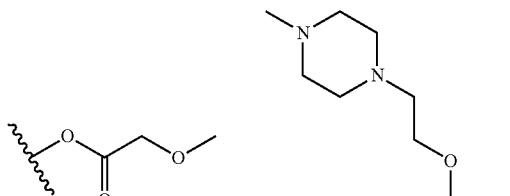
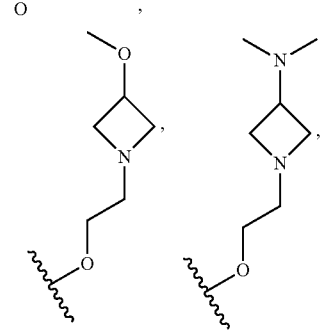
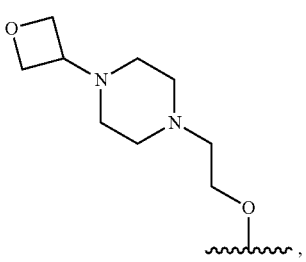
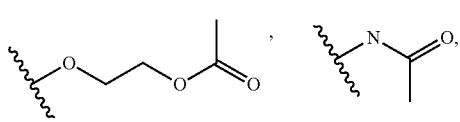

-continued

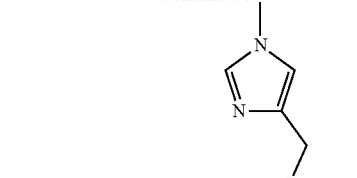
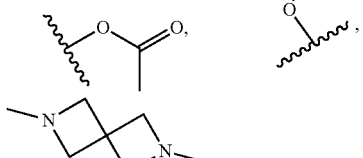
and
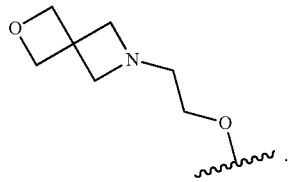

In some embodiments of Formula (I), (II), (III), (IV), or (V), $R^5$ is selected from hydrogen, hydroxyl, and —OCH$_3$. In some embodiments, $R^5$ is hydrogen.

In some embodiments of Formula (I), (II), (III), (IV), or (V), each $R^4$ and $R^5$ is independently selected from halo, hydroxyl, C$_{1-6}$alkyl, C$_{2-6}$alkenyl, C$_{2-6}$alkynyl, C$_1$-haloalkyl, C$_{1-6}$alkoxyl, C$_{1-6}$haloalkoxyl, —NR$^{aa}$R$^{bb}$, —NHC(O)—C$_{1-6}$alkyl, —C(O)NH—C$_{1-6}$alkyl, —O—C$_{2-6}$alkynyl, —OC(O)—C$_{1-6}$alkyl, —O—(CH$_2$CH$_2$O)$_n$—C$_{1-6}$alkyl, C$_{3-10}$cycloalkyl, 3-12 membered heterocyclyl, —O—C$_{3-10}$cycloalkyl, —O-3-12 membered heterocyclyl, —O—C$_{1-4}$alkylene-C$_{3-10}$cycloalkyl, 5-10 membered heteroaryl, —O—C$_{1-4}$alkylene-3-12 membered heterocyclyl, —O-5-10 membered heteroaryl, and —O—C$_{1-4}$alkylene-5-10 membered heteroaryl; wherein each C$_{1-6}$alkyl, C$_{2-6}$alkenyl, C$_{2-6}$alkynyl, C$_{1-6}$haloalkyl, C$_{1-6}$alkoxyl, C$_{1-6}$haloalkoxyl, —NHC(O)—C$_{1-6}$alkyl, —C(O)NH—C$_{1-6}$alkyl, —O—C$_{2-6}$alkynyl, —OC(O)—C$_{1-6}$alkyl, —O—(CH$_2$CH$_2$O)$_n$—C$_{1-6}$alkyl, C$_{3-10}$cycloalkyl, 3-12 membered heterocyclyl, —O—C$_{3-10}$cycloalkyl, —O-3-12 membered heterocyclyl, —O—C$_{1-4}$alkylene-C$_{3-10}$cycloalkyl, 5-10 membered heteroaryl, —O—C$_{1-4}$alkylene-3-12 membered heterocyclyl, —O-5-10 membered heteroaryl, and —O—C$_{1-4}$alkylene-5-10 membered heteroaryl of $R^4$ and $R^5$ is optionally substituted with 1-3 groups independently selected from halo, hydroxyl, oxo, C$_{1-6}$alkyl, C$_{1-6}$alkoxyl, C$_{1-6}$haloalkoxyl, —NR$^{aa}$R$^{bb}$, C$_{3-10}$cycloalkyl, and 3-12 membered heterocyclyl.

In some embodiments of Formula (I), (Ia), (II), (IIa), (IIb), (III), (IIIa), (IIIb), (IV), (IVa), (IVb), (V), (Va), or (Vb), $R^4$ is selected from hydroxyl, C$_{1-6}$alkoxyl, —NHC(O)—C$_{1-6}$alkyl, —O—C$_2$-6alkynyl, —OC(O)—C$_{1-6}$alkyl, —O—(CH$_2$CH$_2$O)$_n$—C$_{1-6}$alkyl, —O—C$_{1-4}$alkylene-C$_{3-10}$cycloalkyl, —O—C$_{1-4}$alkylene-3-12 membered heterocyclyl, —O-5-10 membered heteroaryl, and —O—C$_{1-4}$alkylene-5-10 membered heteroaryl; and $R^5$ is selected from hydroxyl, and —OCH$_3$.

In some embodiments of Formula (I), (Ia), (II), (IIa), (IIb), (III), (IIIa), (IIIb), (IV), (IVa), (IVb), (V), (Va), or (Vb), $R^2$ and $R^4$ together with the atoms to which they are attached form a C$_{5-10}$cycloalkyl or 5-7 membered heterocyclyl; and wherein the C$_{5-10}$cycloalkyl or 5-7 membered heterocyclyl is optionally substituted with halo, hydroxyl, oxo, C$_{1-6}$alkyl, C$_1$-haloalkyl, C$_{2-6}$alkenyl, C$_{2-6}$alkynyl, —NR$^{aa}$R$^{bb}$, and —C$_{1-6}$alkylene-NR$^{aa}$R$^{bb}$.

In some embodiments of Formula (I), (Ia), (II), (IIa), (IIb), (III), (IIIa), (IIIb), (IV), (IVa), (IVb), (V), (Va), or (Vb), R$^6$ is hydrogen.

In some embodiments of Formula (I), (Ia), (II), (IIa), (IIb), (III), (IIIa), (IIIb), (IV), (IVa), (IVb), (V), (Va), or (Vb), R$^4$ and R$^6$ together with the atoms to which they are attached form a C$_{5-10}$cycloalkyl, 3-7 membered heterocyclyl or 5-6 membered heteroaryl; wherein the 3-7 membered heterocyclyl is optionally substituted with 1-3 groups independently selected from halo, oxo, hydroxyl, C$_{1-6}$alkyl, C$_1$-haloalkyl, C$_{2-6}$alkenyl, C$_{2-6}$alkynyl, —NR$^{aa}$R$^{bb}$, and —C$_{1-6}$alkylene-NR$^{aa}$R$^{bb}$. In some embodiments, R$^4$ and R$^6$ together with the atoms to which they are attached form tetrahydrofuranyl; wherein tetrahydrofuranyl is optionally substituted with one group selected from hydroxyl, oxo, —CH$_3$, —CH$_2$CH$_2$N(CH$_3$)$_2$, and —CH$_2$CH=CH$_2$.

In some embodiments of Formula (I), (Ia), (II), (IIa), (IIb), (III), (IIIa), (IIIb), (IV), (IVa), (IVb), (V), (Va), or (Vb), R$^7$ is hydrogen.

In some embodiments of Formula (I), (Ia), (II), (IIa), (IIb), (III), (IIIa), (IIIb), (IV), (IVa), (IVb), (V), (Va), or (Vb), R$^7$ and R$^8$, together with the atoms to which they are attached form a C$_{5-10}$cycloalkyl, 3-7 membered heterocyclyl or 5-6 membered heteroaryl; wherein the 3-7 membered heterocyclyl is optionally substituted with 1-3 groups independently selected from halo, oxo, hydroxyl, C$_{1-6}$alkyl, C$_1$-haloalkyl, C$_{2-6}$alkenyl, C$_{2-6}$alkynyl, —NR$^{aa}$R$^{bb}$, and —C$_{1-6}$alkylene-NR$^{aa}$R$^{bb}$.

In some embodiments of Formula (I), (Ia), (II), (IIa), (IIb), (III), (IIIa), (IIIb), (IV), (IVa), (IVb), (V), (Va), or (Vb), R$^7$ and R$^8$, together with the atoms to which they are attached form a C$_{5-10}$cycloalkyl, 3-7 membered heterocyclyl or 5-6 membered heteroaryl; wherein the 3-7 membered heterocyclyl is optionally substituted with 1-3 groups independently selected from halo, oxo, hydroxyl, C$_{1-6}$alkyl, C$_1$-haloalkyl, C$_{2-6}$alkenyl, C$_{2-6}$alkynyl, —NR$^{aa}$R$^{bb}$, and —C$_{1-6}$alkylene-NR$^{aa}$R$^{bb}$. In some embodiments, R$^7$ and R$^8$, together with the atoms to which they are attached form tetrahydrofuran or tetrahydropyranyl; wherein tetrahydrofuran or tetrahydropyranyl is optionally substituted with one group selected from hydroxyl, oxo, and —CH$_3$.

In some embodiments of Formula (I), (II), (III), (IV), or (V), each R$^8$ and R$^9$ is independently selected from halo, hydroxyl, C$_{1-6}$alkyl, C$_{2-6}$alkenyl, C$_{2-6}$alkynyl, C$_{1-6}$alkoxyl, —O—C$_{2-6}$alkenyl, —O—C$_{2-6}$alkynyl, C$_{3-10}$cycloalkyl, 3-12 membered heterocyclyl, C$_{6-10}$aryl, 5-10 membered heteroaryl, —O—C$_{3-10}$cycloalkyl, —O-3-12 membered heterocyclyl, —O—C$_{6-10}$aryl, —O-5-10 membered heteroaryl, —O—C$_{1-4}$alkylene-C$_{3-10}$cycloalkyl, —O—C$_{1-4}$alkylene-3-12 membered heterocyclyl, —O—C$_{1-4}$alkylene-C$_{6-10}$aryl, and —O—C$_{1-4}$alkylene-5-10 membered heteroaryl; and wherein each of C$_{1-6}$alkyl, C$_{2-6}$alkenyl, C$_{2-6}$alkynyl, C$_{1-6}$alkoxyl, —O—C$_{2-6}$alkenyl, —O—C$_{2-6}$alkynyl, C$_{3-10}$cycloalkyl, 3-12 membered heterocyclyl, C$_{6-10}$aryl, 5-10 membered heteroaryl, —O—C$_{3-10}$cycloalkyl, —O-3-12 membered heterocyclyl, —O—C$_{6-10}$aryl, —O-5-10 membered heteroaryl, —O—C$_{1-4}$alkylene-C$_{3-10}$cycloalkyl, —O—C$_{1-4}$alkylene-3-12 membered heterocyclyl, —O—C$_{1-4}$alkylene-C$_{6-10}$aryl, and —O—C$_{1-4}$alkylene-5-10 membered heteroaryl is independently optionally substituted with 1-5 R$^4$.

In some embodiments of Formula (I), (II), (III), (IV), or (V), each R$^8$ and R$^9$ is independently selected from OH, F, —CH$_3$,

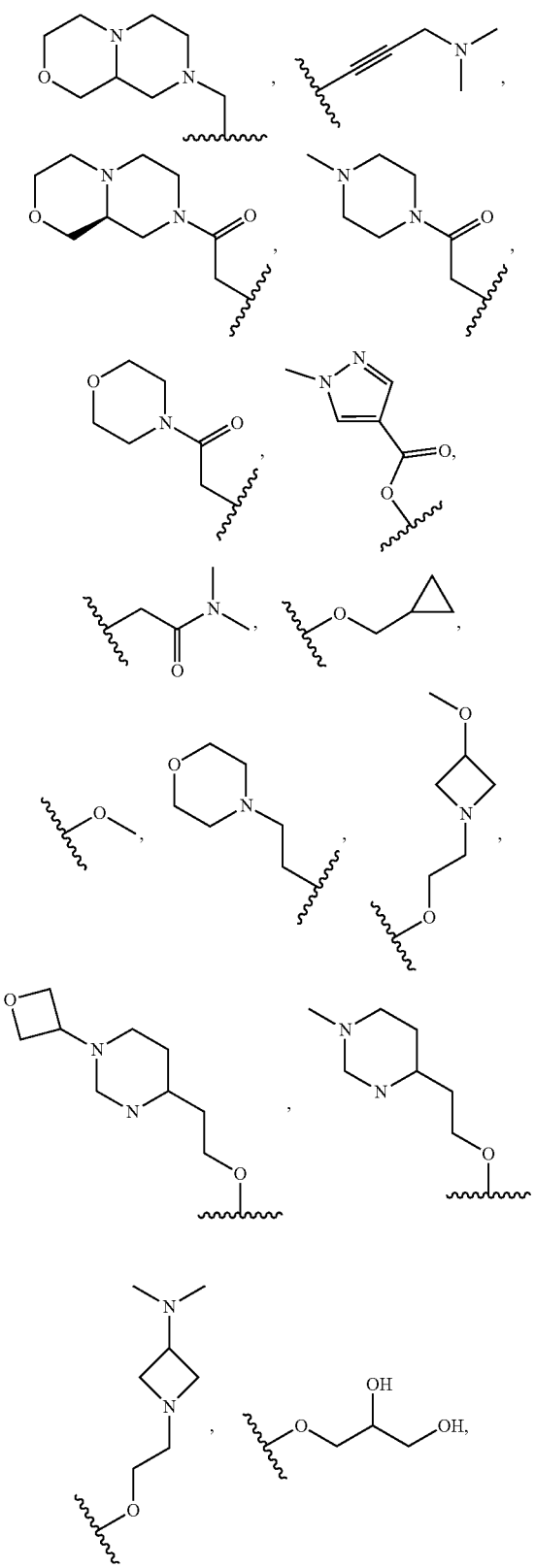

-continued

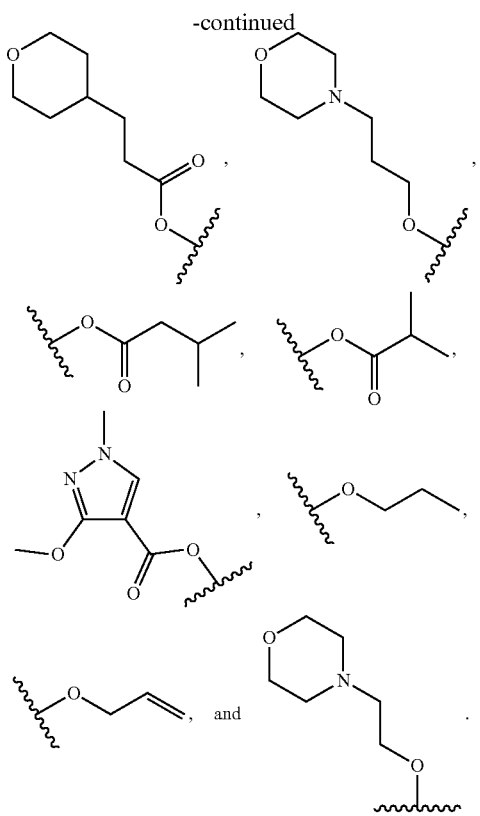

In some embodiments of Formula (I), (Ia), (II), (IIa), (IIb), (III), (IIIa), (IIIb), (IV), (IVa), (IVb), (V), (Va), or (Vb), $R^8$ is

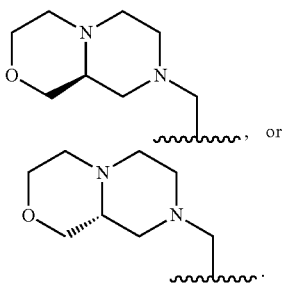

In some embodiments of Formula (I), (Ia), (II), (IIa), (IIb), (III), (IIIa), (IIIb), (IV), (IVa), (IVb), (V), (Va), or (Vb), $R^4$ and $R^8$ together with the atoms to which they are attached form a 10 membered heterocyclyl; wherein the 10 membered heterocyclyl is optionally substituted with 1-3 groups independently selected from halo, oxo, hydroxyl, $C_{1-6}$alkyl, and $C_{1-6}$haloalkyl.

In some embodiments of Formula (I), (Ia), (II), (IIa), (IIb), (III), (IIIa), (IIIb), (IV), (IVa), (IVb), (V), (Va), or (Vb), $R^{10}$ is selected from F, $C_1$, —$CH_3$, and —$CH_2CH_3$. In some embodiments, $R^{10}$ is Cl.

In some embodiments of Formula (I), ═══ is a single bond. In some embodiments, ------ is a double bond. In some embodiments, ═══ is a double bond; and $R^9$ is absent. In some embodiments, ------ is a triple bond, and $R^6$ and $R^7$ are absent.

In some embodiments, the present disclosure provides a compound selected from examples 1-211.

In some embodiments, isotopically labeled forms of the compounds of Formula (I), (Ia), (II), (IIa), (IIb), (III), (IIIa), (IIIb), (IV), (IVa), (IVb), (V), (Va), or (Vb) are provided herein. In some embodiments, isotopically labeled forms of the compounds of Formula (I), (Ia), (II), (IIa), (IIb), (III), (IIIa), (IIIb), (IV), (IVa), (V), (Va), (IVb), or (Vb), are provided herein. Isotopically labeled compounds have structures depicted by the formulas given herein except that one or more atoms are replaced by an isotope having a selected atomic mass or mass number. Isotopically labeled compounds have structures depicted by the formulas given herein except that one or more atoms are replaced by an isotope having a selected atomic mass or mass number. Examples of isotopes that can be incorporated into compounds of the disclosure include isotopes of hydrogen, carbon, nitrogen, oxygen, phosphorus, fluorine and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labeled compounds of the present disclosure, for example those into which radioactive isotopes such as $^3H$, $^{13}C$ and $^{14}C$ are incorporated, are within the ambit of the present disclosure. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in treatment of patients. Such isotopically labeled analogs of compounds of the present disclosure may also be useful for treatment of diseases disclosed herein because they may provide improved pharmacokinetic and/or pharmacodynamic properties over the unlabeled forms of the same compounds. Such isotopically leveled forms of or analogs of compounds herein are within the ambit of the present disclosure. One of skill in the art is able to prepare and use such isotopically labeled forms following procedures for isotopically labeling compounds or aspects of compounds to arrive at isotopic or radiolabeled analogs of compounds disclosed herein.

The compounds disclosed herein may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Likewise, all tautomeric forms are also intended to be included.

In certain embodiments, the present disclosure provides a pharmaceutical composition comprising a compound of the present disclosure, or a pharmaceutically acceptable salt thereof, and a pharmaceutically acceptable excipient. In certain embodiments, the pharmaceutical composition comprises one or more additional therapeutic agents, as described in more detail below.

Pharmaceutical compositions comprising the compounds disclosed herein, or pharmaceutically acceptable salts thereof, may be prepared with one or more pharmaceutically acceptable excipients which may be selected in accord with ordinary practice. "Pharmaceutically acceptable excipient"

includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

In certain embodiments, pharmaceutical compositions are provided as a solid dosage form, including a solid oral dosage form, such as a tablet. Tablets may contain excipients including glidants, fillers, binders and the like. Aqueous compositions may be prepared in sterile form, and when intended for delivery by other than oral administration generally may be isotonic. All compositions may optionally contain excipients such as those set forth in the Rowe et al, Handbook of Pharmaceutical Excipients, $6^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like.

Pharmaceutical compositions disclosed herein include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if necessary, shaping the product. Techniques and formulations generally are found in Remington: The Science and Practice of Pharmacy, $21^{st}$ Edition, Lippincott Wiliams and Wilkins, Philadelphia, Pa., 2006.

Compositions described herein that are suitable for oral administration may be presented as discrete units (a unit dosage form) including but not limited to capsules, cachets or tablets each containing a predetermined amount of the active ingredient. In one embodiment, the pharmaceutical composition is a tablet.

Pharmaceutical compositions disclosed herein comprise one or more compounds disclosed herein, or a pharmaceutically acceptable salt thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 to 1000 mg of active material formulated with an appropriate and convenient amount of a pharmaceutically acceptable excipient. In certain embodiments, the pharmaceutically acceptable excipient varies from about 5 to about 95% of the total compositions (weight:weight).

Methods

In some embodiments, the present disclosure provides a method of inhibiting MCL1. In some embodiments, the present disclosure provides a method of inhibiting MCL1 in an individual (e.g., a human) comprising administering a compound of Formula (I), or a pharmaceutically acceptable salt thereof, to the individual.

In some embodiments, the present disclosure provides a method of treating or preventing cancer. In certain embodiments, the present disclosure provides a method of treating or preventing cancer comprising administering to a patient a therapeutically effective amount a compound of Formula (I), or a pharmaceutically acceptable salt thereof, to the individual. In some embodiments, the cancer is a hematologic malignancy. In some embodiments, the cancer is multiple myeloma. In some embodiments, the cancer is selected from the group consisting of breast cancer, colorectal cancer, skin cancer, melanoma, ovarian cancer, kidney cancer, small cell lung cancer, non-small cell lung cancer, lymphoma, and leukemia.

Compounds disclosed herein can be administered by any route appropriate for use in a method described herein. Suitable routes include oral, rectal, nasal, topical (including buccal and sublingual), transdermal, vaginal and parenteral (including subcutaneous, intramuscular, intravenous, intradermal, intrathecal and epidural), and the like.

Compounds disclosed herein may be administered to an individual in accordance with an effective dosing regimen for a desired period of time or duration, such as at least one week, at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

Therapeutically effective amounts of compounds disclosed herein are from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 µg to about 30 mg per day, or such as from about 0.3 µg to about 30 mg per day.

A compound of Formula (I), (Ia), (II), (IIa), (IIb), (III), (IIIa), (IIIb), (IV), (IVa), (IVb), (V), (Va), or (Vb), or a pharmaceutically acceptable salt thereof, may be combined with one or more additional therapeutic agents in any dosage amount of the compound of the present disclosure (e.g., from 1 mg to 1000 mg of compound). Therapeutically effective amounts of the compound of Formula (I), (Ia), (II), (IIa), (IIb), (III), (IIIa), (IIIb), (IV), (IVa), (IVb), (V), (Va), or (Vb), or a pharmaceutically acceptable salt thereof, can range from about 0.01 mg per dose to about 1000 mg per dose, such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose. Other therapeutically effective amounts of the compound of Formula (I), (Ia), (II), (IIa), (IIb), (III), (IIIa), (IIIb), (IV), (IVa), (IVb), (V), (Va), or (Vb) are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of Formula (I), (Ia), (II), (IIa), (IIb), (III), (IIIa), (IIIb), (IV), (IVa), (IVb), (V), (Va), or (Vb) are about 100 mg per dose, or about 125, 150, 175, 200, 225, 250, 275, 300, 350, 400, 450, or about 500 mg per dose.

Therapeutically effective amounts of the compound of Formula (I), (Ia), (II), (IIa), (IIb), (III), (IIIa), (IIIb), (IV), (IVa), (IVb), (V), (Va), or (Vb), or a pharmaceutically acceptable salt thereof, can range from about 0.01 mg per dose to about 1000 mg per dose, such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose. Other therapeutically effective amounts of the compound of Formula (I), (Ia), (II), (IIa), (IIb), (III), (IIIa), (IIIb), (IV), (IVa), (IVb), (V), (Va), or (Vb), are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of Formula (I), (Ia), (II), (IIa), (IIb), (III), (IIIa), (IIIb), (IV), (IVa), (IVb), (V), (Va), or (Vb), are about 100 mg per dose, or about 125, 150, 175, 200, 225, 250, 275, 300, 350, 400, 450, or about 500 mg per dose.

A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound disclosed herein is administered once daily in a method disclosed herein. In some embodiments, a compound disclosed herein is administered twice daily in a method disclosed herein.

The frequency of dosage of a compound disclosed herein will be determined by the needs of the individual patient and can be, for example, once per day or twice, or more times, per day. Administration of a compound continues for as long as necessary to treat cancer. For example, a compound disclosed herein can be administered to a human having cancer for a period of from 20 days to 180 days or, for example, for a period of from 20 days to 90 days or, for example, for a period of from 30 days to 60 days.

Administration can be intermittent, with a period of several or more days during which a patient receives a daily dose of a compound disclosed herein, followed by a period of several or more days during which a patient does not receive a daily dose of the compound. For example, a patient can receive a dose of a compound every other day, or three times per week. Again by way of non-limiting example, a patient can receive a dose of a compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

Combination Therapy

In various embodiments, a compound as described herein, is combined with one or more additional therapeutic agents, e.g., an inhibitory immune checkpoint blocker or inhibitor, a stimulatory immune checkpoint stimulator, agonist or activator, a chemotherapeutic agent, an anti-cancer agent, a radiotherapeutic agent, an anti-neoplastic agent, an anti-proliferation agent, an anti-angiogenic agent, an anti-inflammatory agent, an immunotherapeutic agent, a therapeutic antigen-binding molecule (mono- and multi-specific antibodies and fragments thereof in any format (e.g., including without limitation DARTs®, Duobodies®, BiTEs®, BiKEs, TriKEs, XmAbs®, TandAbs®, scFvs, Fabs, Fab derivatives), bi-specific antibodies, non-immunoglobulin antibody mimetics (e.g., including without limitation adnectins, affibody molecules, affilins, affimers, affitins, alphabodies, anticalins, peptide aptamers, armadillo repeat proteins (ARMs), atrimers, avimers, designed ankyrin repeat proteins (DARPins®), fynomers, knottins, Kunitz domain peptides, monobodies, and nanoCLAMPs), antibody-drug conjugates (ADC), antibody-peptide conjugate), an oncolytic virus, a gene modifier or editor, a cell comprising a chimeric antigen receptor (CAR), e.g., including a T-cell immunotherapeutic agent, an NK-cell immunotherapeutic agent, or a macrophage immunotherapeutic agent, a cell comprising an engineered T-cell receptor (TCR-T), or any combination thereof.

Illustrative Targets

In some embodiments, the one or more additional therapeutic agents include, without limitation, an inhibitor, agonist, antagonist, ligand, modulator, stimulator, blocker, activator or suppressor of a target (e.g., polypeptide or polynucleotide) including without limitation: Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2BR, A2aR, A3aR), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, 4-1BB ligand (CD137L), Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1, CHK2), chemokine (C-C motif) receptor (such as CCR2, CCR4, CCR5, CCR8), chemokine (C-X-C motif) receptor (such as CXCR1, CXCR2, CXCR3 and CXCR4), Chemokine CC21 ligand, Cholecystokinin CCK2 receptor, Chorionic gonadotropin, c-Kit (tyrosine-protein kinase Kit or CD117), CISH (Cytokine-inducible SH2-containing protein), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e (CEACAM6), CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement $C_3$, Connective tissue growth factor, COP9 signalosome subunit 5, CSF-1 (colony-stimulating factor 1 receptor), CSF2 gene, CTLA-4 (cytotoxic T-lymphocyte protein 4) receptor, C-type lectin domain protein 9A (CLEC9A), Cyclin D1, Cyclin G1, cyclin-dependent kinases (CDK, such as CDK1, CDK12, CDK1B, CDK2-9), cyclooxygenase (such as COX1, COX2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, DEAD-box helicase 6 (DDX6), Death receptor 5 (DR5, TRAILR2), Death receptor 4 (DR4, TRAILR1), Delta-like protein ligand (such as 3, 4), Deoxyribonuclease, Deubiquitinating enzymes (DUBs), Dickkopf-1 ligand, dihydrofolate reductase (DHFR), Dihydropyrimidine dehydrogenase, Dipeptidyl peptidase IV, discoidin domain receptor (DDR, such as DDR1), Diacylglycerol kinase zeta (DGKZ), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, E3 ubiquitin-protein ligase (such as RNF128, CBL-B), echinoderm microtubule like protein 4, EGFR tyrosine kinase receptor, Elastase, Elongation factor 1 alpha 2, Elongation factor 2, Endoglin, Endonuclease, endoplasmic reticulum aminopeptidase (ERAP, such as ERAP 1, ERAP2), Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Hypoxia-inducible factor prolyl hydroxylase (HIF-PH or EGLN), Factor (such as Xa, VIIa), farnesoid x receptor (FXR), Fas ligand, Fatty acid synthase (FASN), Ferritin, FGF-2 ligand, FGF-5 ligand, fibroblast growth factor (FGF, such as FGF1, FGF2, FGF4), Fibronectin, focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Ganglioside GD2, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releasing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heme oxygenase 1 (HO1), Heme oxygenase 2 (HO2), Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOT1L), histone deacetylase (HDAC, such as 1, 2, 3, 6, 10, 11), Histone H1, Histone H3, HLA class I antigen (A-2 alpha), HLA class II antigen, HLA class I antigen alpha G (HLA-G), Non-classical HLA, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha (HIF1α), Imprinted Maternally Expressed Transcript (H19) gene, mitogen-activated protein kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1 and IDO2), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, Interleukin 35 (IL-35), isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KiSS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukocyte immunoglobulin-like receptor subfamily B member 1 (ILT2), Leukocyte immunoglobulin-like receptor subfamily B member 2 (ILT4), Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), 5-Lipoxygenase (5-LOX), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), MCL1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAPi (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyltransferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, NLRP3 (NACHT LRR PYD domain protein 3) modulators, Noradrenaline transporter, Notch (such as Notch-2 receptor, Notch-3 receptor, Notch-4 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Ornithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly (ADP-ribose) polymerase (PARP, such as PARP1, PARP2 and PARP3, PARP7, and mono-PARPs), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), Prostaglandin E2 synthase, prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase) gene, Rosi tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Secreted phospholipase A2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Son of sevenless (SOS), Specific protein 1 (Spi) transcription factor, Sphingomyelin synthase, Sphingosine kinase (such as 1, 2), Sphingosine-1-phosphate receptor-1, spleen tyrosine kinase (SYK), SRC gene, Src tyrosine kinase, Stabilin-1 (STAB1), STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Suppressor of cytokine signaling modulators (SOCS), Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, Three prime repair exonuclease 1 (TREX1), Three prime repair exonuclease 2 (TREX2), Thrombopoietin receptor, Thymidine kinase, Thymidine phosphorylase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, transferrin (TF), transforming growth factor alpha (TGFα), transforming growth factor beta (TGFB) and isoforms thereof, TGF beta 2 ligand, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), tryptophan 2,3-dioxygenase (TDO), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tumor specific neoantigens, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E2I (UBE2I, UBC9), Ubiquitin-specific-processing protease 7 (USP7), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase, Mer (Mer tyrosine kinase receptor modulators), YAP (Yes-associated protein modulators)es, Wee-1 protein kinase, Werner Syndrome RecQ Like Helicase (WRN), Wilms' tumor antigen 1, Wilms' tumor protein, WW domain containing transcription regulator protein 1 (TAZ), X-linked inhibitor of apoptosis protein, Zinc finger protein transcription factor, or any combination thereof.

Illustrative Mechanisms of Action

In various embodiments, the one or more additional therapeutic agents may be categorized by their mechanism of action into, for example, the following groups:

- anti-metabolites/anti-cancer agents, such as pyrimidine analogs floxuridine, capecitabine, cytarabine, CPX-351 (liposomal cytarabine, daunorubicin), and TAS-118;
- purine analogs, folate antagonists (such as pralatrexate), cladribine, pentostatin, fludarabine and related inhibitors;
- antiproliferative/antimitotic agents including natural products, such as vinca alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide);
- DNA damaging agents, such as actinomycin, amsacrine, busulfan, carboplatin, chlorambucil, cisplatin, cyclophosphamide (CYTOXAN®), dactinomycin, daunorubicin, doxorubicin, DEBDOX, epirubicin, iphosphamide, melphalan, merchlorethamine, mitomycin C, mitoxantrone, nitrosourea, procarbazine, taxol, Taxotere, teniposide, etoposide, and triethylenethiophosphoramide;
- DNA-hypomethylating agents, such as guadecitabine (SGI-110), ASTX727;
- antibiotics such as dactinomycin, daunorubicin, doxorubicin, idarubicin, anthracyclines, mitoxantrone, bleomycins, and plicamycin (mithramycin);
- enzymes such as L-asparaginase which systemically metabolizes L-asparagine and deprives cells which do not have the capacity to synthesize their own asparagine;
- DNAi oligonucleotides targeting Bcl-2, such as PNT2258; agents that activate or reactivate latent human immunodeficiency virus (HIV), such as panobinostat and romidepsin;
- asparaginase stimulators, such as crisantaspase (Erwinase®) and GRASPA (ERY-001, ERY-ASP), calaspargase pegol, and pegaspargase;
- pan-Trk, ROS1 and ALK inhibitors, such as entrectinib, and TPX-0005;
- anaplastic lymphoma kinase (ALK) inhibitors, such as alectinib, ceritinib, alecensa (RG7853), and ALUNBRIG® (brigatinib);
- antiproliferative/antimitotic alkylating agents, such as nitrogen mustard cyclophosphamide and analogs (e.g., melphalan, chlorambucil, hexamethylmelamine, thiotepa), alkyl nitrosoureas (e.g., carmustine) and analogs, streptozocin, and triazenes (e.g., dacarbazine);
- antiproliferative/antimitotic antimetabolites, such as folic acid analogs (methotrexate);
- platinum coordination complexes (e.g., cisplatin, oxiloplatinim, and carboplatin), procarbazine, hydroxyurea, mitotane, and aminoglutethimide;
- hormones, hormone analogs (e.g., estrogen, tamoxifen, goserelin, bicalutamide, and nilutamide), and aromatase inhibitors (e.g., letrozole and anastrozole);
- antiplatelet agents; anticoagulants such as heparin, synthetic heparin salts, and other inhibitors of thrombin;
- fibrinolytic agents such as tissue plasminogen activator, streptokinase, urokinase, aspirin, dipyridamole, ticlopidine, and clopidogrel;
- antimigratory agents;
- antisecretory agents (e.g., breveldin);
- immunosuppressives, such as tacrolimus, sirolimus, azathioprine, and mycophenolate;
- growth factor inhibitors, and vascular endothelial growth factor inhibitors;
- fibroblast growth factor inhibitors, such as FPA14;
- AMP activated protein kinase stimulators, such as metformin hydrochloride;
- Alpha 1 adrenoceptor/Alpha 2 adrenoceptor antagonists, such as phenoxybenzamine hydrochloride (injectable, pheochromocytoma);
- androgen receptor antagonists, such as nilutamide;
- anti-VEGFR antibodies, such as IMC-3C5, GNR-011, tanibirumab, LYN-00101; anti-VEGF/DDL4 antibodies, such as ABT-165;
- anti-cadherin antibodies, such as HKT-288;
- anti-leucine-rich repeat containing 15 (LRRC15) antibodies, such as ABBV-085, ARGX-110;
- angiotensin receptor blockers, nitric oxide donors;
- antisense oligonucleotides, such as AEG35156, IONIS-KRAS-2.5Rx, EZN-3042, RX-0201, IONIS-AR-2.5Rx, BP-100 (prexigebersen), and IONIS-STAT3-2.5Rx;
- DNA interference oligonucleotides, such as PNT2258, and AZD-9150;
- anti-angiopoietin (ANG)-2 antibodies, such as MEDI3617, and LY3127804;
- anti-ANG-1/ANG-2 antibodies, such as AMG-780;
- anti-CSF1R antibodies, such as emactuzumab, LY3022855, AMG-820, and FPA-008 (cabiralizumab);
- anti-endoglin antibodies, such as TRC105 (carotuximab);
- anti-MET/EGFR antibodies, such as LY3164530;

anti-EGFR antibodies, such as ABT-414, AMG-595, necitumumab, ABBV-221, depatuxizumab mafodotin (ABT-414), tomuzotuximab, ABT-806, vectibix, modotuximab, and RM-1929;

anti-HER2 antibodies, such as HERCEPTIN® (trastuzumab), trastuzumab biosimilar, margetuximab, MEDI4276, BAT-8001, Pertuzumab (Perjeta), RG6264, and ZW25 (a bispecific HER2-directed antibody targeting the extracellular domains 2 and 4; Cancer Discov. 2019 January; 9(1):8; PMID: 30504239);

anti-HLA-DR antibodies, such as IMMU-114;

anti-IL-3 antibodies, such as JNJ-56022473;

anti-TNF receptor superfamily member 4 (TNFRSF4, OX40; NCBI Gene ID: 7293) antibodies, such as MEDI6469, MEDI6383, MEDI0562 (tavolixizumab), MOXR0916, PF-04518600, RG-7888, GSK-3174998, INCAGN1949, BMS-986178, GBR-8383, ABBV-368; and those described in Intl. Patent Publ. Nos. WO 2016/179517, WO 2017/096179, WO 2017/096182, WO 2017/096281, and WO 2018/089628;

anti-TNF receptor superfamily member 18 (TNFRSF18, GITR; NCBI Gene ID: 8784) antibodies, such as MEDI1873, FPA-154, INCAGN-1876, TRX-518, BMS-986156, MK-1248, GWN-323; and those described, e.g., in Intl. Patent Publ. Nos. WO 2017/096179, WO 2017/096276, WO 2017/096189, and WO 2018/089628;

anti-TNFRSF4 (OX40)/TNFRSF18(GITR) bi-specific antibodies, such as those described in Intl. Patent Publ. Nos. WO 2017/096179 and WO 2018/089628;

anti-EphA3 antibodies, such as KB-004;

anti-CD37 antibodies, such as AGS67E, and otlertuzumab (TRU-016);

anti-ENPP3 antibodies, such as AGS-16C$_3$F;

anti-FGFR-3 antibodies, such as LY3076226, and B-701;

anti-FGFR-2 antibodies, such as GAL-F2;

anti-C$_5$ antibodies, such as ALXN-1210;

anti-TROP-2 antibodies, such as IMMU-132;

anti-EpCAM antibodies, such as VB4-845;

antibodies against TNF receptor superfamily member 17 (TNFRSF17, BCMA), such as GSK-2857916;

anti-CEA antibodies, such as RG-7813;

anti-cluster of differentiation 3 (CD3) antibodies, such as MGD015; anti-folate receptor alpha antibodies, such as IMGN853;

anti-TNF receptor superfamily member 10b (TNFRSF10B, DR5, TRAILR2) antibodies, such as DS-8273, CTB-006, INBRX-109, and GEN-1029;

anti-Carcinoembryonic-antigen-related-cell-adhesion-molecule-6 (CEACAM6, CD66C) antibodies, such as BAY-1834942, and NEO-201 (CEACAM 5/6);

anti-GD2 antibodies, such as APN-301;

anti-interleukin-17 (IL-17) antibodies, such as CJM-112;

anti-interleukin-1 beta antibodies, such as canakinumab (ACZ885), and VPM087;

anti-carbonic anhydrase 9 (CA9, CAIX) antibodies, such as TX-250;

anti-CD38 antibodies, such as isatuximab, MOR-202, and TAK-079;

anti-CD38-attenukine, such as TAK573;

anti-Mucin 1 (MUC1) antibodies, such as gatipotuzumab, and Mab-AR-20.5;

anti-CD33 antibodies, such as IMGN-779;

anti-KMA antibodies, such as MDX-1097;

anti-CD55 antibodies, such as PAT-SC1;

anti-PSMA antibodies, such as ATL-101;

anti-CD100 antibodies, such as VX-15;

anti-EPHA3 antibodies, such as fibatuzumab;

anti-APRIL antibodies, such as BION-1301;

anti-fibroblast activation protein (FAP)/IL-2R antibodies, such as RG7461;

anti-fibroblast activation protein (FAP)/TRAIL-R$^2$ antibodies, such as RG7386;

anti-fucosyl-GM1 antibodies, such as BMS-986012;

anti-TGFb antibodies, such as SAR439459;

ADP ribosyl cyclase-1 inhibitors, such as daratumumab (DARZALEX®);

caspase recruitment domain protein-15 stimulators, such as mifamurtide (liposomal);

CCR5 chemokine antagonists, such as MK-7690 (vicriviroc);

CDC7 protein kinase inhibitors, such as TAK-931;

cholesterol side-chain cleavage enzyme inhibitors, such as ODM-209;

dihydropyrimidine dehydrogenase/Orotate phosphoribosyltransferase inhibitors, such as Cefesone (tegafur+gimeracil+oteracil potassium);

DNA polymerase/Ribonucleotide reductase inhibitors, such as clofarabine;

estrogen receptor modulators, such as bazedoxifene;

estrogen receptor agonists/Progesterone receptor antagonists, such as TRI-CYCLEN LO (norethindrone+ethinyl estradiol);

HLA class I antigen A-2 alpha modulators, such as FH-MCVA2TCR;

HLA class I antigen A-2 alpha/MART-1 melanoma antigen modulators, such as MART-1 F5 TCR engineered PBMC;

human Granulocyte Colony Stimulating Factors, such as PF-06881894;

GNRH receptor agonists, such as leuprorelin acetate, leuprorelin acetate sustained release depot (ATRIGEL), triptorelin pamoate, and goserelin acetate;

GNRH receptor antagonists, such as elagolix, relugolix, and degarelix;

endoplasmin modulators, such as anlotinib;

H+ K+ ATPase inhibitors, such as omeprazole, and esomeprazole;

ICAM-1/CD55 modulators, such as cavatak (V-937);

IL-15/IL-12 modulators, such as SAR441000;

interleukin 23A inhibitors, such as guselkumab;

Lysine specific histone demethylase 1 inhibitors, such as CC-90011;

IL-12 Mrna, such as MEDI1191;

progesterone receptor agonists, such as levonorgestrel;

protein cereblon modulators, such as CC-92480, and CC-90009;

protein cereblon modulators/DNA binding protein Ikaros inhibitors/Zinc finger binding protein Aiolos inhibitors, such as iberdomide;

retinoid X receptor modulators, such as alitretinoin, and bexarotene (oral formulation);

RIP-1 kinase inhibitors, such as GSK-3145095;

selective oestrogen receptor degraders, such as AZD9833;

SUMO inhibitors, such as TAK-981;

thrombopoietin receptor agonists, such as eltrombopag;

thyroid hormone receptor agonists, such as levothyroxine sodium;

TNF agonists, such as tasonermin;

tyrosine phosphatase substrate 1 inhibitors, such as CC-95251;

HER2 inhibitors, such as neratinib, and tucatinib (ONT-380);

EGFR/ErbB2/Ephb4 inhibitors, such as tesevatinib;
EGFR/HER2 inhibitors, such as TAK-788;
EGFR family tyrosine kinase receptor inhibitors, such as DZD-9008;
anti-ERBB antibodies, such as CDX-3379, HLX-02, and seribantumab;
EGFR/ErbB-2 inhibitors, such as varlitinib;
mutant selective EGFR inhibitors, such as PF-06747775, EGF816 (nazartinib), ASP8273, ACEA-0010, and BI-1482694;
epha2 inhibitors, such as MM-310;
raf kinase/VEGFR inhibitors, such as RAF-265;
polycomb protein (EED) inhibitors, such as MAK683;
DHFR inhibitor/Folate transporter 1 modulator/Folate receptor antagonist, such as pralatrexate;
DHFR/GAR transformylase/Thymidylate synthase/Transferase inhibitors, such as pemetrexed disodium;
p38 MAP kinase inhibitors, such as ralimetinib;
PRMT inhibitors, such as MS203, PF-06939999, GSK3368715, and GSK3326595;
sphingosine kinase 2 (SK2) inhibitors, such as opaganib;
nuclear erythroid 2-related factor 2 stimulators, such as omaveloxolone (RTA-408);
tropomyosin receptor kinase (TRK) inhibitors, such as LOXO-195, and ONO-7579;
mucin 1 inhibitors, such as GO-203-2C;
MARCKS protein inhibitors, such as BIO-11006;
folate antagonists, such as arfolitixorin;
galectin-3 inhibitors, such as GR-MD-02;
phosphorylated P68 inhibitors, such as RX-5902;
CD95/TNF modulators, such as ofranergene obadenovec;
PI3K/Akt/mTOR inhibitors, such as ABTL-0812;
pan-PIM kinase inhibitors, such as INCB-053914;
IL-12 gene stimulators, such as EGEN-001, and tavokinogene telseplasmid;
heat shock protein HSP90 inhibitors, such as TAS-116, and PEN-866;
VEGF/HGF antagonists, such as MP-0250;
VEGF ligand inhibitors, such as bevacizumab biosimilar;
VEGF receptor antagonists/VEGF ligand inhibitors, such as ramucirumab;
VEGF-1/VEGF-2/VEGF-3 receptor antagonists; such as fruquintinib;
VEGF-1/VEGF-2 receptor modulators, such as HLA-A2402/HLA-A0201 restricted epitope peptide vaccine;
placenta growth factor ligand inhibitor/VEGF-A ligand inhibitor, such as aflibercept;
SYK tyrosine kinase/JAK tyrosine kinase inhibitors, such as ASN-002;
Trk tyrosine kinase receptor inhibitors, such as larotrectinib sulfate;
JK3/JAK1/TBK1 kinase inhibitors, such as CS-12912;
IL-24 antagonist, such as AD-IL24;
NLRP3 (NACHT LRR PYD domain protein 3) modulators, such as BMS-986299;
RIG-1 agonists, such as RGT-100;
aerolysin stimulators, such as topsalysin;
P-Glycoprotein 1 inhibitors, such as HM-30181A;
CSF-1 antagonists, such as ARRY-382, and BLZ-945;
CCR8 inhibitors, such as 1-309, SB-649701, HG-1013, and RAP-310;
anti-Mesothelin antibodies, such as SEL-403;
thymidine kinase stimulators, such as aglatimagene besadenovec;
polo-like kinase 1 inhibitors, such as PCM-075;
NAE inhibitors, such as pevonedistat (MLN-4924), TAS-4464; pleiotropic pathway modulators, such as avadomide (CC-122);
amyloid protein binding protein-1 inhibitorS/Ubiquitin ligase modulators, such as pevonedistat;
FoxM1 inhibitors, such as thiostrepton;
UBA1 inhibitors, such as TAK-243;
Src tyrosine kinase inhibitors, such as VAL-201;
VDAC/HK inhibitors, such as VDA-1102;
BRAF/PI3K inhibitors, such as ASN-003;
Elf4a inhibitors, such as rohinitib, eFT226;
TP53 gene stimulators, such as ad-p53;
retinoic acid receptor agonists, such as tretinoin;
retinoic acid receptor alpha (RARα) inhibitors, such as SY-1425;
SIRT3 inhibitors, such as YC8-02;
stromal cell-derived factor 1 ligand inhibitors, such as olaptesed pegol (NOX-A12);
IL-4 receptor modulators, such as MDNA-55;
arginase-I stimulators, such as pegzilarginase;
topoisomerase I inhibitors, such as irinotecan hydrochloride and Onivyde;
topoisomerase I inhibitor/hypoxia inducible factor-1 alpha inhibitors, such as PEG-SN38 (firtecan pegol);
hypoxia inducible factor-1 alpha inhibitors, such as PT-2977, PT-2385;
CD122 agonists, such as NKTR-214;
TLR7/TLR8 agonist, such as NKTR-262;
TLR7 agonists, such as DS-0509, GS-9620, LHC-165, and TMX-101 (imiquimod);
p53 tumor suppressor protein stimulators such as kevetrin;
Mdm4/Mdm2 p53-binding protein inhibitors, such as ALRN-6924;
kinesin spindle protein (KSP) inhibitors, such as filanesib (ARRY-520);
CD80-fc fusion protein inhibitors, such as FPT-155;
menin and mixed lineage leukemia (MLL) inhibitors such as KO-539;
Liver x receptor agonists, such as RGX-104;
IL-10 agonists, such as Pegilodecakin (AM-0010);
VEGFR/PDGFR inhibitors, such as vorolanib;
IRAK4 inhibitors, such as CA-4948;
anti-TLR-2 antibodies, such as OPN-305;
Calmodulin modulators, such as CBP-501;
glucocorticoid receptor antagonists, such as relacorilant (CORT-125134);
second mitochondria-derived activator of caspases (SMAC) protein inhibitors, such as BI-891065;
lactoferrin modulators, such as LTX-315;
KIT proto-oncogene, receptor tyrosine kinase (KIT) inhibitors, such as PLX-9486;
platelet derived growth factor receptor alpha (PDGFRA)/KIT proto-oncogene, receptor tyrosine kinase (KIT) mutant-specific antagonists/inhibitors such as BLU-285, and DCC-2618;
exportin 1 inhibitors, such as eltanexor;
CHST15 gene inhibitors, such as STNM-01;
RAS inhibitors, such as NEO-100;
somatostatin receptor antagonist, such as OPS-201;
CEBPA gene stimulators, such as MTL-501;
DKK3 gene modulators, such as MTG-201;
chemokine (CXCR1/CXCR2) inhibitors, such as SX-682;
p70s6k inhibitors, such as MSC2363318A;
methionine aminopeptidase 2 (MetAP2) inhibitors, such as M8891, and APL-1202;

arginine N-methyltransferase 5 inhibitors, such as GSK-3326595;
CD71 modulators, such as CX-2029 (ABBV-2029);
anti-IL-8 (Interleukin-8) antibodies, such as HuMax-Inflam;
ATM (ataxia telangiectasia) inhibitors, such as AZD0156, and AZD1390;
CHK1 inhibitors, such as GDC-0575, LY2606368 (prexasertib), SRA737, and RG7741 (CHK1/2);
CXCR4 antagonists, such as BL-8040, LY2510924, burixafor (TG-0054), X4P-002, X4P-001-IO, and Plerixafor;
EXH2 inhibitors, such as GSK2816126;
KDM1 inhibitors, such as ORY-1001, IMG-7289, INCB-59872, and GSK-2879552;
CXCR2 antagonists, such as AZD-5069;
GM-CSF antibodies, such as lenzilumab;
DNA dependent protein kinase inhibitors, such as MSC2490484A (nedisertib), and VX-984, AsiDNA (DT-01); protein kinase C (PKC) inhibitors, such as LXS-196, and sotrastaurin;
selective estrogen receptor downregulators (SERD), such as fulvestrant (Faslodex®), RG6046, RG6047, RG6171, elacestrant (RAD-1901), SAR439859 and AZD9496;
selective estrogen receptor covalent antagonists (SERCAs), such as H3B-6545;
selective androgen receptor modulator (SARM), such as GTX-024, and darolutamide;
transforming growth factor-beta (TGF-beta) kinase antagonists, such as galunisertib, LY3200882; TGF-beta inhibitors described in WO 2019/103203;
TGF beta receptor 1 inhibitors, such as PF-06952229;
anti-transforming growth factor-beta (TGF-beta) antibodies, such as ABBV-151, LY3022859, NIS793, and XOMA 089;
bispecific antibodies, such as ABT-165 (DLL4/VEGF), MM-141 (IGF-1/ErbB3), MM-111 (Erb2/Erb3), JNJ-64052781 (CD19/CD3), PRS-343 (CD-137/HER2), AFM26 (BCMA/CD16A), JNJ-61186372 (EGFR/cMET), AMG-211 (CEA/CD3), RG7802 (CEA/CD3), ERY-974 (CD3/GPC3) vancizumab (angiopoietins/VEGF), PF-06671008 (Cadherins/CD3), AFM-13 (CD16/CD30), APV0436 (CD123/CD3), flotetuzumab (CD123/CD3), REGN-1979 (CD20/CD3), MCLA-117 (CD3/CLEC12A), MCLA-128 (HER2/HER3), JNJ-0819, JNJ-7564 (CD3/heme), AMG-757 (DLL3-CD3), MGD-013 (PD-1/LAG-3), FS-118 (LAG-3/PD-L1) MGD-019 (PD-1/CTLA-4), KN-046 (PD-1/CTLA-4), MEDI-5752 (CTLA-4/PD-1), RO-7121661 (PD-1/TIM-3), XmAb-20717 (PD-1/CTLA-4), AK-104 (CTLA-4/PD-1), AMG-330 (CD33/CD3), AMG-420 (BCMA/CD3), BI-836880 (VEFG/ANG2), JNJ-63709178 (CD123/CD3), MGD-007 (CD3/gpA33), MGD-009 (CD3/B7H3), AGEN1223, IMCgp100 (CD3/gp100), AGEN-1423, ATOR-1015 (CTLA-4/OX40), LY-3415244 (TIM3/PDL1), INHIBRX-105 (4-1 BB/PDL1), faricimab (VEGF-A/ANG-2), FAP-4-IBBL (4-1BB/FAP), XmAb-13676 (CD3/CD20), TAK-252 (PD-1/OX40L), TG-1801 (CD19/CD47), XmAb-18087 (SSTR2/CD3), catumaxomab (CD3/EpCAM), SAR-156597 (IL4/IL13), EMB-01 (EGFR/cMET), REGN-4018 (MUC16/CD3), REGN-1979 (CD20/CD3), RG-7828 (CD20/CD3), CC-93269 (CD3/BCMA), REGN-5458 (CD3/BCMA), navicixizumab (DLL4/VEGF), GRB-1302 (CD3/Erbb2), vanucizumab (VEGF-A/ANG-2), GRB-1342 (CD38/CD3), GEM-333 (CD3/CD33), IMM-0306 (CD47/CD20), RG6076, and MED15752 (PD-1/CTLA-4);
anti-delta-like protein ligand 3 (DDL3) antibodies, such as rovalpituzumab tesirine;
anti-clusterin antibodies, such as AB-16B5;
anti-Ephrin-A4 (EFNA4) antibodies, such as PF-06647263;
anti-RANKL antibodies, such as denosumab;
anti-mesothelin antibodies, such as BMS-986148, and Anti-MSLN-MMAE;
anti-sodium phosphate cotransporter 2B (NaP2B) antibodies, such as lifastuzumab
anti-c-Met antibodies, such as ABBV-399;
alpha-ketoglutarate dehydrogenase (KGDH) inhibitors, such as CPI-613;
XPO1 inhibitors, such as selinexor (KPT-330);
Isocitrate dehydrogenase 2 (IDH2) inhibitors, such as enasidenib (AG-221);
IDH1 inhibitors such as AG-120, and AG-881 (IDH1 and IDH2), IDH-305, and BAY-1436032;
IDH1 gene inhibitors, such as ivosidenib;
interleukin-3 receptor (IL-3R) modulators, such as SL-401;
arginine deiminase stimulators, such as pegargiminase (ADI-PEG-20);
claudin-18 inhibitors, such as claudiximab;
β-catenin inhibitors, such as CWP-291;
chemokine receptor 2 (CCR) inhibitors, such as PF-04136309, CCX-872, and BMS-813160 (CCR2/CCR5);
thymidylate synthase inhibitors, such as ONX-0801;
ALK/ROS1 inhibtors, such as lorlatinib;
tankyrase inhibitors, such as G007-LK;
Mdm2 p53-binding protein inhibitors, such as CMG-097, and HDM-201; and c-PIM inhibitors, such as PIM447;
BRAF inhibitors, such as dabrafenib, vemurafenib, encorafenib (LGX818), and PLX8394;
sphingosine kinase-2 (SK2) inhibitors, such as Yeliva® (ABC294640);
cell cycle inhibitors, such as selumetinib (MEK1/2), and sapacitabine;
cell cycle/Microtubule inhibitors, such as eribulin mesylate;
AKT inhibitors such as MK-2206, ipatasertib, afuresertib, AZD5363, ARQ-092, capivasertib, and triciribine;
c-MET inhibitors, such as AMG-337, savolitinib, tivantinib (ARQ-197), capmatinib, and tepotinib, ABT-700, AG213, AMG-208, JNJ-38877618 (OMO-1), merestinib, and HQP-8361;
c-Met/VEGFR inhibitors, such as BMS-817378, and TAS-115;
c-Met/RON inhibitors, such as BMS-777607;
BRAF/EGFR inhibitors, such as BGB-283;
BCR/ABL inhibitors, such as rebastinib, asciminib, and ponatinib (ICLUSIG®);
MNK1/MNK2 inhibitors, such as eFT-508;
cytochrome P450 11B2/Cytochrome P450 17/AKT protein kinase inhibitors, such as LAE-201;
mTOR inhibitor/cytochrome P450 3A4 stimulators, such as TYME-88;
cytochrome P450 3A4 stimulators, such as mitotane;
lysine-specific demethylase-1 (LSD1) inhibitors, such as CC-90011;
pan-RAF inhibitors, such as LY3009120, LXH254, and TAK-580;
Raf/MEK inhibitors, such as RG7304;

CSF1R/KIT and FLT3 inhibitors, such as pexidartinib (PLX3397);

Flt3 tyrosine kinase/Kit tyrosine kinase inhibitor and PDGF receptor antagonists, such as quizartinib dihydrochloride;

kinase inhibitors, such as vandetanib;

E selectin antagonists, such as GMI-1271;

differentiation inducers, such as tretinoin;

epidermal growth factor receptor (EGFR) inhibitors, such as osimertinib (AZD-9291), cetuximab;

topoisomerase inhibitors, such as Adriamycin, doxorubicin, daunorubicin, dactinomycin, DaunoXome, Caelyx, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), and irofulven (MGI-114);

corticosteroids, such as cortisone, dexamethasone, hydrocortisone, methylprednisolone, prednisone, and prednisolone;

growth factor signal transduction kinase inhibitors;

nucleoside analogs, such as DFP-10917;

Axl inhibitors, such as BGB-324 (bemcentinib), and SLC-0211;

Inhibitors of bromodomain and extraterminal motif (BET) proteins, including ABBV-744, BRD2 (NCBI Gene ID: 6046), BRD3 (NCBI Gene ID: 8019), BRD4 (NCBI Gene ID: 23476), and bromodomain testis-specific protein (BRDT; NCBI Gene ID: 676), such as INCB-054329, INCB057643, TEN-010, AZD-5153, ABT-767, BMS-986158, CC-90010, GSK525762 (molibresib), NHWD-870, ODM-207, GSK-2820151, GSK-1210151A, ZBC246, ZBC260, ZEN3694, FT-1101, RG-6146, CC-90010, CC-95775, mivebresib, BI-894999, PLX-2853, PLX-51107, CPI-0610, and GS-5829;

PARP inhibitors, such as olaparib (MK7339), rucaparib, veliparib, talazoparib, ABT-767, BGB-290, fluzolepali (SHR-3162), niraparib (JNJ-64091742), and bendamustine hydrochloride;

PARP/Tankyrase inhibitors such as 2X-121 (e-7499);

IMP-4297, SC-10914, IDX-1197, HWH-340, CK-102, and simmiparib;

proteasome inhibitors, such as ixazomib (NINLARO®); carfilzomib (Kyprolis®), marizomib; and bortezomib;

glutaminase inhibitors, such as CB-839 (telaglenastat), and bis-2-(5-phenylacetamido-1,3,4-thiadiazol-2-yl) ethyl sulfide (BPTES);

mitochondrial complex I inhibitors, such as metformin, and phenformin;

vaccines, such as peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU-131, peptide subunit vaccine (acute lymphoblastic leukemia, University Children's Hospital Tuebingen); bacterial vector vaccines such as CRS-207/GVAX, axalimogene filolisbac (ADXS11-001); adenovirus vector vaccines such as nadofaragene firadenovec; autologous Gp96 vaccine; dendritic cells vaccines, such as CVactm, tapuldencel-T, eltrapuldencel-T, SL-701, BSK01TM, rocapuldencel-T (AGS-003), DCVAC, CVactm, stapuldencel-T, eltrapuldencel-T, SL-701, BSK01TM, ADXS31-142, autologous dendritic cell vaccine (metastatic malignant melanoma, intradermal/intravenous, Universitatsklinikum Erlangen); oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, CreaVax-BC, PF-06753512, VBI-1901, TG-4010, ProscaVax™; tumor cell vaccines, such as Vigil® (IND-14205), Oncoquest-L vaccine; live attenuated, recombinant, serotype 1 poliovirus vaccine, such as PVS-RIPO; Adagloxad simolenin; MEDI-0457; DPV-001 a tumor-derived, autophagosome enriched cancer vaccine; RNA vaccines such as, CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; GI-4000; 10-103; Neoantigen peptide vaccines, such as AGEN-2017, GEN-010, NeoVax, RG-6180, GEN-009, PGV-001 (TLR-3 agonist), GRANITE-001, NEO-PV-01; Peptide vaccines that target heat shock proteins, such as PhosphoSynVax™; and Vitespen (HSPPC-96-C), NANT Colorectal Cancer Vaccine containing aldoxorubicin, autologous tumor cell vaccine+systemic CpG-B+IFN-alpha (cancer);

anti-DLL4 (delta like ligand 4) antibodies, such as demcizumab;

STAT-3 inhibitors, such as napabucasin (BBI-608);

ATPase p97 inhibitors, such as CB-5083;

smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole;

interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus)(Inmutag, Inter 2A), interferon alfa-2b follow-on biologic (Biosidus—Bioferon, Citopheron, Ganapar, Beijing Kawin Technology—Kaferon), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-ni (Humoferon, SM-10500, Sumiferon);

interferon gamma ligand modulators, such as interferon gamma (OH-6000, Ogamma 100);

IL-6 receptor modulators, such as tocilizumab, and AS-101 (CB-06-02, IVX-Q-101);

heat shock protein inhibitors/IL-6 receptor antagonists, such as siltuximab;

telomerase modulators, such as, tertomotide (GV-1001, HR-2802, Riavax) and imetelstat (GRN-163, JNJ-63935937);

DNA methyltransferases inhibitors, such as temozolomide (CCRG-81045), decitabine, guadecitabine (S-110, SGI-110), KRX-0402, RX-3117, RRx-001, and azacytidine (CC-486);

DNA gyrase inhibitors, such as pixantrone and sobuzoxane;

DNA gyrase inhibitors/Topoisimerase II inhibitors, such as amrubicin;

Bcl-2 family protein inhibitors, such as ABT-263, venetoclax (ABT-199), ABT-737, RG7601, and AT-101;

Bcl-2/Bcl-XL inhibitors, such as novitoclax;

notch inhibitors, such as LY3039478 (crenigacestat), tarextumab (anti-Notch2/3), and BMS-906024;
anti-myostatin inhibitors, such as landogrozumab;
hyaluronidase stimulators, such as PEGPH-20;
Erbb2 tyrosine kinase receptor inhibitors/Hyaluronidase stimulators, such as Herceptin Hylecta;
Wnt pathway inhibitors, such as SM-04755, PRI-724, and WNT-974;
gamma-secretase inhibitors, such as PF-03084014, MK-0752, and RO-4929097;
Grb-2 (growth factor receptor bound protein-2) inhibitors, such as BP1001;
TRAIL pathway-inducing compounds, such as ONC201, and ABBV-621;
focal adhesion kinase inhibitors, such as VS-4718, defactinib, and GSK2256098;
hedgehog inhibitors, such as saridegib, sonidegib (LDE225), and glasdegib;
aurora kinase inhibitors, such as alisertib (MLN-8237), and AZD-2811, AMG-900, barasertib, and ENMD-2076;
HSPB1 modulators (heat shock protein 27, HSP27), such as brivudine, and apatorsen;
ATR inhibitors, such as BAY-937, AZD6738, AZD6783, VX-803, VX-970 (berzosertib) and VX-970;
mTOR inhibitors, such as sapanisertib and vistusertib (AZD2014), ME-344, and sirolimus (oral nano-amorphous formulation, cancer);
mTOR/PI3K inhibitors, such as gedatolisib, GSK2141795, omipalisib, and RG6114;
Hsp90 inhibitors, such as AUY922, onalespib (AT13387), SNX-2112, and SNX5422;
murine double minute (mdm2) oncogene inhibitors, such as DS-3032b, RG7775, AMG-232, HDM201, and idasanutlin (RG7388);
CD137 agonists, such as urelumab, utomilumab (PF-05082566), AGEN2373, and ADG-106;
STING agonists, such as ADU-S100 (MIW-815), SB-11285, MK-1454, SR-8291, AdVCA0848, GSK-532, SYN-STING, MSA-1, SR-8291, and GSK3745417;
FGFR inhibitors, such as FGF-401, INCB-054828, BAY-1163877, AZD4547, JNJ-42756493, LY2874455, Debio-1347;
fatty acid synthase (FASN) inhibitors, such as TVB-2640;
antigen CD19 inhibitors, such as MOR208, MEDI-551, AFM-11, inebilizumab;
CD44 binders, such as A6;
protein phosphateese 2A (PP2A) inhibitors, such as LB-100;
CYP17 inhibitors, such as seviteronel (VT-464), ASN-001, ODM-204, CFG920, abiraterone acetate;
RXR agonists, such as IRX4204;
hedgehog/smoothened (hh/Smo) antagonists, such as taladegib, patidegib, vismodegib;
complement $C_3$ modulators, such as Imprime PGG;
IL-15 agonists, such as ALT-803, NKTR-255, and hetIL-15;
EZH2 (enhancer of zeste homolog 2) inhibitors, such as tazemetostat, CPI-1205, GSK-2816126, and PF-06821497;
Oncolytic viruses, such as pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, OBP-301, and IMLYGIC®;

DOT1 L (histone methyltransferase) inhibitors, such as pinometostat (EPZ-5676);
toxins such as Cholera toxin, ricin, *Pseudomonas* exotoxin, *Bordetella pertussis* adenylate cyclase toxin, diphtheria toxin, and caspase activators;
DNA plasmids, such as BC-819;
PLK inhibitors of PLK 1, 2, and 3, such as volasertib (PLK1);
WEE1 inhibitors, such as AZD-1775 (adavosertib); Rho kinase (ROCK) inhibitors, such as AT13148, and KD025;
ERK inhibitors, such as GDC-0994, LY3214996, and MK-8353;
apoptosis Protein (IAP) inhibitors, such as ASTX660, debio-1143, birinapant, APG-1387, and LCL-161;
RNA polymerase inhibitors, such has lurbinectedin (PM-1183), and CX-5461;
tubulin inhibitors, such as PM-184, BAL-101553 (lisavanbulin), and OXI-4503, fluorapacin (AC-0001), plinabulin, and vinflunine;
toll-like receptor 4 (TL4) agonists, such as G100, GSK1795091, and PEPA-10;
elongation factor 1 alpha 2 inhibitors, such as plitidepsin;
elongation factor 2 inhibitors/Interleukin-2 ligands/NAD ADP ribosyltransferase stimulators, such as denileukin diftitox;
CD95 inhibitors, such as APG-101, APO-010, asunercept;
WT1 inhibitors, such as DSP-7888;
splicing factor 3B subunit1 (SF3B1) inhibitors, such as H3B-8800;
retinoid Z receptor gamma (RORγ) agonists, such as LYC-55716; and
microbiome modulators, such as SER-401, EDP-1503, and MRx-0518.

In some embodiments, a compound as described herein, is co-administered with one or more additional therapeutic agents comprising an inhibitor or antagonist of: protein tyrosine phosphatase, non-receptor type 11 (PTPN11 or SHP2; NCBI Gene ID: 5781); myeloid cell leukemia sequence 1 (MCL1) apoptosis regulator (NCBI Gene ID: 4170); mitogen-activated protein kinase kinase kinase kinase 1 (MAP4K1) (also called Hematopoietic Progenitor Kinase 1 (HPK1), NCBI Gene ID: 11184); diacylglycerol kinase alpha (DGKA, DAGK, DAGK1 or DGK-alpha; NCBI Gene ID: 1606); 5'-nucleotidase ecto (NT5E or CD73; NCBI Gene ID: 4907); ectonucleoside triphosphate diphosphohydrolase 1 (ENTPD1 or CD39; NCBI Gene ID: 593); transforming growth factor beta 1 (TGFB1 or TGFβ; NCBI Gene ID: 7040); heme oxygenase 1 (HMOX1, HO-1 or HO1; NCBI Gene ID: 3162); heme oxygenase 2 (HMOX2, HO-2 or H02; NCBI Gene ID: 3163); vascular endothelial growth factor A (VEGFA or VEGF; NCBI Gene ID: 7422); erb-b2 receptor tyrosine kinase 2 (ERBB2, HER2, HER2/neu or CD340; NCBI Gene ID: 2064), epidermal growth factor receptor (EGFR, ERBB, ERBB1 or HER1; NCBI Gene ID: 1956); ALK receptor tyrosine kinase (ALK, CD246; NCBI Gene ID: 238); poly(ADP-ribose) polymerase 1 (PARP1; NCBI Gene ID: 142); poly(ADP-ribose) polymerase 2 (PARP2; NCBI Gene ID: 10038); TCDD inducible poly(ADP-ribose) polymerase (TIPARP, PARP7; NCBI Gene ID: 25976); cyclin dependent kinase 4 (CDK4; NCBI Gene ID: 1019); cyclin dependent kinase 6 (CDK6; NCBI Gene ID: 1021); TNF receptor superfamily member 14 (TNFRSF14, HVEM, CD270; NCBI Gene ID: 8764); T cell immunoreceptor with Ig and ITIM domains (TIGIT; NCBI Gene ID: 201633); X-linked inhibitor of apoptosis (XIAP, BIRC4, IAP-3; NCBI Gene ID: 331); baculoviral IAP repeat containing 2 (BIRC2, cIAP1; NCBI Gene ID: 329); baculoviral IAP repeat containing 3 (BIRC3, cIAP2; NCBI Gene ID: 330); baculoviral IAP repeat containing 5 (BIRC5, surviving; NCBI Gene ID: 332); C-C motif chemokine receptor 2 (CCR2, CD192; NCBI Gene ID: 729230); C-C motif chemokine receptor 5 (CCR5, CD195; NCBI Gene ID: 1234); C-C motif chemokine receptor 8 (CCR8, CDw198; NCBI Gene ID: 1237); C-X-C motif chemokine receptor 2 (CXCR2, CD182; NCBI Gene ID: 3579); C-X-C motif chemokine receptor 3 (CXCR3, CD182, CD183; NCBI Gene ID: 2833); C-X-C motif chemokine receptor 4 (CXCR4, CD184; NCBI Gene ID: 7852); arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CASA (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240) and/or soluble epoxide hydrolase 2 (EPHX2, SEH; NCBI Gene ID: 2053); a secreted phospholipase A2 (e.g., PLA2G1B (NCBI Gene ID: 5319); PLA2G7 (NCBI Gene ID: 7941), PLA2G3 (NCBI Gene ID: 50487), PLA2G2A (NCBI Gene ID: 5320); PLA2G4A (NCBI Gene ID: 5321); PLA2G12A (NCBI Gene ID: 81579); PLA2G12B (NCBI Gene ID: 84647); PLA2G10 (NCBI Gene ID: 8399); PLA2G5 (NCBI Gene ID: 5322); PLA2G2D (NCBI Gene ID: 26279); PLA2G15 (NCBI Gene ID: 23659)); indoleamine 2,3-dioxygenase 1 (IDO1; NCBI Gene ID: 3620); indoleamine 2,3-dioxygenase 2 (IDO2; NCBI Gene ID: 169355); hypoxia inducible factor 1 subunit alpha (HIF1A; NCBI Gene ID: 3091); angiopoietin 1 (ANGPT1; NCBI Gene ID: 284); Endothelial TEK tyrosine kinase (TIE-2, TEK, CD202B; NCBI Gene ID: 7010); Janus kinase 1 (JAK1; NCBI Gene ID: 3716); catenin beta 1 (CTNNB1; NCBI Gene ID: 1499); histone deacetylase 9 (HDAC9; NCBI Gene ID: 9734) and/or 5'-3' exoribonuclease 1 (XRN1; NCBI Gene ID: 54464).

Immune Checkpoint Modulators

In various embodiments, a compound as described herein, is combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of cancer cells within the tumor microenvironment. Activation or stimulation of stimulatory immune check points can augment the effect of immune checkpoint inhibitors in cancer therapeutics. In various embodiments, the immune checkpoint proteins or receptors regulate T cell responses (e.g., reviewed in Xu, et al., *J Exp Clin Cancer Res*. (2018) 37:110). In various embodiments, the immune checkpoint proteins or receptors regulate NK cell responses (e.g., reviewed in Davis, et al., *Semin Immunol*. (2017) 31:64-75 and Chiossone, et al., *Nat Rev Immunol*. (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1 E (RAET1 E; ULBP4); retinoic acid early transcript 1G (RAET1G; ULBP5); retinoic acid early transcript 1 L (RAET1 L; ULBP6); lymphocyte activating 3 (CD223); killer cell immunoglobulin like receptor(KIR); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); and killer cell lectin like receptor D1 (KLRD1).

In various embodiments, a compound as described herein, is combined with one or more blockers or inhibitors of one or more T-cell inhibitory immune checkpoint proteins or receptors. Illustrative T-cell inhibitory immune checkpoint proteins or receptors include without limitation CD274 (PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSFi4 (HVEML); CD272

(B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor(KIR); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, a compound as described herein, is combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4); and poliovirus receptor (PVR) cell adhesion molecule (PVR, CD155). See, e.g., Xu, et al., *J Exp Clin Cancer Res.* (2018) 37:110.

In various embodiments, a compound as described herein, is combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In various embodiments, a compound as described herein, is combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); and SLAM family member 7 (SLAMF7). See, e.g., Davis, et al., *Semin Immunol.* (2017) 31:64-75; Fang, et al., *Semin Immunol.* (2017) 31:37-54; and Chiossone, et al., *Nat Rev Immunol.* (2018) 18(11):671-688.

In various embodiments, a compound as described herein, is combined with an inhibitor of CD47 (IAP, MER6, OA3; NCBI Gene ID: 961). Examples of CD47 inhibitors include without limitation to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

anti-CTLA-4 (cytotoxic T-lymphocyte protein-4) antibodies, such as tremelimumab, ipilimumab (BMS-734016), AGEN-1884, BMS-986218, AGEN1181, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, and BA-3071;

CTLA-4 (cytotoxic T-lymphocyte protein-4) inhibitors, such as BPI-002; TLR-3 agonist/interferon inducers, such as Poly-ICLC (NSC-301463);

Examples of inhibitors/antibodies of PD-L1 (CD274) or PD-1 (PDCD1) that can be co-administered include without limitation pembrolizumab, nivolumab, cemiplimab, pidilizumab, AMG-404, AMP-224, MEDI0680 (AMP-514), spartalizumab, atezolizumab, avelumab, durvalumab, BMS-936559, CK-301, PF-06801591, BGB-A317 (tislelizumab), GEN-1046 (PD-L1/4-1BB), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), RG7769 (PD-1/TIM3) and INBRX-105 (4-1BB/PDL1), RG-7446 (Tecentriq, atezolizumab), ABBV-181, nivolumab (OPDIVO®, BMS-936558, MDX-1106), pembrolizumab (KEYTRUDA®, MK-3477, SCH-900475, lambrolizumab, CAS Reg. No. 1374853-91-4), pidilizumab, PF-06801591, BGB-A317 (tislelizumab), GLS-010 (WBP-3055), AK-103 (HX-008), CS-1003, HLX-10, MGA-012, BI-754091, REGN-2810 (cemiplimab), AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, AK-105, PD1-PIK, BAT-1306, and anti-programmed death-ligand 1 (anti-PD-L1) antibodies such as BMS-936559, atezolizumab (MPDL3280A), durvalumab (MEDI-4736), avelumab, CK-301 (MSB0010718C), MEDI-0680, CX-072, CBT-502, PDR-001 (spartalizumab), PDR001+Tafinlar®+Mekinist®, MSB-2311, JTX-4014, BGB-A333, SHR-1316, CS-1001 (WBP-3155), KN-035, IBI-308 (sintilimab), HLX-20, KL-A167, STI-A1014, STI-A1015 (IMC-001), BCD-135, FAZ-053, TQB-2450, and MDX1105-01;

PD-L1/VISTA antagonists such as CA-170;

PD-1/PD-L1 inhibitors, such as INCB086550, GS-4224, and GS-4416;

PD-L1/EGFR inhibitors, such as GNS-1480 (lazertinib);

PD-1/CTLA-4 inhibitors, such as PF-06936308;

PD-L1/PD-L2 vaccines, such as 10-120+IO-103;

anti-PVRIG antibodies, such as COM-701;

anti-TIGIT antibodies, such as BMS-986207, RG-6058, and AGEN-1307;

anti-TIM-3 antibodies, such as TSR-022, LY-3321367, MBG-453; and INCAGN-2390;

anti LAG-3 (Lymphocyte-activation) antibodies, such as relatlimab (ONO-4482), LAG-525, MK-4280, REGN-3767, INCAGN2385, and TSR-033;

anti-killer cell immunoglobulin like receptor, three Ig domains and long cytoplasmic tail 1 (KIR3DL1; KIR; NCBI Gene ID: 3811) monoclonal antibodies, such as lirilumab (IPH-2102), and IPH-4102;

anti-NKG2a antibodies, such as monalizumab;

anti-VISTA antibodies, such as HMBD-002;

anti-CD27 antibodies, such as varlilumab (CDX-1127);

anti-CD70 antibodies, such as AMG-172;

anti-CD20 antibodies, such as obinutuzumab, IGN-002, PF-05280586;

anti-ICOS antibodies, such as JTX-2011, GSK3359609; and

ICOS agonists, such as ICOS-L. COMP (Gariepy, J. et al. 106th Annu Meet Am Assoc Immunologists (AAI) (May 9-13, San Diego) 2019, Abst 71.5).

TNF Receptor Superfamily (TNFRSF) Member Agonists or Activators

In various embodiments, a compound as described herein, is combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MED16469, MED16383, MED10562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be co-administered include without limitation RG7876, SEA-CD40, APX-005M and ABBV-428, and ABBV-927.

In some embodiments, the anti-TNFRSF7 (CD27) antibody varlilumab (CDX-1127) is co-administered.

Example anti-TNFRSF9 (4-1BB, CD137) antibodies that can be co-administered include without limitation urelumab, utomilumab (PF-05082566), AGEN2373 and ADG-106.

In some embodiments, the anti-TNFRSF17 (BCMA) antibody GSK-2857916 is co-administered.

Example anti-TNFRSF18 (GITR) antibodies that can be co-administered include without limitation, MED11873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Example anti-TRAILR1, anti-TRAILR2, anti-TRAILR3, anti-TRAILR4 antibodies that can be co-administered include without limitation ABBV-621.

Bi-specific antibodies targeting TNFRSF family members that can be co-administered include without limitation PRS-343 (CD-137/HER2), AFM26 (BCMA/CD16A), AFM-13 (CD16/CD30), REGN-1979 (CD20/CD3), AMG-420 (BCMA/CD3), INHIBRX-105 (4-1BB/PDL1), FAP-4-IBBL (4-1BB/FAP), XmAb-13676 (CD3/CD20), RG-7828 (CD20/CD3), CC-93269 (CD3/BCMA), REGN-5458 (CD3/BCMA), and IMM-0306 (CD47/CD20), and AMG-424 (CD38.CD3).

Adenosine Generation and Signalling

Adenosin receptor signaling includes A1R, A2AR, A2BR, A3R, CD73, CD39, and CD26.

Anti-CD73 antibodies include such as MEDI-9447 (oleclumab), CPX-006, IPH-53, BMS-986179, and NZV-930.

CD73 inhibitors include AB-680, PSB-12379, PSB-12441, PSB-12425, and CB-708.

CD39/CD73 inhibitors include PBF-1662.

Anti-CD39 antibodies include TTX-030.

Adenosine A2A receptor antagonists include CPI-444, AZD-4635, preladenant, and PBF-509.

Adenosine deaminase inhibitors include pentostatin, and cladribine.

Bi-Specific T-Cell Engagers

In various embodiments, a compound as described herein, is combined with a bi-specific T-cell engager (e.g., not having an Fc) or an anti-CD3 bi-specific antibody (e.g., having an Fc). Illustrative anti-CD3 bi-specific antibodies or BiTEs that can be co-administered include AMG-160 (PSMA/CD3), AMG-212 (PSMA/CD3), AMG-330 (CD33/CD3), AMG-420 (BCMA/CD3), AMG-427 (FLT3/CD3), AMG-562 (CD19/CD3), AMG-596 (EGFRvIII/CD3), AMG-673 (CD33/CD3), AMG-701 (BCMA/CD3), AMG-757 (DLL3/CD3), JNJ-64052781 (CD19/CD3), AMG-211 (CEA/CD3), BLINCYTO® (CD19/CD3), RG7802 (CEA/CD3), ERY-974 (CD3/GPC3), huGD2-BsAb (CD3/GD2), PF-06671008 (Cadherins/CD3), APV0436 (CD123/CD3), ERY974, flotetuzumab (CD123/CD3), GEM333 (CD3/CD33), GEMoab (CD3/PSCA), REGN-1979 (CD20/CD3), REGN-5678 (PSMA/CD28), MCLA-117 (CD3/CLEC12A), JNJ-0819, JNJ-7564 (CD3/heme), JNJ-63709178 (CD123/CD3), MGD-007 (CD3/gpA33), MGD-009 (CD3/B7H3), IMCgp100 (CD3/gp100), XmAb-14045 (CD123/CD3), XmAb-13676 (CD3/CD20), XmAb-18087

(SSTR2/CD3), catumaxomab (CD3/EpCAM), REGN-4018 (MUC16/CD3), RG6026, RG6076, RG6194, RG-7828 (CD20/CD3), CC-93269 (CD3/BCMA), REGN-5458 (CD3/BCMA), GRB-1302 (CD3/Erbb2), GRB-1342 (CD38/CD3), GEM-333 (CD3/CD33), PF-06863135 (BCMA/CD3), SAR440234 (CD3/CDw123). As appropriate, the anti-CD3 binding bi-specific molecules may or may not have an Fc. Illustrative bi-specific T-cell engagers that can be co-administered target CD3 and a tumor-associated antigen as described herein, including, e.g., CD19 (e.g., blinatumomab); CD33 (e.g., AMG330); CEA (e.g., MEDI-565); receptor tyrosine kinase-like orphan receptor 1 (ROR1) (Gohil, et al., *Oncoimmunology*. (2017) May 17; 6(7):e1326437); PD-L1 (Horn, et al., *Oncotarget*. 2017 Aug. 3; 8(35):57964-57980); and EGFRvIII (Yang, et al., *Cancer Lett*. 2017 Sep. 10; 403:224-230).

Bi- and Tri-Specific Natural Killer (NK)-Cell Engagers

In various embodiments, a compound as described herein, is combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. Illustrative bi-specific NK-cell engagers that can be co-administered target CD16 and one or more tumor-associated antigens as described herein, including, e.g., CD19, CD20, CD22, CD30, CD33, CD123, EGFR, EpCAM, ganglioside GD2, HER2/neu, HLA Class II and FOLR1. BiKEs and TriKEs are described, e.g., in Felices, et al., *Methods Mol Biol*. (2016) 1441:333-346; Fang, et al., *Semin Immunol*. (2017) 31:37-54.

MCL1 Apoptosis Regulator, BCL2 Family Member (MCL1) Inhibitors

In various embodiments, a compound as described herein, is combined with an inhibitor of MCL1 apoptosis regulator, BCL2 family member (MCL1, TM; EAT; MCL1 L; MCL1 S; MCL1; BCL2L3; MCL1-ES; bcl2-L-3; MCL1/EAT; NCBI Gene ID: 4170). Examples of MCL1 inhibitors include AMG-176, AMG-397, S-64315, and AZD-5991, 483-LM, A-1210477, UMI-77, JKY-5-037, and those described in WO2018183418, WO2016033486, and WO2017147410.

SHP2 Inhibitors

In various embodiments, a compound as described herein, is combined with an inhibitor of protein tyrosine phosphatase non-receptor type 11 (PTPN11; BPTP3, CFC, JMML, METCDS, NS1, PTP-1D, PTP2C, SH-PTP2, SH-PTP3, SHP2; NCBI Gene ID: 5781). Examples of SHP2 inhibitors include TNO155 (SHP-099), RMC-4550, JAB-3068, RMC-4630, SAR442720, and those described in WO2018172984 and WO2017211303.

Hematopoietic Progenitor Kinase 1 (HPK1) Inhibitors

In various embodiments, a compound as described herein, is combined with an inhibitor of mitogen-activated protein kinase kinase kinase kinase 1 (MAP4K1, HPK1; NCBI Gene ID: 11184). Examples of Hematopoietic Progenitor Kinase 1 (HPK1) inhibitors include without limitation, those described in WO-2018183956, WO-2018183964, WO-2018167147, WO-2018183964, WO-2016205942, WO-2018049214, WO-2018049200, WO-2018049191, WO-2018102366, WO-2018049152 and WO-2016090300.

Apoptosis Signal-Regulating Kinase (ASK) Inhibitors

In various embodiments, a compound as described herein, is combined with an inhibitor of an ASK inhibitor, e.g., mitogen-activated protein kinase kinase kinase 5 (MAP3K5; ASK1, MAPKKK5, MEKK5; NCBI Gene ID: 4217). Examples of ASK1 inhibitors include without limitation, those described in WO 2011/008709 (Gilead Sciences) and WO 2013/112741 (Gilead Sciences).

Bruton Tyrosine Kinase (BTK) Inhibitors

In various embodiments, a compound as described herein, is combined with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include without limitation, (S)-6-amino-9-(1-(but-2-ynoyl) pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, Calquence+AZD6738, Calquence+danvatirsen.

Cyclin-Dependent Kinase (CDK) Inhibitors

In various embodiments, a compound as described herein, is combined with an inhibitor of cyclin dependent kinase 1 (CDK1, CDC2; CDC28A; P34CDC2; NCBI Gene ID: 983); cyclin dependent kinase 2 (CDK2, CDKN2; p33(CDK2); NCBI Gene ID: 1017); cyclin dependent kinase 3 (CDK3; NCBI Gene ID: 1018); cyclin dependent kinase 4 (CDK4, CMM3; PSK-J3; NCBI Gene ID: 1019); cyclin dependent kinase 6 (CDK6, MCPH12; PLSTIRE; NCBI Gene ID: 1021); cyclin dependent kinase 7 (CDK7, CAK; CAK1; HCAK; MO15; STK1; CDKN7; p39MO15; NCBI Gene ID: 1022); cyclin dependent kinase 9 (CDK9, TAK; C-2k; CTK1; CDC2L4; PITALRE; NCBI Gene ID: 1025). Inhibitors of CDK 1, 2, 3, 4, 6, 7 and/or 9, include without limitation abemaciclib, alvocidib (HMR-1275, flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, trilaciclib, PF-06873600, AZD4573, and TG-02.

Discoidin Domain Receptor (DDR) Inhibitors

In various embodiments, a compound as described herein, is combined with an inhibitor of discoidin domain receptor tyrosine kinase 1 (DDR1, CAK, CD167, DDR, EDDR1, HGK2, MCK10, NEP, NTRK4, PTK3, PTK3A, RTK6, TRKE; NCBI Gene ID: 780); and/or discoidin domain receptor tyrosine kinase 2 (DDR2, MIG20a, NTRKR3, TKT, TYRO10, WRCN; NCBI Gene ID: 4921). Examples of DDR inhibitors include without limitation, dasatinib and those disclosed in WO2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO2013/034933 (Imperial Innovations).

Histone Deacetylase (HDAC) Inhibitors

In various embodiments, a compound as described herein, is combined with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, entinostat, romidepsin, and tucidinostat.

Indoleamine-pyrrole-2,3-dioxyqenase (IDO1) inhibitors

In various embodiments, a compound as described herein, is combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

Janus Kinase (JAK) Inhibitors

In various embodiments, a compound as described herein, is combined with an inhibitor of Janus kinase 1 (JAK1, JAK1A, JAK1B, JTK3; NCBI Gene ID: 3716); Janus kinase 2 (JAK2, JTK10, THCYT3; NCBI Gene ID: 3717); and/or Janus kinase 3 (JAK3, JAK-3, JAK3_HUMAN, JAKL, L-JAK, LJAK; NCBI Gene ID: 3718). Examples of JAK inhibitors include without limitation, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB1518), peficitinib (ASP015K), ruxolitinib, tofacitinib (formerly tasocitinib), INCB052793, and XL019.

Matrix Metalloprotease (MMP) Inhibitors

In various embodiments, a compound as described herein, is combined with an inhibitor of a matrix metallopeptidase (MMP), e.g., an inhibitor of MMP1 (NCBI Gene ID: 4312), MMP2 (NCBI Gene ID: 4313), MMP3 (NCBI Gene ID: 4314), MMP7 (NCBI Gene ID: 4316), MMP8 (NCBI Gene ID: 4317), MMP9 (NCBI Gene ID: 4318); MMP10 (NCBI Gene ID: 4319); MMP11 (NCBI Gene ID: 4320); MMP12 (NCBI Gene ID: 4321), MMP13 (NCBI Gene ID: 4322), MMP14 (NCBI Gene ID: 4323), MMP15 (NCBI Gene ID: 4324), MMP16 (NCBI Gene ID: 4325), MMP17 (NCBI Gene ID: 4326), MMP19 (NCBI Gene ID: 4327), MMP20 (NCBI Gene ID: 9313), MMP21 (NCBI Gene ID: 118856), MMP24 (NCBI Gene ID: 10893), MMP25 (NCBI Gene ID: 64386), MMP26 (NCBI Gene ID: 56547), MMP27 (NCBI Gene ID: 64066) and/or MMP28 (NCBI Gene ID: 79148). Examples of MMP9 inhibitors include without limitation, marimastat (BB-2516), cipemastat (Ro 32-3555), GS-5745 (andecaliximab), and those described in WO 2012/027721 (Gilead Biologics).

RAS and RAS Pathway Inhibitors

In various embodiments, a compound as described herein, is combined with an inhibitor of KRAS proto-oncogene, GTPase (KRAS; a.k.a., NS; NS3; CFC2; RALD; K-Ras; KRAS1; KRAS2; RASK2; KI-RAS; C-K-RAS; K-RAS2A; K-RAS2B; K-RAS4A; K-RAS4B; c-Ki-ras2; NCBI Gene ID: 3845); NRAS proto-oncogene, GTPase (NRAS; a.k.a., NS6; CMNS; NCMS; ALPS4; N-ras; NRAS1; NCBI Gene ID: 4893); HRas proto-oncogene, GTPase (HRAS; a.k.a., CTLO; KRAS; HAMSV; HRAS1; KRAS2; RASH1; RASK2; Ki-Ras; p21 ras; C-H-RAS; c-K-ras; H-RASIDX; c-Ki-ras; C-BAS/HAS; C-HA-RAS1; NCBI Gene ID: 3265). The Ras inhibitors can inhibit Ras at either the polynucleotide (e.g., transcriptional inhibitor) or polypeptide (e.g., GTPase enzyme inhibitor) level. In some embodiments, the inhibitors target one or more proteins in the Ras pathway, e.g., inhibit one or more of EGFR, Ras, Raf (A-Raf, B-Raf, C-Raf), MEK (MEK1, MEK2), ERK, PI3K, AKT and mTOR. Illustrative K-Ras inhibitors that can be co-administered include ARS-1620 (G12C), SML-8-73-1 (G12C), Compound 3144 (G12D), Kobe0065/2602 (Ras GTP), RT11, MRTX-849 (G2C) and K-Ras(G12D)-selective inhibitory peptides, including KRpep-2 (Ac-RRCPLYI-SYDPVCRR-NH$_2$) (SEQ ID NO:108) and KRpep-2d (Ac-RRRRCPLYISYDPVCRRRR-NH$_2$) (SEQ ID NO:109). Illustrative KRAS mRNA inhibitors include anti-KRAS U1 adaptor, AZD-4785, siG12D-LODER™, and siG12D exosomes. Illustrative MEK inhibitors that can be co-administered include binimetinib, cobimetinib, PD-0325901, pimasertib, RG-7304, selumetinib, trametinib, and those described below and herein. Illustrative AKT inhibitors that can be co-administered include RG7440. Illustrative Raf dimer inhibitors that can be co-administered BGB-283, HM-95573, LXH-254, LY-3009120, RG7304 and TAK-580. Illustrative ERK inhibitors that can be co-administered include LTT-462, LY-3214996, MK-8353, ravoxertinib and ulixertinib. Illustrative Ras GTPase inhibitors that can be co-administered include rigosertib. Illustrative PI3K inhibitors that can be co-administered include idelalisib (Zydelig®), alpelisib, buparlisib, pictilisib, and those described below and herein. Illustrative PI3K/mTOR inhibitors that can be co-administered include dactolisib, omipalisib and voxtalisib. In certain embodiments, Ras-driven cancers (e.g., NSCLC) having CDKN2A mutations can be inhibited by co-administration of the MEK inhibitor selumetinib and the CDK4/6 inhibitor palbociclib. See, e.g., Zhou, et al., Cancer Lett. 2017 Nov. 1; 408:130-137. Also, K-RAS and mutant N-RAS can be reduced by the irreversible ERBB1/2/4 inhibitor neratinib. See, e.g., Booth, et al., Cancer Biol Ther. 2018 Feb. 1; 19(2):132-137.

K-Ras GTPase inhibitors: Examples of KRAS inhibitors include AMG-510, MRTX-849, COTI-219, MRTX-1257, ARS-3248, ARS-853, and WDB-178.

Mitogen-Activated Protein Kinase (MEK) Inhibitors

In various embodiments, a compound as described herein, is combined with an inhibitor of mitogen-activated protein kinase kinase 7 (MAP2K7, JNKK2, MAPKK7, MEK, MEK 7, MKK7, PRKMK7, SAPKK-4, SAPKK; NCBI Gene ID: 5609). Examples of MEK inhibitors include antroquinonol, binimetinib, CK-127, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, refametinib, TAK-733, $C_{1-1040}$, and RG7421.

Phosphatidylinositol 3-kinase (PI3K) Inhibitors

In various embodiments, a compound as described herein, is combined with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C$_1$; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/or phosphatidylinositol-4,5-bisphosphate 3-kinase catalytic subunit delta (PIK3CD, APDS, IMD14, P110DELTA, PI3K, p110D, NCBI Gene ID: 5293). In some embodiments, the PI3K inhibitor is a pan-PI3K inhibitor. Examples of PI3K inhibitors include without limitation, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Spleen Tyrosine Kinase (SYK) Inhibitors

In various embodiments, a compound as described herein, is combined with an inhibitor of spleen associated tyrosine kinase (SYK, p72-Syk, Gene ID: 6850). Examples of SYK inhibitors include without limitation, 6-(1H-indazol-6-yl)-N-(4-morpholinophenyl)imidaz[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Connecticut) and those described in U.S. 2015/0175616.

Toll-Like Receptor (TLR) Agonists

In various embodiments, a compound as described herein, is combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation DS-0509, GS-9620, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262. Example TLR8 agonists that can be co-administered include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include without limitation AST-008, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, leftolimod (MGN-1703), CYT-003, CYT-003-QbG10 and PUL-042. Examples of TLR3 agonist include rintatolimod, poly-ICLC, RIBOXXON®, Apoxxim, RIBOXXIM®, IPH-33, MCT-465, MCT-475, and ND-1.1.

Toll-like receptor 8 (TLR8) inhibitors: Examples of TLR8 inhibitors include, but are not limited to, E-6887, IMO-8400, IMO-9200 and VTX-763.

Toll-like receptor 8 (TLR8) agonists: Examples of TLR8 agonists include, but are not limited to, MCT-465, motolimod, =GS-9688, and VTX-1463.

Toll-like receptor 9 (TLR9) inhibitors: Examples of TLR9 inhibitors include, but are not limited to, AST-008, IMO-2055, IMO-2125, lefitolimod, litenimod, MGN-1601, and PUL-042.

TLR7/TLR8 agonist, includes NKTR-262, IMO-4200, MEDI-9197 (telratolimod), and resiquimod.

TLR7 agonists include DS-0509, GS-9620, LHC-165, and TMX-101 (imiquimod).

STING agonists include ADU-S100 (MIW-815), SB-11285, MK-1454, SR-8291, AdVCA0848, GSK-532, SYN-STING, MSA-1, and SR-8291.

In certain embodiments, a compound described herein is combined with a TLR agonist. Examples of TLR agonists include without limitation: lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.

In some embodiments, the therapeutic agent is a small organic compound. In some embodiments, the therapeutic agent is an agonist or activator of a toll-like receptor (TLR) or a stimulator of interferon genes (STING) In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP.

In some embodiments, a compound described herein is combined with a RIG-1 modulator such as RGT-100, or NOD2 modulator, such as SB-9200, and IR-103.

In certain embodiments, a compound described herein is combined with an interleukin agonist, such as IL-2, IL-7, IL-15, IL-10, IL-12; examples of IL-2 agonists such as proleukin (aldesleukin, IL-2); pegylated IL-2 (e.g., NKTR-214); modified variants of IL-2 (e.g., THOR-707); examples of IL-15 agonists, such as ALT-803, NKTR-255, and hetIL-15, interleukin-15/Fc fusion protein, AM-0015, and NIZ-985.

In certain embodiments, a compound described herein is combined with a Flt3 agonist.

Indoleamine-pyrrole-2,3-dioxygenase (IDO1) Inhibitors

In various embodiments, a compound as described herein, is combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, and LY-3381916.

In some embodiments, the therapeutic agent is a small organic compound. In some embodiments, the therapeutic agent is an agonist or activator of a toll-like receptor (TLR) or a stimulator of interferon genes (STING) In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP), and cyclic-di-AMP.

In some embodiments, a compound described herein is combined with a RIG-1 modulator such as RGT-100, or NOD2 modulator, such as SB-9200, and IR-103.

Tyrosine-kinase Inhibitors (TKIs)

In various embodiments, a compound as described herein, is combined with a tyrosine kinase inhibitor (TKI). TKIs may target epidermal growth factor receptors (EGFRs) and receptors for fibroblast growth factor (FGF), platelet-derived growth factor (PDGF), and vascular endothelial growth factor (VEGF). Examples of TKIs include without limitation, axitinib, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, olmutinib, osimertinib (AZD-9291), pazopanib, ponatinib, poziotinib, quizartinib, radotinib, rociletinib, sulfatinib (HMPL-012), sunitinib, famitinib L-malate, (MAC-4), tivoanib, TH-4000, tivoanib, and MEDI-575 (anti-PDGFR antibody), TAK-659, and Cabozantinib.

Chemotherapeutic Agents

In various embodiments, a compound as described herein, is combined with a chemotherapeutic agent or anti-neoplastic agent.

As used herein, the term "chemotherapeutic agent" or "chemotherapeutic" (or "chemotherapy" in the case of treatment with a chemotherapeutic agent) is meant to encompass any non-proteinaceous (e.g., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, e.g., bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammal1 and calicheamicin phil1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as cladribine, pentostatin, fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223, 177-Lu-PSMA-617; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-trichlorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFOX (folinic acid, 5-fluorouracil, oxaliplatin); FOLFIRI (folinic acid, 5-fluorouracil, irinotecan); FOLFOXIRI (folinic acid, 5-fluorouracil, oxaliplatin, irinotecan), FOLFIRINOX (folinic acid, 5-fluorouracil, irinotecan, oxaliplatin), and pharmaceutically acceptable salts, acids, or derivatives of any of the above. Such agents can be conjugated onto an antibody or any targeting agent described herein to create an antibody-drug conjugate (ADC) or targeted drug conjugate.

Anti-Hormonal Agents

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204.

An example progesterone receptor antagonist includes onapristone.

Anti-Angiogenic Agents

In various embodiments, a compound as described herein, is combined with an anti-angiogenic agent. Anti-angiogenic agents that can be co-administered include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as I-azetidine-2-carboxylic acid (LACA), cishydroxyproline, d,l-3,4-dehydroproline, thiaproline, α,α'-dipyridyl, beta-aminopropionitrile fumarate, 4-propyl-5-(4-pyridinyl)-2(3 h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

In various embodiments, a compound as described herein, is combined with an anti-fibrotic agent. Anti-fibrotic agents that can be co-administered include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Anti-Inflammatory Agents

In various embodiments, a compound as described herein, is combined with an anti-inflammatory agent. Example anti-inflammatory agents include without limitation inhibitors of one or more of arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240), soluble epoxide hydrolase 2 (EPHX2, SEH; NCBI Gene ID: 2053) and/or mitogen-activated protein kinase kinase kinase 8 (MAP3K8, TPL2; NCBI Gene ID: 1326). In some embodiments, the inhibitor is a dual inhibitor, e.g., a dual inhibitor of COX-2/COX-1, COX-2/SEH, COX-2/CA, and COX-2/5-LOX.

Examples of inhibitors of prostaglandin-endoperoxide synthase 1 (PTGS1, COX-1; NCBI Gene ID: 5742) that can be co-administered include without limitation mofezolac, GLY-230, and TRK-700.

Examples of inhibitors of prostaglandin-endoperoxide synthase 2 (PTGS2, COX-2; NCBI Gene ID: 5743) that can be co-administered include without limitation diclofenac, meloxicam, parecoxib, etoricoxib, AP-101, celecoxib, AXS-06, diclofenac potassium, DRGT-46, AAT-076, meisuoshuli, lumiracoxib, meloxicam, valdecoxib, zaltoprofen, nimesulide, Anitrazafen, Apricoxib, Cimicoxib, Deracoxib, Flumizole, Firocoxib, Mavacoxib, NS-398, Pamicogrel, Parecoxib, Robenacoxib, Rofecoxib, Rutecarpine, Tilmacoxib, and Zaltoprofen. Examples of dual COX1/COX2 inhibitors that can be co-administered include without limitation, HP-5000, lornoxicam, ketorolac tromethamine, bromfenac sodium, ATB-346, HP-5000. Examples of dual COX-2/carbonic anhydrase (CA) inhibitors that can be co-administered include without limitation polmacoxib and imrecoxib.

Examples of inhibitors of secreted phospholipase A2, prostaglandin E synthase (PTGES, PGES; Gene ID: 9536) that can be co-administered include without limitation LY3023703, GRC 27864, and compounds described in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, and WO2008071173. Metformin has further been found to repress the COX2/PGE2/STAT3 axis, and can be co-administered. See, e.g., Tong, et al., *Cancer Lett.* (2017) 389:23-32; and Liu, et al., *Oncotarget.* (2016) 7(19):28235-46.

Examples of inhibitors of carbonic anhydrase (e.g., one or more of CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)) that can be co-administered include without limitation acetazolamide, methazolamide, dorzolamide, zonisamide, brinzolamide, and dichlorphenamide. A dual COX-2/CA1/CA2 inhibitor that can be co-administered includes CG100649.

Examples of inhibitors of arachidonate 5-lipoxygenase (ALOX5, 5-LOX; NCBI Gene ID: 240) that can be co-administered include without limitation meclofenamate sodium, zileuton.

Examples of inhibitors of soluble epoxide hydrolase 2 (EPHX2, SEH; NCBI Gene ID: 2053) that can be co-administered include without limitation compounds described in WO2015148954. Dual inhibitors of COX-2/SEH that can be co-administered include compounds described in WO2012082647. Dual inhibitors of SEH and fatty acid amide hydrolase (FAAH; NCBI Gene ID: 2166) that can be co-administered include compounds described in WO2017160861.

Examples of inhibitors of mitogen-activated protein kinase kinase kinase 8 (MAP3K8, tumor progression loci-2, TPL2; NCBI Gene ID: 1326) that can be co-administered include without limitation GS-4875, GS-5290, BHM-078 and those described, e.g., in WO2006124944, WO2006124692, WO2014064215, WO2018005435, Teli, et al., *J Enzyme Inhib Med Chem.* (2012) 27(4):558-70; Gangwall, et al., *Curr Top Med Chem.* (2013) 13(9):1015-35; Wu, et al., *Bioorg Med Chem Lett.* (2009) 19(13):3485-8; Kaila, et al., *Bioorg Med Chem.* (2007) 15(19):6425-42; and Hu, et al., *Bioorg Med Chem Lett.* (2011) 21(16):4758-61.

Tumor Oxygenation Agents

In various embodiments, a compound as described herein, is combined with an agent that promotes or increases tumor oxygenation or reoxygenation, or prevents or reduces tumor hypoxia. Illustrative agents that can be co-administered include, e.g., Hypoxia inducible factor-1 alpha (HIF-1a) inhibitors, such as PT-2977, PT-2385; VEGF inhibitors, such as bevasizumab, IMC-3C$_5$, GNR-011, tanibirumab, LYN-00101, ABT-165; and/or an oxygen carrier protein (e.g., a heme nitric oxide and/or oxygen binding protein (HNOX)), such as OMX-302 and HNOX proteins described in WO 2007/137767, WO 2007/139791, WO 2014/107171, and WO 2016/149562.

Immunotherapeutic Agents

In various embodiments, a compound as described herein, is combined with an immunotherapeutic agent. Example immunotherapeutic agents that can be co-administered include without limitation abagovomab, ABP-980, adecatumumab, afutuzumab, alemtuzumab, altumomab, amatuximab, anatumomab, arcitumomab, bavituximab, bectumomab, bevacizumab, bevacizumab biosimilar, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, moxetumomab pasudotox, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, trastuzumab biosimilar, tucotuzumab, ubilituximab, veltuzumab, vorsetuzumab, votumumab, zalutumumab, and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

In some embodiments, the immunotherapeutic agent is an antibody-drug conjugate (ADC). Illustrative ADCs that can be co-administered include without limitation drug-conjugated antibodies, fragments thereof, or antibody mimetics targeting the proteins or antigens listed above and herein (e.g., in Table B). Example ADCs that can be co-administered include without limitation gemtuzumab, brentuximab, trastuzumab, inotuzumab, glembatumumab, anetumab, mirvetuximab, depatuxizumab, rovalpituzumab, vadastuximab, labetuzumab, sacituzumab, lifastuzumab, indusatumab, polatzumab, pinatuzumab, coltuximab, indatuximab, milatuzumab, rovalpituzumab, ABBV-011, ABBV-2029, ABBV-321, ABBV-647, MLN0264 (anti-GCC, guanylyl cyclase C), T-DM1 (trastuzumab emtansine, Kadcycla); SYD985 (anti-HER2, Duocarmycin), milatuzumab-doxorubicin (hCD74-DOX), brentuximab vedotin (ADCETRIS®), DCDT2980S, belantamab mafodotin (GSK2857916), polatuzumab vedotin (RG-7596), SGN-CD70A, SGN-CD19A, inotuzumab ozogamicin (CMC-544), lorvotuzumab mertansine, SAR3419, isactuzumab govitecan, enfortumab vedotin (ASG-22ME), ASG-15ME, DS-8201 (trastuzumab deruxtecan), 225Ac-lintuzumab, U3-1402, 177Lu-tetraxetan-tetuloma, tisotumab vedotin, anetumab ravtansine, CX-2009, SAR-566658, W-0101, ABBV-085, gemtuzumab ozogamicin, ABT-414, glembatumumab vedotin (CDX-011), labetuzumab govitecan (IMMU-130), sacituzumab govitecan (IMMU-132), lifastuzumab vedotin, (RG-7599), milatuzumab-doxorubicin (IMMU-110), indatuximab ravtansine (BT-062), pinatuzumab vedotin (RG-7593), SGN-LIV1A, SGN-CD33A, SAR566658, MLN2704, SAR408701, rovalpituzumab tesirine, ABBV-399, AGS-16C3F, ASG-22ME, AGS67E, AMG 172, AMG 595, AGS-15E, BAY1129980, BAY1187982, BAY94-934 (anetumab ravtansine), GSK2857916, Humax-TF-ADC (tisotumab vedotin), IMGN289, IMGN529, IMGN853 (mirvetuximab soravtansine), LOP628, PCA062, MDX-1203, MEDI-547, PF-06263507, PF-06647020, PF-06647263, PF-06664178, PF-06688992, PF-06804103, RG7450, RG7458, RG7598, SAR566658, SGN-CD33A, DS-1602 and DS-7300, DS-6157, DS-6000, TAK-164, MED12228, MED17247; ABBV-399, AGS-16C$_3$F, ASG-22ME, AGS67E, AMG172, AMG575, BAY1129980, BAY1187982, BAY94-9343, GSK2857916, Humax-TF-ADC, IMGN289, IMGN529, IMGN853, LOP628, PCA062, MDX-1203 (BMS936561), MEDI-547, PF-06263507, PF-06647020, PF-06647263, PF-06664178, RG7450, RG7458, RG7598, SAR566658, SGN-CD19A, SGN-CD33A, SGN-CD70A, SGN-LIV1A, and SYD985. ADCs that can be co-administered are described, e.g., in Lambert, et al., Adv Ther (2017) 34:1015-1035 and in de Goeij, Current Opinion in Immunology (2016) 40:14-23.

Illustrative therapeutic agents (e.g., anticancer or antineoplastic agents) that can be conjugated to the drug-conjugated antibodies, fragments thereof, or antibody mimetics include without limitation monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracycline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a *vinca* alkaloid, an epothilone), a pyrrolobenzodiazepine (PBD) or dimer thereof, a duocarmycin (A, B1, B2, C$_1$, C$_2$, D, SA, CC-1065), and other anticancer or anti-neoplastic agents described herein.

Cancer Gene Therapy and Cell Therapy

In various embodiments, a compound as described herein, is combined with a cancer gene therapy and cell therapy. Cancer gene therapies and cell therapies include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Cellular Therapies

In various embodiments, a compound as described herein, is combined with one or more cellular therapies. Illustrative cellular therapies include without limitation co-administration of one or more of a population of natural killer (NK) cells, NK-T cells, T cells, cytokine-induced killer (CIK) cells, macrophage (MAC) cells, tumor infiltrating lymphocytes (TILs) and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC$^T$M T cells. In some embodiments, the cellular therapy entails a NK cell therapy, e.g., co-administering NK-92 cells. As appropriate, a cellular therapy can entail the co-administration of cells that are autologous, syngeneic or allogeneic to the subject.

In some embodiments, the cellular therapy entails co-administering cells comprising chimeric antigen receptors (CARs). In such therapies, a population of immune effector cells engineered to express a CAR, wherein the CAR comprises a tumor antigen-binding domain. In T cell therapies, the T cell receptors (TCRs) are engineered to target tumor derived peptides presented on the surface of tumor cells.

With respect to the structure of a CAR, in some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon RIb), CD79a, CD79b, Fcgamma RIIa, DAP10, and DAP12.

In some embodiments, the costimulatory domain comprises a functional domain of one or more proteins selected from the group consisting of CD27, CD28, 4-1 BB(CD137), OX40, CD30, CD40, PD-1, ICOS, CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, ITGAE, CD103, ITGAL, CD1A (NCBI Gene ID: 909), CD1B (NCBI Gene ID: 910), CD1C (NCBI Gene ID: 911), CD1D (NCBI Gene ID: 912), CD1E (NCBI Gene ID: 913), ITGAM, ITGAX, ITGB1, CD29, ITGB2 (CD18, LFA-1), ITGB7, TNFR2, TRANCE/RANKL, DNAM1 (CD226), SLAMF4 (CD244, 2B4), CD84, CD96 (Tactile), CEACAMi, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, ICOS (CD278), 4-1BB(CD137), GITR, CD40, BAFFR, HVEM (LIGHTR), SLAMF7, NKp80 (KLRF1), CD19, IL2R beta, IL2R gamma, IL7R, ITGA1, VLA1, CD49a, ITGA4, IA4, CD49D, ITGA6, VLA-6, CD49f, ITGAD, CD1A, CD1B, CD1C, CD1D, CD1E, ITGAE, CD103, ITGAL, ITGAM, ITGAX, ITGB1, CD29, ITGB2 (LFA-1, CD18), ITGB7, TNFR2, DNAM1 (CD226), SLAMF4 (CD244, 2B4), CD84, CD96 (TACTILE), CEACAMi, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the TCR or CAR antigen binding domain or the immunotherapeutic agent described herein (e.g., monospecific or multi-specific antibody or antigen-binding fragment thereof or antibody mimetic) binds a tumor-associated antigen (TAA). In some embodiments, the tumor-associated antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvIII); ganglioside G2 (GD2); ganglioside GD3 (aNeuSAc(2-8)aNeuSAc(2-3)pDGaip(1-4)bDGlcp(1-1) Cer); ganglioside GM3 (aNeuSAc(2-3)pDGalp(1-4)pDGlcp(1-1)Cer); TNF receptor superfamily member 17 (TNFRSF17, BCMA); Tn antigen ((Tn Ag) or (GalNAcu-Ser/Thr)); prostate-specific membrane antigen (PSMA); Receptor tyrosine kinase-like orphan receptor 1 (RORI); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11 Ra); prostate stem cell antigen (PSCA); Protease Serine 21 (Testisin or PRSS21); vascular endothelial growth factor receptor 2 (VEGFR2); Lewis(Y)antigen; CD24; Platelet-derived growth factor receptor beta (PDGFR-beta); Stage-specificembryonic antigen-4 (SSEA-4); CD20; delta like 3 (DLL3); Folate receptor alpha; Receptor tyrosine-protein kinase, ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2(EphA2); Fucosyl GM1; sialyl Lewis adhesion molecule (sLe); transglutaminase 5 (TGS5); high molecular weight-melanomaassociatedantigen (HMW-MAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAPi); claudin 6 (CLDN6); thyroid stimulating hormone receptor (TSHR); G protein-coupled receptor class C group 5, member D (GPRCSD); chromosome X open reading frame 61 (CX-ORF61); CD97; CD179a; anaplastic lymphoma kinase (ALK); Polysialic acid; placenta-specific 1 (PLAC1); hexa-saccharide portion of globoH glycoceramide (GloboH); mammary gland differentiation antigen (NY-BR-1); uro-plakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51 E2 (ORS IE2); TCR Gamma Alternate Reading Frame Protein (TARP); Wilms tumor protein (WT1); Cancer/testis antigen 1 (NY-ESO-1); Cancer/testis antigen 2 (LAGE-Ia); Melanoma associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1(CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRI); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLECI2A); bone marrow stromal cell antigen 2 (BST2); EGF-like module containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1). In some embodiments, the target is an epitope of the tumor associated antigen presented in an MHC.

In some embodiments, the tumor antigen is selected from CD150, 5T4, ActRIIA, B7, TNF receptor superfamily member 17 (TNFRSF17, BCMA), CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, LI-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D1), ephrinB2, epithelial tumor antigen, estrogen receptor, fetal acetylcholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, and Fc Receptor-like 5 (FcRL5).

Examples of cell therapies include without limitation: AMG-119, Algenpantucel-L, ALOFISEL®, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, lmilecleucel-T, baltaleucel-T, PNK-007, UCARTCSi, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1 BBL CAR T cells, autologous 4H11-28z/fIL-12/EFGRt T cell, CCR5-SBC-728-HSPC, CAR4-1 BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, CSG-005, LAAP T-cell therapy, PD-1 knockout T cell therapy (esophageal cancer/NSCLC), anti-MUC1 CAR T-cell therapy (esophageal cancer/NSCLC), anti-MUC1 CAR T-cell therapy+PD-1 knockout T cell therapy (esophageal cancer/NSCLC), and anti-KRAS G12D mTCR PBL.

Additional agents for targeting tumors include without limitation:
- alpha-fetoprotein, such as ET-1402, and AFP-TCR;
- anthrax toxin receptor 1, such as anti-TEM8 CAR T-cell therapy;
- TNF receptor superfamily member 17 (TNFRSF17, BCMA), such as bb-2121 (ide-cel), bb-21217, JCARH125, UCART-BCMA, ET-140, KITE-585, MCM-998, LCAR-B38M, CART-BCMA, SEA-BCMA, BB212, UCART-BCMA, ET-140, P-BCMA-101, AUTO-2 (APRIL-CAR), JNJ-68284528;
- anti-CLL-1 antibodies, such as KITE-796;
- anti-PD-L1-CAR tank cell therapy, such as KD-045;
- anti-CD45 antibodies, such as 131 I-BC8 (lomab-B);
- anti-HER3 antibodies, such as LJM716, GSK2849330;
- anti-CD52 antibodies, such as alemtuzumab;
- B7 homolog 6, such as CAR-NKp30 and CAR-B7H6;
- B-lymphocyte antigen CD19, such as TBI-1501, CTL-119 huCART-19 T cells, I iso-cel, JCAR-015 U.S. Pat. No. 7,446,190, JCAR-014, JCAR-017, (WO2016196388, WO2016033570, WO2015157386), axicabtagene ciloleucel (KTE-C$_{19}$, Yescarta®), KTE-X19, U.S. Pat. Nos. 7,741,465, 6,319,494, UCART-19, EBV-CTL, T tisagenlecleucel-T (CTL019), WO2012079000, WO2017049166, CD19CAR-CD28-CD3zeta-EGFRt-expressing T cells, CD19/4-1 BBL armored CAR T cell therapy, C-CAR-011, CIK-CAR.CD19, CD19CAR-28-zeta T cells, PCAR-019, MatchCART, DSCAR-01, IM19 CAR-T, TC-110; anti-CD19 CAR T-cell therapy (B-cell acute lymphoblastic leukemia, Universiti Kebangsaan Malaysia); anti-CD19 CAR T-cell therapy (acute lymphoblastic leukemia/Non-Hodgkin's lymphoma, University Hospital Heidelberg), anti-CD19 CAR T-cell therapy (silenced IL-6 expression, cancer, Shanghai Unicar-Therapy Bio-medicine Technology), and MB-CART2019.1 (CD19/CD20);
- B-lymphocyte antigen CD20, such as ACTR707 ATTCK-20;
- B-lymphocyte antigen CD19/B-lymphocyte antigen 22, such as TC-310;
- B-lymphocyte antigen 22 cell adhesion, such as UCART-22, JCAR-018 WO2016090190;
- NY-ESO-1 modulators, such as GSK-3377794, TBI-1301, and GSK3537142;
- carbonic anhydrase, such as DC-Ad-GMCAIX;
- caspase 9 suicide gene, such as CaspaCIDe DLI, and BPX-501;
- CCR5, such as SB-728;
- CDw123, such as MB-102, and UCART-123;
- CD4, such as ICG-122;
- CD33, such as CIK-CAR.CD33;
- CD38, such as T-007, UCART-38;
- CD40 ligand, such as BPX-201, MED15083;
- CD56, such as allogeneic CD56-positive CD3-negative natural killer cells (myeloid malignancies);
- T-cell antigen CD7 modulator, such as anti-CD7 CAR T-cell therapy (CD7-positive hematological malignancies);
- CEACAM protein 5 modulators, such as MG7-CART;
- claudin 6, such as CSG-002;
- EBV targeted, such as CMD-003;
- MUC16EGFR, such as autologous 4H, 11-28z/fIL-12/EFGRt T cell;
- endonuclease, such as PGN-514, PGN-201;
- epstein-Barr virus specific T-lymphocytes, such as TT-10;
- Erbb2, such as CST-102, CIDeCAR;
- ganglioside (GD2), such as 4SCAR-GD2;
- folate hydrolase 1 (FOLH1, Glutamate carboxypeptidase II, PSMA; NCBI Gene ID: 2346), such as CIK-CAR.PSMA, CART-PSMA-TGFpRDN, P-PSMA-101;
- glypican-3(GPC3), such as TT-16, GLYCAR;
- hemoglobin, such as PGN-236;
- hepatocyte growth factor receptor, such as anti-cMet RNA CAR T;
- human papillomavirus E7 protein, such as KITE-439;
- immunoglobulin gamma Fc receptor III, such as ACTR087;
- IL-12, such as DC-RTS-IL-12;
- IL-12 agonist/mucin 16, such as JCAR-020;
- IL-13 alpha 2, such as MB-101;
- IL-2, such as CST-101;
- K-Ras GTPase, such as anti-KRAS G12V mTCR cell therapy;
- neural cell adhesion molecule L1 L1CAM (CD171), such as JCAR-023;
- latent membrane protein 1/Latent membrane protein 2, such as Ad5f35-LMPdi-2-transduced autologous dendritic cells;
- melanoma associated antigen 10, such as MAGE-A10C796T MAGE-A10 TCR;
- melanoma associated antigen 3/Melanoma associated antigen 6 (MAGE A3/A6) such as KITE-718;
- mesothelin, such as CSG-MESO, TC-210;
- NKG2D, such as NKR-2;
- Ntrkr1 tyrosine kinase receptor, such as JCAR-024;
- PRAMET cell receptor, such as BPX-701;
- roundabout homolog 1 9Robo1), such as ATCG-427;
- PSMA, such as PSMA-CAR T-cell therapy (lentiviral vector, castrate-resistant prostate cancer);
- T-lymphocyte, such as TT-12;
- T-lymphocyte stimulator, such as ATL-001;
- tumor infiltrating lymphocytes, such as LN-144, LN-145; and
- Wilms tumor protein, such as JTCR-016, WT1-CTL, ASP-7517.

Gene Editors

In various embodiments, a compound as described herein, is combined with gene editor. Illustrative gene editing system that can be co-administered include without limitation a CRISPR/Cas9 system, a zinc finger nuclease system, a TALEN system, a homing endonucleases system (e.g., an ARCUS), and a homing meganuclease system.

In various embodiments, a compound as described herein, is combined with others drugs with unspecified targets: for example, human immunoglobulin (10% liquid formulation), Cuvitru (human immunoglobulin (20% solution), levofolinate disodium, IMSA-101, BMS-986288, IMUNO BGC Moreau RJ, R-OKY-034F, GP-2250, AR-23, calcium levofolinate, porfimer sodium, RG6160, ABBV-155, CC-99282, polifeprosan 20 with carmustine, Veregen, gadoxetate disodium, gadobutrol, gadoterate meglumine, gadoteridol, 99mTc-sestamibi, pomalidomide, pacibanil, and valrubicin.

Exemplified Combination Therapies

Lymphoma or Leukemia Combination Therapy

Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), pomalidomide (POMALYST®/IMNOVID®)lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCI-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), and venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP (cyclophosphamide, doxorubicin, vincristine, and prednisone), CVP (cyclophosphamide, vincristine, and prednisone), FCM (fludarabine, cyclophosphamide, and mitoxantrone), MCP (Mitoxantrone, Chlorambucil, Prednisolone), all optionally including rituximab (R) and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP (rituximab, cyclophosphamide, doxorubicin, vincristine, and prednisone), R-FCM, R-CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCI-779), everolimus (RAD001), BMS-345541, curcumin, SAHA, thalidomide, lenalidomide (REVLIMID®, CC-5013), and geldanamycin (17 AAG).

Waldenstrom's Macroqlobulinemia Combination Therapy

Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ibrutinib, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, ulocuplumab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-cell Lymphoma Combination Therapy

Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and R ICE.

Chronic Lymphocytic Leukemia Combination Therapy

Examples of therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

Myelofibrosis Combination Therapy

Myelofibrosis inhibiting agents include, but are not limited to, hedgehog inhibitors, histone deacetylase (HDAC) inhibitors, and tyrosine kinase inhibitors. Non-limiting examples of hedgehog inhibitors are saridegib and vismodegib. Examples of HDAC inhibitors include, but are not limited to, pracinostat and panobinostat. Non-limiting examples of tyrosine kinase inhibitors are lestaurtinib, bosutinib, imatinib, gilteritinib, radotinib, and cabozantinib.

Hyperproliferative Disorder Combination Therapy

Gemcitabine, nab-paclitaxel, and gemcitabine/nab-paclitaxel may be used with a JAK inhibitor and/or PI3Kδ inhibitor to treat hyperproliferative disorders.

Bladder Cancer Combination Therapy

Therapeutic agents used to treat bladder cancer include atezolizumab, carboplatin, cisplatin, docetaxel, doxorubicin, fluorouracil (5-FU), gemcitabine, idosfamide, Interferon alfa-2b, methotrexate, mitomycin, nab-paclitaxel, paclitaxel, pemetrexed, thiotepa, vinblastine, and any combination thereof.

Breast Cancer Combination Therapy

Therapeutic agents used to treat breast cancer include albumin-bound paclitaxel, anastrozole, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, Letrozole, methotrexate, mitoxantrone, paclitaxel, pegylated liposomal doxorubicin, pertuzumab, tamoxifen, toremifene, trastuzumab, vinorelbine, and any combinations thereof.

Triple Negative Breast Cancer Combination Therapy

Therapeutic agents used to treat triple negative breast cancer include cyclophosphamide, docetaxel, doxorubicin, epirubicin, fluorouracil, paclitaxel, and combinations thereof.

Colorectal Cancer Combination Therapy

Therapeutic agents used to treat colorectal cancer include bevacizumab, capecitabine, cetuximab, fluorouracil, irinotecan, leucovorin, oxaliplatin, panitumumab, ziv-aflibercept, and any combinations thereof.

Castration-resistant Prostate Cancer Combination Therapy

Therapeutic agents used to treat castration-resistant prostate cancer include abiraterone, cabazitaxel, docetaxel, enzalutamide, prednisone, sipuleucel-T, and any combinations thereof.

Esophageal and Esophagogastric Junction Cancer Combination Therapy

Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof.

Gastric Cancer Combination Therapy

Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head and Neck Cancer Combination Therapy

Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Hepatobiliary Cancer Combination Therapy

Therapeutic agents used to treat hepatobiliary cancer include capecitabine, cisplatin, fluoropyrimidine, 5-fluorourcil, gemecitabine, oxaliplatin, sorafenib, and any combinations thereof.

Hepatocellular Carcinoma Combination Therapy

Therapeutic agents used to treat hepatocellular carcinoma include capecitabine, doxorubicin, gemcitabine, sorafenib, and any combinations thereof.

Non-Small Cell Lung Cancer Combination Therapy

Therapeutic agents used to treat non-small cell lung cancer (NSCLC) include afatinib, albumin-bound paclitaxel, alectinib, bevacizumab, bevacizumab biosimilar, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof.

Small Cell Lung Cancer Combination Therapy

Therapeutic agents used to treat small cell lung cancer (SCLC) include bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof.

Melanoma Combination Therapy

Therapeutic agents used to treat melanoma cancer include albumin bound paclitaxel, carboplatin, cisplatin, cobiemtinib, dabrafenib, dacrabazine, IL-2, imatinib, interferon alfa-2b, ipilimumab, nitrosourea, nivolumab, paclitaxel, pembrolizumab, pilimumab, temozolomide, trametinib, vemurafenib, vinblastine, and any combinations thereof.

Ovarian Cancer Combination Therapy

Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcitabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.

Pancreatic Cancer Combination Therapy

Therapeutic agents used to treat pancreatic cancer include 5-fluorourcil, albumin-bound paclitaxel, capecitabine, cisplatin, docetaxel, erlotinib, fluoropyrimidine, gemcitabine, irinotecan, leucovorin, oxaliplatin, paclitaxel, and any combinations thereof.

Renal Cell Carcinoma Combination Therapy

Therapeutic agents used to treat renal cell carcinoma include axitinib, bevacizumab, cabozantinib, erlotinib, everolimus, levantinib, nivolumab, pazopanib, sorafenib, sunitinib, temsirolimus, and any combinations thereof.

Compound Preparation

Some embodiments of the instant disclosure are directed to processes and intermediates useful for preparing the subject compounds or pharmaceutically acceptable salts thereof.

Compounds described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," $4^{th}$ ed., Wiley, New York 2006. The protecting groups may be removed at a convenient subsequent stage using methods known from the art.

General Synthetic Schemes

Scheme 1: Preparation of Optically Pure General Intermediates GI-01A, GI-01B

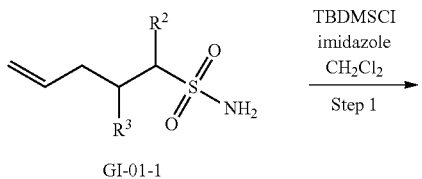

GI-01-1

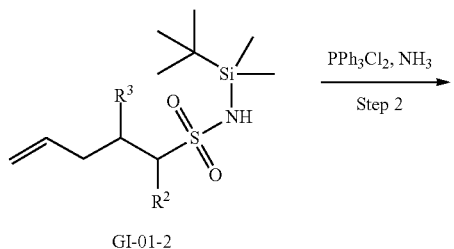

GI-01-2

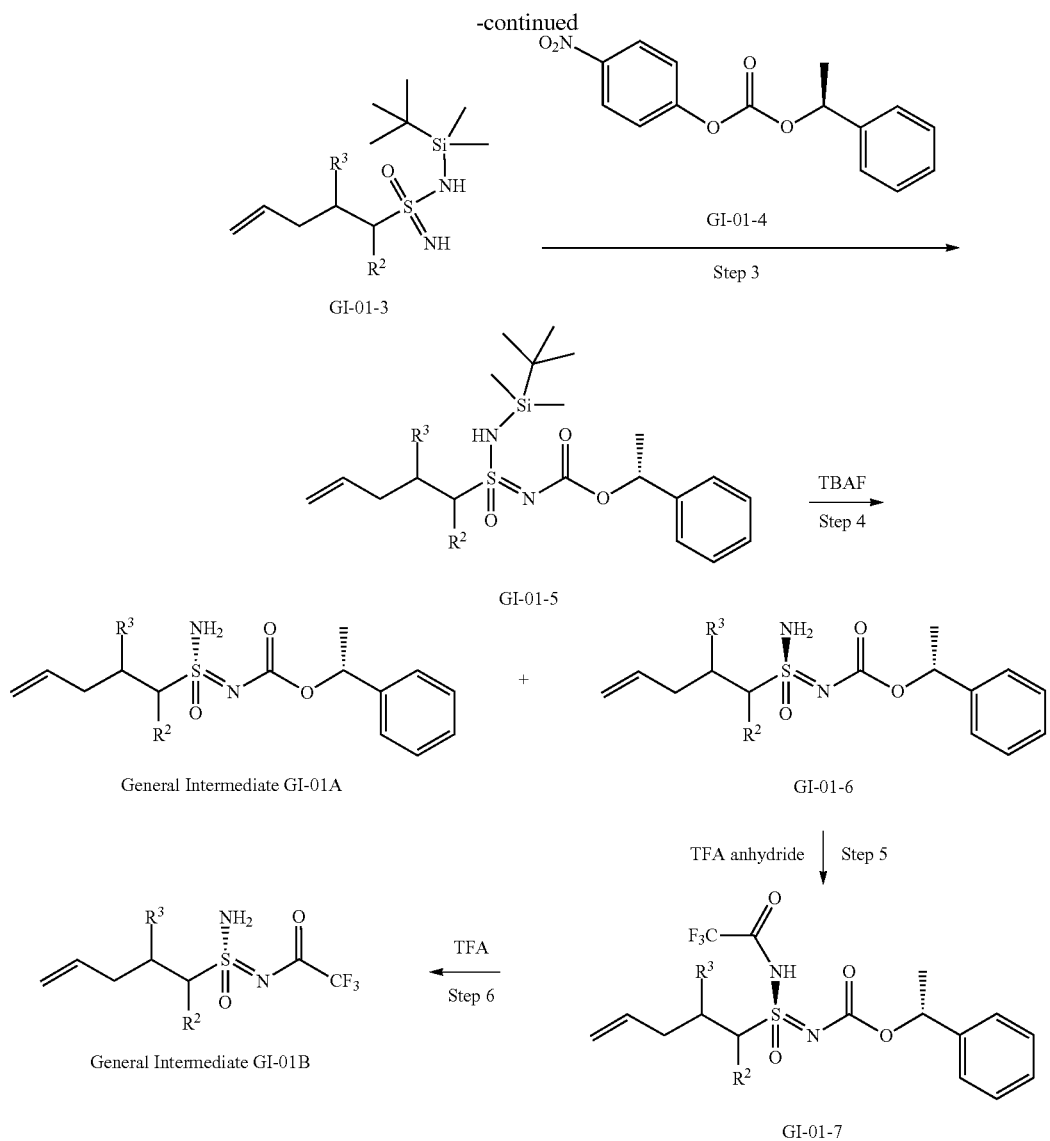

Intermediates exemplified by formula GI-01-1 can be prepared using procedures described in International Publication No. WO 2016033486, or via procedures described in specific Examples below.

Step 1: Intermediate GI-01-2 can be prepared by dissolving Intermediate GI-01-1 in an appropriate solvent such as THF, DMF or $CH_2Cl_2$, treating with an appropriate organic base, such as trimethylamine, diisopropylethylamine or imidazole, and an appropriate silylating agent, such as TBDMSCl or TBDMSOTf, at appropriate temperature, preferably at 0° C.

Step 2: Intermediate GI-01-3 can be prepared as a mixture of stereoisomers by suspending $Ph_3PCl_2$ in an appropriate solvent, such as $CH_2Cl_2$ or 1,2-dichloroethane, under a $N_2$ atmosphere, adding an appropriate organic base, such as trimethylamine or diisopropylethylamine, and then adding a solution of Intermediate GI-01-2 in an appropriate solvent such as $CH_2Cl_2$ or 1,2-dichloroethane followed by bubbling ammonia gas.

Step 3: Intermediate GI-01-5 can be prepared as a mixture of stereoisomers by dissolving Intermediate GI-01-4 (preparation described in the Examples below) in an appropriate solvent such as tetrahydrofuran under a $N_2$ atmosphere, treating with an appropriate strong organic base such as n-butyllithium at an appropriate temperature, preferably −40° C., then adding Intermediate GI-01-3 as a solution in an appropriate solvent such as tetrahydrofuran.

Step 4: General Intermediate GI-01A can be prepared in optically pure form by dissolving Intermediate GI-01-5 in an appropriate solvent such as tetrahydrofuran and treating with an appropriate desilylating agent such as tetrabutylammonium fluoride. The resulting mixture of General Intermediate GI-01A and Intermediate GI-01-6 can be separated by any technique appropriate for separation of mixtures of stereoisomers, such as chiral HPLC or SFC.

Step 5: Intermediate GI-01-7 can be prepared in optically pure form by dissolving Intermediate GI-01-6 in an appropriate solvent such as $CH_2Cl_2$, then treating with a trifluoroacetylating agent such as trifluoroacetic anhydride and an organic base such as triethylamine.

Step 6: General Intermediate GI-01B can be prepared in optically pure form by dissolving Intermediate GI-01-7 in an appropriate solvent such as $CH_2Cl_2$, then treating with a reagent to deprotect the chiral carbamate, preferably trifluoroacetic acid.

Scheme 2: Preparation of Optically Pure General Intermediate GI-02A

Intermediates exemplified by formula GI-02-1 and GI-02-2 can be prepared in optically pure form using procedures described in International Publication No. WO 2016033486, or by the methods described for specific Examples below.

Step 1: Intermediate GI-02-3 can be prepared by dissolving intermediates exemplified by formula GI-02-1 in an appropriate solvent such as 1,2-dichloroethane and treating with Intermediate GI-02-2, an acid such as acetic acid, and a hydride reducing agent, preferably sodium triacetoxyborohydride.

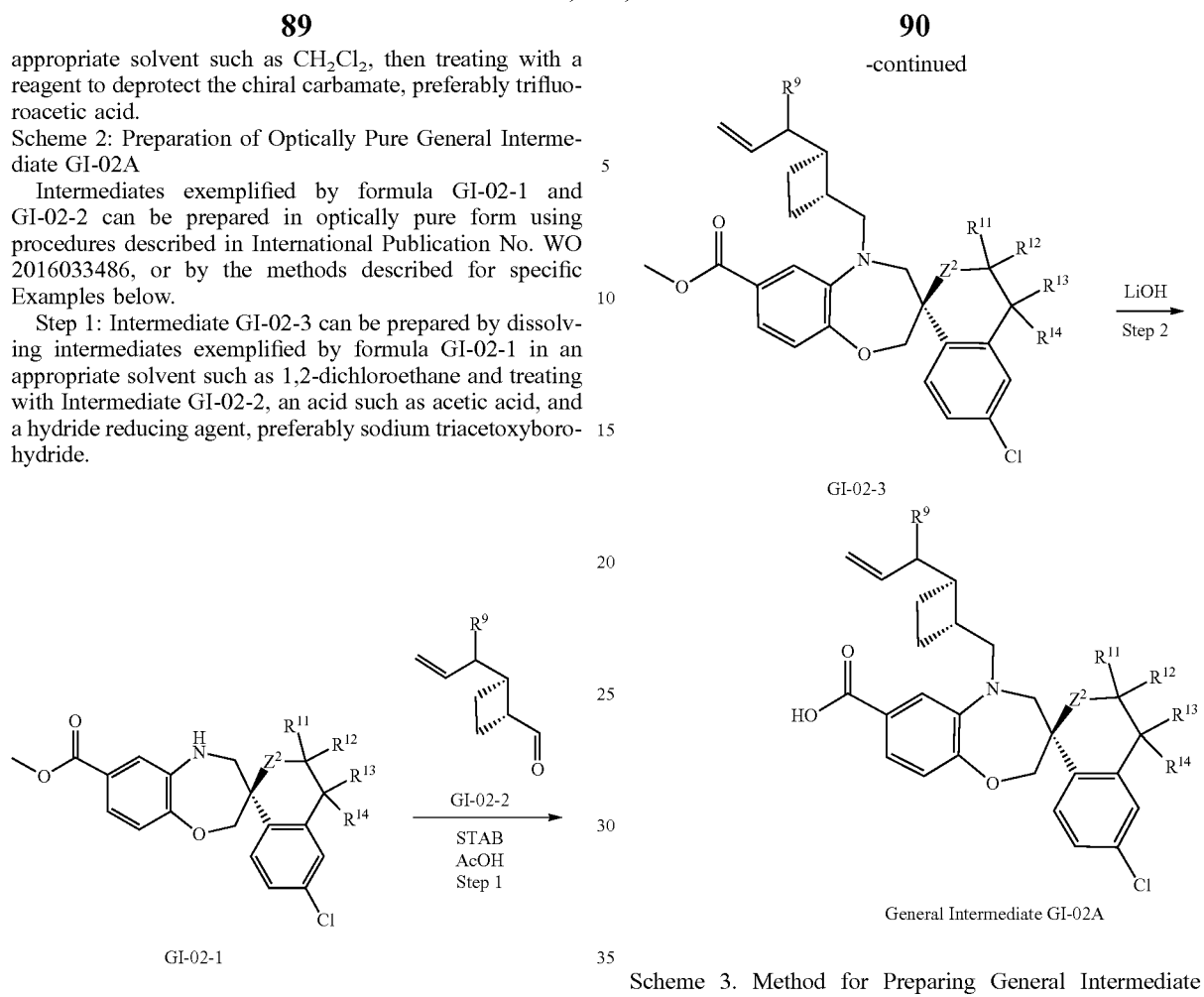

Scheme 3. Method for Preparing General Intermediate GI-03 in Optically Pure Form.

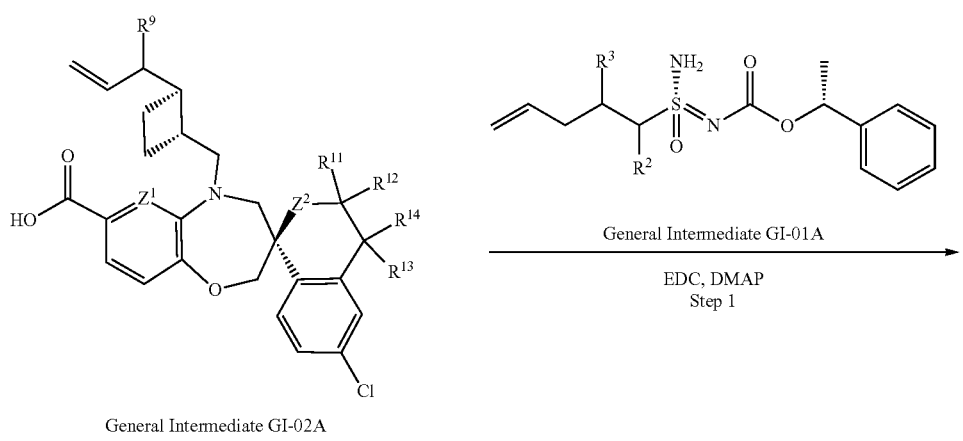

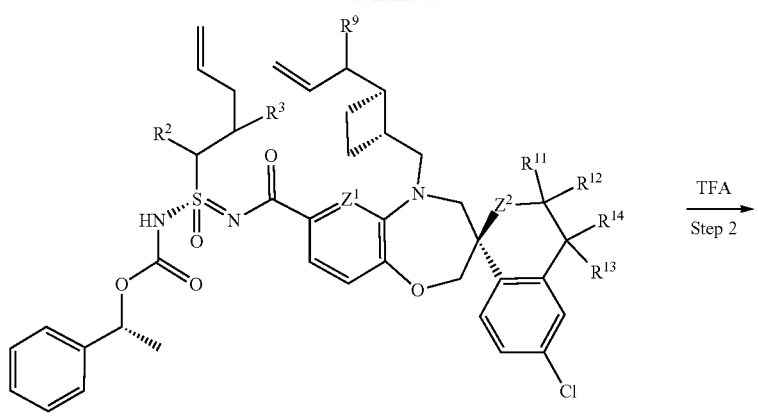
GI-03-1
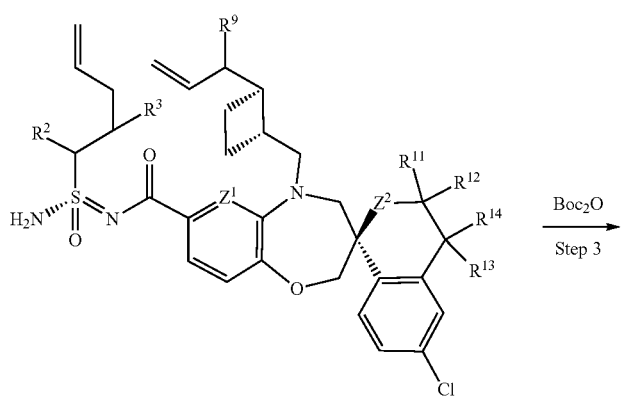
GI-03-2
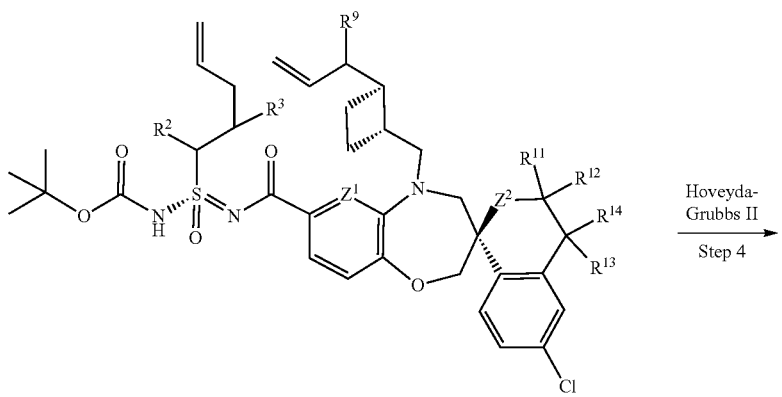
GI-03-3

-continued

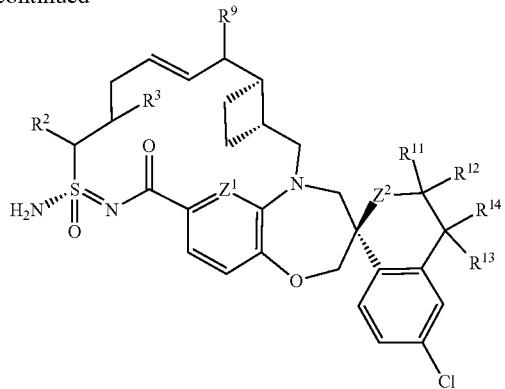

General Intermediate GI-03

Step 1: Intermediate GI-03-1 can be prepared dissolving a mixture of General Intermediate GI-01A and General Intermediate GI-02A in an appropriate solvent such as $CH_2Cl_2$, then treating with an organic base, preferably 4-dimethylaminopyridine, and a coupling agent such as EDCl.

Step 2: Intermediate GI-03-2 can be prepared by dissolving Intermediate GI-03-1 in an appropriate solvent such as $CH_2Cl_2$, and treating with an acid, preferably trifluoroacetic acid.

Step 3: Intermediate GI-03-3 can be prepared by dissolving Intermediate GI-03-2 in an appropriate solvent such as $CH_2Cl_2$, adding an appropriate organic base such as triethylamine and an appropriate acylation catalyst such as 4-dimethylaminopyridine, then treating with an acylating agent, preferably di-tert-butyl dicarbonate.

Step 4: General Intermediate GI-03 can be prepared by stirring Intermediate GI-03-3 with Hoveyda Grubbs $2^{nd}$ generation catalyst in an appropriate solvent, such as $CH_2Cl_2$ or 1,2-dichloroethane, at elevated temperature, preferably at 60° C. After concentrating the reaction mixture, the residue can be purified by preparative HPLC or silica gel column chromatography.

Scheme 4. Method for Preparing General Intermediate GI-03 in Optically Pure Form.

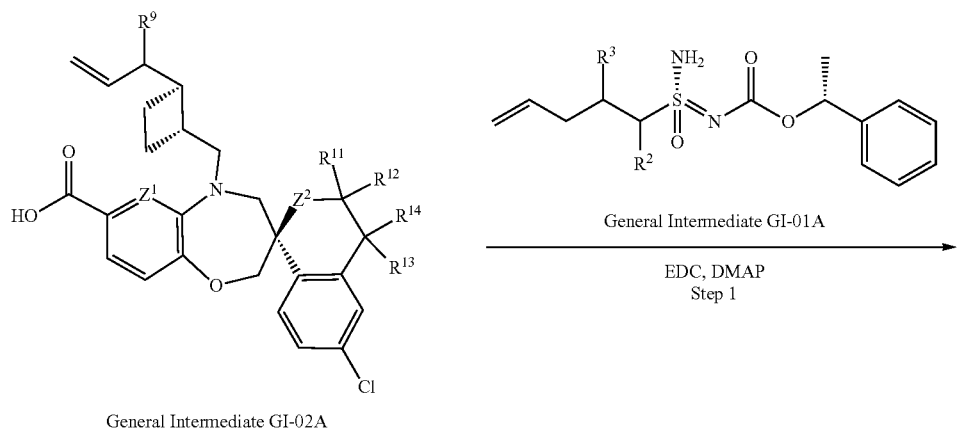

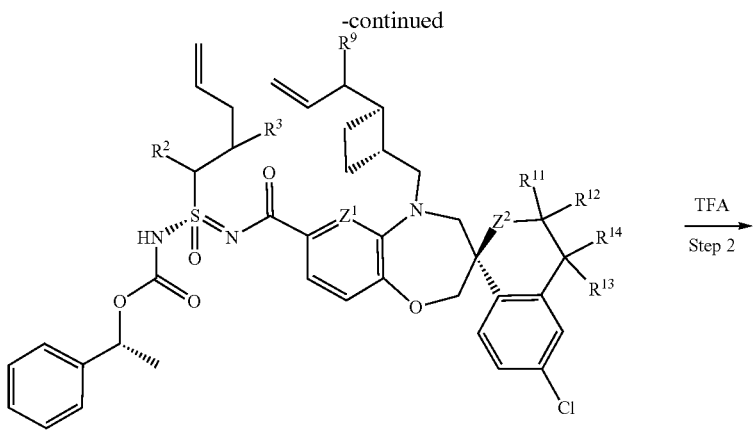

GI-03-1

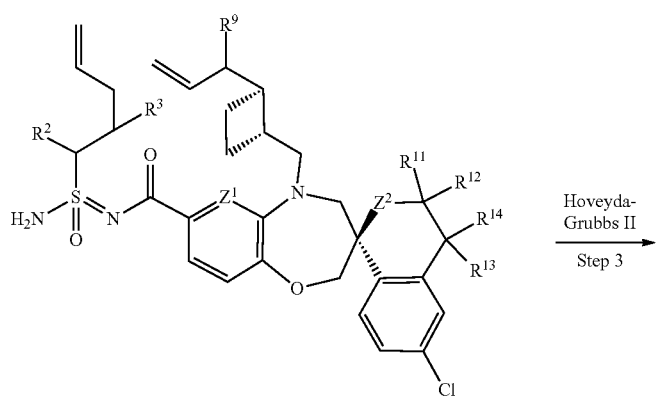

GI-03-2

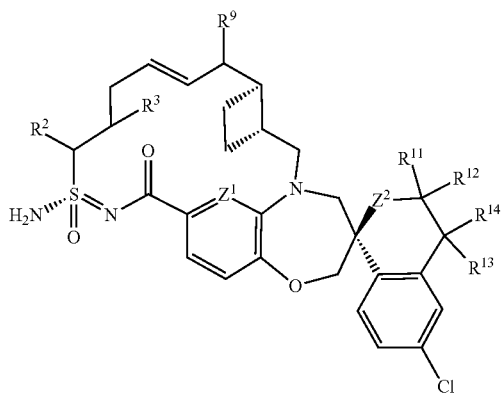

General Intermediate GI-03

Step 1: Intermediate GI-03-1 can be prepared dissolving a mixture of General Intermediate GI-01A and General Intermediate GI-02A in an appropriate solvent such as $CH_2Cl_2$, then treating with an organic base, preferably 4-dimethylaminopyridine, and a coupling agent such as EDCl.

Step 2: Intermediate GI-03-2 can be prepared by dissolving Intermediate GI-03-1 in an appropriate solvent such as $CH_2Cl_2$, and treating with an acid, preferably trifluoroacetic acid.

Step 3: General Intermediate GI-03 can be prepared by stirring Intermediate GI-03-2 with Hoveyda Grubbs $2^{nd}$ generation catalyst in an appropriate solvent, such as $CH_2Cl_2$ or 1,2-dichloroethane, at elevated temperature, preferably at 60° C. After concentrating the reaction mixture, the residue can be purified by preparative HPLC or silica gel column chromatography.

Scheme 5. Method for Preparing General Intermediate GI-03 in Optically Pure Form.

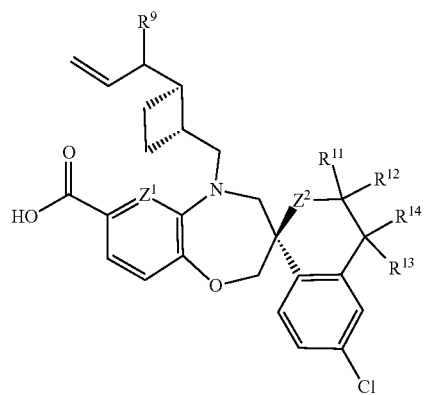
General Intermediate GI-02A
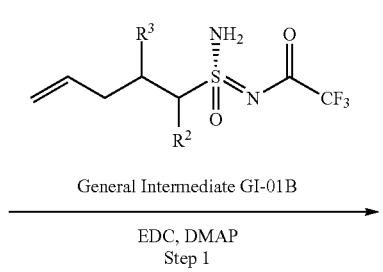
General Intermediate GI-01B
EDC, DMAP
Step 1
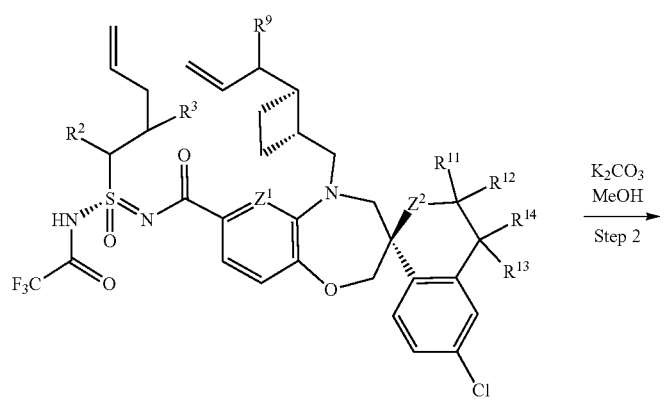
GI-03-4
K$_2$CO$_3$
MeOH
Step 2
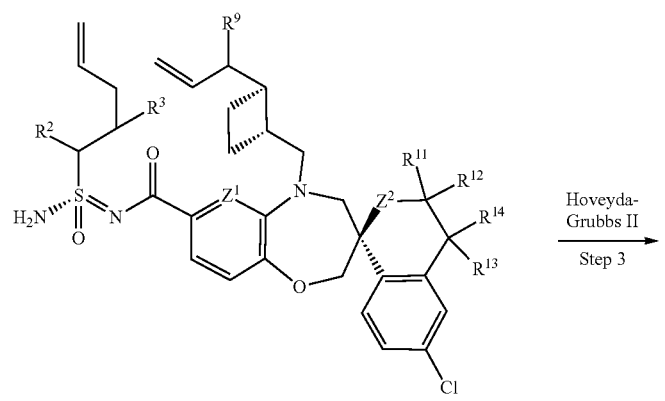
GI-03-2
Hoveyda-
Grubbs II
Step 3

-continued

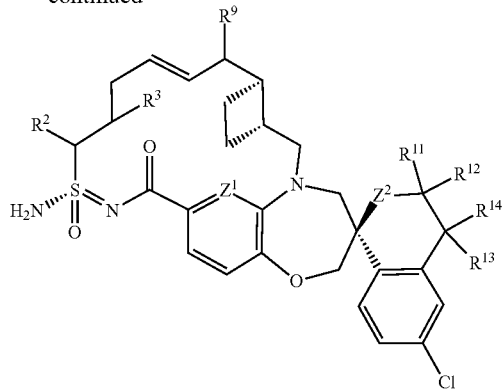

General Intermediate GI-03

Step 1: Intermediate GI-03-4 can be prepared dissolving a mixture of General Intermediate GI-01B and General Intermediate GI-02A in an appropriate solvent such as DCM, then treating with an organic base, preferably 4-dimethylaminopyridine, and a coupling agent such as EDCl.

Step 2: Intermediate GI-03-2 can be prepared by dissolving Intermediate GI-03-4 in an appropriate polar protic solvent such as methanol and treating with a base, preferably potassium carbonate.

Step 3: General Intermediate GI-03 can be prepared by stirring Intermediate GI-03-2 with Hoveyda Grubbs $2^{nd}$ generation catalyst in an appropriate solvent, such as DCM or 1,2-dichloroethane, at elevated temperature, preferably at 60° C. After concentrating the reaction mixture, the residue can be purified by preparative HPLC or silica gel column chromatography.

Scheme 6. Method for Preparing General Intermediate GI-03 in Optically Pure Form.

Step 1: Intermediate GI-03-5 can be prepared by dissolving General Intermediate GI-02A in an appropriate solvent, such as DCM or 1,2-dichloroethane. An appropriate acid chloride forming agent, for example thionyl chloride or oxalyl chloride, can be added to generate Intermediate GI-03-5, which can be used immediately in the next step.

Step 2: Intermediate GI-03-6 can be prepared by dissolving Intermediate GI-01-3 in an appropriate polar solvent, such as acetonitrile, and adding pyridazine, followed by Intermediate GI-03-5 in an appropriate polar solvent such as acetonitrile.

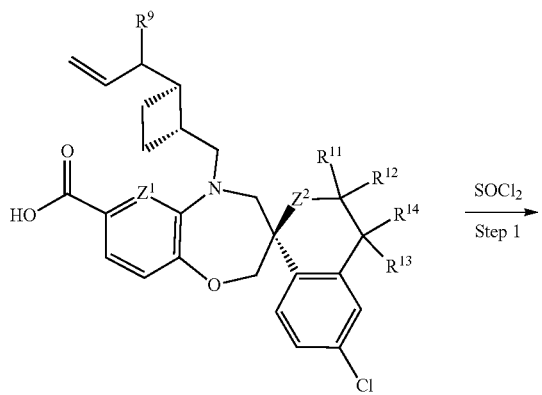

General Intermediate GI-02A

-continued
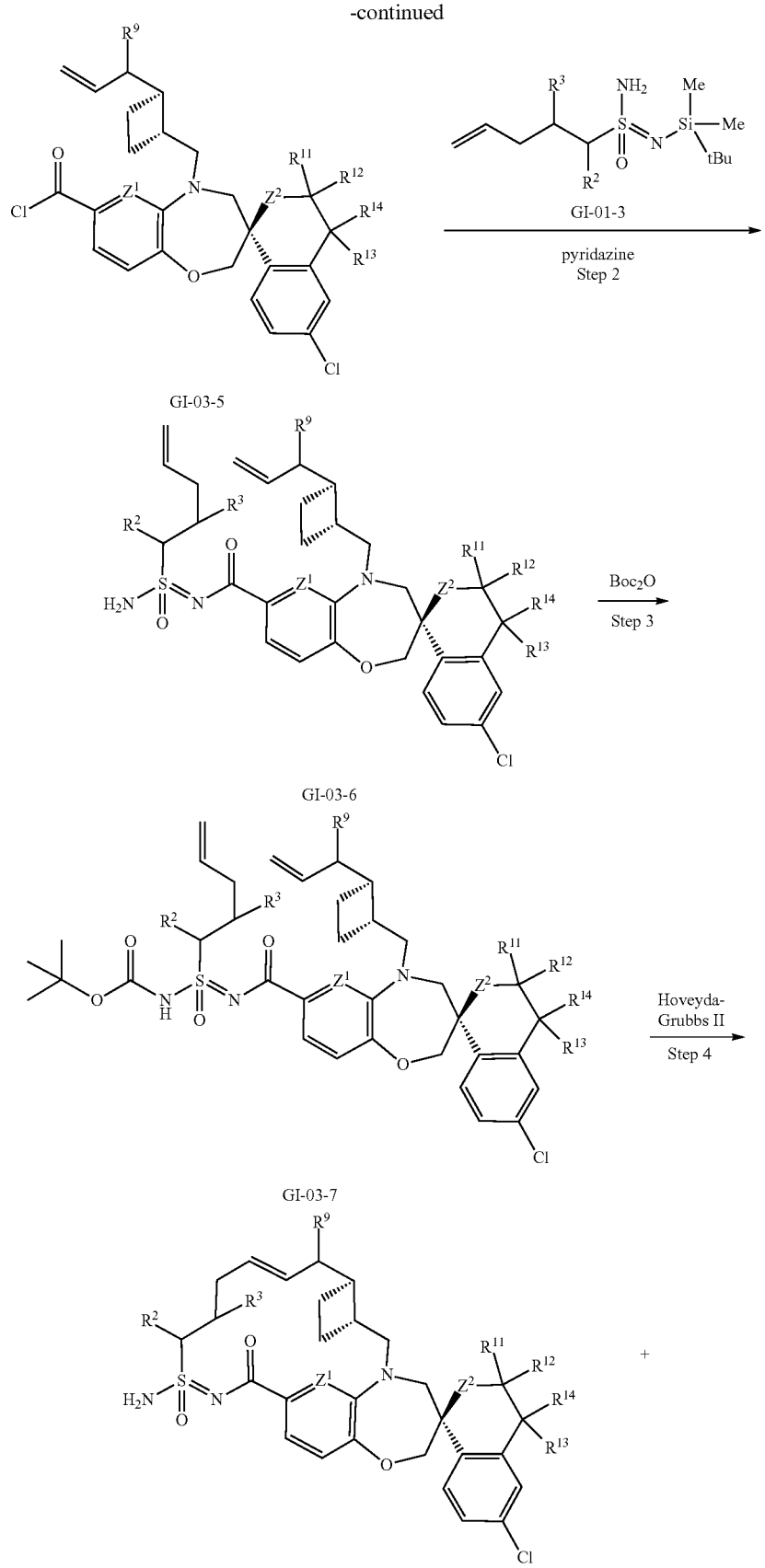

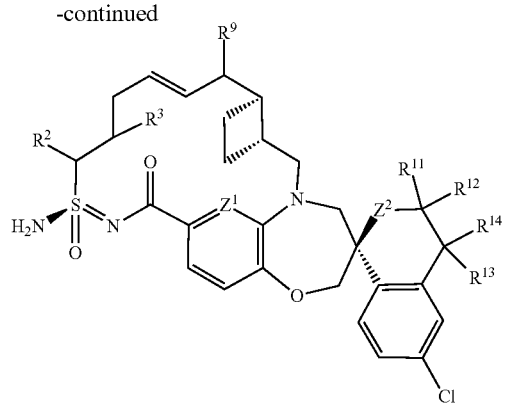

GI-03-8

Step 3: Intermediate GI-03-7 can be prepared by dissolving Intermediate GI-03-6 in an appropriate solvent such as DCM, adding an appropriate organic base such as triethylamine and an appropriate acylation catalyst such as 4-dimethylaminopyridine, then treating with an acylating agent, preferably di-tert-butyl dicarbonate.

Step 4: General Intermediate GI-03 can be prepared by stirring Intermediate GI-03-2 with Hoveyda Grubbs $2^{nd}$ generation catalyst in an appropriate solvent, such as $CH_2Cl_2$ or 1,2-dichloroethane, at elevated temperature, preferably at 60° C. After concentrating the reaction mixture, the residue can be purified by prep HPLC or silica gel column chromatography to separate stereoisomers and provide both General Intermediate GI-03 and stereoisomer Intermediate GI-03-8. Alternatively, the mixture of stereoisomers can be carried forward to subsequent steps and the stereoisomers separated by preparative HPLC or silica gel column chromatography after that subsequent step.

Scheme 7 Methods for $R^5$ or $R^{16}$ Group Installation to Prepare Optically Pure Compounds of Formula (I).

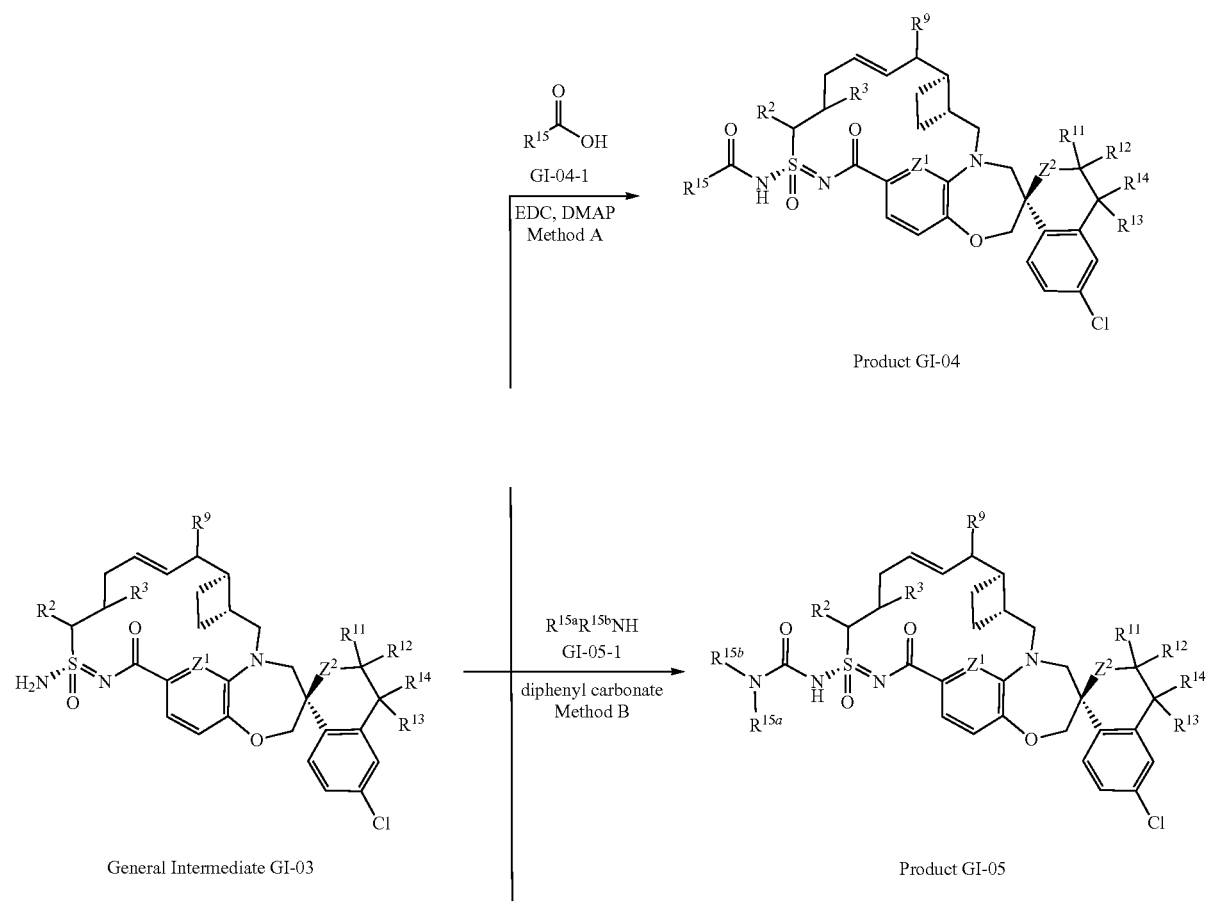

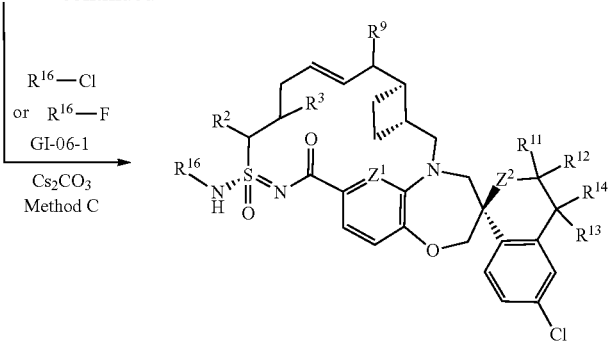

Product GI-06

Method A: Product GI-04 can be prepared by dissolving a mixture of General Intermediate GI-03 and a carboxylic acid Intermediate GI-04-1 in an appropriate solvent such as DCM, then treating with an organic base, preferably 4-dimethylaminopyridine, and a coupling agent such as EDCl. After the reaction is complete, the reaction may be concentrated, and the residue can be purified by preparative HPLC or silica gel column chromatography.

Method B: Product GI-05 can be prepared by treating General Intermediate GI-03 first with a carbonylation reagent such as diphenyl carbonate and an acylation catalyst such as 4-dimethylaminopyridine in an appropriate solvent such as dichloromethane overnight at elevated temperatures, preferably 40° C. Then amine Intermediate GI-05-1 is added, followed by an organic base, such as triethylamine, and the resulting reaction mixture is stirred at elevated temperature, preferably 40° C. When the reaction is complete, the mixture can be purified by aqueous workup with an aqueous acid solution, preferably 1 N hydrochloric acid, followed by an aqueous base solution, preferably aqueous sodium bicarbonate, and the resulting residue can be purified by preparative HPLC or silica gel column chromatography.

Method C: Product GI-06 can be prepared by mixing General Intermediate GI-03 with a heteroaryl chloride or heteroaryl fluoride Intermediate GI-06-1 and an appropriate base, such as cesium carbonate or potassium carbonate, in an appropriate polar solvent, such as N-methylpyrrolidone, N,N-dimethylformamide, or 1,4-dioxane, at elevated temperatures ranging from 80 to 150° C. After cooling, the mixture may be purified by preparative HPLC or silica gel column chromatography.

Scheme 8. Modification of Macrocycles to Prepare Optically Pure Compounds of Formula (I).

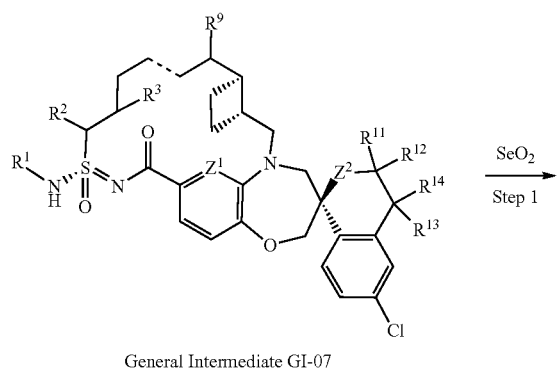

General Intermediate GI-07

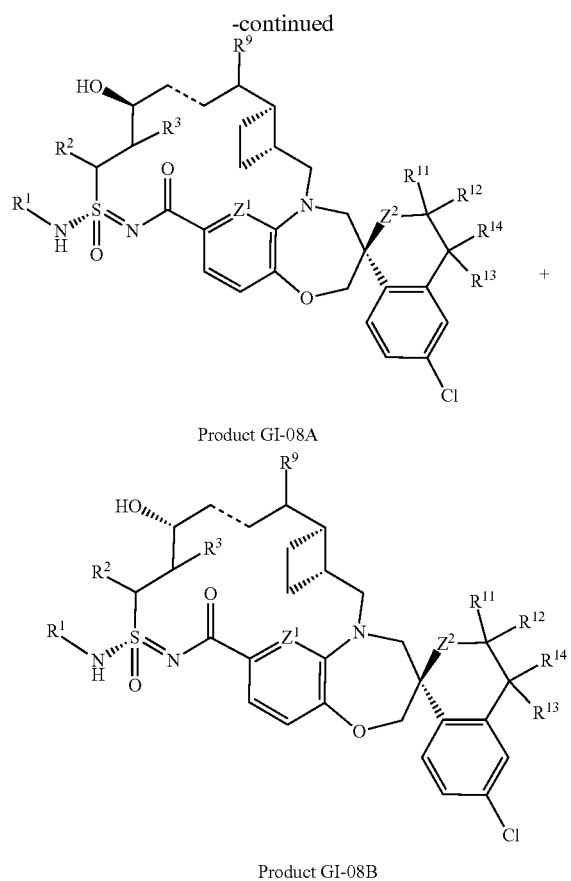

Product GI-08A

Product GI-08B where --- is either a double or triple bond

General Intermediate GI-07 can be prepared via the methods described above in Scheme 7 for Products GI-04, GI-05 or GI-06, or via specific methods described in the Examples below.

Step 1: Products GI-08A and GI-08B can be prepared by mixing General Intermediate GI-07 with an oxidizing agent, preferably selenium dioxide, in an appropriate aprotic solvent such as 1,4-dioxane at elevated temperatures, preferably 100 to 120° C. The resulting residue may be purified by preparative HPLC or silica gel column chromatography to separate stereoisomers and provide Products GI-08A and GI-08B.

Scheme 9. Modification of Macrocycles to Prepare Optically Pure Compounds of Formula (I).

Intermediate GI-09-1 can be prepared via methods described for Products GI-04, GI-05 and GI-06 in Scheme 7.

Step 1: Intermediate GI-09-2 can be prepared by treating Intermediate GI-09-1 with an oxidizing agent such as Dess-Martin periodinane in an appropriate solvent such as dichloromethane.

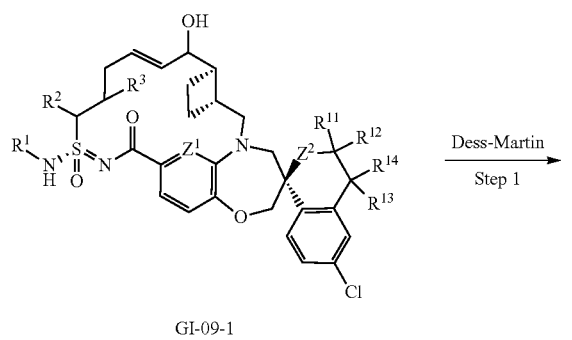

GI-09-1

Dess-Martin
Step 1

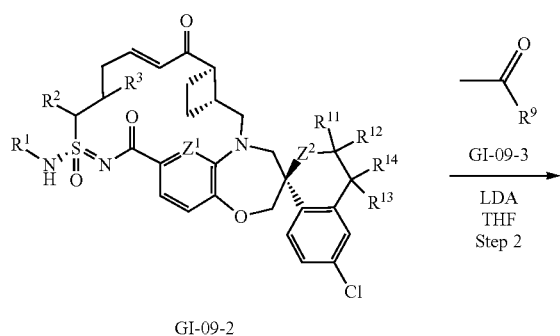

GI-09-2

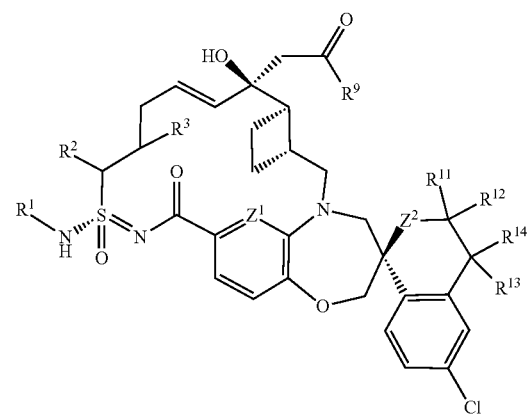

Product GI-09A

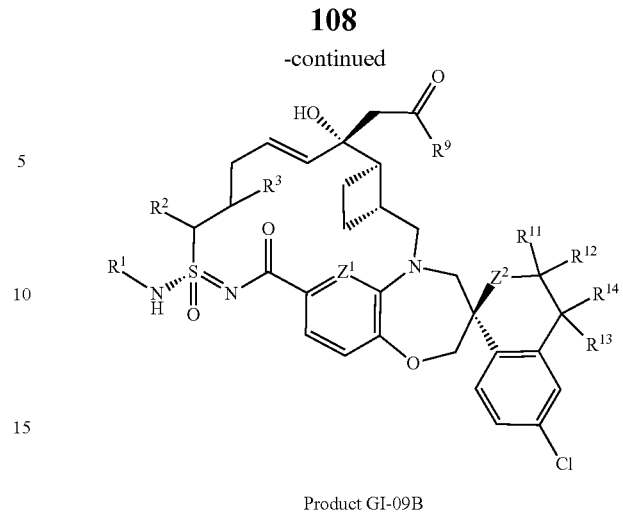

Product GI-09B

Step 2: Products GI-09A and GI-09B can be prepared by first treating a carbonyl compound GI-09-3 with a strong base such as lithium diisopropylamide in an appropriate aprotic solvent such as tetrahydrofuran at an appropriate temperature, preferably −78° C., then adding Intermediate GI-09-2. After workup, the resulting residue may be purified by preparative HPLC or silica gel column chromatography to separate stereoisomers and provide Products GI-09A and GI-09B.

EXAMPLES

Exemplary chemical entities of the present disclosure are provided in the specific examples that follow. Those skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

Intermediate A and Intermediate B

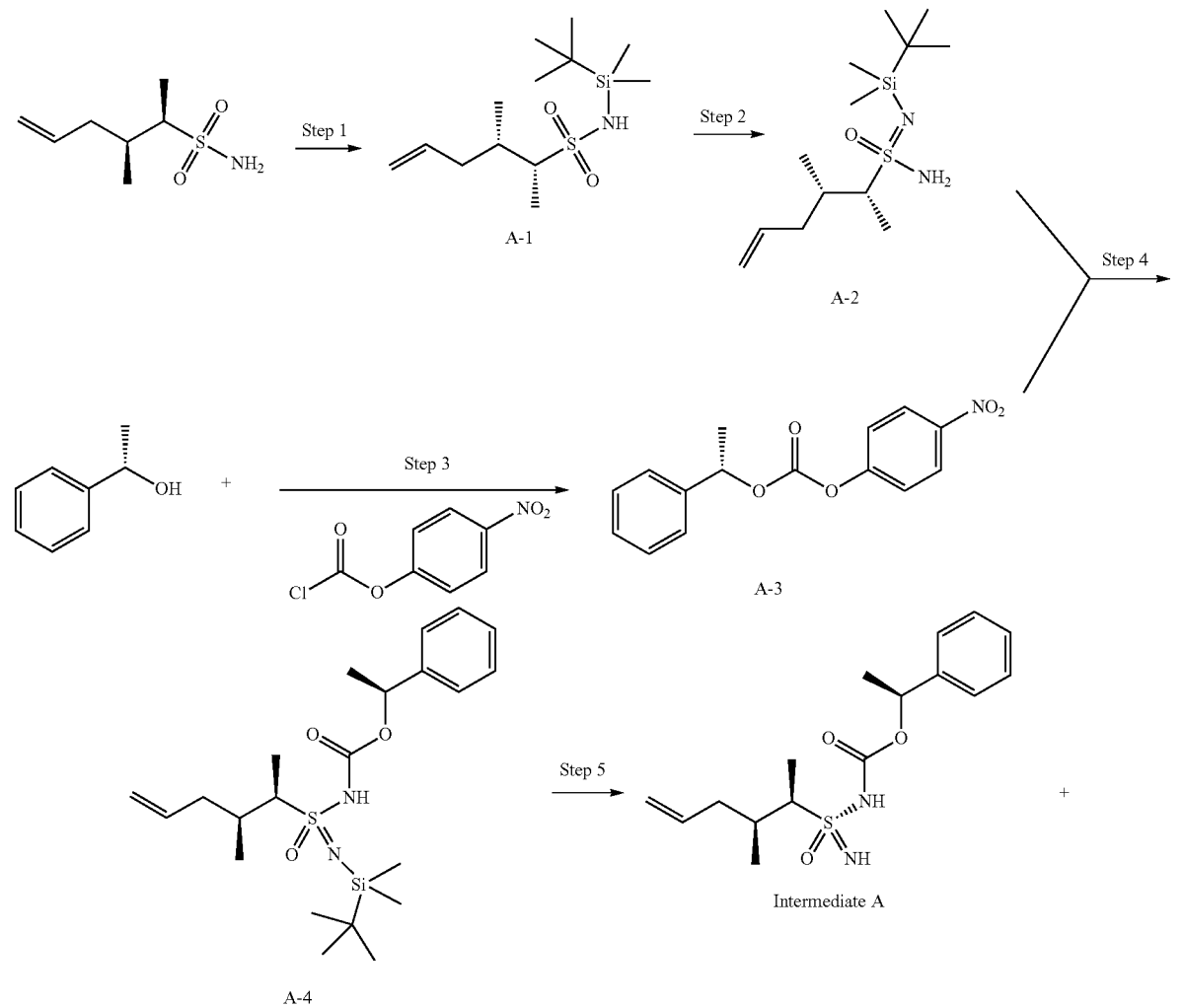

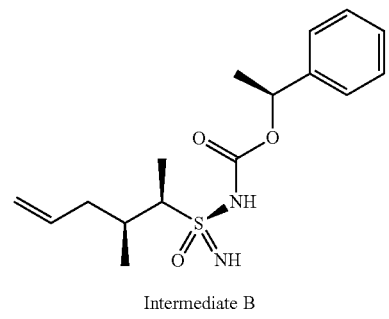

Intermediate B

Step 1: To a stirred solution of (2R,3S)-3-methylhex-5-ene-2-sulfonamide (WO 2016033486) (2.00 g, 11.28 mmol) in THF (16 mL) was added triethylamine (3.15 mL, 22.57 mmol) in an ice bath, followed by TBDMSCl (2.13 g, 14.10 mmol) in THF (8 mL) slowly. The resulting mixture was stirred at rt for 2 days. The precipitate was filtered and washed with ether. The filtrate was concentrated and purified by silica gel column (EtOAc/Hexanes=1/4) to afford A-1. $^1$H NMR (400 MHz, Chloroform-d) δ 5.76-5.67 (m, 1H), 5.08-5.02 (m, 2H), 3.95 (s, 1H), 3.95-2.97 (m, 1H), 2.44-2.41 (m, 1H), 2.14-2.08 (m, 1H), 2.02-1.96 (m, 1H), 1.27 (d, J=8.0 Hz, 3H), 1.02 (d, J=8.0 Hz, 3H), 0.94 (m, 9H), 0.27-0.26 (m, 6H).

Step 2: To a stirred suspension of Ph$_3$PCl$_2$ (754.33 mg, 2.264 mmol) in CH$_2$Cl$_2$ (4.0 mL) under a N$_2$ atmosphere, was added triethylamine (0.43 mL, 3.087 mmol). The mixture was stirred for 10 min at rt, then cooled to 0° C., and a solution of A-1 (600.00 mg, 2.058 mmol) in DCM (4 mL) was added. The reaction mixture was stirred for 1 h at 0° C. Ammonia gas was bubbled in the reaction mixture, and the reaction vessel was sealed, and stirred at 0° C. for 2 h. The resulting precipitate was filtered and washed with CH₂Cl₂. The filtrate was concentrated and purified by silica gel column (EtOAc/Hexanes=1/4) to afford A-2. ¹H NMR (400 MHz, Chloroform-d) δ 5.80-5.69 (m, 1H), 5.08-5.02 (m, 2H), 4.17 (w, 2H), 3.06-2.98 (m, 1H), 2.54-2.46 (m, 1H), 2.11-1.95 (m, 2H), 1.29-1.26 (m, 3H), 1.01-0.98 (m, 3H), 0.92-0.88 (m, 9H), 0.13-0.11 (m, 6H).

Step 3: A mixture of (1S)-1-(4-phenylphenyl)ethanol (8.7 g, 71.2 mmol) was dissolved in MeTHF (90 mL) and cooled to 0° C. To this cold stirred solution was added pyridine (7.1 mL). A solution of 4-nitro-phenyl-chloroformate (14.4 g, 71.2 mmol) in MeTHF (60.0 mL) was then added dropwise via dropping funnel. After addition, the resulting mixture was removed from the cooling bath and stirred at ambient for 2 hrs. Additional (1S)-1-(4-phenylphenyl)ethanol (2.6 g, 21.3 mmol) and pyridine (1.0 mL) were added and reaction was stirred overnight. The reaction was then washed with 1 N HCl (2×), brine (2×), dried over sodium sulfate, filtered, and concentrated. The residue was dissolved in DCM and mixed with silica gel, concentrated to dryness, and purified by normal phase chromatography (silica gel, 0-20% EtOAc/Hexanes). Desired fractions were combined and concentrated to give A-3. ¹H NMR (400 MHz, Chloroform-d) δ 8.34-8.16 (m, 2H), 7.48-7.31 (m, 7H), 5.84 (q, J=6.6 Hz, 1H), 1.70 (d, J=6.6 Hz, 3H).

Step 4: A-2 (5.9 g, 20.1 mmol) was azeotroped with anhydrous toluene (3×20 mL) and dissolved in anhydrous tetrahydrofuran (150 mL) under an atmosphere of argon. The solution was cooled to −50° C. A solution of 2.5M n-BuLi in hexanes (17.3 mL, 43.3 mmol) was added dropwise over 5 min. This mixture was stirred for 15 min. Concurrently A-3 (7.5 g, 26.2 mmol) was azeotroped with toluene (3×20 mL). The material was taken up in anhydrous tetrahydrofuran (60 mL) under an atmosphere of argon. The solution was added to the reaction via cannula over 5 min. After 15 min the reaction was warmed to 0° C. (ice bath) and stirred for 1 hr. The reaction was quenched with water (75 mL) at 0° C. EtOAc (50 mL) was added, the phases were separated, and the aqueous phase was extracted with EtOAc (2×50 mL). The combined organic phases were washed with sat NaHCO₃ (75 mL) and brine (75 mL). The organic phase was dried over sodium sulfate and the solvent was removed under reduced pressure, providing A-4.

Step 5: A solution of TBAF (1.0 M, 19.7 mL, 19.7 mmol) was added to a solution of A-4 (6.64 g, 15.1 mmol) in anhydrous THF at 0° C. and stirred 1 h. Solvent was removed under reduced pressure, and the residue was diluted with water (80 mL) and EtOAc (80 mL). The phases were separated and the aqueous phase was extracted with EtOAc (3×50 mL). The combined organic phases were washed with brine, and dried over sodium sulfate, and concentrated. The residue was subjected to flash chromatography (0-65% EtOAc/hexanes). The purified material was subjected to chiral SFC separation, with methanol as a co-solvent, using a ChiralPak IC column, providing Intermediate A as the earlier eluting diastereomer (stereochemistry tentatively assigned), and Intermediate B as the later (stereochemistry tentatively assigned).

Intermediate A: ¹H NMR (400 MHz, chloroform-d) δ 7.45-7.33 (m, 4H), 7.33-7.30 (m, 1H), 5.73 (q, J=6.7 Hz, 1H), 5.48 (dddd, J=16.4, 10.1, 8.2, 6.0 Hz, 1H), 5.06-4.93 (m, 2H), 3.41 (qd, J=7.0, 2.2 Hz, 1H), 2.53-2.39 (m, 1H), 2.07 (dt, J=14.0, 6.2 Hz, 1H), 2.00-1.86 (m, 1H), 1.59 (d, J=6.7 Hz, 3H), 1.34 (d, J=7.0 Hz, 3H), 1.02 (d, J=6.8 Hz, 3H).

Intermediate B: ¹H NMR (400 MHz, chloroform-d) δ 7.43-7.32 (m, 4H), 7.33-7.29 (m, 1H), 5.75 (q, J=6.6 Hz, 1H), 5.71-5.62 (m, 1H), 5.13-5.03 (m, 2H), 3.38 (qd, J=7.1, 2.3 Hz, 1H), 2.47 (dtd, J=8.9, 6.9, 2.2 Hz, 1H), 2.11 (dtt, J=13.1, 6.5, 1.4 Hz, 1H), 2.07-1.96 (m, 1H), 1.59 (d, J=6.7 Hz, 3H), 1.31 (d, J=7.0 Hz, 3H), 1.04 (d, J=6.9 Hz, 3H).

Intermediate C and Intermediate D

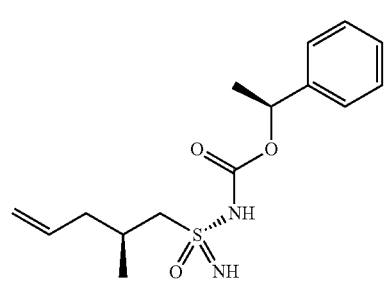

Intermediate C

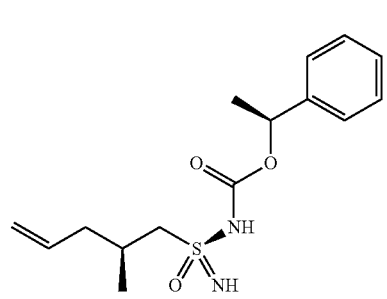

Intermediate D

Intermediate C and Intermediate D were synthesized in the same manner as Intermediate A and Intermediate B starting with (S)-2-methylpent-4-ene-1-sulfonamide (WO 2016033486).

Intermediate C, the first eluted diasteromer (Rt=3.05 min on ChiralPak IC with 15% ethanol co-solvent, absolute stereochemistry tentatively assigned as drawn): ¹H NMR (400 MHz, chloroform-d) δ 7.43-7.33 (m, 4H), 7.33-7.29 (m, 1H), 5.74 (q, J=6.7 Hz, 1H), 5.62 (ddt, J=16.0, 11.0, 7.1 Hz, 1H), 5.05 (d, J=1.3 Hz, 1H), 5.04-4.99 (m, 1H), 3.43 (dd, J=14.4, 4.5 Hz, 1H), 3.06 (dd, J=14.4, 7.9 Hz, 1H), 2.30-2.20 (m, 1H), 2.20-2.04 (m, 2H), 1.59 (d, J=6.7 Hz, 3H), 1.14 (d, J=6.7 Hz, 3H).

Intermediate D, the second eluted diasteromer (Rt=4.92 min on ChiralPak IC with 15% ethanol co-solvent, absolute stereochemistry tentatively assigned as drawn): ¹H NMR (400 MHz, chloroform-d) δ 7.44-7.32 (m, 4H), 7.32-7.30 (m, 1H), 5.79-5.73 (m, 1H), 5.73-5.66 (m, 1H), 5.16-5.05 (m, 2H), 3.38 (dd, J=14.5, 4.4 Hz, 1H), 3.20 (dd, J=14.4, 7.7 Hz, 1H), 2.27 (dq, J=12.5, 6.8 Hz, 1H), 2.22-2.10 (m, 2H), 1.59 (d, J=6.7 Hz, 3H), 1.14 (d, J=6.7 Hz, 3H).

Intermediate E and Intermediate F

Intermediate E and Intermediate F were synthesized in the same manner as Intermediate A and Intermediate B starting with (R)-hept-6-ene-3-sulfonamide (WO 2016033486). The diastereomers were separated by silica gel column chromatography (ethyl acetate/hexanes) after step 4 of the synthetic sequence.

Intermediate E

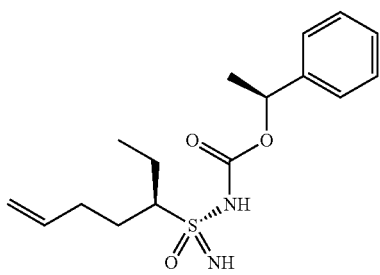

Intermediate F

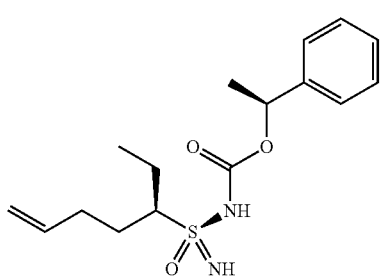

Intermediate E, second eluted diastereomer by silica gel column chromatography (absolute stereochemistry tentatively assigned as drawn): $^1$H NMR (400 MHz, Chloroform-d) b 8.49 (s, 1H), 7.24 (d, J=2.1 Hz, 1H), 7.17 (d, J=5.2 Hz, 1H), 7.13-7.05 (m, 2H), 6.93 (d, J=8.2 Hz, 1H), 4.78 (s, 2H), 4.18-4.01 (m, 2H), 3.62 (q, J=7.4 Hz, 2H), 3.50 (d, J=14.2 Hz, 1H), 3.40 (dd, J=14.6, 6.4 Hz, 1H), 3.32 (d, J=14.2 Hz, 1H), 3.26 (dd, J=14.6, 6.4 Hz, 1H), 2.89-2.75 (m, 1H), 2.69 (dq, J=14.0, 6.8 Hz, 1H), 2.15-2.03 (m, 2H), 2.00-1.70 (m, 4H), 1.61 (ddd, J=13.5, 9.6, 3.7 Hz, 1H), 1.44 (t, J=7.4 Hz, 2H).

Intermediate F, first eluted diastereomer after silica gel column chromatography (absolute stereochemistry tentatively assigned as drawn): $^1$H NMR (400 MHz, Chloroform-d) b 8.38 (s, 1H), 7.23 (d, J=2.1 Hz, 1H), 7.18 (d, J=5.2 Hz, 1H), 7.10 (d, J=5.3 Hz, 1H), 7.06 (dd, J=8.2, 2.1 Hz, 1H), 6.92 (d, J=8.2 Hz, 1H), 4.21-4.01 (m, 2H), 4.02-3.86 (m, 2H), 3.62 (q, J=7.4 Hz, 1H), 3.53-3.15 (m, 3H), 2.87-2.74 (m, 1H), 2.09 (td, J=9.7, 8.7, 6.6 Hz, 1H), 1.97-1.72 (m, 3H), 1.60 (ddd, J=13.4, 9.5, 3.6 Hz, 1H), 1.44 (t, J=7.4 Hz, 3H), 1.25 (s, 1H).

Intermediate G and Intermediate H

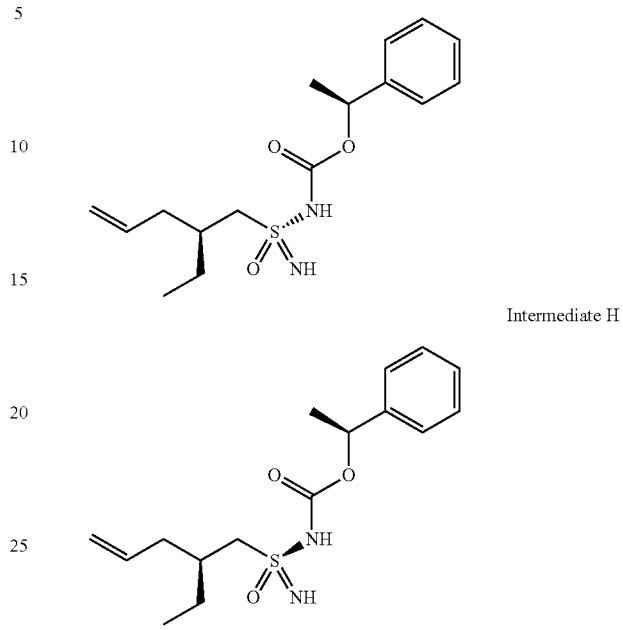

Intermediate G and Intermediate H were synthesized in the same manner as Intermediate A and Intermediate B starting with (S)-2-ethylpent-4-ene-1-sulfonamide (WO 2016033486).

Intermediate G, the first eluted diastereomer (Rt=1.73 min on Chiralpak IC, 40% ethanol co-solvent, absolute stereochemistry tentatively assigned as drawn): $^1$H NMR (400 MHz, DMSO-$d_6$) δ 7.35 (d, J=3.6 Hz, 4H), 7.31-7.23 (m, 3H), 5.77-5.65 (m, 1H), 5.61 (q, J=6.6 Hz, 1H), 5.11-5.00 (m, 2H), 3.33 (s, 1H), 3.31-3.19 (m, 2H), 2.25-2.06 (m, 2H), 1.97 (p, J=6.1 Hz, 1H), 1.42 (d, J=6.6 Hz, 4H), 1.39 (dd, J=8.0, 2.2 Hz, 2H), 0.83 (t, J=7.4 Hz, 3H).

Intermediate H, the second eluted diastereomer (Rt=2.17 min on Chiralpak IC, 40% ethanol co-solvent, absolute stereochemistry tentatively assigned as drawn): $^1$H NMR (400 MHz, DMSO-$d_6$) δ 7.33 (d, J=3.9 Hz, 4H), 7.31-7.22 (m, 3H), 5.72-5.56 (m, 2H), 5.06-4.90 (m, 2H), 3.32 (s, 1H), 3.25 (d, J=5.8 Hz, 2H), 2.17-1.99 (m, 2H), 1.94 (hept, J=6.0 Hz, 1H), 1.51-1.34 (m, 5H), 0.83 (t, J=7.4 Hz, 3H).

Intermediate I
Method 1.

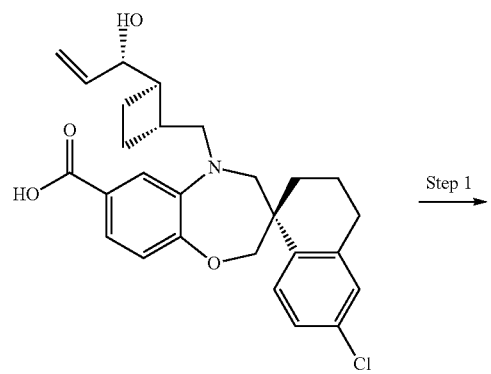

Step 1

-continued
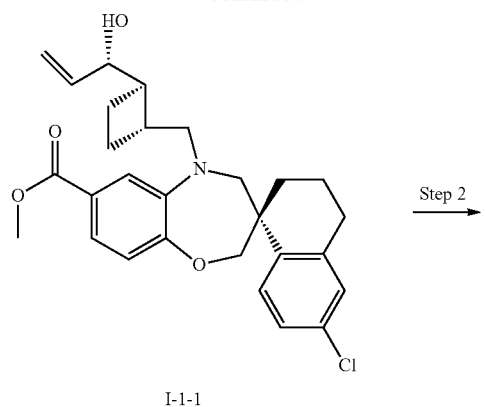
I-1-1
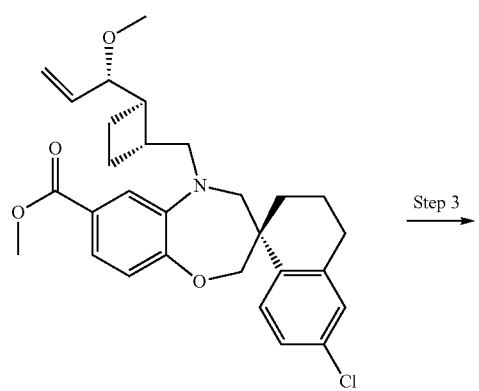
I-1-2
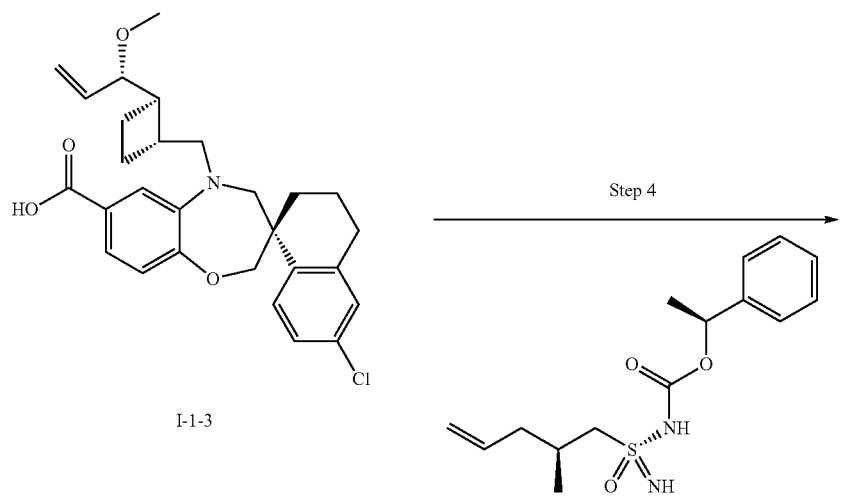
I-1-3   Intermediate C

-continued
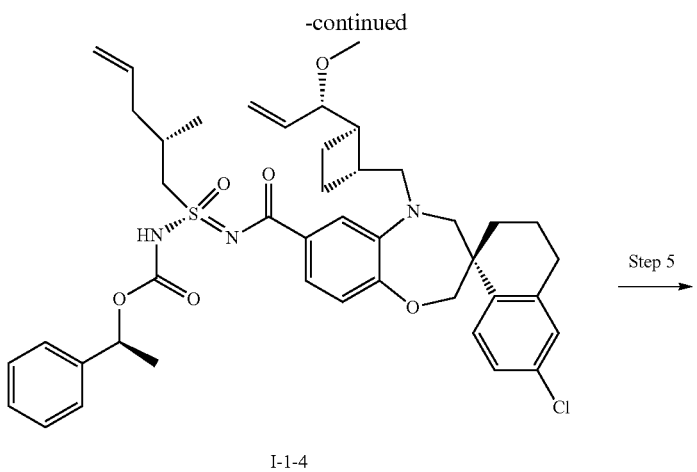
I-1-4
Step 5
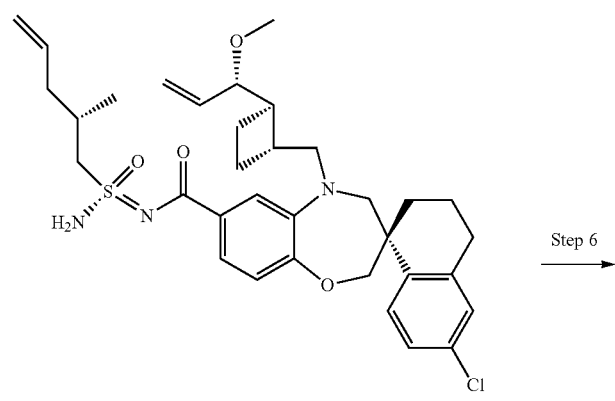
I-1-5
Step 6
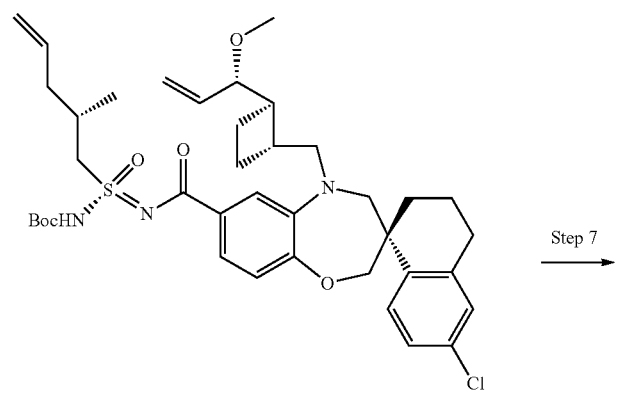
I-1-6
Step 7

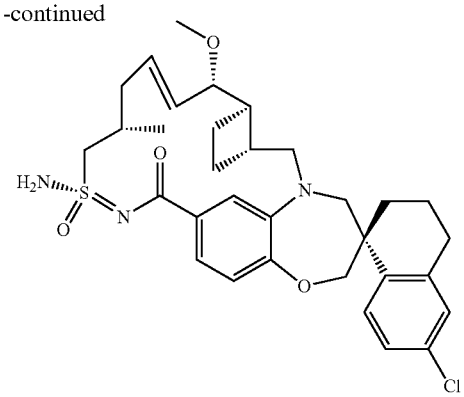

Intermediate I

Step 1: To a stirred solution of (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (WO 2016033486) (1.02 g, 2.18 mmol) in THF (10 mL) at 0° C. was added sodium hydride (60% in mineral oil, 183.1 mg, 4.57 mmol, followed by iodomethane (618.7 mg, 4.359 mmol). The resulting mixture was brought to rt, and stirred for 5 h. The reaction mixture was then poured into ice cold $H_2O$ and extracted with $CH_2Cl_2$. The organic layer was concentrated and purified by silica gel column (EtOAc/Hexanes=2/3) to afford I-1-1. LCMS-ESI+ (m/z): [M+H]$^+$ calcd for $C_{28}H_{32}ClNO_4$: 482.0; found: 482.2.

Step 2: To a stirred solution of I-1-1 (707.0 mg, 1.4 mmol) in DMF (8 mL) at 0° C. was added sodium hydride (60% in mineral oil, 88.0 mg, 2.2 mmol), followed by iodomethane (312.3 mg, 2.2 mmol). The resulting mixture was stirred at rt overnight. The reaction mixture was then poured into ice cold $H_2O$ and extracted with DCM. The organic layer was concentrated and purified by silica gel column (EtOAc/Hexanes=1/4) to afford I-1-2. LCMS-ESI+ (m/z): [M+H]$^+$ calcd for $C_{29}H_{34}ClNO_4$: 496.0; found: 496.2.

Step 3: I-1-2 (659.0 mg, 1.33 mmol) was stirred in 2N aq NaOH (3 mL) and MeOH (8 mL) at 60° C. overnight. After cooling, the mixture was acidified with HCl and concentrated. The resulting solid was treated with $CH_2Cl_2$ and filtered. The filtrate was concentrated to yield crude I-1-3, which was used directly in the next step. LCMS-ESI+ (m/z): [M+H]$^+$ calcd for $C_{28}H_{32}ClNO_4$: 482.2; found: 482.1.

Step 4: To a stirred solution of intermediate I-1-3 (9.68 g, 20.1 mmol) in DCM (200 mL) was added Intermediate C (6.17 g, 19.9 mmol), EDCI (7.62 g, 39.75 mmol) and DMAP (4.21 g, 34.46 mmol). The reaction mixture was stirred at rt overnight. Then the reaction mixture was diluted with DCM, washed with 1 N HCl and brine. The organic phase was dried over $MgSO_4$, filtered, and concentrated to give I-1-4, which was used without further purification.

Step 5: To a solution of intermediate I-1-4 (12.7 g, 16.4 mmol) in DCM (130 mL), was added TFA (25 mL). The reaction mixture was stirred at rt. Upon completion, the solvent was removed under vacuum. The residue was dissolved in DCM, washed with saturated $NaHCO_3$ solution. The organic phase was separated, dried over $MgSO_4$, filtered, and concentrated to give I-1-5 which was used without further purification.

Step 6: To a solution of intermediate I-1-5 (10 g, 15.97 mmol) in DCM, was added triethylamine (4.45 ml, 31.94 mmol), DMAP (500 mg, 4.09 mmol) and di-tert-butyl dicarbonate (5.23 g, 23.95 mmol). The reaction mixture was stirred at rt overnight. The reaction mixture was washed with 1 N HCl (aq) and brine. The organic phase was separated, dried over $MgSO_4$, filtered, concentrated, and purified by silica gel column chromatography (0-100% EtOAc/hexanes) to give I-1-6.

Step 7: A solution of I-1-6 (1 g, 1.38 mmol) and Hoveyda-Grubbs II (258.13 mg, 0.41 mmol) in 1,2-dichloroethane (400 mL) was degassed with argon. The reaction mixture was stirred at 60° C. overnight. The reaction mixture was concentrated and the residue was purified by column chromatography (silica gel, 0-70% EtOAc/hexanes) to give Intermediate 1. $^1$H NMR (400 MHz, chloroform-d) δ 7.76 (d, J=8.5 Hz, 1H), 7.43 (dd, J=8.2, 1.9 Hz, 1H), 7.32 (d, J=2.0 Hz, 1H), 7.20 (dd, J=8.5, 2.3 Hz, 1H), 7.10 (d, J=2.3 Hz, 1H), 6.93 (d, J=8.2 Hz, 1H), 6.27 (ddd, J=15.1, 7.9, 5.2 Hz, 1H), 5.99 (s, 2H), 5.56 (dd, J=15.3, 8.2 Hz, 1H), 4.20 (s, 2H), 4.06 (t, J=11.4 Hz, 2H), 3.92-3.82 (m, 1H), 3.82-3.69 (m, 2H), 3.47 (d, J=5.6 Hz, 2H), 3.36 (d, J=14.6 Hz, 1H), 3.28 (s, 3H), 3.02 (dd, J=15.0, 11.0 Hz, 1H), 2.80 (dt, J=11.3, 5.1 Hz, 2H), 2.63-2.53 (m, 1H), 2.47-2.36 (m, 2H), 2.26 (dt, J=14.4, 7.3 Hz, 2H), 2.03-1.84 (m, 3H), 1.84-1.57 (m, 4H), 1.41 (t, J=13.4 Hz, 1H), 1.16 (d, J=6.1 Hz, 3H). LCMS-ESI+(m/z): [M+H]$^+$ calcd for $C_{32}H_{40}ClN_3O_4S$: 598.2; found: 598.1.

Method 2.

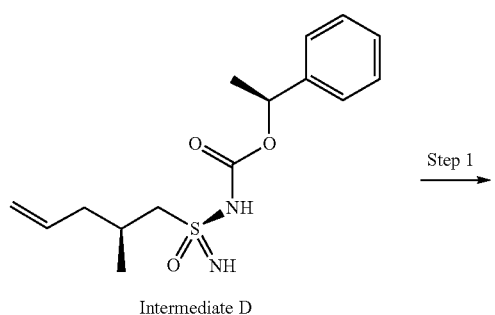

Intermediate D

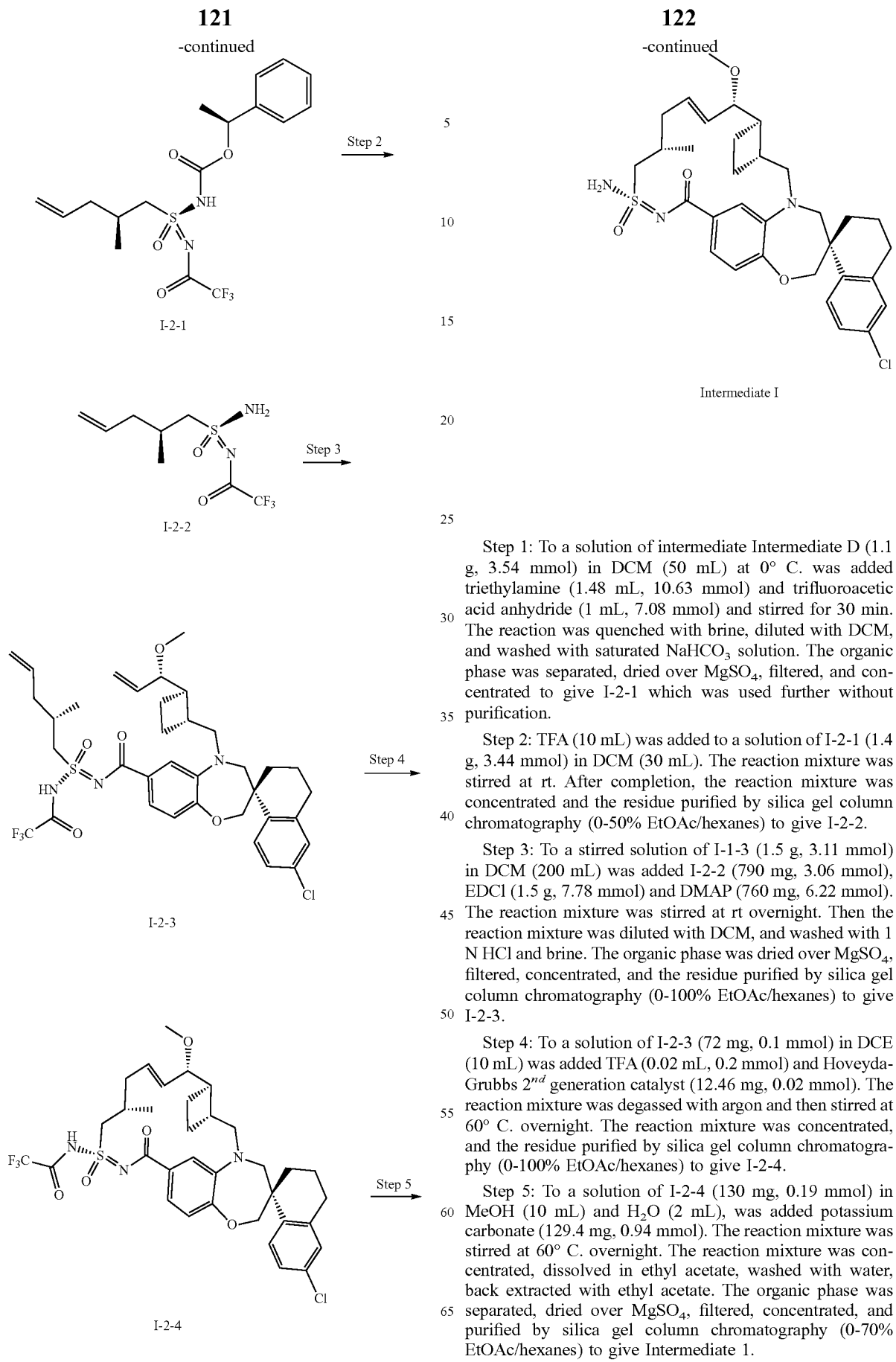

Step 1: To a solution of intermediate Intermediate D (1.1 g, 3.54 mmol) in DCM (50 mL) at 0° C. was added triethylamine (1.48 mL, 10.63 mmol) and trifluoroacetic acid anhydride (1 mL, 7.08 mmol) and stirred for 30 min. The reaction was quenched with brine, diluted with DCM, and washed with saturated NaHCO$_3$ solution. The organic phase was separated, dried over MgSO$_4$, filtered, and concentrated to give I-2-1 which was used further without purification.

Step 2: TFA (10 mL) was added to a solution of I-2-1 (1.4 g, 3.44 mmol) in DCM (30 mL). The reaction mixture was stirred at rt. After completion, the reaction mixture was concentrated and the residue purified by silica gel column chromatography (0-50% EtOAc/hexanes) to give I-2-2.

Step 3: To a stirred solution of I-1-3 (1.5 g, 3.11 mmol) in DCM (200 mL) was added I-2-2 (790 mg, 3.06 mmol), EDCl (1.5 g, 7.78 mmol) and DMAP (760 mg, 6.22 mmol). The reaction mixture was stirred at rt overnight. Then the reaction mixture was diluted with DCM, and washed with 1 N HCl and brine. The organic phase was dried over MgSO$_4$, filtered, concentrated, and the residue purified by silica gel column chromatography (0-100% EtOAc/hexanes) to give I-2-3.

Step 4: To a solution of I-2-3 (72 mg, 0.1 mmol) in DCE (10 mL) was added TFA (0.02 mL, 0.2 mmol) and Hoveyda-Grubbs 2$^{nd}$ generation catalyst (12.46 mg, 0.02 mmol). The reaction mixture was degassed with argon and then stirred at 60° C. overnight. The reaction mixture was concentrated, and the residue purified by silica gel column chromatography (0-100% EtOAc/hexanes) to give I-2-4.

Step 5: To a solution of I-2-4 (130 mg, 0.19 mmol) in MeOH (10 mL) and H$_2$O (2 mL), was added potassium carbonate (129.4 mg, 0.94 mmol). The reaction mixture was stirred at 60° C. overnight. The reaction mixture was concentrated, dissolved in ethyl acetate, washed with water, back extracted with ethyl acetate. The organic phase was separated, dried over MgSO$_4$, filtered, concentrated, and purified by silica gel column chromatography (0-70% EtOAc/hexanes) to give Intermediate 1.

Method 3.

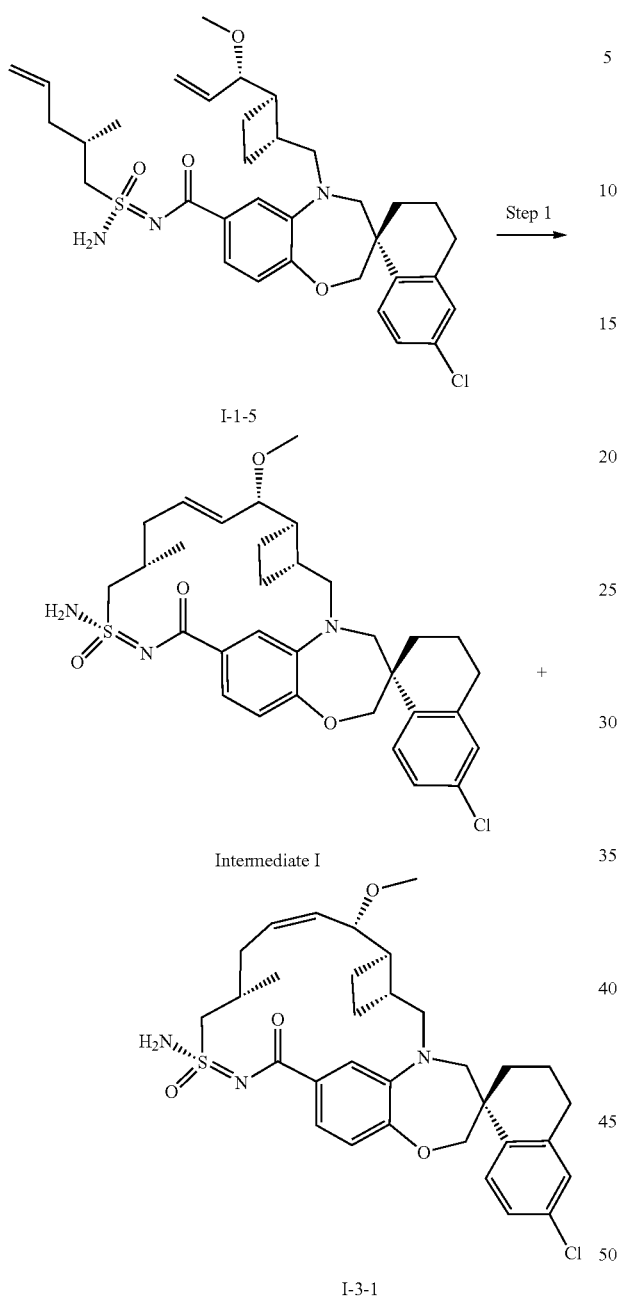

Intermediate I

I-3-1

Step 1: A stirred mixture of I-1-5 (2.14 g, 3.42 mmol), magnesium oxide (413 mg, 10.3 mmol), and Hoveyda-Grubbs 2$^{nd}$ generation catalyst (449 mg, 717 μmol) in 1,2-dichloroethane (485 mL) was heated to 80° C., and stirred for 18.5 h. The resulting mixture was cooled to room temperature, filtered through celite, and concentrated under reduced pressure. The residue was dissolved in a mixture of ethyl acetate (50 mL) and toluene (100 mL). Silica gel (40 g) was added, and the resulting slurry was concentrated under reduced pressure. The residue was purified by flash column chromatography on silica gel (0 to 65% ethyl acetate in hexanes), and repurified by reverse phase preparative HPLC (0.1% trifluoroacetic acid in acetonitrile/water) to give Intermediate I and I-3-1.

I-3-1: $^1$H NMR (400 MHz, Acetone-$d_6$) δ 7.79 (d, J=8.5 Hz, 1H), 7.39 (d, J=1.9 Hz, 1H), 7.31 (dd, J=8.2, 1.9 Hz, 1H), 7.24 (dd, J=8.5, 2.4 Hz, 1H), 7.14 (d, J=2.3 Hz, 1H), 7.07 (s, 1H), 6.89 (d, J=8.2 Hz, 1H), 5.82 (td, J=9.8, 6.1 Hz, 1H), 5.54-5.43 (m, 1H), 4.28-4.17 (m, 1H), 4.11 (d, J=12.1 Hz, 1H), 4.01 (d, J=12.1 Hz, 1H), 3.94 (d, J=15.1 Hz, 1H), 3.78 (d, J=14.3 Hz, 1H), 3.64 (dd, J=14.3, 3.4 Hz, 1H), 3.49 (d, J=14.3 Hz, 1H), 3.40 (dd, J=14.3, 8.1 Hz, 1H), 3.28 (dd, J=15.2, 10.7 Hz, 1H), 3.23 (s, 3H), 2.88-1.27 (m, 15H), 1.17 (d, J=6.9 Hz, 3H). LCMS-ESI+ (m/z): [M+H]$^+$ calcd for $C_{32}H_{40}ClN_3O_4S$: 598.2; found: 598.2.

Intermediate J

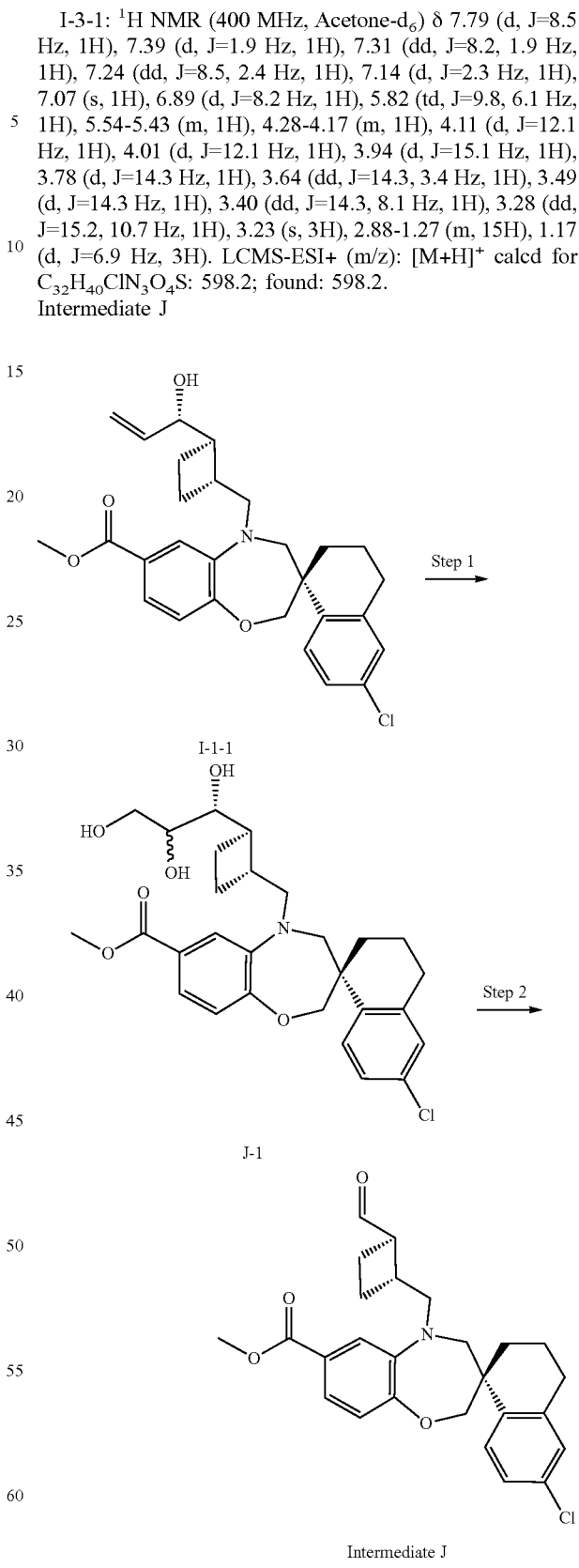

Intermediate J

Step 1: A solution of osmium tetroxide (260 mg, 0.026 mmol) was added to a mixture of I-1-1 (2.5 g, 5.19 mmol), N-methylmorpholine N-oxide (911 mg, 7.78 mmol), and DMAP (6 mg, 0.052 mmol) in tBuOH (2.4 mL), THF (0.8 mL), and water (0.8 mL). The resulting solution was heated to 45° C. for 4 h, then to 80° C. for 4 h, then allowed to cool to ambient temperature. The reaction was quenched by addition of sodium sulfite and water and vigorous stirring of the subsequent mixture for 20 min. The mixture was filtered through celite, and the filter cake washed with EtOAc. The combined organic phases were dried over magnesium sulfate, filtered, and concentrated to yield J-1, which was carried forward crude to the next step.

Step 2: A solution of sodium periodate (3.33 g, 15.6 mmol) in water (33 mL) was added dropwise to J-1 (2.68 g, 5.19 mmol) in acetone (21 mL) at 0° C. The reaction was then warmed to ambient temperature and stirred for 120 min. Acetone was removed under reduced pressure and the aqueous layer was extracted with EtOAc. The combined organic layer was washed with brine, dried over magnesium sulfate, filtered, and concentrated. Purification by silica gel flash column chromatography (0 to 30% ethyl acetate in hexane) gave Intermediate J. LCMS-ESI+: (m/z): [M+H]+ calcd for $C_{26}H_{28}ClNO_4$: 454.2; found: 454.2.

Intermediate K
Method 1.

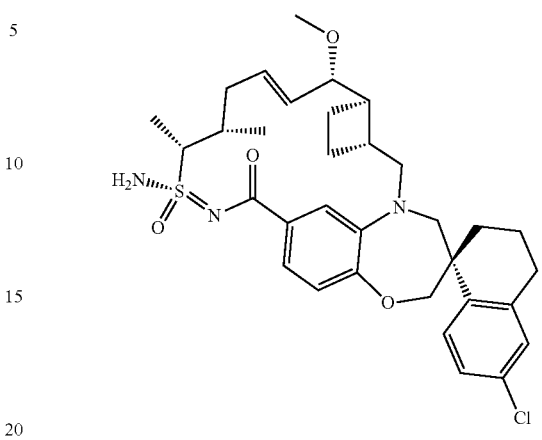

Intermediate K was synthesized in the same manner as Intermediate I (Method 1-Steps 4-7) using Intermediate A instead of Intermediate C. $^1$H NMR (400 MHz, Chloroform-d) δ 7.778 (d, J=8.5 Hz, 1H), 7.45 (dd, J=8.3, 1.9 Hz, 1H), 7.30 (d, J=2.0 Hz, 1H), 7.20 (dd, J=8.5, 2.3 Hz, 1H), 7.10 (d, J=2.4 Hz, 1H), 6.93 (d, J=8.3 Hz, 1H), 5.91 (dt, J=15.8, 5.8 Hz, 1H), 5.69 (dd, J=15.8, 6.8 Hz, 1H), 4.18-3.95 (m, 2H), 3.87 (dd, J=14.9, 3.4 Hz, 1H), 3.73 (s, 5H), 3.41-3.23 (m, 4H), 3.01 (dd, J=15.0, 10.9 Hz, 1H), 2.89-2.72 (m, 2H), 2.62 (s, 2H), 2.46 (s, 1H), 2.31-2.01 (m, 3H), 1.99-1.64 (m, 6H), 1.46 (s, 3H), 1.11 (d, J=6.9 Hz, 3H). LCMS-ESI+ (m/z): [M+H]+ calcd for $C_{33}H_{42}ClN_3O_4S$: 612.26; found: 612.06.
Method 2.

Intermediate K was prepared in a similar manner to Intermediate I (method 2) from Intermediate B.

Intermediate L

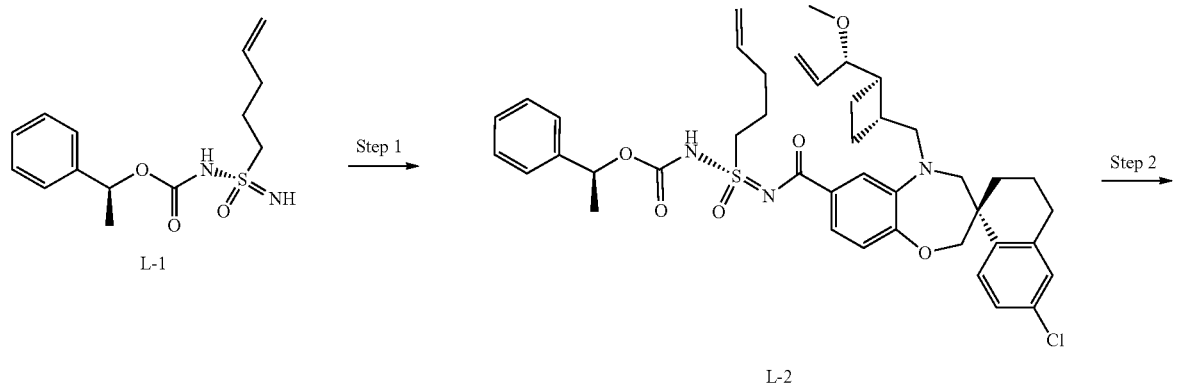

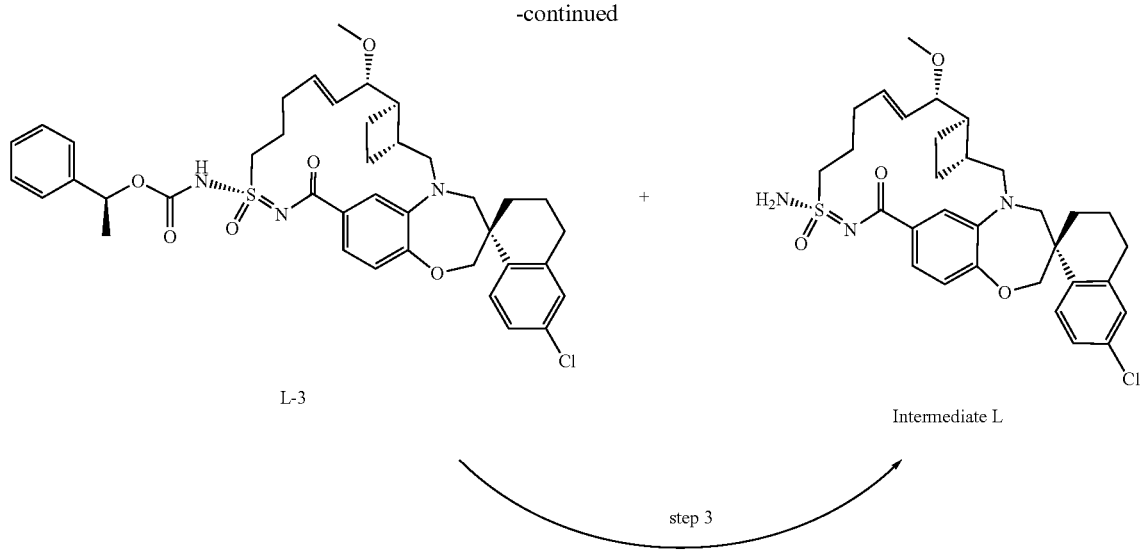

Preparation of L-1: L-1 was prepared in a similar manner to Intermediate A using pent-4-ene-1-sulfonamide instead of (2R,3S)-3-methylhex-5-ene-2-sulfonamide and Step 5 conducted at rt instead of at 0° C. $^1$H NMR (400 MHz, Chloroform-d) δ 7.45-7.31 (m, 4H), 5.83-5.59 (m, 2H), 5.12-4.96 (m, 2H), 3.35-3.21 (m, 2H), 2.28-2.11 (m, 2H), 2.01-1.87 (m, 2H), 1.59 (d, J=6.7 Hz, 3H).

Step 1: To a mixture of I-1-3 (215 mg, 0.45 mmol) in DCM (20 mL) at 0° C. was added EDCl (152 mg, 0.98 mmol) followed by DMAP (120 mg, 0.98 mmol). After 5 min, a solution of L-1 (159 mg, 0.54 mmol) in DCM (3 mL) was added, and the resulting mixture was removed from the cooling bath and stirred at rt overnight. The reaction was further diluted with DCM (30 mL) and washed with 1 N HCl (15 mL), saturated sodium bicarbonate (15 mL) and brine (15 mL), dried over sodium sulfate, filtered, concentrated, and the residue purified by normal phase chromatography (silica gel column, 0-80% EtOAc/Hexanes) to give L-2. LCMS-ESI+ (m/z): [M+H]$^+$ calcd: 761.0, found: 759.9. $^1$H NMR (400 MHz, Chloroform-d) δ 7.67 (d, J=8.5 Hz, 1H), 7.50 (s, 1H), 7.39-7.28 (m, 6H), 7.16 (dd, J=8.5, 2.3 Hz, 1H), 7.08 (d, J=2.3 Hz, 1H), 6.91 (d, J=8.2 Hz, 1H), 5.86 (p, J=6.3 Hz, 1H), 5.77-5.48 (m, 2H), 5.21-5.08 (m, 2H), 5.08-4.96 (m, 2H), 4.14-4.04 (m, 2H), 3.81-3.71 (m, 2H), 3.70-3.48 (m, 3H), 3.39-3.13 (m, 5H), 2.84-2.69 (m, 2H), 2.52 (dd, J=10.7, 7.4 Hz, 1H), 2.16 (dt, J=13.3, 7.6 Hz, 3H), 2.01-1.74 (m, 7H), 1.70-1.39 (m, 7H).

Step 2: A solution L-2 in DCE (10 mL) was sparged with nitrogen for 5 min before Hoveyda-Grubbs 2$^{nd}$ generation catalyst (7 mg, 0.011 mmol) was added. The newly formed mixture was degassed for another 2 minutes and was capped and heated at 60° C. for 16 hrs. The reaction was then cooled to rt, concentrated, and purified by normal phase chromatography (silica gel, 0-5% DCM/MeOH (with 2.0 N NH$_3$)) to give Intermediate L as the earlier eluting peak and L-3 as the later. Intermediate L: LCMS-ESI+ (m/z): [M+H]$^+$ calcd for $C_{31}H_{38}ClN_3O_4S$: 584.2; found: 583.4. L-3: LCMS-ESI+ (m/z): [M+H]$^+$ calcd for $C_{40}H_{46}ClN_3O_6S$: 732.9; found: 730.8.

Step 3: TFA (1.0 mL) was added to a solution of L-3 (15.8 mg, 0.022 mmol) in DCM (1.0 mL) at 0° C. The resulting mixture was stirred at 0° C. for 2 min and then rt for 1 hr. The reaction was cooled back to 0° C. and basified with 1 N NaOH to pH=8. The mixture was extracted with DCM (2×). Combined organic layers were washed with brine (1×), dried over sodium sulfate, filtered, concentrated, and the residue purified by flash column chromatography (silica gel, 0-100% EtOAc/Hexanes) to give Intermediate L. $^1$H NMR (400 MHz, Chloroform-d): δ 7.73 (d, J=8.6 Hz, 1H), 7.44-7.39 (m, 1H), 7.33 (d, J=1.8 Hz, 1H), 7.16 (dd, J=8.5, 2.3 Hz, 1H), 7.06 (d, J=2.3 Hz, 1H), 6.90 (d, J=8.2 Hz, 1H), 6.04-5.93 (m, 1H), 5.73-5.61 (m, 1H), 4.12-3.94 (m, 2H), 3.88-3.68 (m, 2H), 3.62-3.51 (m, 2H), 3.40-3.17 (m, 6H), 3.00 (dd, J=15.0, 11.0 Hz, 1H), 2.82-2.63 (m, 4H), 2.47-2.20 (m, 4H), 1.99-1.59 (m, 6H), 1.37 (t, J=13.1 Hz, 1H). LCMS-ESI+ (m/z): [M+H]$^+$ calcd for $C_{31}H_{38}ClN_3O_4S$: 584.2, found: 583.3.

Intermediate M

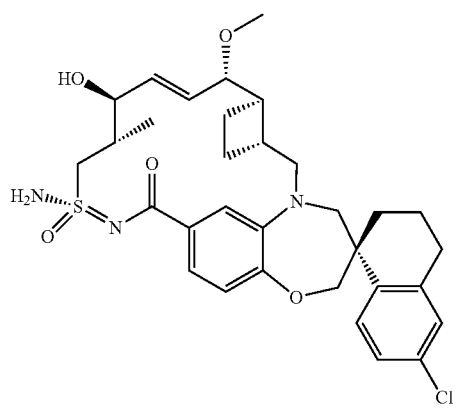 [SMILES: CO[C@H]1/C=C/[C@H](O)[C@H](C)C[S@](N)(=O)=NC(=O)c2ccc3c(c2)N(C[C@@H]2CC[C@H]21)C[C@@]1(CCCc2cc(Cl)ccc21)CO3]

Intermediate I (445 mg, 0.744 mmol) was dissolved in 1,4-dioxane (7 mL). Selenium dioxide (330 mg, 4 equiv.)

was added in one portion. The mixture was heated to reflux until LCMS indicated approximately 50% conversion to the corresponding allylic alcohol. The reaction mixture was then cooled to room temperature and the residue was purified by Gilson reverse phase prep HPLC (40-90% MeCN/H₂O with 0.1% TFA) to give Intermediate M as the major product. ¹H NMR (400 MHz, Methanol-d₄) δ 7.76 (d, J=8.6 Hz, 1H), 7.29 (dd, J=8.2, 1.9 Hz, 1H), 7.18 (dd, J=8.6, 2.3 Hz, 1H), 7.11 (d, J=2.4 Hz, 1H), 7.07 (d, J=1.9 Hz, 1H), 6.84 (d, J=8.2 Hz, 1H), 6.25 (dd, J=15.3, 6.1 Hz, 1H), 5.76 (dd, J=15.5, 9.0 Hz, 1H), 4.38 (d, J=6.0 Hz, 1H), 4.26 (dd, J=15.0, 6.1 Hz, 1H), 4.09-4.00 (m, 2H), 3.93-3.81 (m, 2H), 3.65 (d, J=14.1 Hz, 1H), 3.30 (m, 6H), 3.10-3.03 (m, 1H), 2.87-2.70 (m, 3H), 2.57-2.30 (m, 2H), 2.25-2.09 (m, 2H), 2.01-1.66 (m, 7H), 1.43 (t, J=12.7 Hz, 1H), 1.21 (d, J=6.9 Hz, 3H). LCMS-ESI+ (m/z): [M+H]⁺ calcd for $C_{32}H_{40}ClN_3O_5S$: 614.3; found: 614.1.

Intermediate N

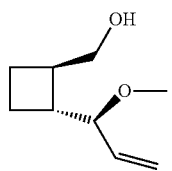

Step 1: A 2.5M solution of n-BuLi in hexane (0.179 L, 448.7 mmol) was added to a stirred solution of (1R,2S)-2-morpholino-1-phenyl-1-propanol (Chemistry Eur. J. 2007, pp. 2587) (99.1 g, 448.7 mmol) in toluene (0.39 L) at −15° C. and stirred for 30 min. Then a 0.28 M solution of divinylzinc in 1:1 ethyl ether:THF (1.6 L, 448.7 mmol) was added, and the reaction mixture was stirred for 1 h. ((1R, 2R)-2-formylcyclobutyl)methyl acetate (WO 2016033486) (35 g, 224.3 mol) in toluene (0.39 L) was added, and reaction was stirred for 2 h. The reaction was quenched with 30% citric acid solution, and diluted with ethyl acetate. The organic layer was separated and the aqueous layer was extracted with ethyl acetate. The combined organic layer was washed with brine, dried over anhydrous Na₂SO₄, filtered, and concentrated under reduced pressure. The crude was purified by silica gel column (10-20% EtOAc in petroleum ether) to afford ((1R,2R)-2-((S)-1-hydroxyallyl)cyclobutyl)methyl acetate. ¹H NMR (400 MHz, Chloroform-d) δ 5.88-5.67 (m, 1H), 5.31-5.19 (m, 1H), 5.19-5.06 (m, 1H), 4.18-4.08 (m, 1H), 4.07-3.91 (m, 1H), 2.60-2.36 (m, 1H), 2.15-2.09 (m, 1H), 2.06 (s, 3H), 2.04 (d, J=3.7 Hz, 1H), 1.99-1.91 (m, 1H), 1.91-1.81 (m, 1H), 1.72-1.56 (m, 1H).

Step 2: Potassium carbonate (79 g, 570 mmol) was added to a stirred solution of ((1R,2R)-2-((S)-1-hydroxyallyl)cyclobutyl)methyl acetate (35 g, 190 mmol) in MeOH (0.35 L) and stirred at rt for 4 h. The reaction mixture cooled to 0° C., water and EtOAc were added and stirred for 20 min at rt. The organic layer was separated, and the aqueous layer extracted with EtOAc. The combined organic layer was washed with brine, dried over anhydrous Na₂SO₄, filtered, and concentrated under reduced pressure. The crude was purified by silica gel column (20-30% EtOAc in petroleum ether) to afford (S)-1-((1R,2R)-2-(hydroxymethyl)cyclobutyl)prop-2-en-1-ol. ¹H NMR (400 MHz, Chloroform-d) δ 5.75 (ddd, J=17.0, 10.4, 6.5 Hz, 1H), 5.33-5.18 (m, 1H), 5.16-5.06 (m, 1H), 3.91 (dd, J=9.6, 6.5 Hz, 1H), 3.69 (d, J=10.3 Hz, 1H), 3.42 (t, J=10.3 Hz, 1H), 2.94 (d, J=40.8 Hz, 2H), 2.41-2.21 (m, 1H), 2.11-1.93 (m, 1H), 1.64-1.61 (m, 1H), 1.70-1.47 (m, 1H).

Step 3: tert-Butyldiphenylchlorosilane (37 g, 134 mmol) was added dropwise to a stirred solution of (S)-1-((1R,2R)-2-(hydroxymethyl)cyclobutyl)prop-2-en-1-ol (19 g, 134 mmol) and imidazole (18 g, 267 mmol) in DCM (0.38 L) at 0° C., and the reaction was stirred for 1 h. The reaction was quenched with cold water and diluted with DCM. The organic layer was separated and aqueous extracted with DCM. The combined organic layer was washed with brine, dried over anhydrous Na₂SO₄, filtered, and concentrated under reduced pressure. The crude was purified by silica gel (5-10% EtOAc in petroleum ether), to afford (S)-1-((1R,2R)-2-(((tert-butyldiphenylsilyl)oxy)methyl)cyclobutyl)prop-2-en-1-ol.

Step 4: Sodium hydride (60% in mineral oil, 11.6 g, 292 mmol) was added to a stirred solution of (S)-1-((1R,2R)-2-(((tert-butyldiphenylsilyl)oxy)methyl)cyclobutyl)prop-2-en-1-ol (37 g, 97.3 mmol) and methyl iodide (30.3 mL, 486 mmol) in THF (0.37 L) at 0° C. and the reaction was brought to rt and stirred for 4 h. The reaction was quenched with cold water and diluted with ethyl acetate. The organic layer was separated and aqueous layer was extracted with ethyl acetate. The combined organic layer was washed with brine, dried over anhydrous Na₂SO₄, filtered, and concentrated under reduced pressure. The crude was diluted with 20% EtOAc in petroleum ether, passed through a plug of silica gel, and concentrated under reduced pressure to afford tert-butyl(((1R,2R)-2-((S)-1-methoxyallyl)cyclobutyl)methoxy)diphenylsilane.

Step 5: A 1.0 M solution of TBAF in THF (141 mL, 141 mmol) was added to a stirred solution of tert-butyl(((1R, 2R)-2-((S)-1-methoxyallyl)cyclobutyl)methoxy)diphenylsilane (37 g, 94 mmol) in THF (0.37 L) at 0° C., and the reaction was brought to rt and stirred for 4 h. The reaction was cooled to 0° C., diluted with water and EtOAc, brought to rt and stirred for 20 min. The organic layer was separated, and the aqueous layer was extracted with EtOAc. The combined organic layer was washed with brine, dried over anhydrous Na₂SO₄, filtered, and concentrated under reduced pressure. The crude was purified by silica gel column (5-10% EtOAc in petroleum ether) to afford Intermediate N. ¹H NMR (400 MHz, DMSO-d₆) δ 5.62-5.49 (m, 1H), 5.24-5.19 (m, 1H), 5.18 (d, J=0.9 Hz, 1H), 4.25 (dd, J=5.9, 4.7 Hz, 1H), 3.45 (t, J=7.7 Hz, 1H), 3.38 (m, 1H), 3.34-3.25 (m, 1H), 3.17 (s, 3H), 2.28-2.15 (m, 1H), 2.13-1.97 (m, 1H), 1.85-1.74 (m, 1H), 1.74-1.64 (m, 1H), 1.64-1.52 (m, 2H).

Intermediate O
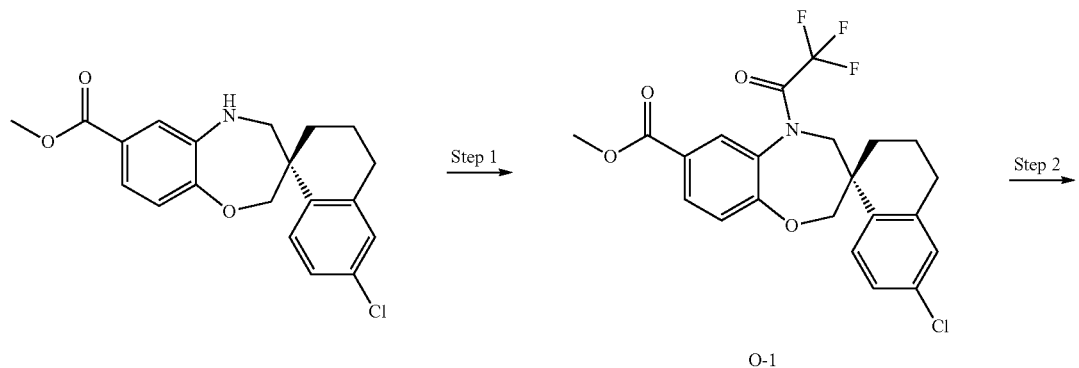
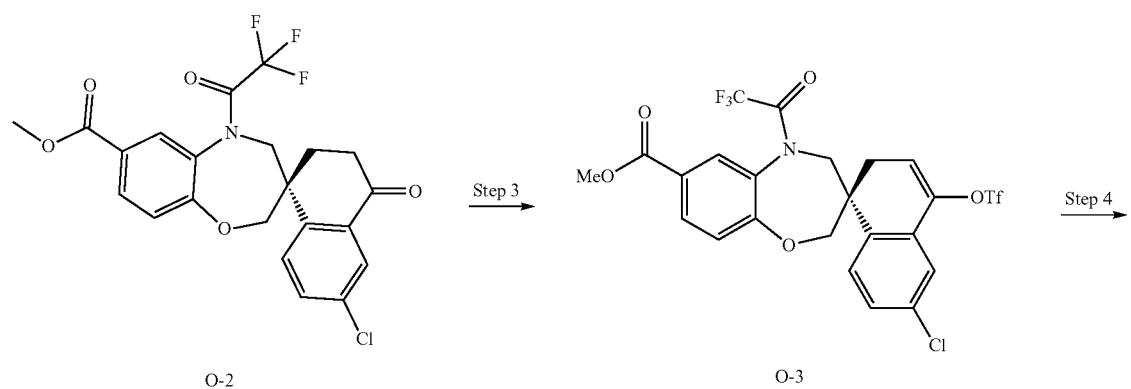
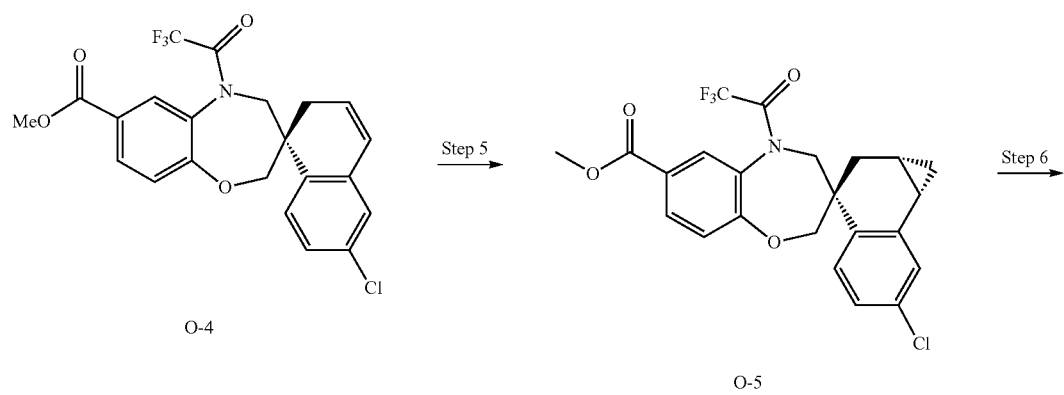

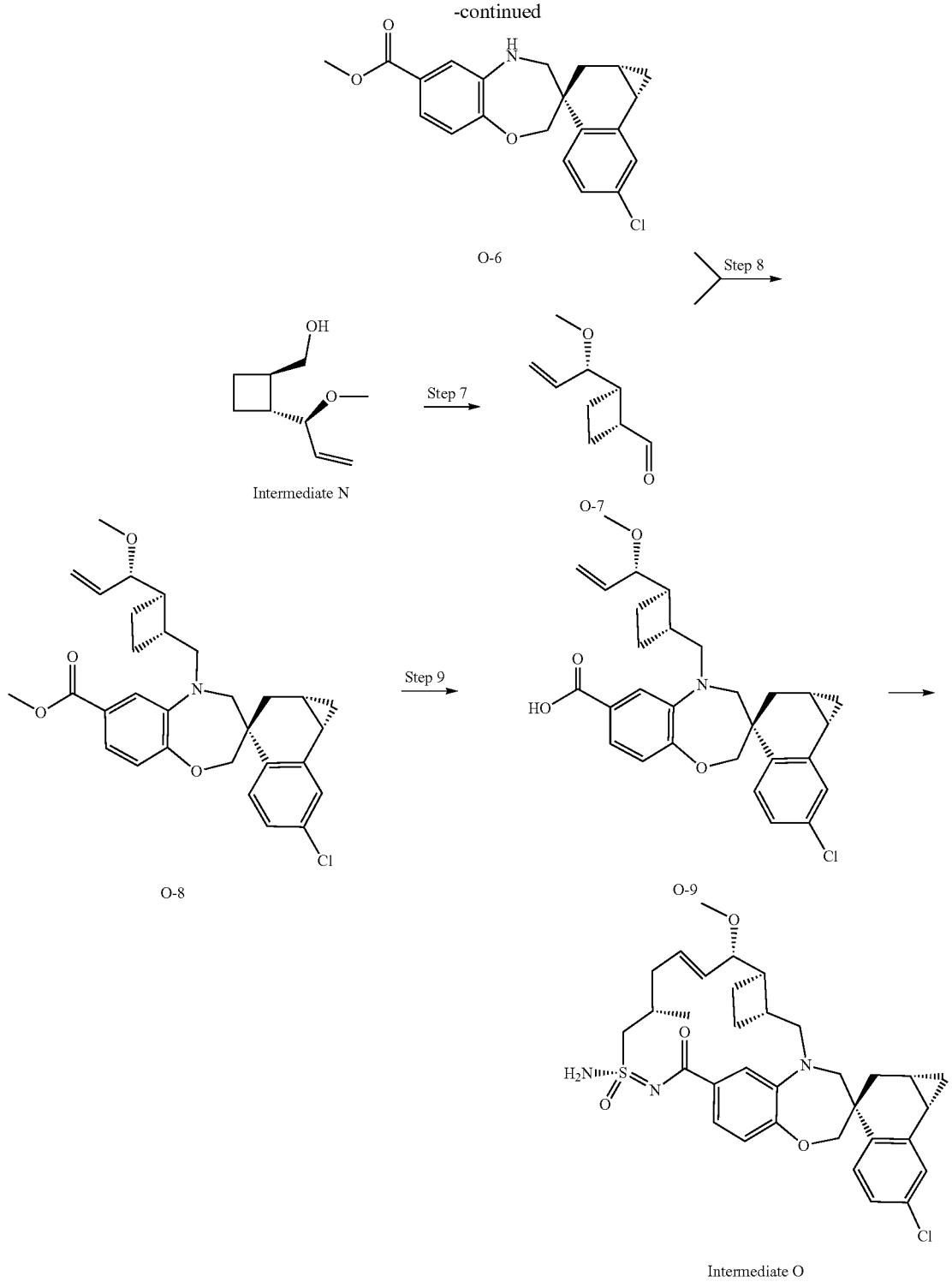

Step 1: To a solution of methyl (3S)-6'-chlorospiro[4,5-dihydro-2H-1,5-benzoxazepine-3,1'-tetralin]-7-carboxylate (5.03 g, 14.06 mmol) in DMF (9 mL), was added DMAP (1.89 g, 15.46 mmol) and triethylamine (14 ml, 0.1 mol). Then, trifluoroacetic anhydride (10 ml, 71.94 mmol) was added slowly at rt. The reaction mixture was stirred at 50° C. overnight. The reaction was cooled to rt, and triethylamine (4 ml, 0.03 mol) and trifluoroacetic anhydride (4 ml, 0.03 mol) was added. The reaction mixture was stirred at 50° C. overnight. The reaction mixture was diluted with EtOAc, washed with water, and back extracted with EtOAc. The combined organic phase was washed with 1 N HCl solution and saturated NaHCO₃ solution, dried over MgSO₄, filtered, concentrated, and purified by silica gel chromatography (0-20% EtOAc/hexane) to give O-1. ¹H NMR (400 MHz, Chloroform-d) δ 8.09 (dd, J=8.4, 2.1 Hz, 1H), 7.99 (s, 1H), 7.27 (s, 1H), 7.19 (d, J=2.2 Hz, 1H), 7.15-7.07 (m, 1H), 7.00 (d, J=8.3 Hz, 1H), 4.91 (d, J=13.8 Hz, 1H), 4.26 (d, J=12.4 Hz, 1H), 3.96 (s, 3H), 3.83 (d, J=12.4 Hz, 1H), 3.23 (d, J=13.8 Hz, 1H), 2.94-2.75 (m, 2H), 2.07 (s, 1H), 2.00 (d, J=12.0 Hz, 2H), 1.91-1.78 (m, 1H).

Step 2: To a solution of O-1 (1.8 g, 3.97 mmol) in benzene (50 mL), was added t-butyl hydroperoxide (70%, 2.72 ml, 19.83 mmol) and pyridinium dichromate (4.47 g, 11.9 mmol). The reaction mixture was stirred at rt for one day. To this mixture was added t-butyl hydroperoxide (70%, 3.81 ml, 0.03 mol) and pyridinium dichromate (4.48 g, 0.01 mol). The reaction mixture was stirred at rt for a day. To the reaction mixture was added water and stirred at rt for 0.5 h. The layers were separated and the organic phase was washed with 10% $Na_2SO_3$ solution, 1% $Na_2S_2O_3$ solution, and brine. The organic phase was dried over $MgSO_4$, filtered, concentrated, and purified by silica gel chromatography (0-30% EtOAc/hexane) to give O-2. $^1$H NMR (400 MHz, Chloroform-d) δ 8.17-8.07 (m, 2H), 8.02 (s, 1H), 7.52 (dd, J=8.4, 2.4 Hz, 1H), 7.31 (s, 1H), 5.04 (d, J=13.9 Hz, 1H), 4.39 (d, J=12.5 Hz, 1H), 4.03 (d, J=12.3 Hz, 1H), 3.96 (s, 3H), 3.33 (d, J=13.9 Hz, 1H), 3.05 (q, J=8.0, 6.9 Hz, 1H), 2.80 (dt, J=18.0, 6.0 Hz, 1H), 2.32 (s, 1H), 1.56 (s, 2H).

Step 3: Lithium bis(trimethylsilyl)amide (1.0M THF, 20.39 ml) was added dropwise to a solution of O-2 (7.95 g, 16.99 mmol) in THF (60 mL) at −78° C., and stirred for 30 min. A solution of Phenyl triflimide (6.37 g, 17.84 mmol) in THF (25 mL) was added dropwise, and the reaction was warmed to 0° C. and stirred for 2.5 h before quenching with $H_2O$. The reaction mixture was then partitioned between EtOAc and $H_2O$, the aqueous layer collected and extracted with EtOAc. The combined organic layers were then washed with brine, dried over $MgSO_4$, filtered, concentrated, and purified by silica gel chromatography (0-100% EtOAc in hexane) to give O-3.

Step 4: A solution of 0-3 (10.08 g, 16.8 mmol) in DMF (100 mL) was sparged with argon for 15 min. Triethylsilane (2.8 ml, 17.5 mmol) and Dichloro 1,1-bis(diphenylphosphino)ferrocene palladium(II) dichloromethane (0.26 g, 0.35 mmol) were added. The resulted mixture was further sparged for 10 min and heated at 65° C. for 4 h. The reaction was cooled to rt, and partitioned between EtOAc and $H_2O$. The organic layer was washed with brine, dried over $MgSO_4$, filtered, concentrated, and purified by silica gel chromatography (0-30% EtOAc in hexane) to give O-4.

Step 5: A 500 mL 2-neck flask was fitted to an addition funnel, dried under vacuum and back-filled with argon, then charged with $CH_2Cl_2$ (24 mL) and cooled to 0° C. A solution of diethyl zinc (1 M hexanes, 5 equiv, 85 mmol, 85 mL) was added followed by $CH_2Cl_2$ (10 mL) to rinse the addition funnel. A solution of TFA (4.9 equiv, 83.2 mmol, 6.4 mL) in $CH_2Cl_2$ (12 mL) was added dropwise over 30 minutes followed by $CH_2Cl_2$ (5 mL). The reaction mixture was stirred for an additional 20 minutes and then a solution of diiodomethane (5 equiv, 84.9 mmol, 6.8 mL) in $CH_2Cl_2$ (12 mL) was added dropwise over 20 minutes, followed by $CH_2Cl_2$ (5 mL). The reaction mixture was stirred for an additional 20 minutes and then a solution of O-4 (1 equiv, 17.0 mmol, 7.67 g) in $CH_2Cl_2$ (12 mL) was added dropwise over 20 minutes, followed by $CH_2Cl_2$ (5 mL). The reaction mixture was then allowed to slowly warm from 0° C. to rt, and stirred for 62 hours. It was quenched with saturated ammonium chloride and extracted into $CH_2Cl_2$. The combined organic layer was washed with half-saturated aqueous sodium bicarbonate and half-saturated brine, dried over sodium sulfate, filtered, concentrated to give a 1.4:1 mixture of diastereomers by $^1$H NMR. It was purified by silica gel chromatography (0-30% EtOAc in hexanes) to afford the diastereomer O-5, as the less polar peak. $^1$H NMR (400 MHz, Methanol-$d_4$) δ 8.10-8.02 (m, 2H), 7.44 (d, J=2.2 Hz, 1H), 7.29 (d, J=8.3 Hz, 1H), 7.18-7.08 (m, 2H), 4.69 (dd, J=13.4, 2.4 Hz, 1H), 4.61 (dd, J=12.3, 2.4 Hz, 1H), 3.92 (s, 3H), 3.72 (d, J=13.4 Hz, 1H), 3.51 (d, J=12.1 Hz, 1H), 2.81 (dd, J=14.3, 8.4 Hz, 1H), 2.02 (td, J=8.8, 4.8 Hz, 1H), 1.52 (dt, J=8.4, 5.5 Hz, 1H), 1.39 (dd, J=14.2, 6.0 Hz, 1H), 1.28 (td, J=8.5, 4.3 Hz, 1H), 0.37 (q, J=4.6 Hz, 1H).

Step 6: A solution of 0-5 (2.59 g, 5.56 mmol) in anhydrous MeOH (56 mL) in an oven-dried 100 mL Schlenk flask was treated with sodium methoxide (1.5 g, 27.8 mmol) under argon, sealed and stirred for 15 hours at 65° C. The reaction mixture was cooled to rt, quenched with water and extracted into EtOAc. The combined organic layer was dried over sodium sulfate, filtered, and concentrated to afford O-6. LCMS-ESI+ (m/z): [M+H]$^+$ calcd for $C_{21}H_{20}ClNO_3$: 370.1; found: 370.2.

Step 7: To a stirred mixture of Intermediate N (67.3 mg, 0.43 mmol) in DCM (2.9 mL) at 0° C. was added Dess-Martin periodinane (238 mg, 0.56 mmol). The resulting mixture was removed from the cooling bath and stirred at rt for 1 hr. The reaction was cooled to 0° C., diluted with DCM (20.0 mL) and quenched with 1:1 mixture of 1 N sodium thiosulfate and saturated sodium bicarbonate (10.0 mL), stirred vigorously for 15 minutes. The layers were separated, and the aqueous layer was extracted with DCM (10.0 mL). Combined organic layers were washed with brine (10.0 mL), dried over sodium sulfate, filtered, and concentrated to afford O-7.

Step 8: A solution of intermediate O-6 (1.0 g, 2.7 mmol) and crude 0-7 (1.5 equiv, 4.06 mmol) in DCE (11 mL) and acetic acid (0.55 mL) was stirred for 30 minutes at room temperature. The reaction mixture was then cooled to 0° C. and treated with STAB (860 mg, 4.06 mmol) split into five portions over 60 minutes, then allowed to warm to rt, and stirred overnight. The reaction mixture was quenched with water and extracted with EtOAc thrice. The combined organic layer was washed with brine, dried over sodium sulfate, filtered, concentrated, and purified by silica gel chromatography (0-50% EtOAc in hexanes) to afford O-8. LCMS-ESI+ (m/z): [M+H]$^+$ calcd for $C_{30}H_{34}ClNO_4$: 508.2; found: 508.3.

Step 9: A solution of intermediate O-8 (1.27 g, 2.5 mmol) in 5/1/1 THF/MeOH/water (25 mL total) was treated with lithium hydroxide (599 mg, 25 mmol,) and heated to 60° C. overnight. The reaction mixture was quenched with 1 N HCl and extracted into $CH_2Cl_2$ thrice. The combined organic layer was washed with half-saturated brine, dried over sodium sulfate, filtered, and concentrated to afford the desired product O-9. LCMS-ESI+ (m/z): [M+H]$^+$ calcd for $C_{29}H_{32}ClNO_4$: 494.2; found: 494.2.

Synthesis of Intermediate O: Intermediate O was synthesized in a similar manner to Intermediate I (Method 1, steps 4-7), using O-9 and Intermediate C. LCMS-ESI+ (m/z): [M+H]$^+$ calcd for $C_{33}H_{40}ClN_3O_4S$: 610.2; found: 610.1.

Intermediate P

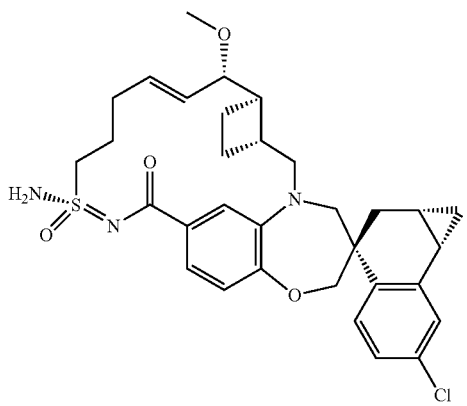 [SMILES: CO[C@H]1/C=C/CCC[S@](N)(=O)=NC(=O)c2ccc3c(c2)N(C[C@@H]2CC[C@H]21)C[C@]1(CO3)C[C@@H]2C[C@@H]2c2cc(Cl)ccc21]

Intermediate P was synthesized in a similar manner to Intermediate I (Method 1, steps 4-7) using L-1 in place of Intermediate C and O-9 in place of I-1-3.

Intermediate Q

Step 1: Ethyl (4-chlorophenyl)acetate (5.0 g, 25.17 mmol) was dissolved in $CCl_4$ (100 mL). To the solution were added azobisisobutyronitrile (124.0 mg, 0.755 mmol) and N-bromosuccinimide (5375.9 mg, 30.20 mmol) at rt. The mixture was heated at 80° C. for 15 h. After cooling to rt, the resulting suspension was filtered through Celite (3 g). Filtrate was washed with brine (30 mL×2), and dried over $Na_2SO_4$. The solvent was removed under reduced pressure to give Q-1, without further purification. $^1$H NMR (400 MHz, Acetone-$d_6$) b 7.65 (dd, J=8.6, 1.9 Hz, 2H), 7.53-7.38 (m, 2H), 5.70 (d, J=1.5 Hz, 1H), 4.33-4.14 (m, 2H), 1.35-1.13 (m, 3H).

Step 2: Thioglycolic acid (2.55 g, 27.69 mmol) was dissolved in DMF (30 mL). To the solution were added DIPEA (6.51 g, 27.69 mmol) and Q-1 (7.0 g, 25.17 mmol) at 0° C. The mixture was stirred at 0° C. for 2 h. To the solution were added HCl (2 mL), brine (30 mL) and EtOAc (100 mL). Layers were separated, and the organic layer was washed with brine (30 mL), dried over $Na_2SO_4$, concentrated and the residue purified by a silica-gel column chromatography (10% to 50% to 67% THF/hexane) to afford Q-2. $^1$H NMR (400 MHz, Acetone-$d_6$) δ 7.57-7.48 (m, 2H), 7.46-7.39 (m, 2H), 4.96 (s, 1H), 4.31-4.10 (m, 2H), 3.38 (d, J=15.3 Hz, 1H), 3.20 (d, J=15.3 Hz, 1H), 1.31-1.13 (m, 3H).

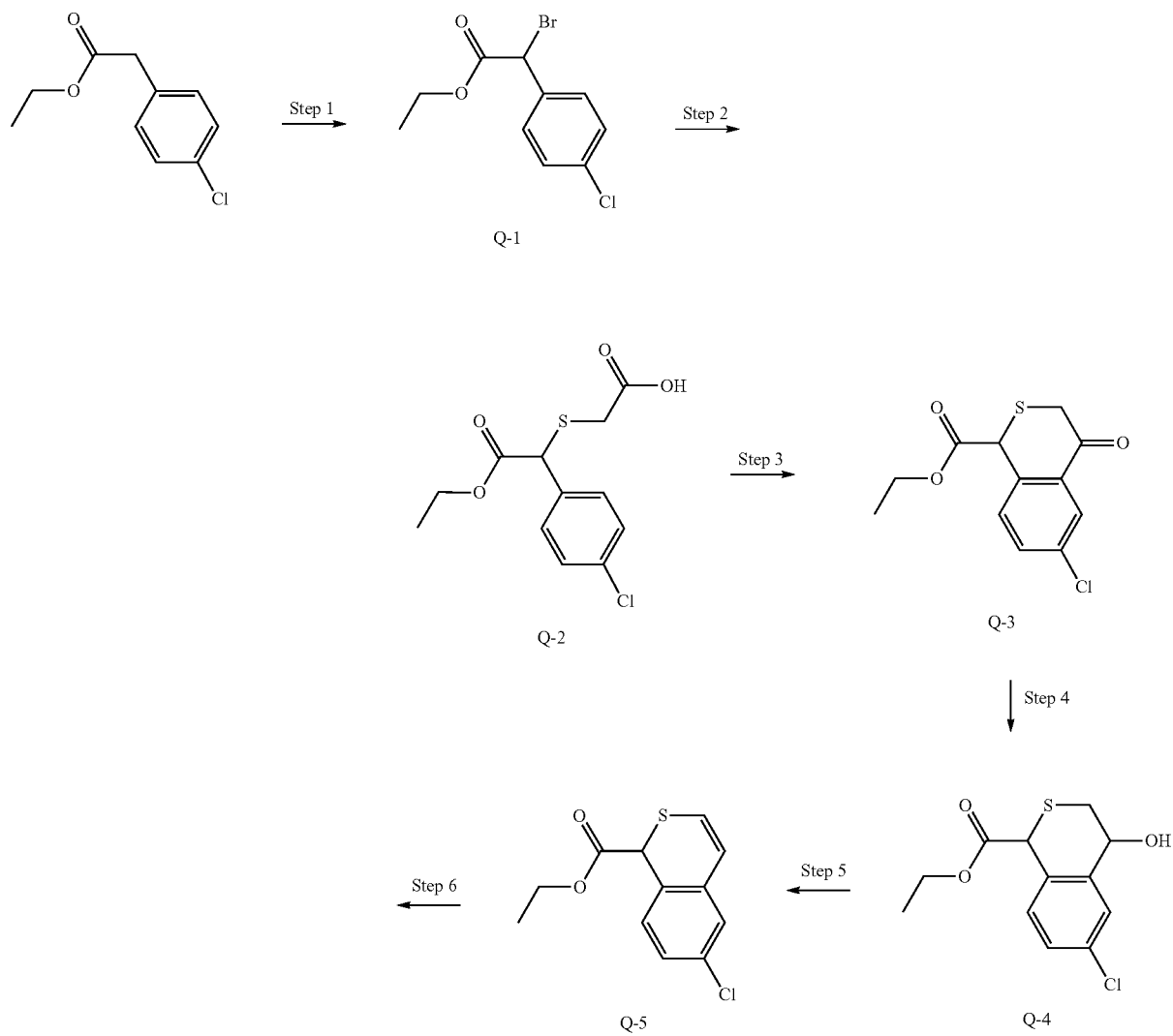

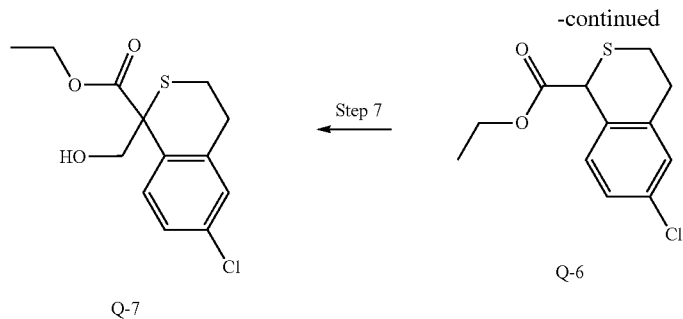
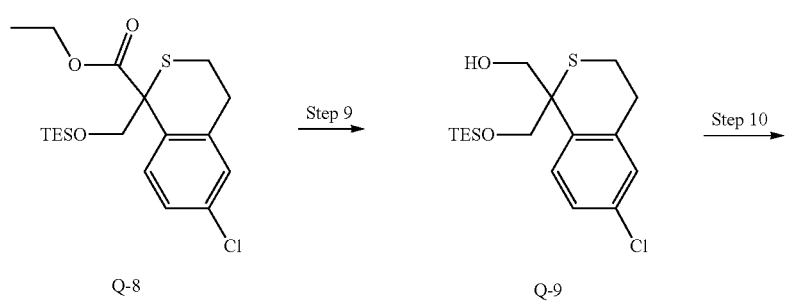
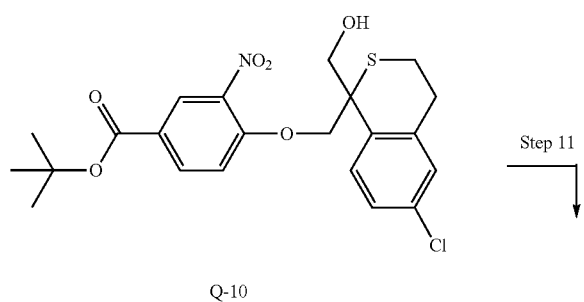
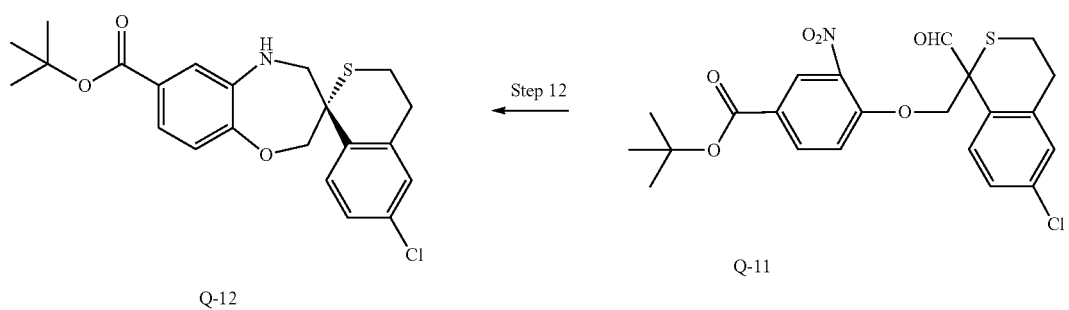

-continued
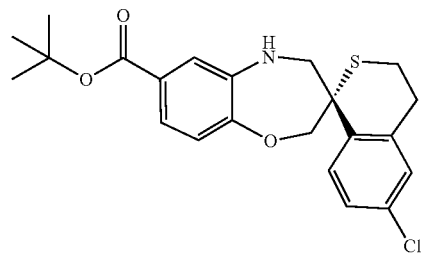
Q-13
↓ Step 13
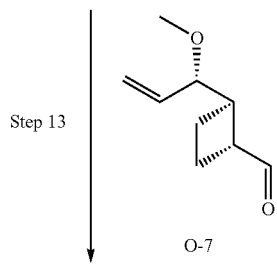
O-7
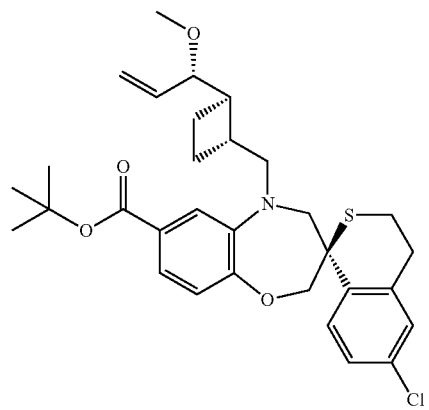
Q-14
→ Step 14
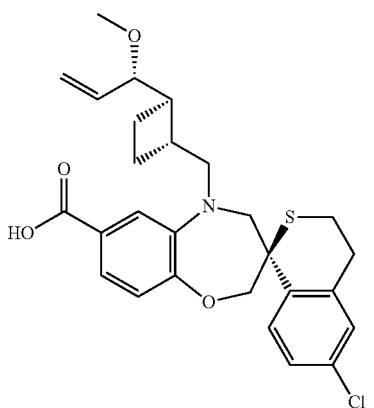
Q-15
→
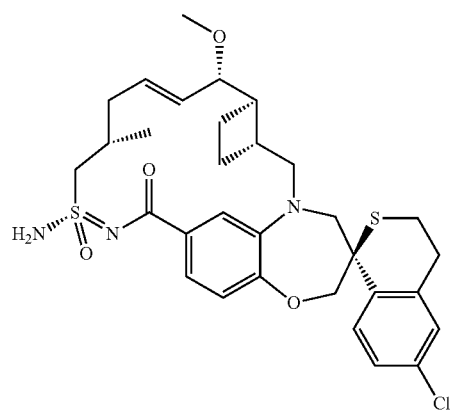
Intermediate Q Step 3: Q-2 (568.4 mg, 1.969 mmol) was dissolved in DCM (4 mL) and DMF (0.1 mL). To the solution was added a solution of oxalyl chloride (299.8 mg, 2.36 mol) in DCM (1 mL) at rt, and the mixture was stirred for 1 h. The solvent was removed under reduced pressure. To the residue was added DCM (20 mL) and the solvent was removed. To the residue were added DCM (5 mL) and $AlCl_3$ (577.4 mg, 4.33 mmol) at rt, and the mixture was stirred for 1 h. To the reaction mixture were added water (30 mL) and EtOAc (100 mL). The bi-phasic solution was filtered through Celite (3 g). The organic layer was washed with brine (30 mL), dried over $Na_2SO_4$, concentrated, and the residue purified by a silica-gel column chromatography (10% to 25% EtOAc/hexane) to give Q-3. $^1$H NMR (400 MHz, Acetone-$d_6$) b 7.97 (d, J=2.4 Hz, 1H), 7.62 (dd, J=8.2, 2.4 Hz, 1H), 7.48 (d, J=8.2 Hz, 1H), 4.80 (s, 1H), 4.23 (q, J=7.1 Hz, 2H), 4.13 (d, J=16.7 Hz, 1H), 3.42 (dd, J=16.7, 1.2 Hz, 1H), 1.26 (t, J=7.1 Hz, 3H).

Step 4: A solution of Q-3 (5.06 g, 18.69 mmol) in EtOH (18 mL) and THF (9 mL) was cooled to −40° C., and $NaBH_4$ (1.06 g, 28.04 mmol) was added. After 45 min, the reaction was brought up to 0° C. After 15 min, the reaction was quenched with water and brine, and extracted with EtOAc. The organic layer was washed with brine and dried over $Na_2SO_4$. Filtration, and removal of solvent gave Q-4 as a mixture of stereoisomers.

Step 5: $InCl_3$ (6.20 g, 28.04 mmol) was added to a solution of Q-4 (5.59 g, 18.69 mmol) in DCE (200 mL). The mixture was heated at 80° C. for 2 h. The mixture was cooled to 0° C., water was added, and aqueous layer was extracted with DCM. Combined organic layers were washed with brine, dried over sodium sulfate, filtered, and concentrated. Purification by silica-gel column chromatography (4% to 13% EtOAc/hexane) gave Q-5.

Step 6: $Et_3SiH$ (20 mL, 125 mmol), was added to a solution of Q-5 (3.20 g, 12.56 mmol) in TFA (100 mL). The mixture was heated at 70° C. for 2 h. Mixture was concentrated under reduced pressure, and purified by silica-gel column chromatography (4% to 25% EtOAc/hexane) to afford Q-6. $^1$H NMR (400 MHz, Acetone-$d_6$) δ 7.24 (m, 3H), 4.61 (s, 1H), 4.14 (qd, J=7.1, 1.5 Hz, 2H), 3.39-2.95 (m, 3H), 2.80-2.75 (m, 1H), 1.23 (t, J=7.1 Hz, 3H). LCMS-ESI+ (m/z): [M+H]$^+$ calcd for $C_{12}H_{13}ClO_2S$: 257.0; found: 257.1.

Step 7: A solution of Q-6 (767 mg, 2.99 mmol) and paraformaldehyde (179 mg, 5.97 mmol) in THF (10.0 mL) at room temperature was degassed and flushed with nitrogen. A solution of 1.0N lithium bis(trimethylsilyl)amide in THF (3.44 mL, 3.44 mmol) was added dropwise. The reaction was degassed and flushed with nitrogen, and stirred at rt for 1.5 hr. The reaction was then quenched with ice, water was added, reaction was stirred for 5 min, and extracted with EtOAc. Combined organic layers were washed with brine, dried over $Na_2SO_4$, filtered, and concentrated. The crude was purified by silica-gel column chromatography (0-30% EtOAc/Hexanes) to give Q-7. $^1$H NMR (400 MHz, Acetonitrile-$d_3$) δ 7.35-7.28 (m, 1H), 7.13 (d, J=7.6 Hz, 2H), 4.11-3.93 (m, 4H), 3.88 (dd, J=11.2, 7.3 Hz, 1H), 3.05-2.93 (m, 3H), 2.82-2.74 (m, 1H), 1.09 (t, J=7.1 Hz, 3H).

Step 8: A solution of Q-7 (7.72 g, 26.9 mmol) in DCM (144 mL) was cooled to 0° C. TEA (5.45 g, 53.8 mmol) was added, followed by triethylsilyl trifluoromethanesulfonate (8.5 DMAP 4 g, 32.3 mmol). After addition, the mixture was removed from the cooling bath and stirred at room temperature for 3 hr. The reaction was diluted with DCM, washed with water, saturated sodium bicarbonate, and brine, dried over $Na_2SO_4$, filtered, and concentrated. The crude was purified by silica-gel column chromatography (0-10% EtOAc/Hexanes, dry loading) to give Q-8. $^1$H NMR (400 MHz, Acetone-$d_6$) δ 7.51-7.41 (m, 1H), 7.30-7.18 (m, 2H), 4.24-4.05 (m, 4H), 3.13-3.01 (m, 3H), 2.95-2.87 (m, 1H), 1.21 (t, J=7.1 Hz, 3H), 0.92 (t, J=7.9 Hz, 9H), 0.66-0.49 (m, 6H).

Step 9: A solution of Q-8 (180 mg, 0.45 mmol) in THF (1.5 mL) was cooled to 0° C., and 1.0N lithium triethylborohydride in THF (0.99 mL, 0.99 mmol) was added dropwise. The resulting mixture was stirred for 10 min. The reaction was quenched with saturated ammonium chloride, and diluted with EtOAc. The organic layer was washed with brine, dried over $Na_2SO_4$, filtered and concentrated to give Q-9. $^1$H NMR (400 MHz, Acetonitrile-$d_3$) δ 7.50-7.45 (m, 1H), 7.25-7.20 (m, 2H), 3.96-3.86 (m, 2H), 3.85 (d, J=6.3 Hz, 2H), 3.10-3.01 (m, 2H), 2.97 (d, J=6.3 Hz, 1H), 2.93-2.76 (m, 2H), 0.92 (t, J=7.9 Hz, 9H), 0.64-0.50 (m, 6H).

Step 10: A solution of Q-9 (2.2 g, 6.13 mmol) and tert-butyl 4-fluoro-3-nitro-benzoate (2.22 g, 9.2 mmol) in THF (35 mL) was cooled to 0° C. A 1.0M solution of lithium bis(trimethylsilyl)amide in THF (7.35 mL, 7.35 mmol) was added dropwise. The resulting mixture was stirred for 1.5 hrs. The reaction was quenched with ice cold saturated aqueous $NH_4Cl$, and diluted with EtOAc. Layers were separated, and the organic layer was washed with water, brine, dried over $Na_2SO_4$, filtered, and concentrated. The residue was re-dissolved in DCM (150 mL) at rt and treated with a solution of TFA (4.35 mL) in DCM (65 mL) dropwise. The resulting mixture was stirred at rt for 40 min. The reaction was basified to pH-7 with sat sodium bicarbonate. Layers were separated, and organic layer was washed with brine, dried over $Na_2SO_4$, filtered, concentrated, and purified by silica-gel column chromatography (0-30% EtOAc/Hexanes) to give Q-10. $^1$H NMR (400 MHz, Acetonitrile-$d_3$) δ 8.34 (d, J=2.2 Hz, 1H), 8.14 (dd, J=8.9, 2.2 Hz, 1H), 7.55 (d, J=8.2 Hz, 1H), 7.31 (d, J=8.9 Hz, 1H), 7.28-7.22 (m, 2H), 4.58-4.46 (m, 2H), 4.05 (d, J=11.5 Hz, 1H), 3.89 (d, J=11.4 Hz, 1H), 3.11 (t, J=5.9 Hz, 2H), 3.01-2.91 (m, 1H), 2.90-2.81 (m, 1H), 1.59 (s, 9H).

Step 11: To a solution of Q-10 (2.17 g, 4.66 mmol) in DCM (31 mL) at rt was added Dess-Martin periodinane (2.97 g, 6.99 mmol). The resulting mixture was stirred for 30 min. The reaction was diluted with DCM, and 1 N sodium thiosulfate, and saturated sodium bicarbonate were added. The resulting mixture was stirred vigorously for 30 min. The layers were separated, and the aqueous layer was extracted with DCM. Combined organic layers were washed with brine, dried over $Na_2SO_4$, filtered, concentrated, and purified by silica-gel chromatography (0-30% EtOAc/Hexanes) to give Q-11. $^1$H NMR (400 MHz, Acetonitrile-$d_3$) b 9.38 (s, 1H), 8.25 (d, J=2.2 Hz, 1H), 8.09 (dd, J=8.8, 2.2 Hz, 1H), 7.45 (d, J=8.8 Hz, 1H), 7.33-7.16 (m, 3H), 4.81-4.57 (m, 2H), 3.09 (dd, J=7.7, 4.8 Hz, 2H), 2.97 (dt, J=13.0, 4.8 Hz, 1H), 2.87-2.74 (m, 1H), 1.49 (s, 9H).

Step 12: Tin(II) chloride (6.13 g, 32.33 mmol) was added to a solution of Q-11 (2.5 g, 5.39 mmol) in EtOH (53 mL) at 45° C. for 1 h. To the reaction mixture were added EtOAc and brine (50 mL). The whole was filtered through Celite. Organic layer was separated from the filtrate, washed with brine, and dried over $Na_2SO_4$. The solvent was removed under reduced pressure. $Na(OAc)_3BH$ (5710.7 mg, 26.95 mmol) and AcOH (11 mL) were added to the residue in $CH_2Cl_2$ (44 mL) at rt, and stirred for 30 min. To the reaction mixture were added EtOAc and brine (50 mL). The whole was filtered through Celite. Organic layer was separated from the filtrate, washed with brine, dried over $Na_2SO_4$, filtered, concentrated, and purified by silica-gel column chromatography (13-25% EtOAc/Hexanes) to give a mixture of stereoisomers. These were separated by a Chiral SFC instrument using Chiral Pak IC giving Q-12 as the less polar eluate and Q-13 as the more polar eluate. LCMS-ESI+ (m/z): [M+H]+ calcd for $C_{22}H_{23}ClNO_3S$: 416.1; found: 416.1.

Step 13: To a solution of Q-13 (150.0 mg, 0.36 mmol) and O-7 (66.4 mg, 0.431 mmol) in DCE (1.44 mL) at rt was added acetic acid (0.087 mL, 1.5 mmol). The resulting mixture was stirred at rt for 1 hr. The reaction was then cooled to 0° C. and STAB (114 mg, 0.54 mmol) was added in two portions with 10 minutes interval. Additional STAB (38 mg, 0.18 mmol) was added after 20 min of stirring. The resulting mixture was stirred at rt overnight. The reaction was quenched with ice, and extracted with DCM. The organic layer was washed with brine, dried over $Na_2SO_4$, filtered, and concentrated to give Q-14. LCMS-ESI+ (m/z): [M+H]+ calcd for $C_{31}H_{38}ClNO_4S$: 556.2; found: 555.9.

Step 14: TFA (0.8 mL) was added to a solution of Q-14 (200 mg, 0.36 mmol) in DCM (0.8 mL) at rt, and stirred for 1.5 hrs. The reaction was concentrated, re-dissolved in DMF (1.2 mL), filtered and purified by Gilson reverse phase prep HPLC, (20-100% ACN/H2O with 0.1% TFA in 15 min) to give Q-15. $^1$H NMR (400 MHz, Methanol-$d_4$) δ 7.67 (d, J=8.6 Hz, 1H), 7.38 (d, J=2.0 Hz, 1H), 7.25 (dd, J=8.2, 1.9 Hz, 1H), 7.14 (dd, J=8.6, 2.4 Hz, 1H), 7.08 (d, J=2.3 Hz, 1H), 6.78 (d, J=8.2 Hz, 1H), 5.56-5.40 (m, 1H), 5.13-5.04 (m, 2H), 4.24-4.08 (m, 2H), 3.78 (d, J=14.6 Hz, 1H), 3.59 (dd, J=15.0, 4.1 Hz, 1H), 3.50-3.37 (m, 3H), 3.21 (s, 3H), 3.01-2.95 (m, 2H), 2.94-2.89 (m, 1H), 2.73-2.64 (m, 1H), 2.50-2.39 (m, 1H), 2.15-2.03 (m, 1H), 1.94-1.83 (m, 1H), 1.73-1.42 (m, 3H). LCMS-ESI+ (m/z): [M+H]+ calcd for $C_{27}H_{30}ClNO_4S$: 500.1; found: 500.0.

Synthesis of Intermediate Q: Intermediate Q was synthesized in a similar manner to Intermediate I (Method 1, steps 4-7), using Q-16 and Intermediate C. $^1$H NMR (400 MHz, Methanol-$d_4$) δ 7.78 (d, J=8.5 Hz, 1H), 7.25 (ddd, J=8.0, 5.4, 2.1 Hz, 2H), 7.18 (d, J=2.4 Hz, 1H), 7.09 (d, J=1.9 Hz, 1H), 6.83 (d, J=8.2 Hz, 1H), 6.16 (dt, J=14.4, 6.7 Hz, 1H), 5.52 (dd, J=15.3, 8.9 Hz, 1H), 4.31 (d, J=12.3 Hz, 1H), 4.13-3.99 (m, 3H), 3.87 (d, J=14.5 Hz, 1H), 3.82-3.73 (m, 2H), 3.47 (d, J=14.4 Hz, 1H), 3.41-3.32 (m, 1H), 3.24 (s, 3H), 3.11-2.99 (m, 3H), 2.82-2.74 (m, 1H), 2.52-2.31 (m, 3H), 2.21-2.06 (m, 2H), 2.00 (s, 1H), 1.90 (q, J=8.2, 7.8 Hz, 1H), 1.75 (tt, J=17.3, 9.3 Hz, 3H), 1.30-1.18 (m, 2H), 1.12 (d, J=6.4 Hz, 3H). LCMS-ESI+ (m/z): [M+H]+ calcd for $C_{31}H_{38}ClN_3O_4S_2$: 616.2, found: 616.0.

Intermediate R

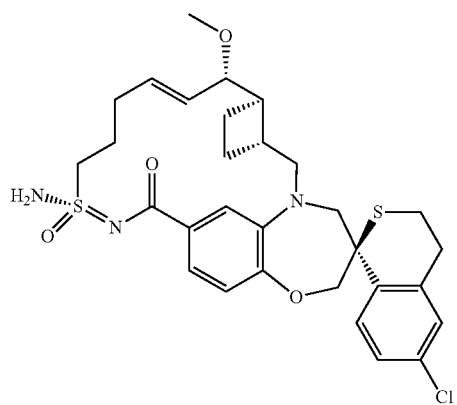 [SMILES: CO[C@H]1/C=C/CCC[S@](N)(=O)=NC(=O)c2ccc3c(c2)N(C[C@@H]2CC[C@H]21)C[C@]1(CO3)SCCc2cc(Cl)ccc21]

Intermediate R was prepared in a manner similar to Intermediate I (Method 1 Steps 4-7) using L-1 in place of Intermediate C and Q-15 in place of I-1-3. LCMS-ESI+ (m/z): [M+H]+ calcd for $C_{30}H_{36}ClN_3O_4S_2$:602.2; found: 602.0.

Intermediate S

Method 1.

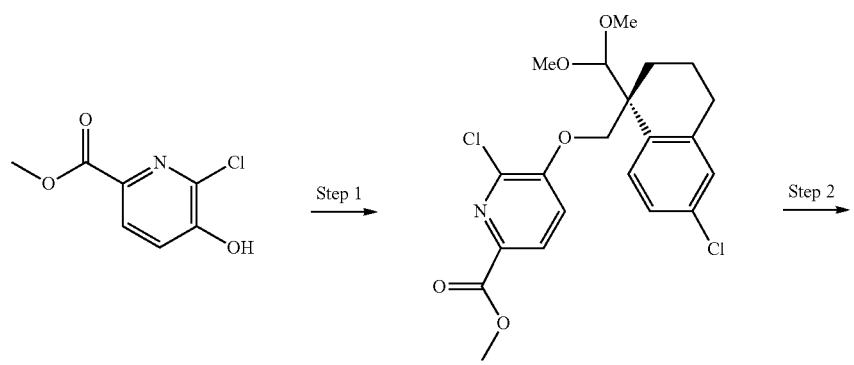

S-1-1

-continued
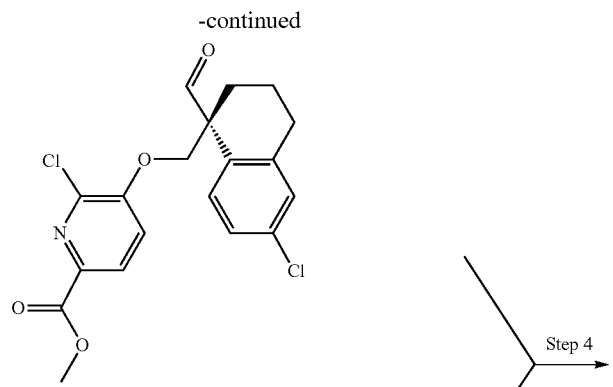
S-1-2
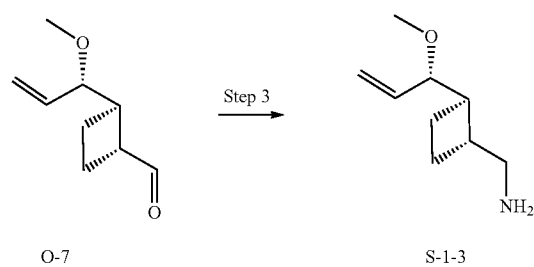
O-7      Step 3      S-1-3
Step 4
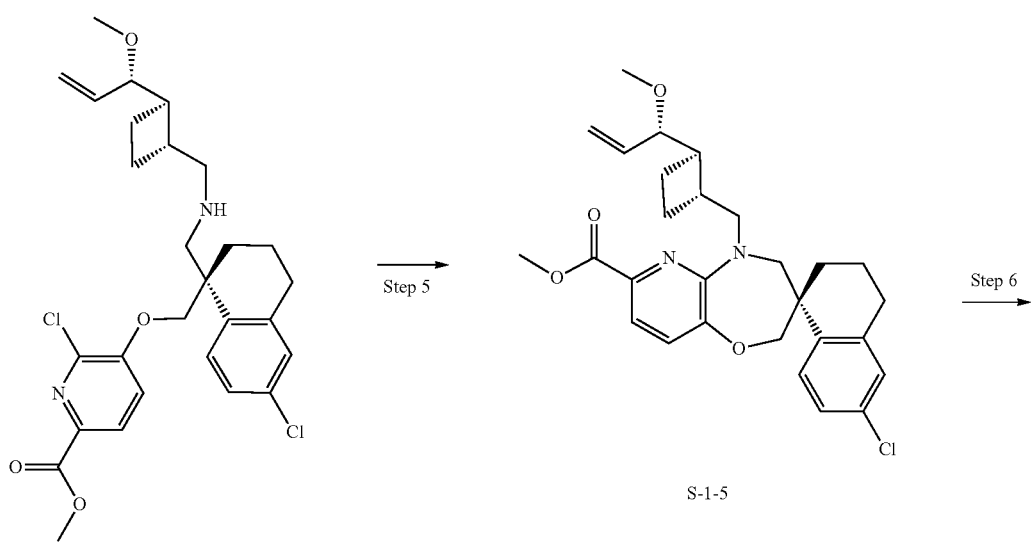
S-1-4     Step 5     S-1-5     Step 6

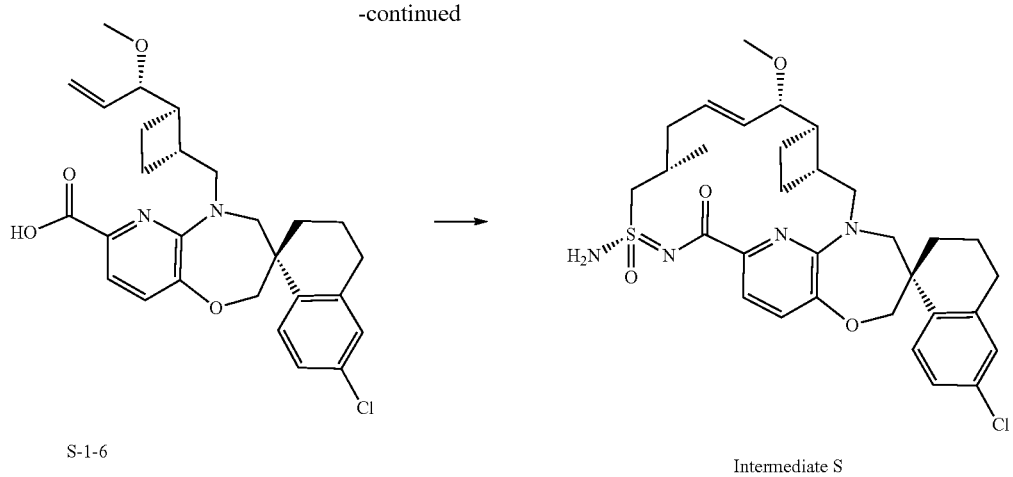

Step 1: To a solution of (R)-(6-chloro-1-(dimethoxymethyl)-1,2,3,4-tetrahydronaphthalen-1-yl)methanol (WO 2016033486) (3.4 g, 12.56 mmol), methyl 6-chloro-5-hydroxypicolinate (2.35 g, 12.56 mmol) in THF (60 mL) under nitrogen atmosphere was added triphenylphosphine (4.44 g, 16.95 mmol). To stirred solution at 0° C. in an ice bath, was added diisopropyl azodicarboxylate (3.2 mL, 16.32 mmol) slowly. The reaction was allowed to warm to rt, and heated at 60° C. overnight. The solvent was concentrated and purified by flash column chromatography (0-20% ethyl acetate in hexane) to afford S-1-1. LCMS-ESI+ (m/z): [M+H]$^+$ calcd for $C_{21}H_{23}Cl_2NO_5$: 440.1; found: 439.8.

Step 2: Water (0.05 mL), and erbium(III) trifluoromethanesulfonate (1.06 g, 1.72 mmol) were added to a solution of S-1-1 (3.8 g, 8.63 mmol) in acetonitrile (47 mL), and reaction was stirred at 90° C. overnight. The solvent was concentrated and crude product purified by flash column chromatography (0-50% ethyl acetate in hexane) to afford S-1-2. LCMS-ESI+(m/z): [M+H]$^+$ calcd for $C_{19}H_{17}Cl_2NO_4$: 434.0; found: 393.8.

Step 3: To 0-7 (3 g, 19.4 mmol) in a 250 mL seal tube was added a saturated solution of $NH_4OAc$ in EtOH (96 mL) and sonicated 5 min to dissolve. $NaBH_3CN$ (4.89 g, 77.82 mmol), followed by 30% Aq. $NH_3OH$ (48 mL) were added. The reaction flask was sealed and stirred at 90° C. for 24 h. The mixture was cooled to 0° C. before opening, and concentrated under reduced pressure. Residue was dissolved in EtOAc (~250 mL), and 2M NaOH (24 mL) followed by sat $Na_2CO_3$ (48 mL) were added. The mixture was stirred for 5 min, and the layers were separated. The aqueous layer was extracted with EtOAc and DCM, the DCM extract was washed with brine, and combined organic layer was dried over $Na_2SO_4$, and concentrated to afford S-1-3. $^1$H NMR (400 MHz, DMSO-d$_6$) δ 5.66-5.42 (m, 1H), 5.37-5.03 (m, 2H), 3.55-3.39 (m, 3H), 3.16 (d, J=9.4 Hz, 4H), 2.72 (dd, J=7.2, 2.4 Hz, 1H), 2.22 (p, J=7.8 Hz, 1H), 2.02 (dp, J=23.3, 8.2 Hz, 1H), 1.92-1.77 (m, 1H), 1.77-1.62 (m, 1H), 1.62-1.44 (m, 2H).

Step 4: To S-1-3 (2.46 g, 9.51 mmol, 60% pure), under Ar was added a solution of S-1-2 (2.5 g, 6.34 mmol) in DCM (50 mL) followed by DIPEA (2.3 mL), and stirred at rt for 40 min. STAB (3.36 g, 15.85 mmol) followed by AcOH (0.22 mL, 3.8 mmol) were added and mixture was sonicated to dissolve STAB. 5 mL DCM was added to bring solids into solution and the mixture stirred at room temperature for 8 h. 2 N NaOH (6 mL) followed by saturated $Na_2CO_3$ (12 mL) were added, the mixture was stirred for 5 min, and then partitioned between DCM/Water. The aqueous layer was extracted with DCM twice. Combined organic layer was dried over $MgSO_4$, filtered, concentrated, and purified by flash column chromatography (0-20% MeOH/DCM) to afford S-1-4. LCMS-ESI+ (m/z): [M+H]$^+$ calcd for $C_{28}H_{34}Cl_2N_2O_4$: 533.1; found: 533.2.

Step 5: DIPEA (2 mL) was added to a solution of S-1-4 (740 mg, 1.38 mmol) in dioxane (15 mL) in a microwave vial. The vial was sealed and heated at 160° C. for 4 h. The solvent was concentrated and the residue purified by flash column chromatography (0-60% EtOAc/hexane) to afford S-1-5. LCMS-ESI+ (m/z): [M+H]$^+$ calcd for $C_{28}H_{33}ClN_2O_4$: 497.2; found: 497.1.

Step 6: To S-1-5 (360 mg, 0.72 mmol) was added THF (20 mL), MeOH (3 mL) followed by 1N solution of LiOH (3 mL). This solution was stirred at 65° C. for 90 min. Solvent was concentrated and the residue was dissolved in water (20 mL). The solution was acidified by drop wise addition of 1.5 N HCl to maintain pH ~2-3 and stirred for 5 min. The precipitating solid was filtered, washed with water, and dried to afford S-1-6. LCMS-ESI+ (m/z): [M+H]$^+$ calcd for $C_{27}H_{31}ClN_2O_4$: 483.2; found: 483.3.

Synthesis of Intermediate S: Intermediate S was prepared in a manner similar to Intermediate I (Method 1 Steps 4-7) using S-1-6 in place of Intermediate C. LCMS-ESI+ (m/z): [M+H]$^+$ calcd for $C_{31}H_{39}ClN_4O_4S$: 599.2; found: 599.1.

Method 2.

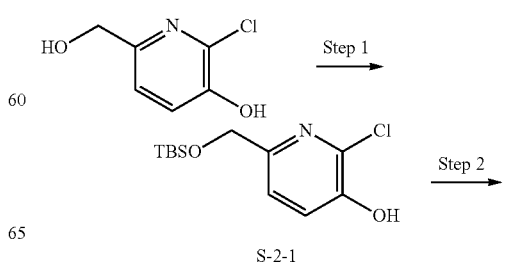

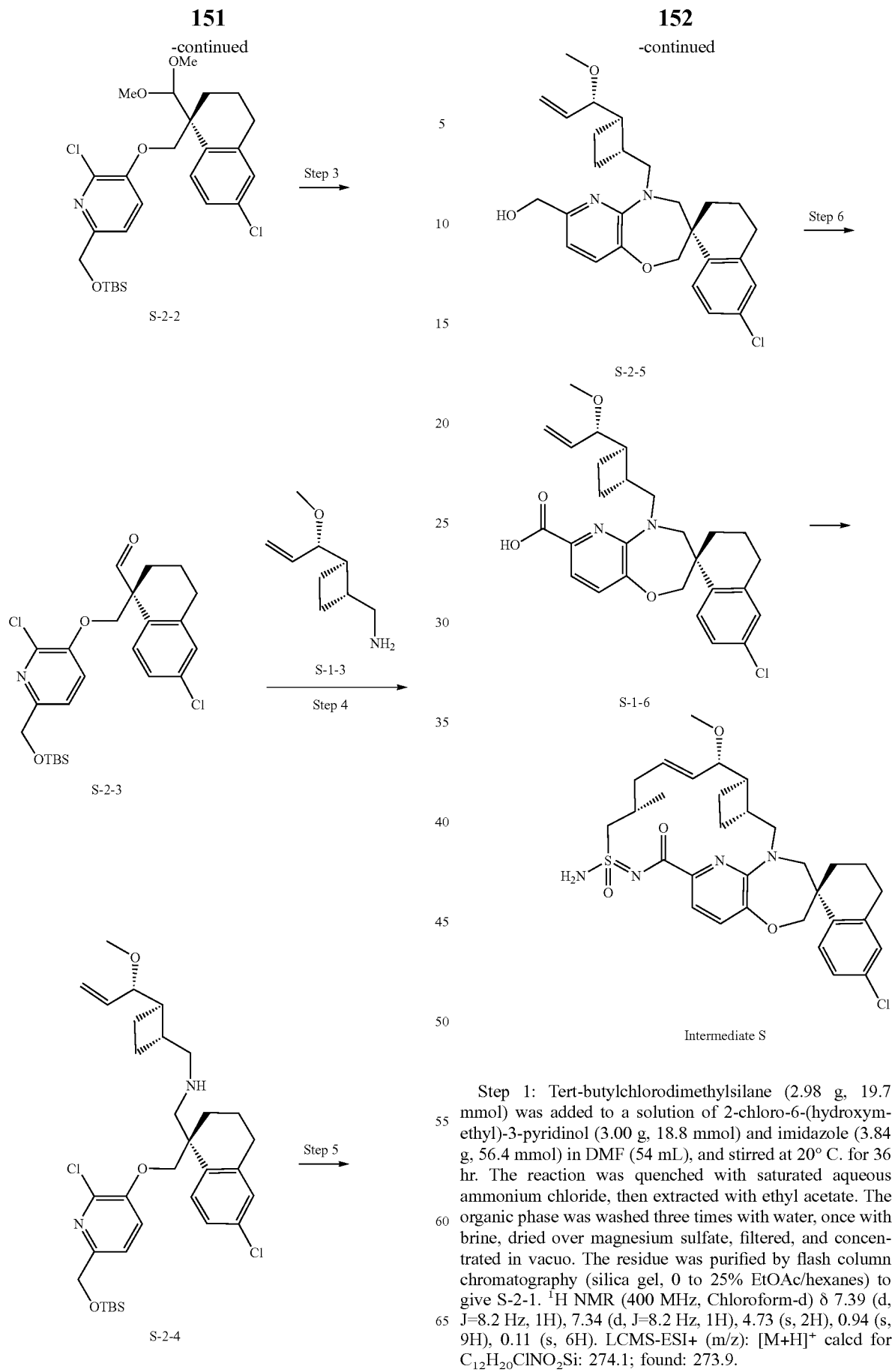

Step 1: Tert-butylchlorodimethylsilane (2.98 g, 19.7 mmol) was added to a solution of 2-chloro-6-(hydroxymethyl)-3-pyridinol (3.00 g, 18.8 mmol) and imidazole (3.84 g, 56.4 mmol) in DMF (54 mL), and stirred at 20° C. for 36 hr. The reaction was quenched with saturated aqueous ammonium chloride, then extracted with ethyl acetate. The organic phase was washed three times with water, once with brine, dried over magnesium sulfate, filtered, and concentrated in vacuo. The residue was purified by flash column chromatography (silica gel, 0 to 25% EtOAc/hexanes) to give S-2-1. $^1$H NMR (400 MHz, Chloroform-d) δ 7.39 (d, J=8.2 Hz, 1H), 7.34 (d, J=8.2 Hz, 1H), 4.73 (s, 2H), 0.94 (s, 9H), 0.11 (s, 6H). LCMS-ESI+ (m/z): [M+H]$^+$ calcd for $C_{12}H_{20}ClNO_2Si$: 274.1; found: 273.9.

Step 2: To a glass roundbottom flask charged with S-2-1 (2.43 g, 8.86 mmol) under nitrogen atmosphere was added triphenylphosphine (3.14 g, 12.0 mmol), then (R)-(6-chloro-1-(dimethoxymethyl)-1,2,3,4-tetrahydronaphthalen-1-yl)methanol (2.40 g, 8.86 mmol) as a solution in THF (44 mL). The flask was cooled to 0° C., then diisopropyl azodicarboxylate (2.26 mL, 11.5 mmol) was added with a significant exotherm observed during addition. The reaction was stirred at 20° C. for 30 min, then warmed to 50° C., and stirred for 24 hr. The reaction was then concentrated in vacuo, and purified by flash column chromatography (0 to 20% EtOAc/hexanes) to give S-2-2. $^1$H NMR (400 MHz, Chloroform-d) δ 7.77 (d, J=8.5 Hz, 1H), 7.35 (d, J=8.2 Hz, 1H), 7.17 (d, J=8.3 Hz, 1H), 7.13 (dd, J=8.5, 2.4 Hz, 1H), 7.10 (d, J=2.4 Hz, 1H), 4.76 (s, 1H), 4.73 (s, 2H), 4.09 (d, J=8.7 Hz, 1H), 4.05 (d, J=8.6 Hz, 1H), 3.49 (s, 3H), 3.41 (s, 3H), 2.86-2.64 (m, 2H), 2.12 (t, J=10.6 Hz, 1H), 2.00-1.86 (m, 2H), 1.78-1.66 (m, 1H), 0.94 (s, 9H), 0.10 (s, 6H). LCMS-ESI+ (m/z): [M+H]$^+$ calcd for $C_{26}H_{37}Cl_2NO_4Si$: 526.2; found: 525.9.

Step 3: Water (0.4 mL) was added to a solution of S-2-2 (2.1 g, 3.99 mmol) and erbium(III) trifluoromethanesulfonate (123 mg, 0.199 mmol) in acetonitrile (40 mL). The reaction was stirred at 80° C. for 90 min and allowed to cool to 20° C. The reaction was partitioned between ethyl acetate and saturated aqueous sodium bicarbonate. The organic phase was washed with saturated aqueous sodium bicarbonate and brine, dried over magnesium sulfate, filtered, concentrated in vacuo, and the residue purified by flash column chromatography (0 to 100% EtOAc/hexanes) to give S-2-3. $^1$H NMR (400 MHz, Chloroform-d) b 9.61 (s, 1H), 7.36 (d, J=8.3 Hz, 1H), 7.26-7.18 (m, 4H), 4.73 (d, J=0.9 Hz, 2H), 4.40 (d, J=9.0 Hz, 1H), 4.17 (d, J=9.1 Hz, 1H), 2.90-2.79 (m, 2H), 2.23 (dd, J=7.0, 5.0 Hz, 2H), 1.96 (h, J=6.6 Hz, 2H), 0.94 (s, 9H), 0.10 (s, 6H). LCMS-ESI+ (m/z): [M+H]$^+$ calcd for $C_{24}H_{31}Cl_2NO_3Si$: 480.2; found: 479.9.

Step 4: DIPEA (0.54 mL, 3.00 mmol) was added to a solution of S-2-3 (720 mg, 1.50 mmol) and S-1-3 (250 mg, 1.62 mmol) in DCM (8 mL) and stirred at 20° C. for 60 min. Then STAB (780 mg, 3.67 mmol) was added, followed by acetic acid (90 μL, 1.5 mmol), and the reaction was stirred at 20° C. for 16 hr. The reaction was quenched by dropwise addition of 2M aqueous sodium hydroxide (10 mL), then saturated aqueous sodium bicarbonate, until the pH of the aqueous phase was 10-11. The resulting mixture was extracted twice with ethyl acetate. The combined organic phase was washed with brine, dried over magnesium sulfate, filtered, concentrated, and the residue purified by flash column chromatography (0 to 100% EtOAc/hexanes) to give S-2-4. LCMS-ESI+ (m/z): [M+H]$^+$ calcd for $C_{33}H_{48}Cl_2N_2O_3Si$: 619.3; found: 619.4.

Step 5: DIPEA (0.53 mL, 2.94 mmol) was added to a solution of S-2-4 (365 mg, 0.589 mmol) in N-methylpyrrolidone (11.3 mL) and heated at 180° C. for 18 hr. The reaction was allowed to cool to 20° C., and TBAF (1 M solution in THF, 1.2 mL, 1.2 mmol) was added and reaction was stirred at for 1 hr. The reaction was diluted with ethyl acetate, washed twice with saturated aqueous ammonium chloride, then twice with water, and once with brine. The combined organic phases were dried over magnesium sulfate, filtered, concentrated, and the residue purified by flash column chromatography (0 to 25% EtOAc/hexanes) to give S-2-5. $^1$H NMR (400 MHz, Acetonitrile-d$_3$) δ 7.70 (d, J=8.5 Hz, 1H), 7.18 (dd, J=8.5, 2.4 Hz, 1H), 7.15-7.09 (m, 1H), 7.05 (d, J=7.7 Hz, 1H), 6.53 (d, J=7.7 Hz, 1H), 5.60 (ddd, J=16.6, 11.0, 8.0 Hz, 1H), 5.16 (s, 1H), 5.13 (ddd, J=8.7, 2.1, 0.8 Hz, 1H), 4.52-4.38 (m, 2H), 4.05 (d, J=12.1 Hz, 1H), 3.98 (dd, J=13.8, 4.5 Hz, 1H), 3.91 (d, J=12.2 Hz, 1H), 3.77 (d, J=14.9 Hz, 1H), 3.50 (t, J=5.6 Hz, 1H), 3.44-3.34 (m, 2H), 3.27 (dd, J=13.8, 8.7 Hz, 1H), 3.17 (s, 3H), 2.84-2.65 (m, 2H), 2.66-2.52 (m, 1H), 2.15-2.06 (m, 1H), 2.05-1.98 (m, 1H), 1.94 (p, J=2.5 Hz, 1H), 1.91-1.77 (m, 2H), 1.76-1.39 (m, 3H). LCMS-ESI+ (m/z): [M+H]$^+$ calcd for $C_{27}H_{33}ClN_2O_3$: 469.3; found: 469.2.

Step 6: Dess-Martin periodinane (191 mg, 0.435 mmol) was added to a solution of S-2-5 (135 mg, 0.290 mmol) in DCM (2.9 mL) and stirred at 20° C. for 30 min. The reaction was quenched by addition of 1.0 M aqueous sodium thiosulfate and saturated aqueous sodium bicarbonate. The resulting biphasic mixture was stirred vigorously for 5 min, the phases were separated, and the aqueous phase was extracted three times with DCM. The combined organic phase was washed with a mixture of 1.0 M aqueous sodium thiosulfate and saturated aqueous sodium bicarbonate, then once with brine, dried over magnesium sulfate, filtered and concentrated in vacuo. The crude material was dissolved in tert-butanol (3.1 mL), and 2-methyl-2-butene (0.65 mL, 6.12 mmol) was added. A solution of sodium chlorite (83 mg, 0.92 mmol) and sodium dihydrogen phosphate (287 mg, 1.84 mmol) in water (0.9 mL) was added dropwise, and the reaction was stirred at 20° C. for 30 min. The reaction was quenched with 1 M sodium thiosulfate, and acidified to pH 2-3 by dropwise addition of 1 N aqueous HCl. The resulting mixture was extracted four times with ethyl acetate. The combined organic phase was washed with brine, dried over magnesium sulfate, filtered, and concentrated in vacuo to give S-1-6. $^1$H NMR (400 MHz, Chloroform-d) δ 7.66 (d, J=8.5 Hz, 1H), 7.52 (d, J=7.8 Hz, 1H), 7.24-7.17 (m, 2H), 7.10 (d, J=2.3 Hz, 1H), 5.50 (ddd, J=16.6, 10.9, 8.2 Hz, 1H), 5.21 (s, 1H), 5.17 (dd, J=8.3, 1.3 Hz, 1H), 4.29 (dd, J=14.2, 3.8 Hz, 1H), 4.20 (d, J=12.2 Hz, 1H), 4.09-4.04 (m, 1H), 3.88 (d, J=14.5 Hz, 1H), 3.47 (q, J=7.8, 6.8 Hz, 2H), 3.25 (s, 3H), 3.09 (dd, J=14.2, 9.3 Hz, 1H), 2.77 (dd, J=10.6, 5.4 Hz, 2H), 2.70 (q, J=9.6, 7.8 Hz, 1H), 2.00-1.71 (m, 6H), 1.69-1.45 (m, 3H). LCMS-ESI+ (m/z): [M+H]$^+$ calcd for $C_{27}H_{31}ClN_2O_4$: 483.2; found: 483.1.

Synthesis of Intermediate S: Intermediate S was prepared in a manner similar to Intermediate I (Method 1 Steps 4-7) using S-1-6 in place of Intermediate C.

Intermediate T

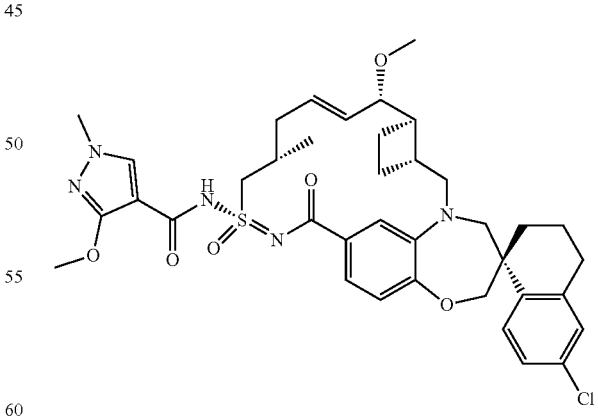

3-Methoxy-1-methyl-1H-pyrazole-4-carboxylic acid (324 mg, 2.08 mmol, 2 equiv.) and EDCl (400 mg, 2.08 mmol, 2 equiv.) were added to a solution of Intermediate I (620 mg, 1.04 mmol) in dichloromethane (12 mL). The reaction mixture was stirred for 5 minutes at room temperature. DMAP (253 mg, 2.08 mmol, 2 equiv.) was added, and the reaction mixture was stirred overnight at room temperature. The reaction mixture was concentrated under reduced pressure, and the residue purified by Gilson reverse phase prep HPLC (60-100% ACN/H₂O with 0.1% TFA) to give Intermediate T. ¹H NMR (400 MHz, Methanol-d₄) δ 8.07 (s, 1H), 7.76 (d, J=8.6 Hz, 1H), 7.34 (d, J=8.2 Hz, 1H), 7.22-7.10 (m, 3H), 6.92 (d, J=8.2 Hz, 1H), 6.20-6.05 (m, 1H), 5.63 (dd, J=15.5, 8.0 Hz, 1H), 4.10 (d, J=12.0 Hz, 1H), 4.06 (s, 4H), 3.91-3.83 (m, 1H), 3.82 (s, 3H), 3.79 (s, 1H), 3.72 (d, J=14.4 Hz, 1H), 3.38 (d, J=14.5 Hz, 1H), 3.30 (s, 3H), 3.09 (dd, J=15.1, 10.0 Hz, 1H), 2.89-2.72 (m, 2H), 2.51 (d, J=26.7 Hz, 2H), 2.24 (dd, J=10.9, 6.0 Hz, 2H), 2.12 (d, J=13.7 Hz, 1H), 2.02-1.70 (m, 4H), 1.54-1.40 (m, 1H), 1.14 (d, J=6.1 Hz, 3H). LCMS-ESI+ (m/z): [M+H]⁺ calcd for $C_{38}H_{46}ClN_5O_6S$: 735.3; found: 735.9.

Intermediate U

Intermediate U was synthesized in the same manner as Intermediate M using Intermediate T in place of Intermediate 1. Final purification by preparative reverse-phase HPLC (0.1% trifluoroacetic acid in acetonitrile/water) gave Intermediate U and U-1 (stereochemistry of U-1 assigned tentatively).

U-1 (first eluting diastereomer, stereochemistry tentatively assigned): ¹H NMR (400 MHz, Methanol-d4) δ 8.05 (s, 1H), 7.74 (d, J=8.5 Hz, 1H), 7.31 (d, J=8.3 Hz, 1H), 7.27 (s, 1H), 7.16 (dd, J=8.4, 2.4 Hz, 1H), 7.10 (d, J=2.4 Hz, 1H), 6.88 (d, J=8.2 Hz, 1H), 6.39 (d, J=15.9 Hz, 1H), 5.85 (dd, J=15.5, 5.9 Hz, 1H), 4.38-4.27 (m, 1H), 4.25-4.12 (m, 1H), 4.12-3.94 (m, 7H), 3.86 (d, J=11.6 Hz, 2H), 3.79 (s, 3H), 3.75-3.63 (m, 2H), 3.40 (d, J=14.5 Hz, 1H), 3.06 (dd, J=15.2, 10.2 Hz, 1H), 2.89-2.60 (m, 3H), 2.45-2.31 (m, 1H), 2.08 (d, J=12.9 Hz, 2H), 1.99-1.85 (m, 5H), 1.83-1.67 (m, 2H), 1.59-1.49 (m, 2H), 1.30 (d, J=7.4 Hz, 3H). LCMS-ESI+ (m/z): [M+H]⁺ calcd for $C_{38}H_{46}ClN_5O_7S$: 752.3; found: 752.0.

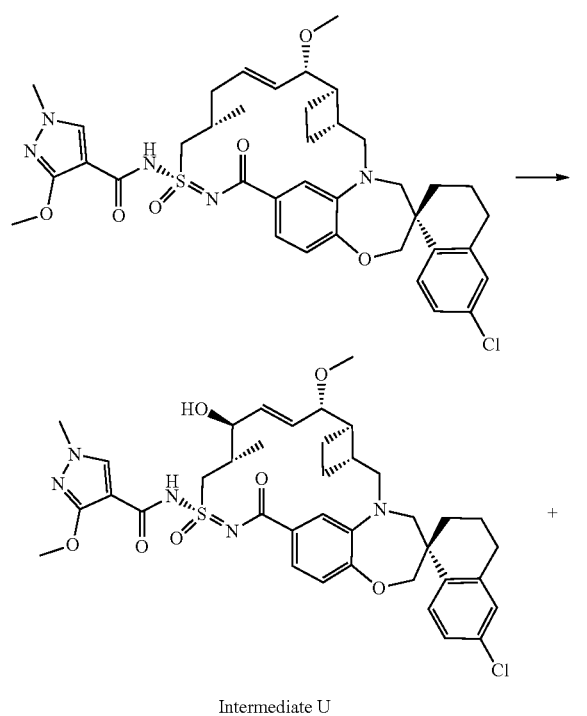

Intermediate U

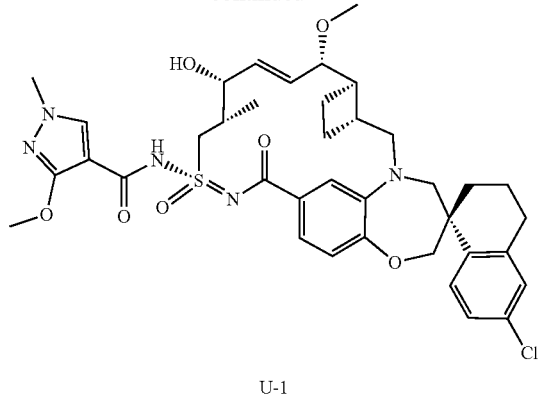

U-1

Intermediate U (second eluting diastereomer): ¹H NMR (400 MHz, Methanol-d₄) δ 8.15 (s, 1H), 7.72 (d, J=9.1 Hz, 1H), 7.37 (dd, J=8.3, 1.8 Hz, 1H), 7.19 (s, 1H), 7.16-7.07 (m, 2H), 6.89 (d, J=8.2 Hz, 1H), 6.15 (dd, J=15.5, 5.3 Hz, 1H), 5.83 (ddd, J=15.5, 8.0, 1.5 Hz, 1H), 4.54 (s, 1H), 4.05 (m, 7H), 3.90-3.82 (m, 3H), 3.81 (s, 3H), 3.69 (d, J=14.3 Hz, 1H), 3.41 (d, J=14.4 Hz, 1H), 3.29 (s, 3H), 3.18-3.04 (m, 1H), 2.92-2.69 (m, 2H), 2.51 (br, 2H), 2.44-2.25 (m, 1H), 2.16-2.03 (m, 1H), 2.02-1.92 (m, 3H), 1.88-1.74 (m, 3H), 1.43 (t, J=11.9 Hz, 1H), 1.15 (d, J=6.9 Hz, 3H). LCMS-ESI+ (m/z): [M+H]⁺ calcd for $C_{38}H_{46}ClN_5O_7S$: 752.3; found: 751.9.

Intermediate V

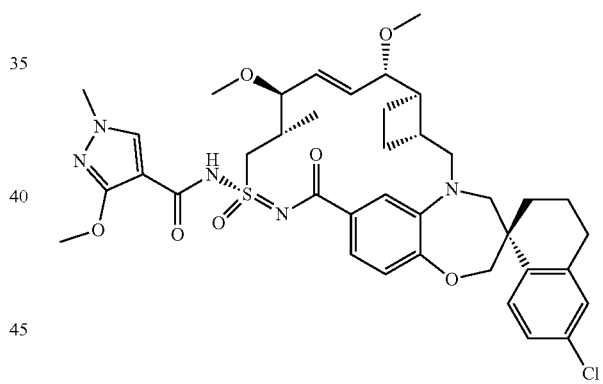

Intermediate U (200 mg, 0.27 mmol) was dissolved in DMF (2.7 mL) and sodium hydride (60% dispersion in oil, 22 mg, 0.53 mmol, 2 equiv.) was added in one portion. The mixture was stirred at room temperature for 5 min before iodomethane (76 mg, 0.53 mmol, 2 equiv.) was added. The reaction was then heated to 50° C. and the progress of the reaction was monitored by LCMS. Upon observing significant conversion (approx. 4:1 product: starting material), the reaction was cooled to 0° C. and water was added (ca. 5 drops). The residue was then purified directly by Gilson reverse phase prep HPLC (60-100% ACN/H₂O with 0.1% TFA) to give Intermediate V. ¹H NMR (400 MHz, Methanol-d₄) δ 8.08 (s, 1H), 7.76 (d, J=8.5 Hz, 1H), 7.36 (d, J=7.9 Hz, 1H), 7.24-7.15 (m, 2H), 7.12 (d, J=2.3 Hz, 1H), 6.92 (d, J=8.2 Hz, 1H), 6.01 (dd, J=15.4, 7.8 Hz, 1H), 5.83 (dd, J=15.3, 8.6 Hz, 1H), 4.06 (m, 6H), 3.9-3.8 (m, 7H), 3.73 (d, J=14.5 Hz, 1H), 3.41 (d, J=14.4 Hz, 1H), 3.31 (s, 3H), 3.30 (s, 3H), 3.19-3.06 (m, 1H), 2.92-2.70 (m, 2H), 2.52 (br, 2H), 2.24 (m, 1H), 2.05 (m, 2H), 1.96 (m, 3H), 1.83 (m, 3H), 1.46

(m, 1H), 1.19 (d, J=6.8 Hz, 3H). LCMS-ESI+ (m/z): [M+H]+ calcd for $C_{39}H_{48}ClN_5O_7S$: 766.3; found: 766.0.

Intermediate W

Method 1.

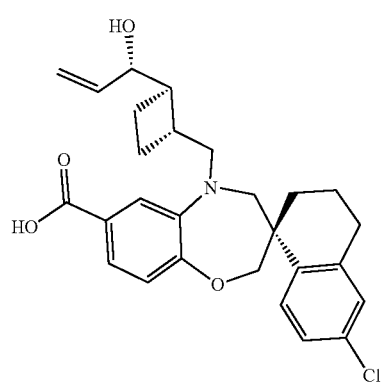

Step 1

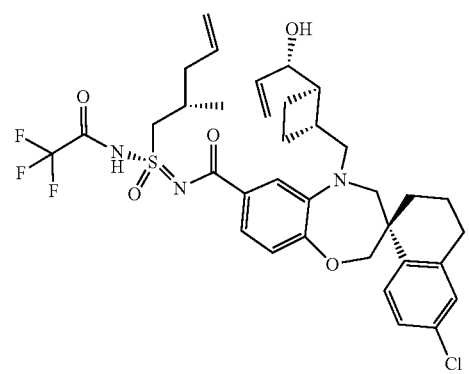

W-1-1

Step 2

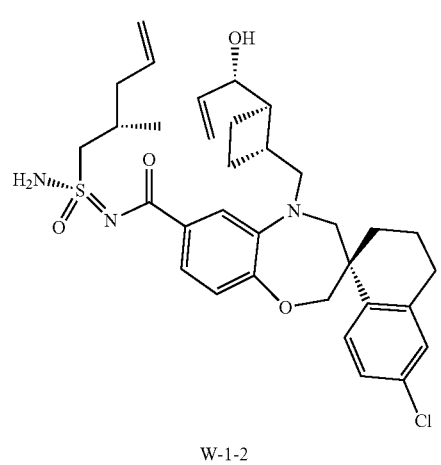

W-1-2

Step 3

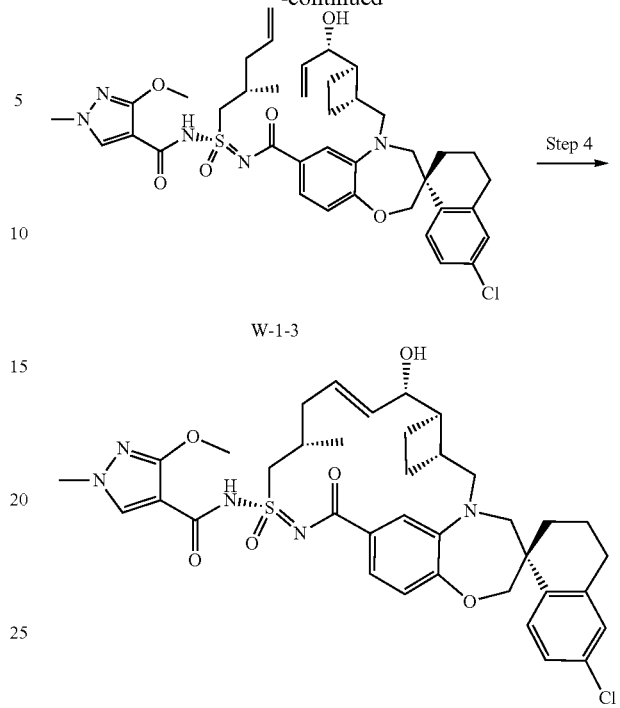

Intermediate W

Step 1: To a stirred solution of (S)-6'-chloro-5-(((1R,2R)-2-((S)-1-hydroxyallyl)cyclobutyl)methyl)-3',4,4',5-tetrahydro-2H,2'H-spiro[benzo[b][1,4] oxazepine-3,1'-naphthalene]-7-carboxylic acid (1.14 g, 2.4 mmol) in DCM (100 mL) was added I-2-2 (703 mg, 2.55 mmol), EDCI (756 mg, 4.87 mmol) and DMAP (595 mg, 4.87 mmol). The reaction mixture was stirred at room temperature for 4 hr. Then the reaction mixture was diluted with DCM, washed with 1 N HCl and brine. The organic phase was dried over $MgSO_4$, filtered, and concentrated to give W-1-1.

Step 2: To a stirred solution of W-1-1 (1300 mg, 1.83 mmol) in methanol (50 mL) was added water (5 mL) and $K_2CO_3$ (899 mg, 9.17 mmol), and stirred at 60° C. for 24 hrs. Water was added and the mixture extracted with dichloromethane. The organic phase was dried over magnesium sulfate, and the solvent removed under reduced pressure to yield W-1-2.

Step 3: To a solution of W-1-2 (1.0 g, 1.63 mmol) in DCM (25 mL) was added 3-methoxy-1-methyl-1H-pyrazole-4-carboxylic acid (280 mg, 1.79 mmol), EDCI (507 mg, 3.26 mmol) and DMAP (399 mg, 3.26 mmol). The reaction mixture was stirred at room temperature for 24 h. Then the reaction mixture was diluted with DCM, washed with 1N HCl and brine. The organic phase was dried over $MgSO_4$, filtered, concentrated and the residue purified on normal phase chromatography (0-10% DCM/MeOH) to yield W-1-3.

Step 4: A stirred solution of W-1-3 (1.0 g, 1.33 mmol), Hoveyda-Grubbs II (339 mg, 0.40 mmol) and TFA (455 mg, 3.99 mmol) in 1,2-dichloroethane (370 mL) was degassed with argon. The reaction mixture was stirred at 80° C. for 1 hr. The reaction mixture was concentrated and purified on reversed phase chromatography (0.1% TFA, 70-95% acetonitrile/water) to give Intermediate W. $^1$H NMR (400 MHz, Chloroform-d) δ 7.83 (s, 1H), 7.77 (d, J=8.5 Hz, 1H), 7.50 (dd, J=8.2, 1.9 Hz, 1H), 7.40 (d, J=2.0 Hz, 1H), 7.20 (dd, J=8.5, 2.4 Hz, 1H), 7.11 (d, J=2.3 Hz, 1H), 6.96 (d, J=8.2 Hz, 1H), 5.64 (t, J=7.3 Hz, 2H), 4.74-4.64 (m, 1H), 4.21-4.01 (m, 4H), 3.96 (d, J=15.1 Hz, 1H), 3.86-3.63 (m, 4H), 3.35 (d, J=14.4 Hz, 1H), 3.16 (dd, J=15.3, 9.1 Hz, 1H), 2.79 (dd, J=10.0, 5.3 Hz, 2H), 2.67-2.48 (m, 2H), 2.45-2.21 (m, 5H), 1.46 (td, J=14.8, 6.9 Hz, 2H), 1.28 (s, 4H), 1.13 (d, J=7.1 Hz, 4H), 0.96-0.77 (m, 3H). LCMS-ESI+ (m/z): [M+H]$^+$ calcd for $C_{37}H_{44}ClN_5O_6S$: 722.3; found: 722.3. Method 2.

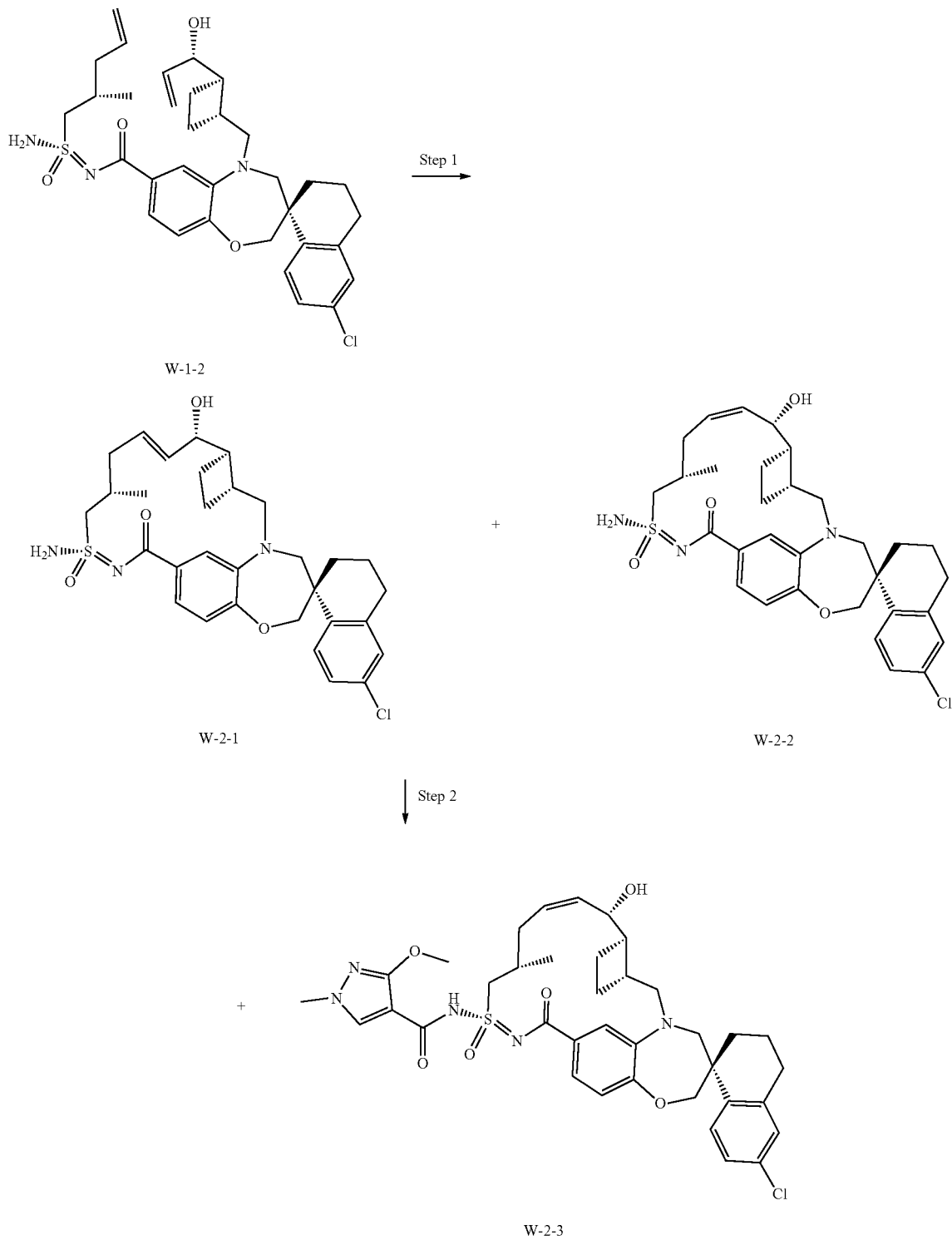

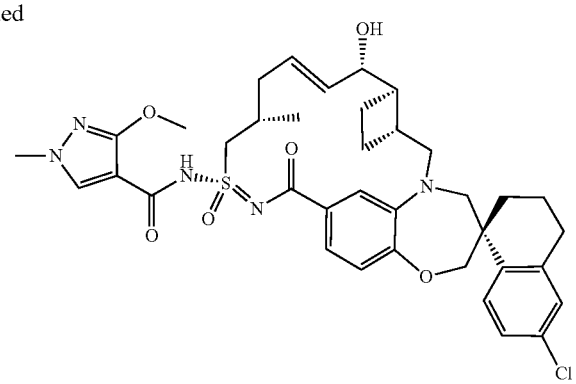

Intermediate W

Step 1: A stirred solution of W-1-2 (500 mg, 0.817 mmol) and Hoveyda-Grubbs II (102 mg, 0.163 mmol) in 1,2-dichloroethane (270 mL) was degassed with argon. The reaction mixture was stirred at 80° C. for 16 hr. The reaction mixture was concentrated, and purified on reversed phase chromatography (0.1% TFA, 70-95% acetonitrile/water to give a mixture of W-2-1 (major product) and W-2-2 (minor product). LCMS-ESI+ (m/z): [M+H]+ calcd for $C_{31}H_{38}ClN_3O_4S$: 584.2; found: 584.1.

Step 2: Intermediate W and W-2-3 were synthesized in a manner similar to Intermediate T using 3-methoxy-1-methyl-1H-pyrazole-4-carboxylic acid and a mixture of W-2-1 and W-2-2.

Example 1

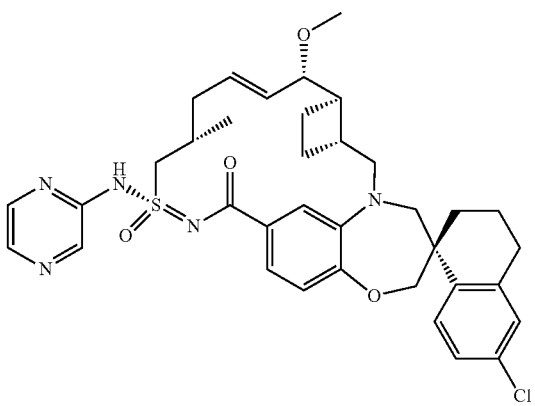 [SMILES: CO[C@H]1/C=C/C[C@H](C)C[S@@](=O)(Nc2cnccn2)=NC(=O)c2ccc3c(c2)N(C[C@@H]2CC[C@H]21)C[C@@]1(CCCc2cc(Cl)ccc21)CO3]

Intermediate 1 (6 mg, 0.010 mmol) was combined with potassium carbonate (14 mg, 10 equiv.), 2-fluoropyrazine (1 mg, 1 equiv.) and N-methylpyrrolidone (0.2 mL) was added. The reaction mixture was heated to reflux. After full consumption of the starting material, the residue was purified by Gilson reverse phase prep HPLC (50-100% ACN/H2O with 0.1% TFA) to give Example 1. $^1$H NMR (400 MHz, Methanol-d4) δ 8.41 (d, J=1.4 Hz, 1H), 8.28 (t, J=2.2 Hz, 1H), 8.21 (d, J=2.9 Hz, 1H), 7.75 (d, J=8.5 Hz, 1H), 7.24 (dd, J=8.1, 1.8 Hz, 1H), 7.17 (dd, J=8.6, 2.4 Hz, 1H), 7.11 (d, J=2.3 Hz, 1H), 7.07 (d, J=1.9 Hz, 1H), 6.88 (d, J=8.2 Hz, 1H), 6.16 (dt, J=14.5, 6.7 Hz, 1H), 5.63 (dd, J=15.4, 8.6 Hz, 1H), 4.25 (dd, J=14.7, 6.6 Hz, 1H), 4.13-3.96 (m, 3H), 3.86 (d, J=15.0 Hz, 1H), 3.79 (d, J=8.2 Hz, 1H), 3.69 (d, J=14.2 Hz, 1H), 3.36 (s, 1H), 3.30 (s, 3H), 3.14-2.68 (m, 3H), 2.54 (dd, J=12.6, 6.6 Hz, 1H), 2.45 (s, 2H), 2.37-2.18 (m, 1H), 2.12 (d, J=13.7 Hz, 1H), 1.95-1.71 (m, 6H), 1.44 (t, J=12.2 Hz, 1H), 1.33 (d, J=17.1 Hz, 2H), 1.14 (d, J=6.6 Hz, 3H). LCMS-ESI+ (m/z): [M+H]+ calcd for $C_{36}H_{42}ClN_5O_4S$: 676.3; found: 676.0.

Example 2

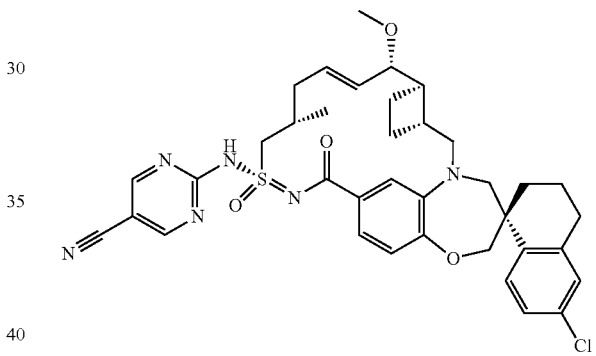

Intermediate 1 (13 mg, 0.021 mmol), 2-chloropyrimidine-5-carbonitrile (6.1 mg, 0.044 mmol) and cesium carbonate (14 mg, 0.033 mmol) were combined in 1,4-dioxane (1.5 mL). The reaction vessel was sealed and heated to 105° C. overnight. Upon cooling, the reaction mixture was diluted with i-PrOAc and washed with 5% (v/v) aqueous AcOH. The aqueous washing was back-extracted with i-PrOAc and the combined organics were washed with H2O, dried over MgSO4, filtered and concentrated under reduced pressure. The crude residue was purified by silica column chromatography (30% to 50% EtOH/EtOAc), affording Example 2. $^1$H NMR (400 MHz, Methanol-d4) δ 8.68 (s, 2H), 7.74 (d, J=8.5 Hz, 1H), 7.26 (ddd, J=19.4, 8.2, 1.8 Hz, 1H), 7.14 (dd, J=8.5, 2.3 Hz, 2H), 7.09 (d, J=2.3 Hz, 2H), 6.80 (dd, J=14.7, 8.2 Hz, 1H), 6.17 (dt, J=14.1, 6.7 Hz, 1H), 5.67-5.42 (m, 1H), 4.10 (q, J=7.1 Hz, 2H), 4.00 (dd, J=12.1, 6.4 Hz, 4H), 3.86 (d, J=15.2 Hz, 1H), 3.79 (dd, J=8.5, 3.6 Hz, 1H), 3.67 (d, J=14.3 Hz, 1H), 3.25 (s, 3H), 3.04 (dd, J=14.9, 9.9 Hz, 1H), 2.82-2.72 (m, 2H), 2.60-2.37 (m, 2H), 2.10 (d, J=14.0 Hz, 1H), 2.01 (s, 2H), 1.91 (d, J=8.6 Hz, 3H), 1.74 (d, J=7.0 Hz, 3H), 1.44 (d, J=12.9 Hz, 1H), 1.13 (d, J=6.5 Hz, 1H), 0.91 (dd, J=10.8, 6.8 Hz, 3H). LCMS-ESI+: [M+H]+ calcd for $C_{37}H_{42}ClN_6O_4S$: 701.3; found: 701.1.

Example 3

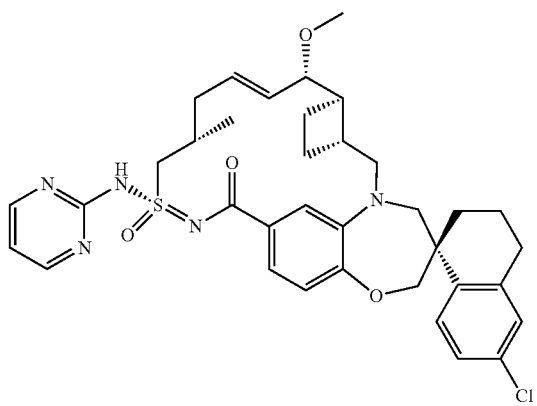 [SMILES: CO[C@H]1/C=C/C[C@H](C)C[S@@](=O)(Nc2ncccn2)=NC(=O)c2ccc3c(c2)N(C[C@@H]2CC[C@H]21)C[C@@]1(CCCc2cc(Cl)ccc21)CO3]

Example 3 was synthesized in a similar manner to Example 1 using Intermediate I and 2-chloropyrimidine. $^1$H NMR (400 MHz, Methanol-$d_4$) δ 8.66 (d, J=5.1 Hz, 2H), 7.77 (d, J=8.6 Hz, 1H), 7.30-7.04 (m, 4H), 6.89 (d, J=8.2 Hz, 1H), 6.16 (dt, J=14.8, 6.9 Hz, 1H), 5.59 (dd, J=15.3, 8.8 Hz, 1H), 4.34 (dd, J=14.6, 6.8 Hz, 1H), 4.17-4.03 (m, 2H), 3.88 (d, J=15.0 Hz, 1H), 3.80 (dd, J=8.8, 3.2 Hz, 1H), 3.69 (d, J=14.2 Hz, 1H), 3.51-3.45 (m, 2H), 3.28 (s, 3H), 3.13-3.01 (m, 2H), 2.85 (t, J=0.9 Hz, 3H), 2.83-2.42 (m, 4H), 2.38 (t, J=8.1 Hz, 2H), 2.27-2.02 (m, 4H), 2.00-1.71 (m, 4H), 1.43 (d, J=14.1 Hz, 1H), 1.09 (d, J=6.7 Hz, 3H). LCMS-ESI+ (m/z): [M+H]$^+$ calcd for $C_{36}H_{42}ClN_5O_4S$: 676.3; found: 676.0.

Example 4

A vigorously stirred mixture of Intermediate 1 (10.0 mg, 16.7 μmol), 4-chloro-1-methyl-1H-pyrazolo[3,4-d]pyrimidine (8.5 mg, 50 μmol), and cesium carbonate (27 mg, 84 μmol) in 1-methylpyrrolidin-2-one (0.7 mL) was heated to 90° C. After 60 min, the reaction mixture was allowed to cool to room temperature, trifluoroacetic acid (100 μL) was added, and the resulting mixture was purified by reverse phase preparative HPLC (0.1% trifluoroacetic acid in acetonitrile/water) to give Example 4. $^1$H NMR (400 MHz, Acetone-$d_6$) δ 8.56 (s, 1H), 8.25 (s, 1H), 7.77 (d, J=8.5 Hz, 1H), 7.28 (dq, J=4.0, 1.9 Hz, 2H), 7.23 (dd, J=8.5, 2.4 Hz, 1H), 7.13 (d, J=2.3 Hz, 1H), 6.82 (d, J=8.6 Hz, 1H), 6.25 (dt, J=14.5, 6.9 Hz, 1H), 5.64 (dd, J=15.5, 8.1 Hz, 1H), 4.13-3.98 (m, 2H), 4.06 (s, 3H), 3.91-3.82 (m, 2H), 3.78 (dd, J=8.1, 3.7 Hz, 1H), 3.72 (d, J=14.4 Hz, 1H), 3.44 (d, J=14.4 Hz, 1H), 3.27 (s, 3H), 3.16 (dd, J=15.1, 10.9 Hz, 1H), 2.94-1.27 (m, 16H), 1.21 (d, J=6.9 Hz, 3H). LCMS-ESI+ (m/z): [M+H]$^+$ calcd for $C_{38}H_{44}ClN_7O_4S$: 730.3; found: 730.1.

Example 5

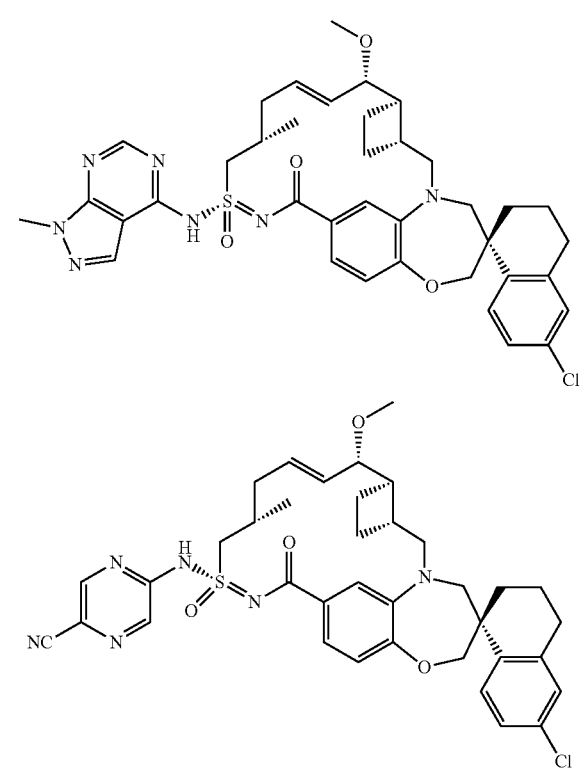

Example 5 was synthesized in a similar manner to Example 1 using Intermediate I and 5-chloropyrazine-2-carbonitrile. $^1$H NMR (400 MHz, Methanol-$d_4$) δ 8.63 (d, J=1.4 Hz, 1H), 8.29 (d, J=1.5 Hz, 1H), 7.74 (d, J=8.5 Hz, 1H), 7.26-7.04 (m, 3H), 7.00-6.85 (m, 2H), 6.03 (dd, J=14.7, 7.3 Hz, 1H), 5.61 (dd, J=15.1, 9.1 Hz, 1H), 4.41 (dd, J=14.8, 6.3 Hz, 1H), 4.08 (d, J=2.6 Hz, 2H), 3.96-3.82 (m, 2H), 3.78 (dd, J=9.0, 3.6 Hz, 1H), 3.68 (d, J=14.2 Hz, 1H), 3.28 (s, 3H), 3.14-3.01 (m, 1H), 2.89-2.71 (m, 3H), 2.57-2.07 (m, 7H), 2.01-1.70 (m, 8H), 1.45 (t, J=12.5 Hz, 1H), 1.14 (d, J=6.3 Hz, 3H). LCMS-ESI+ (m/z): [M+H]$^+$ calcd for $C_{37}H_{41}ClN_6O_4S$: 701.3; found: 700.8.

Example 6

Example 6 was synthesized in a similar manner to Example 1 using Intermediate I and 6-chloropyrazine-2-carbonitrile. $^1$H NMR (400 MHz, Methanol-$d_4$) δ 8.46 (d, J=2.5 Hz, 1H), 8.25 (d, J=2.5 Hz, 1H), 7.73 (d, J=8.5 Hz, 1H), 7.18 (dd, J=8.5, 2.4 Hz, 1H), 7.12 (d, J=2.4 Hz, 1H), 6.99 (dd, J=8.1, 1.9 Hz, 1H), 6.96-6.87 (m, 2H), 5.98 (dd, J=14.6, 7.0 Hz, 1H), 5.60 (dd, J=15.2, 9.1 Hz, 1H), 4.48 (dd, J=15.0, 6.1 Hz, 1H), 4.09 (s, 2H), 3.86 (d, J=15.3 Hz, 1H), 3.81-3.62 (m, 3H), 3.27 (s, 4H), 3.21-3.03 (m, 1H), 2.89-2.70 (m, 3H), 2.59-2.04 (m, 6H), 2.01-1.68 (m, 4H), 1.45 (t, J=12.6 Hz, 1H), 1.24 (d, J=6.5 Hz, 3H). LCMS-ESI+(m/z): [M+H]$^+$ calcd for $C_{37}H_{41}ClN_6O_4S$: 701.3; found: 700.8.

Example 7

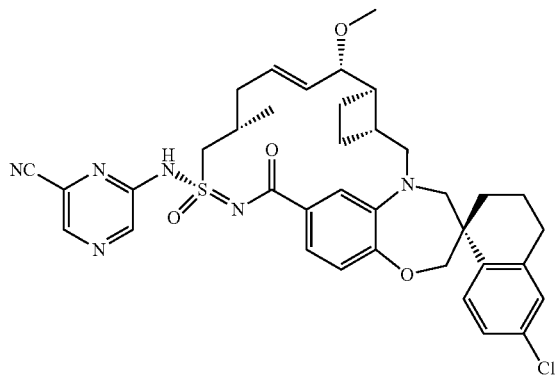

Example 8

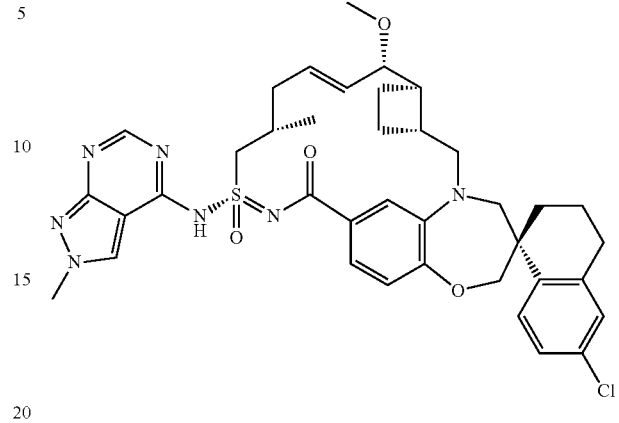

Example 8 was synthesized in a manner similar to Example 4 using 4-chloro-2-methyl-2H-pyrazolo[3,4-d]pyrimidine in place of 4-chloro-1-methyl-1H-pyrazolo[3,4-d]pyrimidine. $^1$H NMR (400 MHz, Acetone-$d_6$) δ 8.59 (s, 1H), 8.40 (s, 1H), 7.77 (d, J=8.5 Hz, 1H), 7.32-7.26 (m, 2H), 7.23 (dd, J=8.5, 2.5 Hz, 1H), 7.13 (d, J=2.3 Hz, 1H), 6.82 (d, J=8.1 Hz, 1H), 6.24 (dt, J=14.5, 6.9 Hz, 1H), 5.64 (dd, J=15.3, 8.3 Hz, 1H), 4.20 (s, 3H), 4.08 (d, J=12.0 Hz, 1H), 4.02 (d, J=12.0 Hz, 1H), 3.91-3.65 (m, 4H), 3.44 (d, J=14.4 Hz, 1H), 3.27 (s, 3H), 3.26-3.10 (m, 1H), 2.98-1.22 (m, 16H), 1.20 (d, J=6.9 Hz, 3H). LCMS-ESI+ (m/z): [M+H]$^+$ calcd for $C_{38}H_{44}ClN_7O_4S$: 730.3; found: 730.1.

Example 9

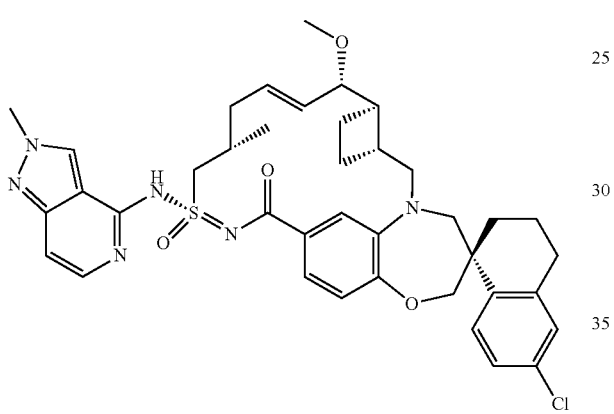

Intermediate I (11 mg, 0.018 mmol), 4-chloro-2-methyl-pyrazolo[4,3-c]pyridine (4.6 mg, 0.028 mmol), cesium carbonate (12 mg, 0.037 mmol) and Xantphos Pd G3 (3.5 mg, 0.0037 mmol) were combined in PhMe (1 mL). The suspension was sparged with N$_2$ for 10 min, then the reaction vessel was sealed and heated to 100° C. overnight. Upon cooling, the reaction mixture was diluted with i-PrOAc and washed with saturated aqueous NH$_4$Cl. The aqueous washing was back-extracted with i-PrOAc and the combined organics were washed 2× with H$_2$O, dried over MgSO$_4$, filtered and concentrated under reduced pressure. The crude residue was purified by silica column chromatography (5% EtOAc/hexanes to 5% MeOH/EtOAc to 30% MeOH/EtOAc). The resulting isolate was repurified by silica column chromatography (20% EtOAc/hexanes to 100% EtOAc to 10% acetone/EtOAc to 30% acetone/EtOAc), affording Example 7. $^1$H NMR (400 MHz, Acetonitrile-$d_3$) δ 11.85 (s, 1H), 8.44 (s, 1H), 7.75 (d, J=8.5 Hz, 1H), 7.45-7.05 (m, 6H), 6.88 (dd, J=28.4, 7.7 Hz, 2H), 6.23-5.94 (m, 1H), 5.58 (dd, J=15.5, 8.5 Hz, 1H), 4.13 (s, 3H), 4.10-3.93 (m, 3H), 3.86-3.60 (m, 4H), 3.34 (d, J=14.3 Hz, 1H), 3.24 (s, 3H), 3.20-2.99 (m, 1H), 2.79 (qd, J=16.8, 10.3 Hz, 2H), 2.60 (d, J=4.3 Hz, 1H), 2.39 (d, J=28.7 Hz, 4H), 1.94-1.57 (m, 5H), 1.25-1.19 (m, 3H), 1.13 (d, J=6.9 Hz, 3H). LCMS-ESI+ (m/z): [M+H]$^+$ calcd for $C_{39}H_{46}ClN_6O_4S$: 729.3; found: 729.3.

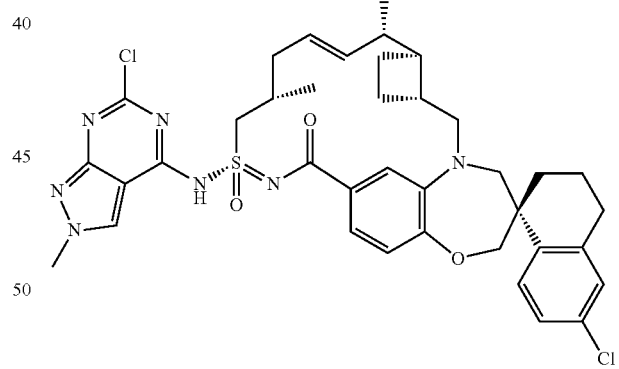

A vigorously stirred mixture of Intermediate I (50.0 mg, 83.6 μmol), 4,6-dichloro-2-methyl-2H-pyrazolo[3,4-d]pyrimidine (22.1 mg, 109 μmol), and cesium carbonate (81.7 mg, 251 μmol) in acetonitrile (2.0 mL) and tetrahydrofuran (0.4 mL) was heated to 95° C. After 75 min, the reaction mixture was allowed to cool to room temperature, trifluoroacetic acid (100 μL) was added, and the resulting mixture was filtered through a pad of celite. The filter cake was extracted with acetone (10 mL), and the combined filtrates were concentrated under reduced pressure. The residue was purified by reverse phase preparative HPLC (0.1% trifluoroacetic acid in acetonitrile/water) to give Example 9. $^1$H NMR (400 MHz, Acetone-$d_6$) δ 8.60 (s, 1H), 7.78 (d, J=8.5

Hz, 1H), 7.31 (d, J=8.1 Hz, 1H), 7.27-7.20 (m, 1H), 7.19-7.11 (m, 2H), 6.90 (d, J=8.1 Hz, 1H), 6.17 (dt, J=14.5, 7.0 Hz, 1H), 5.60 (dd, J=15.4, 8.5 Hz, 1H), 4.20 (s, 3H), 4.10 (d, J=12.1 Hz, 1H), 4.05 (d, J=12.1 Hz, 1H), 3.88 (d, J=15.0 Hz, 1H), 3.82-3.34 (m, 4H), 3.24 (s, 3H), 3.15 (dd, J=15.4, 10.0 Hz, 1H), 2.87-1.22 (m, 16H), 1.15 (d, J=6.9 Hz, 3H). LCMS-ESI+ (m/z): [M+H]$^+$ calcd for $C_{38}H_{43}Cl_2N_7O_4S$: 764.3; found: 764.1.

Example 10

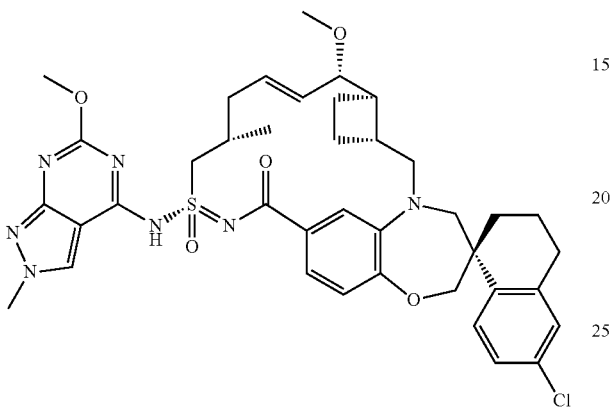

Sodium methoxide solution (25% wt. in methanol, 600 µL, 2.62 mmol) was added via syringe to a stirred solution of Example 9 (4.00 mg, 5.23 µmol) in methanol (1.0 mL) at room temperature. After 17 min, the resulting mixture was heated to 50° C. After 130 min, the resulting mixture was allowed to cool to room temperature. Trifluoroacetic acid (250 µL) was added, and the resulting mixture was purified by reverse phase preparative HPLC (0.1% trifluoroacetic acid in acetonitrile/water) to give Example 10. $^1$H NMR (400 MHz, Acetone-d$_6$) b 8.51 (s, 1H), 7.78 (d, J=8.5 Hz, 1H), 7.30 (dd, J=8.1, 1.9 Hz, 1H), 7.27-7.21 (m, 2H), 7.13 (d, J=2.3 Hz, 1H), 6.86 (d, J=8.2 Hz, 1H), 6.21 (dt, J=14.5, 6.8 Hz, 1H), 5.61 (dd, J=15.4, 8.3 Hz, 1H), 4.12 (s, 3H), 4.12 (s, 3H), 4.11-3.58 (m, 6H), 3.42 (d, J=14.4 Hz, 1H), 3.25 (s, 3H), 3.15 (dd, J=15.2, 10.4 Hz, 1H), 2.89-1.25 (m, 16H), 1.16 (d, J=6.9 Hz, 3H). LCMS-ESI+ (m/z): [M+H]$^+$ calcd for $C_{39}H_{46}ClN_7O_5S$: 760.3; found: 760.2.

Example 11

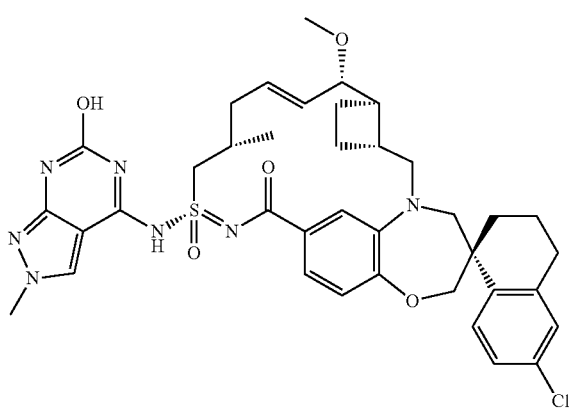 [SMILES: CO[C@H]1/C=C/C[C@H](C)C[S@@](=O)(Nc2nc(O)nc3nn(C)cc23)=NC(=O)c2ccc3c(c2)N(C[C@@H]2CC[C@H]21)C[C@@]1(CCCc2cc(Cl)ccc21)CO3]

Sodium cyanide (5.1 mg, 110 µmol) was added to a stirred solution of Example 9 (4.00 mg, 5.23 µmol) in dimethylsulfoxide (1.0 mL) at room temperature, and the resulting mixture was heated to 100° C. After 115 min, the resulting mixture was heated to 160° C. After 40 min, water (0.1 mL) was added, and the resulting mixture was heated to 180° C. After 110 min, the resulting mixture was allowed to cool to room temperature and was purified by reverse phase preparative HPLC (0.1% trifluoroacetic acid in acetonitrile/water) to give Example 11. $^1$H NMR (400 MHz, Acetone-d$_6$) δ 10.84 (s, 1H), 8.39 (s, 1H), 7.78 (d, J=8.6 Hz, 1H), 7.32 (d, J=8.2 Hz, 1H), 7.30-7.19 (m, 2H), 7.13 (d, J=2.3 Hz, 1H), 6.85 (d, J=8.2 Hz, 1H), 6.21 (dt, J=14.5, 6.9 Hz, 1H), 5.63 (dd, J=15.5, 8.2 Hz, 1H), 4.08 (d, J=12.1 Hz, 1H), 4.04 (d, 1H), 4.02 (s, 3H), 3.98-3.84 (m, 2H), 3.82-3.59 (m, 2H), 3.43 (d, J=14.4 Hz, 1H), 3.26 (s, 3H), 3.15 (dd, J=15.2, 10.6 Hz, 1H), 3.01-1.37 (m, 16H), 1.17 (d, J=6.9 Hz, 3H). LCMS-ESI+ (m/z): [M+Na]+ calcd for $C_{38}H_{44}ClN_7O_5S$: 768.3; found: 768.1.

Example 12

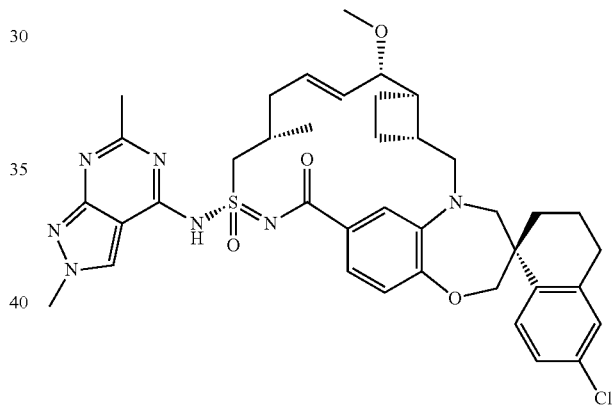

A stirred mixture of Example 9 (6.60 mg, 8.63 µmol), tetramethylstannane (23.9 µL, 173 µmol), and [1,1'-bis(diphenylphosphino)ferrocene]dichloropalladium(II) (3 mg, 4 µmol) in N,N-dimethylformamide (0.5 mL) was heated to 110° C. After 100 min, the resulting mixture was allowed to cool to room temperature. Trifluoroacetic acid (100 µL) was added, and the resulting mixture was purified by reverse phase preparative HPLC (0.1% trifluoroacetic acid in acetonitrile/water) to give Example 12. $^1$H NMR (400 MHz, Acetone-d$_6$) δ 8.62 (s, 1H), 7.78 (d, J=8.5 Hz, 1H), 7.29 (dd, J=8.2, 1.8 Hz, 1H), 7.24 (dd, J=8.5, 2.4 Hz, 1H), 7.20 (d, J=1.9 Hz, 1H), 7.13 (d, J=2.3 Hz, 1H), 6.85 (d, J=8.2 Hz, 1H), 6.22 (dt, J=14.5, 7.0 Hz, 1H), 5.59 (dd, J=15.5, 8.4 Hz, 1H), 4.18 (s, 3H), 4.12-3.98 (m, 3H), 3.87 (dd, J=15.0, 2.0 Hz, 1H), 3.79-3.68 (m, 2H), 3.40 (d, J=14.3 Hz, 1H), 3.25 (s, 3H), 3.21-3.05 (m, 1H), 2.89-1.35 (m, 16H), 2.60 (s, 3H), 1.15 (d, J=6.9 Hz, 3H). LCMS-ESI+ (m/z): [M+H]$^+$ calcd for $C_{39}H_{46}ClN_7O_4S$: 744.3; found: 744.2.

Example 13

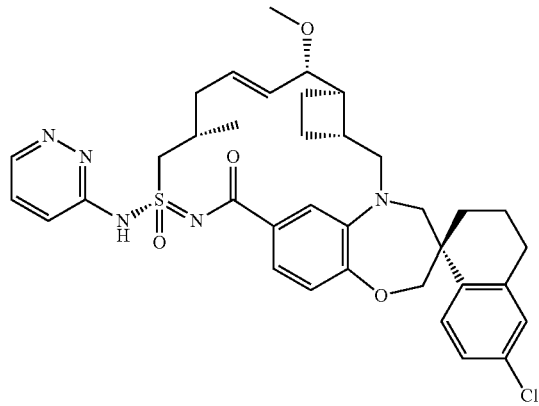 [SMILES: CO[C@H]1/C=C/C[C@H](C)C[S@@](=O)(Nc2cccnn2)=NC(=O)c2ccc3c(c2)N(C[C@@H]2CC[C@H]21)C[C@@]1(CCCc2cc(Cl)ccc21)CO3]

A vigorously stirred mixture of Intermediate 1 (7.0 mg, 12 μmol), cesium carbonate (19.1 mg, 58.5 μmol), 3-bromopyridazine (5.6 mg, 35 μmol), and [(2-di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate (1.5 mg, 1.8 μmol) in 1,4-dioxane (0.7 mL) was heated to 130° C. After 1 d, the resulting mixture was cooled to room temperature and was purified by reverse phase preparative HPLC (0.1% trifluoroacetic acid in acetonitrile/water) to give Example 13. $^1$H NMR (400 MHz, Acetone-$d_6$) δ 8.36 (dd, J=4.0, 1.6 Hz, 1H), 7.88-7.71 (m, 3H), 7.33 (dd, J=8.2, 1.9 Hz, 1H), 7.29-7.22 (m, 2H), 7.13 (d, J=2.3 Hz, 1H), 6.83 (d, J=8.2 Hz, 1H), 6.25 (dt, J=14.7, 7.1 Hz, 1H), 5.61 (dd, J=15.5, 8.1 Hz, 1H), 4.07 (d, J=12.0 Hz, 1H), 4.02 (d, J=12.0 Hz, 1H), 3.92-3.60 (m, 4H), 3.43 (d, J=14.4 Hz, 1H), 3.26 (s, 3H), 3.21-3.10 (m, 1H), 2.99-1.37 (m, 16H), 1.17 (d, J=6.9 Hz, 3H). LCMS-ESI+ (m/z): [M+H]$^+$ calcd for $C_{36}H_{42}ClN_5O_4S$: 676.3; found: 676.1.

Example 14

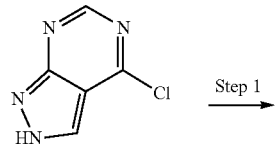

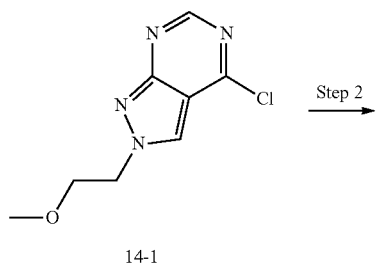

14-1

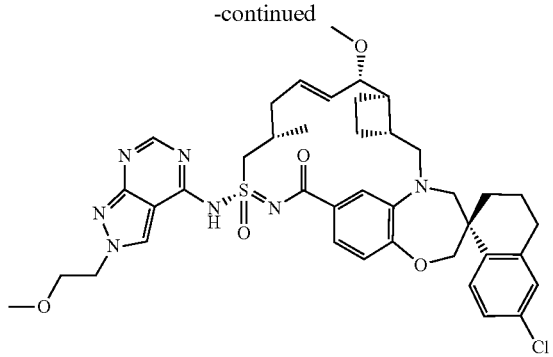

Example 14

Step 1: Trimethylphosphine solution (1.0 M in tetrahydrofuran, 2.59 mL, 2.6 mmol) was added over 5 min via syringe to a vigorously stirred mixture of 4-chloro-2H-pyrazolo[3,4-d]pyrimidine (308 mg, 1.99 mmol), 2-methoxyethanol (188 μL, 2.39 mmol), and diisopropyl azodicarboxylate (509 μL, 2.59 mmol) in tetrahydrofuran (10 mL) at room temperature. After 35 min, silica gel (12 g) was added, and the resulting mixture was concentrated under reduced pressure. The residue was purified by flash column chromatography on silica gel (0 to 100% ethyl acetate in hexanes) to give 14-1.

Step 2: Example 14 was synthesized in a manner similar to Example 4 using 14-1. $^1$H NMR (400 MHz, Acetone-$d_6$) δ 8.54 (s, 1H), 8.16 (s, 1H), 7.86-6.75 (m, 6H), 6.41-6.02 (m, 1H), 5.75-5.47 (m, 1H), 4.88-3.17 (m, 18H), 3.12-0.97 (m, 19H). LCMS-ESI+ (m/z): [M+H]$^+$ calcd for $C_{40}H_{48}ClN_7O_5S$: 774.3; found: 774.2.

Example 15

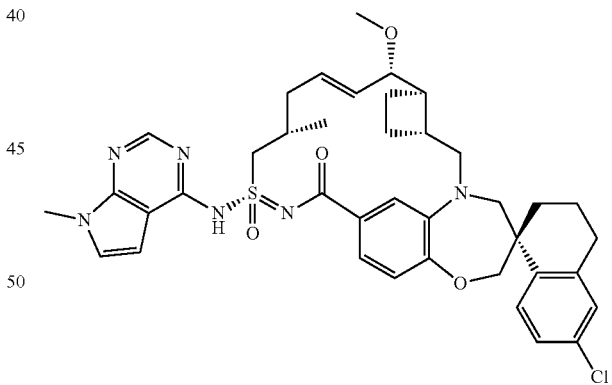

Example 15 was prepared in a manner similar to Example 4 using 4-chloro-7-methyl-pyrrolo[2,3-d]pyrimidine. $^1$H NMR (400 MHz, Methanol-$d_4$) δ 8.28 (s, 1H), 7.75 (d, J=8.5 Hz, 1H), 7.34 (d, J=3.6 Hz, 1H), 7.22-7.03 (m, 5H), 6.80 (d, J=8.1 Hz, 1H), 6.20 (dt, J=14.4, 7.0 Hz, 1H), 5.57 (dd, J=15.3, 8.8 Hz, 1H), 4.22 (dd, J=14.3, 7.7 Hz, 1H), 4.12-3.97 (m, 3H), 3.91 (s, 2H), 3.87-3.77 (m, 2H), 3.66 (d, J=14.2 Hz, 1H), 3.29 (s, 3H), 3.06 (dd, J=15.0, 9.8 Hz, 1H), 2.79 (d, J=18.8 Hz, 2H), 2.66 (d, J=12.1 Hz, 1H), 2.51-2.36 (m, 3H), 2.24-2.06 (m, 3H), 1.93-1.69 (m, 5H), 1.33 (d, J=16.0 Hz, 2H), 1.19 (d, J=7.0 Hz, 3H). LCMS-ESI+ (m/z): [M+H]$^+$ calcd for $C_{39}H_{45}ClN_6O_4S$: 729.3; found: 728.0.

Example 16

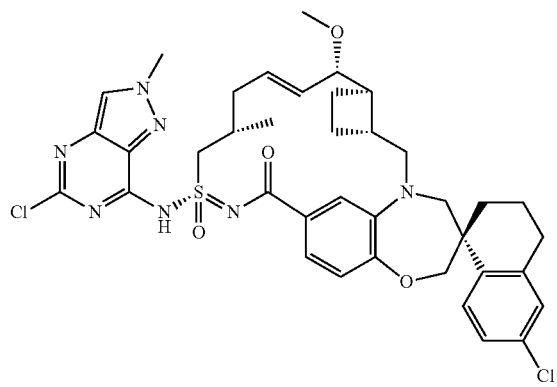 [SMILES: CO[C@H]1/C=C/C[C@H](C)C[S@@](=O)(Nc2nc(Cl)nc3cn(C)nc23)=NC(=O)c2ccc3c(c2)N(C[C@@H]2CC[C@H]21)C[C@@]1(CCCc2cc(Cl)ccc21)CO3]

Example 16 was prepared in a manner similar to Example 4 using 4-chloro-7-methyl-pyrrolo[2,3-d]pyrimidine. $^1$H NMR (400 MHz, Methanol-$d_4$) δ 8.27 (s, 1H), 7.75 (d, J=8.5 Hz, 1H), 7.19 (ddd, J=8.4, 6.0, 2.1 Hz, 2H), 7.12 (d, J=2.3 Hz, 1H), 7.00 (d, J=1.9 Hz, 1H), 6.95 (d, J=8.2 Hz, 1H), 6.12-6.02 (m, 1H), 5.60 (dd, J=15.2, 9.0 Hz, 1H), 4.47 (dd, J=14.9, 7.6 Hz, 1H), 4.26 (s, 3H), 4.13-4.04 (m, 2H), 3.96 (dd, J=14.8, 5.0 Hz, 1H), 3.87 (d, J=15.1 Hz, 1H), 3.80 (dd, J=9.1, 3.7 Hz, 1H), 3.69 (d, J=14.3 Hz, 1H), 3.29 (s, 3H), 3.14-3.05 (m, 1H), 2.90-2.75 (m, 2H), 2.62-2.44 (m, 2H), 2.38 (dd, J=20.3, 11.8 Hz, 2H), 2.27-2.08 (m, 2H), 2.00-1.88 (m, 3H), 1.86-1.70 (m, 4H), 1.50-1.39 (m, 1H), 1.13 (d, J=6.8 Hz, 3H). LCMS-ESI+ (m/z): [M+H]$^+$ calcd for $C_{38}H_{43}Cl_2N_7O_4S$: 764.3, found: 764.0.

Example 17

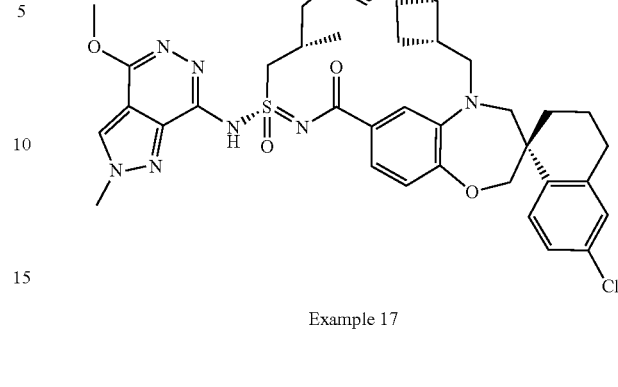

Step 1: Sodium methoxide solution (25% wt in methanol, 67.6 µL, 296 µmol) was added over 1 min via syringe to a stirred solution of 4,7-dichloro-2-methyl-2H-pyrazolo[3,4-d]pyridazine (60.0 mg, 296 µmol) in methanol (1.0 mL) and tetrahydrofuran (3.0 mL) at room temperature. After 30 min, the resulting mixture was warmed to 50° C. After 32 min, sodium methoxide solution (25% wt in methanol, 67.6 µL, 296 µmol) was added via syringe. After 30 min, the resulting mixture was cooled to room temperature. Silica gel (12 g) was added, and the resulting mixture was concentrated under reduced pressure. The residue was purified by flash column chromatography on silica gel (0 to 1% methanol in dichloromethane) to give a 1:1 mixture of 17-1 and 17-2, regioisomers assigned tentatively.

Step 2: A vigorously stirred mixture of Intermediate I (30.0 mg, 50.2 µmol), the 1:1 mixture of 17-2 and 17-3 (25.5 mg, 125 µmol), potassium carbonate (69.3 mg, 502 µmol), tris(dibenzylideneacetone)dipalladium(0) (11.5 mg, 12.5 µmol), and 5-(di-tert-butylphosphino)-1',3',5'-triphenyl-1'H-[1,4']bipyrazole (25.4 mg, 50.2 µmol) in 1,4-dioxane was warmed to 90° C. After 15 min, the resulting mixture was warmed to 130° C. After 165 min, the resulting mixture was cooled to room temperature and was purified by reverse phase preparative HPLC (0.1% trifluoroacetic acid in acetonitrile/water) to give Example 17 (regioisomer assigned tentatively). $^1$H NMR (400 MHz, Acetone-$d_6$) δ 8.79 (s, 1H), 7.78 (d, J=8.5 Hz, 1H), 7.32 (d, J=7.0 Hz, 1H), 7.28-7.19 (m, 2H), 7.13 (s, 1H), 6.85 (d, J=8.2 Hz, 1H), 6.32-6.17 (m, 1H), 5.61 (dd, J=15.9, 8.2 Hz, 1H), 4.32 (s, 3H), 4.09 (s, 3H), 4.09-3.99 (m, 2H), 3.96-3.82 (m, 1H), 3.80-3.69 (m, 2H), 3.43 (d, J=14.6 Hz, 1H), 3.26 (s, 3H), 3.21-3.10 (m, 2H), 2.87-1.41 (m, 16H), 1.17 (d, J=6.9 Hz, 3H). LCMS-ESI+ (m/z): [M+H]$^+$ calcd for $C_{39}H_{46}ClN_7O_5S$: 760.3; found: 760.2.

Example 18

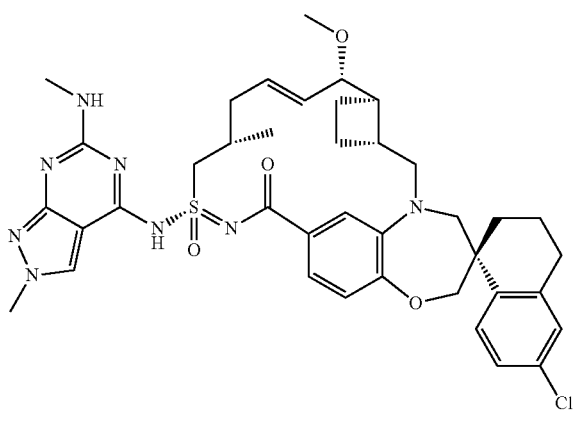 [SMILES: CNc1nc(N[S@@]2(=O)=NC(=O)c3ccc4c(c3)N(C[C@@H]3CC[C@H]3[C@@H](OC)/C=C/C[C@H](C)C2)C[C@@]2(CCCc3cc(Cl)ccc32)CO4)c2cn(C)nc2n1]

A mixture of Example 9 (3.0 mg, 3.9 μmol) and methylamine solution (9.8 M in methanol, 1.0 mL, 9.8 mmol) was heated in a microwave reactor to 100° C. After 30 min, the resulting mixture was allowed to cool to room temperature and was then heated in a microwave reactor to 115° C. After 2.5 h, the resulting mixture was allowed to cool to room temperature and was purified by reverse phase preparative HPLC (0.1% trifluoroacetic acid in acetonitrile/water) to give Example 18. $^1$H NMR (400 MHz, Acetone-$d_6$) δ 8.30 (s, 1H), 7.78 (d, J=8.5 Hz, 1H), 7.30 (dd, J=8.3, 1.8 Hz, 1H), 7.27-7.20 (m, 2H), 7.13 (d, J=2.3 Hz, 1H), 6.83 (d, J=8.2 Hz, 1H), 6.32-6.17 (m, 1H), 5.61 (dd, J=15.5, 8.2 Hz, 1H), 4.08 (d, J=12.1 Hz, 1H), 4.04-4.00 (m, 1H), 4.03 (s, 3H), 3.86 (d, J=15.0 Hz, 1H), 3.82-3.58 (m, 3H), 3.44 (d, J=14.4 Hz, 1H), 3.26 (s, 3H), 3.15 (dd, J=15.1, 10.8 Hz, 1H), 3.04-1.38 (m, 16H), 1.18 (d, J=6.9 Hz, 3H). LCMS-ESI+ (m/z): [M+H]$^+$ calcd for $C_{39}H_{47}ClN_3O_4S$: 759.3; found: 759.3.

Example 19

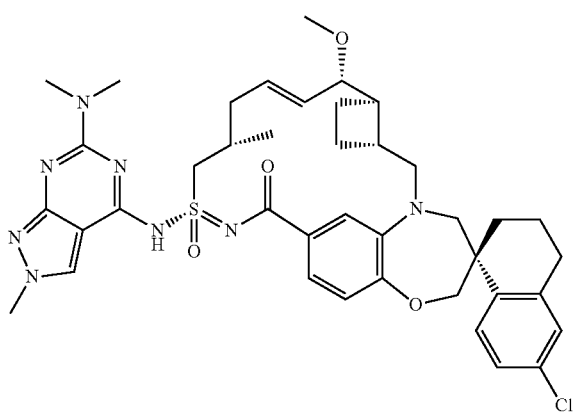 [SMILES: CO[C@H]1/C=C/C[C@H](C)C[S@@](=O)(Nc2nc(N(C)C)nc3nn(C)cc23)=NC(=O)c2ccc3c(c2)N(C[C@@H]2CC[C@H]21)C[C@@]1(CCCc2cc(Cl)ccc21)CO3]

A mixture of Example 9 (3.0 mg, 3.9 μmol) and dimethylamine solution (2.0 M in methanol, 1.5 mL, 3.0 mmol) was heated to 120° C. in a microwave reactor. After 120 min, the resulting mixture was allowed too cool to room temperature and was purified by reverse phase preparative HPLC (0.1% trifluoroacetic acid in acetonitrile/water) to give Example 19. $^1$H NMR (400 MHz, Acetone-$d_6$) δ 8.27 (s, 1H), 7.78 (d, J=8.5 Hz, 1H), 7.37 (dd, J=8.2, 1.8 Hz, 1H), 7.31 (s, 1H), 7.24 (dd, J=8.6, 2.4 Hz, 1H), 7.13 (d, J=2.2 Hz, 1H), 6.84 (d, J=8.2 Hz, 1H), 6.37-6.21 (m, 1H), 5.67 (dd, J=15.8, 7.9 Hz, 1H), 4.08 (d, J=12.0 Hz, 1H), 4.05-3.99 (m, 1H), 4.03 (s, 3H), 3.85 (d, J=15.1 Hz, 1H), 3.79 (dd, J=7.9, 3.7 Hz, 1H), 3.73 (d, J=14.4 Hz, 1H), 3.48 (d, J=14.6 Hz, 1H), 3.34-3.23 (m, 1H), 3.28 (s, 3H), 3.26 (s, 6H), 3.18 (dd, J=15.2, 11.1 Hz, 1H), 2.97-1.38 (m, 16H), 1.21 (d, J=6.9 Hz, 3H). LCMS-ESI+ (m/z): [M+H]$^+$ calcd for $C_{40}H_{49}ClN_8O_4S$: 773.3; found: 773.3.

Example 20

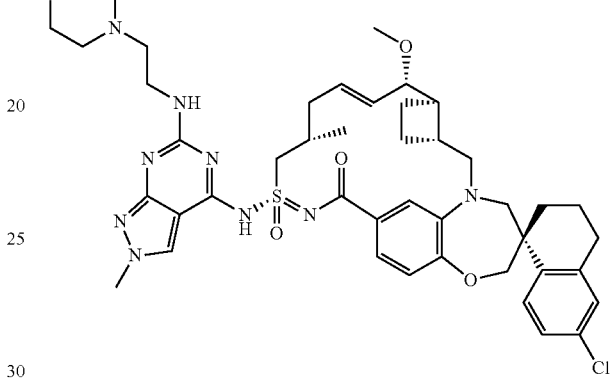

A stirred mixture of Example 9 (3.0 mg, 3.9 μmol) and 2-morpholinoethan-1-amine (257 μL, 1.96 mmol) in dimethylsulfoxide (250 μL) was heated to 130° C. After 180 min, the resulting mixture was allowed too cool to room temperature. Trifluoroacetic acid (200 μL) was added, and the resulting mixture was purified by reverse phase preparative HPLC (0.1% trifluoroacetic acid in acetonitrile/water) to give Example 20. $^1$H NMR (400 MHz, Acetone-$d_6$) b 8.15 (s, 1H), 7.78 (d, J=8.6 Hz, 1H), 7.23 (d, J=9.5 Hz, 3H), 7.13 (d, J=2.4 Hz, 1H), 6.79 (d, J=8.1 Hz, 1H), 6.25 (s, 1H), 5.56 (dd, J=15.5, 8.2 Hz, 1H), 4.23-3.32 (m, 22H), 3.23 (s, 3H), 3.19-3.04 (m, 1H), 2.99-1.23 (m, 16H), 1.17 (d, J=6.8 Hz, 3H). LCMS-ESI+ (m/z): [M+H]$^+$ calcd for $C_{44}H_{56}ClN_9O_5S$: 858.4; found: 858.4.

Example 21

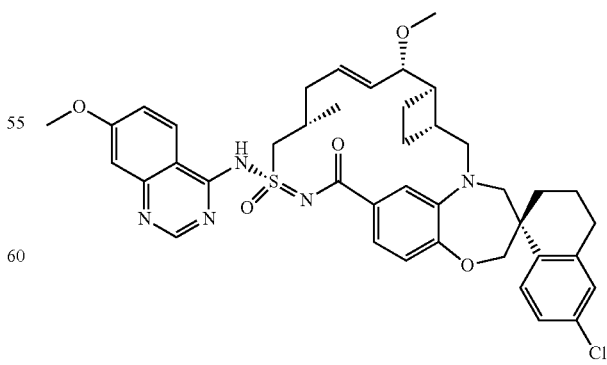

Example 21 was synthesized in a similar manner to Example 1 using Intermediate I and 4-chloro-7-methoxyquinazoline. ¹H NMR (400 MHz, Methanol-d₄) δ 8.50 (s, 1H), 8.38 (d, J=9.1 Hz, 1H), 7.76 (d, J=8.5 Hz, 1H), 7.34-7.21 (m, 2H), 7.21-7.09 (m, 4H), 6.87 (d, J=8.2 Hz, 1H), 6.32-6.17 (m, 1H), 5.62 (dd, J=15.4, 8.8 Hz, 1H), 4.24-4.03 (m, 2H), 4.02 (s, 3H), 3.92-3.77 (m, 2H), 3.69 (d, J=14.1 Hz, 2H), 3.31 (s, 3H), 3.19-2.63 (m, 2H), 2.53-2.04 (m, 4H), 1.96 (s, 2H), 1.78 (s, 2H), 1.45 (t, J=13.8 Hz, 1H), 1.18 (d, J=6.8 Hz, 3H). LCMS-ESI+ (m/z): [M+H]⁺ calcd for $C_{41}H_{46}ClN_5O_5S$: 756.3; found: 756.3.

Example 22

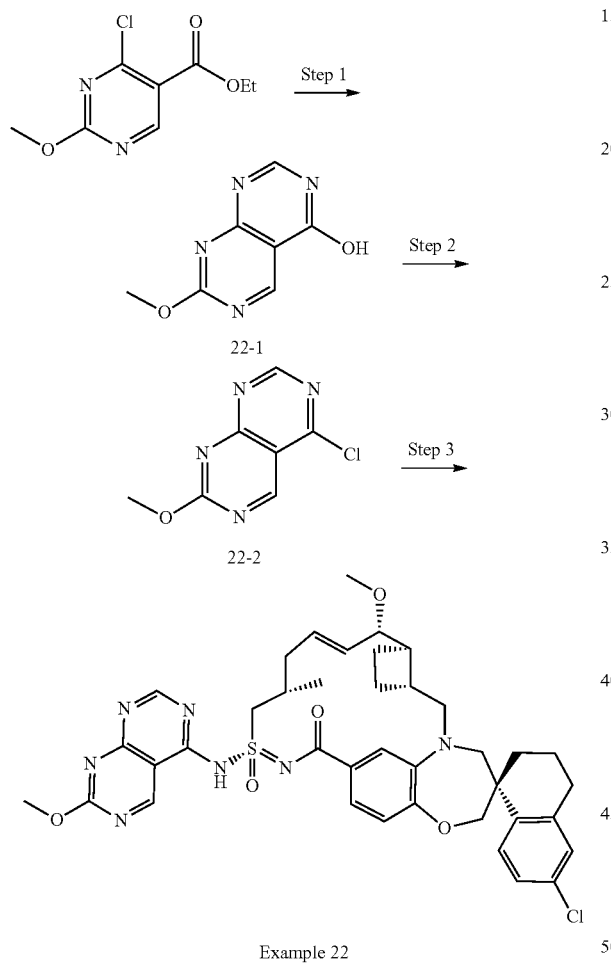

Example 22

Step 1: A stirred mixture of ethyl 4-chloro-2-methoxypyrimidine-5-carboxylate (300 mg, 1.38 mmol), formamidine hydrochloride (298 mg, 3.70 mmol), and triethylamine (965 µL, 6.92 mmol) in N,N,-dimethylformamide (7.0 mL) was heated to 80° C. After 45 min, a mixture of brine (15 mL), ice (15 g), phosphoric acid (679 mg), and water (10 mL) was added, and the resulting mixture was swirled until all of the ice had melted. The resulting mixture was filtered, and the filter cake was washed with water (15 mL) and was dried under reduced pressure to give 22-1.

Step 2: A stirred mixture of 22-1 (100 mg, 561 µmol) and phosphoryl chloride (2.30 mL, 24.7 mmol) was heated to 110° C. After 70 min, the resulting mixture was cooled to room temperature and was concentrated under reduced pressure. Ethyl acetate (75 mL), tetrahydrofuran (20 mL), dichloromethane (10 mL), ice (50 g) and brine (25 mL) were added sequentially to the residue, and the resulting biphasic mixture was agitated. The layers were separated, and the organic layer was washed with a mixture of water and brine (1:1 v:v, 50 mL), was dried over anhydrous magnesium sulfate, was filtered, and was concentrated under reduced pressure to give 22-2.

Step 3: Example 22 was synthesized in a manner similar to Example 4 using 22-2, potassium carbonate, N,N-dimethylformamide, and Intermediate I. ¹H NMR (400 MHz, Acetone-d₆) δ 9.53 (s, 1H), 8.86 (s, 1H), 7.77 (d, J=8.5 Hz, 1H), 7.40-7.16 (m, 3H), 7.13 (d, J=2.3 Hz, 1H), 6.85 (d, J=8.2 Hz, 1H), 6.28 (dt, J=15.7, 7.2 Hz, 1H), 5.69 (dd, J=15.7, 8.1 Hz, 1H), 4.14 (s, 3H), 4.13-4.06 (m, 1H), 4.03 (d, J=12.0 Hz, 1H), 3.91-3.62 (m, 3H), 3.53-3.10 (m, 3H), 3.29 (s, 3H), 3.05-1.27 (m, 16H), 1.24 (d, J=6.9 Hz, 3H). LCMS-ESI+ (m/z): [M+H]⁺ calcd for $C_{39}H_{44}ClN_7O_5S$: 758.3; found: 758.2.

Example 23

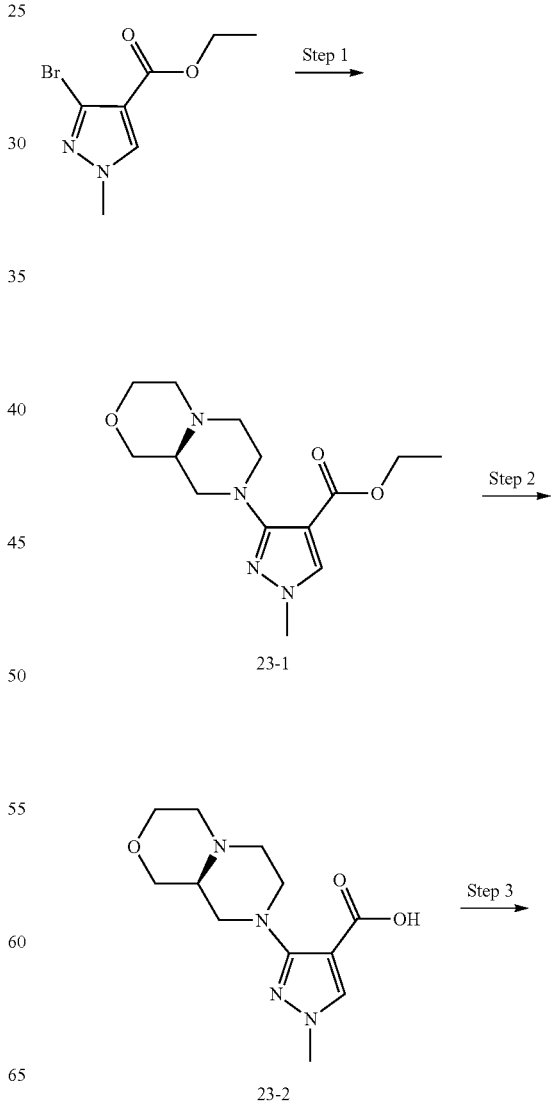

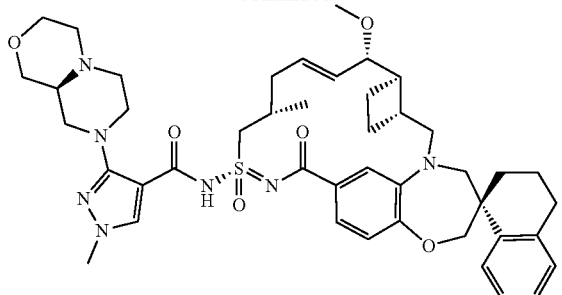

Example 23

Step 1: To a 20-mL glass microwave vial was added ethyl 3-bromo-1-methyl-pyrazole-4-carboxylate (250 mg, 1 equiv.), then (9aS)-1,3,4,6,7,8,9,9a-octahydropyrazino[2,1-c][1,4]oxazine dihydrochloride (462 mg, 2 equiv.), then RuPhos Pd G3 precatalyst (80 mg, 0.1 equiv.), then cesium carbonate (2.5 g, 7 equiv.), then 1,4-dioxane (5 mL). The resulting suspension was degassed by stirring vigorously while bubbling through nitrogen gas for 5 min. The vial was then sealed under nitrogen atmosphere and stirred in a metal heating block at 100° C. for 18 hr. The vial was removed from the heating block and allowed to cool to 20° C. The reaction was diluted with water, then extracted with ethyl acetate. The combined organic phases were dried over magnesium sulfate, filtered and concentrated in vacuo to a residue. The residue was redissolved in dichloromethane and purified by flash column chromatography (silica gel, 0 to 20% methanol in dichloromethane) to give 23-1. $^1$H NMR (400 MHz, Chloroform-d) δ 7.67 (s, 1H), 4.15 (q, J=7.1 Hz, 2H), 3.78 (d, J=11.4 Hz, 2H), 3.67 (s, 3H), 3.67-3.58 (m, 2H), 3.55-3.43 (m, 1H), 3.23 (dq, J=9.9, 7.2 Hz, 1H), 2.87 (td, J=11.8, 2.9 Hz, 1H), 2.72 (d, J=11.2 Hz, 1H), 2.61 (d, J=11.5 Hz, 1H), 2.55-2.26 (m, 4H), 1.23 (t, J=7.1 Hz, 3H). LCMS-ESI+ (m/z): [M+H]$^+$ calcd for $C_{14}H_{22}N_4O_3$: 295.2; found: 295.1.

Step 2: To a glass screwtop vial charged with 23-1 (107 mg, 1 equiv.) was added THF (3.5 mL), then sodium hydroxide in water (2 M, 3.6 mL, 20 equiv.), then ethanol (1 mL). The vial was sealed under ambient atmosphere and stirred vigorously at 80° C. in a metal heating block for 5 hr. The reaction was filtered to remove insoluble solids, rinsing with ethanol. Then 1 N aqueous HCl was added dropwise until pH ~2 by pH paper. The resulting solution was concentrated and dried overnight in vacuo to yield 23-2, which was carried forward crude to the next step without further purification. $^1$H NMR (400 MHz, Methanol-d$_4$) δ 8.00 (s, 1H), 4.21-3.98 (m, 4H), 3.97-3.84 (m, 1H), 3.71-3.56 (m, 2H), 3.56-3.37 (m, 3H), 3.28-3.18 (m, 2H), 2.89 (dd, J=13.5, 10.7 Hz, 1H), 2.04 (s, 3H). LCMS-ESI+ (m/z): [M+H]$^+$ calcd for $C_{12}H_１N_4O_3$: 267.1; found: 267.1.

Step 3: Example 23 was synthesized in a manner similar to Intermediate T using 23-2, and Intermediate I. 1H NMR (400 MHz, Acetonitrile-d3) δ 8.44 (s, 1H), 7.53 (d, J=8.0 Hz, 1H), 7.38-7.29 (m, 1H), 7.10-6.99 (m, 2H), 6.95-6.82 (m, 1H), 6.80 (d, J=8.3 Hz, 1H), 6.08 (dt, J=14.8, 6.9 Hz, 1H), 5.64 (dd, J=15.5, 8.0 Hz, 1H), 4.10-3.82 (m, 6H), 3.74 (s, 3H), 3.74-3.56 (m, 4H), 3.53 (d, J=13.7 Hz, 2H), 3.46 (d, J=12.1 Hz, 2H), 3.40 (d, J=12.3 Hz, 2H), 3.30-3.18 (m, 2H), 3.21 (s, 3H), 3.16-3.02 (m, 2H), 2.87-2.64 (m, 3H), 2.54-2.37 (m, 2H), 2.37-2.27 (m, 1H), 2.28-2.16 (m, 2H), 2.10 (d, J=10.1 Hz, 1H), 2.01 (s, 3H), 1.79 (ddd, J=36.9, 19.6, 9.0 Hz, 6H), 1.39-1.28 (m, 1H), 1.08 (d, J=6.8 Hz, 3H). LCMS-ESI+ (m/z): [M+H]$^+$ calcd for $C_{44}H_{56}ClN_7O_6S$: 846.4; found: 846.5.

Example 24

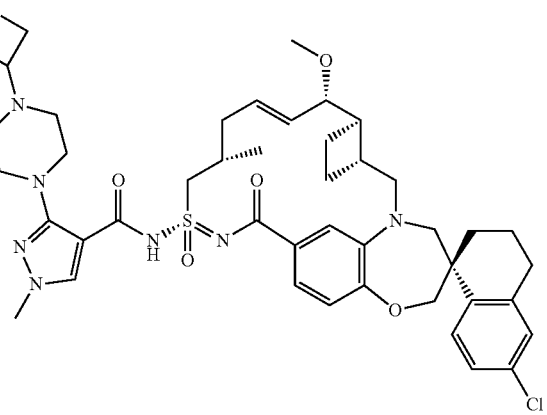

Example 24 was synthesized in a manner similar to Example 23 using 1-(oxetan-3-yl)piperazine, in place of (9aS)-1,3,4,6,7,8,9,9a-octahydropyrazino[2,1-c][1,4]oxazine dihydrochloride. $^1$H NMR (400 MHz, Acetonitrile-d$_3$) δ 8.40 (s, 1H), 7.55 (d, J=8.3 Hz, 1H), 7.32 (d, J=8.2 Hz, 1H), 7.10-6.99 (m, 2H), 6.98-6.85 (m, 1H), 6.82 (d, J=8.5 Hz, 1H), 6.07 (dt, J=14.6, 7.0 Hz, 1H), 5.64 (dd, J=15.5, 8.1 Hz, 1H), 4.93-4.82 (m, 2H), 4.82-4.68 (m, 2H), 4.26-4.15 (m, 1H), 4.03-3.82 (m, 4H), 3.75 (s, 3H), 3.74-3.67 (m, 2H), 3.61 (d, J=14.5 Hz, 2H), 3.54-3.29 (m, 4H), 3.23 (s, 3H), 3.21-2.90 (m, 4H), 2.85-2.60 (m, 3H), 2.54-2.37 (m, 2H), 2.37-2.28 (m, 1H), 2.23 (dt, J=14.6, 7.5 Hz, 1H), 2.17-2.05 (m, 1H), 2.05-1.98 (m, 1H), 1.91-1.62 (m, 6H), 1.41-1.29 (m, 1H), 1.08 (d, J=6.7 Hz, 3H). LCMS-ESI+(m/z): [M+H]$^+$ calcd for $C_{44}H_{56}ClN_7O_6S$: 846.4; found: 846.4.

Example 25

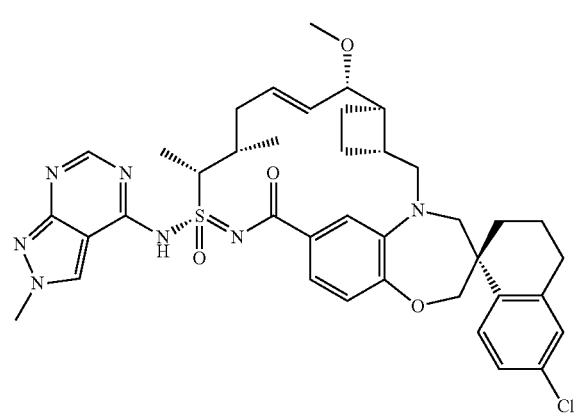 [SMILES: CO[C@H]1/C=C/C[C@H](C)[C@@H](C)[S@@](=O)(Nc2ncnc3nn(C)cc23)=NC(=O)c2ccc3c(c2)N(C[C@@H]2CC[C@H]21)C[C@@]1(CCCc2cc(Cl)ccc21)CO3]

Example 25 was synthesized in a manner similar to Example 4 using Intermediate K and 4-chloro-2-methyl-2H-pyrazolo[3,4-d]pyrimidine. $^1$H NMR (400 MHz, Acetone-d$_6$) δ 8.56 (s, 1H), 8.40 (d, J=1.9 Hz, 1H), 7.80-7.74 (m, 1H), 7.37-7.20 (m, 3H), 7.13 (d, J=2.5 Hz, 1H), 6.82 (d, J=8.2 Hz, 1H), 6.16-6.06 (m, 1H), 5.69 (dd, J=15.6, 8.0 Hz, 1H), 4.20 (s, 3H), 4.19-3.62 (m, 6H), 3.48 (d, J=14.5 Hz, 1H), 3.22 (s, 3H), 3.22-3.15 (m, 1H), 3.14-1.26 (m, 15H), 1.42 (d, J=7.0 Hz, 3H), 1.19 (d, J=6.9 Hz, 3H). LCMS-ESI+ (m/z): [M+H]+ calcd for C$_{39}$H$_{46}$ClN$_{7}$O$_{4}$S: 744.3; found: 744.2.

Example 26

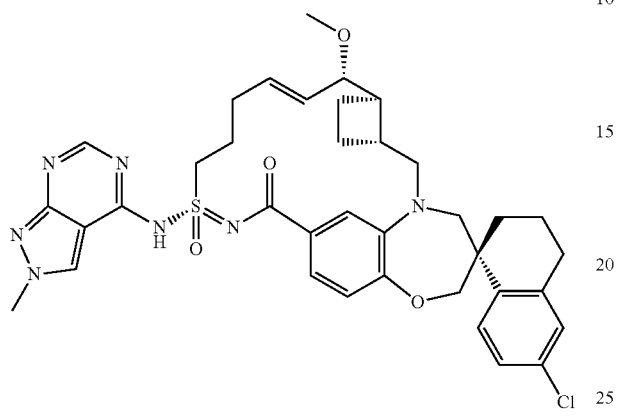

Example 26 was synthesized in a manner similar to Example 4 using Intermediate L and 4-chloro-2-methyl-2H-pyrazolo[3,4-d]pyrimidine. $^{1}$H NMR (400 MHz, Acetone-d$_{6}$) δ 8.52 (s, 1H), 8.40 (d, J=2.4 Hz, 1H), 7.79 (d, J=8.5 Hz, 1H), 7.55 (d, J=1.9 Hz, 1H), 7.34 (dd, J=8.2, 1.9 Hz, 1H), 7.24 (dd, J=8.5, 2.4 Hz, 1H), 7.13 (d, J=2.3 Hz, 1H), 6.86 (d, J=8.2 Hz, 1H), 6.00-5.85 (m, 2H), 4.18 (s, 3H), 4.10 (d, J=12.0 Hz, 1H), 4.00 (d, J=12.0 Hz, 1H), 3.87-3.81 (m, 1H), 3.78 (d, J=14.5 Hz, 1H), 3.66 (ddd, J=14.2, 10.3, 4.4 Hz, 1H), 3.59-3.54 (m, 1H), 3.49 (d, J=14.5 Hz, 1H), 3.30 (s, 3H), 3.27-3.16 (m, 1H), 2.98-1.61 (m, 16H), 1.54-1.39 (m, 1H). LCMS-ESI+ (m/z): [M+H]+ calcd for C$_{37}$H$_{42}$ClN$_{7}$O$_{4}$S: 716.3; found: 716.1.

Example 27

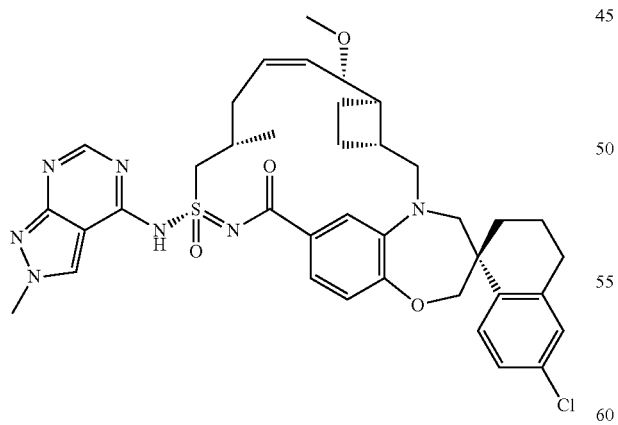

Example 27 was synthesized in a manner similar to Example 4 using I-3-1 (10:1 E:Z olefin isomer mixture) and 4-chloro-2-methyl-2H-pyrazolo[3,4-d]pyrimidine. $^{1}$H NMR (400 MHz, Acetone-d$_{6}$) δ 8.61 (s, 1H), 8.41 (s, 1H), 7.77 (d, J=8.5 Hz, 1H), 7.38 (d, J=1.9 Hz, 1H), 7.33-7.20 (m, 2H), 7.13 (d, J=2.4 Hz, 1H), 6.84 (d, J=8.2 Hz, 1H), 5.83 (td, J=10.8, 3.9 Hz, 1H), 5.44 (t, J=9.7 Hz, 1H), 4.26 (d, J=9.3 Hz, 1H), 4.19 (s, 3H), 4.17-3.75 (m, 4H), 3.58 (d, J=14.4 Hz, 1H), 3.49-3.11 (m, 2H), 3.23 (s, 3H), 2.97-1.59 (m, 15H), 1.50 (t, J=13.0 Hz, 1H), 1.15 (d, J=6.9 Hz, 3H). LCMS-ESI+ (m/z): [M+H]+ calcd for C$_{38}$H$_{44}$ClN$_{7}$O$_{4}$S: 730.3; found: 730.1.

Example 28

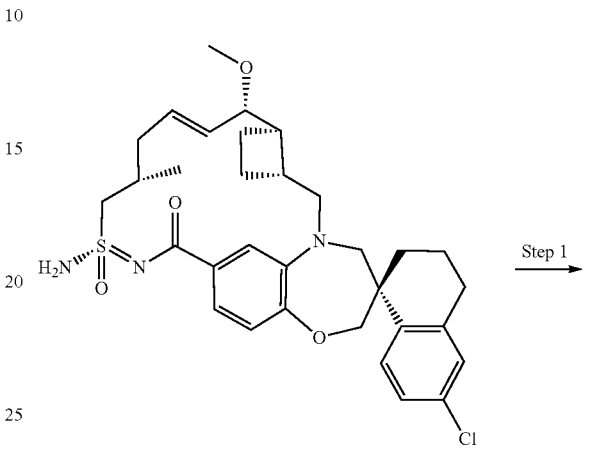

Intermediate I

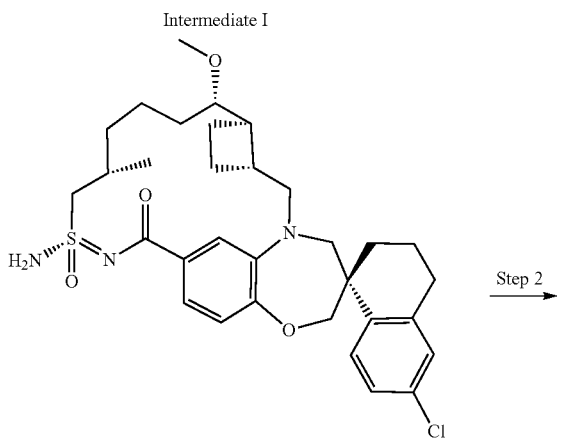

28-1

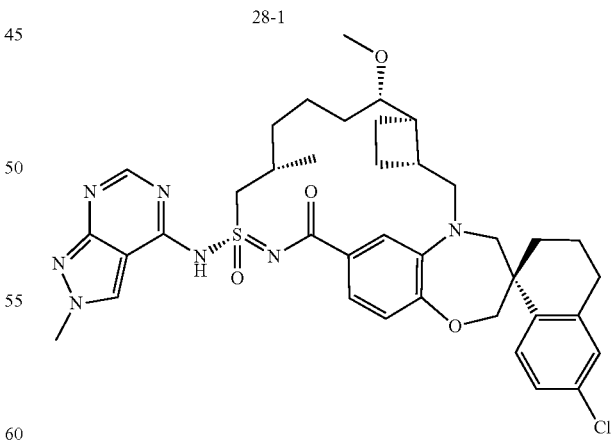

Example 28

Step 1: A vigorously stirred mixture of Intermediate 1 (30.0 mg, 50.2 µmol) and platinum(IV) oxide (5.7 mg, 25.1 µmol) in ethanol (1.5 mL) was placed under an atmosphere of hydrogen gas (balloon) at room temperature. After 220 min, the resulting mixture was filtered through celite and was concentrated under reduced pressure to give 28-1 which was carried forward without further purification.

Step 2: 2-tert-Butylimino-2-diethylamino-1,3-dimethylperhydro-1,3,2-diazaphosphorine (polymer-bound, 200-400 mesh, 2.0-2.5 mmol/g loading, 1% cross-linked, 90.9 mg, 180-230 µmol) was added to a vigorously stirred solution of 28-1 (20.0 mg, 33.3 µmol) in dimethylsulfoxide (1.0 mL) at room temperature. After 1 min, 4-chloro-2-methyl-2H-pyrazolo[3,4-d]pyrimidine (22.5 mg, 133 µmol) was added, and the resulting mixture was warmed to 110° C. After 60 min, trifluoroacetic acid (200 µL) and methanol (1 mL) were added. The resulting mixture was filtered and was purified by reverse phase preparative HPLC (0.1% trifluoroacetic acid in acetonitrile/water) to give Example 28. $^1$H NMR (400 MHz, Acetone-$d_6$) δ 8.59 (s, 1H), 8.40 (s, 1H), 7.79 (d, J=8.4 Hz, 1H), 7.36 (d, J=1.9 Hz, 1H), 7.30 (d, J=8.1 Hz, 1H), 7.24 (dd, J=8.5, 2.4 Hz, 1H), 7.13 (d, J=2.3 Hz, 1H), 6.84 (d, J=8.2 Hz, 1H), 4.20 (s, 3H), 4.09 (d, J=12.0 Hz, 1H), 4.04 (d, J=12.0 Hz, 1H), 3.93-3.60 (m, 3H), 3.42 (d, J=14.2 Hz, 1H), 3.34 (s, 3H), 3.18 (dd, J=15.0, 9.6 Hz, 1H), 3.06 (dd, J=14.0, 8.5 Hz, 1H), 3.01-1.28 (m, 20H), 1.26 (d, J=6.6 Hz, 3H). LCMS-ESI+ (m/z): [M+H]$^+$ calcd for $C_{38}H_{46}ClN_7O_4S$: 732.3; found: 732.2.

Example 29

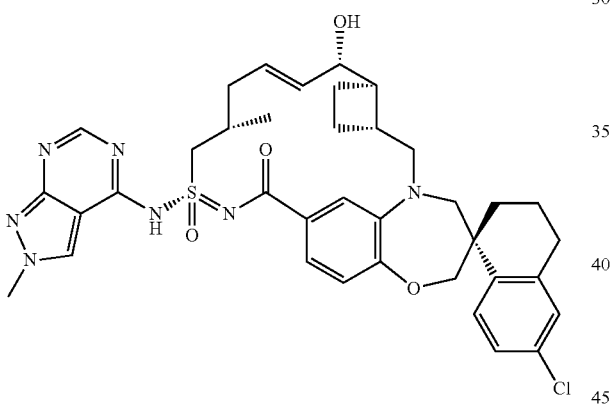

A mixture of W-2-1 (30.0 mg, 51.4 µmol), 4-chloro-2-methyl-2H-pyrazolo[3,4-d]pyrimidine (8.7 mg, 51 µmol), and cesium carbonate (100 mg, 308 µmol) in dimethylsulfoxide (0.4 mL) was heated to 120° C. in a microwave reactor. After 45 min, the resulting mixture was allowed to cool to room temperature. More 4-chloro-2-methyl-2H-pyrazolo[3,4-d]pyrimidine (8.7 mg, 51 µmol) was added, and the resulting mixture was heated to 120° C. in a microwave reactor. After 75 min, the resulting mixture was allowed to cool to room temperature. Trifluoroacetic acid (100 µL) was added, and the resulting mixture was purified by reverse phase preparative HPLC (0.1% trifluoroacetic acid in acetonitrile/water) to give Example 29. $^1$H NMR (400 MHz, Acetone-$d_6$) δ 8.57 (s, 1H), 8.40 (s, 1H), 7.78 (d, J=8.5 Hz, 1H), 7.34-7.27 (m, 2H), 7.24 (dd, J=8.6, 2.4 Hz, 1H), 7.13 (d, J=2.3 Hz, 1H), 6.83 (d, J=8.2 Hz, 1H), 6.25-6.12 (m, 1H), 5.84 (dd, J=15.6, 6.7 Hz, 1H), 4.31-4.24 (m, 1H), 4.20 (s, 3H), 4.08 (d, J=12.0 Hz, 1H), 4.02 (d, J=12.0 Hz, 1H), 3.86 (d, J=15.0 Hz, 1H), 3.81-3.61 (m, 2H), 3.46 (d, J=14.4 Hz, 1H), 3.25 (dd, J=14.3, 5.6 Hz, 1H), 3.20-3.09 (m, 1H), 2.94-1.37 (m, 16H), 1.24 (d, J=6.8 Hz, 3H). LCMS-ESI+ (m/z): [M+H]$^+$ calcd for $C_{37}H_{42}ClN_7O_4S$: 716.3; found: 716.2.

Example 30

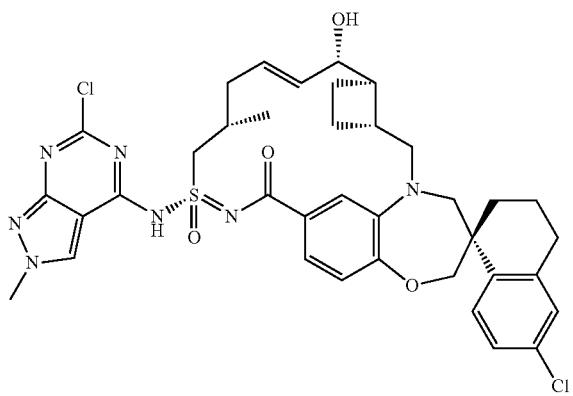 [SMILES: C[C@H]1C/C=C/[C@H](O)[C@@H]2CC[C@H]2CN2C[C@@]3(CCCc4cc(Cl)ccc43)COc3ccc(cc32)C(=O)N=[S@](=O)(Nc2nc(Cl)nc3nn(C)cc23)C1]

A vigorously stirred mixture of W-2-1 (40.0 mg, 68.5 µmol), cesium carbonate (134 mg, 411 µmol), and 4,6-dichloro-2-methyl-2H-pyrazolo[3,4-d]pyrimidine (14.6 mg, 71.9 µmol) in dimethylsulfoxide (1.0 mL) was heated to 120° C. After 60 min, the resulting mixture was allowed too cool to room temperature and was purified by reverse phase preparative HPLC (0.1% trifluoroacetic acid in acetonitrile/water) to give Example 30. $^1$H NMR (400 MHz, Acetone-$d_6$) δ 8.56 (s, 1H), 7.78 (d, J=8.6 Hz, 1H), 7.31 (d, J=9.0 Hz, 1H), 7.28-7.20 (m, 2H), 7.13 (d, J=2.3 Hz, 1H), 6.88 (d, J=8.2 Hz, 1H), 6.13 (dt, J=14.3, 6.8 Hz, 1H), 5.77 (dd, J=15.4, 7.2 Hz, 1H), 4.24 (dd, J=7.2, 3.8 Hz, 1H), 4.18 (s, 3H), 4.14-3.95 (m, 3H), 3.87 (d, J=15.0 Hz, 1H), 3.72 (d, J=14.4 Hz, 1H), 3.42 (d, J=14.3 Hz, 1H), 3.14 (dd, J=15.1, 10.6 Hz, 1H), 2.86-1.39 (m, 16H), 1.16 (d, J=6.8 Hz, 3H). LCMS-ESI+ (m/z): [M+H]$^+$ calcd for $C_{37}H_{41}Cl_2N_7O_4S$: 750.2; found: 750.2.

Example 31

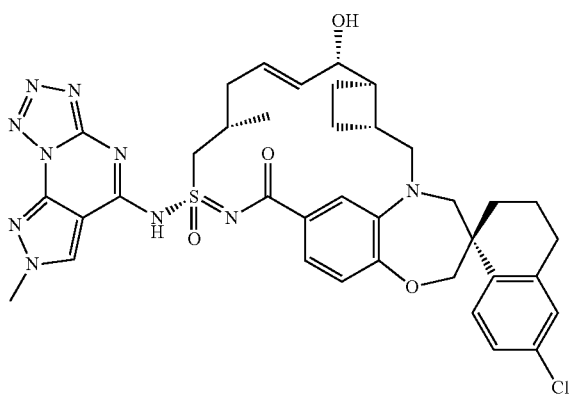 [SMILES: C[C@H]1C/C=C/[C@H](O)[C@@H]2CC[C@H]2CN2C[C@@]3(CCCc4cc(Cl)ccc43)COc3ccc(cc32)C(=O)N=[S@](=O)(Nc2nc3nnnn3c3nn(C)cc23)C1]

A stirred mixture of Example 30 (9.0 mg, 12 µmol), sodium azide (25.0 mg, 385 µmol), and acetic acid (2.1 µL, 36 µmol) in dimethylsulfoxide (0.7 mL) was heated to 120° C. After 120 min, the resulting mixture was allowed too cool to room temperature and was purified by reverse phase preparative HPLC (0.1% trifluoroacetic acid in acetonitrile/ water) to give Example 31 (7:3 mixture of isomers by ¹H NMR). ¹H NMR (400 MHz, Acetone-d₆) δ 8.62 (s, 0.7H), 8.56 (s, 0.3H), 7.83-7.73 (m, 1H), 7.33-7.21 (m, 2H), 7.21-7.16 (m, 0.3H), 7.16-7.11 (m, 0.7H), 6.97-6.86 (m, 1H), 6.24-6.05 (m, 1H), 5.79 (dd, J=15.2, 7.4 Hz, 1H), 4.32-3.81 (m, 5H), 4.25 (s, 2.1H), 4.16 (s, 0.9H), 3.72 (d, J=14.4 Hz, 1H), 3.52-3.36 (m, 1H), 3.15 (dd, J=15.1, 10.3 Hz, 1H), 2.90-1.36 (m, 16H), 1.18 (d, J=6.8 Hz, 0.9H), 1.15 (d, J=6.1 Hz, 2.1H). LCMS-ESI+ (m/z): [M+H]⁺ calcd for C₃₇H₄₁ClN₁₀O₄S: 757.3; found: 757.3.

Example 32

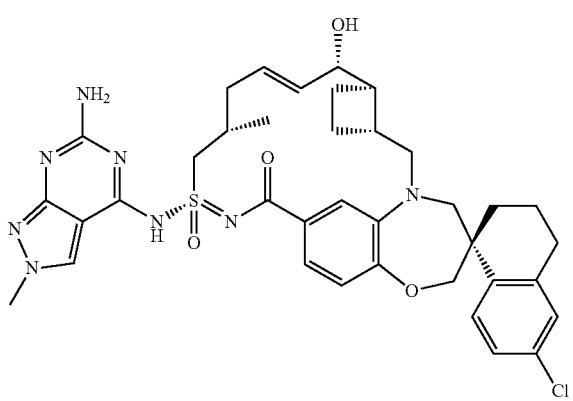 [SMILES: C[C@H]1C/C=C/[C@H](O)[C@@H]2CC[C@H]2CN2C[C@@]3(CCCc4cc(Cl)ccc43)COc3ccc(cc32)C(=O)N=[S@](=O)(Nc2nc(N)nc3nn(C)cc23)C1]

Tin(II) chloride (25.0 mg, 132 µmol) was added to a vigorously stirred solution of Example 31 (5.0 mg, 6.6 µmol) in DCM (0.5 mL) and methanol (0.1 mL) at room temperature. After 25 min, the resulting mixture was concentrated, and the residue was purified by reverse phase preparative HPLC (0.1% trifluoroacetic acid in acetonitrile/water) to give Example 32. ¹H NMR (400 MHz, Acetone-d₆) δ 8.30 (s, 1H), 7.79 (s, 1H), 7.30 (dd, J=8.3, 1.8 Hz, 1H), 7.28-7.21 (m, 2H), 7.13 (d, J=2.3 Hz, 1H), 6.83 (d, J=8.2 Hz, 1H), 6.30-6.17 (m, 1H), 5.61 (dd, J=15.5, 8.2 Hz, 1H), 4.08 (d, J=12.1 Hz, 1H), 4.05-3.98 (m, 1H), 4.03 (s, 3H), 3.86 (d, J=15.0 Hz, 1H), 3.77 (dd, J=8.0, 3.7 Hz, 1H), 3.71 (d, J=14.5 Hz, 1H), 3.69-3.61 (m, 1H), 3.44 (d, J=14.4 Hz, 1H), 3.26 (s, 3H), 3.15 (dd, J=15.1, 10.8 Hz, 1H), 2.90-1.55 (m, 15H), 1.46 (s, 1H), 1.18 (d, J=6.9 Hz, 3H). LCMS-ESI+ (m/z): [M+H]⁺ calcd for C₃₇H₄₃ClN₈O₄S: 731.3; found: 731.3.

Example 33

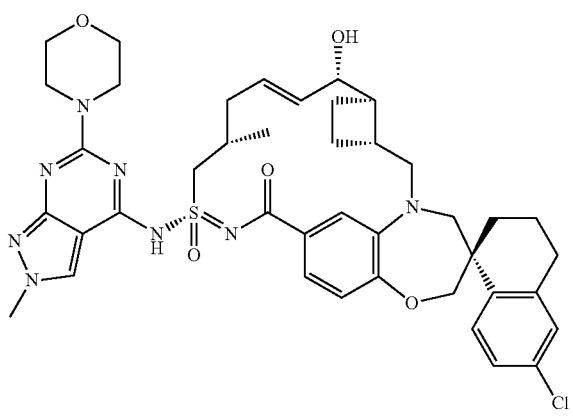 [SMILES: C[C@H]1C/C=C/[C@H](O)[C@@H]2CC[C@H]2CN2C[C@@]3(CCCc4cc(Cl)ccc43)COc3ccc(cc32)C(=O)N=[S@](=O)(Nc2nc(N3CCOCC3)nc3nn(C)cc23)C1]

A stirred mixture of Example 30 (5.0 mg, 6.7 µmol) and morpholine (600 µL, 6.86 mmol) in methanol (0.6 mL) was heated in a microwave reactor to 120° C. After 30 min, the resulting mixture was allowed too cool to room temperature and was purified by reverse phase preparative HPLC (0.1% trifluoroacetic acid in acetonitrile/water) to give Example 33. ¹H NMR (400 MHz, Acetone-d₆) δ 8.34-8.26 (m, 1H), 7.78 (d, J=8.5 Hz, 1H), 7.36 (dd, J=8.2, 1.9 Hz, 1H), 7.32 (d, J=2.0 Hz, 1H), 7.24 (dd, J=8.5, 2.4 Hz, 1H), 7.13 (d, J=2.3 Hz, 1H), 6.86 (d, J=8.2 Hz, 1H), 6.22 (dt, J=14.3, 6.4 Hz, 1H), 5.84 (dd, J=15.6, 6.4 Hz, 1H), 4.29-4.22 (m, 1H), 4.09 (d, J=12.0 Hz, 1H), 4.05 (s, 3H), 4.03 (d, J=12.2 Hz, 1H), 3.92-3.56 (m, 1 OH), 3.49 (d, J=14.5 Hz, 1H), 3.35 (dd, J=14.4, 4.8 Hz, 1H), 3.16 (dd, J=15.1, 11.1 Hz, 1H), 2.97-1.65 (m, 15H), 1.55-1.41 (m, 1H), 1.24 (d, J=6.7 Hz, 3H). LCMS-ESI+ (m/z): [M+H]⁺ calcd for C₄₁H₄₉ClN₈O₅S: 801.3; found: 801.3.

Example 34

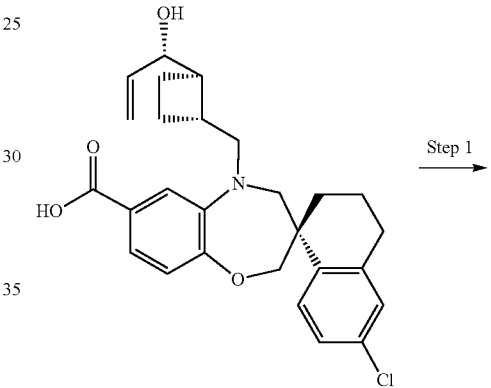

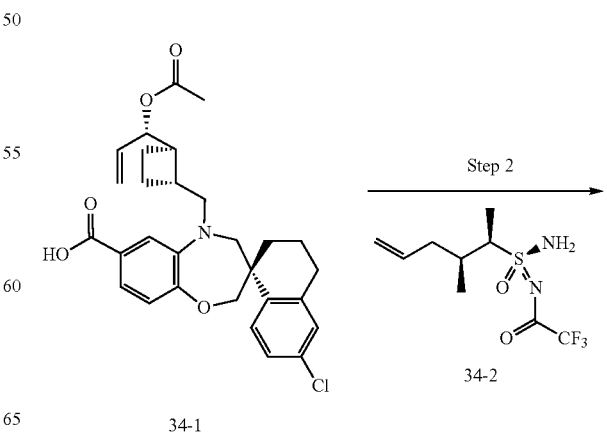

-continued

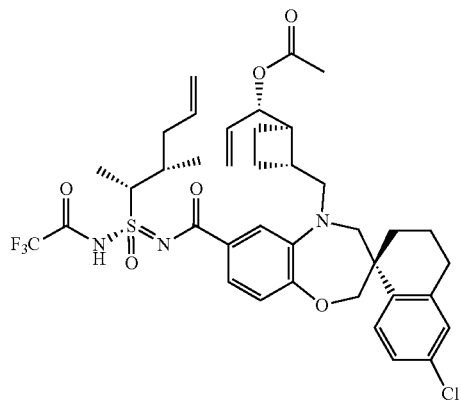

34-3

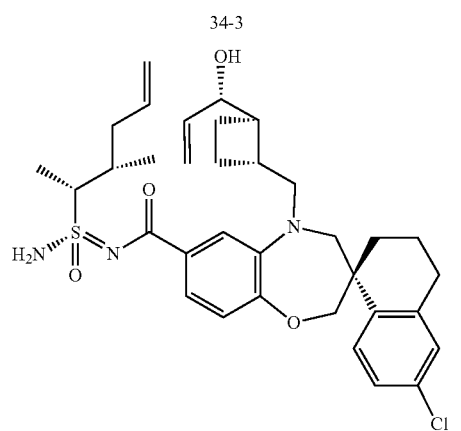

34-4

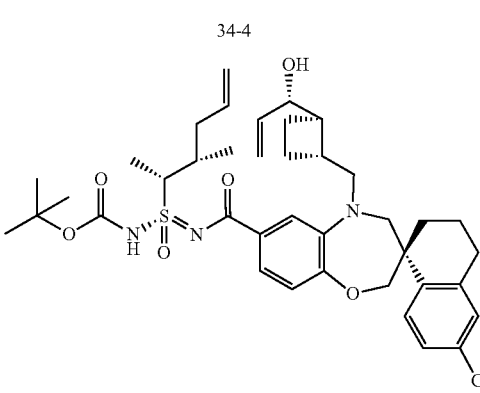

34-5

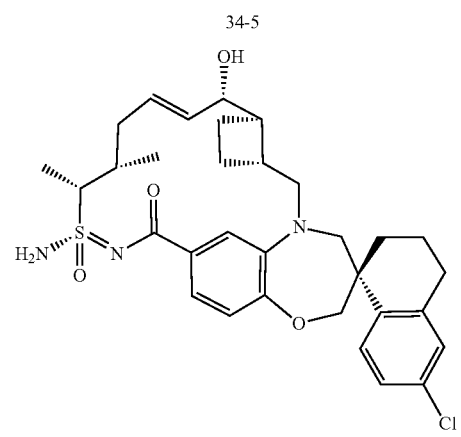

34-6

-continued

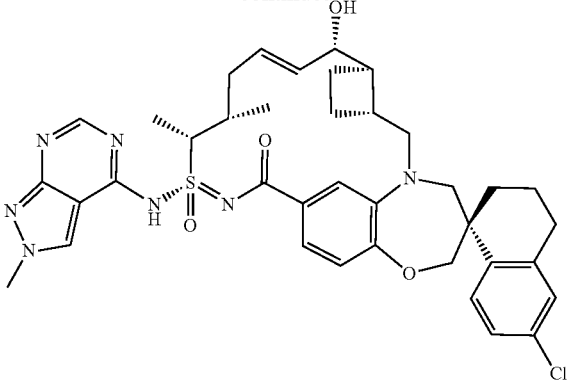

Example 34

Step 1: Acetic anhydride (505 µL, 5.34 mmol) was added via syringe to a stirred mixture of (S)-6'-chloro-5-(((1R,2R)-2-((S)-1-hydroxyallyl)cyclobutyl)methyl)-3',4,4',5-tetrahydro-2H,2'H-spiro[benzo[b][1,4] oxazepine-3,1'-naphthalene]-7-carboxylic acid (500 mg, 1.07 mmol) and pyridine (345 µL, 4.27 mmol) in tetrahydrofuran (8.0 mL) at room temperature. After 1 h, the resulting mixture was heated to 60° C. After stirring overnight, the resulting mixture was concentrated under reduced pressure, redissolved in dichloromethane, and concentrated under reduced pressure. The residue was redissolved in dichloromethane (8.0 mL), and the resulting mixture was cooled to 0° C. and stirred. Thionyl chloride (2.0 mL, 27 mmol) was added via syringe, and the resulting mixture was warmed to room temperature. After 2 h, the resulting mixture was cooled to 0° C., and water was added. After 2 h, the aqueous layer was diluted with water and was extracted with dichloromethane. The organic layer was dried over anhydrous magnesium sulfate, was filtered, and was concentrated under reduced pressure to give 34-1.

Step 2: 34-2 was prepared in a similar manner to I-2-2 from Intermediate B. DMAP (96.0 mg, 784 µmol), 3-(((ethylimino)methylene)amino)-N,N-dimethylpropan-1-amine hydrochloride (122 mg, 784 µmol), and 34-2 (112 mg, 412 µmol) were added sequentially as solids to a stirred solution of 34-1 (200 mg, 392 µmol) in dichloromethane (10 mL) at room temperature. After 4 h, the organic layer was washed sequentially with water, 1 M aqueous hydrogen chloride solution (twice), water, and saturated aqueous sodium bicarbonate solution. The organic layer was dried over anhydrous magnesium sulfate, was filtered, and was concentrated under reduced pressure to give 34-3.

Step 3: Potassium carbonate (321 mg, 3.27 mmol) was added as a solid to a stirred solution of 34-3 (250 mg, 327 µmol) in methanol (5.0 mL) and water (0.5 mL) at room temperature, and the resulting mixture was heated to 60° C. After stirring overnight, the resulting mixture was concentrated under reduced pressure, and the residue was extracted with dichloromethane. The organic layer was dried over anhydrous magnesium sulfate, was filtered, and was concentrated under reduced pressure to give 34-4.

Step 4: Di-tert-butyl dicarbonate (139 mg, 639 µmol) was added as a solid to a stirred mixture of 34-4 (400 mg, 639 µmol), N,N-diisopropylethylamine (178 µL, 1.28 mmol), and DMAP (39.0 mg, 319 µmol) in dichloromethane (10 mL) at room temperature. After 135 min, ethyl acetate (100 mL) was added, and the organic layer was washed sequentially with aqueous citric acid solution (2% w/v, 80 mL) and a mixture of water and brine (2:1 v:v, 80 mL), was dried over anhydrous magnesium sulfate, was filtered, and was concentrated under reduced pressure. The residue was purified by flash column chromatography on silica gel (0 to 45% ethyl acetate in hexanes) to give 34-5.

Step 5: A stirred solution of 34-5 (460 mg, 633 μmol) in 1,2-dichloroethane (300 mL) was sparged with a stream of argon at room temperature. After 20 min, (1,3-bis-(2,4,6-trimethylphenyl)-2-imidazolidinylidene)dichloro(o-isopropoxyphenylmethylene)ruthenium (119 mg, 190 μmol) was added as a solid, and the resulting mixture was heated to 75° C. After 15.75 h, the resulting mixture was allowed too cool to room temperature and was concentrated under reduced pressure. The residue was purified by flash column chromatography on silica gel (0 to 100% dichloromethane in hexanes, then 0 to 100% ethyl acetate in hexanes) to give 34-6.

Step 6: Example 34 was synthesized in a manner similar to Example 29 using 34-6 instead of W-2-1. $^1$H NMR (400 MHz, Acetone-d$_6$) δ 8.54 (s, 1H), 8.40 (d, J=2.7 Hz, 1H), 7.78 (d, J=8.5 Hz, 1H), 7.41-7.10 (m, 4H), 6.82 (d, J=8.2 Hz, 1H), 6.10-5.88 (m, 2H), 4.33 (d, J=4.7 Hz, 1H), 4.20 (s, 3H), 4.15-3.28 (m, 6H), 3.23-3.13 (m, 1H), 3.06-1.40 (m, 16H), 1.37 (d, J=7.0 Hz, 3H), 1.20 (d, J=6.9 Hz, 3H). LCMS-ESI+ (m/z): [M+H]$^+$ calcd for $C_{38}H_{44}ClN_7O_4S$: 730.3; found: 730.1.

Example 35 and Example 36

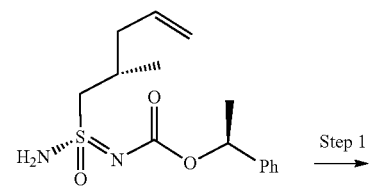

Intermediate D

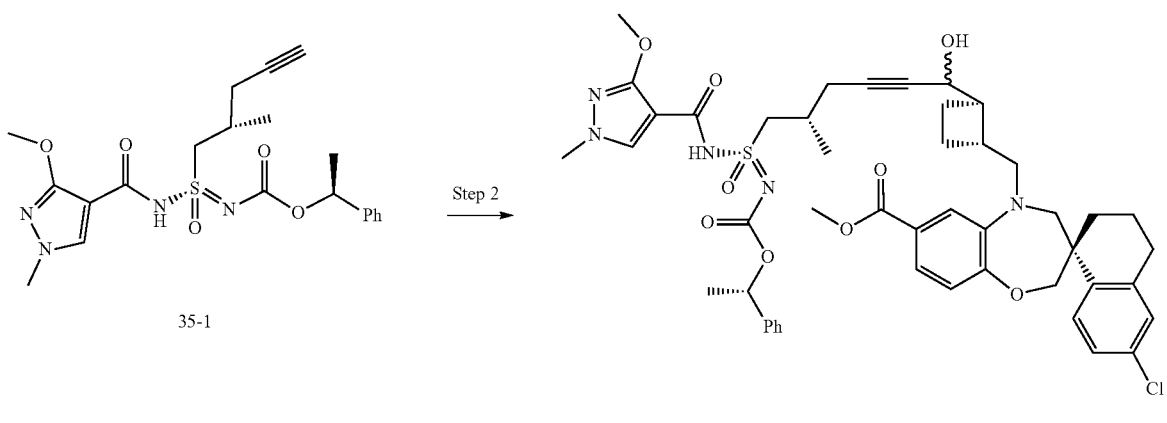

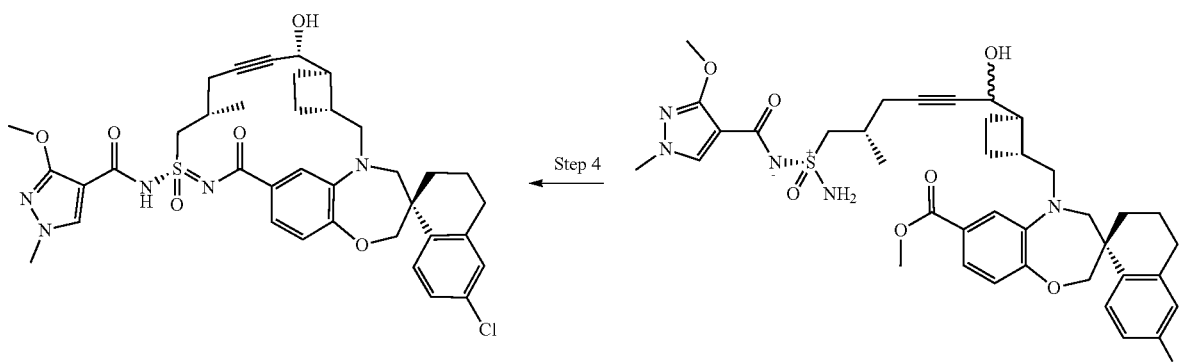

-continued

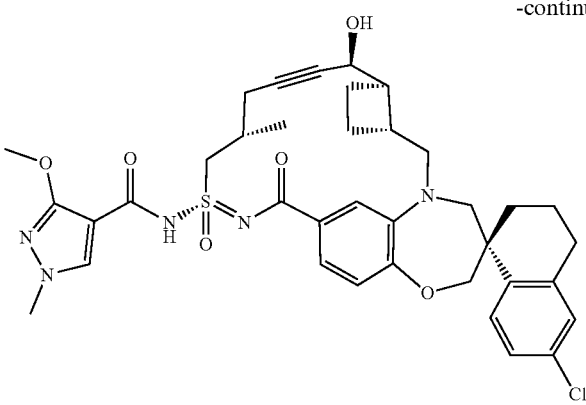

Step 1: 3-(((Ethylimino)methylene)amino)-N,N-dimethylpropan-1-amine hydrochloride (1.41 g, 7.35 mmol) was added to a stirred mixture of Intermediate D (1.63 g, 5.25 mmol), 3-methoxy-1-methyl-pyrazole-4-carboxylic acid (984 mg, 6.30 mmol), and DMAP (321 mg, 2.63 mmol) in dichloromethane (40 mL) at 0° C., and the resulting mixture was warmed to room temperature. After 15 h, ethyl acetate and aqueous citric acid solution were added sequentially. The organic layer was washed sequentially with brine and a mixture of water and brine (1:1 v:v), was dried over anhydrous magnesium sulfate, filtered, and concentrated under reduced pressure. The residue was dissolved in tert-butyl alcohol (8.5 mL), tetrahydrofuran (2.8 mL), and water (2.8 mL), and was stirred at room temperature. 4-methylmorpholine (577 µL, 5.25 mmol), 4-methylmorpholine-4-oxide (923 mg, 7.88 mmol), DMAP (128 mg, 1.05 mmol), and osmium tetroxide solution (2.5% wt in tert-butyl alcohol, 1.66 mL, 130 µmol) were added sequentially, and the resulting mixture was warmed to 80° C. After 60 min, the resulting mixture was cooled to room temperature, sodium sulfite (662 mg, 5.25 mmol) was added, and the resulting mixture was stirred vigorously. After 5 min, ethyl acetate was added, and the resulting mixture was filtered through celite. Aqueous citric acid solution (9.3% wt) and brine were added sequentially to the filtrate, the resulting biphasic mixture was agitated, and the layers were separated. The aqueous layer was extracted with ethyl acetate, and the combined organic layers were washed with a mixture of water and brine (1:1 v:v), dried over anhydrous magnesium sulfate, filtered, and concentrated under reduced pressure. The residue was dissolved in tetrahydrofuran (20 mL), and the resulting solution was stirred vigorously and was cooled to 0° C. A solution of sodium periodate (1.35 g, 6.30 mmol) in water (7.0 mL) was added over 1 min via syringe, and the resulting mixture was warmed to room temperature. After 26 min, aqueous citric acid solution (2% wt) and ethyl acetate were added sequentially, and the organic layer was washed sequentially with brine and a mixture of water and brine (1:1 v:v), dried over anhydrous magnesium sulfate, filtered, and concentrated under reduced pressure. The residue was dissolved in methanol (24 mL), potassium carbonate (2.90 g, 21.0 mmol) was added, and the resulting mixture was stirred vigorously and was cooled to 0° C. Dimethyl (1-diazo-2-oxopropyl)phosphonate (946 µL, 6.30 mmol) was added over 1 min via syringe, and the resulting mixture was warmed to room temperature. After 15 min, the resulting mixture was warmed to 50° C., and cesium carbonate (3.42 g, 10.5 mmol) was added. The resulting mixture was warmed to 55° C. After 5 min, the resulting mixture was cooled to room temperature, and aqueous citric acid solution (27% wt) and ethyl acetate were added sequentially. The organic layer was washed sequentially with bine and a mixture of water and brine (1:1 v:v), dried over anhydrous magnesium sulfate, filtered, and concentrated under reduced pressure. The residue was purified by flash column chromatography on silica gel (0 to 5% methanol in dichloromethane) to give 35-1.

Step 2: 2,2,6,6-Tetramethylpiperidinylmagnesium chloride lithium chloride complex solution (1.0 M in tetrahydrofuran/toluene, 1.97 mL, 1.97 mmol) was added via syringe to a stirred solution of 35-1 (366 mg, 821 µmol) in tetrahydrofuran (5.0 mL) at −20° C. After 30 min, the resulting mixture was transferred via syringe to a stirred solution of Intermediate J (190 mg, 419 µmol) in tetrahydrofuran (3.0 mL) at 0° C. After 36 min, aqueous citric acid solution (6% wt) and ethyl acetate were added sequentially. The organic layer was washed sequentially with brine, a mixture of water and saturated aqueous sodium bicarbonate solution (10:1 v:v), and a mixture of aqueous citric acid solution (2% wt) and brine (1:1 v:v), dried over anhydrous magnesium sulfate, filtered, and concentrated under reduced pressure. The residue was purified by flash column chromatography on silica gel (0 to 5% methanol in dichloromethane) to give 35-2.

Step 3: Trifluoroacetic acid (6.0 mL) was added over 1 min via syringe to a stirred mixture of 35-2 (377 mg, 419 µmol) and methanol (85 µL, 2.1 mmol) in dichloromethane (30 mL) at room temperature. After 60 min, aqueous sodium hydroxide solution (2.0 M), citric acid and brine were added sequentially, and the aqueous layer was extracted with dichloromethane. The organic layer was dried over anhydrous magnesium sulfate, filtered, and concentrated under reduced pressure. The residue was purified by flash column chromatography on silica gel (0 to 5% methanol in dichloromethane) to give 35-3.

Step 4: Aqueous lithium hydroxide solution (2.13 M, 300 µL, 640 µmol) was added via syringe to a stirred solution of 35-3 (146 mg, 194 µL) in tetrahydrofuran (0.5 mL) and methanol (0.2 mL) at room temperature, and the resulting mixture was warmed to 50° C. After 37 min, the resulting mixture was cooled to room temperature, and an aqueous phosphoric acid solution (1% wt) and ethyl acetate were added sequentially. The organic layer was washed with brine and a mixture of water and brine (1:1 v:v), dried over anhydrous magnesium sulfate, filtered, and concentrated under reduced pressure. The residue was dissolved in dichloromethane (9.0 mL), and the resulting mixture was added over 77 min via syringe pump to a vigorously stirred mixture of EDCl (50.1 mg, 261 µmol) and DMAP (118 mg, 968 µmol) in dichloromethane (20 mL) at 35° C. After 45 min, the resulting mixture was concentrated under reduced pressure, and the residue was purified by reverse phase preparative HPLC (0.1% trifluoroacetic acid in acetonitrile/water) to give Example 35 (faster eluting diastereomer [the stereochemistry of the propargylic alcohol stereocenter was tentatively assigned] on reverse phase HPLC) and Example 36 (slower eluting diastereomer [the stereochemistry of the propargylic alcohol stereocenter was tentatively assigned] on reverse phase HPLC).

Example 35: $^1$H NMR (400 MHz, Acetone-d$_6$) δ 8.05 (s, 1H), 7.80 (d, J=8.5 Hz, 1H), 7.56 (s, 1H), 7.43 (d, J=8.2 Hz, 1H), 7.26 (dd, J=8.5, 2.4 Hz, 1H), 7.14 (d, J=2.3 Hz, 1H), 6.90 (d, J=8.2 Hz, 1H), 4.62 (s, 1H), 4.50-3.55 (m, 5H), 4.07 (s, 3H), 3.84 (s, 3H), 3.48 (d, J=14.5 Hz, 1H), 3.24-3.12 (m, 1H), 3.03-1.25 (m, 16H), 1.18 (d, J=6.7 Hz, 3H). LCMS-ESI+ (m/z): [M+H]$^+$ calcd for C$_{37}$H$_{42}$ClN$_5$O$_6$S: 720.3; found: 720.1.

Example 36: $^1$H NMR (400 MHz, Acetone-d$_6$) δ 8.12 (s, 1H), 7.82-7.78 (m, 1H), 7.58-7.56 (m, 1H), 7.52-7.46 (m, 1H), 7.28-7.20 (m, 1H), 7.14 (d, J=3.5 Hz, 1H), 6.96-6.89 (m, 1H, 4.49-2.97 (m, 14H), 2.97-1.17 (m, 16H), 1.14 (d, J=6.7 Hz, 3H). LCMS-ESI+(m/z): [M+H]$^+$ calcd for C$_{37}$H$_{42}$ClN$_5$O$_6$S: 720.3; found: 720.1.

Example 37

Potassium bis(trimethylsilyl)amide solution (1.0 M in tetrahydrofuran, 97 µL, 97 µmol) was added over 1 min via syringe to a stirred mixture of Example 35 (7.0 mg, 9.7 µmol) and iodomethane (12 µL, 190 µmol) in tetrahydrofuran (0.5 mL) at −40° C. After 5 min, the resulting mixture was warmed to room temperature. After 15 min, acetic acid (8 µL) was added, and the resulting mixture was concentrated under reduced pressure. The residue was purified by reverse phase preparative HPLC (0.1% trifluoroacetic acid in acetonitrile/water) to give Example 37 (the stereochemistry of the propargylic ether stereocenter was tentatively assigned). $^1$H NMR (400 MHz, Acetone-d$_6$) δ 8.11 (s, 1H), 7.80 (d, J=8.5 Hz, 1H), 7.50 (s, 2H), 7.26 (dd, J=8.5, 2.4 Hz, 1H), 7.14 (s, 1H), 6.93 (s, 1H), 4.42 (s, 1H), 4.36-3.44 (m, 6H), 4.09 (s, 3H), 3.86 (s, 3H), 3.40 (s, 3H), 3.20 (t, J=13.1 Hz, 1H), 3.02-1.54 (m, 15H), 1.53-1.42 (m, 1H), 1.16 (s, 3H). LCMS-ESI+ (m/z): [M+H]$^+$ calcd for C$_{38}$H$_{44}$ClN$_5$O$_6$S: 734.3; found: 734.1.

Example 38

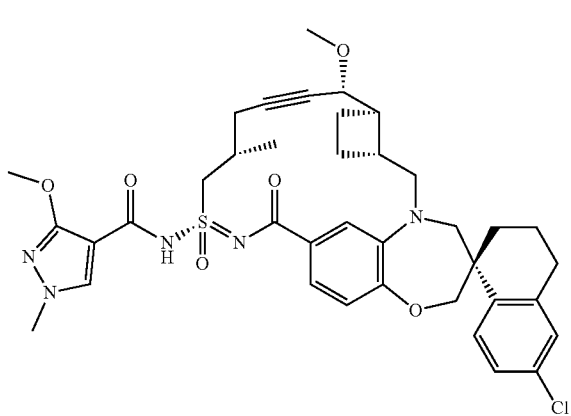

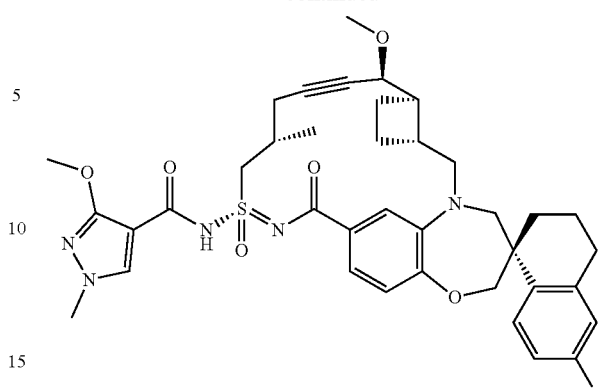

Example 38 (the stereochemistry of the propargylic ether stereocenter was tentatively assigned) was synthesized in a manner similar to Example 37 using Example 36 instead of Example 35. $^1$H NMR (400 MHz, Acetone-d$_6$) δ 8.10 (s, 1H), 7.80 (d, J=8.5 Hz, 1H), 7.60 (s, 1H), 7.46 (d, J=8.2 Hz, 1H), 7.29-7.24 (m, 1H), 7.14 (d, J=2.5 Hz, 1H), 6.92 (d, J=8.3 Hz, 1H), 4.30-3.30 (m, 7H), 4.08 (s, 3H), 3.85 (s, 3H), 3.47 (s, 3H), 3.18-3.10 (m, 1H), 3.09-1.35 (m, 16H), 1.18 (d, J=6.2 Hz, 3H). LCMS-ESI+ (m/z): [M+H]$^+$ calcd for C$_{38}$H$_{44}$ClN$_5$O$_6$S: 734.3; found: 734.2.

Example 39

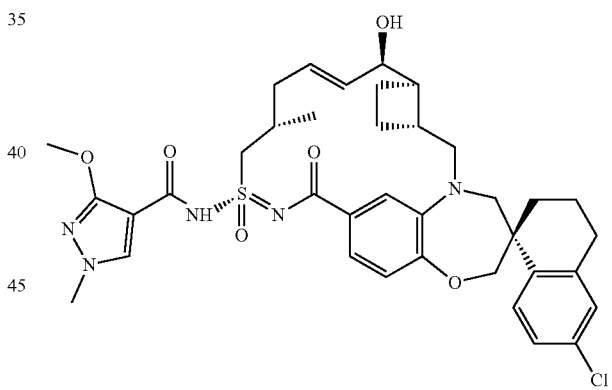

Triphenylsilyl perrhenate (5.3 mg, 10 µmol) was added to a stirred solution of Intermediate W (26.0 mg, 36.0 µmol) in dichloromethane (2.0 mL) at 0° C. After 68 min, the resulting mixture was warmed to room temperature. After 15 min, triethylamine (0.1 mL) and methanol (2.0 mL) were added sequentially, and the resulting mixture was concentrated under reduced pressure. The residue was purified by reverse phase preparative HPLC (0.1% trifluoroacetic acid in acetonitrile/water) to give Example 39. $^1$H NMR (400 MHz, Chloroform-d) δ 7.84 (s, 1H), 7.77 (d, J=8.5 Hz, 1H), 7.56-7.44 (m, 2H), 7.20 (dd, J=8.5, 2.4 Hz, 1H), 7.10 (d, J=2.3 Hz, 1H), 6.95 (d, J=8.2 Hz, 1H), 5.79-5.63 (m, 2H), 4.21-3.55 (m, 6H), 4.14 (s, 3H), 3.82 (s, 3H), 3.32 (d, J=14.5 Hz, 1H), 3.03 (dd, J=15.3, 8.0 Hz, 1H), 2.88-1.30 (m, 16H), 1.17 (d, J=6.8 Hz, 3H). LCMS-ESI+ (m/z): [M+H]$^+$ calcd for C$_{37}$H$_{44}$ClN$_5$O$_6$S: 722.3; found: 722.2.

Example 40

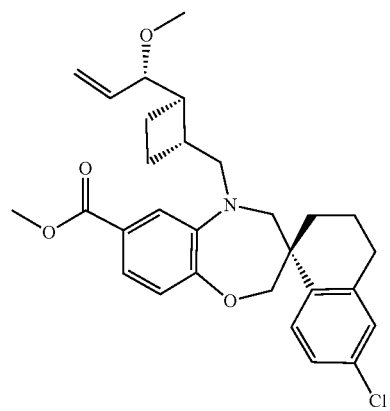

I-1-2

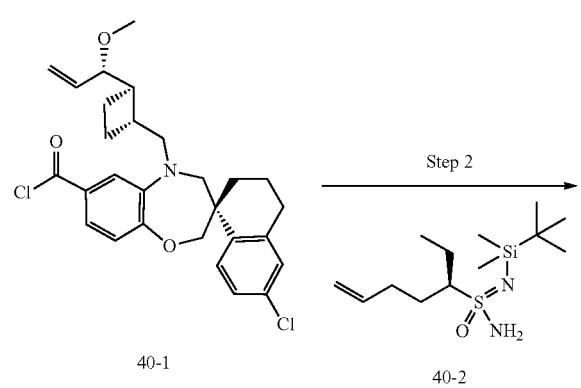

40-1      40-2

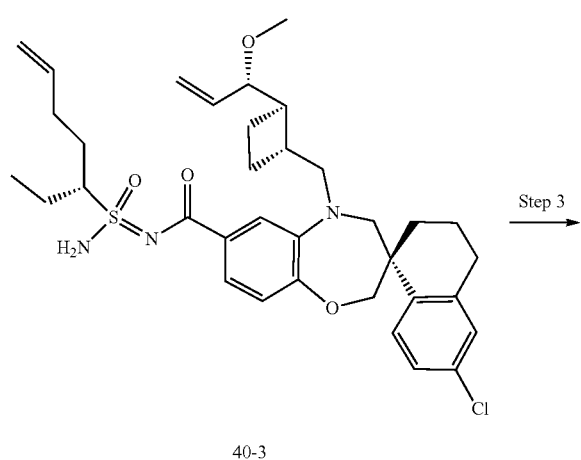

40-3

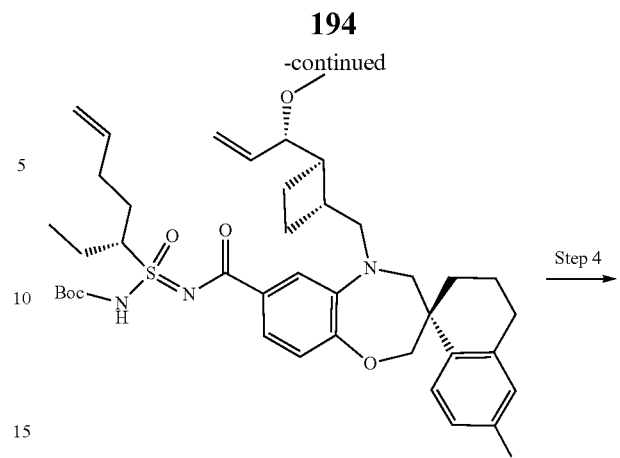

40-4

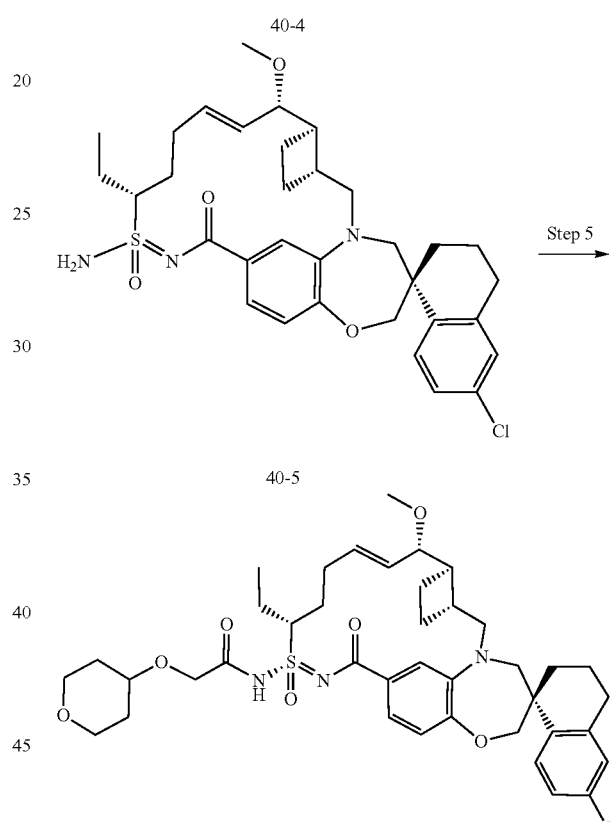

40-5

Example 40

Step 1: I-1-2 (605 mg, 1.2 mmol) was stirred in 2N aq NaOH (10 mL) and MeOH (29 mL) at 60° C. overnight. After cooling, the mixture was acidified with HCl and concentrated. The resulting solid was treated with DCM and filtered. The filtrate was concentrated, and re-dissolved in DCM (21 mL) at 0° C. Thionyl chloride (5.35 mL, 7.4 mmol) was added, and the resulting mixture was brought to rt, and stirred for 2 h. The reaction was concentrated to give 40-1, which was used subsequently without further purification.

Step 2: 40-2 was prepared in a similar manner to A-2 from (R)-hept-6-ene-3-sulfonamide. To a stirred solution of 40-1 (600 mg, 1.2 mmol) in acetonitrile (12 mL) was added pyridazine (0.1 mL, 1.3 mmol), followed by 40-2 (383 mg, 1.3 mmol) in acetonitrile (2.0 mL). The resulting mixture was stirred at rt overnight. The reaction was partitioned between water and DCM. The organic layer was dried over magnesium sulfate, and concentrated, to give 40-3, which was used subsequently without further purification.

Step 3: A solution of 40-3 (700 mg, 1.09 mmol), triethylamine (0.2 mL, 1.31 mmol), DMAP (13.3 mg, 0.11 mmol), and di-tert-butyl dicarbonate (334 mg, 1.53 mmol) in DCM (14 mL) was stirred at rt for 20 min. The reaction was washed with water, 1 N HCl, and saturated sodium bicarbonate. The organic layer was dried over magnesium sulfate, and concentrated, to give 40-4, which was used subsequently without further purification.

Step 4: 40-5 was prepared in a similar manner to Intermediate I (Method 1, Step 7) using 40-4 in place of I-1-6, and isolated as a mixture of diastereomers.

Step 5: Example 40 was synthesized in a similar manner to Intermediate T using 2-((tetrahydro-2H-pyran-4-yl)oxy)acetic acid and 40-5, and adding triethylamine. It was isolated as the earlier of two eluting diastereomers, and the stereochemistry was tentatively assigned. $^1$H NMR (400 MHz, Chloroform-d) δ 7.71 (d, J=8.5 Hz, 1H), 7.45 (dd, J=8.3, 1.9 Hz, 1H), 7.37 (d, J=2.0 Hz, 1H), 7.16 (dd, J=8.5, 2.3 Hz, 1H), 7.07 (d, J=2.3 Hz, 1H), 6.91 (d, J=8.2 Hz, 1H), 5.75 (td, J=11.0, 5.2 Hz, 1H), 5.38 (t, J=10.3 Hz, 1H), 4.16 (s, 3H), 4.11-3.92 (m, 5H), 3.84 (d, J=15.3 Hz, 1H), 3.78-3.67 (m, 2H), 3.55 (ddd, J=11.8, 8.7, 4.1 Hz, 3H), 3.41 (d, J=14.7 Hz, 2H), 3.31 (s, 5H), 2.96-2.64 (m, 3H), 2.39 (q, J=8.8 Hz, 1H), 2.28 (t, J=13.7 Hz, 2H), 2.19-1.58 (m, 15H), 1.42 (t, J=12.8 Hz, 1H), 1.25 (s, 2H), 1.02 (t, J=7.4 Hz, 3H). LCMS-ESI+ (m/z): [M+H]$^+$ calcd for $C_{40}H_{52}ClN_3O_7S$: 754.3; found: 754.2.

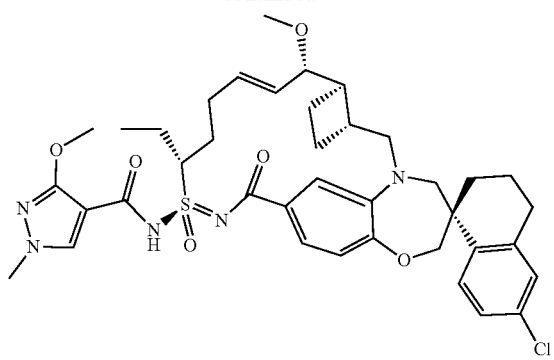

Example 41

Synthesis of 41-1: 41-1 was prepared in a similar manner to I-1-5 using Intermediate F in place of Intermediate C.

Synthesis of Example 41: Example 41 was synthesized in a similar manner to Intermediate W (Method 1, Steps 3-4) using 41-1 in place of W-1-2 (absolute stereochemistry at sulfur tentatively assigned as drawn). $^1$H NMR (400 MHz, Chloroform-d) δ 7.89-7.66 (m, 2H), 7.36 (d, J=7.9 Hz, 1H), 7.26-7.15 (m, 2H), 7.11 (d, J=2.3 Hz, 1H), 6.95 (d, J=8.2 Hz, 1H), 6.27-6.02 (m, 1H), 5.52 (dd, J=15.4, 8.6 Hz, 1H), 4.26 (d, J=27.3 Hz, 1H), 4.09 (d, J=10.3 Hz, 5H), 3.87-3.64 (m, 5H), 3.30 (s, 4H), 3.03 (dd, J=15.0, 10.3 Hz, 1H), 2.86-2.68 (m, 2H), 2.55-2.29 (m, 3H), 2.25-1.54 (m, 13H), 1.44 (t, J=12.5 Hz, 1H), 1.13 (t, J=7.5 Hz, 3H). LCMS-ESI+ (m/z): [M+H]$^+$ calcd for $C_{39}H_{48}ClN_5O_6S$: 750.3; found: 750.5.

Example 41

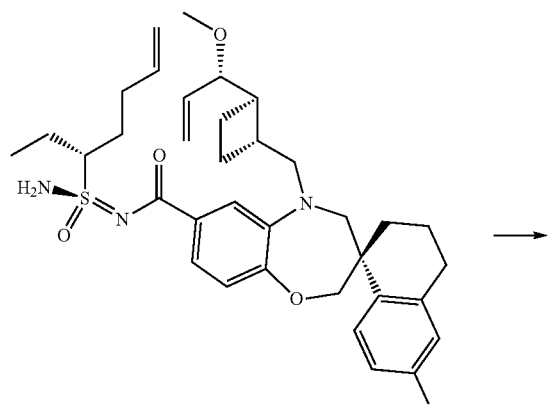

41-1

Example 42

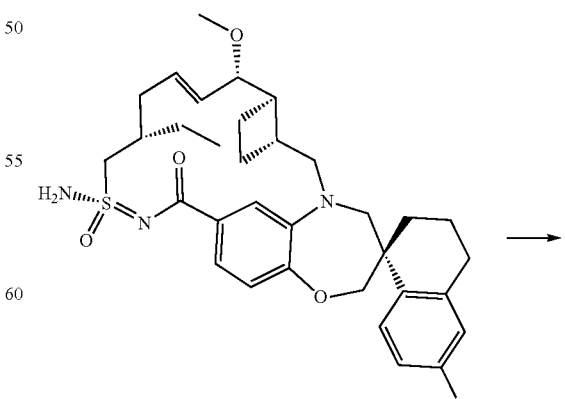

42-1

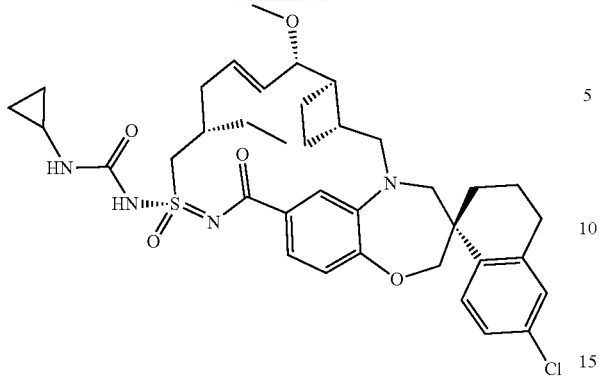

Example 42

Example 43

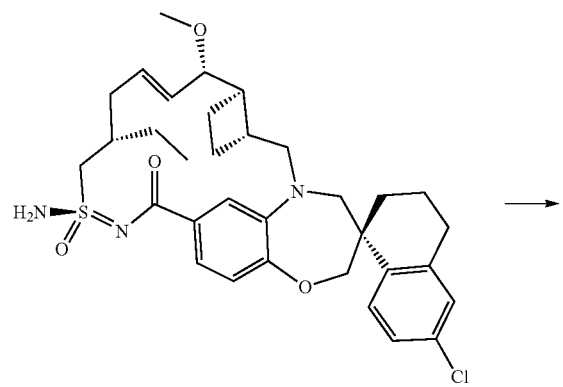

43-1

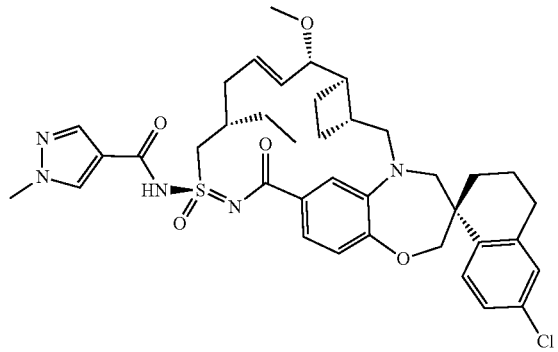

Example 43

Synthesis of 42-1: 42-1 was prepared in a similar manner to Intermediate I (Method 1) using Intermediate G in place of Intermediate C. $^1$H NMR (400 MHz, Chloroform-d) δ 7.76 (d, J=8.5 Hz, 1H), 7.43 (dd, J=8.2, 1.9 Hz, 1H), 7.32 (d, J=2.0 Hz, 1H), 7.20 (dd, J=8.5, 2.4 Hz, 1H), 7.10 (d, J=2.3 Hz, 1H), 6.93 (d, J=8.2 Hz, 1H), 6.33 (dt, J=14.8, 7.1 Hz, 1H), 5.89 (s, 2H), 5.53 (dd, J=15.3, 8.4 Hz, 1H), 4.11-4.01 (m, 2H), 3.87 (d, J=14.7 Hz, 1H), 3.84-3.75 (m, 1H), 3.71 (dd, J=8.5, 3.9 Hz, 1H), 3.61 (dd, J=14.5, 3.6 Hz, 1H), 3.42 (d, J=9.5 Hz, 1H), 3.39 (d, J=9.5 Hz, 1H), 3.27 (s, 3H), 3.01 (dd, J=15.0, 11.1 Hz, 1H), 2.88-2.71 (m, 2H), 2.58 (d, J=9.6 Hz, 1H), 2.46 (dq, J=20.6, 10.6, 9.1 Hz, 1H), 2.32 (dt, J=14.3, 6.9 Hz, 1H), 2.07 (s, 2H), 1.99-1.85 (m, 1H), 1.74 (dq, J=33.7, 9.2, 8.8 Hz, 2H), 1.50 (t, J=7.2 Hz, 2H), 1.42 (q, J=13.3, 12.9 Hz, 1H), 0.96 (t, J=7.4 Hz, 3H). LCMS-ESI+ (m/z): [M+H]$^+$ calcd for $C_{33}H_{42}ClN_3O_4S$: 612.3; found: 612.5.

Synthesis of Example 42: A solution of 4-dimethylaminopyridine (10 mg, 82 µmol), diphenyl carbonate (28 mg, 131 µmol), and 42-1 (10 mg, 16 µmol) in dichloromethane (1.0 mL) was heated at 40° C. overnight. Triethylamine (0.05 mL, 359 µmol) and cyclopropylamine (38.7 mg, 678 µmol) were added, and reaction was stirred at 40° C. for 1 hour. The reaction was diluted with dichloromethane (8 mL), washed with hydrochloric acid (1 N, 2×5 mL) and saturated sodium bicarbonate (2×5 mL). The organic layer was dried over sodium sulfate, concentrated, purified by silica gel chromatography (0-100% [20% methanol/ethyl acetate]/hexanes). The fractions containing product were combined and the solvent was removed under reduced pressure. The residue was repurified by reverse phase preparatory HPLC. The fractions containing product were combined and subjected to lyophilization to give Example 42. $^1$H NMR (400 MHz, Methanol-d$_4$) δ 7.72 (d, J=9.0 Hz, 1H), 7.20 (d, J=8.2 Hz, 1H), 7.10 (d, J=1.9 Hz, 2H), 6.97 (s, 1H), 6.89 (d, J=8.2 Hz, 1H), 6.05 (dt, J=14.3, 7.4 Hz, 1H), 5.61 (dd, J=15.3, 8.8 Hz, 1H), 4.24 (dd, J=15.0, 8.6 Hz, 1H), 4.13-4.00 (m, 2H), 3.90 (s, 1H), 3.84 (d, J=15.2 Hz, 1H), 3.77 (dd, J=8.9, 3.6 Hz, 1H), 3.68 (d, J=14.2 Hz, 1H), 3.28 (s, 3H), 3.06 (dd, J=15.2, 10.2 Hz, 1H), 2.89-2.69 (m, 2H), 2.69-2.54 (m, 2H), 2.54-2.25 (m, 2H), 2.11 (d, J=13.8 Hz, 1H), 2.07-1.87 (m, 3H), 1.87-1.69 (m, 3H), 1.60-1.36 (m, 2H), 1.31 (s, 4H), 0.99 (t, J=7.3 Hz, 3H), 0.75 (d, J=7.0 Hz, 2H), 0.56 (s, 2H). LCMS-ESI+: [M+H]$^+$ calcd for $C_{37}H_{47}ClN_4O_5S$: 695.3; found: 695.3.

Synthesis of 43-1: 43-1 was prepared in a similar manner to Intermediate I (Method 1) using Intermediate H in place of Intermediate C.

Synthesis of Example 43: Example 43 was synthesized in a similar manner to Intermediate T using 43-1. $^1$H NMR (400 MHz, Methanol-d$_4$) δ 8.03 (s, 1H), 7.89 (s, 1H), 7.78 (d, J=8.5 Hz, 1H), 7.26 (d, J=8.2 Hz, 1H), 7.17 (dd, J=8.5, 2.4 Hz, 1H), 7.11 (d, J=2.6 Hz, 2H), 6.83 (d, J=7.9 Hz, 1H), 6.40-6.28 (m, 1H), 5.46 (dd, J=15.3, 9.0 Hz, 1H), 4.22 (t, J=11.8 Hz, 1H), 4.08-3.98 (m, 2H), 3.96-3.86 (m, 4H), 3.84-3.76 (m, 2H), 3.68 (d, J=14.3 Hz, 1H), 3.21 (s, 3H), 3.04 (dd, J=15.1, 9.8 Hz, 1H), 2.89-2.70 (m, 2H), 2.64 (d, J=14.2 Hz, 1H), 2.45 (s, 3H), 2.27-2.02 (m, 3H), 2.02-1.85 (m, 2H), 1.78 (dd, J=16.2, 8.2 Hz, 3H), 1.57-1.39 (m, 2H), 1.31 (s, 2H), 0.97 (t, J=7.3 Hz, 3H). LCMS-ESI+: [M+H]$^+$ calcd for $C_{38}H_{46}ClN_5O_5S$: 720.3; found: 720.4.

Example 44

Step 1: 44-1 (1.0 g, 2.38 mmol) in THF (10.0 mL) was cooled to −40° C. 1.0M LHMDS in THF (3.81 mL, 3.81 mmol) was added, stirred at −40° C. for 15 min, and MeI (1.67 g, 11.9 mmol) was added. The cooling bath was switched to ice-water bath, stirred at 0° C. for 3 hrs, additional LHMDS (2.38 mL) was added followed by MeI (0.7 mL), and stirred at 0° C. to rt for overnight. The reaction was quenched with ice cold saturated NH$_4$Cl, partitioned between EtOAc and water. The organic layer was washed with brine, dried over sodium sulfate, filtered and concentrated to give a mixture. The mixture was purified by flash column chromatography (24 g silica gel, 0-40% EtOAc/Hexanes) gave 44-2.

Step 2: 44-2 (759 mg, 1.75 mmol) was dissolved in DCM (1.2 mL) at room temperature. To the stirred mixture was added anisole (5.11 g, 47.3 mmol) followed by TFA (6.3 g, 43.8 mmol) dropwise. The resulting mixture was stirred overnight. The reaction was diluted with EtOAc, basified with 1 N NaOH to pH-5 and then saturated sodium bicarbonate to pH-7. The organic layer was washed with brine, dried over sodium sulfate, filtered and concentrated to give a mixture. The mixture was purified by flash column chromatography (12 g silica gel, 0-100% EtOAc/Hexanes) gave 44-3. $^1$H NMR (400 MHz, Chloroform-d) δ 5.86-5.63 (m, 1H), 5.22-5.00 (m, 4H), 3.52 (dd, J=9.6, 4.4 Hz, 1H), 3.42 (dd, J=9.6, 6.4 Hz, 1H), 3.36 (s, 3H), 3.27 (dd, J=14.5, 7.0 Hz, 1H), 3.15 (dd, J=14.5, 5.1 Hz, 1H), 2.45-2.32 (m, 1H), 2.31-2.21 (m, 2H).

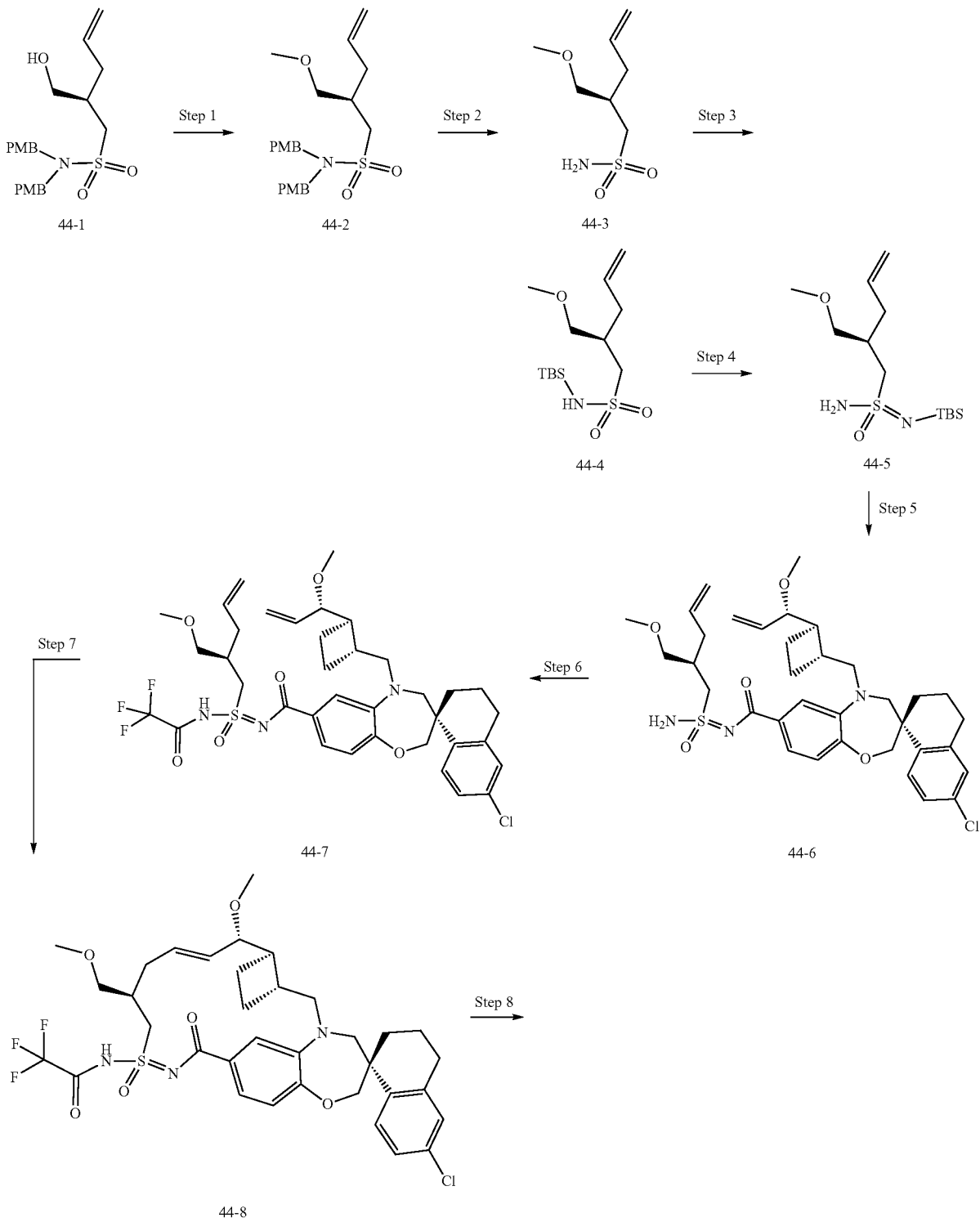

-continued

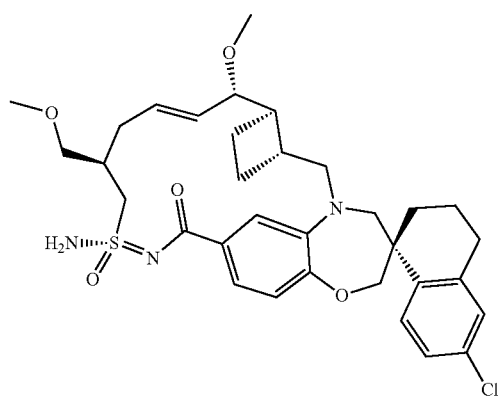

44-9

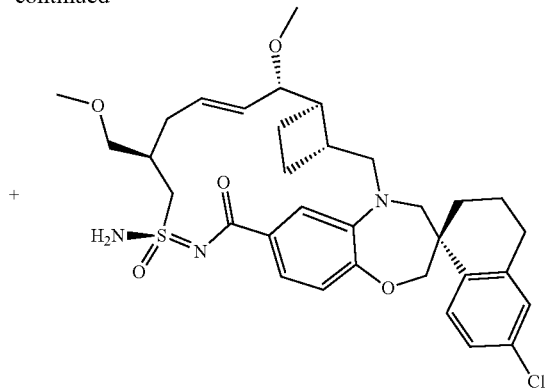

44-10

Step 9

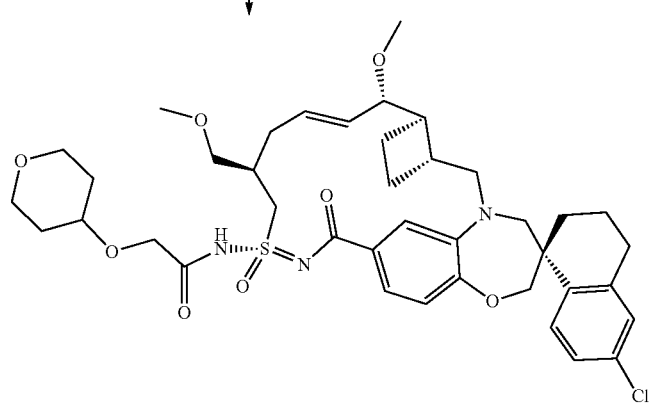

Example 44

Step 3: 44-3 (284 mg, 1.47 mmol) was dissolved in THF (1.5) mL, Et₃N (0.41 mL, 2.94 mmol) was added, and solution was cooled to 0° C. A solution of TBSCl (239 mg, 2.20 mmol) in THF (2.0 mL) was added. The resulting mixture was stirred at rt. overnight. Additional Et₃N (0.307 mL, 2.20 mmol) and TBSCl (160 mg, 1.47 mmol) was added, and stirred for 2 hours. The reaction was partitioned between EtOAc and water. The organic layer was dried over sodium sulfate, filtered and concentrated to give a mixture. The mixture was purified by flash column chromatography (12 g silica gel, 0-40% EtOAc/Hexanes) gave 44-4.

Step 4: To a suspension of dichlorotriphenylphosphorane (784 mg, 2.35 mmol) in DCM (6.7 mL) at rt was added triethylamine (317 mg, 3.14 mmol). The mixture was stirred at rt for 10 min and then cooled to 0° C. 44-4 (608 mg, 1.57 mmol) in DCM (2.5 mL) was added and the newly formed mixture was stirred at 0° C. for 1.5 hrs. Ammonium gas was bubbled in for 3 min. The vial was sealed and stirred at rtovernight. The reaction was filtered, and rinsed with DCM. Filtrate was concentrated to give a mixture. The mixture was purified by flash column chromatography (24 g silica gel, 0-40% EtOAc/Hexanes) gave 44-5.

Step 5: A solution of I-1-3 (195 mg, 0.405 mmol) in DCM (6.0 mL) was cooled to O ° C. Thionyl chloride (2.65 g, 22.2 mmol) was added dropwise followed by 2 drops of DMF. The resulting mixture was removed from the cooling bath and stirred at room temperature for 2 hrs. The reaction was then concentrated, the resulting residue was coevaporated with DCM (3×5.0 mL), further dried over vacuum to give a mixture. The mixture was then treated with ACN (3.0 mL) and cooled to 0° C., pyridazine (32.4 mg, 0.405 mmol) was added. After stirring for 3 min, a solution of 44-5 in ACN (2.0 mL) was added. The resulting reaction was stirred at room temperature overnight. The reaction was concentrated to remove ACN, redissolved in EtOAc, washed with water, dried over sodium sulfate, filtered and concentrated to give a mixture. The mixture was purified by flash column chromatography (4 g silica gel, 0-80% EtOAc/Hexanes gave 44-6. LCMS-ESI+ (m/z): [M+H]⁺ calcd for $C_{35}H_{46}ClN_3OsS$: 655.28; found: 656.07.

Step 6: A solution of 44-6 (80.0 mg, 0.122 mmol) in DCM (2.0 mL) was cooled to 0° C. Triethylamine (24.7 mg, 0.244 mmol) was added followed by trifluoroacetic anhydride (38.4 mg, 0.183 mmol) in DCM (1.0 mL) dropwise. The resulting reaction was stirred at room temperature for 1 hr. The reaction was diluted with DCM, washed with 1 N HCl, saturated sodium bicarbonate, brine, dried over sodium sulfate, filtered and concentrated to give a mixture. The mixture was purified by flash column chromatography (4 g silica gel, 0-70% EtOAc/Hexanes) gave 44-7. LCMS-ESI+ (m/z): [M+H]⁺ calcd for $C_{35}H_{46}ClN_3OsS$: 751.27; found: 752.00.

Step 7: 44-7 (60.0 mg, 0.079 mmol) was dissolved in DCE (6.0 mL) at room temperature, and the solution was sparged with nitrogen. Hoveyda-Grubbs II (10.0 mg, 0.016 mmol) was added. The vial was capped and heated at 65° C.

for 13 hrs. The reaction was concentrated, and purified by flash column chromatography (4 g silica gel, 0-100% EtOAc/Hexanes) to give 44-8.

Step 8: 44-8 (50.0 mg, 0.069 mmol) in a mixture of MeOH/THF/water (2/1/1 mL) was treated with $K_2CO_3$ (47.7 mg, 0.345 mmol) at room temperature for 30 min. The mixture was then heated at 50° C. for 2 hr. The reaction was concentrated to remove MeOH, the resulting residue was partitioned between EtOAc and water. The organic layer was dried over sodium sulfate, filtered and concentrated. The resulting residue was then redissolved in DMF (1.0 mL) and water (0.2 mL), filtered and purified by reverse phase prep HPLC. The first eluted peak on reverse phase HPLC was assigned tentatively as 44-9, and the second one tentatively as 44-10.

44-9: $^1$H NMR (400 MHz, Methanol-$d_4$) δ 7.77 (d, J=8.5 Hz, 1H), 7.28 (dd, J=8.2, 1.8 Hz, 1H), 7.18 (dd, J=8.4, 2.3 Hz, 1H), 7.10 (dd, J=5.6, 2.1 Hz, 2H), 6.85 (d, J=8.1 Hz, 1H), 6.26-6.16 (m, 1H), 5.59-5.49 (m, 1H), 4.11-3.99 (m, 3H), 3.87 (d, J=15.3 Hz, 1H), 3.78 (dd, J=9.1, 3.7 Hz, 1H), 3.72-3.59 (m, 2H), 3.46 (dd, J=9.4, 5.4 Hz, 1H), 3.42-3.36 (m, 1H), 3.31 (s, 3H) 3.26 (s, 3H), 3.04 (dd, J=14.9, 10.0 Hz, 1H), 2.91-2.71 (m, 2H), 2.57-2.21 (m, 5H), 2.12 (d, J=13.2 Hz, 1H), 1.95 (d, J=5.3 Hz, 4H), 1.86-1.69 (m, 3H), 1.43 (t, J=12.0 Hz, 1H). LCMS-ESI+ (m/z): [M+H]$^+$ calcd for $C_{33}H_{42}ClN_3O_5S$: 627.25; found: 627.92.

44-10: $^1$H NMR (400 MHz, Methanol-$d_4$) δ 7.77 (d, J=8.5 Hz, 1H), 7.26 (dd, J=8.2, 1.9 Hz, 1H), 7.21-7.16 (m, 1H), 7.09 (dd, J=17.2, 2.2 Hz, 2H), 6.86 (d, J=8.2 Hz, 1H), 6.11-6.01 (m, 1H), 5.56 (dd, J=15.4, 8.5 Hz, 1H), 4.15-3.97 (m, 4H), 3.83 (d, J=14.9 Hz, 1H), 3.75 (dd, J=8.6, 3.3 Hz, 1H), 3.68 (d, J=14.2 Hz, 1H), 3.49-3.36 (m, 2H), 3.35 (s, 3H), 3.26 (s, 3H), 3.11-3.00 (m, 1H), 2.86-2.77 (m, 2H), 2.63-2.20 (m, 5H), 2.12 (d, J=13.6 Hz, 1H), 1.96-1.90 (m, 3H), 1.85-1.68 (m, 4H), 1.44 (t, J=13.1 Hz, 1H). LCMS-ESI+ (m/z): [M+H]$^+$ calcd for $C_{33}H_{42}ClN_3O_5S$: 627.25; found: 627.97.

Step 9: A mixture of 2-tetrahydropyran-4-yloxyacetic acid in DCM (0.5 mL) was cooled to 0° C. EDCl (3.46 mg, 0.0233 mmol) was added followed by DMAP (2.72 mg, 0.0233 mmol). The resulting mixture was stirred at 0° C. for 5 minutes before a solution of 44-9 (7.0 mg, 0.011 mmol) in DCM (0.5 mL) was added. The newly formed mixture was removed from the cooling bath and stirred at rt for overnight. The reaction was concentrated to give a residue. The residue was then redissolved in a mixture of DMF (1.0 mL) and water (0.2 mL), filtered and purified by reverse phase prep HPLC (Gilson, Gemini 5 um column, 40-100% ACN/H2O with 0.1% TFA). Desired fractions were combined and frozen dried to give Example 44. $^1$H NMR (400 MHz, Methanol-$d_4$) δ 7.76 (d, J=8.6 Hz, 1H), 7.27 (dd, J=8.3, 1.8 Hz, 1H), 7.19 (dd, J=8.6, 2.3 Hz, 1H), 7.12 (d, J=2.2 Hz, 2H), 6.91 (d, J=8.2 Hz, 1H), 6.19-6.07 (m, 1H), 5.64 (dd, J=15.4, 8.2 Hz, 1H), 4.23 (s, 2H), 4.16-4.01 (m, 4H), 4.00-3.90 (m, 3H), 3.84 (d, J=15.1 Hz, 1H), 3.78-3.65 (m, 3H), 3.53-3.40 (m, 4H), 3.34 (s, 3H), 3.29 (s, 3H), 3.12-3.04 (m, 1H), 2.85-2.74 (m, 2H), 2.58-2.24 (m, 5H), 2.16-2.07 (m, 1H), 2.06-1.87 (m, 6H), 1.84-1.73 (m, 3H), 1.73-1.58 (m, 2H). LCMS-ESI+ (m/z): [M+H]$^+$ calcd for $C_{40}H_{52}ClN_3O_8S$: 769.32; found: 769.91.

Example 45

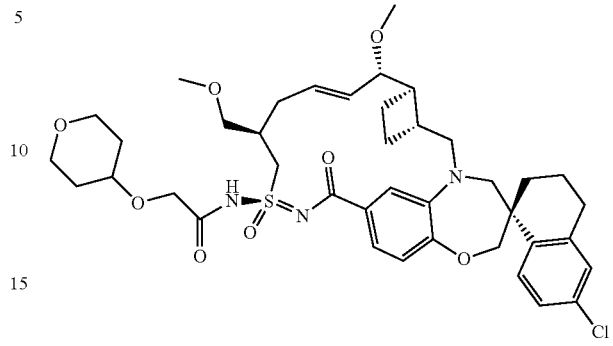

Example 45 was prepared in a similar manner to 44 (Step 9) using 44-10. $^1$H NMR (400 MHz, Methanol-$d_4$) δ 7.76 (d, J=8.5 Hz, 1H), 7.28 (d, J=8.2 Hz, 1H), 7.19 (dd, J=8.5, 2.3 Hz, 1H), 7.12 (d, J=2.4 Hz, 2H), 6.90 (d, J=8.2 Hz, 1H), 6.16-6.02 (m, 1H), 5.63 (dd, J=15.5, 8.0 Hz, 1H), 4.19 (s, 2H), 4.16-4.00 (m, 3H), 3.98-3.88 (m, 2H), 3.88-3.61 (m, 5H), 3.52-3.40 (m, 5H), 3.36 (s, 3H), 3.29 (s, 3H), 3.17-3.11 (m, 1H), 2.89-2.75 (m, 2H), 2.67-2.36 (m, 5H), 2.11 (d, J=13.8 Hz, 1H), 2.00-1.89 (m, 6H), 1.79 (d, J=6.6 Hz, 3H), 1.61 (dtd, J=13.5, 9.0, 3.6 Hz, 2H). LCMS-ESI+ (m/z): [M+H]$^+$ calcd for $C_{40}H_{52}ClN_3O_8S$: 769.32; found: 769.89.

Example 46

Step 1: To a mixture of 44-1(2.00 g, 4.77 mmol) and 1-ethyl-1H-pyrazol-3-ol (802 mg, 7.15 mmol) in DCM (15.9 mL) at 0° C. was added TRI-N-BUTYLPHOSPHINE (1.93 g, 9.53 mmol) followed by DEAD (1.66 g, 9.53 mmol) dropwise. The resulting mixture was removed from the cooling bath and stirred at rt for 2 days. The reaction was concentrated, purified by flash column chromatography (80 g silica gel, 0-80% EtOAc/Hexanes) to give a 46-1.

Steps 2-4 were conducted in a similar manner to Example 44 (Steps 2-4).

Step 5: A solution of 46-4 (362 mg, 0.936 mmol) in THF (13 mL) was cooled to −40° C. 1.6M n-BuLi in hexanes (1.29 mL, 2.06 mmol) was added dropwise to this cold solution. The newly formed mixture was stirred at −40° C. for 20 min before a solution of (4-nitrophenyl) [(1S)-1-phenylethyl] carbonate (350 mg, 1.22 mmol) in THF (8 mL) was added dropwise slowly. The resulting mixture was stirred at −40° C. for 15 min and then switched to ice-water bath and stirred at 0° C. for 3 hrs. The reaction was quenched with ice and extracted with EtOAc. The organic layer was washed with 1 N NaOH, brine, dried over sodium sulfate, filtered and concentrated to give a mixture. The mixture was purified by flash column chromatography (24 g silica gel, 0-30% EtOAc/Hexanes with ELS detector) gave a mixture of diastereomers. The mixture was subjected to chiral SFC for separation to give 46-5, as the first eluting product, and 46-6 as the second eluting product (stereochemistry assigned tentatively).

Step 6: 46-6 (51.1 mg, 0.096 mmol) in THF (1.5 mL) at rt was treated with 1 N tetrabutylammonim fluoride in THF (0.19 mL, 0.19 mmol) at rt for 2 hrs. The reaction solution was concentrated, purified by flash column chromatography (4 g silica gel, 0-100% EtOAc/Hexanes, detected by ELS detector to give 46-7. $^1$H NMR (400 MHz, Chloroform-d) b 7.44-7.22 (m, 5H), 7.18 (d, J=2.4 Hz, 1H), 5.76-5.68 (m, 2H), 5.63 (d, J=2.4 Hz, 1H), 5.17-5.01 (m, 2H), 4.23 (d, J=5.0 Hz, 2H), 3.99 (q, J=7.3 Hz, 2H), 3.61-3.39 (m, 2H), 2.62-2.47 (m, 1H), 2.45-2.21 (m, 2H), 1.54 (d, J=6.6 Hz, 3H), 1.43 (t, J=7.3 Hz, 3H).

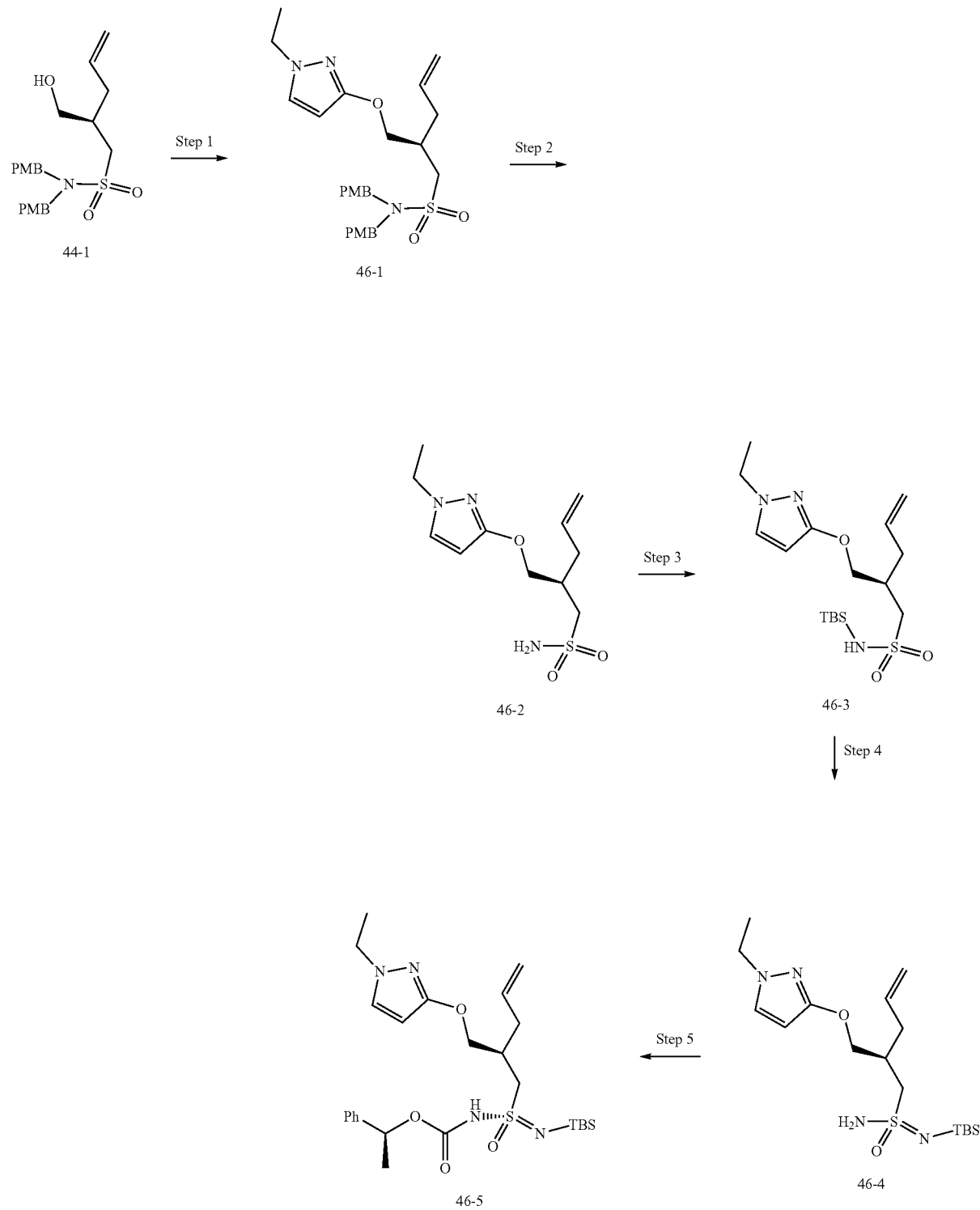

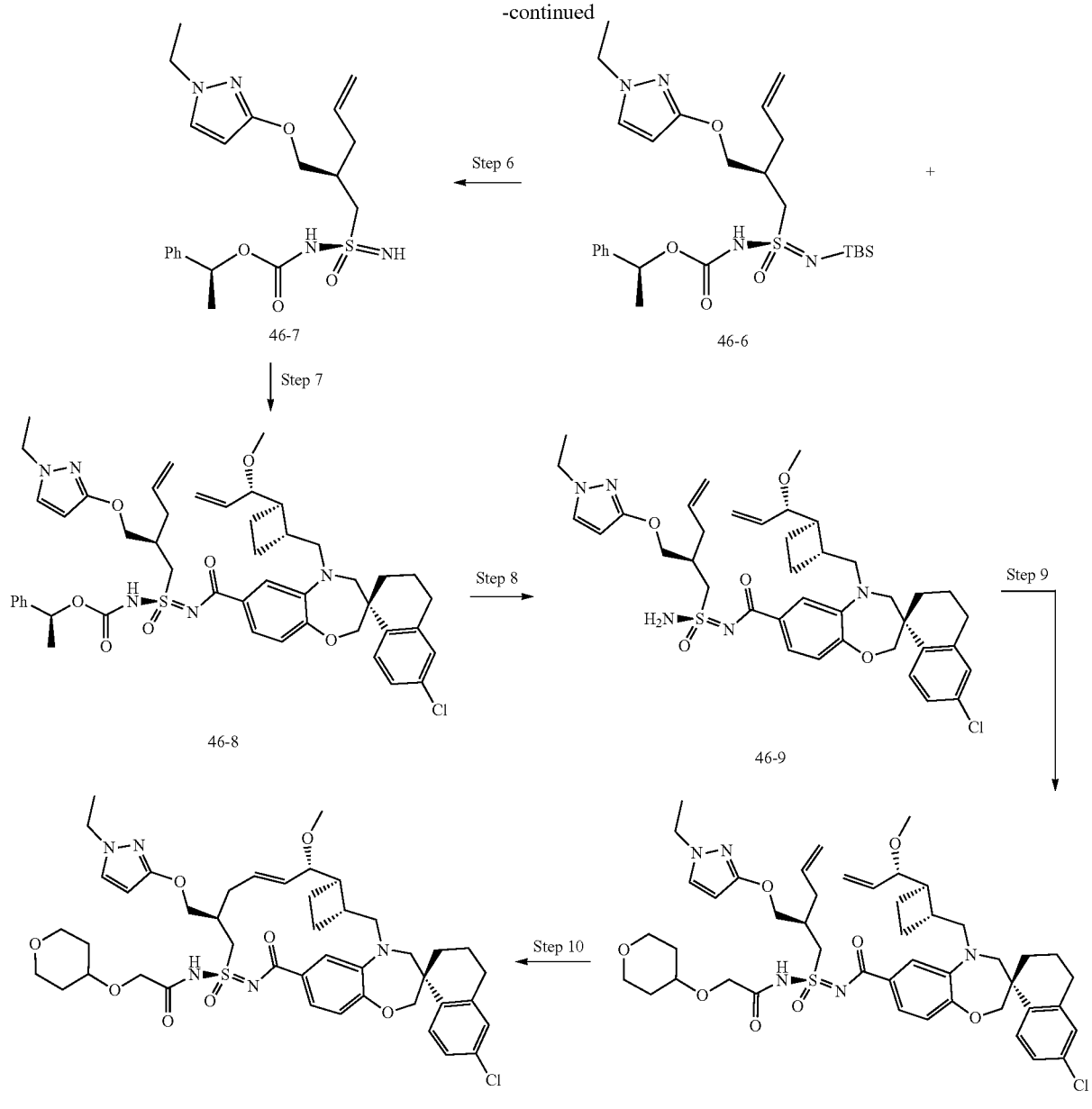

Step 7: A mixture of I-1-3 (53.5 mg, 0.10 mmol) in DCM (3.0 mL) was cooled to 0° C. EDCl (38.7 mg, 0.20 mmol) was added followed by DMAP (24.6 mg, 0.20 mmol). The resulting mixture was stirred at 0° C. for 5 minutes before a solution of 46-7 (42.4 mg, 0.10 mmol) in DCM (1.5 mL) was added. The newly formed mixture was removed from the cooling bath and stirred at rt for overnight. The reaction was diluted with DCM, washed with 0.5 N aq HCl, saturated sodium bicarbonate, brine, dried over sodium sulfate, filtered, and concentrated to give a residue. The residue was then purified by flash column chromatography (4 g silica gel, 0-100% EtOAc/Hexanes) to give 46-8. LCMS-ESI+ (m/z): [M+H]+ calcd for $C_{46}H_{60}ClN_5O_8S$: 883.37; found: 883.92.

Step 8: 46-8 (50.0 mg, 0.056 mmol) was dissolved in DCM (0.3 mL) at 0° C. and treated with TFA (0.3 mL) for 1 hr. The reaction was diluted with EtOAc, basified to pH-5 with 1 N NaOH, then saturated sodium bicarbonate to pH-7 at 0° C. The organic layer was washed with brine, dried over sodium sulfate, filtered, and concentrated to give 46-9, which was used subsequently without additional purification. $^1$H NMR (400 MHz, Chloroform-d) δ 7.71 (d, J=8.5 Hz, 1H), 7.56-7.46 (m, 2H), 7.18 (dd, J=7.0, 2.4 Hz, 2H), 7.10 (d, J=2.3 Hz, 1H), 6.89 (d, J=8.2 Hz, 1H), 5.80 (ddt, J=18.9, 9.6, 7.1 Hz, 1H), 5.65-5.53 (m, 2H), 5.24-5.11 (m, 5H), 4.32 (dd, J=10.4, 4.5 Hz, 1H), 4.24 (dd, J=10.4, 5.7 Hz, 1H), 4.16-4.05 (m, 2H), 3.99 (q, J=7.3 Hz, 2H), 3.67-3.50 (m, 5H), 3.36-3.25 (m, 5H), 2.85-2.74 (m, 2H), 2.73-2.63 (m, 1H), 2.59-2.33 (m, 3H), 2.21-2.09 (m, 1H), 2.09-1.96 (m, 2H), 1.93-1.75 (m, 3H), 1.68-1.52 (m, 3H), 1.43 (t, J=7.3 Hz, 3H). LCMS-ESI+ (m/z): [M+H]+ calcd for $C_{46}H_{60}ClN_5O_8S$: 735.32; found: 736.11.

Step 9: A mixture of 2-tetrahydropyran-4-yloxyacetic acid (20.6 mg, 0.128 mmol) in DCM (3.0 mL) was cooled to 0° C. EDCl (24.6 mg, 0.128 mmol) was added followed by DMAP (15.7 mg, 0.128 mmol). The resulting mixture was stirred at 0° C. for 5 minutes before a solution of 46-9 (47.3 mg, 0.064 mmol) in DCM (2.0 mL) was added. The newly formed mixture was removed from the cooling bath and stirred at rt overnight. The reaction was diluted with DCM, washed with 0.5N aq HCl, saturated sodium bicarbonate, brine, dried over sodium sulfate, filtered, and concentrated. Purification by flash column chromatography (0-100% EtOAc/Hexanes) gave 46-10. LCMS-ESI+ (m/z): [M+H]+ calcd for $C_{46}H_{60}ClN_5O_8S$: 877.39; found: 878.15.

Step 10: A solution of 46-10 (25.3 mg) in DCE (10.0 mL) was degassed with nitrogen for 5 min before Hoveyda-Grubbs catalyst (3.61 mg) was added. The newly formed mixture was degassed for another 2 minutes and then it was capped and heated at 65° C. for 16 hrs. The reaction was then cooled to rt, concentrated, purified by Gilson reverse phase prep HPLC (40-100% AN/H2O with 0.1% TFA) to give Example 46. $^1$H NMR (400 MHz, Methanol-$d_4$) δ 7.76 (d, J=8.6 Hz, 1H), 7.39 (d, J=2.4 Hz, 1H), 7.28 (d, J=8.7 Hz, 1H), 7.18 (d, J=8.5 Hz, 1H), 7.13 (d, J=7.8 Hz, 2H), 6.92 (d, J=8.3 Hz, 1H), 6.20-6.09 (m, 1H), 5.72-5.61 (m, 2H), 4.26-4.01 (m, 8H), 3.95 (dd, J=15.6, 8.8 Hz, 4H), 3.85 (d, J=15.0 Hz, 1H), 3.80-3.74 (m, 1H), 3.74-3.61 (m, 2H), 3.52-3.41 (m, 2H), 3.41-3.36 (m, 1H), 3.27 (s, 3H), 3.18-3.02 (m, 1H), 2.87-2.74 (m, 2H), 2.65-2.40 (m, 5H), 2.17-2.06 (m, 1H), 2.02-1.86 (m, 5H), 1.84-1.55 (m, 5H), 1.50-1.42 (m, 1H), 1.37 (t, J=7.2 Hz, 3H). LCMS-ESI+ (m/z): [M+H]+ calcd for $C_{44}H_{56}ClN_5O_8S$: 849.35; found: 850.09.

Example 47

Method #1

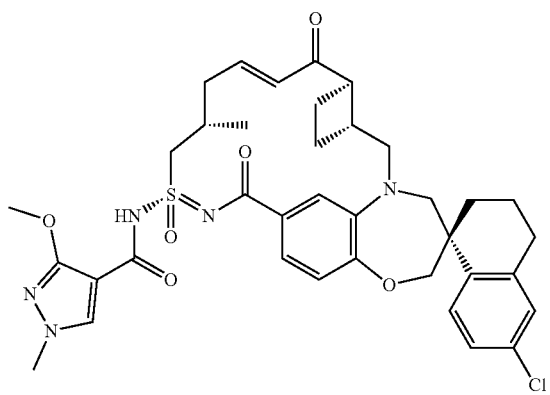 [SMILES: COc1nn(C)cc1C(=O)N[S@@]1(=O)=NC(=O)c2ccc3c(c2)N(C[C@@H]2CC[C@H]2C(=O)/C=C/C[C@H](C)C1)C[C@@]1(CCCc2cc(Cl)ccc21)CO3]

Intermediate W (20.0 mg, 0.0277 mmol) was treated with Dess-Martin periodinane (17.6 mg, 0.0415 mmol, 1.5 equiv.) in dichloromethane (2 mL) in the presence of pyridine (0.5 mL) at rt for 1 h. The organic solvent was removed under a reduced pressure. The crude mixture obtained was directly injected into preparative-HPLC. To the fraction containing the desired product was added EtOAc. The whole was washed with saturated NaHCO3 and brine. The organic solvent was removed under a reduced pressure. The crude mixture was purified by preparative-HPLC to give Example 47. LCMS-ESI+ (m/z): [M+H]+ calcd for $C_{37}H_{42}ClN_5O_6S$: 720.25; found: 720.07.

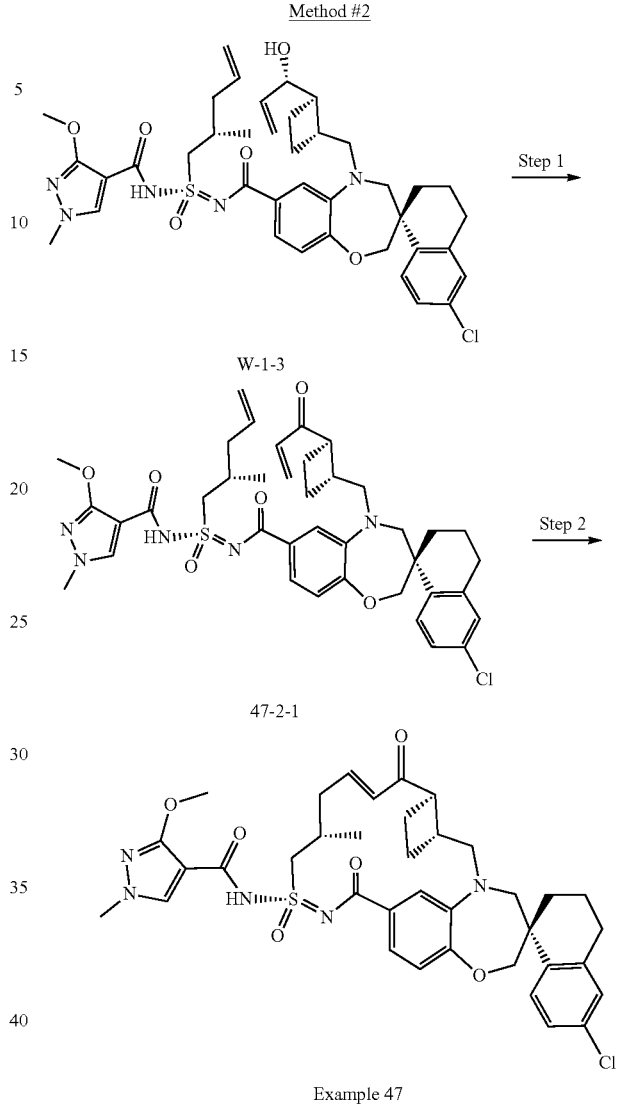

Step 1: 47-2-1 was prepared in a similar manner to Example 47 using W-1-3.

Step 2: Example 47 was prepared in a similar manner to Intermediate I (Method 1, step 7), using 47-2-1.

Example 48

Synthesis of 48-1: 48-1 was synthesized in a similar manner to W-1-3 from 34-3.

Synthesis of Example 48: Example 48 was synthesized in a similar manner to Example 47 (Method 2), using 48-1. $^1$H NMR (400 MHz, Chloroform-d) δ 7.90-7.69 (m, 2H), 7.47 (d, J=2.0 Hz, 1H), 7.23 (dd, J=8.5, 2.3 Hz, 1H), 7.16-7.04 (m, 2H), 6.87 (d, J=8.2 Hz, 1H), 6.64 (dt, J=15.5, 7.6 Hz, 1H), 5.91 (d, J=15.8 Hz, 1H), 4.44 (q, J=7.3 Hz, 1H), 4.09 (d, J=21.6 Hz, 4H), 3.98-3.83 (m, 2H), 3.81 (s, 3H), 3.24 (d, J=14.4 Hz, 2H), 3.14-2.68 (m, 4H), 2.25-1.98 (m, 5H), 1.96-1.71 (m, 4H), 1.58 (d, J=7.2 Hz, 2H), 1.41 (t, J=12.6 Hz, 1H), 1.28 (s, 3H), 1.07 (d, J=6.7 Hz, 3H). LCMS-ESI+ (m/z): [M+H]+ calcd for $C_{38}H_{44}ClN_5O_6S$: 734.27; found: 734.15.

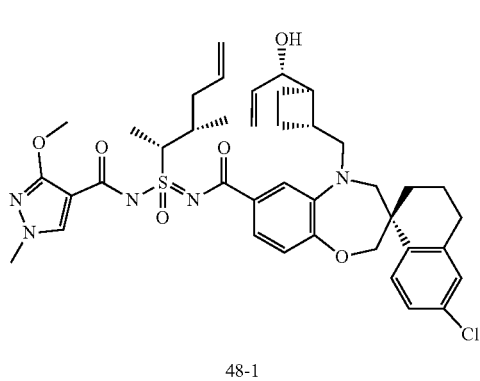

48-1

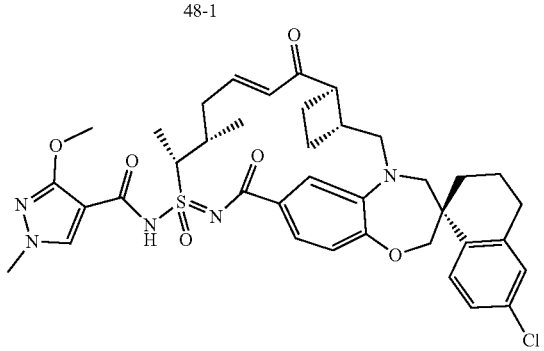

Example 48

Example 49

Step 1: To a stirred solution of I-1-1 (300 mg, 1.0 equiv.) in DMF (15 mL) was added NaH (60% in mineral oil, 124 mg, 5 equiv.) in an ice-bath, followed by 4-(2-iodoethyl)morpholine hydrochloride (518 mg, 3 equiv.). The resulting mixture was stirred at ambient temperature overnight and poured into water. The solution was concentrated and purified by preparative reverse-phase HPLC (acetonitrile/water with 0.1% trifluoroacetic acid modifier) to give 49-1. LCMS-ESI+ (m/z): [M+H]$^+$ calcd for $C_{33}H_{41}ClN_2O_5$: 581.3; found: 581.2.

Step 2: 49-2 was prepared in a similar manner to A-2 from pent-4-ene-1-sulfonamide. To a stirred solution of 49-1 (84 mg, 1 equiv) in dichloromethane in an ice bath was added thionyl chloride. The resulting mixture was stirred at ambient temperature for 2 hr, then concentrated in vacuo. The residue was dissolved in acetonitrile, then pyridazine (12 mg, 1 equiv.) in 1 ml of acetonitrile, followed by 49-2 (46 mg, 1.2 equiv.) in acetonitrile solution were added. The resulting mixture was stirred at ambient temperature for 3 hr and concentrated. The resulting residue was purified by preparative reverse-phase HPLC (acetonitrile/water with 0.1% trifluoroacetic acid modifier) to give 49-3. LCMS-ESI+ (m/z): [M+H]$^+$ calcd for $C_{38}H_{51}ClN_4O_5S$: 711.3; found: 711.3.

Step 3: To a stirred solution of 49-3 (35 mg, 1 equiv.) in dichloromethane (8 mL) was added triethylamine (13 µL, 2 equiv.) in an ice bath, followed by di-tert-butyl dicarbonate (16 mg, 1.5 equiv.) and DMAP (2.4 mg, 0.4 equiv.). The resulting mixture was stirred at ambient temperature for 3 hr, then concentrated. The resulting residue was purified by preparative reverse-phase HPLC (acetonitrile/water with 0.1% trifluoroacetic acid modifier) to give 49-4. LCMS-ESI+ (m/z): [M+H]$^+$ calcd for $C_{43}H_{59}ClN_4O_7S$: 811.4; found: 811.3.

Step 4: A solution of 49-4 (17 mg, 1 equiv.) and Hoveyda-Grubbs second generation catalyst (1.3 mg, 0.1 equiv.) were stirred in 1,2-dichloroethane (20 mL) at 60° C. for 6 h, then concentrated. The resulting residue was purified by preparative reverse-phase HPLC (acetonitrile/water with 0.1% trifluoroacetic acid modifier) to give 49-5. LCMS-ESI+ (m/z): [M+H]$^+$ calcd for $C_{36}H_{47}ClN_4O_5S$: 683.3; found: 683.3.

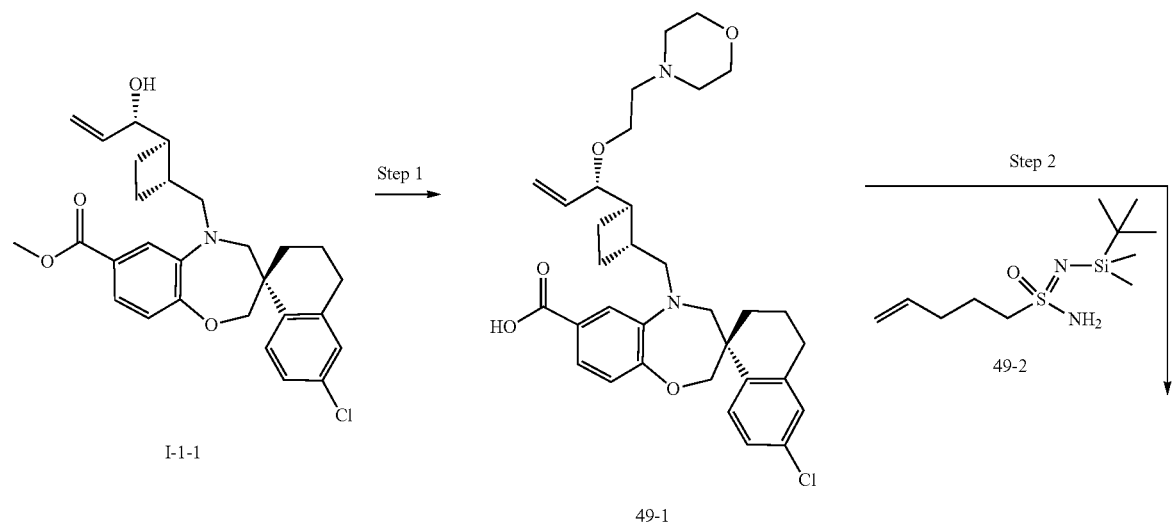

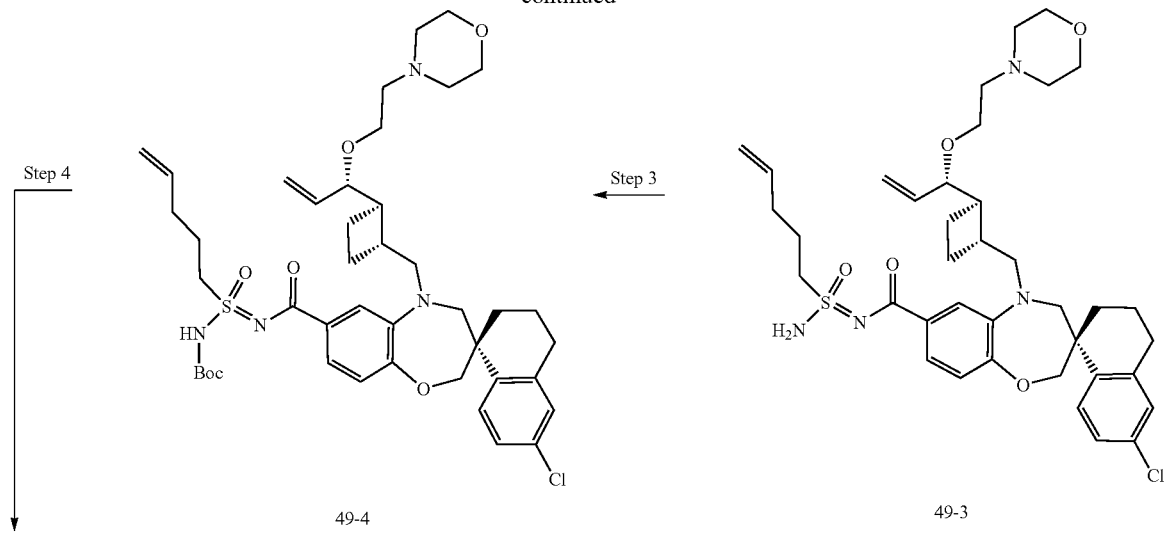

49-4            49-3

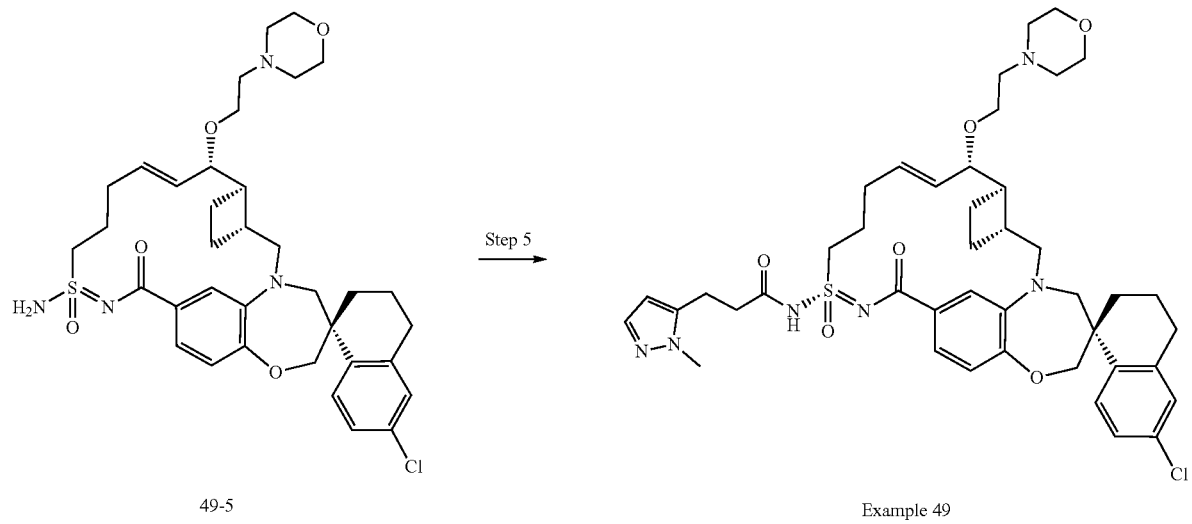

49-5            Example 49

Step 5: To a stirred solution of 3-(1-methyl-1H-pyrazol-5-yl)propanoic acid (3.4 mg, 1.5 equiv.) in dichloromethane (2 mL) was added DMAP (3.6 mg, 2 equiv.) and EDCl (4.5 mg, 2 equiv.), followed by 49-5 (10 mg, 1 equiv.). The resulting mixture was stirred at ambient temperature for 2 hr, then concentrated. The resulting residue was purified by preparative reverse-phase HPLC (acetonitrile/water with 0.1% trifluoroacetic acid modifier) to give Example 49 (the less polar diastereomer). $^1$H NMR (400 MHz, Methanol-$d_4$) δ 7.78 (d, J=8.4 Hz, 1H), 7.46 (d, J=2.0 Hz, 1H), 7.38 (dd, J=8.4, 2.0 Hz, 1H), 7.36 (d, J=2.0 Hz, 1H), 7.20 (dd, J=8.4, 2.4 Hz, 1H), 7.12 (d, J=2.4 Hz, 1H), 6.93 (d, J=8.4 Hz, 1H), 6.15 (d, J=2.0 Hz, 1H), 5.97-5.96 (m, 2H), 4.14-3.97 (m, 4H), 3.90-3.76 (m, 7H), 3.65-3.45 (m, 2H), 3.41-3.23 (m, 9H), 3.17-3.11 (m, 3H), 3.07-2.97 (m, 4H), 2.90-2.73 (m, 4H), 2.58-1.78 (m, 1 OH), 1.48-1.42 (m, 1H). LCMS-ESI+ (m/z): [M+H]$^+$ calcd for $C_{43}H_{55}ClN_6O_6S$: 819.4; found: 819.3.

Example 50

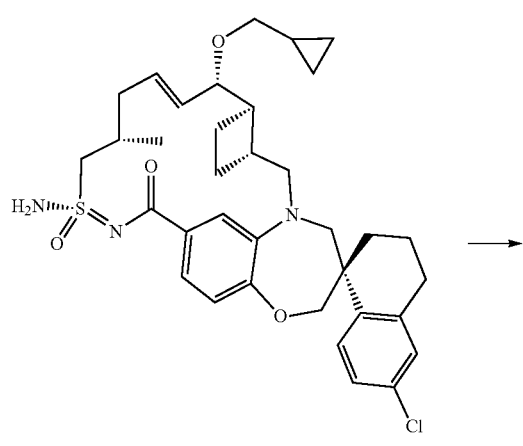

50-1

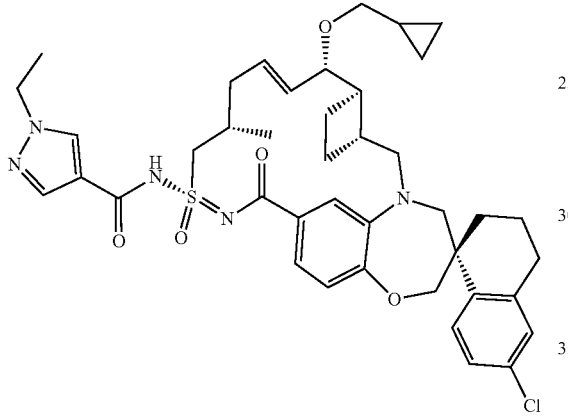

Example 50

Synthesis of 50-1: 50-1 was prepared in a similar manner to Intermediate I (Method 1, Steps 2-7), using bromomethylcyclopropane in place of iodomethane.

Synthesis of Example 50: 50-1 (29 mg, 0.045 mmol), EDCl (70 mg, 0.36 mmol), and DMAP (44 mg, 0.36 mmol) were suspended in DCM (2 mL). 1-Ethylpyrazole-4-carboxylic acid (38 mg, 0.27 mmol) and triethylamine (0.051 mL, 0.36 mmol) were added and the reaction mixture was stirred o/n at RT. Upon completion, the reaction was quenched by addition of MeOH then partially concentrated under reduced pressure. The crude material was purified by reverse phase HPLC, then repurified by silica column chromatography (0% to 20% MeOH/EtOAc) to afford Example 50. $^1$H NMR (400 MHz, Chloroform-d) δ 8.09-8.04 (m, 1H), 8.02-7.94 (m, 3H), 7.71 (d, J=8.6 Hz, 2H), 7.33 (s, 1H), 7.18-7.07 (m, 6H), 6.94 (s, 1H), 5.92 (d, J=14.2 Hz, 1H), 5.61 (dd, J=15.6, 8.1 Hz, 2H), 5.49-5.40 (m, 1H), 4.23 (d, J=11.8 Hz, 5H), 4.10 (dd, J=20.7, 8.1 Hz, 3H), 3.85 (t, J=9.5 Hz, 3H), 3.73 (d, J=14.1 Hz, 2H), 3.57 (s, 1H), 3.44 (s, 1H), 3.37-3.17 (m, 7H), 3.17-2.96 (m, 4H), 2.78 (dt, J=22.4, 8.3 Hz, 5H), 2.46 (s, 2H), 2.23 (s, 1H), 2.19-2.02 (m, 4H), 2.02-1.93 (m, 3H), 1.84 (s, 4H), 1.64 (dt, J=18.0, 8.8 Hz, 3H), 1.53 (d, J=7.4 Hz, 6H), 1.46-1.33 (m, 3H), 1.32-1.24 (m, 3H), 1.19 (s, 1H), 1.15-0.96 (m, 9H), 0.94-0.88 (m, 1H), 0.87 (d, J=9.0 Hz, 1H), 0.60-0.47 (m, 5H), 0.26-0.06 (m, 7H). LCMS-ESI+: (m/z): [M+H]$^+$ calcd for $C_{41}H_{50}ClN_5O_5S$: 760.3; found: 760.2.

Example 51

A solution of W-2-1 (1 equiv, 0.017 mmol, 10 mg), 1-methylpyrazole-4-carboxylic acid (1.5 equiv, 0.026 mmol, 3.2 mg), EDCl (2.5 equiv, 0.043 mmol, 6.6 mg), and 4-dimethylaminopyridine (2 equiv, 0.034 mmol, 4.2 mg) in CH$_2$Cl$_2$ (0.35 mL) was stirred overnight at room temperature. The reaction mixture was concentrated and purified by preparative HPLC (MeCN in water, 0.1% TFA) to afford Example 51. $^1$H NMR (400 MHz, Methanol-d$_4$) δ 8.17 (s, 1H), 7.90 (s, 1H), 7.83 (s, 1H), 7.76 (s, 1H), 7.59 (d, J=8.5 Hz, 1H), 7.31-7.22 (m, 2H), 7.18-7.02 (m, 2H), 6.90 (dd, J=8.1, 1.6 Hz, 1H), 6.08 (dt, J=14.5, 7.0 Hz, 1H), 5.84 (dd, J=15.4, 7.0 Hz, 1H), 5.53-5.45 (m, 1H), 4.11-4.00 (m, 3H), 3.94 (s, 3H), 3.89 (s, 3H), 3.88-3.81 (m, 2H), 3.57 (d, J=14.3 Hz, 1H), 3.19-3.07 (m, 1H), 2.87-2.53 (m, 4H), 2.46-2.32 (m, 1H), 2.31-2.19 (m, 1H), 2.19-1.99 (m, 3H), 1.99-1.72 (m, 6H), 1.42 (t, J=13.0 Hz, 1H), 1.16 (d, J=6.8 Hz, 3H). LCMS-ESI+ (m/z): [M+H]$^+$ calcd for $C_{41}H_{46}ClN_7O_6S$: 800.3; found: 799.9.

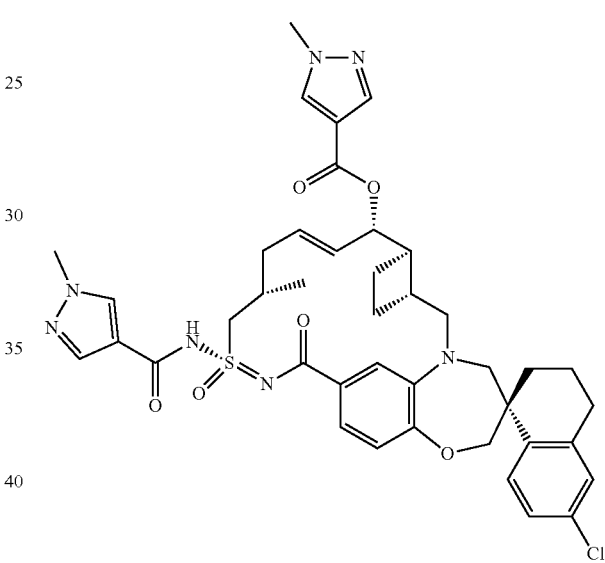

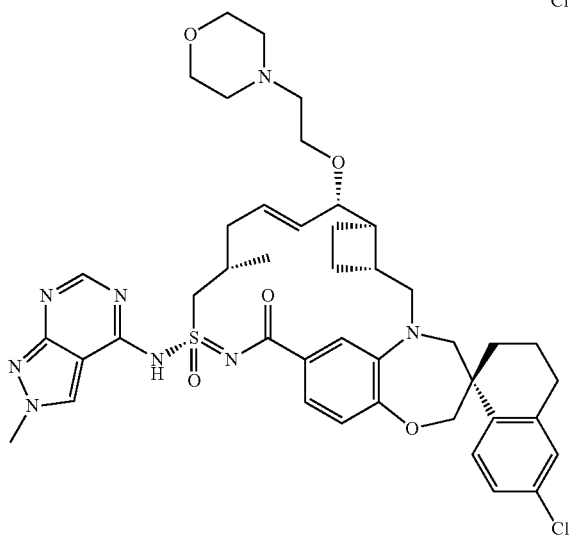

Potassium bis(trimethylsilyl)amide solution (1.0 M in tetrahydrofuran, 98 μL, 98 μmol) was added via syringe to a stirred solution of Example 29 (5.0 mg, 7.0 μmol) in N,N-dimethylformamide (0.4 mL) at 0° C. After 5 min, 4-(2-bromoethyl)morpholine hydrobromide (15.4 mg, 55.8 μmol) was added, and the resulting mixture was allowed to warm to room temperature. After 60 min, cesium fluoride (29.7 mg, 195 μmol) and sodium hydride (60% wt. dispersion in mineral oil, 16.8 mg, 420 μmol) were added sequentially, and the resulting mixture was heated to 80° C. After 4 h, the reaction mixture was allowed to cool to room temperature. Trifluoroacetic acid (100 μL) was added, and the resulting mixture was purified by reverse phase preparative HPLC (0.1% trifluoroacetic acid in acetonitrile/water) to give Example 52. $^1$H NMR (400 MHz, Acetone-d$_6$) δ 8.65 (s, 1H), 8.39 (s, 1H), 7.77 (d, J=8.5 Hz, 1H), 7.30 (dd, J=8.2, 1.8 Hz, 1H), 7.29-7.21 (m, 2H), 7.13 (d, J=2.4 Hz, 1H), 6.84 (d, J=8.2 Hz, 1H), 6.29 (dt, J=14.4, 6.9 Hz, 1H), 5.77 (dd, J=15.6, 8.0 Hz, 1H), 4.27-3.21 (m, 19H), 4.20 (s, 3H), 3.14 (dd, J=15.2, 10.6 Hz, 1H), 2.92-1.34 (m, 16H), 1.22 (d, J=6.9 Hz, 3H). LCMS: LCMS-ESI+(m/z): [M+H]$^+$ calcd for C$_{43}$H$_{53}$ClN$_8$O$_5$S: 829.43; found: 829.1.

Example 53

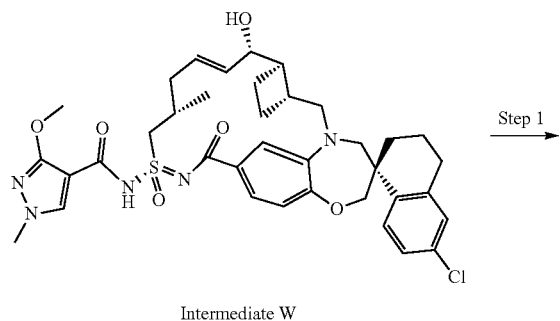

Intermediate W

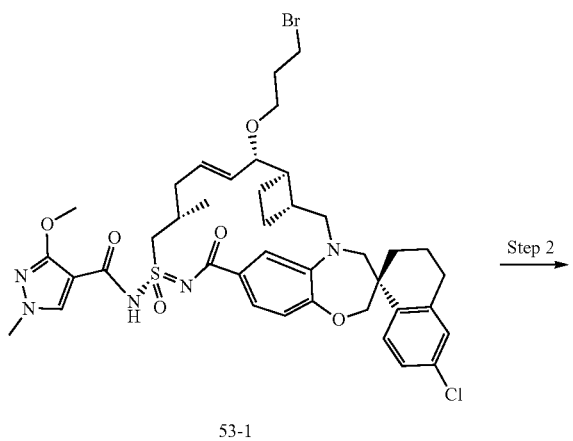

53-1

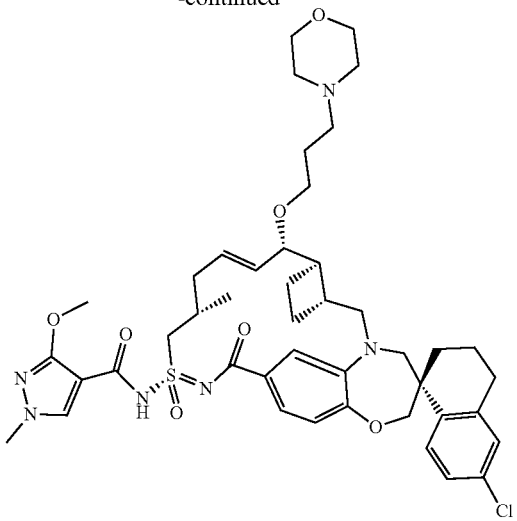

Example 53

Step 1: To a stirred solution of Intermediate W (100 mg, 0.138 mmol) in DMF (5 mL) was added sodium hydride (60% in mineral oil, 33.2 mg, 1.38 mmol) in an ice bath, followed by 3-bromopropyl trifluoromethanesulfonate (188 mg, 0.69 mmol). The resulting mixture was stirred at 80° C. overnight. Reaction mixture extracted with CH$_2$Cl$_2$. The organic layer was concentrated and purified by preparative HPLC to afford intermediate 53-1.

Step 2: A stirred solution of 53-1 (10 mg, 0.012 mmol) in morpholine (5 mL) was heated at 60° C. for 1 hr. Reaction mixture was concentrated and purified by preparative HPLC to afford Example 53. $^1$H NMR (400 MHz, Chloroform-d) δ 8.04 (s, 1H), 7.76 (d, J=8.5 Hz, 1H), 7.47 (d, J=8.2 Hz, 1H), 7.26 (s, 1H), 7.20 (dd, J=8.5, 2.3 Hz, 1H), 7.11 (d, J=2.3 Hz, 1H), 6.94 (d, J=8.3 Hz, 1H), 6.18-5.97 (m, 1H), 5.63 (dd, J=15.7, 6.2 Hz, 1H), 4.25-3.90 (m, 7H), 3.87-3.49 (m, 7H), 3.41-2.96 (m, 6H), 2.79 (d, J=15.0 Hz, 4H), 2.61 (s, 2H), 2.36 (s, 3H), 2.16-1.60 (m, 10H), 1.50-1.06 (m, 6H), 0.94-0.75 (m, 2H). LCMS-ESI+ (m/z): [M+H]$^+$ calcd for C$_{44}$H$_{57}$ClN$_6$O$_7$S: 849.37 found: 849.25.

Example 54 and Example 55

To a solution of a mixture of Intermediate W and W-2-3 (20.0 mg, 0.0266 mmol) in THF (3.0 mL) at −40° C. was added allyl bromide (19.3 mg, 0.16 mmol) followed by KHMDS (1.0 M in THF, 0.775 mL, 0.775 mmol). The reaction was warmed to rt and stirred for 40 min. Acetic acid was added and the mixture was concentrated in vacuo. The residue was redissolved in a mixture of methanol, water, acetonitrile and trifluoroacetic acid, filtered, and purified by reverse phase preparative HPLC to give Example 54 as the earlier eluting of two isomers and Example 55 as the later-eluting of two isomers (olefin stereochemistry assigned tentatively).

Example 54

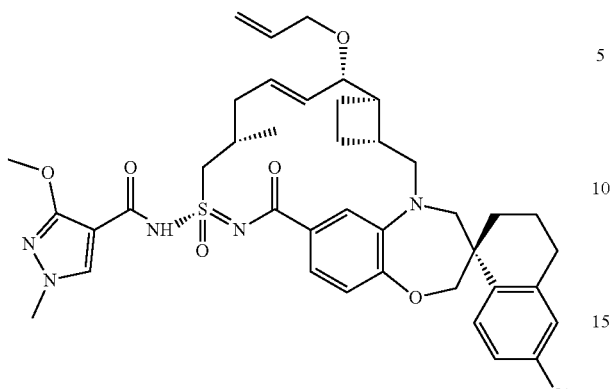

Example 55

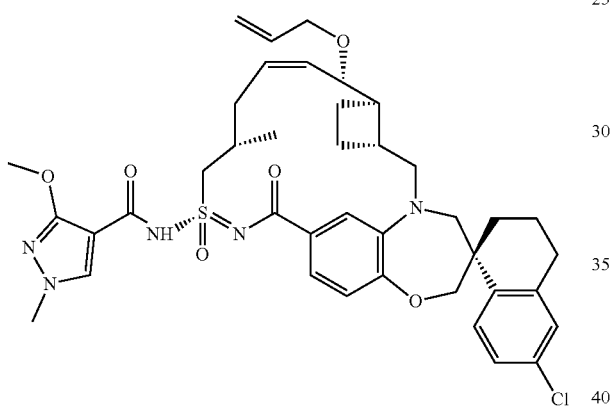

Example 56

Example 54: $^1$H NMR (400 MHz, Acetone-$d_6$) δ 8.12 (s, 1H), 7.79 (dd, J=8.5, 1.9 Hz, 1H), 7.57-7.32 (m, 2H), 7.25 (dd, J=8.5, 2.4 Hz, 1H), 7.14 (d, J=2.3 Hz, 1H), 6.93 (d, J=8.2 Hz, 1H), 6.16 (dt, J=14.5, 6.7 Hz, 1H), 5.98-5.83 (m, 1H), 5.69 (dd, J=15.6, 7.2 Hz, 1H), 5.24 (dq, J=17.3, 1.9 Hz, 1H), 5.09 (dq, J=10.4, 1.5 Hz, 1H), 4.18-3.39 (m, 9H), 4.08 (s, 3H), 3.86 (s, 3H), 3.16 (dd, J=15.1, 10.8 Hz, 1H), 3.07-1.10 (m, 16H), 1.13 (d, J=6.8 Hz, 3H). LCMS-ESI+ (m/z): [M+H]$^+$ calcd for $C_{40}H_{48}ClN_5O_6S$: 762.3 found: 762.2.

Example 55: $^1$H NMR (400 MHz, Acetone-$d_6$) δ 8.08 (s, 1H), 7.80 (d, J=8.5 Hz, 1H), 7.48 (s, 1H), 7.39 (d, J=8.2 Hz, 1H), 7.25 (d, J=8.7 Hz, 1H), 7.14 (s, 1H), 6.91 (d, J=8.3 Hz, 1H), 6.25-5.59 (m, 3H), 5.25 (d, J=17.0 Hz, 1H), 5.15-4.99 (m, 1H), 4.29-3.49 (m, 14H), 3.45 (d, J=14.3 Hz, 1H), 3.15 (dd, J=15.0, 10.9 Hz, 1H), 3.06-1.10 (m, 16H), 1.24 (d, J=6.8 Hz, 3H). LCMS-ESI+ (m/z): [M+H]$^+$ calcd for $C_{40}H_{48}ClN_5O_6S$: 762.3 found: 762.1.

To a stirred solution of Intermediate W (10 mg, 0.01 mmol) in DCM (5 mL) was added 3-(tetrahydro-2H-pyran-4-yl)propanoic acid (3 mgs, 0.015 mmol), EDCl (4.3 mg, 0.03 mmol) and 4-dimethylaminopyridine (3.4 mg, 0.02 mmol). The reaction mixture was stirred at room temperature for 24 hr. Then the reaction mixture was diluted with DCM, washed with 1 N HCl and brine. The organic phase was dried over $MgSO_4$, filtered, concentrated, and purified on normal phase chromatography 0-10% DCM/MeOH to yield Example 56. $^1$H NMR (400 MHz, Chloroform-d) δ 7.83 (s, 1H), 7.78-7.72 (m, 1H), 7.49 (ddd, J=10.9, 8.2, 1.9 Hz, 1H), 7.39 (d, J=2.0 Hz, 1H), 7.19 (dd, J=8.5, 2.3 Hz, 1H), 7.10 (d, J=2.2 Hz, 1H), 6.94 (dd, J=8.3, 4.8 Hz, 1H), 5.88 (dt, J=13.5, 6.6 Hz, 1H), 5.71 (dd, J=15.7, 5.8 Hz, 1H), 5.29 (t, J=5.7 Hz, 1H), 4.22-3.96 (m, 6H), 3.82 (s, 4H), 3.77-3.63 (m, 3H), 3.48-3.23 (m, 3H), 3.05 (dd, J=15.3, 8.9 Hz, 2H), 2.90-2.72 (m, 2H), 2.69-2.37 (m, 4H), 2.35-2.14 (m, 3H), 2.13-2.02 (m, 2H), 2.01-1.76 (m, 4H), 1.76-1.64 (m, 2H), 1.63-1.46 (m, 4H), 1.35-1.19 (m, 3H), 1.11 (dd, J=10.6, 6.9 Hz, 3H). LCMS-ESI+ (m/z): [M+H]$^+$ calcd for $C_{45}H_{56}ClN_5O_8S$: 863.35 found: 863.18.

Example 57

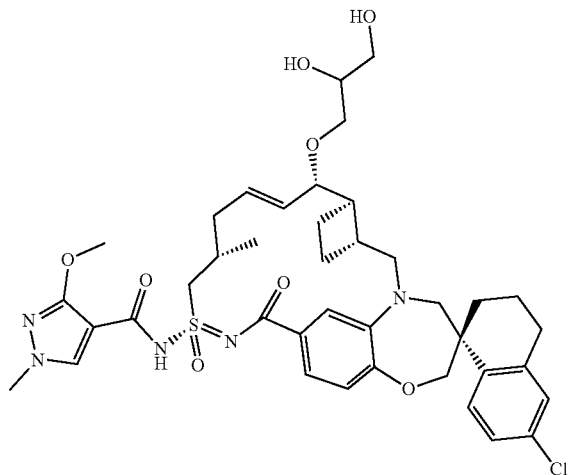 [SMILES: COc1nn(C)cc1C(=O)N[S@@]1(=O)=NC(=O)c2ccc3c(c2)N(C[C@@H]2CC[C@H]2[C@@H](OCC(O)CO)/C=C/C[C@H](C)C1)C[C@@]1(CCCc2cc(Cl)ccc21)CO3]

NaIO₄ (60 mg, 0.29 mmol) and OsO₄ 2.5% in ᵗBuOH (40 mg, 0.004 mmol) were added to a stirred solution of Example 54 (30 mg, 0.04 mmol) in a mixture of tBuOH (0.7 mL), THF (0.2 mL) and water (3.5 mL). The resulting mixture was stirred at room temperature for 90 min. Reaction mixture was quenched with a 1 N solution of sodium thiosulfate, stirred vigorously at room temperature for 10 minutes, and extracted with DCM. Combined organic layer was washed with brine, dried over magnesium sulfate, filtered and concentrated. The residue was purified by preparative HPLC to afford Example 57 as mixture of diastereomers. H NMR (400 MHz, Chloroform-d) δ 7.85 (d, J=7.0 Hz, 1H), 7.76 (d, J=8.5 Hz, 1H), 7.47 (dd, J=8.4, 1.8 Hz, 1H), 7.25 (s, 1H), 7.21 (dd, J=8.5, 2.4 Hz, 1H), 7.10 (d, J=2.3 Hz, 1H), 6.94 (dd, J=8.2, 1.6 Hz, 1H), 6.08 (ddd, J=21.8, 15.0, 7.2 Hz, 1H), 5.70 (dt, J=15.1, 6.7 Hz, 1H), 4.27-3.96 (m, 6H), 3.94-3.59 (m, 8H), 3.55-3.22 (m, 4H), 3.02 (dd, J=15.3, 10.9 Hz, 1H), 2.89-2.55 (m, 4H), 2.47-1.62 (m, 1 OH), 1.48-1.01 (m, 6H). LCMS-ESI+ (m/z): [M+H]⁺ calcd for $C_{40}H_{50}ClN_5O_8S$: 796.31; found: 796.22.

Example 58

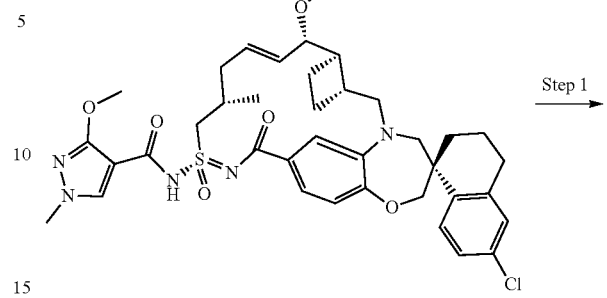

Example 54

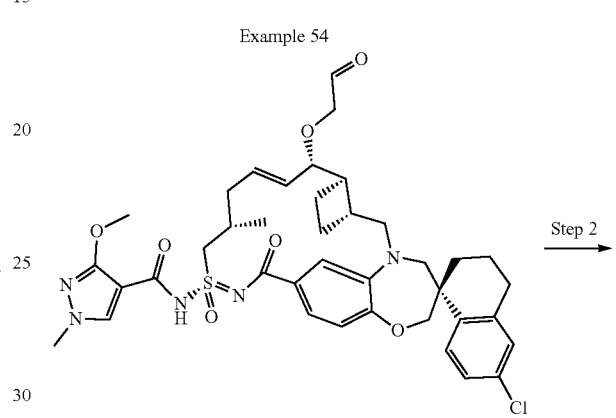

58-1

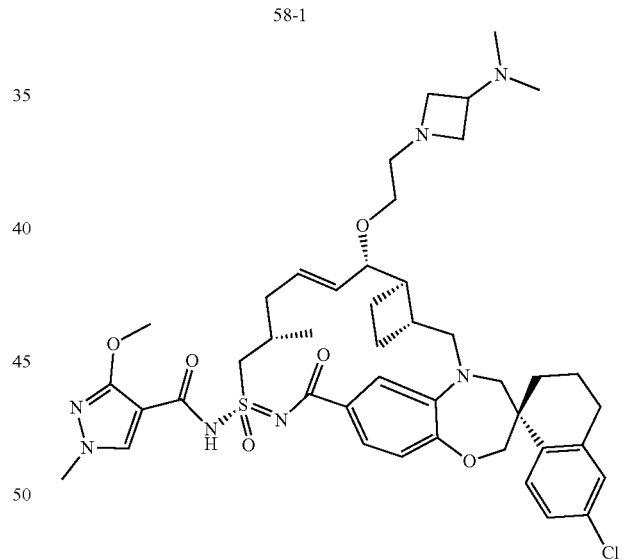

Example 58

Step 1: NaIO₄ (314 mg, 0.15 mmol) and OsO₄ 2.5% in tBuOH (200 mg, 0.019 mmol) were added to a stirred solution of Example 54 (150 mg, 0.19 mmol) in a mixture of tBuOH (7 ml), THF (2.1 ml) and water (3.5 ml). The resulting mixture was stirred at room temperature for 90 min. Reaction mixture was quenched with a 1 N solution of sodium thiosulfate stirred vigorously at room temperature for 10 minutes, extracted with DCM. Combined organic layer was washed with brine, dried over magnesium sulfate, filtered, and concentrated to give 58-1.

Step 2: DIPEA (0.011 mL 0.065 mmol), and STAB (5.7 mg, 0.03 mmol) were added to a stirred solution of 58-1 (10 mg, 0.01 mmol) and 3-dimethylaminoazetidine (15.7 mg, 0.157 mmol) at 0° C. in DCM (3 mL). The reaction was stirred at room temperature overnight. Product was extracted with DCM. Organic layer was washed with brine, dried over magnesium sulfate, filtered and concentrated. The residue was purified by preparative HPLC to afford Example 58. ¹H NMR (400 MHz, Methanol-d₄) δ 8.12 (s, 1H), 7.75 (d, J=8.5 Hz, 1H), 7.35 (dd, J=8.2, 1.9 Hz, 1H), 7.22-7.08 (m, 3H), 6.92 (d, J=8.2 Hz, 1H), 6.26 (dt, J=14.8, 7.0 Hz, 1H), 5.73 (dd, J=15.5, 6.9 Hz, 1H), 4.53 (q, J=10.7 Hz, 2H), 4.36 (dt, J=12.7, 6.9 Hz, 2H), 4.27-4.15 (m, 1H), 4.13-3.97 (m, 3H), 3.92-3.69 (m, 5H), 3.61 (d, J=15.9 Hz, 2H), 3.4 (s, 12), 3.19-2.94 (m, 2H), 2.91-2.66 (m, 3H), 2.29-2.05 (m, 2H), 2.04-1.71 (m, 5H), 1.53-0.96 (m, 5H). LCMS-ESI+ (m/z): calcd for H+C$_{44}$H$_{58}$ClN$_{7}$O$_{6}$S: 848.39; found: 848.28.

Example 59

Example 59 was synthesized in a similar manner to Example 58 using 1-methylpiperazine. $^1$H NMR (400 MHz, Chloroform-d) δ 8.01 (s, 1H), 7.75 (d, J=8.5 Hz, 1H), 7.48 (dd, J=8.2, 1.9 Hz, 1H), 7.37 (s, 1H), 7.20 (dd, J=8.5, 2.3 Hz, 1H), 7.11 (d, J=2.3 Hz, 1H), 6.96 (d, J=8.2 Hz, 1H), 6.50 (dd, J=15.3, 9.8 Hz, 1H), 5.74 (dd, J=15.2, 9.3 Hz, 1H), 4.44 (dd, J=14.3, 10.5 Hz, 3H), 4.09 (d, J=12.9 Hz, 5H), 3.79 (d, J=17.7 Hz, 10H), 3.62-3.37 (m, 7H), 3.29 (s, 3H), 3.07 (dd, J=15.2, 10.2 Hz, 2H), 2.92 (s, 3H), 2.86-2.67 (m, 3H), 2.49 (s, 3H), 2.17-1.65 (m, 6H), 1.50-1.05 (m, 5H). LCMS-ESI+ (m/z): calcd for H+C$_{44}$H$_{58}$ClN$_{7}$O$_{6}$S: 848.39; found: 848.26.

Example 60

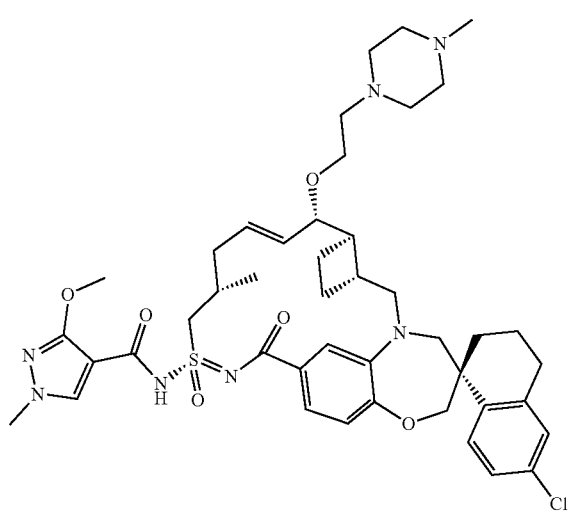

Example 60 was synthesized in a similar manner to Example 58 using 1-(oxetan-3-yl)piperazine. $^1$H NMR (400 MHz, Chloroform-d) δ 7.91 (s, 1H), 7.75 (d, J=8.6 Hz, 1H), 7.48 (dd, J=8.2, 1.9 Hz, 1H), 7.34 (d, J=1.9 Hz, 1H), 7.20 (dd, J=8.5, 2.4 Hz, 1H), 7.11 (d, J=2.3 Hz, 1H), 6.96 (d, J=8.2 Hz, 1H), 6.40 (dd, J=15.2, 9.5 Hz, 1H), 5.76 (dd, J=15.2, 9.1 Hz, 1H), 4.83 (dt, J=28.0, 6.9 Hz, 4H), 4.35 (dd, J=14.4, 9.3 Hz, 2H), 4.09 (d, J=15.5 Hz, 6H), 3.96-3.54 (m, 9H), 3.35 (d, J=52.1 Hz, 8H), 3.15-2.92 (m, 4H), 2.80 (d, J=15.5 Hz, 3H), 2.49 (s, 4H), 2.17-1.64 (m, 2H), 1.50-0.78 (m, 5H). LCMS-ESI+ (m/z): calcd for H+C$_{46}$H$_{60}$ClN$_{7}$O$_{7}$S: 890.4; found: 890.26.

Example 61

Example 61 was synthesized in a similar manner to Example 58 using 3-methoxyazetidine. $^1$H NMR (400 MHz, Chloroform-d) δ $^1$H NMR (400 MHz, Methanol-d$_4$) δ 8.10 (s, 1H), 7.76 (d, J=8.6 Hz, 1H), 7.35 (dd, J=8.2, 1.8 Hz, 1H), 7.30-7.03 (m, 2H), 6.92 (d, J=8.2 Hz, 1H), 6.23 (s, 1H), 5.75 (s, 1H), 4.45 (d, J=62.3 Hz, 2H), 4.29-3.69 (m, 9H), 3.64-3.38 (m, 2H), 3.38-3.30 (m, 10) 3.29-2.94 (m, 4H), 2.92-2.64 (m, 2H), 2.51 (d, J=48.2 Hz, 3H), 2.34-1.65 (m, 6H), 1.59-0.81 (m, 6H). LCMS-ESI+ (m/z): [M+H]$^+$ calcd for C$_{43}$H$_{55}$ClN$_{6}$O$_{7}$S: 835.35; found: 835.24.

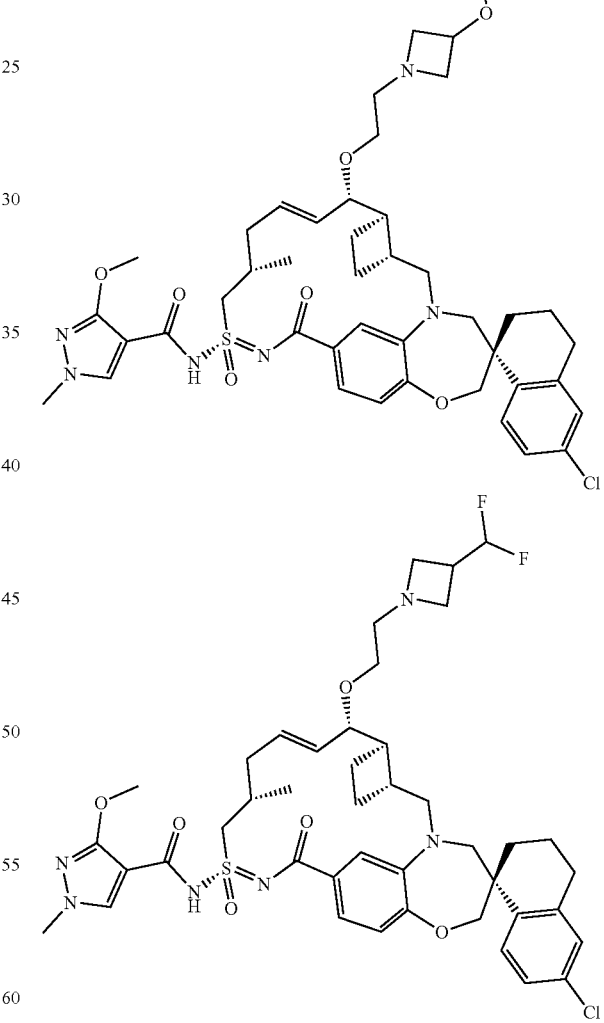

Example 62 was synthesized in a similar manner to Example 58 using 3-(difluoromethyl)azetidine. $^1$H NMR (400 MHz, Methanol-d$_4$) δ 8.09 (s, 1H), 7.76 (d, J=8.5 Hz, 1H), 7.35 (dd, J=8.3, 1.8 Hz, 2H), 7.23-7.06 (m, 2H), 6.92 (d, J=8.2 Hz, 1H), 6.24 (d, J=15.7 Hz, 1H), 6.12 (s, 1H), 5.98

(s, 1H), 5.73 (s, 1H), 4.52-3.95 (m, 8H), 3.94-3.67 (m, 5H), 3.59 (s, 3H), 3.07 (dd, J=15.2, 10.6 Hz, 2H), 2.94-2.61 (m, 3H), 2.50 (d, J=39.3 Hz, 3H), 2.35-1.54 (m, 8H), 1.55-0.98 (m, 5H). LCMS-ESI+ (m/z): calcd for H+C$_{43}$H$_{53}$ClF$_2$N$_6$O$_6$S: 855.34; found: 855.68.

Example 63

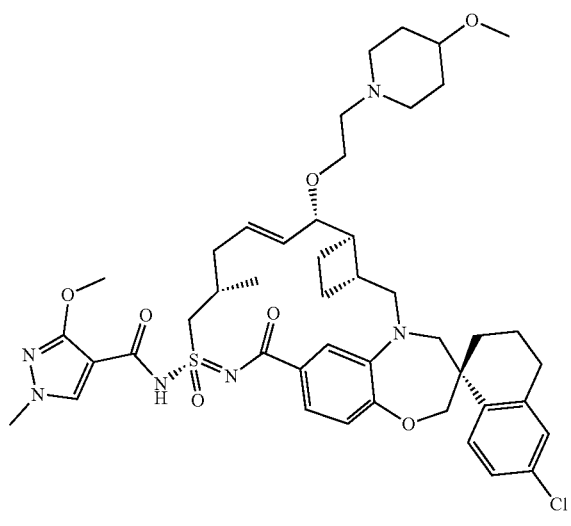 [SMILES: COc1nn(C)cc1C(=O)N[S@@]1(=O)=NC(=O)c2ccc3c(c2)N(C[C@@H]2CC[C@H]2[C@@H](OCCN2CCC(OC)CC2)/C=C/C[C@H](C)C1)C[C@@]1(CCCc2cc(Cl)ccc21)CO3]

Example 63 was synthesized in a similar manner to Example 58 using 4-methoxypiperidine. $^1$H NMR (400 MHz, Methanol-d$_4$) δ 8.08 (s, 1H), 7.77 (d, J=8.6 Hz, 1H), 7.35 (d, J=8.3 Hz, 1H), 7.25-7.16 (m, 1H), 7.12 (d, J=2.3 Hz, 1H), 6.93 (d, J=8.2 Hz, 1H), 6.23 (dt, J=14.7, 7.0 Hz, 1H), 5.77 (dd, J=15.8, 7.3 Hz, 1H), 4.22-3.98 (m, 4H), 3.95 (dd, J=7.5, 3.6 Hz, 2H), 3.82 (s, 3H), 3.78-3.54 (m, 4H), 3.54-3.38 (m, 4H), 3.08 (dd, J=15.6, 10.3 Hz, 2H), 2.95-2.71 (m, 4H), 2.67-2.33 (m, 4H), 2.28-1.73 (m, 1 OH), 1.53 (dt, J=60.6, 12.7 Hz, 3H), 1.21 (d, J=6.9 Hz, 3H). LCMS-ESI+ (m/z): calcd for H+C$_{43}$H$_{59}$ClN$_6$O$_7$S: 863.80; found: 863.39.

Example 64

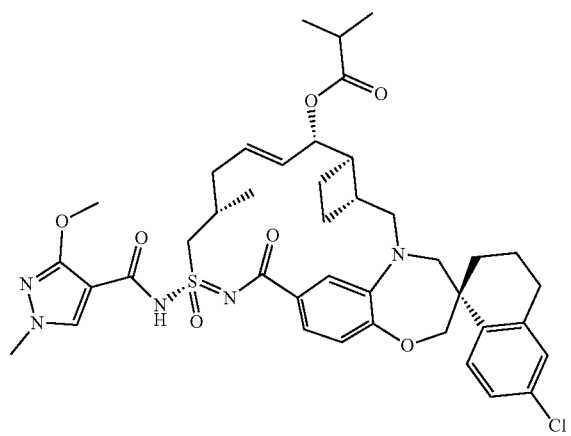

Example 64 was synthesized in a similar manner to Example 56 using isobutyric acid. $^1$H NMR (400 MHz, Chloroform-d) δ 7.83-7.68 (m, 2H), 7.32-7.28 (m, 2H), 7.21 (dd, J=8.5, 2.4 Hz, 1H), 7.10 (d, J=2.3 Hz, 1H), 6.94 (d, J=8.2 Hz, 1H), 6.04-5.89 (m, 1H), 5.64 (dd, J=15.4, 7.5 Hz, 1H), 5.27 (s, 1H), 4.20-3.99 (m, 4H), 3.93 (d, J=14.8 Hz, 1H), 3.80 (s, 3H), 3.71 (d, J=14.3 Hz, 1H), 3.27 (d, J=14.3 Hz, 1H), 3.00 (dd, J=15.1, 8.5 Hz, 1H), 2.90-2.70 (m, 3H), 2.43 (h, J=6.7 Hz, 2H), 2.32-1.75 (m, 13H), 1.56 (d, J=7.1 Hz, 2H), 1.47-1.31 (m, 2H), 1.18-0.97 (m, 6H), 0.96-0.80 (m, 2H). LCMS-ESI+ (m/z): [M+H]$^+$ calcd for C$_{42}$H$_{52}$ClN$_5$O$_7$S: 806.33; found: 806.64.

Example 65

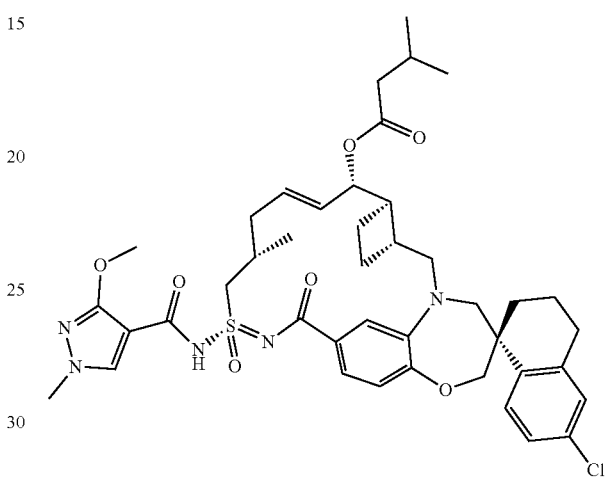

Example 65 was synthesized in a similar manner to Example 56 using 3-methylbutanoic acid. $^1$H NMR (400 MHz, Chloroform-d) δ 7.85-7.64 (m, 2H), 7.31 (s, 2H), 7.21 (dd, J=8.5, 2.3 Hz, 1H), 7.10 (d, J=2.3 Hz, 1H), 6.94 (d, J=8.2 Hz, 1H), 5.88 (s, 1H), 5.62 (dd, J=15.2, 7.2 Hz, 1H), 5.27 (s, 1H), 4.20-4.04 (m, 3H), 3.93 (d, J=15.8 Hz, 1H), 3.86-3.66 (m, 3H), 3.26 (d, J=14.5 Hz, 1H), 3.01 (dd, J=15.3, 8.1 Hz, 1H), 2.87-2.67 (m, 2H), 2.58-2.40 (m, 2H), 2.31 (dd, J=31.6, 7.1 Hz, 2H), 2.23-1.67 (m, 13H), 1.57 (d, J=7.1 Hz, 2H), 1.28 (s, 4H), 0.98 (ddd, J=34.5, 6.5, 4.7 Hz, 9H). LCMS-ESI+ (m/z): [M+H]$^+$ calcd for C$_{43}$H$_{54}$ClN$_5$O$_7$S: 819.34; found: 820.58.

Example 66

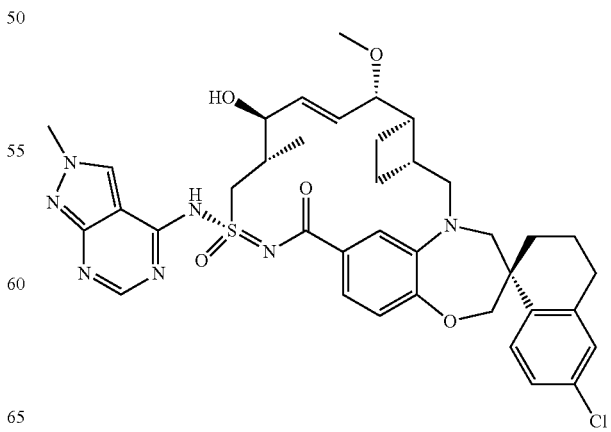

Example 66 was prepared in a similar manner to Intermediate M using Example 8. $^1$H NMR (400 MHz, Methanol-d$_4$) δ 8.77 (s, 1H), 8.24 (s, 1H), 7.74 (d, J=8.6 Hz, 1H), 7.22-7.07 (m, 5H), 6.81 (d, J=8.1 Hz, 1H), 6.33 (dd, J=15.5, 5.2 Hz, 1H), 5.83 (dd, J=15.6, 8.2 Hz, 1H), 4.68 (s, 1H), 4.18 (s, 3H), 4.10-3.97 (m, 3H), 3.96-3.81 (m, 2H), 3.67 (d, J=14.4 Hz, 1H), 3.39 (s, 1H), 3.19-3.03 (m, 1H), 2.90-2.55 (m, 3H), 2.50 (s, 2H), 2.12 (d, J=13.6 Hz, 1H), 1.96-1.76 (m, 7H), 1.44 (t, J=12.6 Hz, 1H), 1.24 (d, J=6.9 Hz, 3H). LCMS-ESI+(m/z): [M+H]$^+$ calcd for C$_{38}$H$_{44}$ClN$_7$O$_5$S: 746.3; found: 746.3.

Example 67

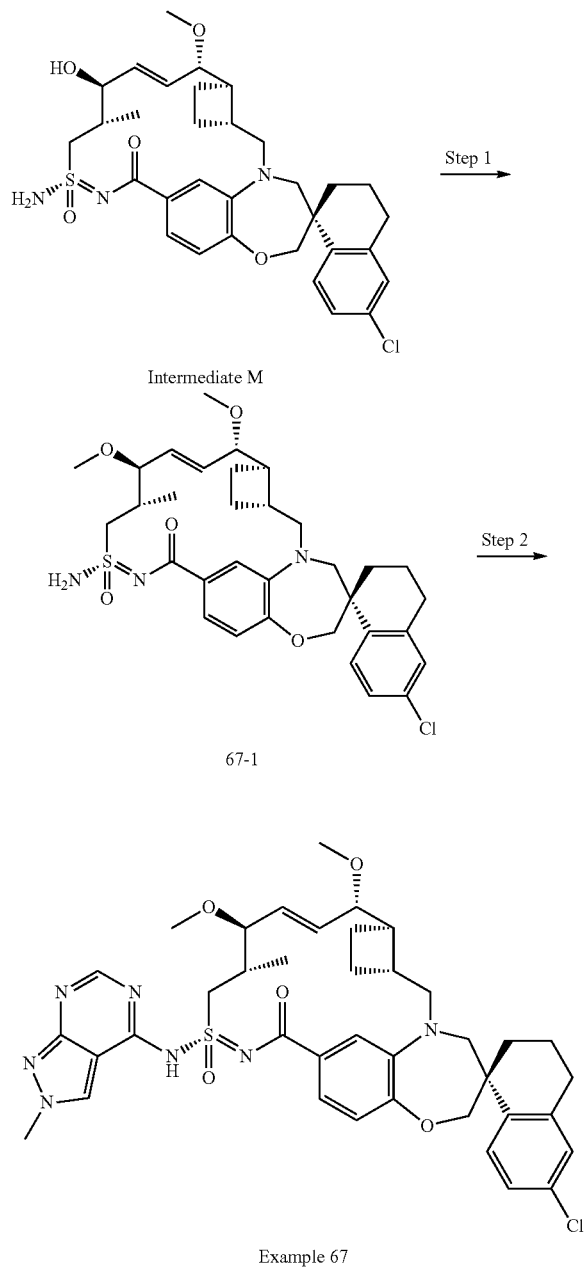

Intermediate M 67-1

Example 67

Step 1: Di-tert-butyl dicarbonate (16.9 mg, 77.4 µmol) was added to a stirred mixture of Intermediate M (31.7 mg, 51.6 µmol), triethylamine (21.6 µL, 155 µmol), and DMAP (18.9 mg, 155 µmol) in dichloromethane (3.0 mL) at 0° C., and the resulting mixture was warmed to room temperature. After 40 min, aqueous citric acid solution (4% w/v) and ethyl acetate were added. The organic layer was washed sequentially with water and a mixture of water and brine (1:1 v:v), dried over anhydrous magnesium sulfate, filtered, and concentrated under reduced pressure. The residue was dissolved in tetrahydrofuran (1.0 mL), and the resulting mixture was cooled with stirring to −40° C. Iodomethane (32.2 µL, 516 µmol) was added via syringe. After 1 min, potassium bis(trimethylsilyl)amide solution (1.0 M in tetrahydrofuran, 258 µL, 258 µmol) was added over 1 min via syringe. After 1 min, the resulting mixture was warmed to room temperature. After 30 min, a mixture of phosphoric acid (260 mg) and sodium dihydrogen phosphate dehydrate (90 mg) in water (10 mL) was added. Ethyl acetate was added, and the organic layer was washed sequentially with a mixture of water and brine (1:1 v:v) and brine, dried over anhydrous magnesium sulfate, filtered, and concentrated under reduced pressure. The residue was dissolved in dichloromethane (10 mL) and the resulting mixture was stirred at room temperature. Trifluoroacetic acid (1.0 mL) was added via syringe. After 20 min, trifluoroacetic acid (550 µL) was added via syringe. After 30 min, a mixture of sodium dihydrogen phosphate dehydrate (6.3 g) in water (15 mL) was added. Brine was added, and the aqueous layer was extracted with dichloromethane. The combined organic layers were dried over anhydrous magnesium sulfate, filtered, and concentrated under reduced pressure. The residue was purified by flash column chromatography on silica gel (0 to 70% ethyl acetate in hexanes) to give 67-1.

Step 2: 2-tert-Butylimino-2-diethylamino-1,3-dimethylperhydro-1,3,2-diazaphosphorine (polymer-bound. 200-400 mesh, 2.0-2.5 mmol/g loading, 1% cross-linked, 92.6 mg, 190-230 µmol) was added to a vigorously stirred solution of 67-1 (16.0 mg, 25.5 µmol) in dimethylsulfoxide (0.5 mL) at room temperature. After 5 min, 4-chloro-2-methyl-2H-pyrazolo[3,4-d]pyrimidine (21.5 mg, 127 µmol) was added, and the resulting mixture was warmed to 110° C. After 40 min, 2-tert-butylimino-2-diethylamino-1,3-dimethylperhydro-1,3,2-diazaphosphorine (polymer-bound. 200-400 mesh, 2.0-2.5 mmol/g loading, 1% cross-linked, 300 mg, 600-750 µmol) and 4-chloro-2-methyl-2H-pyrazolo[3,4-d]pyrimidine (8.6 mg, 51 µmol) were added sequentially. After 90 min, the resulting mixture was cooled to room temperature, trifluoroacetic acid (200 µL) was added, and the resulting mixture was purified by reverse phase preparative HPLC (0.1% trifluoroacetic acid in acetonitrile/water) to give Example 67. $^1$H NMR (400 MHz, Acetone-d$_6$) δ 8.58 (s, 1H), 8.41 (s, 1H), 7.77 (d, J=8.4 Hz, 1H), 7.34-7.28 (m, 2H), 7.23 (d, J=8.4 Hz, 1H), 7.13 (s, 1H), 6.82 (d, J=8.6 Hz, 1H), 6.17 (dd, J=15.5, 7.1 Hz, 1H), 5.81 (dd, J=15.6, 8.9 Hz, 1H), 4.20 (s, 3H), 4.08 (d, J=12.1 Hz, 1H), 4.03 (d, J=12.1 Hz, 1H), 3.95-3.78 (m, 3H), 3.73 (d, J=14.4 Hz, 1H), 3.49 (d, J=14.4 Hz, 1H), 3.33 (s, 3H), 3.32-3.17 (m, 1H), 3.28 (s, 3H), 3.11 (dd, J=14.5, 7.2 Hz, 1H), 2.93-1.36 (m, 14H), 1.29 (d, J=7.2 Hz, 3H). LCMS-ESI+ (m/z): [M+H]$^+$ calcd for C$_{39}$H$_{46}$ClN$_7$O$_5$S: 760.3; found: 760.2.

Example 68 and Example 69

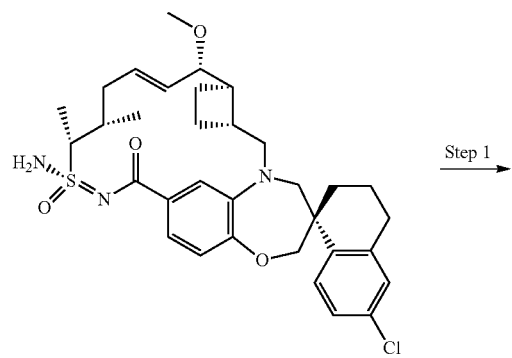

Intermediate K

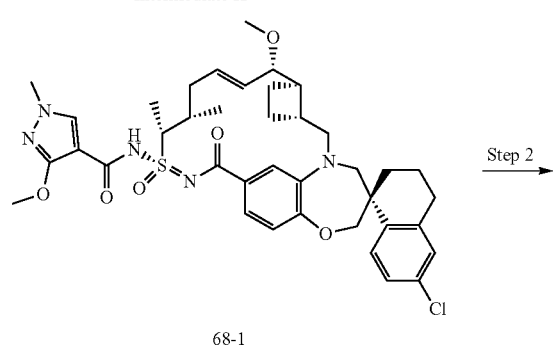

68-1

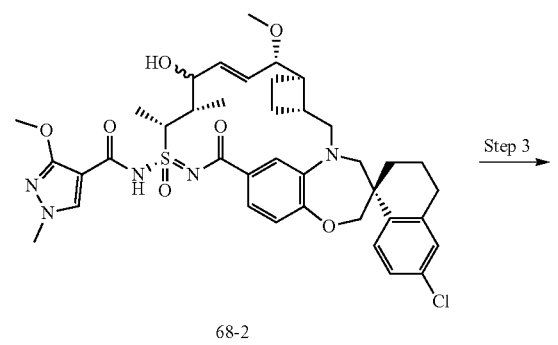

68-2

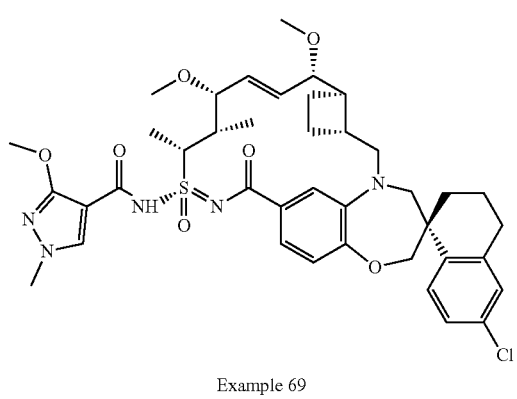

Example 69

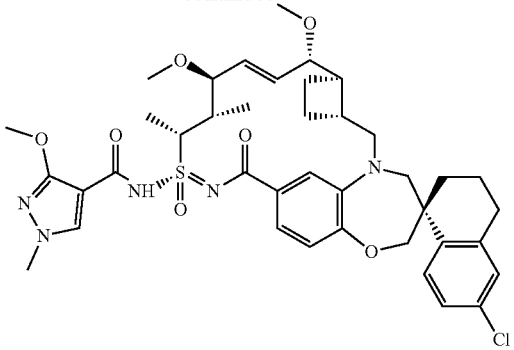

Example 68

Step 1: 68-1 was synthesized in a similar manner to Intermediate T using 3-methoxy-1-methyl-1H-pyrazole-4-carboxylic acid and Intermediate K. $^1$H NMR (400 MHz, Methanol-$d_4$) δ 7.93 (s, 1H), 7.75 (d, J=8.5 Hz, 1H), 7.18 (dd, J=8.5, 2.5 Hz, 1H), 7.12 (d, J=2.3 Hz, 1H), 6.99 (d, J=16.9 Hz, 1H), 6.93 (d, J=8.2 Hz, 1H), 6.00 (m, 1H), 5.58 (dd, J=15.3, 8.9 Hz, 1H), 4.38 (d, J=7.5 Hz, 1H), 4.09 (s, 2H), 3.96 (s, 3H), 3.84 (d, J=15.0 Hz, 1H), 3.78 (s, 3H), 3.72 (dd, J=8.9, 3.1 Hz, 1H), 3.66 (d, J=14.3 Hz, 1H), 3.35 (m, 2H), 3.24 (s, 3H), 3.17-3.05 (m, 1H), 2.89-2.72 (m, 2H), 2.52-2.06 (m, 6H), 2.05-1.70 (m, 6H), 1.60 (d, J=7.0 Hz, 3H), 1.52-1.41 (m, 1H), 1.19 (d, J=6.8 Hz, 3H). LCMS-ESI+ (m/z): [M+H]$^+$ calcd for $C_{39}H_{48}ClN_5O_6S$: 750.3; found: 749.9.

Step 2: 68-2 was synthesized in a manner similar to Intermediate M using 68-1 instead of Intermediate T.

Step 3: Example 68 and Example 69 were synthesized in a manner similar to Example 37 using 68-2.

Example 68: $^1$H NMR (400 MHz, Acetone-$d_6$) δ 7.94 (s, 1H), 7.78 (d, J=8.5 Hz, 1H), 7.31 (d, J=8.2 Hz, 1H), 7.26-7.16 (m, 2H), 7.14 (d, J=2.3 Hz, 1H), 6.91 (s, 1H), 6.16-5.85 (m, 1H), 5.77 (dd, J=15.4, 8.6 Hz, 1H), 4.14-4.03 (m, 2H), 4.02-3.67 (m, 11H), 3.45 (d, J=14.5 Hz, 1H), 3.30 (s, 3H), 3.24 (s, 3H), 3.24-3.16 (m, 1H) 2.88-1.22 (m, 16H), 1.18 (d, J=7.0 Hz, 3H). LCMS-ESI+ (m/z): [M+H]$^+$ calcd for $C_{40}H_{50}ClN_5O_7S$: 780.3; found: 780.2.

Example 69: $^1$H NMR (400 MHz, Acetone-$d_6$) δ 8.01 (s, 1H), 7.80 (d, J=8.6 Hz, 1H), 7.48 (s, 1H), 7.39 (d, J=8.2 Hz, 1H), 7.25 (dd, J=8.5, 2.4 Hz, 1H), 7.15 (d, J=2.4 Hz, 1H), 6.91 (d, J=8.3 Hz, 1H), 6.20 (s, 1H), 5.89-5.67 (m, 1H), 4.27-3.57 (m, 13H), 3.46 (d, J=14.4 Hz, 1H), 3.29 (s, 3H), 3.27-3.18 (m, 1H), 3.24 (s, 3H), 2.95-1.24 (m, 16H), 1.14 (d, J=6.9 Hz, 3H). LCMS-ESI+ (m/z): [M+H]$^+$ calcd for $C_{40}H_{50}ClN_5O_7S$: 780.3; found: 780.2.

Example 70

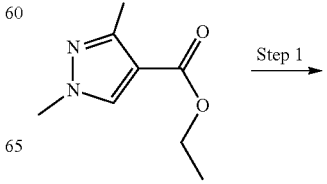

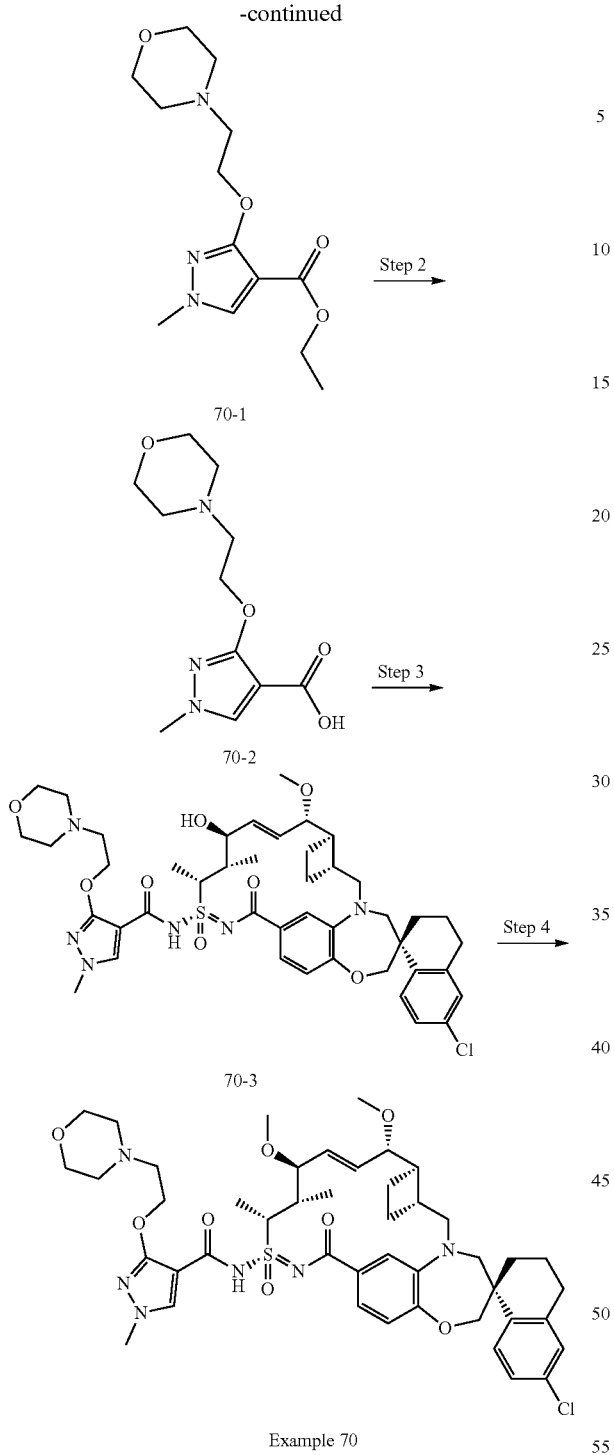

sium sulfate, filtered, and concentrated in vacuo to provide 120 mg crude product. The resulting residue was dissolved in dichloromethane and purified by flash column chromatography (silica gel, 0 to 10% methanol in dichloromethane) to give 70-1. $^1$H NMR (400 MHz, Chloroform-d) δ 7.63 (s, 1H), 4.37 (t, J=5.7 Hz, 2H), 4.21 (q, J=7.1 Hz, 2H), 3.71 (s, 3H), 3.72-3.69 (m, 4H), 2.82 (t, J=5.7 Hz, 2H), 2.61 (t, J=4.7 Hz, 4H), 1.28 (t, J=7.1 Hz, 3H). LCMS-ESI+ (m/z): [M+H]$^+$ calcd for $C_{13}H_{21}N_3O_4$: 284.2; found: 284.1.

Step 2: To a glass screwtop vial charged with 70-1 (120 mg, 0.424 mmol) was added THF (4.2 mL), then sodium hydroxide (2 M in water, 0.96 mL). The resulting mixture was stirred vigorously in a metal heating block warmed to 60° C. for 12 hr. The reaction was quenched with 1 N HCl (approx. 2 mL), added dropwise until pH 4-5 by pH paper. The resulting mixture was extracted three times with ethyl acetate. Then the aqueous phase was concentrated in vacuo to give 70-2, which was carried forward crude without further purification. $^1$H NMR (400 MHz, Methanol-d$_4$) δ 7.80 (s, 1H), 4.49 (t, J=4.9 Hz, 2H), 3.88 (t, J=4.6 Hz, 4H), 3.74 (s, 3H), 3.27 (t, J=5.0 Hz, 2H), 3.11 (t, J=4.5 Hz, 4H). LCMS-ESI+ (m/z): [M+H]$^+$ calcd for $C_{11}H_{17}N_3O_4$: 256.1; found: 256.1.

Step 3: 70-3 was prepared in a similar manner to Intermediate T using 70-2 and Intermediate M. $^1$H NMR (400 MHz, Acetonitrile-d$_3$) δ 8.02 (s, 1H), 7.75 (d, J=8.5 Hz, 1H), 7.33 (dd, J=8.1, 1.9 Hz, 1H), 7.30 (d, J=1.9 Hz, 1H), 7.23 (dd, J=8.5, 2.4 Hz, 1H), 7.17 (d, J=2.3 Hz, 1H), 6.93 (d, J=8.2 Hz, 1H), 6.07 (dd, J=15.6, 4.7 Hz, 1H), 5.77 (ddd, J=15.7, 7.8, 1.6 Hz, 1H), 4.77-4.64 (m, 3H), 4.53 (s, 1H), 4.14-4.00 (m, 4H), 3.92-3.81 (m, 3H), 3.79 (s, 3H), 3.77-3.51 (m, 7H), 3.43 (d, J=14.5 Hz, 1H), 3.22 (s, 3H), 3.19-3.02 (m, 3H), 2.92-2.69 (m, 3H), 2.59-2.44 (m, 2H), 2.41-2.29 (m, 1H), 2.13-2.02 (m, 1H), 1.92 (d, J=3.5 Hz, 2H), 1.86-1.63 (m, 4H), 1.45 (dt, J=15.9, 7.3 Hz, 1H), 1.08 (d, J=6.9 Hz, 3H). LCMS-ESI+(m/z): [M+H]$^+$ calcd for $C_{43}H_{55}ClN_6O_8S$: 851.4; found: 851.4.

Step 4: Example 70 was prepared in a similar manner to Intermediate V using 70-3. $^1$H NMR (400 MHz, Acetonitrile-d$_3$) δ 8.09 (s, 1H), 7.83 (s, 1H), 7.74 (d, J=8.5 Hz, 1H), 7.20 (dd, J=8.7, 2.6 Hz, 1H), 7.16-7.10 (m, 2H), 6.83 (d, J=8.1 Hz, 1H), 6.03 (dd, J=15.3, 7.4 Hz, 1H), 5.69 (dd, J=15.4, 9.1 Hz, 1H), 4.43 (dd, J=10.2, 4.8 Hz, 2H), 4.03 (d, J=7.0 Hz, 2H), 3.93-3.61 (m, 8H), 3.73 (s, 3H), 3.21 (s, 3H), 3.20 (s, 3H), 3.10-3.00 (m, 2H), 2.88-2.65 (m, 6H), 2.48-2.39 (m, 2H), 2.08-2.03 (m, 1H), 1.88-1.65 (m, 7H), 1.49-1.33 (m, 5H), 1.06 (d, J=6.9 Hz, 3H). LCMS-ESI+ (m/z): [M+H]$^+$ calcd for $C_{44}H_{57}ClN_6O_8S$: 865.4; found: 865.4.

Example 71

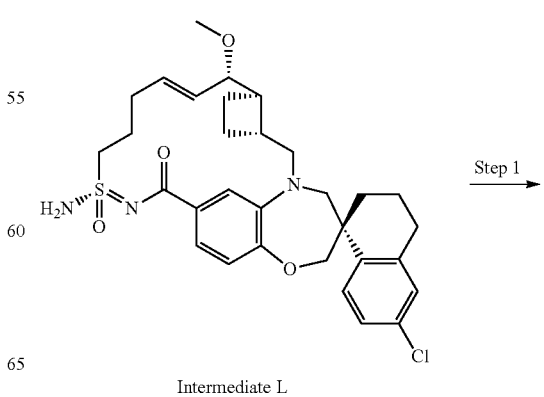

Intermediate L

Step 1: To a round bottom flask was charged with starting ethyl 3-hydroxy-1-methyl-4-pyrazolecarboxylate (100 mg, 0.588 mmol) under nitrogen atmosphere was added DMF (3 mL), followed by sodium hydride (60% dispersion in mineral oil, 27 mg, 1.2 equiv.) at 20° C. The flask was stirred at 20° C. for 60 min, then 4-(2-iodoethyl)morpholine (184 mg, 1.3 equiv.) was added. The reaction was stirred at 80° C. for 16 hr. The reaction was removed from heating and allowed to cool to 20° C., then the reaction was quenched with water and extracted five times into ethyl acetate. The combined organic phases were washed with brine, dried over magne-

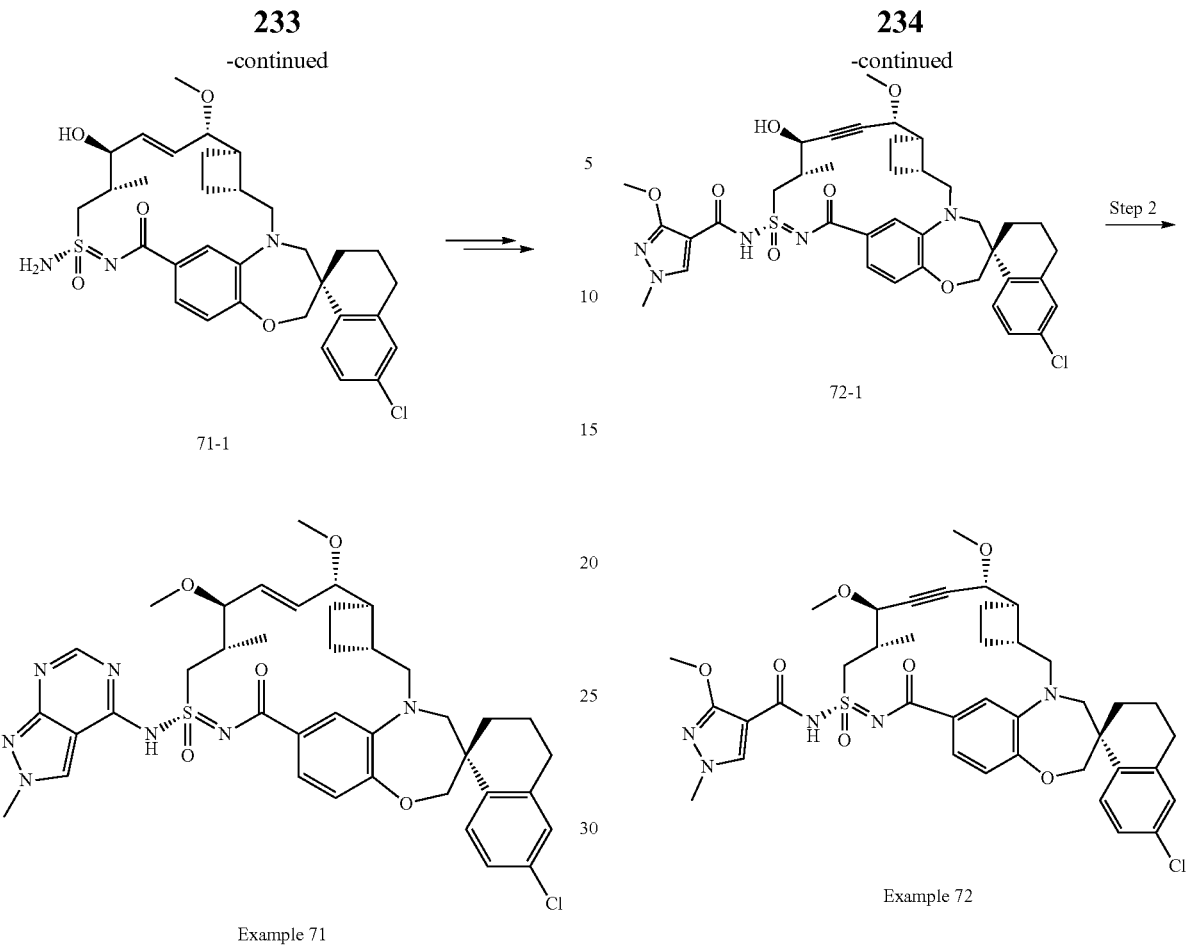

Example 71

Example 72

Step 1: 71-1 was prepared in a similar manner to Intermediate M, using Intermediate L.

Synthesis of Example 71: Example 71 was synthesized in a manner similar to Example 67 using 71-1 instead of Intermediate M. $^1$H NMR (400 MHz, Acetone-$d_6$) δ 8.30 (s, 1H), 8.15 (s, 1H), 7.77 (d, J=8.4 Hz, 1H), 7.50 (d, J=1.9 Hz, 1H), 7.29 (dd, J=8.2, 1.8 Hz, 1H), 7.23 (dd, J=8.5, 2.4 Hz, 1H), 7.13 (d, J=2.4 Hz, 1H), 6.80 (d, J=8.1 Hz, 1H), 5.94-5.88 (m, 2H), 4.14-3.03 (m, 9H), 4.09 (s, 3H), 3.31 (s, 3H), 3.28 (s, 3H), 3.01-1.03 (m, 15H). LCMS-ESI$^+$ (m/z): [M+H]$^+$ calcd for $C_{38}H_{44}ClN_7O_5S$: 746.3; found: 746.1.

Example 72

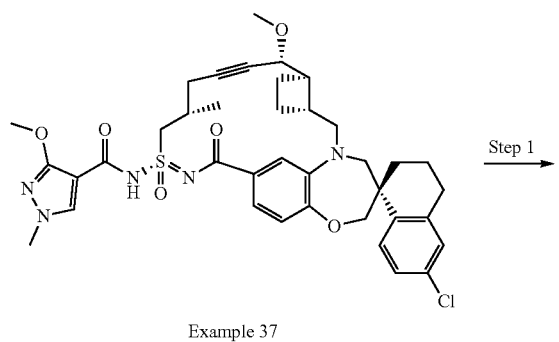

Example 37

Step 1: 72-1 was synthesized in a manner similar to Intermediate M using Example 37.

Step 2: Example 72 was synthesized in a manner similar to Example 37 using 72-1 instead of Example 10. $^1$H NMR (400 MHz, Acetone-$d_6$) δ 8.12 (s, 1H), 7.79 (d, J=8.5 Hz, 1H), 7.56-7.46 (m, 2H), 7.26 (dd, J=8.5, 2.4 Hz, 1H), 7.15 (d, J=2.4 Hz, 1H), 6.94 (d, J=8.2 Hz, 1H), 4.52 (dd, J=4.4, 1.7 Hz, 1H), 4.41 (s, 1H), 4.15-4.03 (m, 2H), 4.10 (s, 3H), 4.00-3.84 (m, 2H), 3.86 (s, 3H), 3.78 (d, J=14.4 Hz, 1H), 3.53 (d, J=14.5 Hz, 1H), 3.43 (s, 3H), 3.41 (s, 3H), 3.24 (dd, J=15.1, 11.4 Hz, 1H), 2.96-1.69 (m, 13H), 1.48 (td, J=13.1, 12.1, 3.8 Hz, 1H), 1.18 (d, J=6.9 Hz, 3H). LCMS-ESI+ (m/z): [M+H]$^+$ calcd for $C_{39}H_{46}ClN_5O_7S$: 764.3; found: 764.2.

Example 73

Example 73 was synthesized in a similar manner to Intermediate V using 2-methoxyacetyl chloride and Intermediate U. $^1$H NMR (400 MHz, Methanol-$d_4$) δ 8.10 (s, 1H), 7.76 (d, J=8.5 Hz, 1H), 7.40 (dd, J=8.3, 1.8 Hz, 1H), 7.22 (s, 1H), 7.17 (d, J=8.7 Hz, 1H), 7.12 (d, J=2.3 Hz, 1H), 6.92 (d, J=8.2 Hz, 1H), 6.15 (dd, J=15.5, 5.9 Hz, 1H), 5.88 (dd, J=15.5, 8.0 Hz, 1H), 5.77 (s, 1H), 4.18-4.09 (m, 2H), 4.07 (d, J=3.1 Hz, 4H), 3.87 (d, J=12.0 Hz, 2H), 3.82 (s, 3H), 3.72 (d, J=14.4 Hz, 1H), 3.40 (s, 2H), 3.26 (s, 3H), 3.16-3.05 (m, 1H), 2.80 (d, J=20.0 Hz, 3H), 2.51 (s, 4H), 2.11 (d, J=13.6 Hz, 1H), 1.96 (s, 2H), 1.77 (s, 3H), 1.46 (s, 1H), 1.15 (d, J=6.8 Hz, 3H). LCMS-ESI+ (m/z): [M+H]$^+$ calcd for $C_{42}H_{50}ClN_5O_9S$: 823.3; found: 823.1.

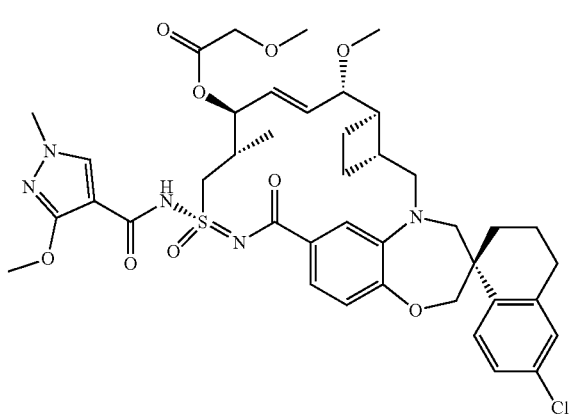 [SMILES: COCC(=O)O[C@H]1/C=C/[C@H](OC)[C@@H]2CC[C@H]2CN2C[C@@]3(CCCc4cc(Cl)ccc43)COc3ccc(cc32)C(=O)N=[S@](=O)(NC(=O)c2cn(C)nc2OC)C[C@H]1C]

Example 74

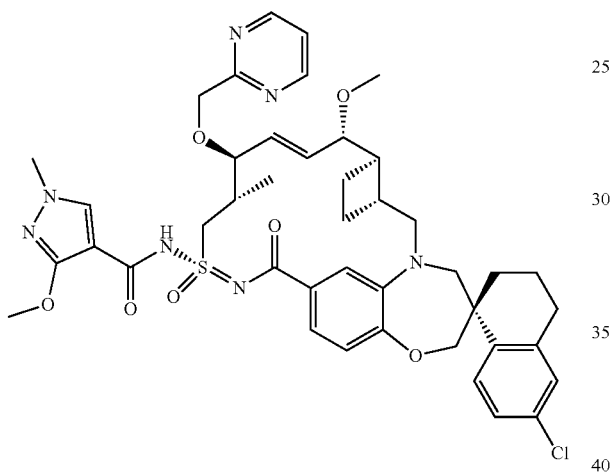

Example 75

Example 74 was synthesized in a similar manner to Intermediate V using 2-(chloromethyl)pyrimidine and Intermediate U. $^1$H NMR (400 MHz, Methanol-$d_4$) δ 8.64 (dd, J=5.0, 1.8 Hz, 2H), 8.09 (s, 1H), 7.79 (d, J=8.6 Hz, 1H), 7.37 (d, J=8.3 Hz, 1H), 7.35-7.25 (m, 1H), 7.20 (d, J=8.5 Hz, 1H), 7.12 (d, J=9.3 Hz, 2H), 6.94 (dd, J=8.2, 1.9 Hz, 1H), 6.10-6.03 (m, 1H), 5.90 (dd, J=15.7, 8.0 Hz, 1H), 4.79-4.61 (m, 2H), 4.39 (s, 1H), 4.10 (dd, J=13.9, 5.0 Hz, 7H), 3.94-3.81 (m, 6H), 3.74 (d, J=14.1 Hz, 1H), 3.40 (d, J=15.1 Hz, 2H), 3.30 (d, J=1.9 Hz, 3H), 3.11 (dd, J=24.6, 12.7 Hz, 2H), 2.83 (s, 2H), 2.51 (s, 1H), 2.40 (s, 2H), 2.11 (d, J=13.1 Hz, 1H), 1.98-1.87 (m, 4H), 1.79 (d, J=7.4 Hz, 3H), 1.46 (s, 1H), 1.16 (d, J=6.8 Hz, 3H). LCMS-ESI+ (m/z): [M+H]$^+$ calcd for $C_{43}H_{51}ClFN_7O_7S$: 844.3; found: 844.4.

Example 75

Example 75 was synthesized in a similar manner to Intermediate V using 1-chloro-4-methoxybut-2-yne and Intermediate U. $^1$H NMR (400 MHz, Methanol-$d_4$) δ 8.08 (d, J=6.5 Hz, 1H), 7.76 (d, J=8.6 Hz, 1H), 7.37 (dd, J=11.6, 8.1 Hz, 1H), 7.27-7.06 (m, 3H), 6.93 (d, J=8.2 Hz, 1H), 6.02 (dd, J=15.3, 7.5 Hz, 1H), 5.89 (dd, J=15.5, 8.3 Hz, 1H), 4.40-4.31 (m, 1H), 4.15-4.03 (m, 5H), 4.03-3.99 (m, 2H), 3.90 (d, J=14.8 Hz, 1H), 3.82 (d, J=4.8 Hz, 3H), 3.73 (d, J=14.3 Hz, 1H), 3.41 (d, J=14.3 Hz, 1H), 3.31 (s, 2H), 3.29 (s, 2H), 3.17-3.08 (m, 1H), 2.89-2.76 (m, 2H), 2.52 (s, 2H), 2.30 (s, 1H), 2.11 (d, J=13.7 Hz, 1H), 1.96 (s, 1H), 1.81 (s, 3H), 1.48 (d, J=12.9 Hz, 1H), 1.34-1.24 (m, 1H), 1.19 (d, J=6.8 Hz, 2H). LCMS-ESI+ (m/z): [M+H]$^+$ calcd for $C_{43}H_{54}ClFN_5O_8S$: 834.3; found: 834.3.

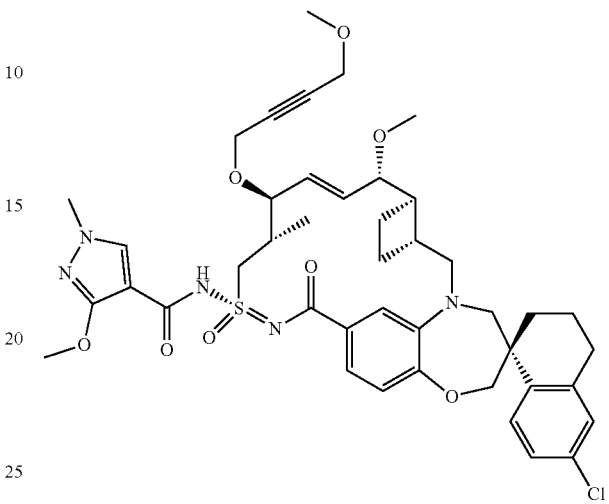

Example 76

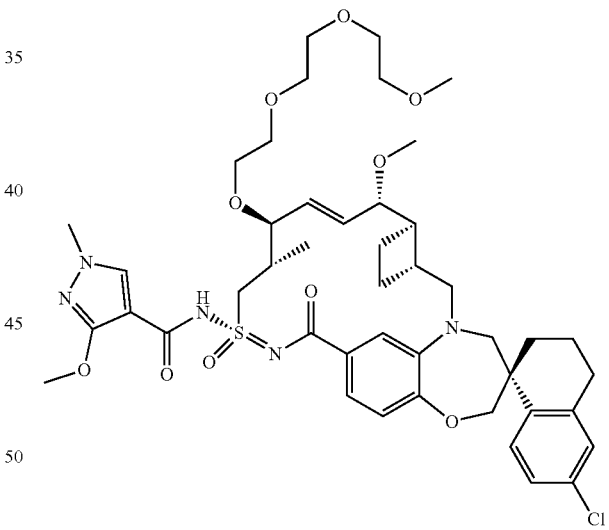

Example 76 was synthesized in a similar manner to Intermediate V using 1-bromo-2-(2-(2-methoxyethoxy)ethoxy)ethane and Intermediate U. $^1$H NMR (400 MHz, Methanol-$d_4$) b 8.09 (s, 1H), 7.75 (d, J=8.4 Hz, 1H), 7.40-7.30 (m, 1H), 7.25-7.15 (m, 2H), 7.12 (d, J=2.3 Hz, 1H), 6.92 (d, J=8.3 Hz, 1H), 6.04 (dd, J=15.4, 7.2 Hz, 1H), 5.85 (dd, J=15.4, 8.6 Hz, 1H), 4.08 (d, J=10.2 Hz, 8H), 3.82 (s, 4H), 3.76-3.46 (m, 14H), 3.34 (s, 3H), 3.30 (s, 3H), 3.19-3.08 (m, 1H), 2.89-2.71 (m, 2H), 2.51 (s, 3H), 2.27 (d, J=7.1 Hz, 1H), 2.11 (d, J=13.5 Hz, 1H), 1.96 (s, 1H), 1.82 (d, J=6.8 Hz, 3H), 1.40 (dd, J=57.4, 14.8 Hz, 3H), 1.20 (d, J=6.8 Hz, 3H). LCMS-ESI+ (m/z): [M+H]$^+$ calcd for $C_{45}H_{61}ClN_5O_{10}S$: 898.4; found: 898.4.

Example 77

To a glass vial charged with Intermediate U (5 mg) under nitrogen atmosphere was added DMF (0.30 mL), then sodium hydride (60% dispersion in mineral oil, 1.3 mg, 5 equiv.), then 2-fluoropyridine (6.5 mg, 10 equiv.). The resulting suspension was sealed under nitrogen atmosphere and stirred in a metal heating block at 80° C. for 90 min. Then the reaction was quenched with 10% aqueous citric acid, and extracted into ethyl acetate. The combined organic phases were washed three times with water, then once with brine. The combined organic phases were dried over magnesium sulfate, filtered, and concentrated in vacuo. The crude product was dissolved in 1:1 acetonitrile:methanol, and purified by preparative reverse-phase HPLC (40 to 100% acetonitrile in water with 0.1% trifluoroacetic acid modifier) to give Example 77. $^1$H NMR (400 MHz, Acetonitrile-$d_3$) δ 7.97-7.87 (m, 2H), 7.74 (d, J=8.5 Hz, 1H), 7.70 (ddd, J=8.7, 7.2, 2.0 Hz, 1H), 7.43 (dd, J=8.3, 2.0 Hz, 1H), 7.29 (d, J=2.0 Hz, 1H), 7.20 (dd, J=8.5, 2.4 Hz, 1H), 7.13 (d, J=2.3 Hz, 1H), 6.96-6.87 (m, 2H), 6.83 (d, J=8.4 Hz, 1H), 6.13 (dd, J=15.6, 5.0 Hz, 1H), 6.03 (s, 1H), 5.80 (ddd, J=15.5, 7.8, 1.3 Hz, 1H), 4.19 (dd, J=15.1, 5.6 Hz, 1H), 4.11-3.96 (m, 2H), 4.03 (s, 3H), 3.80 (dd, J=8.1, 4.5 Hz, 2H), 3.77-3.66 (m, 1H), 3.72 (s, 3H), 3.36 (d, J=14.4 Hz, 1H), 3.10 (s, 4H), 3.05 (dd, J=15.1, 10.7 Hz, 2H), 2.74 (ddd, J=28.8, 14.6, 6.8 Hz, 3H), 2.51 (t, J=9.6 Hz, 1H), 2.48-2.35 (m, 1H), 2.05 (d, J=13.8 Hz, 1H), 1.89 (d, J=6.9 Hz, 2H), 1.71 (q, J=8.8 Hz, 2H), 1.58 (q, J=8.2, 6.8 Hz, 1H), 1.47-1.32 (m, 2H), 1.11 (d, J=6.9 Hz, 3H). LCMS-ESI+ (m/z): [M+H]$^+$ calcd for $C_{43}H_{49}ClN_6O_7S$: 829.3; found: 828.8.

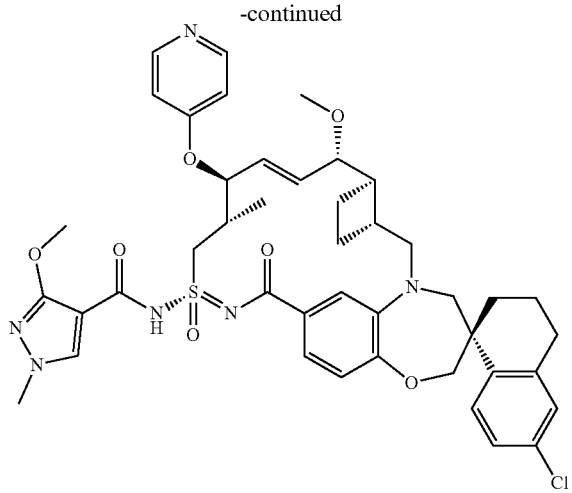

Example 78 was prepared in a manner similar to Example 77, using 4-fluoropyridine. $^1$H NMR (400 MHz, Acetonitrile-$d_3$) δ 8.46 (d, J=7.4 Hz, 2H), 7.92 (s, 1H), 7.75 (d, J=8.5 Hz, 1H), 7.44 (dd, J=8.2, 1.9 Hz, 1H), 7.33 (d, J=2.0 Hz, 1H), 7.28 (d, J=7.4 Hz, 2H), 7.22 (dd, J=8.5, 2.4 Hz, 1H), 7.15 (d, J=2.3 Hz, 1H), 6.92 (d, J=8.2 Hz, 1H), 6.10 (dd, J=15.9, 5.7 Hz, 1H), 5.91 (dd, J=15.7, 7.7 Hz, 1H), 5.58-5.48 (m, 1H), 4.23 (dd, J=15.2, 6.1 Hz, 1H), 4.10 (d, J=12.1 Hz, 1H), 4.06-3.93 (m, 2H), 4.02 (s, 3H), 3.85-3.77 (m, 2H), 3.74 (s, 3H), 3.39 (d, J=14.4 Hz, 2H), 3.17-3.01 (m, 1H), 3.09 (s, 3H), 2.86-2.63 (m, 4H), 2.58-2.38 (m, 3H), 2.05 (d, J=13.8 Hz, 1H), 1.92-1.86 (m, 1H), 1.82-1.69 (m, 2H), 1.69-1.57 (m, 1H), 1.53-1.35 (m, 2H), 1.19 (d, J=6.9 Hz, 3H). LCMS-ESI+ (m/z): [M+H]$^+$ calcd for $C_{43}H_{49}ClN_6O_7S$: 829.3; found: 829.0.

Example 78

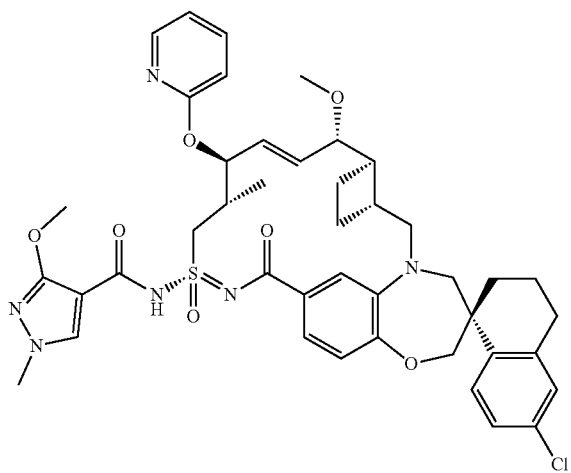

Example 79

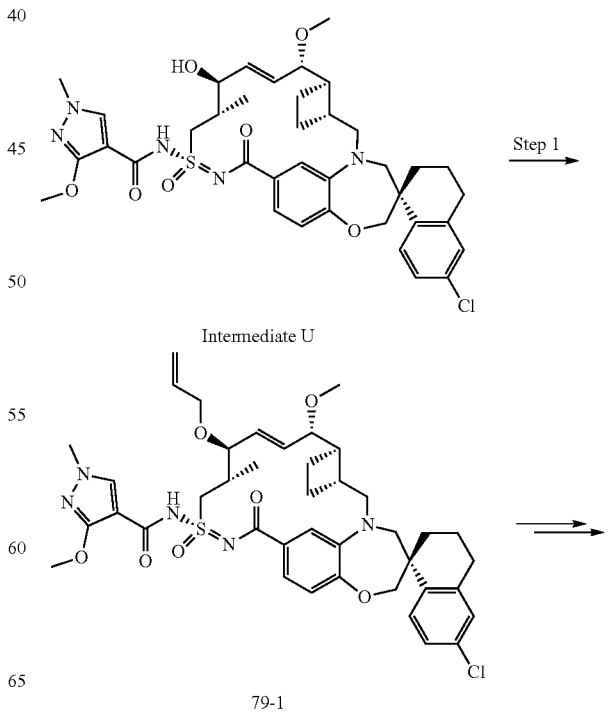

Intermediate U 79-1

239

-continued

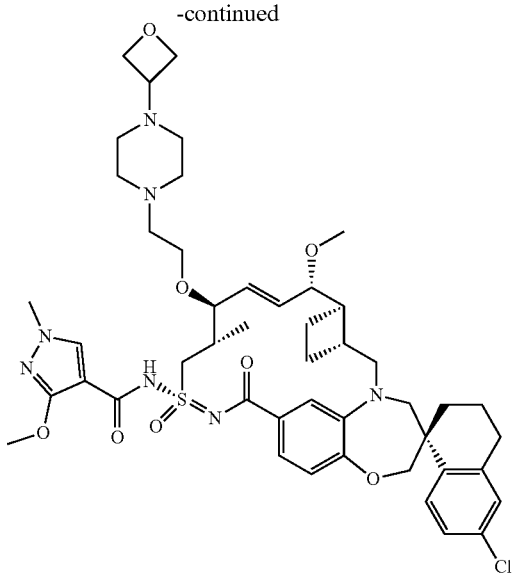

Example 79

Step 1: 79-1 was synthesized in a similar manner to Example 54 using Intermediate U.

Preparation of Example 79: Example 79 was synthesized in a similar manner to Example 58 using 1-(oxetan-3-yl)piperazine in place of 3-dimethylaminoazetidine and 79-1 in place of Example 54. $^1$H NMR (400 MHz, Chloroform-d) δ 7.91 (s, 1H), 7.75 (d, J=8.6 Hz, 1H), 7.48 (dd, J=8.2, 1.9 Hz, 1H), 7.34 (d, J=1.9 Hz, 1H), 7.20 (dd, J=8.5, 2.4 Hz, 1H), 7.11 (d, J=2.3 Hz, 1H), 6.96 (d, J=8.2 Hz, 1H), 6.40 (dd, J=15.2, 9.5 Hz, 1H), 5.76 (dd, J=15.2, 9.1 Hz, 1H), 4.83 (dt, J=28.0, 6.9 Hz, 4H), 4.35 (dd, J=14.4, 9.3 Hz, 2H), 4.09 (d, J=15.5 Hz, 5H), 3.96-3.53 (m, 11H), 3.35 (d, J=52.1 Hz, 8H), 3.06 (dd, J=15.2, 9.4 Hz, 3H), 2.80 (d, J=15.5 Hz, 3H), 2.49 (s, 3H), 2.12-1.67 (m, 7H), 1.29-1.12 (m, 4H). LCMS-ESI+ (m/z): calcd for H+C$_{47}$H$_{62}$ClN$_7$O$_8$S: 920.4; found: 920.2.

Example 80

Example 80 was synthesized in a similar manner to Example 79 using N,N-dimethylazetidin-3-amine. $^1$H NMR (400 MHz, Chloroform-d) δ 7.91 (s, 1H), 7.75 (d, J=8.5 Hz, 1H), 7.47 (d, J=8.0 Hz, 1H), 7.33 (s, 1H), 7.20 (dd, J=8.5, 2.3 Hz, 1H), 7.11 (d, J=2.3 Hz, 1H), 6.95 (d, J=8.2 Hz, 1H), 6.30 (dd, J=15.1, 9.1 Hz, 1H), 5.73 (dd, J=15.2, 9.0 Hz, 1H), 5.32 (s, 1H), 4.64 (t, J=54.9 Hz, 6H), 4.36-4.00 (m, 7H), 3.98-3.61 (m, 1 OH), 3.58-3.36 (m, 4H), 3.30 (s, 3H), 3.05 (dd, J=15.0, 10.0 Hz, 2H), 2.82 (s, 6H), 2.56 (d, J=51.1 Hz, 4H), 2.16-1.64 (m, 8H), 1.55-1.09 (m, 5H). LCMS-ESI+ (m/z): calcd for H+C$_{45}$H$_{60}$ClN$_7$O$_7$S: 878.4; found: 878.4.

240

Example 81

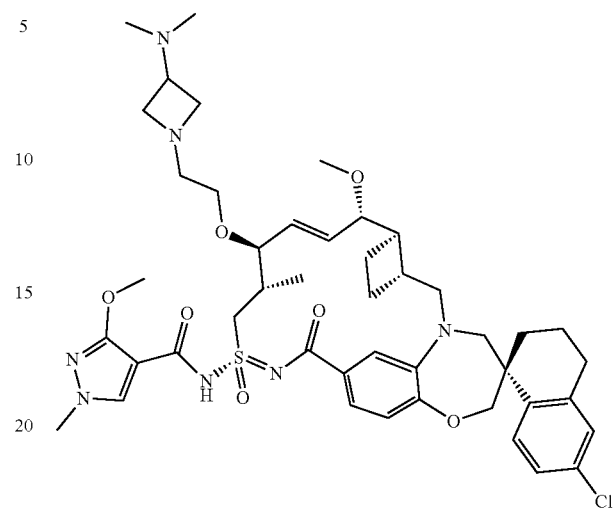

Example 81 was synthesized in a similar manner to Example 79 using 3-methoxyazetidine. $^1$H NMR (400 MHz, Chloroform-d) δ 7.83 (s, 1H), 7.76 (d, J=8.5 Hz, 1H), 7.47 (d, J=8.2 Hz, 1H), 7.26 (s, 1H), 7.21 (dd, J=8.5, 2.3 Hz, 1H), 7.11 (d, J=2.3 Hz, 1H), 6.95 (d, J=8.2 Hz, 1H), 6.09 (dd, J=15.4, 8.3 Hz, 1H), 5.79 (dd, J=15.4, 8.3 Hz, 1H), 5.32 (s, 1H), 4.72 (s, 2H), 4.39 (d, J=5.5 Hz, 2H), 4.09 (d, J=19.6 Hz, 6H), 3.92-3.70 (m, 8H), 3.61 (dd, J=11.1, 5.3 Hz, 1H), 3.52 (s, 1H), 3.45-3.22 (m, 7H), 3.11-2.97 (m, 1H), 2.80 (d, J=14.6 Hz, 3H), 2.49 (s, 9H), 2.21-1.63 (m, 4H), 1.51-1.08 (m, 3H). LCMS-ESI+ (m/z): calcd for H+C$_{44}$H$_{57}$ClN$_6$O$_8$S: 865.3; found: 865.5.

Example 82

Example 82 was synthesized in a similar manner to Example 79 using 1-methylpiperazine. $^1$H NMR (400 MHz, Chloroform-d) δ 8.01 (s, 1H), 7.75 (d, J=8.5 Hz, 1H), 7.48 (dd, J=8.2, 1.9 Hz, 1H), 7.37 (s, 1H), 7.20 (dd, J=8.5, 2.3 Hz, 1H), 7.11 (d, J=2.3 Hz, 1H), 6.96 (d, J=8.2 Hz, 1H), 6.50 (dd, J=15.3, 9.8 Hz, 2H), 5.74 (dd, J=15.2, 9.3 Hz, 1H), 4.44 (dd, J=14.3, 10.5 Hz, 2H), 4.09 (d, J=12.9 Hz, 4H), 3.79 (d, J=17.7 Hz, 10H), 3.55 (d, J=24.5 Hz, 3H), 3.47-3.20 (m, 6H), 2.92 (s, 4H), 2.87-2.68 (m, 3H), 2.49 (s, 3H), 2.12-1.58

(m, 7H), 1.50-1.03 (m, 5H). LCMS-ESI+ (m/z): calcd for H+C$_{45}$H$_{60}$ClN$_7$O$_7$S: 878.4 found: 878.5.

Example 83

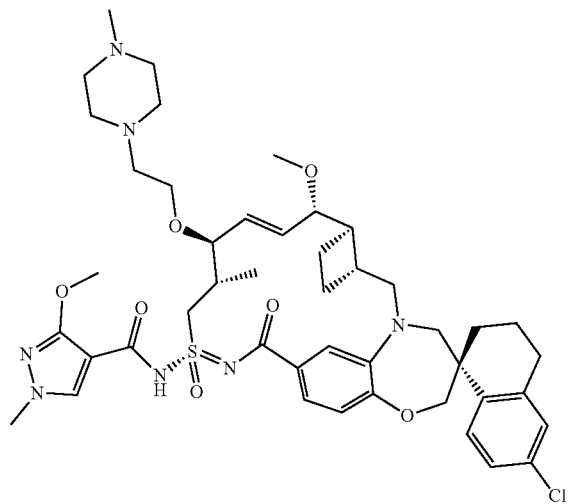

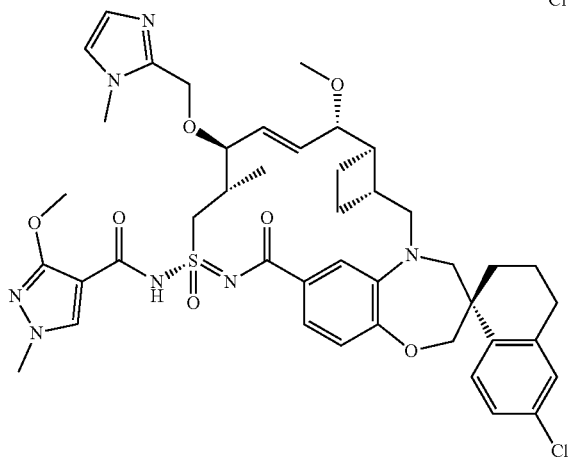 [SMILES: COc1nn(C)cc1C(=O)N[S@@]1(=O)=NC(=O)c2ccc3c(c2)N(C[C@@H]2CC[C@H]2[C@@H](OC)/C=C/[C@H](OCc2ccncc2)[C@H](C)C1)C[C@@]1(CCCc2cc(Cl)ccc21)CO3]

Intermediate U (28 mg, 0.034 mmol) in DMF (2 mL) was cooled to 0° C. and then sodium hydride (60%, 7 mg, 0.17 mmol) was added followed by 2-(chloromethyl)-1-methyl-1H-imidazole (17 mg, 0.1 mmol). The reaction mixture was warmed to room temperature after 1 h, and stirred for 5 h. 1 mL DMSO was added, and the mixture was filtered and purified by reverse phase HPLC to afford Example 83. $^1$H NMR (400 MHz, Methanol-d$_4$) δ 8.04 (d, J=7.7 Hz, 1H), 7.74 (dd, J=8.5, 2.3 Hz, 1H), 7.55 (d, J=2.0 Hz, 1H), 7.53-7.47 (m, 1H), 7.35 (dd, J=8.2, 1.9 Hz, 1H), 7.20-7.14 (m, 2H), 7.11 (d, J=2.4 Hz, 1H), 6.89 (dd, J=14.3, 8.3 Hz, 1H), 6.13 (dd, J=15.4, 8.1 Hz, 1H), 6.05-5.88 (m, 1H), 4.83 (s, 1H), 4.75-4.61 (m, 1H), 4.23-4.14 (m, 2H), 4.14-3.93 (m, 3H), 4.04 (s, 3H), 3.86 (d, J=12.3 Hz, 1H), 3.86 (s, 3H), 3.79 (s, 3H), 3.73-3.63 (m, 2H), 3.39 (d, J=14.3 Hz, 1H), 3.32 (s, 1H), 3.30 (s, 3H), 3.29 (s, OH), 3.19-3.03 (m, 1H), 2.88-2.68 (m, 2H), 2.56 (dt, J=12.1, 6.5 Hz, 1H), 2.51-2.22 (m, 2H), 2.14-2.02 (m, 1H), 2.00-1.89 (m, 3H), 1.86-1.74 (m, 2H), 1.58-1.37 (m, 1H), 1.21 (d, J=6.9 Hz, 3H). LCMS-ESI+ (m/z): [M+H]+ calcd for C$_{43}$H$_{52}$ClN$_7$O$_7$S: 846.3; found: 846.3.

Example 84

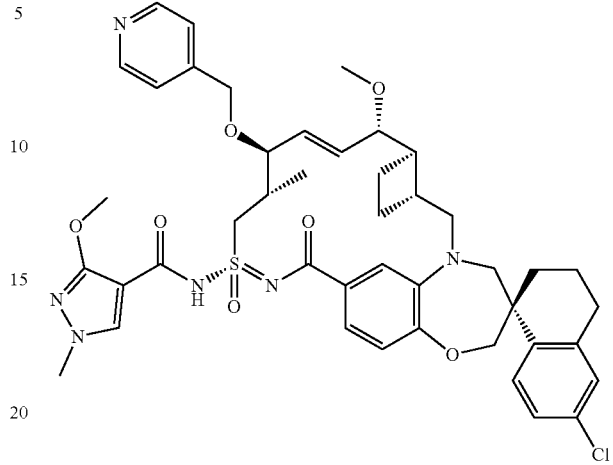

Example 84 was prepared in a manner similar to Example 83, using 4-(chloromethyl)pyridine. $^1$H NMR (400 MHz, Methanol-d$_4$) δ 8.64 (d, J=5.7 Hz, 2H), 8.06 (s, 1H), 7.85 (d, J=5.7 Hz, 2H), 7.75 (d, J=8.5 Hz, 1H), 7.35 (dd, J=8.2, 1.9 Hz, 1H), 7.17 (dd, J=9.1, 2.2 Hz, 2H), 7.11 (d, J=2.3 Hz, 1H), 6.91 (d, J=8.2 Hz, 1H), 6.14 (dd, J=15.5, 7.7 Hz, 1H), 5.93 (dd, J=15.4, 8.4 Hz, 1H), 4.81 (s, 1H), 4.69 (d, J=15.5 Hz, 1H), 4.30-4.15 (m, 3H), 4.05 (s, 3H), 4.17-3.98 (m, 3H), 3.85 (dd, J=8.4, 3.7 Hz, 2H), 3.81 (s, 3H), 3.71 (d, J=14.4 Hz, 1H), 3.39 (d, J=14.4 Hz, 1H), 3.25 (s, 3H), 3.17-3.00 (m, 1H), 2.88-2.69 (m, 2H), 2.60-2.29 (m, 1H), 2.16-2.02 (m, 1H), 2.01-1.86 (m, 3H), 1.80 (d, J=7.0 Hz, 3H), 1.45 (t, J=10.4 Hz, 1H), 1.27 (t, J=7.4 Hz, 3H). LCMS-ESI+ (m/z) [M+H]+ calcd for C$_{44}$H$_{51}$ClN$_6$O$_7$S: 843.3; found: 843.2.

Example 85

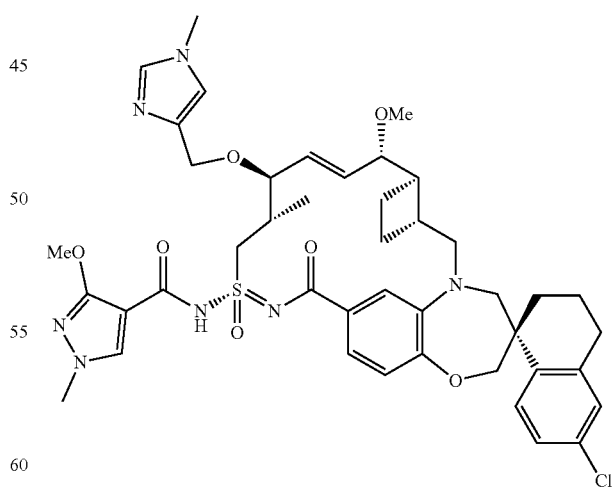

Example 85 was synthesized in a similar manner to Example 83 using 4-(chloromethyl)-1-methyl-imidazole hydrochloride. $^1$H NMR (400 MHz, Methanol-d$_4$) δ 8.87 (d, J=1.4 Hz, 1H), 8.08 (s, 1H), 7.75 (d, J=8.4 Hz, 1H), 7.49 (d, J=1.5 Hz, 1H), 7.37 (m, 1H), 7.24-7.08 (m, 3H), 6.93 (d, J=8.2 Hz, 1H), 6.10 (m, 1H), 5.93 (m, 1H), 4.71-4.60 (m, 1H), 4.47 (d, J=13.0 Hz, 1H), 4.22-3.98 (m, 7H), 3.93-3.84 (m, 4H), 3.82 (s, 3H), 3.72 (d, J=14.3 Hz, 1H), 3.41 (d, J=14.3 Hz, 1H), 3.31 (m, 6H), 3.13 (m, 1H), 2.90-2.72 (m, 2H), 2.56 (m, 1H), 2.45 (d, J=9.5 Hz, 1H), 2.29 (m, 1H), 2.11 (d, J=13.6 Hz, 1H), 2.00-1.91 (m, 2H), 1.84 (m, 3H), 1.53-1.40 (m, 1H), 1.18 (d, J=6.9 Hz, 3H). LCMS-ESI+ (m/z) [M+H]+ calc'd for $C_{43}H_{52}ClN_7O_7S$: 846.3; found: 846.3.

Example 86

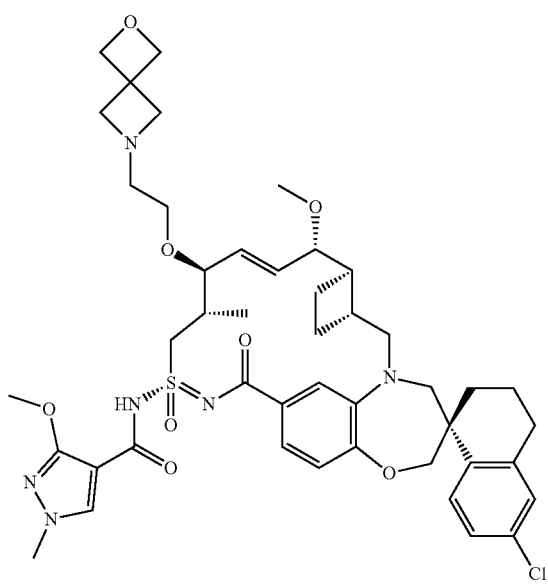 [SMILES: COc1nn(C)cc1C(=O)N[S@@]1(=O)=NC(=O)c2ccc3c(c2)N(C[C@@H]2CC[C@H]2[C@@H](OC)/C=C/[C@H](OCCN2CC4(COC4)C2)[C@H](C)C1)C[C@@]1(CCCc2cc(Cl)ccc21)CO3]

Example 86 was synthesized in a similar manner to Example 79, using DCE in place of DCM, 2-oxa-6-azaspiro[3.3]heptane in place of 1-(oxetan-3-yl)piperazine, and omitting DIPEA. 1H NMR (400 MHz, Methanol-d4) δ 8.09 (s, 1H), 7.73 (d, J=8.5 Hz, 1H), 7.37 (dd, J=8.2, 1.9 Hz, 1H), 7.23 (d, J=2.0 Hz, 1H), 7.19-7.12 (m, 1H), 7.10 (d, J=2.2 Hz, 1H), 6.91 (d, J=8.3 Hz, 1H), 6.16 (dd, J=15.4, 8.6 Hz, 1H), 5.88 (dd, J=15.4, 8.7 Hz, 1H), 4.76 (s, 2H), 4.54 (dd, J=30.0, 10.9 Hz, 2H), 4.37 (t, J=10.4 Hz, 2H), 4.22 (dd, J=15.1, 5.5 Hz, 1H), 4.15-3.96 (m, 9H), 3.81 (s, 6H), 3.77-3.65 (m, 2H), 3.57-3.35 (m, 3H), 3.28 (s, 3H), 3.11 (dd, J=15.3, 9.9 Hz, 1H), 2.91-2.67 (m, 3H), 2.51 (d, J=10.3 Hz, 2H), 2.30 (d, J=6.7 Hz, 1H), 2.09 (d, J=12.9 Hz, 1H), 1.94 (s, 1H), 1.86-1.71 (m, 3H), 1.46 (d, J=13.0 Hz, 1H), 1.22 (d, J=6.9 Hz, 3H). LCMS-ESI+ (m/z): [M+H]+ calcd for $C_{45}H_{57}ClN_6O_8S$: 877.3; found: 877.5.

Example 87

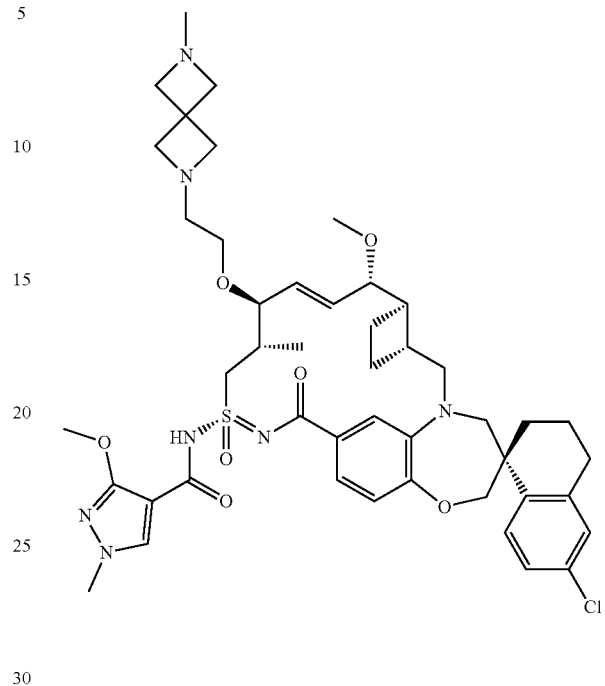

Example 87 was synthesized in a similar manner to Example 86 using 2-methyl-2,6-diazaspiro[3.3]heptane. 1H NMR (400 MHz, Methanol-d4) δ 8.08 (s, 1H), 7.74 (d, J=8.5 Hz, 1H), 7.36 (d, J=8.2 Hz, 1H), 7.24 (s, 1H), 7.17 (d, J=8.3 Hz, 1H), 7.11 (s, 1H), 6.91 (d, J=8.2 Hz, 1H), 6.20 (dd, J=15.3, 8.9 Hz, 1H), 5.87 (dd, J=15.3, 8.9 Hz, 1H), 4.57 (d, J=29.5 Hz, 5H), 4.25 (dd, J=14.6, 5.8 Hz, 3H), 4.17-3.92 (m, 8H), 3.94-3.61 (m, 8H), 3.61-3.35 (m, 3H), 3.28 (s, 3H), 3.17-3.07 (m, 1H), 2.94 (s, 2H), 2.78 (d, J=18.1 Hz, 2H), 2.51 (s, 1H), 2.28 (d, J=6.9 Hz, 1H), 2.10 (d, J=13.7 Hz, 1H), 2.00-1.85 (m, 3H), 1.81 (d, J=6.8 Hz, 4H), 1.45 (s, 1H), 1.23 (d, J=7.0 Hz, 3H). LCMS-ESI+ (m/z): [M+H]+ calcd for $C_{46}H_{60}ClN_7O_7S$: 890.4; found: 890.4.

Example 88

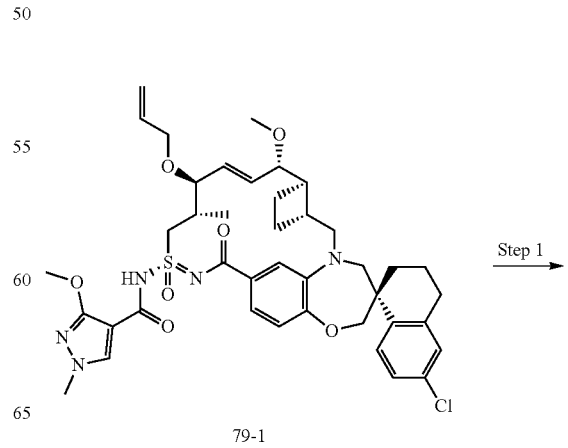

79-1

Step 1

-continued

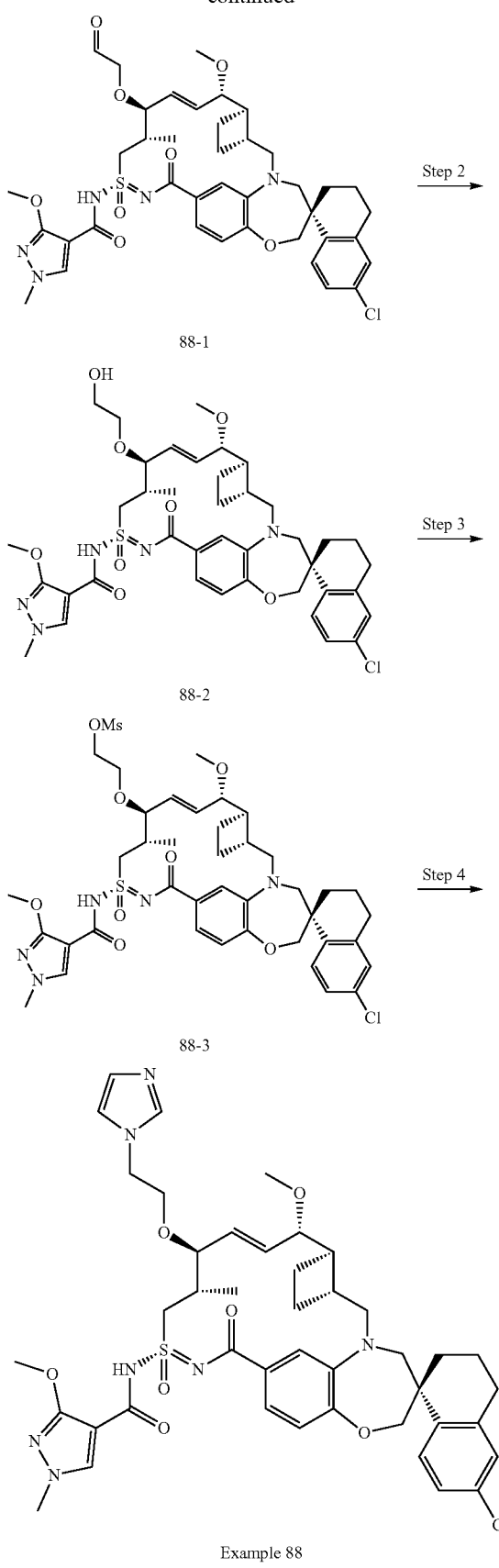

88-1

88-2

88-3

Example 88

Step 1: 88-1 was prepared in a similar manner to 58-1 from 79-1.

Step 2: 88-1 (23.7 mg, 0.0298 mmol) was treated with sodium borohydride (5.6 mg, 0.149 mmol, 5 equiv.) in MeOH (3 mL) and THF (0.5 mL) at rt for 30 min. The organic solvent was removed under a reduced pressure. The crude mixture obtained was directly injected into preparative-HPLC to give 88-2. LCMS-ESI+ (m/z): [M+H]+ calcd for $C_{40}H_{50}ClN_5O_8S$: 796.3; found: 796.1.

Step 3: 88-2 (15.2 mg, 0.0191 mmol) was treated with methanesulfonyl chloride (33.5 mg, 0.287 mmol, 15 equiv.) in the presence of DIPEA (24.7 mg, 0.382 mmol, 20 equiv.) in 1,2-dichloroethane (3 mL) at rt for total 2.5 h. The organic solvent was removed under a reduced pressure. The crude mixture obtained was purified by preparative reverse-phase HPLC to give 88-3. LCMS-ESI+ (m/z): [M+H]+ calcd for $C_{41}H_{52}ClN_5O_{10}S_2$: 874.3; found: 874.1.

Step 4: Imidazole (13.0 mg, 0.191 mmol, 10 equiv.) was treated with KHMDS (0.2 mL, 0.191 mmol, 10 equiv.) in THF (3 mL) under a nitrogen atmosphere at −78° C. for 10 min. The solution was transferred to the flask with a solution of 88-3 in THF (3 mL) at rt. The reaction mixture was stirred at rt for 40 min and then 40° C. for 2 h. The reaction mixture was quenched with brine (30 mL) and the whole was extracted with EtOAc (30 mL×3). Obtained organic layer was washed with brine (30 mL) and dried over $Na_2SO_4$. The solvent was removed under a reduced pressure. Crude material obtained was purified by preparative reverse-phase HPLC to give Example 88. 1H NMR (400 MHz, Methanol-$d_4$) δ 9.01 (s, 1H), 8.07 (s, 1H), 7.72 (d, J=8.5 Hz, 1H), 7.66 (t, J=0.5 Hz, 1H), 7.57 (t, J=0.5 Hz, 1H), 7.34 (dd, J=8.1, 1.8 Hz, 1H), 7.23-7.12 (m, 2H), 7.10 (d, J=2.3 Hz, 1H), 6.89 (d, J=8.2 Hz, 1H), 6.00 (dd, J=15.4, 8.2 Hz, 1H), 5.77 (dd, J=15.4, 8.6 Hz, 2H), 4.56-4.37 (m, 2H), 4.19-3.92 (m, 8H), 3.92-3.62 (m, 8H), 3.39 (d, J=14.3 Hz, 1H), 3.21 (s, 3H), 3.10 (dd, J=15.2, 10.1 Hz, 1H), 2.89-2.64 (m, 2H), 2.54-2.39 (m, 2H), 2.22 (d, J=7.2 Hz, 1H), 2.08 (d, J=14.4 Hz, 1H), 1.83-1.98 (s, 3H), 1.79 (d, J=7.3 Hz, 3H), 1.44 (t, J=12.4 Hz, 1H), 1.09 (d, J=6.9 Hz, 3H). LCMS-ESI+ (m/z): [M+H]+ calcd for $C_{43}H_{52}ClN_7O_7S$: 846.3; found: 846.5.

Example 89

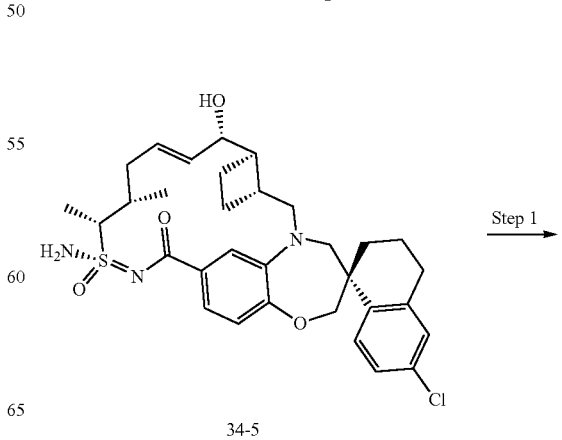

34-5

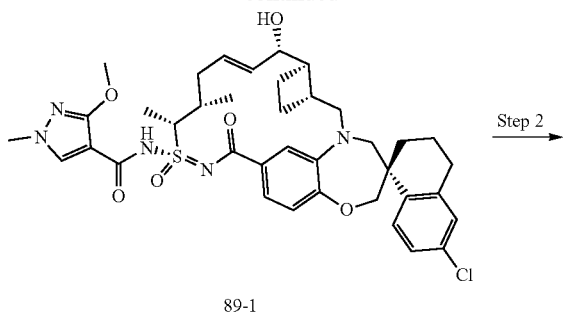

89-1

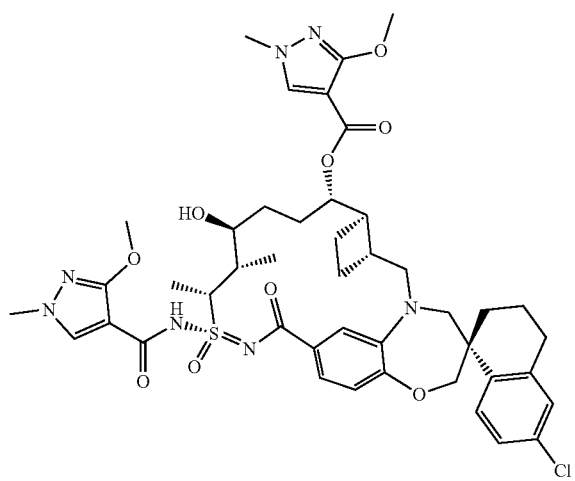

Example 90

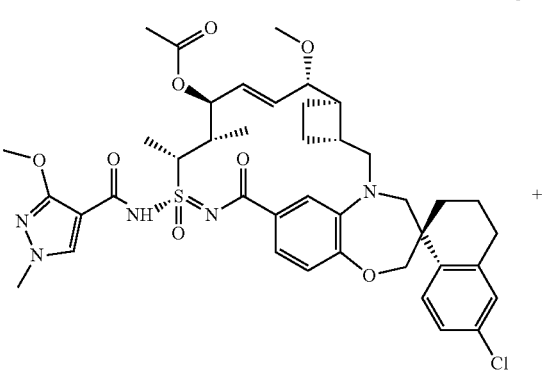

Example 89

Step 1: 89-1 was synthesized in the same manner as Intermediate T using 34-5 and 3-methoxy-1-methyl-pyrazole-4-carboxylic acid. LCMS-ESI+ (m/z): [M+H]+ calcd for $C_{44}H_{52}ClN_7O_8S$: 873.33; found: 872.85.

Step 2: Example 89 was synthesized in a similar manner to Intermediate U using 89-1. $^1$H NMR (400 MHz, Methanol-$d_4$) δ 8.05 (s, 1H), 7.78-7.67 (m, 1H), 7.45 (d, J=8.1 Hz, 1H), 7.32 (dd, J=23.0, 8.5 Hz, 1H), 7.18 (dd, J=8.5, 2.3 Hz, 1H), 7.09 (d, J=2.2 Hz, 1H), 6.93-6.84 (m, 1H), 6.59 (s, 1H), 5.98-5.82 (m, 1H), 5.69 (dd, J=15.7, 7.9 Hz, 1H), 5.50 (dd, J=8.7, 3.1 Hz, 1H), 4.12-3.95 (m, 5H), 3.88-3.65 (m, 13H), 3.27-3.18 (m, 2H), 2.93-2.66 (m, 4H), 2.26-2.16 (m, 1H), 2.15-1.95 (m, 3H), 1.91-1.77 (m, 3H), 1.74-1.66 (m, 1H), 1.58 (d, J=7.3 Hz, 3H), 1.46-1.36 (m, 1H), 1.13 (d, J=6.8 Hz, 3H). LCMS-ESI+ (m/z): [M+H]+ calcd for $C_{44}H_{52}ClN_7O_9S$: 889.3; found: 889.7.

Example 90 was synthesized in a similar manner to Example 28 (step 1) using Example 89 and purifying using reverse phase preparatory HPLC. $^1$H NMR (400 MHz, Methanol-$d_4$) δ 7.97 (s, 1H), 7.64 (s, 1H), 7.41-7.26 (m, 2H), 7.17 (dd, J=8.5, 2.3 Hz, 1H), 7.09 (d, J=2.3 Hz, 1H), 6.94 (d, J=8.2 Hz, 2H), 5.20-5.11 (m, 1H), 4.02 (d, J=9.0 Hz, 6H), 3.84-3.79 (m, 8H), 3.75 (s, 4H), 3.25-3.18 (m, 2H), 2.86-2.68 (m, 4H), 2.10-1.97 (m, 4H), 1.91-1.64 (m, 8H), 1.55 (d, J=7.1 Hz, 3H), 1.46-1.41 (m, 1H), 1.08 (d, J=6.7 Hz, 3H). LCMS-ESI+ (m/z): [M+H]+ calcd for $C_{44}H_{54}ClN_7O_9$: 891.3; found: 891.8.

Example 91 and Example 92

Example 91

Example 92

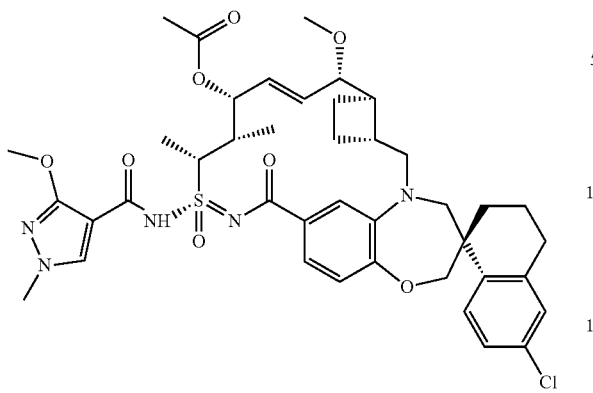

Acetic anhydride (4.9 μL, 52.2 μmol) was added via syringe to a stirred mixture of 68-2 (4.0 mg, 5.2 μmol) and DMAP (7.7 mg, 62.6 μmol) in dichloromethane (0.6 mL) at room temperature, and the resulting mixture was warmed to 45° C. After 30 min, the resulting mixture was cooled to room temperature and was concentrated under reduced pressure. The residue was purified by reverse phase preparative HPLC (0.1% trifluoroacetic acid in acetonitrile/water) to give Example 91 and Example 92.

Example 91: $^1$H NMR (400 MHz, Acetone-d$_6$) δ 8.00 (s, 1H), 7.78 (d, J=8.5 Hz, 1H), 7.36 (d, J=8.3 Hz, 1H), 7.30-7.20 (m, 2H), 7.14 (d, J=2.3 Hz, 1H), 6.91 (d, J=8.2 Hz, 1H), 6.25 (s, 1H), 5.98-5.68 (m, 2H), 4.36-3.59 (m, 12H), 3.44 (d, J=14.5 Hz, 1H), 3.25-3.12 (m, 1H), 3.18 (s, 3H), 2.86-1.68 (m, 12H), 1.64 (d, J=6.9 Hz, 3H), 1.55-1.43 (m, 1H), 1.19 (d, J=7.0 Hz, 3H). LCMS-ESI+ (m/z): [M+H]$^+$ calcd for C$_{41}$H$_{50}$ClN$_5$OsS: 808.3; found: 808.2.

Example 92: $^1$H NMR (400 MHz, Acetone-d$_6$) δ 8.05 (s, 1H), 7.80 (d, J=8.5 Hz, 1H), 7.47-7.32 (m, 2H), 7.25 (dd, J=8.5, 2.4 Hz, 1H), 7.14 (d, J=2.3 Hz, 1H), 6.94 (d, J=8.4 Hz, 1H), 6.11 (dd, J=15.8, 4.8 Hz, 1H), 5.77 (dd, J=15.8, 6.5 Hz, 1H), 5.69-5.47 (m, 1H), 4.42-3.63 (m, 6H), 4.02 (s, 3H), 3.83 (s, 3H), 3.44 (d, J=14.3 Hz, 1H), 3.22 (s, 3H), 3.18-3.09 (m, 1H), 2.94-1.38 (m, 16H), 1.17 (d, J=7.0 Hz, 3H). LCMS-ESI+ (m/z): [M+H]$^+$ calcd for C$_{41}$H$_{50}$ClN$_5$O$_8$S: 808.3; found: 808.3.

Example 93

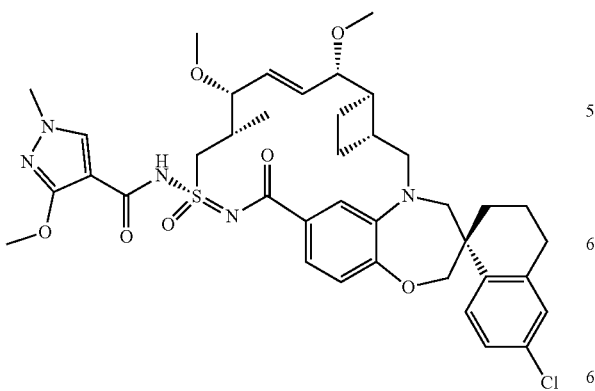

Example 93 was prepared in a similar manner to Intermediate V using iodomethane and U-1. $^1$H NMR (400 MHz, Methanol-d$_4$) δ 8.15 (s, 1H), 7.72 (d, J=9.1 Hz, 1H), 7.37 (dd, J=8.3, 1.8 Hz, 1H), 7.19 (s, 1H), 7.16-7.07 (m, 2H), 6.89 (d, J=8.2 Hz, 1H), 6.15 (dd, J=15.5, 5.3 Hz, 1H), 5.83 (ddd, J=15.5, 8.0, 1.5 Hz, 1H), 4.54 (s, 1H), 4.05 (m, 7H), 3.90-3.82 (m, 3H), 3.81 (s, 3H), 3.69 (d, J=14.3 Hz, 1H), 3.41 (d, J=14.4 Hz, 1H), 3.29 (s, 3H), 3.18-3.04 (m, 1H), 2.92-2.69 (m, 2H), 2.51 (br, 2H), 2.44-2.25 (m, 1H), 2.16-2.03 (m, 1H), 2.02-1.92 (m, 3H), 1.88-1.74 (m, 3H), 1.43 (t, J=11.9 Hz, 1H), 1.15 (d, J=6.9 Hz, 3H). LCMS-ESI+ (m/z): [M+H]$^+$ calcd for C$_{39}$H$_{48}$ClN$_5$O$_7$S: 766.3; found: 766.0.

Example 94

Example 47 (20 mg, 0.028 mmol), was taken in a 6 mL vial, added THF (1 mL) under Ar atmosphere. The solution was cooled to 0° C., and added methyl magnesium bromide, (93 μL, 0.27 mmol, 3 M solution in diethyl ether) dropwise. The solution was allowed warm to room temperature and stirred overnight. The reaction was quenched with two drops of water. The solvent was concentrated, dissolved in MeOH (2 mL), filtered and purified by reverse phase preparative HPLC, eluted with 60-100% ACN/H$_2$O with 0.1% TFA to afford Example 94 (stereochemistry tentatively assigned). $^1$H NMR (400 MHz, Acetonitrile-d$_3$) δ 7.93 (s, 1H), 7.76 (d, J=8.5 Hz, 1H), 7.40 (d, J=8.1 Hz, 1H), 7.34 (s, 1H), 7.27-7.19 (m, 1H), 7.16 (s, 1H), 6.92 (d, J=8.3 Hz, 1H), 5.99-5.83 (m, 2H), 4.15-3.94 (m, 8H), 3.76 (s, 7H), 3.39 (d, J=14.3 Hz, 1H), 3.05 (dd, J=15.0, 11.2 Hz, 1H), 2.92-2.68 (m, 3H), 2.36 (s, 1H), 2.16-2.02 (m, 1H), 1.85-1.58 (m, 4H), 1.45 (dd, J=14.4, 7.5 Hz, 1H), 1.27 (d, J=18.9 Hz, 4H), 1.17 (d, J=5.7 Hz, 3H), 1.12-0.97 (m, 1H). LCMS-ESI+ (m/z): [M+H]$^+$ calcd for C$_{38}$H$_{46}$ClN$_5$O$_6$S: 736.3; found: 736.0.

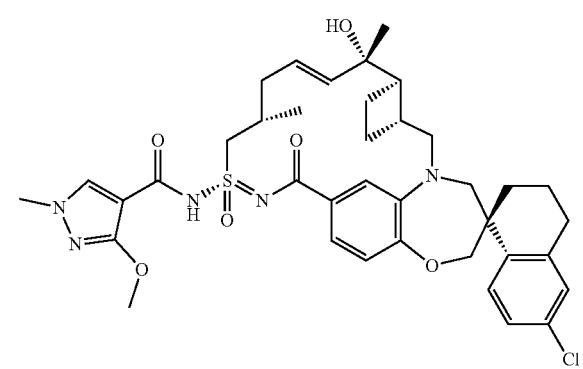

Example 95

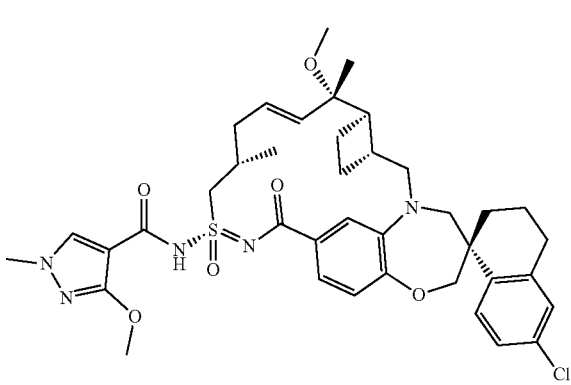 [SMILES: COc1nn(C)cc1C(=O)N[S@@]1(=O)=NC(=O)c2ccc3c(c2)N(C[C@@H]2CC[C@H]2[C@@](C)(OC)/C=C/C[C@H](C)C1)C[C@@]1(CCCc2cc(Cl)ccc21)CO3]

To a stirred solution crude mix of Example 94 (10 mg, 0.013 mmol) in DMF (1 mL) was added sodium hydride (2.2 mg, 0.05 mmol) at once and stirred for 5 min at 0° C. To well stirred solution was added iodomethane (169 uL, 0.27 mmol). The resulting mixture was warmed to room temperature and stirred 4 h. The reaction mixture was poured into ice-cold solution of sat NH$_4$Cl (50 ml) and extracted with EtOAc (2×50 ml). The organic layer was washed with 5% LiCl aq solution (50 ml) once, dried over Na$_2$SO$_4$, and concentrated to dryness. The crude was dissolved in MeOH (2 mL), filtered and purified by reverse phase preparative HPLC, eluted with 60-100% ACN/H$_2$O with 0.1% TFA to afford Example 95 (stereochemistry tentatively assigned). $^1$H NMR (400 MHz, Methanol-d$_4$) δ 8.00 (s, 1H), 7.77 (d, J=8.5 Hz, 1H), 7.47 (s, 2H), 7.19 (d, J=9.2 Hz, 1H), 7.12 (s, 1H), 6.94 (s, 1H), 5.83 (s, 2H), 4.08 (s, 4H), 3.82 (s, 4H), 3.73-3.59 (m, 1H), 3.56-3.42 (m, 5H), 3.15 (p, J=1.7 Hz, 4H), 3.02 (s, 2H), 2.88 (d, J=0.7 Hz, 2H), 2.74 (d, J=67.4 Hz, 3H), 2.25-2.05 (m, 2H), 1.96 (s, 2H), 1.64 (s, 1H), 1.18 (s, 3H), 1.14 (d, J=6.7 Hz, 3H), 0.97-0.82 (m, 2H). LCMS-ESI+ (m/z): [M+H]$^+$ calcd for C$_{39}$H$_{48}$ClN$_5$O$_6$S: 750.3; found: 749.9.

Example 96 and Example 97

Example 96

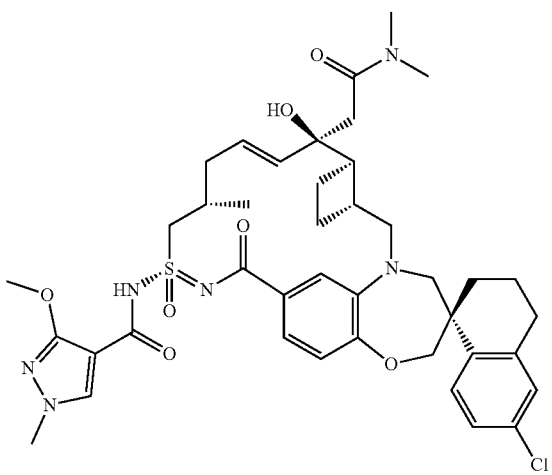

Example 97

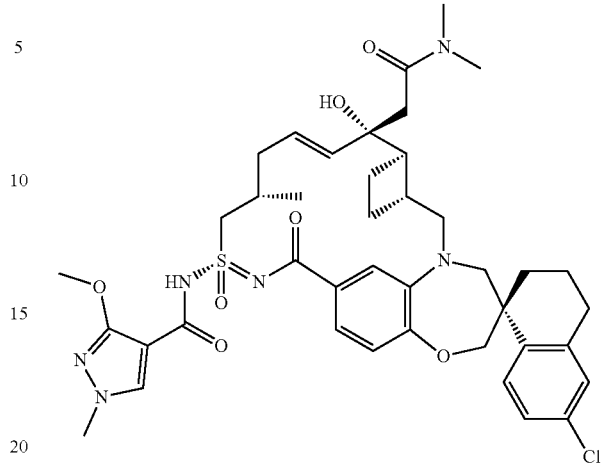

N,N'-Dimethylacetamide (8.8 mg, 0.101 mmol, 5 equiv.) was treated with lithium diisopropylamide (1M in THF, 0.1 mL, 0.1 mmol) in THF (2 mL) at −78° C. for 10 min. To the reaction mixture was added a solution of Example 47 (14.6 mg, 0.0203 mmol) in THF (2 mL) at the same temperature. The reaction mixture was stirred at −78° C. for 1 h. The reaction mixture was quenched with brine (30 mL) and the whole was extracted with EtOAc (30 mL×3). Obtained organic layer was washed with brine (30 mL) and dried over Na$_2$SO$_4$. The solvent was removed under a reduced pressure. The crude mixture was purified by preparative reverse-phase HPLC to give Example 96 as the earlier-eluting of two diastereomers (stereochemistry tentatively assigned) and Example 97 as the later-eluting of two diastereomers (stereochemistry also tentatively assigned).

Example 96: $^1$H NMR (400 MHz, Methanol-d$_4$) δ 8.05 (s, 1H), 7.74 (d, J=8.5 Hz, 1H), 7.38 (s, 1H), 7.32 (br s, 1H), 7.15 (d, J=9.2 Hz, 1H), 7.09 (s, 1H), 6.89 (d, J=8.2 Hz, 1H), 6.13-5.95 (m, 1H), 5.80 (d, J=15.6 Hz, 1H), 4.04 (m, 7H), 3.91 (s, 1H), 3.79 (s, 3H), 3.69 (d, J=14.2 Hz, 1H), 3.36 (d, J=10.7 Hz, 1H), 3.05 (s, 3H), 3.09-3.00 (m, 1H), 2.91 (s, 3H), 2.84-2.55 (m, 3H), 2.32 (dd, J=20.1, 12.4 Hz, 3H), 2.09 (m, 2H), 1.98-1.75 (m, 2H), 1.70 (d, J=9.2 Hz, 1H), 1.61-1.49 (m, 2H), 1.42 (s, 1H), 1.02 (d, J=6.8 Hz, 3H). LCMS-ESI+ (m/z): [M+H]$^+$ calcd for C$_{41}$H$_{51}$ClN$_6$O$_7$S: 807.3; found: 807.1.

Example 97: $^1$H NMR (400 MHz, Methanol-d$_4$) δ 8.07 (s, 1H), 7.75 (d, J=8.6 Hz, 1H), 7.44 (d, J=8.4 Hz, 1H), 7.30 (s, 1H), 7.16 (d, J=9.3 Hz, 1H), 7.10 (s, 1H), 6.92 (d, J=8.3 Hz, 1H), 6.06 (d, J=16.0 Hz, 1H), 5.87 (d, J=15.9 Hz, 1H), 4.07 (s, 3H), 4.16-3.99 (m, 2H), 3.83 (d, J=13.7 Hz, 1H), 3.80 (s, 4H), 3.71 (t, J=13.7 Hz, 2H), 3.40 (d, J=14.4 Hz, 1H), 3.13 (s, 3H), 3.13 (d, J=14.4 Hz, 1H), 2.93 (s, 3H), 2.87 (d, J=15.3 Hz, 1H), 2.84-2.64 (m, 2H), 2.43 (d, J=15.2 Hz, 2H), 2.38-2.19 (m, 3H), 2.10 (d, J=13.9 Hz, 1H), 1.93 (d, J=8.4 Hz, 3H), 1.83-1.63 (m, 3H), 1.45 (s, 1H), 1.16 (d, J=6.7 Hz, 3H). LCMS-ESI+ (m/z): [M+H]$^+$ calcd for C$_{41}$H$_{51}$ClN$_6$O$_7$S: 807.3; found: 807.1.

Example 98 and Example 99

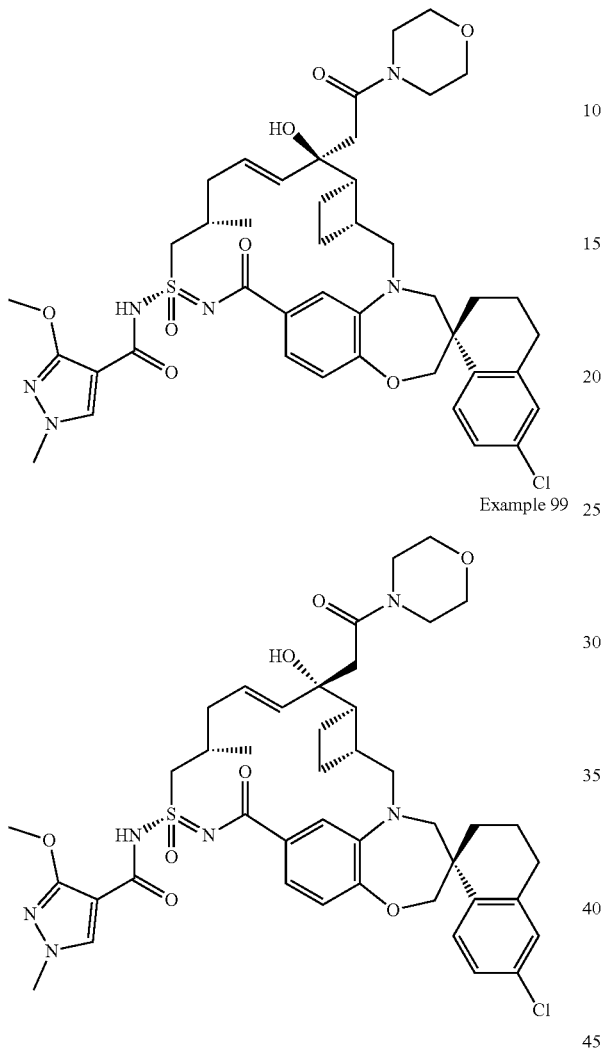

Example 98

Example 99

Example 98 and Example 99 were synthesized in a similar manner to Example 96 and Example 97 using 1-morpholinoethanone and Example 47. Example 98 was the earlier-eluting of two diastereomers by preparative HPLC (stereochemistry tentatively assigned), and Example 99 was the later-eluting of two diastereomers (stereochemistry also tentatively assigned).

Example 98: $^1$H NMR (400 MHz, Methanol-$d_4$) δ 8.07 (s, 1H), 7.72 (d, J=8.5 Hz, 1H), 7.39 (s, 1H), 7.33 (s, 1H), 7.13 (d, J=8.6 Hz, 1H), 7.09 (s, 1H), 6.88 (d, J=8.2 Hz, 1H), 6.04 (dt, J=11.4, 6.7 Hz, 1H), 5.79 (d, J=15.6 Hz, 1H), 5.49 (s, 2H), 4.04 (s, 7H), 3.90 (d, J=14.4 Hz, 1H), 3.79 (s, 3H), 3.74-3.57 (m, 6H), 3.51 (d, J=15.8 Hz, 3H), 3.37 (d, J=14.8 Hz, 2H), 3.04 (dd, J=15.2, 10.5 Hz, 1H), 2.78 (d, J=20.7 Hz, 2H), 2.66 (d, J=15.1 Hz, 3H), 2.33 (dd, J=23.8, 12.3 Hz, 3H), 2.05 (d, J=16.6 Hz, 2H), 2.00-1.76 (m, 2H), 1.76-1.65 (m, 1H), 1.63-1.53 (m, 1H), 1.42 (d, J=12.9 Hz, 1H), 1.03 (d, J=6.9 Hz, 3H). LCMS-ESI+ (m/z): [M+H]$^+$ calcd for $C_{43}H_{53}ClN_6O_8S$: 849.3; found: 849.0.

Example 99: $^1$H NMR (400 MHz, Methanol-$d_4$) δ 8.06 (s, 1H), 7.75 (d, J=8.5 Hz, 1H), 7.41 (d, J=8.2 Hz, 1H), 7.29 (s, 1H), 7.16 (d, J=8.4 Hz, 1H), 7.10 (s, 1H), 6.91 (d, J=8.3 Hz, 1H), 6.10 (d, J=15.6 Hz, 1H), 5.87 (d, J=15.9 Hz, 1H), 5.49 (s, 2H), 4.05 (m, 7H), 3.80 (m, 5H), 3.78-3.54 (m, 8H), 3.55-3.44 (m, 1H), 3.40 (d, J=14.5 Hz, 1H), 3.17-3.02 (m, 1H), 2.92-2.63 (m, 3H), 2.51 (d, J=15.1 Hz, 1H), 2.46-2.20 (m, 4H), 2.09 (d, J=14.0 Hz, 1H), 1.99-1.83 (m, 3H), 1.82-1.62 (m, 3H), 1.50-1.40 (m, 1H), 1.18 (d, J=5.0 Hz, 3H). LCMS-ESI+ (m/z): [M+H]$^+$ calcd for $C_{43}H_{53}ClN_6O_8S$: 849.3; found: 849.1.

Example 100 and Example 101

Example 100 and Example 101 were synthesized in a similar manner to Example 96 and Example 97 using 1-(4-methylpiperazin-1-yl)ethanone and Example 47. Example 100 was the earlier-eluting of two diastereomers by preparative HPLC (stereochemistry tentatively assigned), and Example 101 was the later-eluting of two diastereomers (stereochemistry also tentatively assigned).

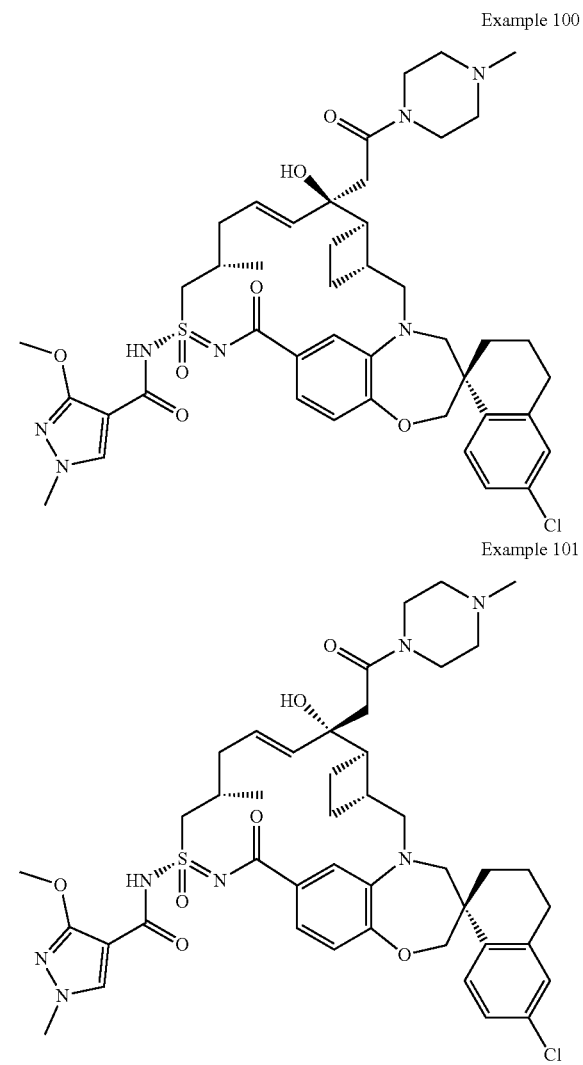

Example 100

Example 101

Example 100: $^1$H NMR (400 MHz, Methanol-$d_4$) δ 8.10 (s, 1H), 7.70 (d, J=8.3 Hz, 1H), 7.34 (d, J=9.9 Hz, 1H), 7.09 (d, J=8.4 Hz, 2H), 6.87 (d, J=8.1 Hz, 1H), 6.10 (dt, J=14.6, 6.6 Hz, 1H), 5.80 (d, J=15.7 Hz, 1H), 4.80-4.50 (br s, 4H), 4.40-4.10 (br s, 2H), 4.16-3.86 (m, 9H), 3.79 (s, 3H), 3.67 (d, J=14.4 Hz, 1H), 3.49 (br s, 2H), 3.36 (d, J=14.4 Hz, 1H), 3.03 (dd, J=15.2, 10.7 Hz, 1H), 2.95 (s, 3H), 2.87-2.72 (m, 2H), 2.67 (d, J=15.0 Hz, 2H), 2.50 (d, J=15.0 Hz, 1H), 2.40-2.24 (m, 2H), 2.05 (dd, J=14.3, 8.4 Hz, 2H), 2.00-1.78 (m, 4H), 1.70 (p, J=9.4 Hz, 1H), 1.57 (q, J=9.8 Hz, 1H), 1.45-1.31 (m, 1H), 1.03 (d, J=6.8 Hz, 3H). LCMS-ESI+ (m/z): [M+H]+ calcd for $C_{44}H_{56}ClN_7O_7S$: 862.4; found: 862.2.

Example 101: $^1$H NMR (400 MHz, Methanol-$d_4$) δ 8.07 (s, 1H), 7.74 (d, J=8.5 Hz, 1H), 7.49-7.39 (m, 1H), 7.31 (s, 1H), 7.16 (dd, J=8.5, 2.4 Hz, 1H), 7.10 (d, J=2.2 Hz, 1H), 6.93 (d, J=8.3 Hz, 1H), 6.08-5.80 (m, 2H), 4.71 (br s, 4H), 4.33 (br s, 2H), 4.06 (d, J=11.9 Hz, 6H), 3.89 (d, J=14.8 Hz, 2H), 3.80 (s, 3H), 3.71 (d, J=14.4 Hz, 1H), 3.38 (d, J=14.4 Hz, 1H), 3.13 (dd, J=15.2, 11.0 Hz, 1H), 3.15-2.90 (br s, 3H), 2.91 (s, 3H), 2.88-2.73 (m, 1H), 2.80-2.60 (br s, 3H), 2.63 (d, J=15.2 Hz, 1H), 2.54-2.14 (m, 3H), 2.09 (d, J=13.5 Hz, 1H), 1.93 (d, J=9.9 Hz, 2H), 1.83-1.59 (m, 3H), 1.45 (t, J=12.6 Hz, 1H), 1.14 (d, J=6.7 Hz, 3H). LCMS-ESI+ (m/z): [M+H]+ calcd for $C_{44}H_{56}ClN_7O_7S$: 862.4; found: 862.3.

Example 102 and Example 103

Step 1: (9aS)-1,3,4,6,7,8,9,9a-octahydropyrazino[2,1-c][1,4]oxazine dihydrochloride (300 mg, 1.39 mmol) was treated with acetic anhydride (157 mg, 1.53 mmol) in the presence of sodium carbonate (739 mg, 7.0 mmol, 5 equiv) in 1,2-dichloroethane (3 mL) at rt for 14 h. Filtration of the reaction mixture through Celite (3 g) and removal of the solvent under a reduced pressure gave 1-[(9aS)-3,4,6,7,9,9a-Hexahydro-1H-pyrazino[2,1-c][1,4]oxazin-8-yl]ethanone. $^1$H NMR (400 MHz, Chloroform-d) 4.57 (d, J=13.2 Hz, 4/10×1H), 4.40 (d, J=12.7 Hz, 6/10×1H), 3.86 (d, J=11.4 Hz, 1H), 3.73 (s, 2H), 3.50 (d, J=13.1 Hz, 6/10×1H), 3.34 (d, J=12.7 Hz, 4/10×1H), 3.24 (q, J=10.5, 9.6 Hz, 1H), 2.86-2.72 (m, 2H), 2.67 (d, J=11.6 Hz, 1H), 2.44-2.33 (m, 1H), 2.27 (d, J=11.8 Hz, 1H), 2.23-2.12 (m, 2H), 2.10 (s, 6/10×3H), 2.09 (s, 4/10×3H).

Example 102

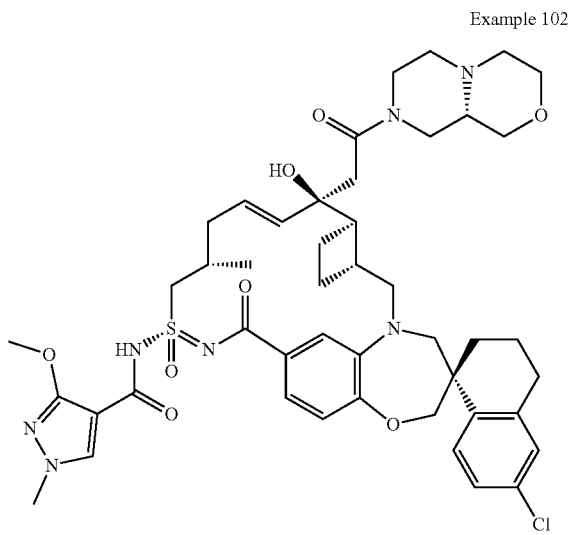

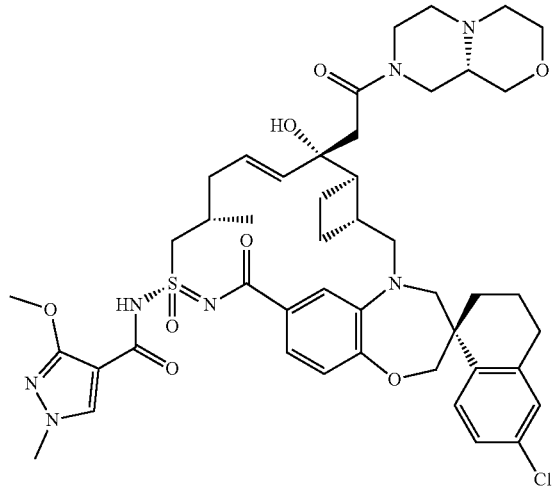

Example 103

Step 2: Example 102 and Example 103 were synthesized in a similar manner to Example 96 and Example 97 using 1-[(9aS)-3,4,6,7,9,9a-Hexahydro-1H-pyrazino[2,1-c][1,4]oxazin-8-yl]ethanone and Example 47. Example 102 was the earlier-eluting of two diastereomers by preparative HPLC (stereochemistry tentatively assigned), and Example 103 was the later-eluting of two diastereomers (stereochemistry also tentatively assigned).

Example 102: $^1$H NMR (400 MHz, Methanol-$d_4$) δ 8.12 (s, 1H), 7.68 (d, J=9.1 Hz, 1H), 7.35 (s, 2H), 7.06 (d, J=2.1 Hz, 2H), 6.85 (d, J=8.5 Hz, 1H), 6.09 (dd, J=15.3, 7.5 Hz, 1H), 5.80 (t, J=16.2 Hz, 1H), 4.22 (d, J=14.0 Hz, 2H), 4.16-3.82 (m, 11H), 3.79 (s, 3H), 3.72-3.42 (m, 4H), 3.36 (d, J=14.4 Hz, 1H), 3.25 (d, J=13.0 Hz, 2H), 3.04 (q, J=13.8, 13.2 Hz, 2H), 2.91-2.57 (m, 3H), 2.51 (d, J=14.9 Hz, 1H), 2.40-2.23 (m, 2H), 2.04 (d, J=13.4 Hz, 2H), 1.92 (d, J=14.0 Hz, 6H), 1.71 (q, J=9.3 Hz, 1H), 1.55 (t, J=9.9 Hz, 1H), 1.33 (dd, J=24.7, 11.9 Hz, 1H), 1.03 (dd, J=10.6, 6.8 Hz, 3H). LCMS-ESI+ (m/z): [M+H]+ calcd for $C_{46}H_{58}ClN_7O_8S$: 904.4; found: 904.3.

Example 103: $^1$H NMR (400 MHz, Methanol-$d_4$) δ 8.12 (s, 1H), 7.68 (d, J=9.1 Hz, 1H), 7.35 (s, 2H), 7.06 (d, J=2.1 Hz, 2H), 6.85 (d, J=8.5 Hz, 1H), 6.09 (dd, J=15.3, 7.5 Hz, 1H), 5.80 (t, J=16.2 Hz, 1H), 4.22 (d, J=14.0 Hz, 2H), 4.16-3.82 (m, 11H), 3.79 (s, 3H), 3.72-3.42 (m, 4H), 3.36 (d, J=14.4 Hz, 1H), 3.25 (d, J=13.0 Hz, 2H), 3.04 (q, J=13.8, 13.2 Hz, 2H), 2.91-2.57 (m, 3H), 2.51 (d, J=14.9 Hz, 1H), 2.40-2.23 (m, 2H), 2.04 (d, J=13.4 Hz, 2H), 1.92 (d, J=14.0 Hz, 6H), 1.71 (q, J=9.3 Hz, 1H), 1.55 (t, J=9.9 Hz, 1H), 1.33 (dd, J=24.7, 11.9 Hz, 1H), 1.03 (dd, J=10.6, 6.8 Hz, 3H). [M+H]+ calcd for $C_{46}H_{58}ClN_7O_8S$: 904.4; found: 904.7.

Example 104 and Example 105

Step 2: Example 104 and Example 105 were synthesized in a similar manner to Example 102 and Example 103 using 1-(Oxetan-3-yl)piperazine and Example 47. Example 104 was the earlier-eluting of two diastereomers by preparative HPLC (stereochemistry tentatively assigned), and Example 105 was the later-eluting of two diastereomers (stereochemistry also tentatively assigned).

Example 104

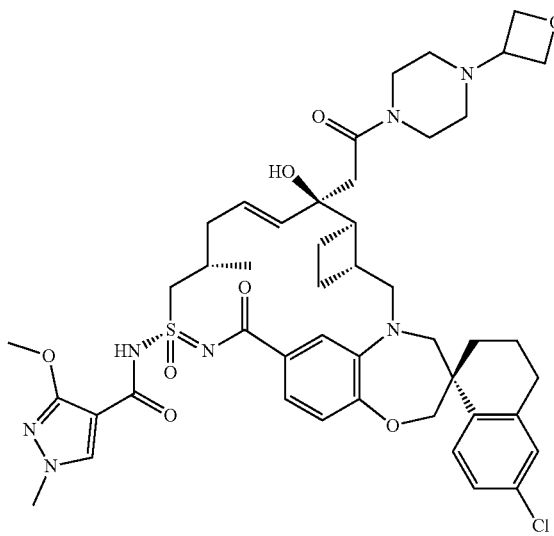

Example 106 and Example 107

Example 106

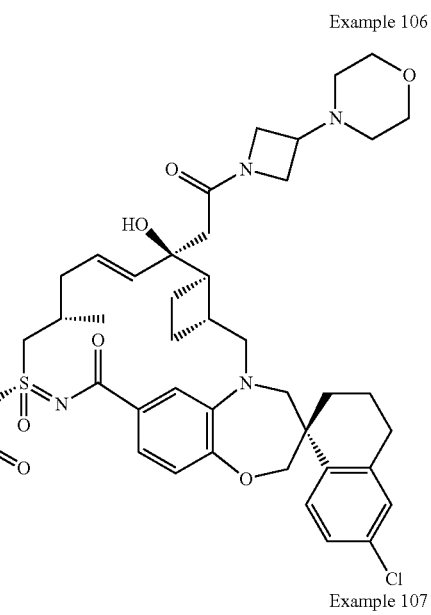

Example 105

Example 107

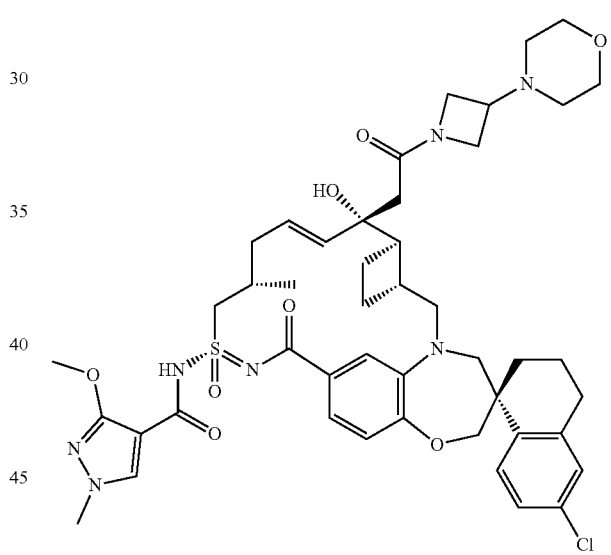

Example 106 and Example 107 were synthesized in a similar manner to Example 102 and Example 103 using 4-(azetidin-3-yl)morpholine and Example 47. Example 106 was the earlier-eluting of two diastereomers by preparative HPLC (stereochemistry tentatively assigned), and Example 107 was the later-eluting of two diastereomers (stereochemistry also tentatively assigned).

Example 104: $^1$H NMR (400 MHz, Methanol-$d_4$) δ 8.10-6.70 (m, 7H), 6.20 (m, 1H), 5.25 (m, 1H), 3.93 (s, 3H), 3.80 (s, 3H), 4.79-3.36 (m, 19H), 3.25-1.25 (m, 19H), 0.90 (d, J=6.8 Hz, 3H). LCMS-ESI+ (m/z): [M+H]$^+$ calcd for $C_{46}H_{58}ClN_7O_8S$: 904.4; found: 904.7.

Example 105: $^1$H NMR (400 MHz, Methanol-$d_4$) δ 8.02 (s, 1H), 7.73 (t, J=8.6 Hz, 1H), 7.64 (m, 1H), 7.30-7.12 (m, 2H), 7.09 (s, 1H), 6.83 (br s, 1H), 6.23 (m, 1H), 5.60 (m, 1H), 4.68 (t, J=6.6 Hz, 2H), 4.62-4.50 (m, 4H), 4.25-4.19 (m, 1H), 4.13-3.82 (m, 6H), 3.77 (s, 3H), 3.66 (s, 3H), 3.60-3.40 (m, 6H), 3.12-1.17 (m, 19H), 1.04 (s, 3H). LCMS-ESI+ (m/z): [M+H]$^+$ calcd for $C_{46}H_{58}ClN_7O_8S$: 904.4; found: 904.4.

Example 106: $^1$H NMR (400 MHz, Methanol-$d_4$) δ 8.10 (s, 1H), 7.70 (d, J=8.3 Hz, 1H), 7.42-7.24 (m, 2H), 7.09 (d, J=7.1 Hz, 2H), 6.88 (dd, J=10.2, 8.4 Hz, 1H), 6.20-6.03 (m, 1H), 5.80 (d, J=15.6 Hz, 1H), 4.51 (ddd, J=27.0, 13.4, 8.1 Hz, 2H), 4.36-3.84 (m, 12H), 3.79 (s, 3H), 3.67 (d, J=14.3 Hz, 1H), 3.49-3.32 (m, 1H), 3.27 (s, 5H), 3.03 (dd, J=15.6, 10.3 Hz, 1H), 2.91-2.50 (m, 4H), 2.43-1.99 (m, 7H), 1.99-1.62 (m, 6H), 1.53 (q, J=9.5 Hz, 1H), 1.45-1.31 (m, 1H), 1.04 (d, J=6.8 Hz, 3H). LCMS-ESI+ (m/z): [M+H]$^+$ calcd for $C_{46}H_{58}ClN_7O_8S$: 904.4; found: 904.0.

Example 107: $^1$H NMR (400 MHz, Methanol-$d_4$) δ 8.08 (s, 1H), 7.74 (d, J=8.5 Hz, 1H), 7.50 (dd, J=8.3, 1.8 Hz, 1H), 7.32 (d, J=2.0 Hz, 1H), 7.16 (dd, J=8.7, 2.4 Hz, 1H), 7.10 (d, J=2.1 Hz, 1H), 6.99-6.91 (m, 1H), 6.08-5.79 (m, 2H), 4.70-4.58 (m, 1H), 4.54 (dd, J=10.4, 4.5 Hz, 1H), 4.36-4.25 (m, 1H), 4.24-3.99 (m, 7H), 3.97-3.76 (m, 7H), 3.72 (d, J=15.2 Hz, 1H), 3.38 (dd, J=14.5, 7.3 Hz, 1H), 3.29-3.03 (m, 7H), 2.77 (dt, J=37.7, 15.2 Hz, 3H), 2.55 (dd, J=31.6, 14.7 Hz, 1H), 2.46-2.22 (m, 2H), 2.12 (dd, J=38.1, 13.0 Hz, 1H), 1.94 (m, 5H), 1.81-1.58 (m, 5H), 1.44 (d, J=10.1 Hz, 1H), 1.13 (d, J=6.7 Hz, 3H). LCMS-ESI+ (m/z): [M+H]+ calcd for $C_{46}H_{58}ClN_7O_8S$: 904.4; found: 904.4.

Example 108, Example 109, and Example 110

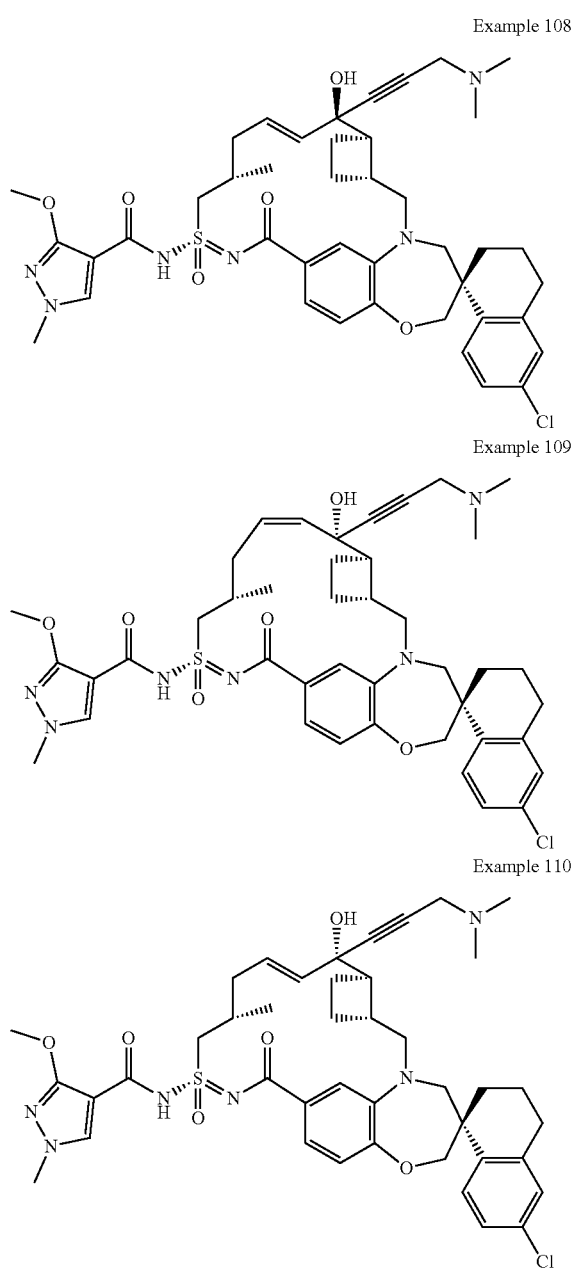

Example 108

Example 109

Example 110

Potassium bis(trimethylsilyl)amide solution (1.0 M in tetrahydrofuran, 704 μL, 704 μmol) was added over 2 min via syringe to a stirred mixture of N,N-dimethylprop-2-yn-1-amine (126 μL, 1.17 mmol) in tetrahydrofuran (0.5 mL) at 0° C. After 20 min, the resulting mixture was transferred via syringe to a stirred solution of Example 47 (33.8 mg, 46.9 μmol) in tetrahydrofuran (1.0 mL) at −78° C. The resulting mixture was warmed to −30° C. over 76 min, and trifluoroacetic acid (110 μL) was added via syringe. The resulting mixture was warmed to room temperature and was concentrated under reduced pressure. The residue was purified by reverse phase preparative HPLC (0.1% trifluoroacetic acid in acetonitrile/water) to give Example 108 (faster eluting E-olefin diastereomer on reverse phase HPLC; the stereochemistry of the propargylic alcohol stereocenter was tentatively assigned), Example 109 (Z-olefin diastereomer, the stereochemistry of the propargylic alcohol stereocenter was tentatively assigned), and Example 110 (slower eluting E-olefin diastereomer on reverse phase HPLC; the stereochemistry of the propargylic alcohol stereocenter was tentatively assigned).

Example 108: $^1$H NMR (400 MHz, Methanol-$d_4$) δ 8.03 (s, 1H), 7.74 (d, J=8.5 Hz, 1H), 7.33 (dd, J=8.3, 1.8 Hz, 1H), 7.27 (d, J=1.9 Hz, 1H), 7.20-7.13 (m, 1H), 7.10 (d, J=2.3 Hz, 1H), 6.93 (d, J=8.2 Hz, 1H), 6.34 (dt, J=15.4, 6.1 Hz, 1H), 5.91 (d, J=15.6 Hz, 1H), 4.33 (d, J=16.3 Hz, 1H), 4.23 (d, J=16.3 Hz, 1H), 4.18-3.96 (m, 5H), 4.04 (s, 3H), 3.79 (s, 3H), 3.69 (d, J=14.3 Hz, 1H), 3.22-3.06 (m, 1H), 3.00 (s, 6H), 2.94-1.26 (m, 16H), 1.13 (d, J=6.4 Hz, 3H). LCMS-ESI+ (m/z): [M+H]+ calcd for $C_{42}H_{51}ClN_6O_6S$: 803.3; found: 803.3.

Example 109: $^1$H NMR (400 MHz, Methanol-$d_4$) δ 8.07 (s, 1H), 7.75 (d, J=8.5 Hz, 1H), 7.40 (d, J=2.0 Hz, 1H), 7.35 (dd, J=8.3, 1.8 Hz, 1H), 7.21-7.14 (m, 1H), 7.11-7.09 (m, 1H), 6.91 (d, J=8.2 Hz, 1H), 5.77 (td, J=10.6, 9.8, 6.2 Hz, 1H), 5.53 (d, J=11.9 Hz, 1H), 4.37-3.07 (m, 9H), 4.05 (s, 3H), 3.80 (s, 3H), 2.95 (s, 6H), 2.92-1.28 (m, 16H), 1.21 (d, J=6.9 Hz, 3H). LCMS-ESI+ (m/z): [M+H]+ calcd for $C_{42}H_{51}ClN_6O_6S$: 803.3; found: 803.3.

Example 110: $^1$H NMR (400 MHz, Methanol-$d_4$) δ 8.06 (s, 1H), 7.74 (d, J=8.5 Hz, 1H), 7.37 (d, J=8.6 Hz, 1H), 7.26 (s, 1H), 7.17 (dd, J=8.5, 2.4 Hz, 1H), 7.10 (d, J=2.3 Hz, 1H), 6.90 (d, J=8.3 Hz, 1H), 6.62-6.43 (m, 1H), 5.83 (d, J=15.8 Hz, 1H), 4.34 (d, J=16.3 Hz, 1H), 4.24 (d, J=16.2 Hz, 1H), 4.08 (d, J=12.1 Hz, 1H), 4.05 (s, 3H), 3.99 (d, J=12.1 Hz, 1H), 3.89 (d, J=15.1 Hz, 1H), 3.80 (s, 3H), 3.77-3.67 (m, 2H), 3.37 (d, J=14.4 Hz, 1H), 3.04 (dd, J=15.2, 11.1 Hz, 1H), 2.91 (s, 6H), 2.88-1.65 (m, 15H), 1.42 (d, J=11.9 Hz, 1H), 1.24 (d, J=6.6 Hz, 3H). LCMS-ESI+ (m/z): [M+H]+ calcd for $C_{42}H_{51}ClN_6O_6S$: 803.3; found: 803.3.

Example 111

Step 1: n-BuLi (1.6 M in hexane, 0.24 mL, 4.9 equiv.) was added to a solution of 1,3-dithiane (46 mg, 5 equiv.) in THF (4 mL) under nitrogen atmosphere at −80° C. The resulting mixture was stirred at −80° C. for 60 min, then Example 47 (55 mg) was added as a solution in THF (2 mL). The resulting solution was stirred at −80° C. for 30 min. Then the reaction was quenched with brine at −80° C. The mixture was allowed to warm to 20° C., then the resulting mixture was extracted three times with ethyl acetate. The combined organic phases were washed with brine, dried over magnesium sulfate, filtered, and concentrated in vacuo to a residue. The residue was purified by preparative reverse-phase HPLC (70 to 100% acetonitrile in water with 0.1% trifluoroacetic acid modifier) to yield 111-1 as a ~1:1 mixture of diastereomers. LCMS-ESI+ (m/z): [M+H]+ calcd for $C_4H_{50}ClN_5O_6S_3$: 840.3; found: 840.0.

Step 2: To a glass screwtop vial charged with diastereomeric mixture 111-1 (45 mg) under nitrogen atmosphere was added DMF (1.1 mL). The vial was cooled to 0° C., then potassium bis(trimethylsilyl)amide (1 M in THF, 0.54 mL, 10 equiv.) was added, followed immediately by iodomethane (137 mg, 18 equiv). The vial was stirred at 0° C. for 5 min, then the cooling bath was removed and the vial was allowed to warm to 20° C. for 15 min. The reaction was quenched with 10% aqueous citric acid and extracted with ethyl acetate. The combined organic phases were washed twice with water, once with brine, dried over magnesium sulfate, filtered, and concentrated in vacuo to a residue. The resulting residue was purified by preparative reverse-phase HPLC (40 to 100% acetonitrile in water with 0.1% trifluoroacetic acid modifier) to give 111-2 as the earlier-eluting of two diastereomeric products and 111-3 as the later-eluting (stereochemistry tentatively assigned).

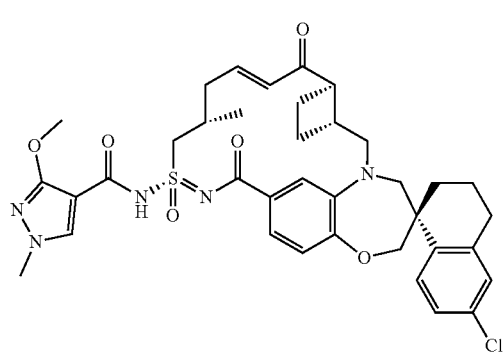

Example 47

Step 1 →

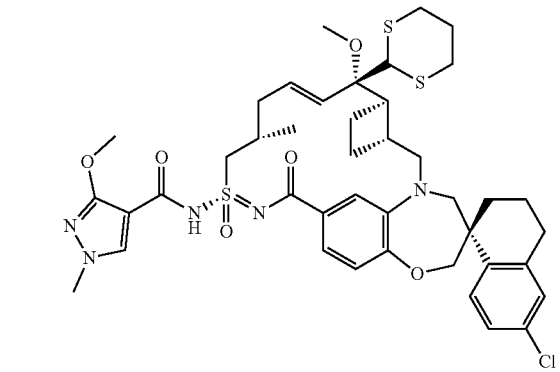 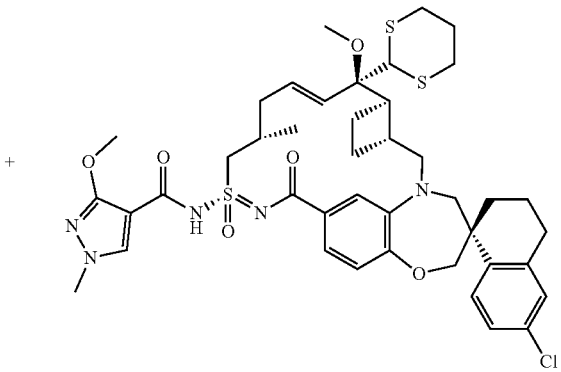

111-1

Step 2 ↓

111-3     +     111-2

Step 3 ↓

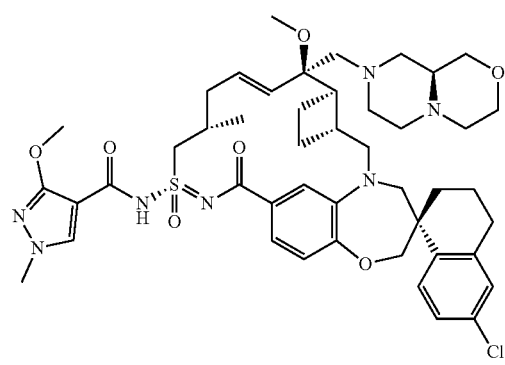 ← Step 4 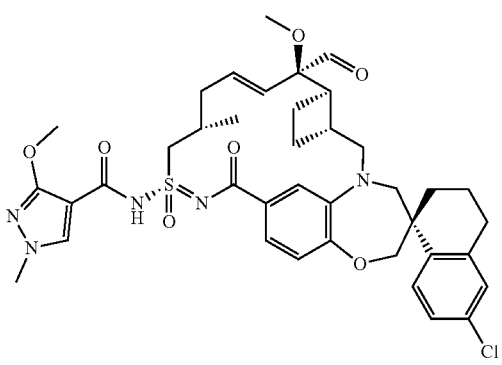

Example 111                                    111-4

111-2: $^1$H NMR (400 MHz, Acetone-$d_6$) δ 8.11 (s, 1H), 7.77 (d, J=8.5 Hz, 1H), 7.45 (d, J=8.4 Hz, 1H), 7.40 (d, J=2.0 Hz, 1H), 7.23 (dd, J=8.5, 2.4 Hz, 1H), 7.12 (d, J=2.4 Hz, 1H), 6.90 (d, J=8.2 Hz, 1H), 6.28 (ddd, J=14.8, 9.3, 4.3 Hz, 1H), 5.70 (d, J=16.1 Hz, 1H), 4.52 (s, 1H), 4.13-3.95 (m, 3H), 4.07 (s, 3H), 3.85 (s, 3H), 3.75 (d, J=14.4 Hz, 2H), 3.53-3.39 (m, 1H), 3.49 (s, 3H), 3.12-2.92 (m, 3H), 2.81 (ddd, J=20.6, 16.4, 10.5 Hz, 8H), 2.46 (s, 1H), 2.20-2.08 (m, 4H), 1.98 (dd, J=7.0, 4.1 Hz, 2H), 1.87-1.68 (m, 3H), 1.57-1.39 (m, 2H), 1.10 (d, J=6.9 Hz, 3H). LCMS-ESI+ (m/z): [M+H]$^+$ calcd for $C_{42}H_{52}ClN_5O_6S_3$: 854.3; found: 854.0.

111-3: $^1$H NMR (400 MHz, Acetone-$d_6$) δ 8.10 (s, 1H), 7.77 (d, J=8.5 Hz, 1H), 7.52 (dd, J=8.2, 1.9 Hz, 1H), 7.48 (d, J=2.0 Hz, 1H), 7.23 (dd, J=8.4, 2.4 Hz, 1H), 7.12 (d, J=2.5 Hz, 1H), 6.93 (d, J=8.2 Hz, 1H), 5.92 (s, 2H), 4.51 (s, 1H), 4.40 (dd, J=15.1, 3.8 Hz, 1H), 4.16 (d, J=14.9 Hz, 1H), 4.11-4.03 (m, 2H), 4.10 (s, 3H), 3.85 (s, 3H), 3.75 (d, J=14.4 Hz, 1H), 3.47 (d, J=14.5 Hz, 1H), 3.39 (s, 3H), 3.25-3.13 (m, 2H), 3.12-2.71 (m, 8H), 2.59 (dd, J=7.0, 3.6 Hz, 1H), 2.51-2.41 (m, 1H), 2.25-2.09 (m, 3H), 1.96 (d, J=8.8 Hz, 2H), 1.92-1.68 (m, 5H), 1.53-1.39 (m, 1H), 1.13 (d, J=6.7 Hz, 3H). LCMS-ESI+ (m/z): [M+H]$^+$ calcd for $C_{42}H_{52}ClN_5O_6S_3$: 854.3; found: 854.0.

Step 3: To a glass screwtop vial charged with a solution of 111-2 (15 mg, 1 equiv.) in 5:1 acetonitrile:water (1.1 mL) cooled to 0° C. was added 2,6-lutidine (120 μL, 60 equiv.), then N-chlorosuccinimide (70 mg, 30 equiv.), then silver nitrate (120 mg, 40 equiv.). The resulting mixture was stirred at 0° C. for 20 min. Then more 2,6-lutidine (120 μL, 60 equiv.) was added, followed by more N-chlorosuccinimide (70 mg, 30 equiv.), then more silver nitrate (120 mg, 40 equiv.). The resulting mixture was stirred at 0° C. for 20 min. Then the reaction was quenched with 1 N aqueous sodium thiosulfate, then 10% aqueous citric acid. The combined aqueous phases were checked for pH and found to be <4 by pH paper. The combined aqueous phases were extracted with ethyl acetate. The combined organic phases were washed with brine, dried over magnesium sulfate, filtered and concentrated in vacuo to a residue. The residue was diluted with 1:1 acetonitrile:methanol, plus several drops of trifluoroacetic acid, filtered and purified by preparative reverse-phase HPLC (60 to 100% acetonitrile in water with 0.1% trifluoroacetic acid modifier) to obtain 111-4 (stereochemistry tentatively assigned). $^1$H NMR (400 MHz, Acetone-d6) δ 9.63 (s, 1H), 8.12 (s, 1H), 7.77 (d, J=8.5 Hz, 1H), 7.49 (d, J=8.8 Hz, 1H), 7.44 (d, J=2.0 Hz, 1H), 7.23 (dd, J=8.5, 2.4 Hz, 1H), 7.12 (d, J=2.3 Hz, 1H), 6.93 (d, J=8.3 Hz, 1H), 6.28 (ddd, J=16.4, 7.8, 4.4 Hz, 1H), 5.87 (d, J=16.6 Hz, 1H), 4.19-3.96 (m, 3H), 3.85 (s, 3H), 3.75 (d, J=14.5 Hz, 1H), 3.49 (d, J=10.8 Hz, 1H), 3.44 (s, 3H), 3.21-3.10 (m, 1H), 2.97-2.65 (m, 6H), 2.58-2.41 (m, 2H), 2.35-2.11 (m, 3H), 1.97 (d, J=8.1 Hz, 2H), 1.86-1.74 (m, 2H), 1.60 (t, J=6.5 Hz, 2H), 1.56-1.39 (m, 3H), 1.09 (d, J=6.8 Hz, 3H). LCMS-ESI+ (m/z): [M+H]$^+$ calcd for $C_{39}H_{46}ClN_5O_7S$: 764.3; found: 764.0.

Step 4: A glass screwtop vial charged with 111-4 (2.0 mg, 2.6 μmol) and (S)-octahydropyrazino[2,1-c][1,4]oxazine dihydrochloride (4.5 mg, 12 equiv.) was dried on high vacuum for 5 min, then placed under nitrogen. The solids were suspended in dichloromethane (0.2 mL), then diisopropylethylamine (13.5 mg, 40 equiv.) was added. The resulting solution was sealed under nitrogen with a screwtop Teflon cap and stirred at 20° C. for 16 hr. Then sodium triacetoxyborohydride (18.3 mg, 33 equiv.) was added. The reaction was stirred at 20° C. for 28 hr. The reaction was concentrated in vacuo, then resuspended in 1:1 methanol: acetonitrile plus one drop of trifluoroacetic acid, filtered, and purified by preparative reverse-phase HPLC (30 to 100% acetonitrile in water with 0.1% trifluoroacetic acid modifier) to give Example 111. $^1$H NMR (400 MHz, Acetone-$d_6$) δ 8.11 (s, 1H), 7.78 (d, J=8.5 Hz, 1H), 7.52 (dd, J=8.3, 1.8 Hz, 1H), 7.49 (d, J=1.7 Hz, 1H), 7.24 (dd, J=8.6, 2.4 Hz, 1H), 7.13 (d, J=2.4 Hz, 1H), 6.93 (d, J=8.2 Hz, 1H), 5.94-5.84 (m, 2H), 4.17 (dd, J=15.2, 7.5 Hz, 1H), 4.09 (d, J=1.4 Hz, 3H), 4.04-3.88 (m, 4H), 3.85 (s, 3H), 3.79-3.65 (m, 3H), 3.59-3.51 (m, 1H), 3.44 (d, J=14.4 Hz, 1H), 3.34 (s, 3H), 3.24-3.02 (m, 7H), 3.02-2.48 (m, 14H), 2.18-2.11 (m, 1H), 2.00-1.93 (m, 2H), 1.73 (s, 2H), 1.55-1.37 (m, 2H), 1.10 (d, J=6.8 Hz, 3H). LCMS-ESI+ (m/z): [M+H]$^+$ calcd for $C_{46}H_{60}ClN_7O_7S$: 890.4; found: 890.2.

Example 112

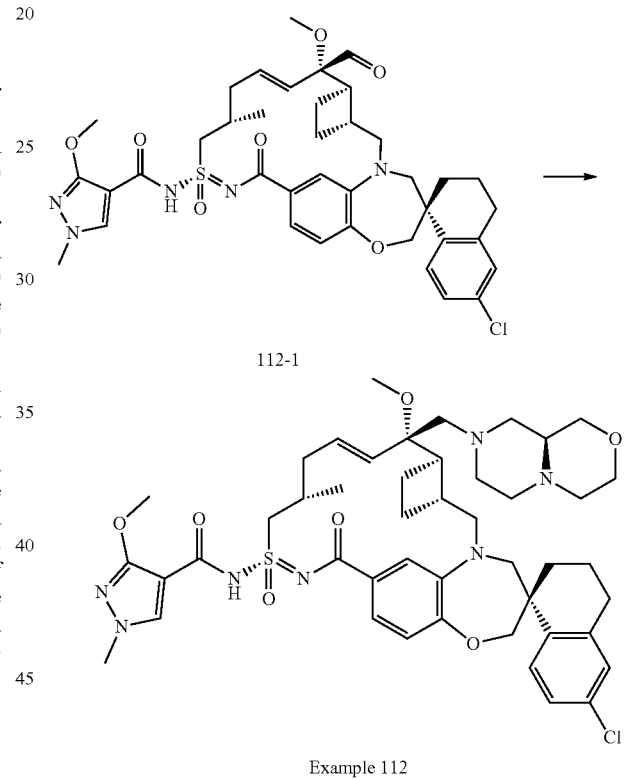

Example 112

Preparation of 112-1: 112-1 was prepared in a similar manner to 111-4 from 111-3. $^1$H NMR (400 MHz, Acetone-$d_6$) δ 9.68 (s, 1H), 8.10 (d, J=0.6 Hz, 1H), 7.77 (d, J=8.5 Hz, 1H), 7.46 (dd, J=8.2, 1.9 Hz, 1H), 7.34 (d, J=2.0 Hz, 1H), 7.23 (dd, J=8.5, 2.4 Hz, 1H), 7.12 (d, J=2.3 Hz, 2H), 6.91 (d, J=8.3 Hz, 2H), 6.27 (dt, J=16.3, 5.9 Hz, 1H), 5.85 (d, J=16.1 Hz, 1H), 4.21-4.10 (m, 2H), 4.08 (s, 3H), 4.05-3.92 (m, 2H), 3.84 (s, 3H), 3.77 (d, J=14.6 Hz, 1H), 3.70 (dd, J=14.9, 4.5 Hz, 1H), 3.46 (d, J=14.6 Hz, 1H), 3.39 (s, 3H), 3.11 (dd, J=15.1, 11.4 Hz, 1H), 2.79 (dt, J=25.7, 16.5 Hz, 4H), 2.63-2.45 (m, 2H), 2.45-2.35 (m, 1H), 2.13 (d, J=13.6 Hz, 1H), 2.00-1.63 (m, 7H), 1.52-1.39 (m, 1H), 1.18 (d, J=6.6 Hz, 3H). LCMS-ESI+ (m/z): [M+H]$^+$ calcd for $C_{39}H_{46}ClN_5O_7S$: 764.3; found: 764.2.

Preparation of Example 112: Example 112 was prepared in a similar manner to Example 111 (step 4) using 112-1 in place of 111-4. $^1$H NMR (400 MHz, Acetone-$d_6$) δ 8.13 (s, 1H), 7.77 (d, J=8.5 Hz, 1H), 7.53 (dd, J=8.3, 1.8 Hz, 1H), 7.41 (d, J=1.9 Hz, 1H), 7.24 (dd, J=8.4, 2.4 Hz, 1H), 7.13 (d, J=2.3 Hz, 1H), 6.95 (d, J=8.3 Hz, 1H), 5.94 (d, J=16.5 Hz, 1H), 5.87 (d, J=17.2 Hz, 1H), 4.40 (d, J=15.0 Hz, 1H), 4.17 (d, J=8.5 Hz, 1H), 4.13 (t, J=4.2 Hz, 1H), 4.10 (s, 3H), 4.05 (d, J=12.1 Hz, 1H), 3.96 (d, J=7.2 Hz, 2H), 3.89 (d, J=11.1 Hz, 1H), 3.86 (s, 3H), 3.75 (d, J=14.4 Hz, 1H), 3.67 (d, J=11.5 Hz, 1H), 3.64-3.54 (m, 1H), 3.47 (d, J=14.4 Hz, 1H), 3.44-3.38 (m, 1H), 3.23 (s, 3H), 3.20-3.12 (m, 3H), 3.07 (d, J=12.7 Hz, 2H), 2.88 (d, J=13.7 Hz, 2H), 2.85-2.76 (m, 3H), 2.59 (d, J=14.2 Hz, 2H), 2.53 (d, J=9.0 Hz, 1H), 2.44 (d, J=17.3 Hz, 2H), 2.12 (d, J=13.3 Hz, 2H), 2.00-1.93 (m, 2H), 1.83-1.61 (m, 5H), 1.52-1.40 (m, 2H), 1.12 (d, J=6.7 Hz, 3H). LCMS-ESI+ (m/z): [M+H]+ calcd for $C_{46}H_{60}ClN_7O_7S$: 890.4; found: 890.5.

Example 113 and Example 114

Step 1: To a stirred solution of 1 M lithium diisopropylamide (87 mg, 0.82 mmol) in THF (6 mL) was added ethyl acetate (73 mg, 0.82 mmol) at −78° C. The resulting mixture was stirred for 10 min. To this solution Example 47 (118 mg, 0.164 mmol) was added, stirred for 1 hr and then quenched with methanol. After stirring for 10 min, mixture was evaporated, solids re-dissolved in $CH_2Cl_2$, water was added and product was extracted with $CH_2Cl_2$. The organic layer was concentrated to yield 113-1.

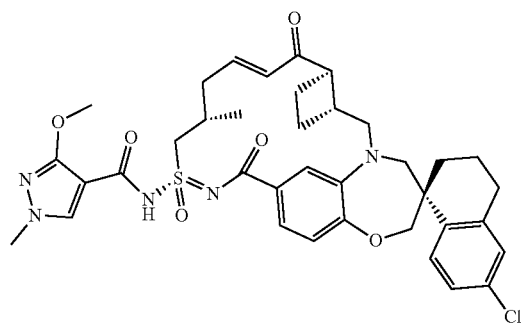

Example 47

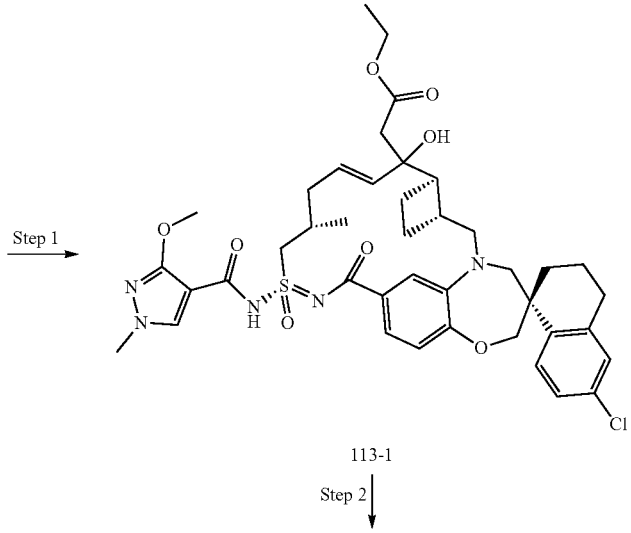

113-1

Step 2

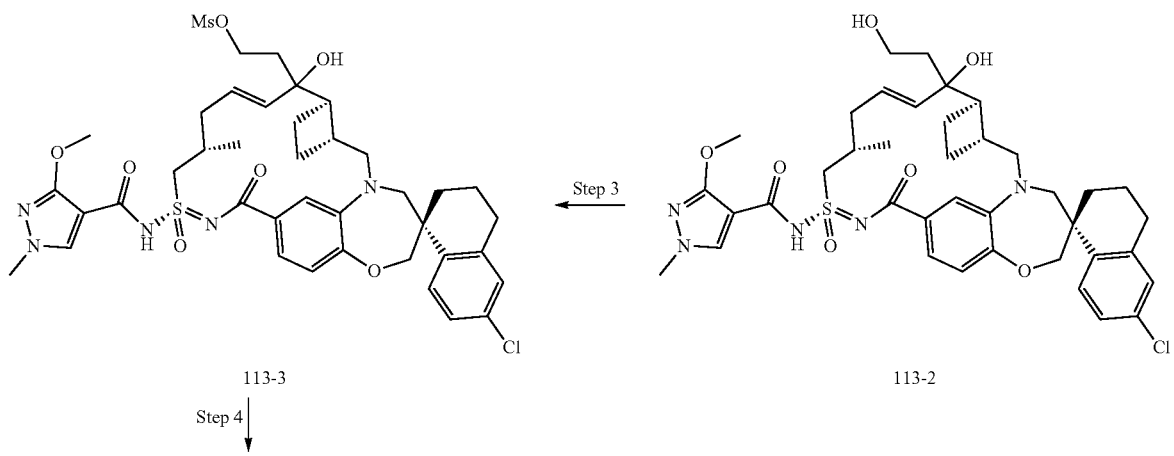

113-3

Step 4

113-2

Step 3

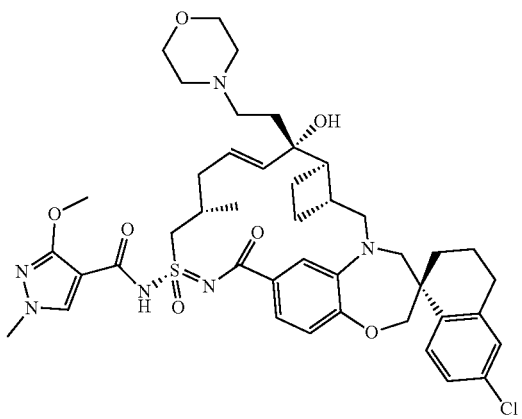

Example 114

+

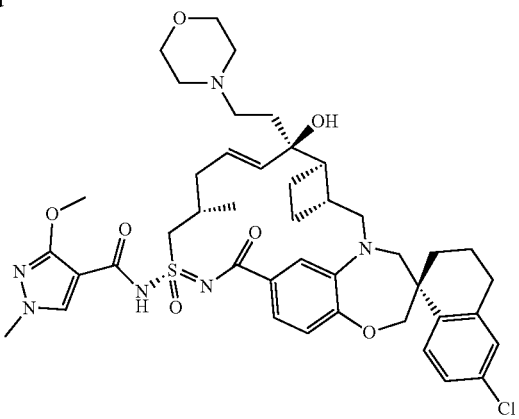

Example 113

Step 2: To a stirred solution of 113-1 (80 mg, 0.099 mmol) in THF (8 mL) at 0° C. was added LAH (11 mgs, 0.29 mmol), and stirred at 0° C. for 1 h. The mixture was diluted with water, and organic solvent was removed using an evaporator. The remaining aqueous solution was extracted with DCM. The organic layer was washed with saturated brine, dried over $Mg_2SO_4$, and concentrated to yield 113-2.

Step 3: To a stirred solution of 113-2 (80 mg, 0.1 mmol) in DCM (8 mL) at 0° C. was added pyridine (41 mg, 0.52 mmol) followed by dropwise addition of methanesulfonyl chloride (14 mg, 0.12 mmol). The reaction mixture was stirred overnight, concentrated under reduced pressure and purified by preparative HPLC to afford 113-3.

Step 4: A stirred solution of 113-3 (10 mg, 0.012 mmol) in Morpholine (3 mL) was heated at 80° C. for 2 hr. Reaction mixture was concentrated and purified by preparative HPLC to afford Example 113 and Example 114 (stereochemistry of the isomers is tentative).

Example 113: $^1$H NMR (400 MHz, Methanol-$d_4$) δ 8.09 (s, 1H), 7.78 (d, J=8.6 Hz, 1H), 7.44 (dd, J=8.3, 1.9 Hz, 1H), 7.32 (d, J=2.0 Hz, 1H), 7.20 (dd, J=8.5, 2.4 Hz, 1H), 7.13 (d, J=2.3 Hz, 1H), 6.95 (d, J=8.2 Hz, 1H), 6.10 (d, J=16.4 Hz, 1H), 5.80 (d, J=16.1 Hz, 1H), 4.47 (q, J=7.1 Hz, 1H), 4.31-3.98 (m, 6H), 3.92-3.68 (m, 5H), 3.62-3.36 (m, 4H), 3.35-3.28 (m, 6H), 3.26-3.04 (m, 3H), 2.92-2.58 (m, 3H), 2.54-2.20 (m, 4H), 2.17-1.64 (m, 8H), 1.57-1.00 (m, 6H). LCMS-ESI+ (m/z): [M+H]$^+$ calcd for $C_{43}H_{55}ClN_6O_7S$: 835.4; found: 835.7.

Example 114: $^1$H NMR (400 MHz, Methanol-$d_4$) δ 8.07 (s, 1H), 7.81-7.70 (m, 1H), 7.35 (d, J=5.8 Hz, 2H), 7.19 (dd, J=8.5, 2.3 Hz, 1H), 7.12 (d, J=2.4 Hz, 1H), 6.93 (d, J=8.7 Hz, 1H), 6.17 (dt, J=14.2, 6.7 Hz, 1H), 5.77 (d, J=15.6 Hz, 1H), 4.52-4.30 (m, 2H), 4.18-3.92 (m, 9H), 3.90-3.60 (m, 7H), 3.47 (d, J=45.4 Hz, 3H), 3.25-2.94 (m, 6H), 2.93-2.53 (m, 6H), 2.43-2.06 (m, 6H), 2.00-1.55 (m, 4H), 1.53-0.88 (m, 4H). LCMS-ESI+ (m/z): [M+H]$^+$ calcd for $C_{43}H_{55}ClN_6O_7S$: 835.4; found: 835.5.

Example 115

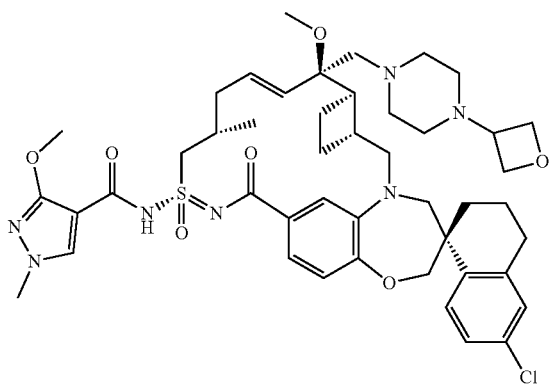 [SMILES: COc1nn(C)cc1C(=O)N[S@@]1(=O)=NC(=O)c2ccc3c(c2)N(C[C@@H]2CC[C@H]2[C@](CN2CCN(C4COC4)CC2)(OC)/C=C/C[C@H](C)C1)C[C@@]1(CCCc2cc(Cl)ccc21)CO3]

Example 115 was prepared in a similar manner to Example 111 (step 4) using 111-4, and 1-(oxetan-3-yl)piperazine. $^1$H NMR (400 MHz, Acetone-$d_6$) δ 7.89 (s, 1H), 7.83-7.70 (m, 1H), 7.53-7.41 (m, 1H), 7.36 (d, J=8.4 Hz, 1H), 7.28-7.17 (m, 1H), 7.11 (s, 1H), 6.92-6.73 (m, 1H), 6.18-6.03 (m, 1H), 5.89-5.74 (m, 1H), 5.68 (d, J=16.2 Hz, 1H), 4.55 (t, J=6.4 Hz, 2H), 4.50-4.39 (m, 2H), 4.13-3.99 (m, 3H), 3.91 (d, J=14.7 Hz, 1H), 3.87-3.79 (m, 2H), 3.76 (s, 2H), 3.67 (d, J=14.1 Hz, 1H), 3.58-3.36 (m, 3H), 3.30 (s, 3H), 3.20-2.97 (m, 3H), 2.70-2.58 (m, 3H), 2.58-2.40 (m, 2H), 2.40-2.21 (m, 4H), 2.19-2.08 (m, 2H), 2.00-1.92 (m, 6H), 1.84-1.55 (m, 3H), 1.52-1.39 (m, 2H), 1.21-1.13 (m, 2H), 1.13-1.02 (m, 1H), 0.87 (d, J=6.7 Hz, 3H). LCMS-ESI+ (m/z): [M+H]$^+$ calcd for $C_{46}H_{60}ClN_7O_7S$: 890.4; found: 890.3.

Example 116

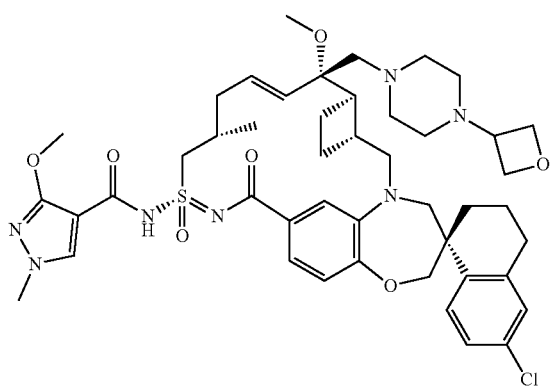 [SMILES: COc1nn(C)cc1C(=O)N[S@@]1(=O)=NC(=O)c2ccc3c(c2)N(C[C@@H]2CC[C@H]2[C@@](CN2CCN(C4COC4)CC2)(OC)/C=C/C[C@H](C)C1)C[C@@]1(CCCc2cc(Cl)ccc21)CO3]

Example 116 was prepared in a similar manner to Example 115 using 112-1 in place of 111-4. $^1$H NMR (400 MHz, Acetone-$d_6$) δ 8.13 (s, 1H), 7.76 (d, J=8.8 Hz, 2H), 7.52 (d, J=8.4 Hz, 1H), 7.40 (s, 1H), 7.23 (d, J=8.4 Hz, 1H), 7.12 (s, 1H), 6.93 (d, J=8.4 Hz, 1H), 6.05-5.81 (m, 2H), 4.89-4.74 (m, 2H), 4.73-4.59 (m, 2H), 4.16-4.00 (m, 4H), 3.95-3.80 (m, 4H), 3.78-3.61 (m, 4H), 3.46 (d, J=14.5 Hz, 2H), 3.23 (s, 3H), 2.80 (dd, J=16.1, 7.3 Hz, 6H), 2.65-2.38 (m, 6H), 2.17-2.08 (m, 2H), 1.96 (s, 3H), 1.82-1.39 (m, 6H), 1.10 (d, J=6.6 Hz, 3H), 0.87 (d, J=6.6 Hz, 3H). LCMS-ESI+ (m/z): [M+H]$^+$ calcd for $C_{46}H_{60}ClN_7O_7S$: 890.4; found: 890.5.

Example 117

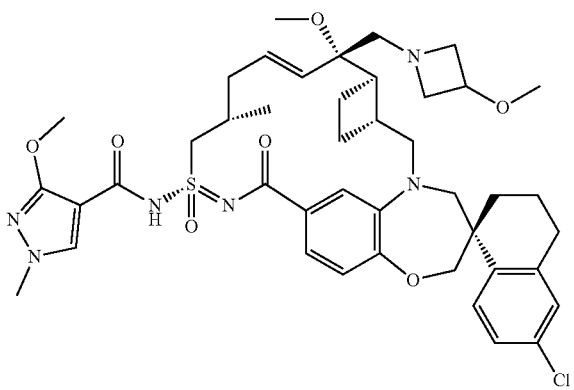 [SMILES: COc1nn(C)cc1C(=O)N[S@@]1(=O)=NC(=O)c2ccc3c(c2)N(C[C@@H]2CC[C@H]2[C@@](CN2CC(OC)C2)(OC)/C=C/C[C@H](C)C1)C[C@@]1(CCCc2cc(Cl)ccc21)CO3]

Example 117 was prepared in a similar manner to Example 112 using 3-methoxyazetidine. $^1$H NMR (400 MHz, Acetone-$d_6$) δ 8.11 (s, 1H), 7.76 (d, J=8.5 Hz, 1H), 7.50 (dd, J=8.3, 1.8 Hz, 1H), 7.37 (d, J=1.9 Hz, 1H), 7.23 (dd, J=8.5, 2.4 Hz, 1H), 7.13 (d, J=2.3 Hz, 1H), 6.94 (d, J=8.2 Hz, 1H), 6.16 (dt, J=16.4, 5.5 Hz, 1H), 5.87 (d, J=16.3 Hz, 1H), 4.83-4.63 (m, 2H), 4.44-4.33 (m, 1H), 4.21-4.10 (m, 3H), 4.08 (s, 3H), 4.01 (d, J=12.1 Hz, 1H), 3.96 (d, J=15.0 Hz, 1H), 3.89-3.80 (m, 2H), 3.84 (s, 3H), 3.77 (d, J=14.9 Hz, 2H), 3.47 (d, J=14.2 Hz, 2H), 3.31 (s, 3H), 3.29 (s, 3H), 3.27-3.21 (m, 1H), 2.95-2.84 (m, 1H), 2.84-2.72 (m, 2H), 2.72-2.60 (m, 1H), 2.58-2.48 (m, 1H), 2.48-2.39 (m, 1H), 2.34-2.24 (m, 1H), 2.13-2.07 (m, 1H), 2.00-1.90 (m, 2H), 1.90-1.75 (m, 4H), 1.51-1.43 (m, 1H), 1.12 (d, J=6.7 Hz, 3H). LCMS-ESI+ (m/z): [M+H]$^+$ calcd for $C_{43}H_{55}ClN_6O_7S$: 835.4; found: 835.4.

Example 118 and Example 119

Chlorotrimethylsilane (12.7 µL, 99.7 µmol) was added via syringe to a stirred mixture of Intermediate U (9.0 mg, 12 µmol) and silver tetrafluoroborate (19.4 mg, 99.7 µmol) in acetonitrile (2.0 mL) at 0° C. After 11 min, the resulting mixture was warmed to room temperature. After 1 hr, trifluoromethanesulfonic anhydride (16.8 µL, 99.7 µmol) was added via syringe. After 5 min, aqueous sodium acetate solution (25% wt, 200 µL) was added via syringe, and the resulting mixture was stirred vigorously. After 2 min, the resulting mixture was purified by reverse phase preparative HPLC (0.1% trifluoroacetic acid in acetonitrile/water) to give Example 118 as the earlier-eluting of two products (stereochemistry tentatively assigned) and Example 119 as the later-eluting of two products (stereochemistry tentatively assigned).

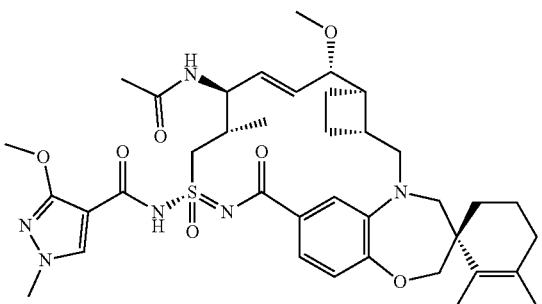

Example 118

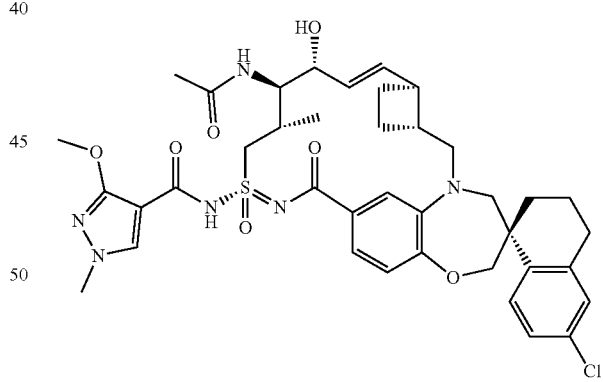

Example 119

Example 118: $^1$H NMR (400 MHz, Acetone-$d_6$) δ 8.13 (s, 0.83H), 8.11 (s, 0.17H), 7.79 (dd, J=8.6, 1.9 Hz, 0.83H), 7.74 (d, J=8.6 Hz, 0.17H), 7.51-7.07 (m, 4H), 6.97-6.89 (m, 1H), 6.29 (dd, J=15.8, 4.9 Hz, 0.83H), 6.10 (dd, J=15.8, 4.7 Hz, 0.17H), 5.91-5.75 (m, 1H), 5.14-5.07 (s, 0.17H), 4.83-4.68 (m, 0.83H), 4.42-2.98 (m, 14H), 3.28 (s, 2.5H), 3.24 (s, 0.5H), 2.94-1.37 (m, 17H), 1.19 (d, J=6.9 Hz, 2.5H), 1.07 (d, J=6.9 Hz, 0.5H). LCMS-ESI+ (m/z): [M+H]$^+$ calcd for $C_{40}H_{49}ClN_6O_7S$: 793.3; found: 793.2.

Example 119: $^1$H NMR (400 MHz, Acetone-$d_6$) δ 8.13 (s, 1H), 7.79 (d, J=8.5 Hz, 1H), 7.55-7.48 (m, 2H), 7.26 (dd, J=8.5, 2.4 Hz, 1H), 7.14 (d, J=2.3 Hz, 1H), 6.96 (d, J=8.0

Hz, 1H), 6.67 (dd, J=15.6, 4.5 Hz, 1H), 6.05 (dd, J=15.8, 8.7 Hz, 1H), 5.43 (d, J=10.8 Hz, 1H), 5.40-5.30 (m, 1H), 4.41 (dd, J=15.2, 10.2 Hz, 1H), 4.19-3.98 (m, 3H), 4.08 (s, 3H), 3.98-3.90 (m, 1H), 3.86 (s, 3H), 3.74 (d, J=14.4 Hz, 1H), 3.44 (d, J=14.3 Hz, 1H), 3.25 (dd, J=15.3, 10.7 Hz, 1H), 3.08-1.56 (m, 12H), 2.13 (s, 3H), 1.55-1.41 (m, 1H), 1.16 (d, J=6.9 Hz, 3H). LCMS-ESI+ (m/z): [M+H]$^+$ calcd for $C_{39}H_{47}ClN_6O_7S$: 779.3; found: 779.2.

Example 120 and Example 121

Step 1: To a glass vial charged with Intermediate U (18 mg, 1.0 equiv.) was added dichloromethane (1 mL), then pyridine (0.25 mL), then Dess-Martin periodinane (15.2 mg, 1.5 equiv.). The suspension was stirred at ambient temperature for 60 min, then it was concentrated in vacuo, redissolved in DMSO, and purified by preparative reverse-phase HPLC to yield 120-1.

Step 2: To a glass vial charged with 120-1 (5 mg, 1 equiv.) was added tetrahydrofuran (2 mL). The solution was cooled to −80° C., then methyl lithium (1.6 M in diethyl ether, 0.5 mL, 12 equiv.) was added. The solution was stirred at −80° C. for 60 min, then quenched with water and concentrated in vacuo. The residue was redissolved in DMSO and purified by preparative reverse-phase HPLC to yield Example 120 as the later-eluting of two diastereomeric products and Example 121 as the earlier-eluting (stereochemistry tentatively assigned).

Example 120: $^1$H NMR (400 MHz, Methanol-d$_4$) δ 8.07 (s, 1H), 7.76 (d, J=8.5 Hz, 1H), 7.48 (s, 1H), 7.41 (dd, J=8.2, 1.9 Hz, 1H), 7.18 (dd, J=8.5, 2.3 Hz, 1H), 7.11 (d, J=2.3 Hz, 1H), 6.90 (d, J=8.3 Hz, 1H), 5.86 (s, 2H), 4.09 (d, J=4.7 Hz, 5H), 3.81 (s, 3H), 3.73 (ddt, J=9.1, 7.5, 2.9 Hz, 4H), 3.66 (s, 1H), 3.39 (d, J=14.6 Hz, 1H), 3.24 (s, 3H), 3.20-3.08 (m, 1H), 2.91-2.68 (m, 2H), 2.57 (s, 2H), 2.31-2.16 (m, 1H), 2.07 (t, J=13.6 Hz, 1H), 1.95 (d, J=8.4 Hz, OH), 1.90-1.84 (m, 3H), 1.84-1.64 (m, 2H), 1.54-1.39 (m, 1H), 1.31 (d, J=16.5 Hz, 1H), 1.24 (s, 3H), 1.15 (d, J=6.9 Hz, 3H). LCMS-ESI+ (m/z): [M+H]$^+$ calcd for $C_{39}H_{43}ClN_5O_7S$: 766.3; found: 766.1.

Example 121: $^1$H NMR (400 MHz, Methanol-d$_4$) δ 8.06 (d, J=2.1 Hz, 1H), 7.75 (d, J=8.5 Hz, 1H), 7.36 (dd, J=8.2, 1.9 Hz, 1H), 7.32 (s, 1H), 7.17 (dd, J=8.5, 2.5 Hz, 1H), 7.11 (d, J=2.3 Hz, 1H), 6.89 (dd, J=8.2, 2.1 Hz, 1H), 6.23 (d, J=15.5 Hz, 1H), 5.90 (dd, J=15.5, 7.6 Hz, 1H), 4.07 (s, 4H), 4.05 (s, 3H), 3.95-3.73 (m, 3H), 3.80 (s, 3H), 3.68 (dd, J=14.4, 7.8 Hz, 1H), 3.38 (dd, J=14.3, 6.1 Hz, 1H), 3.23 (s, 2H), 3.18-3.04 (m, 1H), 2.88-2.70 (m, 2H), 2.66 (s, OH), 2.63-2.42 (m, 3H), 2.25 (dt, J=23.2, 6.5 Hz, 1H), 2.09 (d, J=13.7 Hz, 1H), 2.03-1.64 (m, 3H), 1.51-1.21 (m, 2H), 1.21-1.04 (m, 5H). LCMS-ESI+ (m/z): [M+H]$^+$ calcd for $C_{39}H_{48}ClN_5O_7S$: 766.3; found: 766.1.

Example 122

To a scintillation vial charged with Example 121 (1.5 mg, 1 equiv.) in DMF (1 mL) at 0° C. was added KHMDS (1 M in THF, 75 μL, 38 equiv.). The mixture was stirred for 30 seconds, then iodomethane (15 μL, 120 equiv.) was added.

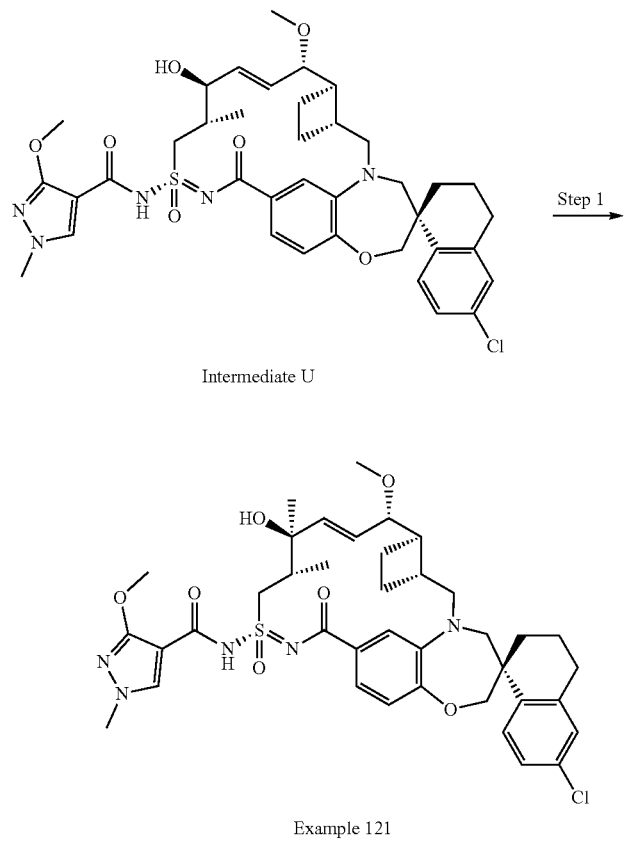

Intermediate U 120-1

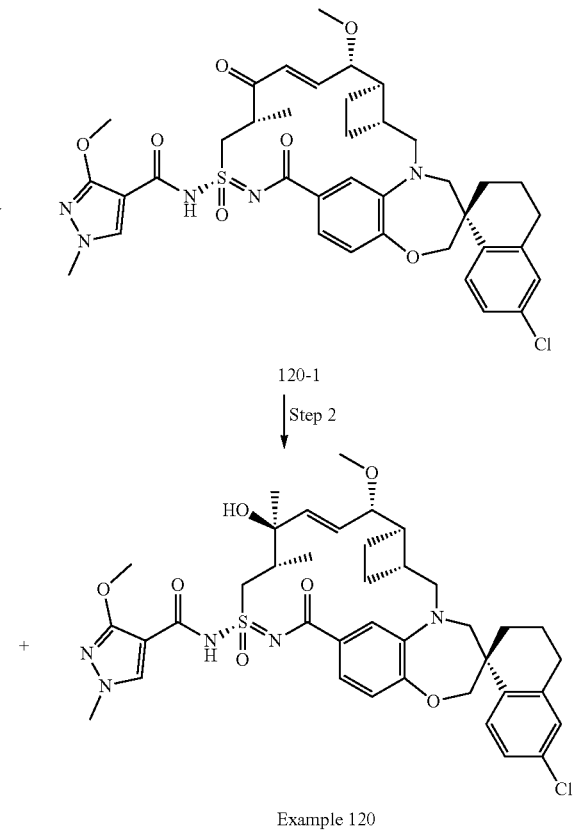

Example 121

Example 120

The mixture was stirred at 0° C. for 5 min, then warmed to ambient temperature and stirred for 45 min, 1 mL DMSO was added, the mixture was filtered, and purified by preparative reverse-phase HPLC (65-100% acetonitrile in water with 0.1% TFA) to give Example 122. ¹H NMR (400 MHz, Methanol-d₄) δ 8.08 (s, 1H), 7.78 (d, J=8.5 Hz, 1H), 7.43 (d, J=6.3 Hz, 2H), 7.19 (dd, J=8.5, 2.4 Hz, 1H), 7.12 (d, J=2.3 Hz, 1H), 6.93 (d, J=8.7 Hz, 1H), 5.94-5.75 (m, 2H), 4.15-4.06 (m, 6H), 3.94-3.85 (m, 1H), 3.83 (s, 3H), 3.71 (d, J=14.5 Hz, 2H), 3.27 (s, 3H), 3.23-3.12 (m, 1H), 3.02 (s, 3H), 2.90-2.71 (m, 2H), 2.68 (s, OH), 2.59 (s, 2H), 2.45 (t, J=7.2 Hz, 1H), 2.12 (d, J=13.4 Hz, 1H), 2.05-1.89 (m, 3H), 1.92-1.63 (m, 2H), 1.48 (t, J=11.9 Hz, 1H), 1.31 (s, 1H), 1.19 (s, 3H), 1.13 (d, J=6.8 Hz, 3H). LCMS-ESI+ (m/z): [M+H]⁺ calcd for $C_{40}H_{50}ClN_5O_7S$: 780.3; found: 780.1.

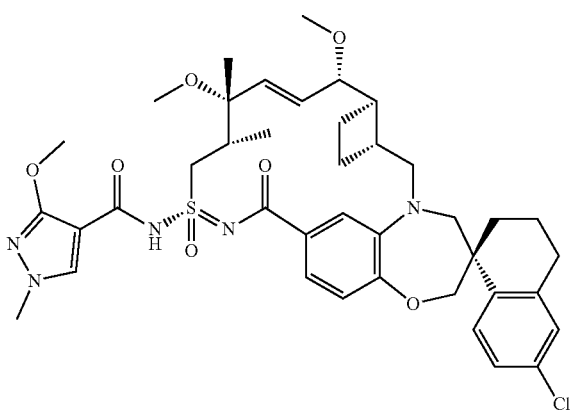 [SMILES: COc1nn(C)cc1C(=O)N[S@@]1(=O)=NC(=O)c2ccc3c(c2)N(C[C@@H]2CC[C@H]2[C@@H](OC)/C=C/[C@@](C)(OC)[C@H](C)C1)C[C@@]1(CCCc2cc(Cl)ccc21)CO3]

Example 123

Example 123 was prepared in a manner similar to Example 122, starting with Example 120. ¹H NMR (400 MHz, Methanol-d4) δ 8.08 (s, 1H), 7.77 (d, J=8.5 Hz, 1H), 7.41 (d, J=7.9 Hz, 2H), 7.19 (dd, J=8.5, 2.4 Hz, 1H), 7.13 (d, J=2.3 Hz, 1H), 6.92 (d, J=8.1 Hz, 1H), 5.96 (d, J=16.0 Hz, 1H), 5.80 (dd, J=16.0, 6.7 Hz, 1H), 4.17-4.02 (m, 6H), 3.95 (d, J=15.3 Hz, 1H), 3.89-3.78 (m, 5H), 3.73 (d, J=14.4 Hz, 1H), 3.43 (d, J=14.4 Hz, 1H), 3.29 (s, 3H), 3.21 (s, 3H), 2.86-2.73 (m, 2H), 2.68 (s, 2H), 2.57 (s, 2H), 2.26 (t, J=7.6 Hz, 1H), 2.11 (d, J=13.1 Hz, 1H), 2.03-1.70 (m, 3H), 1.61-1.43 (m, 1H), 1.35-1.26 (m, 4H), 1.16 (d, J=6.8 Hz, 3H). LCMS-ESI+ (m/z): [M+H]⁺ calcd for $C_{40}H_{50}ClN_5O_7S$: 780.3; found: 780.1.

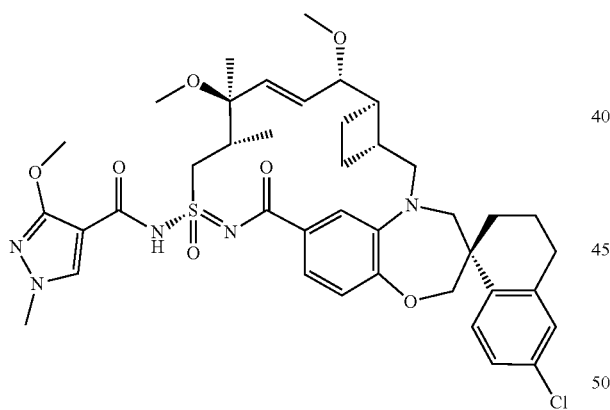

Example 124

Example 124 was prepared in a manner similar to Example 96 and Example 97, starting with 120-1, and isolated as a mixture of stereoisomers. ¹H NMR (400 MHz, Methanol-d₄) δ 8.08 (s, 1H), 7.73 (dd, J=8.6, 5.1 Hz, 1H), 7.54-7.31 (m, 1H), 7.27 (d, J=2.0 Hz, 1H), 7.18-7.04 (m, 2H), 6.89 (d, J=8.2 Hz, 1H), 6.32 (d, J=15.4 Hz, 1H), 5.92-5.76 (m, 1H), 4.17-4.07 (m, 3H), 4.05 (s, 3H), 4.00 (d, J=12.1 Hz, 1H), 3.80 (s, 3H), 3.84-3.73 (m, 3H), 3.67 (dd, J=23.1, 14.5 Hz, 1H), 3.39 (dd, J=14.5, 7.5 Hz, 1H), 3.19 (s, 3H), 3.05 (s, 3H), 2.87 (s, 3H), 2.83-2.68 (m, 3H), 2.67-2.52 (m, 2H), 2.52-2.27 (m, 1H), 2.14-2.00 (m, 1H), 2.00-1.87 (m, 3H), 1.79 (ddt, J=17.4, 12.2, 8.9 Hz, 2H), 1.50-1.08 (m, 2H), 1.25 (d, J=6.9 Hz, 3H). LCMS-ESI+ (m/z): [M+H]⁺ calcd for $C_{42}H_{53}ClN_6O_8S$: 837.3; found: 837.0.

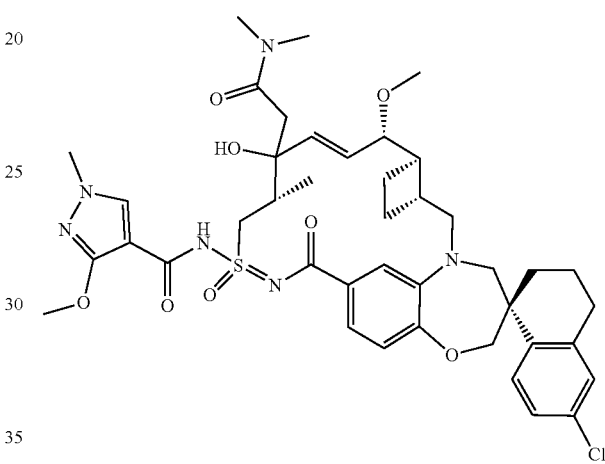

Example 125 and Example 126

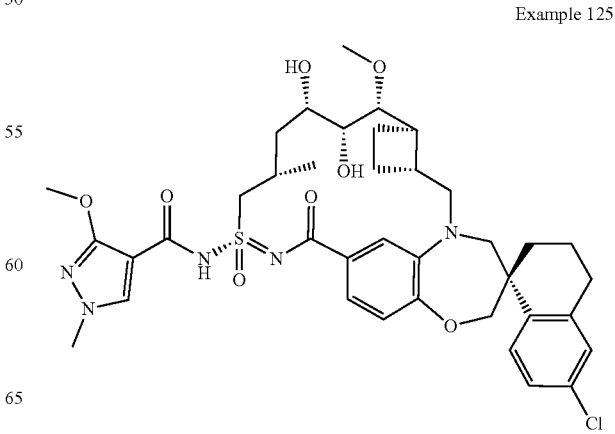

Example 125

Example 126

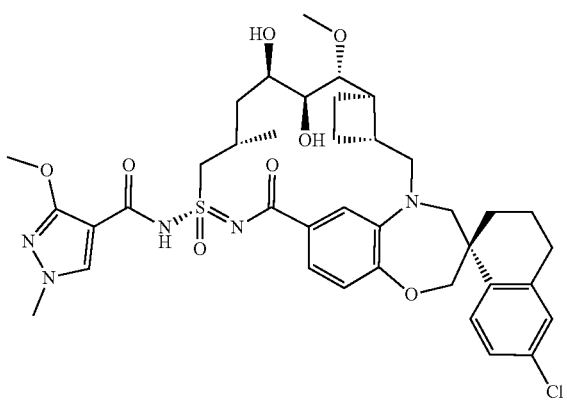

Osmium tetroxide solution (2.5% wt in tert-butyl alcohol, 2.77 mL, 220 µmol) was added over 1 min via syringe to a stirred mixture of Intermediate T (155 mg, 211 µmol) and DMAP (54.0 mg, 442 µmol) in tert-butyl alcohol (4.5 mL), tetrahydrofuran (2.5 mL), and water (1.0 mL) at room temperature. After 28 min, the resulting mixture was warmed to 70° C. After 9 min, the resulting mixture was cooled to room temperature over 3 min DMAP (27.0 mg, 221 µmol) was added, and the resulting mixture was warmed to 80° C. After 81 min, the resulting mixture was cooled to room temperature, sodium sulfite (318 mg, 2.53 mmol) was added, and the resulting mixture was stirred vigorously. After 2 min, water (1.5 mL) was added. After 28 min, the resulting mixture was filtered, and the filter cake was extracted with ethyl acetate (100 mL). Citric acid (1.2 g) was added to the filtrate, and the resulting mixture was washed with a mixture of water and brine (1:1 v:v, 2×70 mL), dried over anhydrous magnesium sulfate, filtered, and concentrated under reduced pressure. The residue was purified by flash column chromatography on silica gel (0 to 10% methanol in dichloromethane) to give a mixture of Example 125 and Example 126. A portion of this mixture (15 mg) was purified by reverse phase preparative HPLC (0.1% trifluoroacetic acid in acetonitrile/water) to give Example 125 (faster eluting diastereomer on reverse phase HPLC; the stereochemistry of dihydroxylation was tentatively assigned) and Example 126 (slower eluting diastereomer on reverse phase HPLC; the stereochemistry of dihydroxylation was tentatively assigned).

Example 125: $^1$H NMR (400 MHz, Acetone-$d_6$) δ 8.13 (s, 1H), 7.80 (d, J=8.5 Hz, 1H), 7.54-7.42 (m, 2H), 7.26 (dd, J=8.5, 2.3 Hz, 1H), 7.15 (d, J=2.3 Hz, 1H), 6.94 (d, J=8.1 Hz, 1H), 4.55 (dt, J=9.2, 5.0 Hz, 1H), 4.38 (dd, J=5.0, 2.3 Hz, 1H), 4.26-3.16 (m, 8H), 4.08 (s, 3H), 3.86 (s, 3H), 3.44 (s, 3H), 3.02-1.23 (m, 16H), 1.20 (d, J=6.8 Hz, 3H). LCMS-ESI+ (m/z): [M+H]$^+$ calcd for $C_{38}H_{48}ClN_5O_8S$: 770.3; found: 770.0.

Example 126: $^1$H NMR (400 MHz, Acetone-$d_6$) δ 8.09 (s, 1H), 7.81 (d, J=8.5 Hz, 1H), 7.50-7.20 (m, 3H), 7.14 (d, J=2.2 Hz, 1H), 6.91 (d, J=8.1 Hz, 1H), 4.38-3.03 (m, 16H), 3.43 (s, 3H), 2.91-0.80 (m, 19H). LCMS-ESI+ (m/z): [M+H]$^+$ calcd for $C_{38}H_{48}ClN_5O_8S$: 770.3; found: 770.2.

Example 127

Intermediate U (5 mg) was dissolved in DCM and 50 µL of diethylaminosulfur trifluoride (DAST) was added via pipette. Upon completion, the reaction mixture was purified directly via Gilson reverse phase prep HPLC (40-100% ACN/$H_2O$ with 0.1% TFA) to give Example 127. $^1$H NMR (400 MHz, Methanol-$d_4$) δ 8.07 (s, 1H), 7.77 (d, J=8.5 Hz, 1H), 7.38-7.15 (m, 2H), 7.12 (s, 1H), 6.91 (d, J=8.3 Hz, 1H), 6.51 (m, 1H), 5.94 (dd, J=15.7, 5.7 Hz, 1H), 5.25 (m, 1H), 4.27-4.04 (m, 5H), 3.94-3.65 (m, 6H), 3.42 (d, J=14.5 Hz, 1H), 3.35 (s, 2H), 3.12-2.99 (m, 1H), 2.86-2.66 (m, 2H), 2.39 (s, 2H), 2.11 (d, J=14.1 Hz, 1H), 1.95 (d, J=5.6 Hz, 4H), 1.79 (q, J=7.9 Hz, 2H), 1.47 (d, J=14.4 Hz, 1H), 1.36 (d, J=7.0 Hz, 3H). LCMS-ESI+ (m/z): [M+H]$^+$ calcd for $C_{38}H_{46}ClFN_5O_6S$: 754.3; found: 754.1.

Example 128, Example 129, and Example 130

Rhodium(III) chloride (1.1 mg, 5.4 µmol) was added to a vigorously stirred solution of Intermediate T (20.0 mg, 27.2 µmol) in ethanol (1.0 mL), tetrahydrofuran (1.0 mL), and water (0.15 mL) at room temperature, and the resulting mixture was warmed to 80° C. After 35 min, rhodium(III) chloride (11.4 mg, 54.5 µmol) was added, and the resulting mixture was warmed to 90° C. After 20 h, the resulting mixture was cooled to room temperature and was filtered through celite. The filter cake was extracted with methanol, and the combined filtrates were concentrated under reduced pressure. The residue was purified by reverse phase preparative HPLC (0.1% trifluoroacetic acid in acetonitrile/water) to give Example 128 (mixture of E- and Z-olefin isomers, stereochemistry tentatively assigned), Example 129 (mixture of E- and Z-olefin isomers, stereochemistry tentatively assigned), and Example 130 (mixture of E- and Z-olefin isomers, stereochemistry tentatively assigned).

Example 128

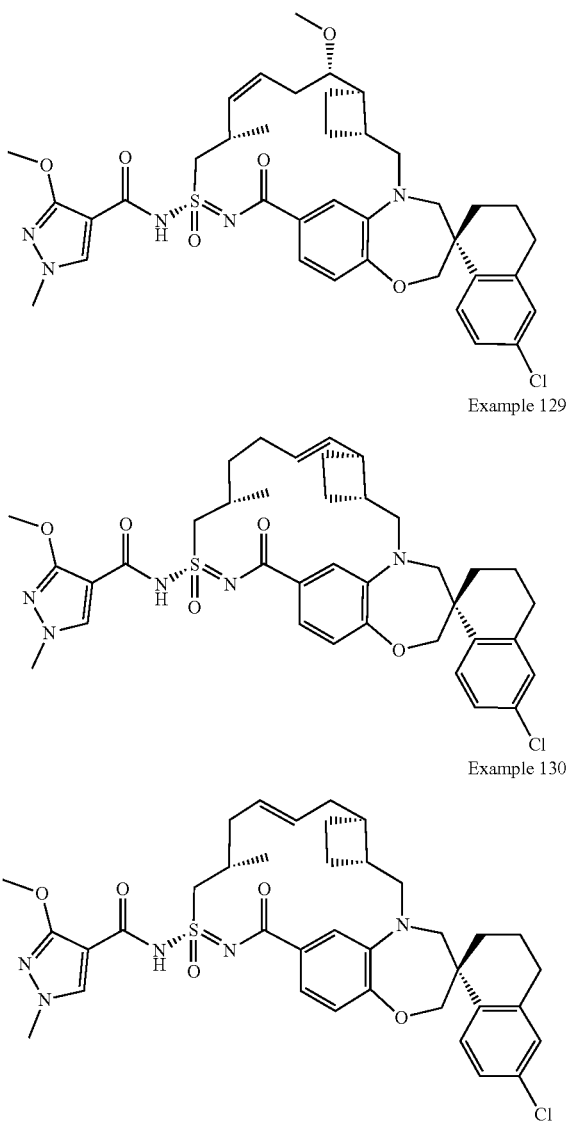

Example 129

Example 130

Example 128: ¹H NMR (400 MHz, Acetone-d₆) δ 8.12 (s, 0.5H), 8.10 (s, 0.5H), 7.84-7.78 (m, 0.5H), 7.78-7.72 (m, 0.5H), 7.64 (d, J=1.9 Hz, 0.5H), 7.57 (d, J=2.0 Hz, 0.5H), 7.48-7.37 (m, 1H), 7.29-7.19 (m, 1H), 7.14 (d, J=4.4 Hz, 1H), 6.93 (d, J=8.3 Hz, 0.5H), 6.91-6.85 (m, 0.5H), 5.93 (dt, J=17.1, 9.5 Hz, 0.5H), 5.76 (dd, J=7.2, 6.3 Hz, 0.5H), 5.65-5.04 (m, 1H), 4.36-3.06 (m, 8H), 4.07 (s, 1.5H), 4.06 (s, 1.5H), 3.86 (s, 1.5H), 3.85 (s, 1.5H), 3.40 (s, 1.5H), 3.35 (s, 1.5H), 2.95-1.03 (m, 16H), 1.15 (d, J=6.6 Hz, 1.5H), 1.07 (d, J=6.6 Hz, 1.5H). LCMS-ESI+ (m/z): [M+H]⁺ calcd for $C_{38}H_{46}ClN_5O_6S$: 736.3; found: 736.1.

Example 129: ¹H NMR (400 MHz, Acetone-d₆) δ 8.12 (s, 1H), 7.80 (d, J=9.0 Hz, 1H), 7.57-7.41 (m, 2H), 7.26 (dd, J=8.5, 2.3 Hz, 1H), 7.15 (s, 1H), 6.94 (dd, J=8.2, 1.5 Hz, 1H), 5.81 (dd, J=15.4, 6.0 Hz, 0.67H), 5.66 (dd, J=9.1, 6.0 Hz, 0.33H), 5.49 (dt, J=15.4, 6.3 Hz, 0.67H), 5.44-5.25 (m, 0.33H), 4.19-3.65 (m, 4.33H), 4.09 (s, 1H), 4.07 (s, 2H), 3.86 (s, 3H), 3.58 (dd, J=14.9, 3.6 Hz, 0.67H), 3.46 (d, J=14.6 Hz, 0.33H), 3.44 (d, J=14.2 Hz, 0.67H), 3.23-3.10 (m, 1H), 2.88-1.15 (m, 18H), 1.11 (d, J=6.7 Hz, 1H), 1.08 (d, J=6.6 Hz, 2H). LCMS-ESI+ (m/z): [M+H]⁺ calcd for $C_{37}H_{44}ClN_5O_5S$: 706.3; found: 706.1.

Example 130: ¹H NMR (400 MHz, Acetone-d₆) δ 8.13 (s, 1H), 7.80 (d, J=8.5 Hz, 1H), 7.49 (dd, J=8.1, 1.9 Hz, 1H), 7.38 (d, J=2.0 Hz, 1H), 7.25 (dd, J=8.5, 2.5 Hz, 1H), 7.15 (d, J=2.3 Hz, 1H), 6.94 (d, J=8.2 Hz, 1H), 4.27 (dd, J=15.1, 9.3 Hz, 1H), 4.20-3.60 (m, 6H), 4.09 (s, 3H), 3.86 (s, 3H), 3.54 (d, J=11.2 Hz, 1H), 3.47 (d, J=7.6 Hz, 1H), 3.41 (s, 1H), 3.36 (s, 3H), 3.22 (dd, J=15.1, 10.1 Hz, 1H), 2.95-1.25 (m, 19H), 1.18 (d, J=6.9 Hz, 3H). LCMS-ESI+ (m/z): [M+H]⁺ calcd for $C_{37}H_{44}ClN_5O_5S$: 706.3; found: 706.1.

Example 131

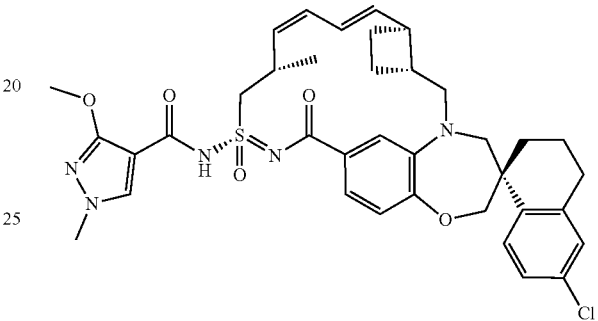

A solution of Intermediate W (150 mg, 208 μmol) in N,N-dimethylformamide (1.5 mL) at −40° C. was added via syringe to potassium hydride (63.8 mg, 1.59 mmol) at −40° C., and the resulting mixture was stirred. After 1 min, the resulting mixture was warmed to room temperature. After 15 min, the resulting mixture was cooled to −40° C. over 2 min, and 2-chloroethyl 4-methylbenzenesulfonate (377 μL, 2.08 mmol) was added via syringe. After 5 min, the resulting mixture was warmed to room temperature. After 15 min, the resulting mixture was warmed to 80° C. After 27 min, the resulting mixture was warmed to 100° C. After 5 h, the resulting mixture was cooled to room temperature and was purified by reverse phase preparative HPLC (0.1% trifluoroacetic acid in acetonitrile/water) to give Example 131 (stereochemistry tentatively assigned). ¹H NMR (400 MHz, Acetone-d₆) δ 8.11 (s, 1H), 7.82 (d, J=8.5 Hz, 1H), 7.60 (d, J=2.0 Hz, 1H), 7.49 (dd, J=8.2, 1.9 Hz, 1H), 7.27 (dd, J=8.5, 2.4 Hz, 1H), 7.15 (d, J=2.3 Hz, 1H), 6.97 (d, J=8.3 Hz, 1H), 6.72 (dd, J=15.4, 10.6 Hz, 1H), 6.05 (t, J=10.7 Hz, 1H), 5.96 (dd, J=15.4, 5.1 Hz, 1H), 5.30 (t, J=10.4 Hz, 1H), 4.14 (d, J=12.1 Hz, 1H), 4.11-3.98 (m, 2H), 4.06 (s, 3H), 3.93-3.79 (m, 2H), 3.86 (s, 3H), 3.77-3.60 (m, 2H), 3.52 (d, J=14.3 Hz, 1H), 3.20 (dd, J=15.2, 10.9 Hz, 1H), 3.11-1.39 (m, 12H), 1.16 (d, J=6.4 Hz, 3H). LCMS-ESI+ (m/z): [M+H]⁺ calcd for $C_{37}H_{42}ClN_5O_5S$: 704.3; found: 704.2.

Example 132

Step 1: AD-mix p (68.0 mg) was added to a vigorously stirred mixture of Example 131 (34.2 mg, 48.6 μmol), methanesulfonamide (18.5 mg, 194 μmol), in tert-butyl alcohol (0.8 mL), tetrahydrofuran (0.5 mL), and water (0.4 mL) at room temperature. After 30 min, AD-mix p (120 mg) was added, and the resulting mixture was warmed to 50° C. After 20 h, the resulting mixture was cooled to room temperature, and sodium sulfite (100 mg) was added. After 5 min, ethyl acetate (30 mL) and aqueous citric acid solution (10% wt, 10 mL) were added sequentially. The organic layer was washed sequentially with water (20 mL) and a mixture of water and brine (1:1 v:v, 20 mL), dried over anhydrous magnesium sulfate, filtered, and concentrated under reduced pressure. The residue was purified by reverse phase preparative HPLC (0.1% trifluoroacetic acid in acetonitrile/water) to give 132-1 (faster eluting diastereomer on reverse phase HPLC [the stereochemistry of dihydroxylation was tentatively assigned]) and 132-2 (slower eluting diastereomer on reverse phase HPLC [the stereochemistry of dihydroxylation was tentatively assigned]).

1H), 7.53 (d, J=2.0 Hz, 1H), 7.45 (dd, J=8.3, 1.9 Hz, 1H), 7.26 (dd, J=8.5, 2.4 Hz, 1H), 7.15 (d, J=2.3 Hz, 1H), 6.95 (d, J=8.2 Hz, 1H), 5.70-5.52 (m, 2H), 4.58 (d, J=4.9 Hz, 1H), 4.13 (d, J=12.1 Hz, 1H), 4.08 (s, 3H), 4.05 (d, J=12.1 Hz, 1H), 4.01-3.77 (m, 4H), 3.86 (s, 3H), 3.77-3.59 (m, 1H), 3.56 (d, J=14.5 Hz, 1H), 3.37 (s, 6H), 3.32-3.19 (m, 2H), 2.95-2.64 (m, 3H), 2.59-2.47 (m, 1H), 2.31-1.73 (m, 7H), 1.55-1.42 (m, 1H), 1.25 (d, J=6.7 Hz, 3H). LCMS-ESI+ (m/z): [M+H]+ calcd for $C_{39}H_{43}ClN_5O_7S$: 766.3; found: 766.2.

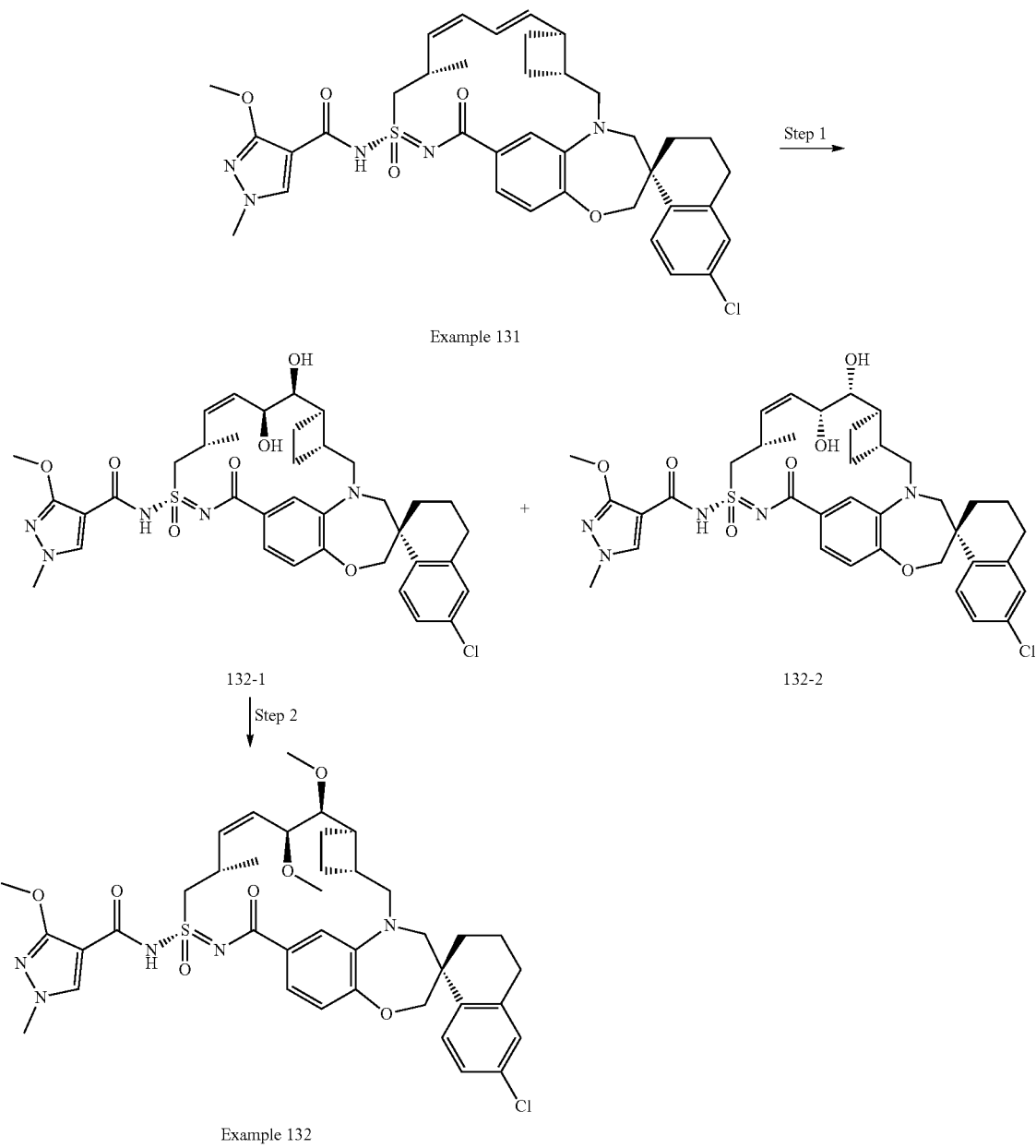

Example 131

132-1

132-2

Step 2

Example 132

Step 2: Example 132 (stereochemistry of the two methyl ether stereocenters tentatively assigned based on the stereochemistry of 132-1) was synthesized in a manner similar to Example 37 using 132-1 instead of Example 35. $^1$H NMR (400 MHz, Acetone-$d_6$) b 8.12 (s, 1H), 7.80 (d, J=8.5 Hz, Example 133

Example 133 (stereochemistry of the two methyl ether stereocenters tentatively assigned based on the stereochemistry of 132-2) was synthesized in a manner similar to Example 132 (Step 2) using 132-1 instead of 132-1. $^1$H NMR (400 MHz, Acetone-$d_6$) δ 8.11 (s, 1H), 7.80 (d, J=8.5 Hz, 1H), 7.78-7.71 (m, 1H), 7.40 (dd, J=8.2, 1.9 Hz, 1H), 7.26 (dd, J=8.5, 2.4 Hz, 1H), 7.14 (d, J=2.3 Hz, 1H), 6.91 (d, J=8.2 Hz, 1H), 5.88-5.63 (m, 1H), 5.36-5.18 (m, 1H), 4.19-3.60 (m, 6H), 4.07 (s, 3H), 3.85 (s, 3H), 3.51 (d, J=14.5 Hz, 1H), 3.47-3.01 (m, 2H), 3.36 (s, 3H), 3.17 (s, 3H), 2.95-1.61 (m, 13H), 1.60-1.43 (m, 1H), 1.20 (d, J=6.8 Hz, 3H). LCMS-ESI+ (m/z): [M+H]$^+$ calcd for $C_{39}H_{48}ClN_5O_7S$: 766.3; found: 766.2.

Example 134

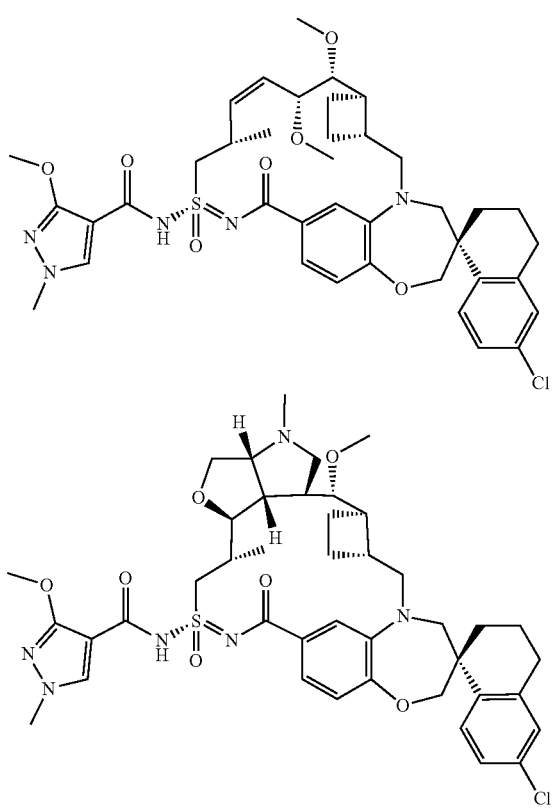

A vigorously stirred mixture of 88-1 (11.5 mg, 14.5 μmol) and sarcosine (25.9 mg, 290 μmol) in toluene (3.0 mL) was warmed to 120° C. After 45 min, the resulting mixture was cooled to room temperature and was concentrated under reduced pressure. The residue was purified by reverse phase preparative HPLC (0.1% trifluoroacetic acid in acetonitrile/water) to give Example 134 (faster eluting diastereomer on reverse phase HPLC (the triplet of stereochemical assignments of the $C_2$-, $C_3$-, and $C_4$-stereocenters on the pyrrolidine ring relative to the stereochemistry at the $C_2$-position of the tetrahydrofuran ring were tentatively assigned)). $^1$H NMR (400 MHz, Methanol-$d_4$) δ 8.17-6.85 (m, 7H), 5.59 (t, J=5.9 Hz, 1H), 5.09-5.02 (m, 1H), 4.46 (d, J=3.0 Hz, 1H), 4.36 (d, J=3.1 Hz, 1H), 4.28-3.03 (m, 18H), 3.03-1.24 (m, 19H), 1.20 (dd, J=6.9, 3.5 Hz, 3H). LCMS-ESI+ (m/z): [M+H]$^+$ calcd for $C_{42}H_{53}ClN_6O_7S$: 821.3; found: 821.3.

Example 135

Step 1: Sodium borohydride (18.3 mg, 484 μmol) was added to a stirred solution of 88-1 (19.2 mg, 24.2 μmol) in methanol (5.0 mL) and tetrahydrofuran (5.0 mL) at 0° C., and the resulting mixture was warmed to room temperature. After 8 min, aqueous phosphoric acid solution (20% wt, 10 mL) and ethyl acetate were added sequentially. The organic layer was washed with water, dried over anhydrous magnesium sulfate, filtered, and concentrated under reduced pressure to give 135-1.

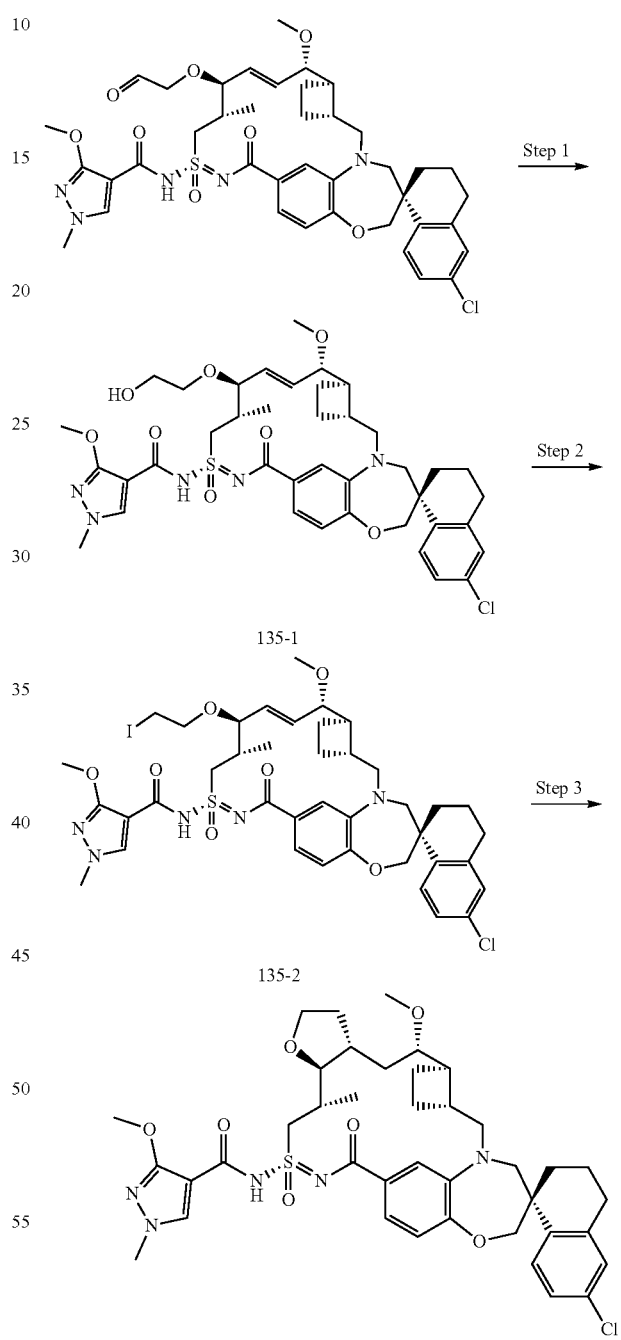

Step 2: Iodine (24.6 mg, 96.8 μmol) was added to a vigorously stirred mixture of 135-1 (19.2 mg, 24.1 μmol), diphenyl-2-pyridylphosphine (26.1 mg, 99.2 μmol), and imidazole (16.5 mg, 242 μmol) in dichloromethane (1.5 mL) at room temperature. After 180 min, ethyl acetate (60 mL)

and aqueous hydrogen chloride solution (2.0 M, 2.0 mL) were added sequentially. The organic layer was washed sequentially with water (40 mL), aqueous hydrogen chloride solution (0.005 M, 40 mL), and water (40 mL), dried over anhydrous magnesium sulfate, filtered, and concentrated under reduced pressure to give 135-2.

Step 3: A solution of 2,2'-(diazene-1,2-diyl)bis(2-methyl-propanenitrile) (8.0 mg, 48.6 µmol) in benzene (0.62 mL) was added over 45 min via syringe pump to a stirred mixture of 135-2 (22.0 mg, 24.3 µmol), tributylstannane (65.3 µL, 243 µmol), and bromobenzene (30.7 µL, 291 µmol) in benzene (5.0 mL) at 90° C. After 25 min, the resulting mixture was cooled to room temperature and was concentrated under reduced pressure. The residue was purified by reverse phase preparative HPLC (0.1% trifluoroacetic acid in acetonitrile/water) to give Example 135. $^1$H NMR (400 MHz, Acetone-d$_6$) δ 8.13 (s, 1H), 7.80 (d, J=8.5 Hz, 1H), 7.49 (dd, J=8.1, 1.9 Hz, 1H), 7.38 (d, J=2.0 Hz, 1H), 7.25 (dd, J=8.5, 2.5 Hz, 1H), 7.15 (d, J=2.3 Hz, 1H), 6.94 (d, J=8.2 Hz, 1H), 4.27 (dd, J=15.1, 9.3 Hz, 1H), 4.20-3.60 (m, 6H), 4.09 (s, 3H), 3.86 (s, 3H), 3.54 (d, J=11.2 Hz, 1H), 3.47 (d, J=7.6 Hz, 1H), 3.41 (s, 1H), 3.36 (s, 3H), 3.22 (dd, J=15.1, 10.1 Hz, 1H), 2.95-1.25 (m, 19H), 1.18 (d, J=6.9 Hz, 3H). LCMS-ESI+(m/z): [M+H]$^+$ calcd for C$_{40}$H$_{50}$ClN$_5$O$_7$S: 780.3; found: 780.2.

Example 136

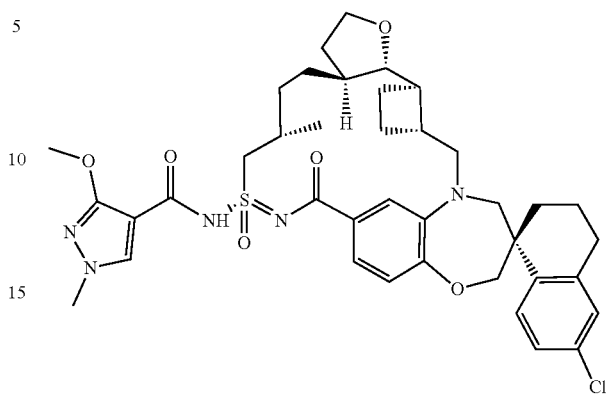

Example 136 was synthesized in a manner similar to Example 135 using 58-1 instead of 88-1. $^1$H NMR (400 MHz, Acetone-d$_6$) δ 8.11 (s, 1H), 7.80 (d, J=8.5 Hz, 1H), 7.44 (d, J=7.9 Hz, 2H), 7.25 (dd, J=8.5, 2.3 Hz, 1H), 7.15 (d, J=2.3 Hz, 1H), 6.94 (d, J=8.0 Hz, 1H), 4.16 (d, J=12.1 Hz, 1H), 4.07 (s, 3H), 4.05 (d, J=12.1 Hz, 1H), 3.95 (dd, J=15.1, 3.9 Hz, 1H), 3.86 (s, 3H), 3.82-3.59 (m, 4H), 3.56 (dd, J=6.7, 3.1 Hz, 1H), 3.48 (d, J=14.4 Hz, 1H), 3.23 (dd, J=15.1, 9.6 Hz, 1H), 2.91-1.39 (m, 21H), 1.08 (d, J=6.8 Hz, 3H). LCMS-ESI+(m/z): [M+H]$^+$ calcd for C$_{39}$H$_{48}$ClN$_5$O$_6$S: 750.3; found: 750.2.

Example 137 and Example 138

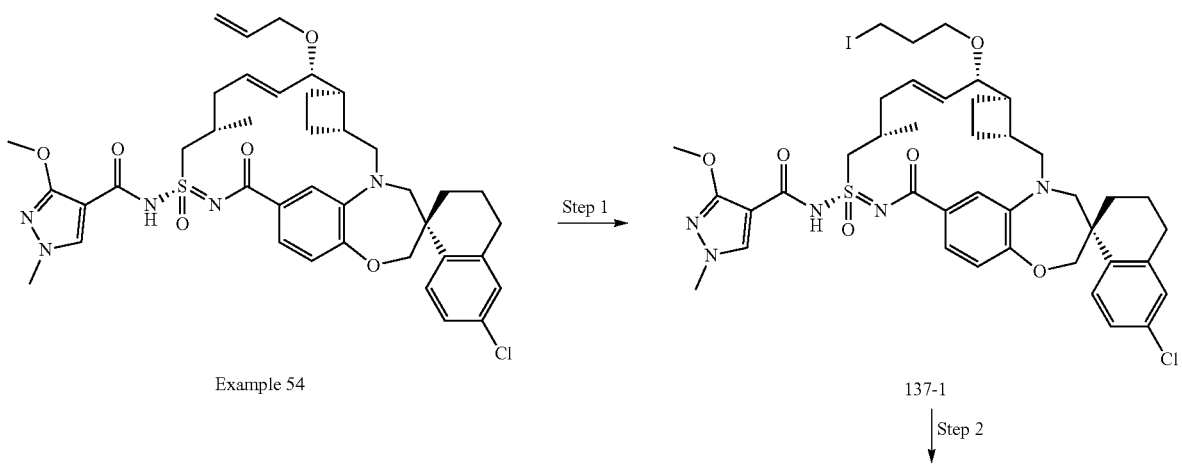

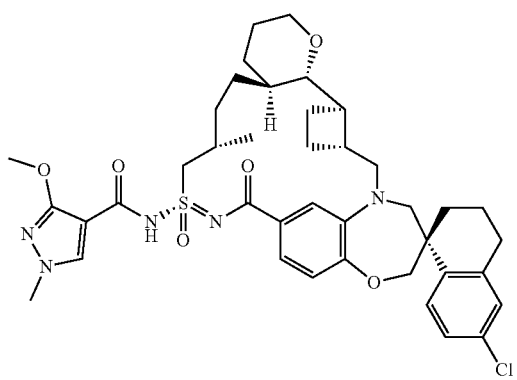

Example 138

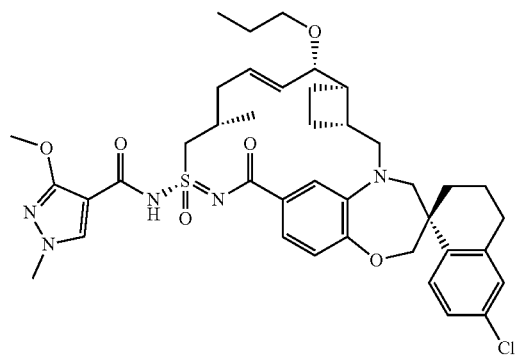

Example 137

Step 1: 9-Borabicyclo[3.3.1]nonane solution (0.50 M in tetrahydrofuran, 130 μL, 65 μmol) was added via syringe to a stirred solution of Example 54 (16.5 mg, 21.6 μmol) in tetrahydrofuran (1.0 mL) at 0° C. After 18 min, the resulting mixture was warmed to room temperature. After 2 min, 9-borabicyclo[3.3.1]nonane solution (0.50 M in tetrahydrofuran, 100 μL, 50 μmol) was added via syringe. After 22 min, 9-borabicyclo[3.3.1]nonane solution (0.50 M in tetrahydrofuran, 300 μL, 150 μmol) was added via syringe. After 150 min, the resulting mixture was cooled to 0° C. Water (0.3 mL) and sodium perborate tetrahydrate (133 mg, 866 μmol) were added sequentially, and the resulting mixture was warmed to room temperature and was stirred vigorously. After 19.5 h, sodium sulfite (300 mg) was added. After 5 min, ethyl acetate (60 mL) was added. The organic layer was washed sequentially with aqueous citric acid solution (10% wt, 50 mL) and water (50 mL), dried over anhydrous magnesium sulfate, filtered, and concentrated under reduced pressure. The residue was dissolved in dichloromethane (2.5 mL), and the resulting mixture was stirred at room temperature. diphenyl-2-pyridylphosphine (93.0 mg, 353 μmol), imidazole (50.4 mg, 740 μmol), and iodine (88.6 mg, 349 μmol) were added sequentially. After 105 min, ethyl acetate (20 mL), diethyl ether (40 mL), and aqueous hydrogen chloride solution (2.0 M, 5.0 mL) were added sequentially. The organic layer was washed with water (2×40 mL), dried over anhydrous magnesium sulfate, filtered, and concentrated under reduced pressure to give 137-1.

Step 2: Example 137 and Example 138 (2:1 mixture epimers at the $C_3$-position of the tetrahydropyran ring; the stereochemistry of the major diastereomer was tentatively assigned) were synthesized in a manner similar to Example 135 (Step 3) using 137-1 instead of 135-2.

Example 137: $^1$H NMR (400 MHz, Acetone-$d_6$) δ 8.13 (d, J=2.7 Hz, 1H), 7.79 (d, J=8.5 Hz, 1H), 7.56-7.40 (m, 1H), 7.38-7.21 (m, 2H), 7.14 (d, J=2.3 Hz, 1H), 6.96-6.91 (m, 1H), 6.14 (dt, J=14.2, 6.8 Hz, 1H), 5.69 (dd, J=15.6, 7.2 Hz, 1H), 4.22-3.99 (m, 4H), 4.08 (s, 3H), 3.96-3.83 (m, 2H), 3.86 (s, 3H), 3.77 (d, J=14.5 Hz, 1H), 3.53-3.39 (m, 1H), 3.35-3.23 (m, 1H), 3.15 (dd, J=15.2, 10.9 Hz, 1H), 2.93-1.17 (m, 21H), 1.13 (d, J=6.7 Hz, 3H). LCMS-ESI+ (m/z): [M+H]$^+$ calcd for $C_{40}H_{50}ClN_5O_6S$: 764.3; found: 764.2.

Example 138: $^1$H NMR (400 MHz, Acetone-$d_6$) δ 8.12 (s, 1H), 7.86-7.75 (m, 1H), 7.73-7.17 (m, 3H), 7.15 (d, J=2.5 Hz, 1H), 6.93 (d, J=8.2 Hz, 0.67H), 6.88 (d, J=8.1 Hz, 0.33H), 4.20-2.99 (m, 13H), 3.86 (s, 3H), 3.00-0.97 (m, 23H), 1.15 (d, J=6.8 Hz, 1H), 1.04 (d, J=6.7, 2H). LCMS-ESI+ (m/z): [M+H]$^+$ calcd for $C_{40}H_{50}ClN_5O_6S$: 764.3; found: 764.3.

Example 139

Step 1: N-Iodosuccinimide (71.8 mg, 319 μmol) and ethyl vinyl ether (45.8 μL, 479 μmol) were added sequentially to a stirred solution of Intermediate U (60.0 mg, 79.8 μmol) in dichloromethane (0.8 mL) at −78° C. and the resulting mixture was warmed to 0° C. over 52 min and then warmed to room temperature. After 45 min, the resulting mixture was purified by flash column chromatography on silica gel (0 to 5% methanol in dichloromethane) to give 139-1.

Step 2: A solution of 2,2'-(diazene-1,2-diyl)bis(2-methylpropanenitrile) (26.3 mg, 160 μmol) in benzene (3.0 mL) was added over 45 min via syringe pump to a stirred mixture of 139-1 (76.0 mg, 80.0 μmol), tributylstannane (215 μL, 800 μmol), and bromobenzene (101 μL, 960 μmol) in benzene (100 mL) at 90° C. After 15 min, the resulting mixture was cooled to room temperature and was concentrated under reduced pressure. The residue was purified by flash column chromatography on silica gel (0 to 5% methanol in dichloromethane) to give 139-2.

Intermediate U

287
-continued

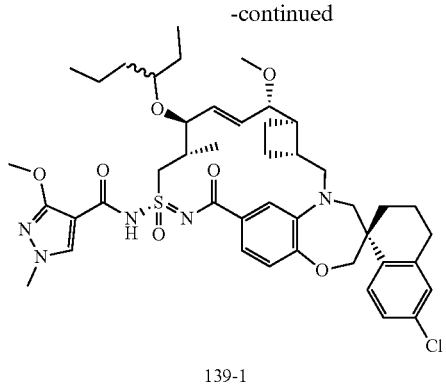

139-1

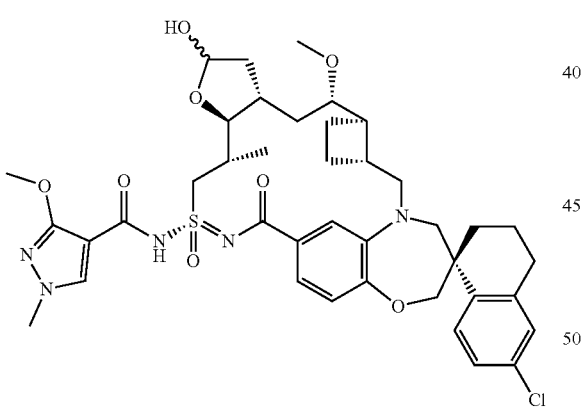

139-2

HO

Example 139

Step 3: Aqueous hydrogen chloride solution (2.0 M, 1.0 mL, 2.0 mmol) was added via syringe to a stirred solution of 139-2 (65.9 mg, 80 µmol) in acetonitrile (4.0 mL) and dimethylsulfoxide (0.2 mL) at room temperature. After 60 min, the resulting mixture was purified by reverse phase preparative HPLC (0.1% trifluoroacetic acid in acetonitrile/water) to give Example 139. $^1$H NMR (400 MHz, Acetone-$d_6$) δ 8.20-8.10 (m, 1H), 7.86-6.82 (m, 6H), 5.56-5.14 (m, 1H), 4.36-3.12 (m, 18H), 3.11-0.97 (m, 22H). LCMS-ESI+ (m/z): [M+H]$^+$ calcd for $C_{40}H_{50}ClN_5O_8S$: 796.3; found: 796.3.

288
Example 140

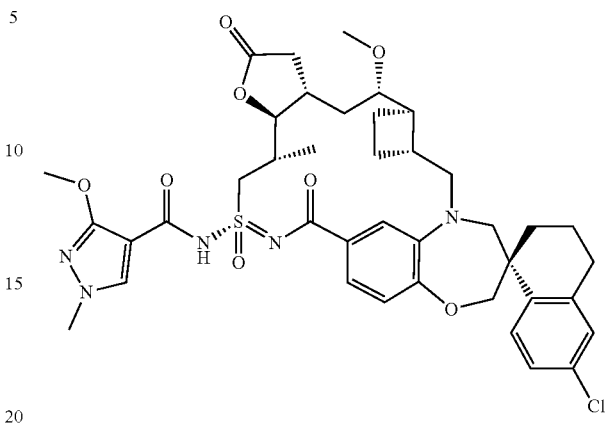

Tetrapropylammonium perruthenate (0.1 mg, 0.4 µmol) was added to a stirred mixture of Example 139 (6.0 mg, 7.5 µmol), 4-methylmorpholine (1.7 µL, 15 µmol), 4-methylmorpholine-4-oxide (1.8 mg, 15 µmol), and 4 Å molecular sieves (10.0 mg) in acetonitrile (1.0 mL) at room temperature. After 15 min, the resulting mixture was purified by reverse phase preparative HPLC (0.1% trifluoroacetic acid in acetonitrile/water) to give Example 140 (stereochemistry tentatively assigned). $^1$H NMR (400 MHz, Acetone-$d_6$) δ 8.15 (s, 1H), 7.79 (d, J=8.5 Hz, 1H), 7.49 (dd, J=8.2, 1.9 Hz, 1H), 7.33 (d, J=1.9 Hz, 1H), 7.25 (dd, J=8.5, 2.4 Hz, 1H), 7.15 (d, J=2.3 Hz, 1H), 6.95 (d, J=8.2 Hz, 1H), 4.32-4.19 (m, 2H), 4.14-4.06 (m, 2H), 4.10 (s, 3H), 3.99 (d, J=15.1 Hz, 1H), 3.92-3.83 (m, 1H), 3.87 (s, 3H), 3.69 (d, J=14.3 Hz, 1H), 3.57 (d, J=11.3 Hz, 1H), 3.43-3.33 (m, 1H), 3.39 (s, 3H), 3.22 (dd, J=15.3, 9.7 Hz, 1H), 2.98-1.28 (m, 18H), 1.25 (d, J=7.0 Hz, 3H). LCMS-ESI+ (m/z): [M+H]$^+$ calcd for $C_{40}H_{48}ClN_5O_8S$: 794.3; found: 794.2.

Example 141

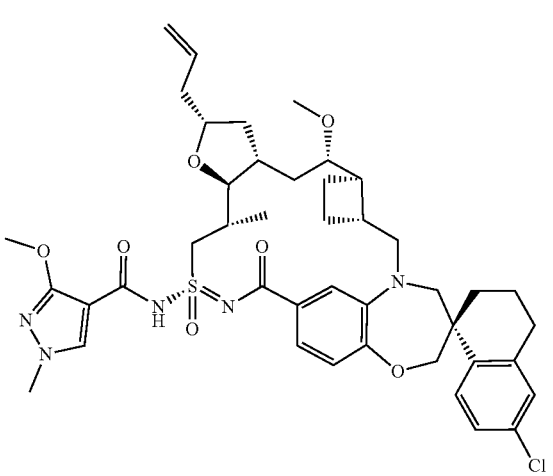

141-1

Example 141

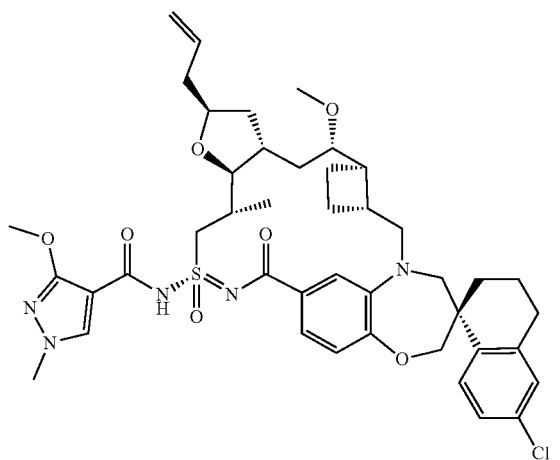

Boron trifluoride diethyl etherate (12.7 µL, 103 µmol) was added via syringe to a stirred mixture of Example 139 (16.4 mg, 20.6 µmol) and allyl(trimethyl)silane (81.8 µL, 515 µmol) in dichloromethane (1.8 mL) at −78° C., and the resulting mixture was warmed to room temperature over 190 min. After 50 min, aqueous sodium acetate solution (25% wt, 200 µL) was added via syringe, and the resulting mixture was concentrated under reduced pressure. The residue was purified by reverse phase preparative HPLC (0.1% trifluoroacetic acid in acetonitrile/water) to give 141-1 (faster eluting diastereomer on reverse phase HPLC, the stereochemistry of $C_5$-position of the tetrahydrofuran ring tentatively assigned) and Example 141 (slower eluting diastereomer on reverse phase HPLC, the stereochemistry of $C_5$-position of the tetrahydrofuran ring tentatively assigned).

Example 141: $^1$H NMR (400 MHz, Acetone-$d_6$) δ 8.13 (s, 1H), 7.81 (d, J=8.5 Hz, 1H), 7.41-7.33 (m, 2H), 7.26 (dd, J=8.5, 2.5 Hz, 1H), 7.14 (d, J=2.3 Hz, 1H), 6.94 (d, J=8.5 Hz, 1H), 5.94-5.77 (m, 1H), 5.17-5.06 (m, 1H), 5.03 (d, J=10.3 Hz, 1H), 4.26-4.18 (m, 1H), 4.15 (d, J=12.1 Hz, 1H), 4.13-3.71 (m, 5H), 4.06 (s, 3H), 3.86 (s, 3H), 3.49-3.34 (m, 1H), 3.42 (s, 3H), 3.31 (d, J=10.6 Hz, 1H), 3.18 (dd, J=15.1, 10.6 Hz, 1H), 2.97-1.22 (m, 21H), 1.06 (d, J=6.8 Hz, 3H). LCMS-ESI+ (m/z): [M+H]$^+$ calcd for $C_{43}H_{54}ClN_5O_7S$: 820.3; found: 820.3.

Example 142 and Example 143

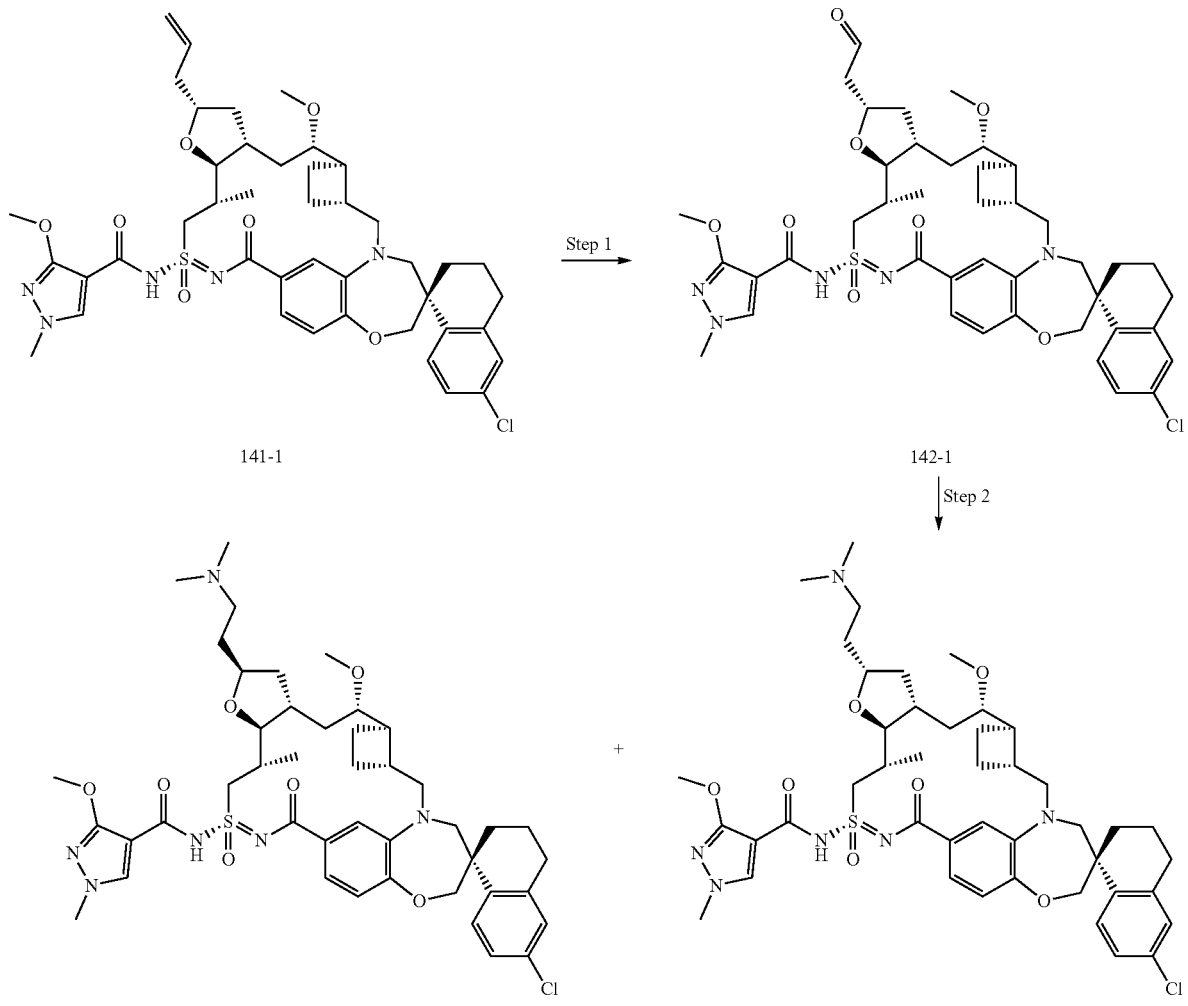

Step 1: 142-1 was synthesized in a manner similar to 58-1 using 141-1 instead of Example 54.

Step 2: Sodium triacetoxyborohydride (47.1 mg, 222 µmol) and dimethylamine solution (2.0 M in tetrahydrofuran, 68.0 µL, 140 µmol) were added concurrently to a stirred mixture of 142-1 (9.0 mg, 11 µmol) and acetic acid (7.7 µL, 140 µmol) in dichloromethane (1.5 mL) at room temperature, and the resulting mixture was warmed to 40° C. After 105 min, the resulting mixture was cooled to room temperature and was concentrated under reduced pressure. The residue was purified by reverse phase preparative HPLC (0.1% trifluoroacetic acid in acetonitrile/water) to give Example 142 (faster eluting diastereomer [the stereochemistry of C5-position of the tetrahydrofuran ring was tentatively assigned] on reverse phase HPLC) and Example 143 (slower eluting diastereomer [the stereochemistry of C5-position of the tetrahydrofuran ring was tentatively assigned] on reverse phase HPLC).

Example 142: $^1$H NMR (400 MHz, Methanol-$d_4$) δ 8.06 (s, 1H), 7.78 (d, J=8.5 Hz, 1H), 7.42 (dd, J=8.2, 1.8 Hz, 1H), 7.24-7.17 (m, 2H), 7.13 (d, J=2.3 Hz, 1H), 6.95 (d, J=8.2 Hz, 1H), 4.28 (dd, J=14.9, 9.8 Hz, 1H), 4.16-3.96 (m, 4H), 4.07 (s, 3H), 3.90-3.82 (m, 1H), 3.82 (s, 3H), 3.67 (d, J=14.1 Hz, 1H), 3.61 (d, J=9.2 Hz, 1H), 3.56-3.47 (m, 1H), 3.40 (s, 3H), 3.36-3.07 (m, 3H), 2.93 (s, 3H), 2.91 (s, 3H), 2.86-1.27 (m, 21H), 1.24 (d, J=6.9 Hz, 3H). LCMS-ESI+ (m/z): [M+H]$^+$ calcd for $C_{44}H_{59}ClN_6O_7S$: 851.4; found: 851.4.

Example 143: $^1$H NMR (400 MHz, Methanol-$d_4$) δ 8.03 (s, 1H), 7.76 (d, J=8.6 Hz, 1H), 7.42 (dd, J=8.2, 1.9 Hz, 1H), 7.22 (s, 1H), 7.18 (dd, J=8.5, 2.3 Hz, 1H), 7.11 (d, J=2.3 Hz, 1H), 6.91 (d, J=8.2 Hz, 1H), 4.18 (dd, J=14.7, 8.7 Hz, 1H), 4.12-4.08 (m, 2H), 4.08-3.88 (m, 3H), 4.01 (s, 3H), 3.84 (d, J=15.3 Hz, 1H), 3.79 (s, 3H), 3.64 (d, J=14.2 Hz, 1H), 3.53 (d, J=10.6 Hz, 1H), 3.38 (s, 3H), 3.35-3.09 (m, 3H), 2.97 (s, 3H), 2.96 (s, 3H), 2.94-1.27 (m, 21H), 1.21 (d, J=6.9 Hz, 3H). LCMS-ESI+ (m/z): [M+H]$^+$ calcd for $C_{44}H_{59}ClN_6O_7S$: 851.4; found: 851.4.

Example 144, Example 145, Example 146, Example 147, and Example 148

Step 1: A mixture of 1-[(1-cyanocyclohexyl)azo]cyclohexanecarbonitrile (22.7 mg, 93.0 µmol) and thiophenol (14.3 µL, 140 µmol) in toluene (1.8 mL) was added over 60 min via syringe pump to a stirred mixture of 79-1 (36.9 mg, 46.6 µmol) and thiophenol (14.7 µL, 140 µmol) in toluene (22 mL) at 120° C. After 30 min, 1-[(1-cyanocyclohexyl)azo]cyclohexane carbonitrile (34.1 mg, 140 µmol) and thiophenol (100 µL, 979 µmol) were added sequentially, and the resulting mixture was warmed to 130° C. After 20 h, the resulting mixture was cooled to room temperature and was concentrated under reduced pressure. The residue was purified by flash column chromatography on silica gel (0 to 5% methanol in dichloromethane) to give a mixture of 144-1 and 144-2.

Step 2: Sodium borohydride (38.0 mg, 1.00 mmol) was added in two equal portions over 1 min to a stirred mixture of the mixture of 144-1 and 144-2 (42.0 mg, 46.5 µmol) and nickel(II) chloride (130 mg, 1.00 mmol) in methanol (1.0 mL), ethanol (2.0 mL), and tetrahydrofuran (0.5 mL) at 0° C. After 1 min, the resulting mixture was warmed to room temperature. After 15 min, the resulting mixture was filtered through celite, and the filter cake was extracted with acetone. The combined filtrates were concentrated under reduced pressure. The residue was purified by reverse phase preparative HPLC (0.1% trifluoroacetic acid in acetonitrile/water) to give Example 144, Example 145 (faster eluting diastereomer on reverse phase HPLC [stereochemistry of C4-position of the tetrahydrofuran ring tentatively assigned]), Example 146 (slower eluting diastereomer on reverse phase HPLC [stereochemistry of C4-position of the tetrahydrofuran ring tentatively assigned]), Example 147 (faster eluting diastereomer on reverse phase HPLC [the stereochemistry of C4-position of the tetrahydrofuran ring was tentatively assigned]), and Example 148 (slower eluting diastereomer on reverse phase HPLC [stereochemistry of C4-position of the tetrahydrofuran ring tentatively assigned]).

Example 144: $^1$H NMR (400 MHz, Acetone-$d_6$) δ 8.13 (s, 1H), 7.79 (d, J=8.5 Hz, 1H), 7.45 (dd, J=8.2, 2.0 Hz, 1H), 7.36 (d, J=1.9 Hz, 1H), 7.25 (dd, J=8.5, 2.3 Hz, 1H), 7.15 (d, J=2.4 Hz, 1H), 6.93 (d, J=8.2 Hz, 1H), 6.12 (dd, J=15.5, 7.5 Hz, 1H), 5.85 (dd, J=15.4, 8.5 Hz, 1H), 4.22-3.24 (m, 10H), 4.08 (s, 3H), 3.86 (s, 3H), 3.19 (dd, J=15.0, 10.6 Hz, 1H), 3.26 (s, 3H), 2.97-1.25 (m, 16H), 1.18 (d, J=6.8 Hz, 3H), 0.91 (t, J=7.4 Hz, 3H). LCMS-ESI+(m/z): [M+H]$^+$ calcd for $C_{41}H_{52}ClN_5O_7S$: 794.3; found: 794.3.

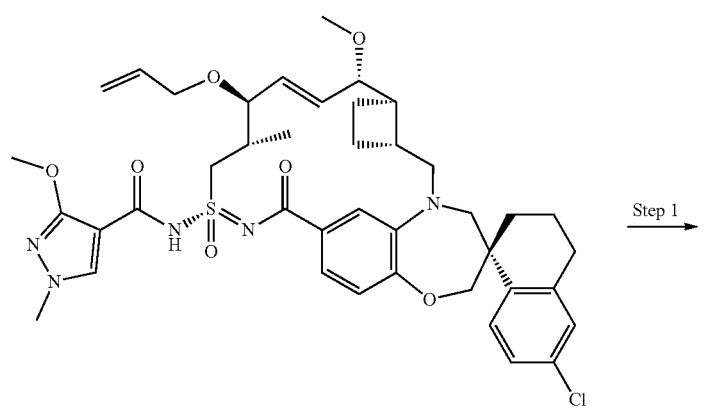

79-1

293 294
-continued
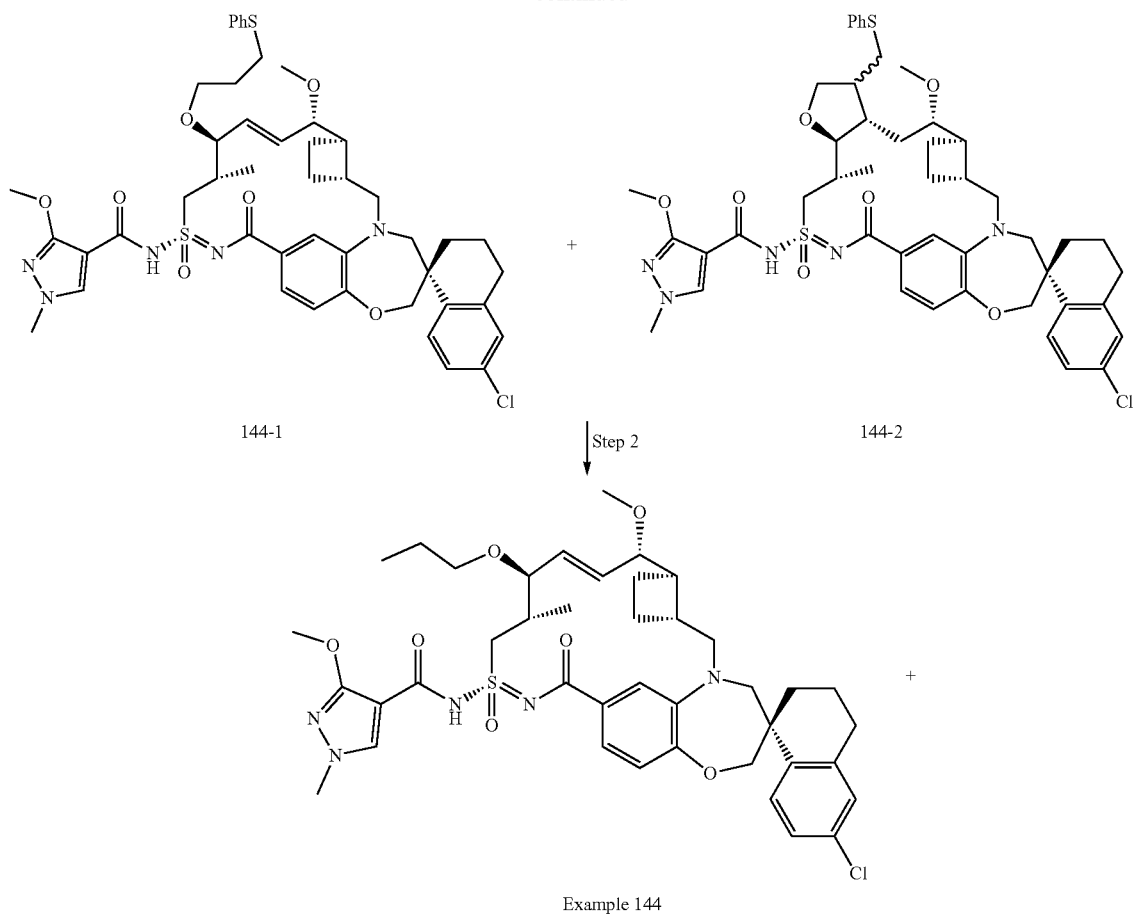
144-1 + 144-2
Step 2
Example 144 +
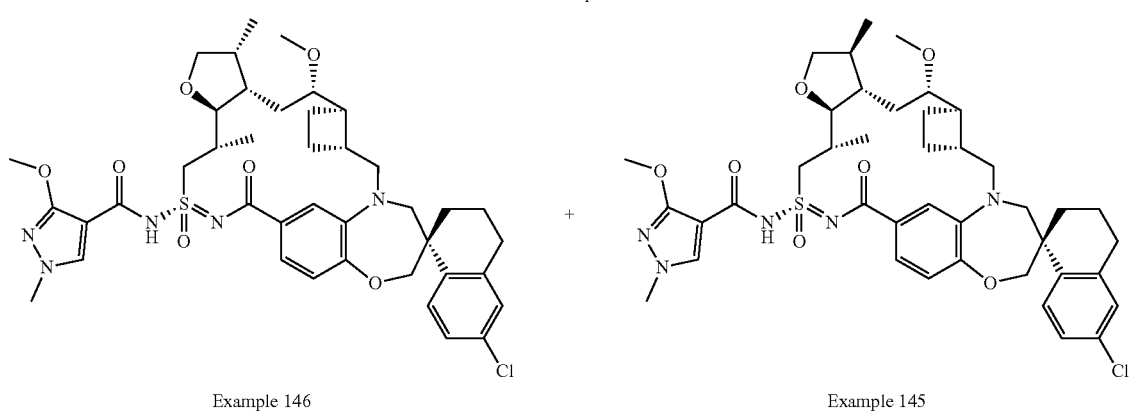
Example 146 Example 145
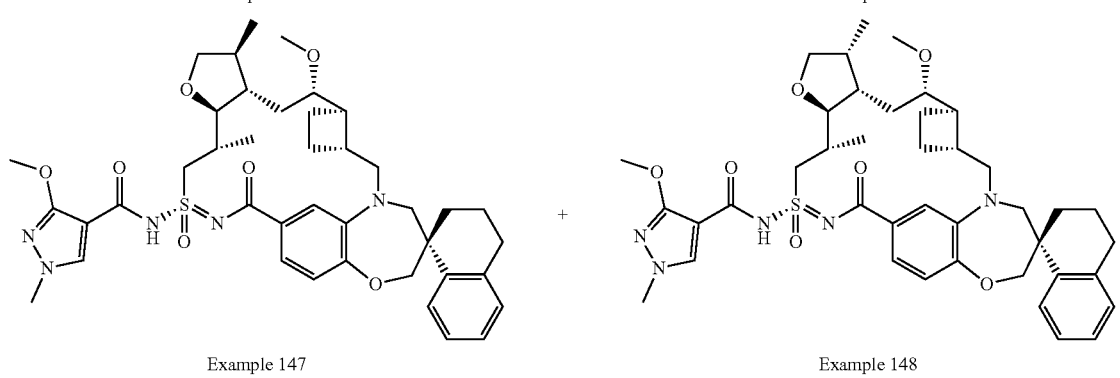
Example 147 + Example 148

Example 145: ¹H NMR (400 MHz, Acetone-d₆) δ 8.13 (s, 1H), 7.82-7.76 (m, 1H), 7.51 (dd, J=8.2, 1.9 Hz, 1H), 7.45-7.43 (m, 1H), 7.26 (d, J=8.3 Hz, 1H), 7.21-7.10 (m, 1H), 6.94 (d, J=8.3 Hz, 1H), 4.30 (dd, J=15.0, 9.3 Hz, 1H), 4.25-3.12 (m, 1 OH), 4.10 (s, 3H), 3.86 (s, 3H), 3.36 (s, 3H), 2.92-1.24 (m, 18H), 1.19 (d, J=6.9 Hz, 3H), 0.96 (d, J=7.1 Hz, 3H). LCMS-ESI+ (m/z): [M+H]⁺ calcd for $C_{41}H_{52}ClN_5O_7S$: 794.3; found: 794.2.

Example 146: ¹H NMR (400 MHz, Acetone-d₆) δ 8.12 (s, 1H), 7.80 (d, J=8.5 Hz, 1H), 7.59 (d, J=2.0 Hz, 1H), 7.51 (dd, J=8.2, 1.9 Hz, 1H), 7.25 (dd, J=8.5, 2.4 Hz, 1H), 7.14 (d, J=2.4 Hz, 1H), 6.94 (d, J=8.2 Hz, 1H), 4.34 (dd, J=14.9, 10.9 Hz, 1H), 4.13-4.04 (m, 2H), 4.09 (s, 3H), 3.99-3.91 (m, 1H), 3.91-3.62 (m, 3H), 3.86 (s, 3H), 3.53 (d, J=8.8 Hz, 1H), 3.44-3.34 (m, 2H), 3.27-3.17 (m, 1H), 2.91-1.21 (m, 18H), 1.19 (d, J=6.9 Hz, 3H), 1.11 (d, J=6.6 Hz, 3H). LCMS-ESI+ (m/z): [M+H]⁺ calcd for $C_{41}H_{52}ClN_5O_7S$: 794.3; found: 794.3.

Example 147: ¹H NMR (400 MHz, Acetone-d₆) δ 8.13 (s, 1H), 7.86-6.87 (m, 7H), 4.41-3.00 (m, 11H), 4.10 (s, 3H), 3.86 (s, 3H), 3.37 (s, 3H), 3.00-1.35 (m, 18H), 1.19 (d, J=6.9 Hz, 3H), 0.97 (d, J=7.0 Hz, 3H). LCMS-ESI+ (m/z): [M+H]⁺ calcd for $C_{41}H_{53}N_5O_7S$: 760.4; found: 760.3.

Example 148: ¹H NMR (400 MHz, Acetone-d₆) δ 8.12 (s, 1H), 7.83-7.76 (m, 1H), 7.58 (d, J=2.0 Hz, 1H), 7.51 (dd, J=8.2, 1.9 Hz, 1H), 7.29-7.07 (m, 3H), 6.94 (d, J=8.2 Hz, 1H), 4.34 (dd, J=14.9, 10.9 Hz, 1H), 4.20-3.29 (m, 9H), 4.09 (s, 3H), 3.86 (s, 3H), 3.34 (s, 3H), 3.29-3.17 (m, 1H), 3.13-1.36 (m, 18H), 1.20 (d, J=6.8 Hz, 3H), 1.11 (d, J=6.6 Hz, 3H). LCMS-ESI+ (m/z): [M+H]⁺ calcd for $C_{41}H_{53}N_5O_7S$: 760.4; found: 760.3.

Example 149

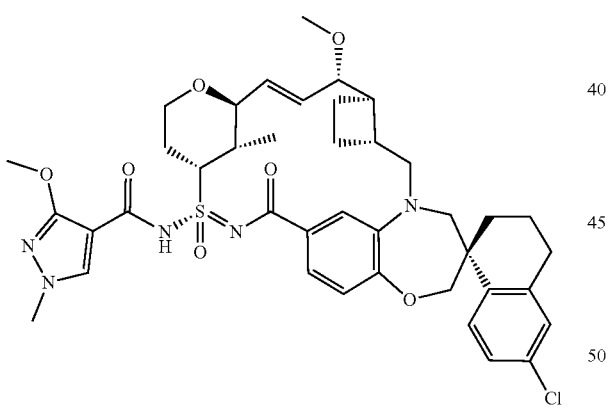

Lithium diisopropylamide solution (1.5 M in tetrahydrofuran/toluene/ethylbenzene, 64.7 μL, 97 μmol) was added over 9 min via syringe pump to a stirred mixture of 135-2 (17.6 mg, 19.4 μmol) and 1,3-dimethyl-3,4,5,6-tetrahydro-2(1H)-pyrimidinone (47.0 μL, 388 μmol) in tetrahydrofuran (5.0 mL) at −78° C. After 90 min, acetic acid (22.2 μL, 388 μmol) was added via syringe, and the resulting mixture was warmed to room temperature and was concentrated under reduced pressure. The residue was purified by reverse phase preparative HPLC (0.1% trifluoroacetic acid in acetonitrile/water) to give Example 149 (the stereochemistry of the new carbon stereocenter was tentatively assigned). ¹H NMR (400 MHz, Acetone-d₆) δ 8.13 (s, 1H), 7.80 (d, J=8.5 Hz, 1H), 7.46 (dd, J=8.2, 2.0 Hz, 1H), 7.35 (d, J=2.0 Hz, 1H), 7.24 (dd, J=8.5, 2.4 Hz, 1H), 7.17 (d, J=2.3 Hz, 1H), 7.00 (d, J=8.2 Hz, 1H), 5.58 (dd, J=16.1, 7.3 Hz, 1H), 5.36 (dd, J=16.0, 6.5 Hz, 1H), 4.36 (ddd, J=11.7, 9.6, 5.2 Hz, 1H), 4.22 (d, J=12.0 Hz, 1H), 4.11 (d, J=12.0 Hz, 1H), 4.08-4.01 (m, 1H), 4.07 (s, 3H), 3.86 (s, 3H), 3.72-3.66 (m, 2H), 3.66-3.61 (m, 1H), 3.53 (td, J=11.6, 2.0 Hz, 1H), 3.49-3.40 (m, 3H), 3.22 (s, 3H), 2.91-2.71 (m, 2H), 2.70-2.57 (m, 1H), 2.48 (qd, J=8.1, 3.6 Hz, 1H), 2.32-2.17 (m, 2H), 2.15-1.58 (m, 9H), 1.13 (d, J=6.5 Hz, 3H). LCMS-ESI+ (m/z): [M+Na]⁺ calcd for $C_{40}H_{48}ClN_5O_7S$: 800.3; found: 800.3.

Example 150

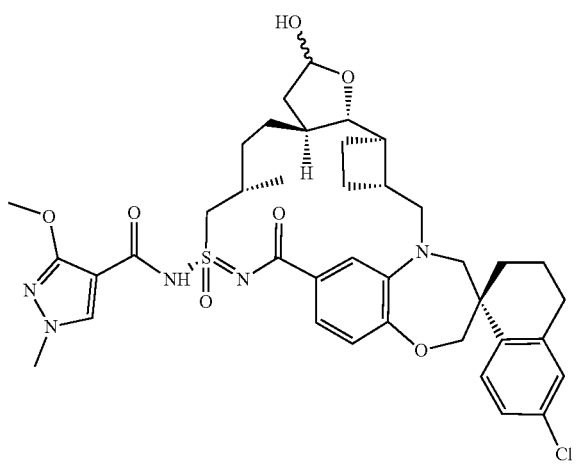

Example 150 (mixture of epimers at the C₂-position of the tetrahydrofuran ring) was synthesized in a manner similar to Example 139 using Intermediate W instead of Intermediate U. ¹H NMR (400 MHz, Acetone-d₆) δ 8.12-8.05 (m, 1H), 7.87-7.72 (m, 1H), 7.52-7.30 (m, 2H), 7.30-7.07 (m, 2H), 6.97-6.87 (m, 1H), 5.33 (d, J=5.2 Hz, 0.33H), 5.19 (d, J=4.6 Hz, 0.67H), 4.24-2.91 (m, 12H), 3.84 (s, 2H), 3.83 (s, 1H), 2.91-1.16 (m, 21H), 1.12-0.99 (m, 3H). LCMS-ESI+ (m/z): [M+H]⁺ calcd for $C_{39}H_{48}ClN_5O_7S$: 766.3; found: 766.3.

Example 151

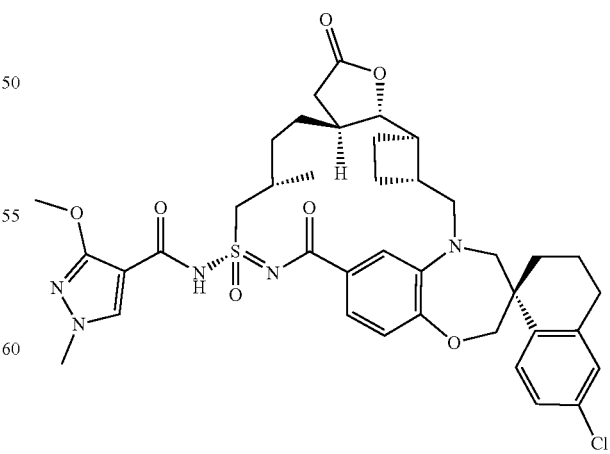

Example 151 was synthesized in a manner similar to Example 140 using Example 150 instead of Example 139.

$^1$H NMR (400 MHz, Acetone-d$_6$) δ 8.10 (s, 1H), 7.79 (d, J=8.6 Hz, 1H), 7.44 (d, J=8.6 Hz, 1H), 7.41 (s, 1H), 7.23 (d, J=9.2 Hz, 1H), 7.13 (d, J=2.3 Hz, 1H), 6.94 (d, J=8.1 Hz, 1H), 4.40-4.33 (m, 1H), 4.15 (d, J=12.1 Hz, 1H), 4.06 (s, 3H), 4.06-3.95 (m, 2H), 3.84 (s, 3H), 3.82-3.71 (m, 2H), 3.48 (d, J=14.4 Hz, 1H), 3.27 (dd, J=14.9, 9.3 Hz, 1H), 2.94-1.11 (m, 21H), 1.08 (d, J=6.9 Hz, 3H). LCMS-ESI+ (m/z): [M+H]$^+$ calcd for C$_{39}$H$_{46}$ClN$_5$O$_7$S: 764.3; found: 764.2.

Example 152

Example 152 (stereochemistry of the C$_5$-position of the tetrahydrofuran ring assigned tentatively) was synthesized using a similar procedure to Example 141 followed by a similar procedure to Example 142 using Example 150 instead of Example 139. $^1$H NMR (400 MHz, Methanol-d$_4$) δ 8.05 (s, 1H), 7.78 (d, J=8.5 Hz, 1H), 7.35 (dt, J=8.2, 2.5 Hz, 1H), 7.29 (d, J=12.3 Hz, 1H), 7.20 (dd, J=8.5, 2.4 Hz, 1H), 7.17-7.09 (m, 1H), 6.95 (dd, J=8.2, 1.5 Hz, 1H), 4.14 (dd, J=12.3, 2.2 Hz, 1H), 4.12-3.72 (m, 6H), 4.06 (s, 3H), 3.81 (s, 3H), 3.72-3.63 (m, 1H), 3.43-3.08 (m, 3H), 3.25-3.08 (m, 1H), 2.98-1.15 (m, 21H), 2.91 (s, 3H), 2.81 (s, 3H), 1.15-1.10 (m, 3H). LCMS-ESI+ (m/z): [M+H]$^+$ calcd for C$_{43}$H$_{57}$ClN$_6$O$_6$S: 821.4; found: 821.3.

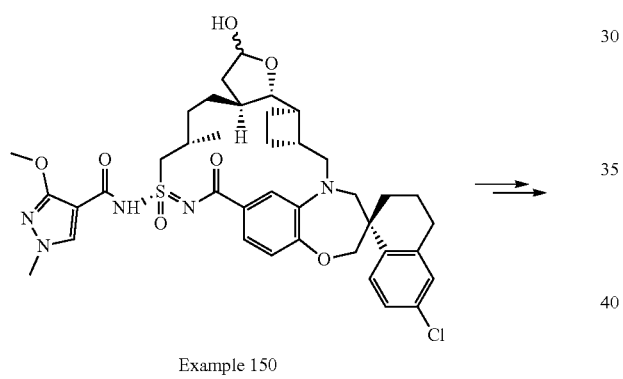

Example 150

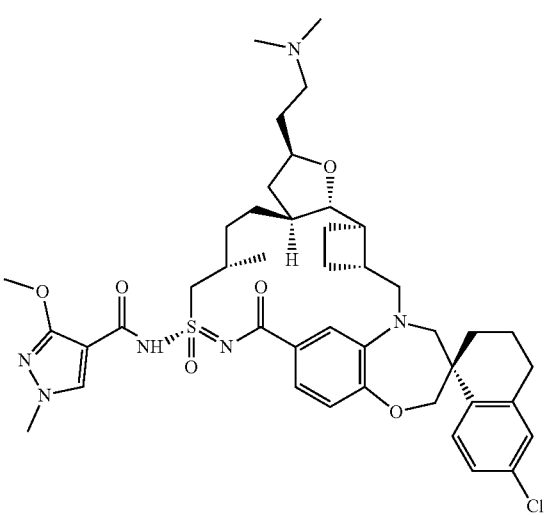

Example 152

Example 153 and Example 154

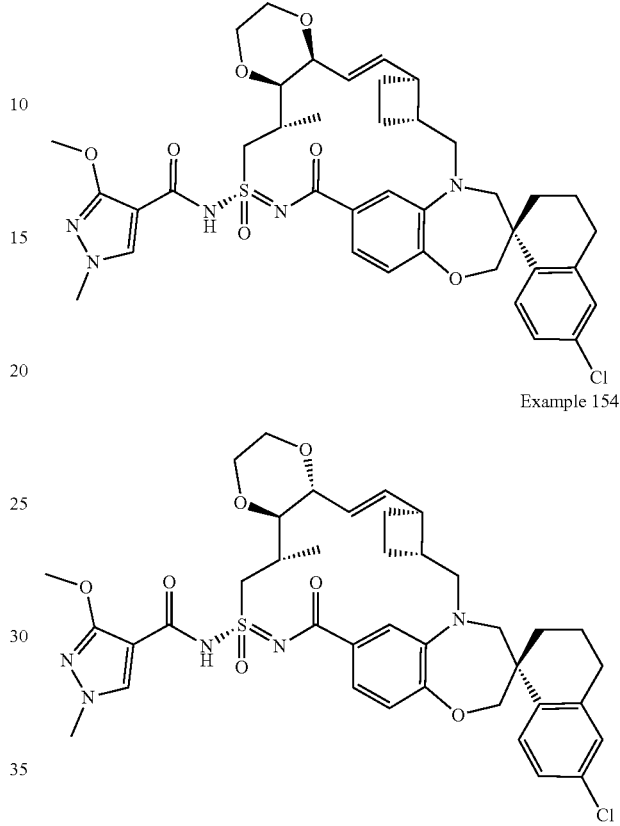

Example 153

Example 154

Trifluoromethanesulfonic acid (10.0 μL, 113 μmol) was added via syringe to a stirred solution of 135-1 (23.0 mg, 28.9 μmol) in dichloromethane (3.0 mL) at 0° C. After 16 min, trifluoromethanesulfonic acid (25.0 μL, 283 μmol) was added via syringe. After 11 min, triethylamine (100 μL) was added. After 1 min, the resulting mixture was warmed to room temperature and was concentrated under reduced pressure. The residue was purified by reverse phase preparative HPLC (0.1% trifluoroacetic acid in acetonitrile/water) to give Example 153 (earlier eluting diastereomer on reverse phase HPLC [stereochemistry of the C$_3$-position on the 1,4-dioxane ring tentatively assigned]) and Example 154 (later eluting diastereomer on reverse phase HPLC [stereochemistry of the C$_3$-position on the 1,4-dioxane ring tentatively assigned]).

Example 153: $^1$H NMR (400 MHz, Acetone-d$_6$) δ 8.10 (s, 1H), 7.78 (d, J=8.5 Hz, 1H), 7.52 (s, 1H), 7.50 (dd, J=8.1, 1.9 Hz, 1H), 7.24 (dd, J=8.5, 2.4 Hz, 1H), 7.13 (d, J=2.3 Hz, 1H), 6.93 (d, J=8.1 Hz, 1H), 6.32 (dd, J=15.8, 4.3 Hz, 1H), 5.43 (dd, J=15.5, 7.7 Hz, 1H), 4.56 (dd, J=15.4, 11.4 Hz, 1H), 4.20-4.03 (m, 3H), 4.07 (s, 3H), 4.03-3.93 (m, 1H), 3.85 (s, 3H), 3.80 (d, J=10.4 Hz, 1H), 3.73 (d, J=14.7 Hz, 1H), 3.70-3.65 (m, 1H), 3.66-3.55 (m, 2H), 3.43 (d, J=14.5 Hz, 1H), 3.25 (d, J=9.5 Hz, 1H), 3.24-3.18 (m, 1H), 2.90-1.20 (m, 14H), 1.16 (d, J=6.9 Hz, 3H). LCMS-ESI+ (m/z): [M+H]$^+$ calcd for C$_{39}$H$_{46}$ClN$_5$O$_7$S: 764.3; found: 764.2.

Example 154: $^1$H NMR (400 MHz, Acetone-d$_6$) δ 8.12 (s, 1H), 7.82-7.72 (m, 1H), 7.43 (s, 1H), 7.36 (dd, J=8.2, 1.9 Hz, 1H), 7.23-7.19 (m, 1H), 7.13 (d, J=2.3 Hz, 1H), 6.91 (d, J=8.1 Hz, 1H), 6.39 (dd, J=15.7, 1.4 Hz, 1H), 5.83 (dd, J=15.7, 6.7 Hz, 1H), 4.39-3.00 (m, 13H), 4.07 (s, 3H), 3.85 (s, 3H), 2.97-1.19 (m, 14H), 1.17 (d, J=6.9 Hz, 3H). LCMS-ESI+(m/z): [M+H]+ calcd for $C_{39}H_{46}ClN_5O_7S$: 764.3; found: 764.1.

Example 155

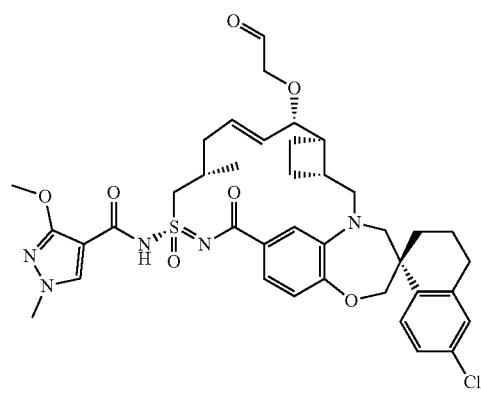

58-1

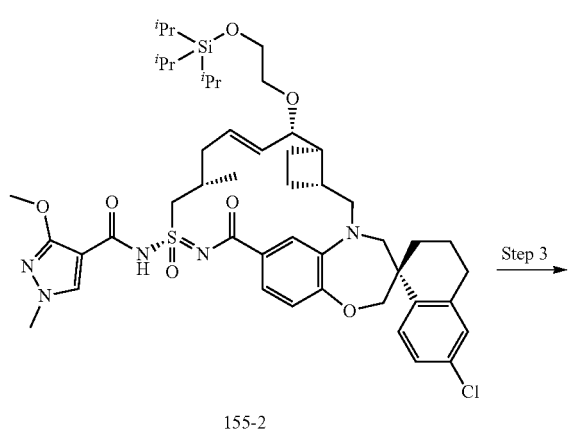

155-1

155-2

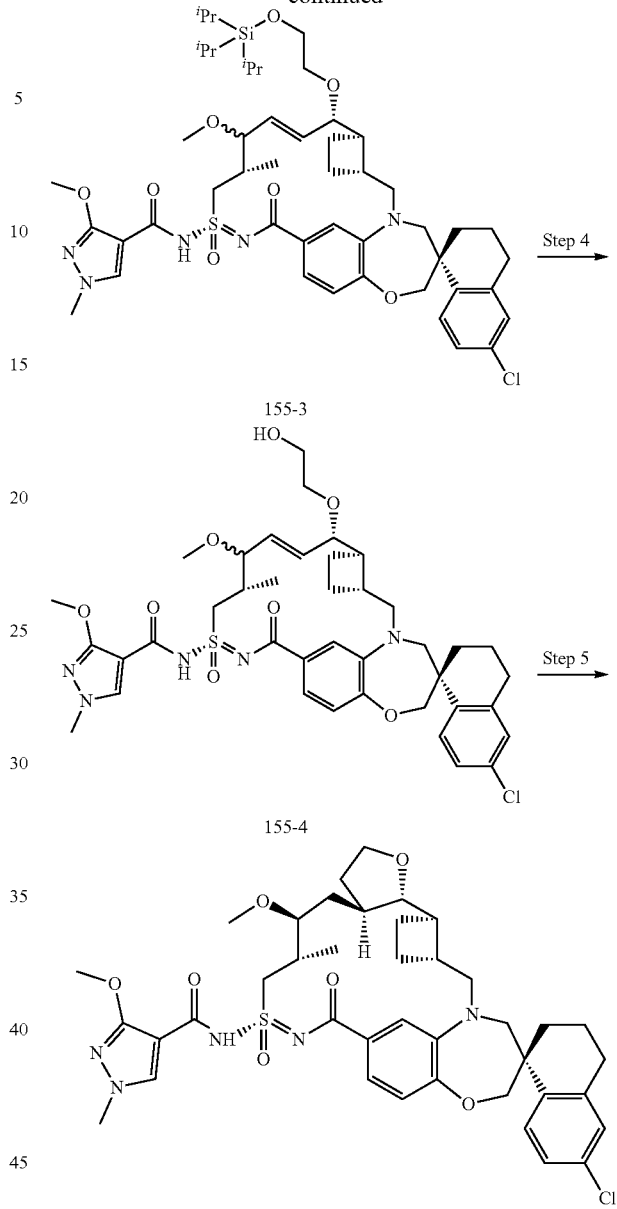

155-3

155-4

Example 55

Step 1: 155-1 was synthesized in a manner similar to 135-1 using 58-1 instead of 88-1.

Step 2: Chloro(triisopropyl)silane (254 μL, 1.19 mmol) was added via syringe to a stirred mixture of 155-1 (135 mg, 176 μmol) and imidazole (120 mg, 1.76 mmol) in dichloromethane (1.5 mL) at room temperature. After 80 min, ethyl acetate (60 mL) and aqueous citric acid solution (10% wt, 10 mL) were added sequentially. The organic layer was washed sequentially with water (40 mL) and a mixture of water and brine (1:1, 40 mL), dried over anhydrous magnesium sulfate, filtered, and concentrated under reduced pressure. The residue was purified by flash column chromatography on silica gel (0 to 7% methanol in dichloromethane) to give 155-2.

Step 3: 155-3 was synthesized in a manner similar to Example 68 using 155-2 instead of 68-1.

Step 4: Tetrabutylammonium fluoride solution (1.0 M in tetrahydrofuran, 591 μL, 590 μmol) was added via syringe to a stirred mixture of 155-2 (113 mg, 118 µmol) and sodium bicarbonate (29.8 mg, 355 µmol) in tetrahydrofuran (6.0 mL) at room temperature. After 40 min, tetrabutylammonium fluoride solution (1.0 M in tetrahydrofuran, 2.50 mL, 2.5 mmol) was added via syringe. After 20 min, the resulting mixture was warmed to 70° C. After 29 min, the resulting mixture was cooled to room temperature, and aqueous citric acid solution (10% wt, 10 mL), saturated aqueous ammonium chloride solution (5 mL), ethyl acetate (40 mL), and diethyl ether (40 mL) were added sequentially. The organic layer was washed sequentially with water (2×50 mL) and a mixture of water and brine (1:1 v:v, 50 mL), dried over anhydrous magnesium sulfate, filtered, and concentrated under reduced pressure. The residue was purified by flash column chromatography on silica gel (0 to 10% methanol in dichloromethane) to give 155-4.

Step 5: Example 155 (4:1 mixture of epimers [major epimer shown, tentatively assigned] at the methoxy-substituted stereocenter) was synthesized in a manner similar to Example 135 (Steps 2-3) using 155-4 instead of 135-1. $^1$H NMR (400 MHz, Acetone-$d_6$) δ 8.13 (s, 0.8H), 8.12 (s, 0.2H), 7.84-7.77 (m, 1H), 7.55 (d, J=2.0 Hz, 1H), 7.50-7.43 (m, 1H), 7.28-7.21 (m, 1H), 7.17-7.11 (m, 1H), 6.96-6.90 (m, 1H), 4.21-3.10 (m, 14H), 3.87 (s, 2.4H), 3.86 (s, 0.6H), 3.26 (s, 0.6H), 3.20 (s, 2.4H), 2.94-1.16 (m, 19H), 1.13 (d, J=6.8 Hz, 0.6H), 1.03 (d, J=7.1 Hz, 2.4H). LCMS-ESI+ (m/z): [M+H]$^+$ calcd for $C_{40}H_{50}ClN_5O_7S$: 780.3; found: 780.2.

Example 156 and Example 157

Step 1: A mixture of 4-bromobutanoic acid (0.013 mL, 0.062 mmol), EDCl (16 mg, 0.083 mmol) in DCM (2 mL) was stirred at room temperature for 5 min. Then Intermediate W (30 mg, 0.042 mmol) was added followed by DMAP (10 mg, 0.083 mmol). The reaction mixture was stirred at room temperature overnight. It was diluted with EtOAc (40 mL), washed with water (20 mL) and brine (10 mL), dried, and concentrated to dryness. The crude residue was purified by column chromatography using 0-10% MeOH in DCM to obtain 156-1. LCMS-ESI$^+$ (m/z): [M+H]$^+$ calcd for $C_{41}H_{49}BrClN_5O_7S$: 870.2; found: 869.8.

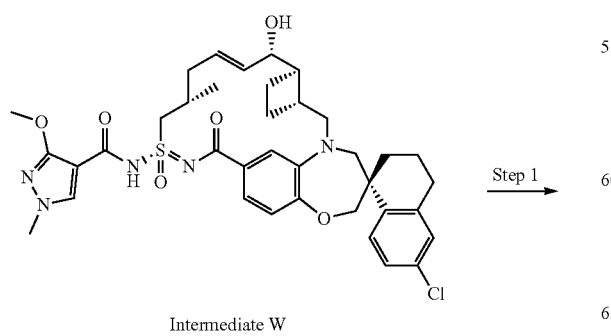

Intermediate W

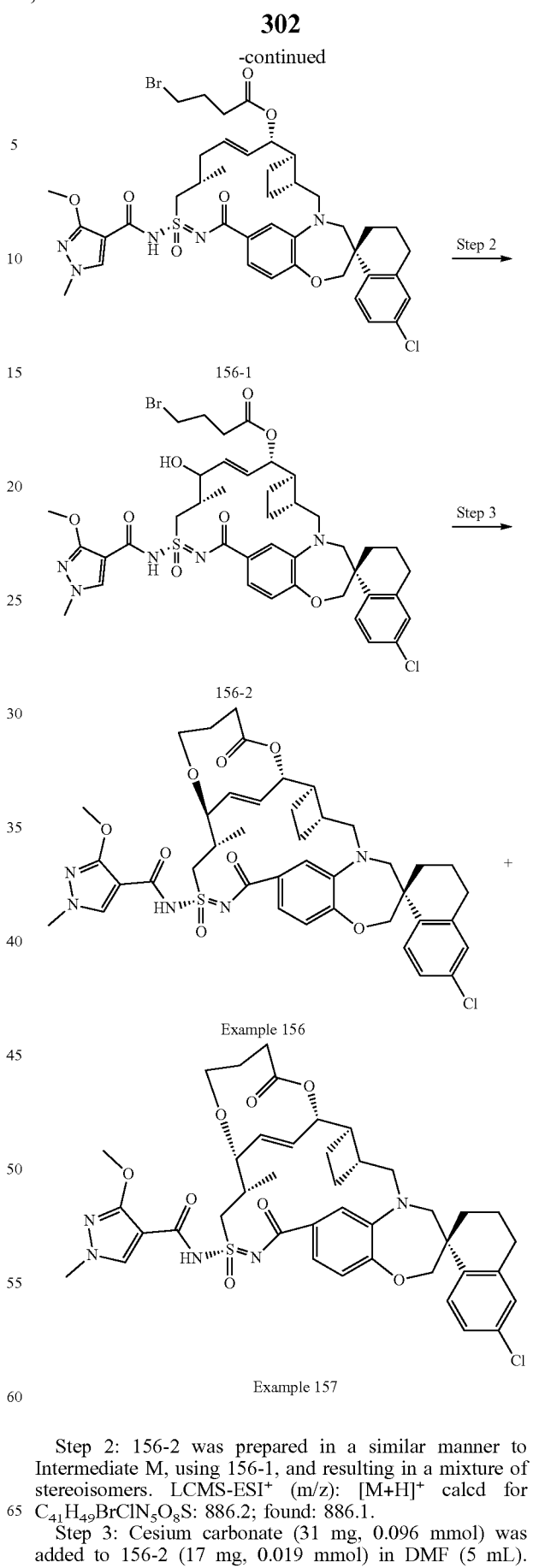

156-1

156-2

Example 156

Example 157

Step 2: 156-2 was prepared in a similar manner to Intermediate M, using 156-1, and resulting in a mixture of stereoisomers. LCMS-ESI$^+$ (m/z): [M+H]$^+$ calcd for $C_{41}H_{49}BrClN_5O_8S$: 886.2; found: 886.1.

Step 3: Cesium carbonate (31 mg, 0.096 mmol) was added to 156-2 (17 mg, 0.019 mmol) in DMF (5 mL).

Reaction mixture was heated at 60° C. overnight. The solid was filtered off and the filtrate was purified by reverse phase HPLC (0.1% trifluoroacetic acid in acetonitrile/water) to obtain two diastereomeric products Example 156 (second eluting diastereomer, stereochemistry tentatively assigned) and Example 157 (first eluting diastereomer, stereochemistry tentatively assigned).

Example 156 (second eluting diastereomer): $^1$H NMR (400 MHz, Methanol-$d_4$) δ 8.11 (s, 1H), 7.78 (d, J=8.5 Hz, 1H), 7.38 (d, J=7.0 Hz, 1H), 7.21 (m, 1H), 7.12 (s, 1H), 7.03-7.00 (m, 1H), 6.86 (d, J=8.2 Hz, 1H), 5.91 (d, J=16.1, 1H), 5.64 (d, J=16.1 Hz, 1H), 5.28 (s, 1H), 4.19-4.01 (m, 4H), 3.88-3.73 (m, 3H), 3.72-3.63 (m, 1H), 3.27 (s, 6H), 3.21-3.10 (m, 3H), 2.90 (s, 3H), 2.81 (m, 2H), 2.58 (s, 1H), 2.40-2.27 (m, 2H), 2.11-2.01 (m, 2H), 1.97-1.85 (m, 3H), 1.82-1.72 (m, 1H), 1.59 (m, 2H), 1.44 (m, 1H), 1.13 (q, J=7.2 Hz, 3H). LCMS-ESI$^+$ (m/z): [M+H]$^+$ calcd for $C_{41}H_{48}ClN_5O_8S$: 806.3; found: 806.0.

Example 157 (first eluting diastereomer): $^1$H NMR (400 MHz, Methanol-$d_4$) δ 8.08 (s, 1H), 7.77 (m, 1H), 7.38 (m, 1H), 7.27-7.15 (m, 2H), 7.12 (s, 1H), 6.97-6.82 (m, 1H), 6.07-5.92 (m, 1H), 5.92-5.77 (m, 1H), 5.26 (m, 1H), 4.26 (m, 1H), 4.18-3.96 (m, 6H), 3.91-3.55 (m, 6H), 3.41 (m, 1H), 3.22-3.04 (m, 2H), 2.81 (m, 3H), 2.65-2.34 (m, 3H), 2.34-2.20 (m, 2H), 2.17-1.98 (m, 3H), 1.79 (d, J=6.2 Hz, 3H), 1.66-1.41 (m, 4H), 1.15 (d, J=6.0 Hz, 3H). LCMS-ESI$^+$ (m/z): [M+H]$^+$ calcd for $C_{41}H_{48}ClN_5O_8S$: 806.3; found: 805.9.

Example 158 and Example 159

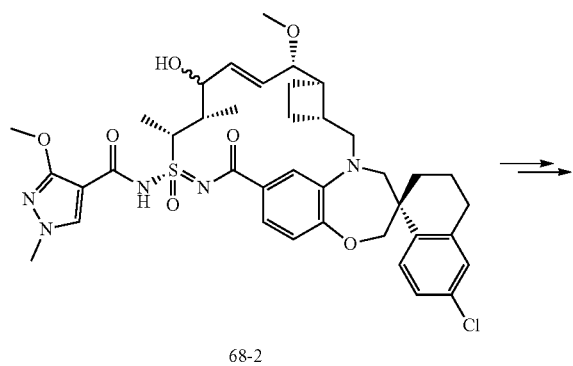

68-2

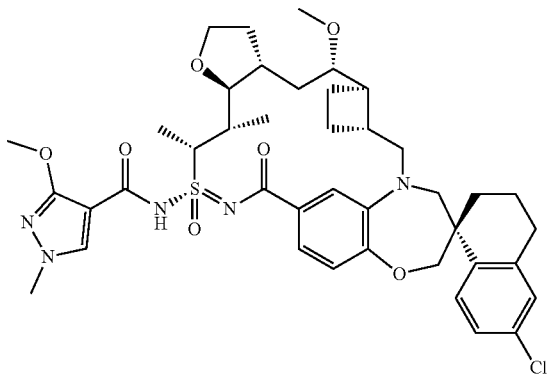

Example 159

Example 158 and Example 159 were synthesized using a similar procedure to Example 79 (Steps 1-2) followed by a similar procedure to Example 135, using 68-2 instead of Intermediate U.

Example 158: $^1$H NMR (400 MHz, Acetone-$d_6$) δ 8.04 (d, J=4.5 Hz, 1H), 7.93-7.74 (m, 1H), 7.67-7.47 (m, 1H), 7.37-7.17 (m, 2H), 7.17-7.10 (m, 1H), 6.98-6.91 (m, 1H), 6.09-5.66 (m, 2H), 4.50-4.00 (m, 5H), 4.00-3.59 (m, 3H), 3.98 (s, 3H), 3.84 (s, 3H), 3.58-3.16 (m, 2H), 3.19 (s, 3H), 3.16-3.04 (m, 1H), 2.96-1.00 (m, 19H), 0.97 (d, J=6.6 Hz, 3H). LCMS-ESI$^+$ (m/z): [M+H]$^+$ calcd for $C_{41}H_{52}ClN_5O_7S$: 794.3; found: 794.3.

Example 159: $^1$H NMR (400 MHz, Acetone-$d_6$) δ 8.04 (s, 1H), 7.78 (d, J=8.5 Hz, 1H), 7.36-7.17 (m, 3H), 7.15 (d, J=2.4 Hz, 1H), 7.01 (d, J=8.1 Hz, 1H), 4.25 (s, 1H), 4.14 (s, 2H), 3.98 (s, 3H), 3.91-3.83 (m, 1H), 3.83 (s, 3H), 3.77 (dt, J=8.3, 6.7 Hz, 1H), 3.74-3.61 (m, 2H), 3.54 (d, J=7.2 Hz, 1H), 3.50-3.41 (m, 1H), 3.36 (d, J=14.2 Hz, 1H), 3.32 (s, 3H), 3.22 (dd, J=15.3, 9.1 Hz, 1H), 2.91-1.22 (m, 21H), 1.18 (d, J=7.1 Hz, 3H). LCMS-ESI+(m/z): [M+H]$^+$ calcd for $C_{41}H_{52}ClN_5O_7S$: 794.3; found: 794.3.

Example 160

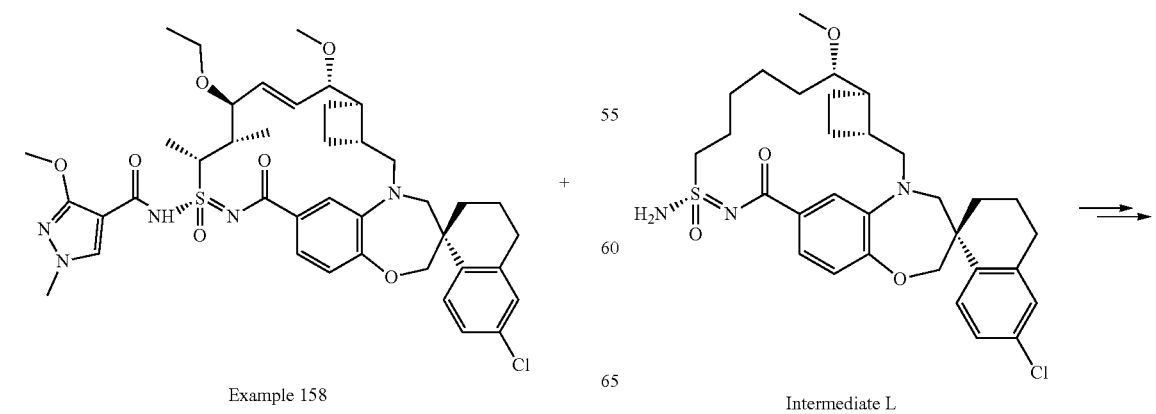

Example 158

Intermediate L

Example 160

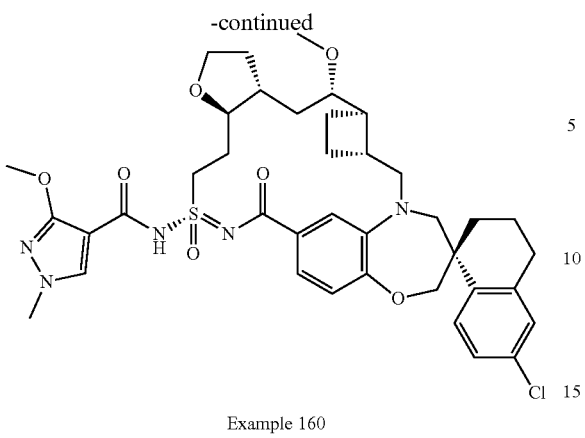

Example 160

Example 160 was synthesized using a similar procedure to Intermediate T, followed by a similar procedure to Intermediate M, followed by a similar procedure to Example 159, using Intermediate L. $^1$H NMR (400 MHz, Acetone-d$_6$) δ 8.11 (d, J=0.6 Hz, 1H), 7.79 (d, J=8.5 Hz, 1H), 7.55 (d, J=1.9 Hz, 1H), 7.49 (dd, J=8.2, 1.9 Hz, 1H), 7.25 (dd, J=8.5, 2.4 Hz, 1H), 7.14 (d, J=2.4 Hz, 1H), 6.94 (d, J=8.2 Hz, 1H), 4.25-4.08 (m, 3H), 4.07 (s, 3H), 4.01-3.65 (m, 5H), 3.86 (s, 3H), 3.63-3.54 (m, 1H), 3.40 (d, J=14.3 Hz, 1H), 3.34 (s, 3H), 3.23 (dd, J=15.1, 10.0 Hz, 1H), 2.91-1.10 (m, 23H). LCMS-ESI$^+$ (m/z): [M+H]$^+$ calcd for C$_{39}$H$_{48}$ClN$_5$O$_7$S: 766.3; found: 766.2.

Example 161

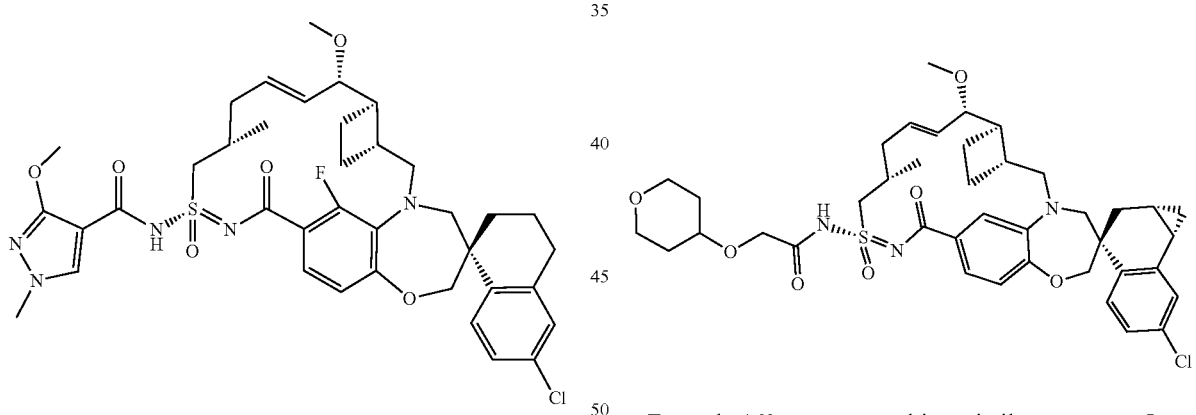

Intermediate M (60 mg, 0.082 mmol), RuCl$_3$ (2 mg, 0.008 mmol), 10 mg of 4 Å molecule sieves and NFSI (36 mg, 0.114 mmol) were added into toluene (8 mL) in sequence. After degassing and with nitrogen gas several times, reaction mixture was heated at 50° C. for 16 h. It was then diluted with EtOAc (50 mL), washed with water (30 mL) and brine (30 mL), dried and concentrated. The crude residue was purified by silica gel flash column chromatography (ISCO) using 0-10% MeOH in DCM followed by reverse phase HPLC to afford Example 161. $^1$H NMR (400 MHz, Methanol-d$_4$) δ 8.08 (s, 1H), 7.72 (s, 1H), 7.34 (t, J=8.0 Hz, 1H), 7.13 (d, J=6.1 Hz, 2H), 6.78 (d, J=8.5 Hz, 1H), 5.98 (m, 1H), 5.56 (m, 1H), 4.12 (s, 2H), 4.05 (s, 3H), 4.01-3.84 (m, 2H), 3.82 (s, 3H), 3.70-3.55 (m, 2H), 3.44 (s, 2H), 3.25 (s, 3H), 2.83 (m, 2H), 2.59 (m, 1H), 2.50-2.19 (m, 4H), 2.11-2.00 (m, 2H), 1.92 (d, J=5.4 Hz, 1H), 1.85-1.63 (m, 4H), 1.31 (s, 1H), 1.10 (d, J=6.8 Hz, 3H), 0.92 (m, 1H). LCMS-ESI$^+$ (m/z): [M+H]$^+$ calcd for C$_3$H$_{45}$ClFN$_5$O$_6$S: 754.3; Found: 754.1.

Example 162

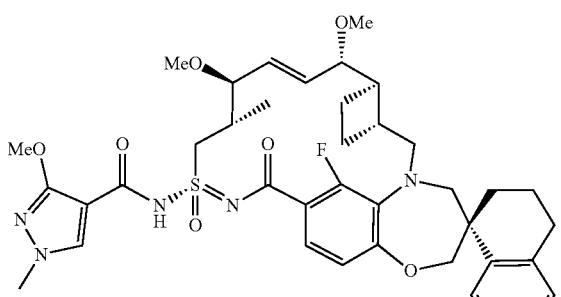

Example 162 was synthesized in a similar manner to Example 161 from Intermediate V. $^1$H NMR (400 MHz, Methanol-d$_4$) δ 8.08 (s, 1H), 7.67 (s, 1H), 7.37 (t, J=8.0 Hz, 1H), 7.18-7.09 (m, 2H), 6.78 (m, 1H), 5.86 (m, 2H), 4.21 (d, J=14.1 Hz, 1H), 4.13-3.95 (m, 6H), 3.88-3.77 (m, 5H), 3.66 (m, 1H), 3.44 (s, 2H), 3.31 (s, 3H), 3.27 (s, 3H), 2.84 (m, 2H), 2.56-2.40 (m, 3H), 2.06 (d, J=8.0 Hz, 1H), 1.96 (s, 2H), 1.86 (m, 2H), 1.75 (m, 3H), 1.31 (s, 1H), 1.20 (d, J=6.9 Hz, 3H). LCMS-ESI$^+$ (m/z): [M+H]$^+$ calcd for C$_{39}$H$_{47}$ClFN$_5$O$_7$S: 784.3; Found: 784.1.

Example 163

Example 163 was prepared in a similar manner to Intermediate T using Intermediate O and 2-((tetrahydro-2H-pyran-4-yl)oxy)acetic acid. $^1$H NMR (400 MHz, Methanol-d$_4$) δ 7.73 (d, J=8.5 Hz, 1H), 7.35 (d, J=2.3 Hz, 1H), 7.27 (dd, J=8.2, 1.9 Hz, 1H), 7.17 (dd, J=8.5, 2.4 Hz, 1H), 7.10 (s, 1H), 6.88 (d, J=8.2 Hz, 1H), 6.11 (dt, J=14.4, 6.9 Hz, 1H), 5.63 (dd, J=15.4, 8.3 Hz, 1H), 4.21 (s, 2H), 4.19-4.10 (m, 2H), 4.06 (d, J=12.0 Hz, 1H), 4.01-3.83 (m, 4H), 3.82-3.65 (m, 3H), 3.54-3.43 (m, 2H), 3.30 (s, 3H), 3.27-3.09 (m, 3H), 2.47 (d, J=9.4 Hz, 2H), 2.33-2.20 (m, 2H), 2.17 (s, 1H), 2.10-1.91 (m, 4H), 1.89-1.66 (m, 5H), 1.66-1.57 (m, 2H), 1.25-1.11 (m, 4H), 0.59 (q, J=4.8 Hz, 1H). LCMS-ESI$^+$: [M+H]$^+$ calcd for C$_{40}$H$_{50}$ClN$_3$O$_7$S: 752.3; found: 752.0.

Example 164

Example 164 was prepared in a similar manner to Intermediate T using Intermediate O and 1-ethylpyrazole-4- carboxylic acid. ¹H NMR (400 MHz, Methanol-d₄) δ 8.26 (s, 1H), 7.97 (s, 1H), 7.70 (d, J=8.5 Hz, 1H), 7.34 (d, J=2.3 Hz, 1H), 7.22 (dd, J=8.2, 1.8 Hz, 1H), 7.13 (dd, J=8.6, 2.3 Hz, 1H), 6.99 (d, J=1.9 Hz, 1H), 6.89 (d, J=8.2 Hz, 1H), 6.08 (dt, J=14.3, 6.7 Hz, 1H), 5.61 (dd, J=15.3, 8.9 Hz, 1H), 4.36 (dd, J=14.8, 6.6 Hz, 1H), 4.24 (q, J=7.3 Hz, 2H), 4.15-4.02 (m, 2H), 3.96-3.83 (m, 2H), 3.79 (dd, J=8.9, 3.6 Hz, 1H), 3.71 (d, J=14.3 Hz, 1H), 3.29 (s, 3H), 3.26-3.10 (m, 2H), 2.57-2.35 (m, 3H), 2.33-2.15 (m, 3H), 2.10-1.96 (m, 2H), 1.89-1.59 (m, 5H), 1.49 (t, J=7.3 Hz, 3H), 1.33 (d, J=16.2 Hz, 1H), 1.25-1.08 (m, 4H), 0.63-0.51 (m, 1H). LCMS-ESI⁺: [M+H]⁺ calcd for $C_{39}H_{46}ClN_5O_5S$: 732.3; found: 731.9.

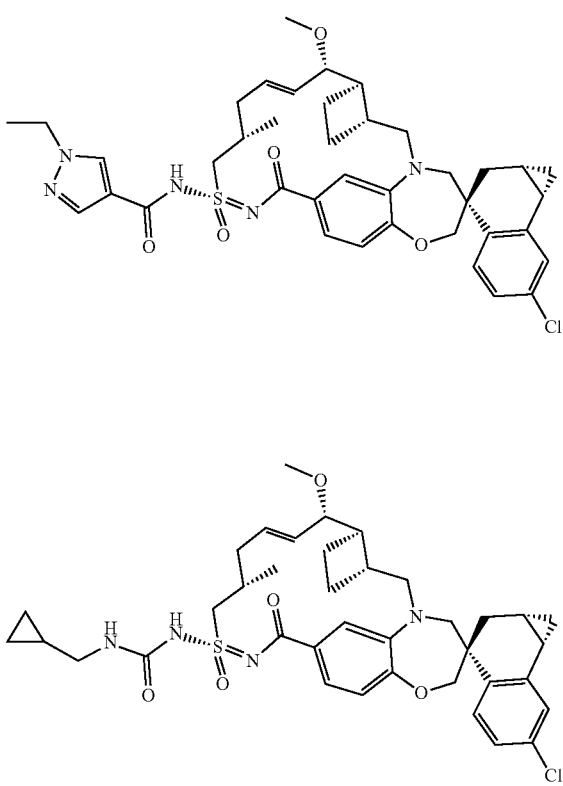

Example 165

Example 165 was prepared in a similar manner to Example 42 (Step 2) using cyclopropylmethanamine, Intermediate O, acetonitrile in place of DCM, and omitting the use of TEA. ¹H NMR (400 MHz, Methanol-d₄) δ 7.71 (d, J=8.5 Hz, 1H), 7.34 (d, J=2.3 Hz, 1H), 7.23 (d, J=8.2 Hz, 1H), 7.15 (dd, J=8.5, 2.4 Hz, 1H), 7.03 (s, 1H), 6.87 (d, J=8.1 Hz, 1H), 6.12-6.01 (m, 1H), 5.59 (dd, J=15.3, 8.9 Hz, 1H), 4.26 (dd, J=14.8, 6.6 Hz, 1H), 4.15-4.02 (m, 2H), 3.87 (d, J=14.6 Hz, 2H), 3.79 (dd, J=8.8, 3.8 Hz, 1H), 3.72 (d, J=14.2 Hz, 1H), 3.28 (s, 3H), 3.24-3.03 (m, 4H), 2.48 (d, J=8.9 Hz, 2H), 2.38 (t, J=9.3 Hz, 1H), 2.33-2.10 (m, 3H), 2.10-1.93 (m, 3H), 1.89-1.63 (m, 5H), 1.31 (s, 1H), 1.16 (dd, J=24.4, 5.7 Hz, 4H), 1.08-0.97 (m, 1H), 0.58 (q, J=4.9 Hz, 1H), 0.55-0.47 (m, 2H), 0.25 (dd, J=4.8, 1.4 Hz, 2H). LCMS-ESI⁺: [M+H]⁺ calcd for $C_{38}H_{47}ClN_4O_5S$: 707.3; found: 706.7.

Example 166

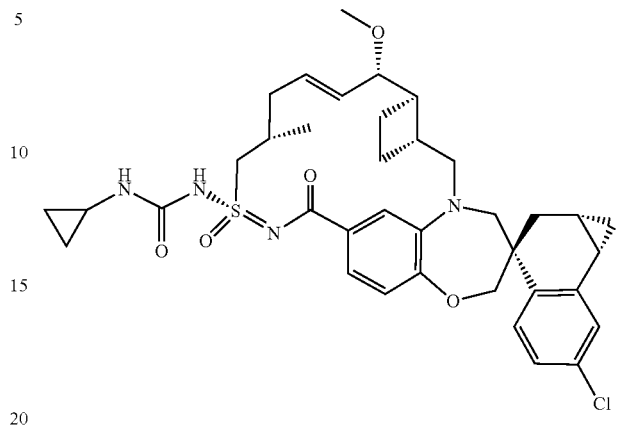

Example 166 was prepared in a similar manner to Example 165 using cyclopropylamine in place of cyclopropylmethanamine. ¹H NMR (400 MHz, Methanol-d₄) δ 7.68 (d, J=8.5 Hz, 1H), 7.32 (d, J=2.3 Hz, 1H), 7.18 (d, J=8.2 Hz, 1H), 7.15-7.08 (m, 1H), 6.98 (s, 1H), 6.85 (d, J=8.2 Hz, 1H), 6.03 (dt, J=14.4, 6.6 Hz, 1H), 5.58 (dd, J=15.3, 8.8 Hz, 1H), 4.31-4.16 (m, 1H), 4.11-3.99 (m, 2H), 3.85 (d, J=15.1 Hz, 1H), 3.77 (dd, J=8.9, 3.7 Hz, 1H), 3.69 (d, J=14.3 Hz, 1H), 3.27 (s, 3H), 3.19 (d, J=14.3 Hz, 1H), 3.16-3.07 (m, 1H), 2.60 (dt, J=7.1, 3.5 Hz, 1H), 2.54-2.42 (m, 2H), 2.36 (t, J=9.2 Hz, 1H), 2.27 (d, J=13.2 Hz, 1H), 2.23-2.08 (m, 1H), 2.08-2.00 (m, 1H), 2.00-1.88 (m, 1H), 1.81 (q, J=10.1 Hz, 2H), 1.76-1.55 (m, 2H), 1.29 (s, 1H), 1.18 (td, J=8.6, 4.6 Hz, 1H), 1.12 (d, J=6.6 Hz, 3H), 0.72 (d, J=7.0 Hz, 2H), 0.61-0.45 (m, 3H). LCMS-ESI+: [M+H]⁺ calcd for $C_{37}H_{45}ClN_4O_5S$: 693.3; found: 693.9.

Example 167

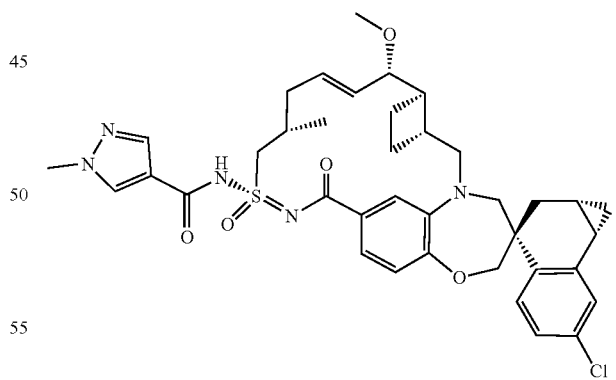

Example 167 was prepared in a similar manner to Intermediate T using Intermediate O and 1-methylpyrazole-4-carboxylic acid. ¹H NMR (400 MHz, Methanol-d₄) b 8.23 (s, 1H), 7.92 (s, 1H), 7.65 (d, J=8.5 Hz, 1H), 7.31 (d, J=2.3 Hz, 1H), 7.20 (dd, J=8.2, 1.8 Hz, 1H), 7.07 (d, J=7.2 Hz, 1H), 6.96 (d, J=2.0 Hz, 1H), 6.86 (d, J=8.2 Hz, 1H), 6.06 (dt, J=14.4, 6.7 Hz, 1H), 5.61 (dd, J=15.3, 8.8 Hz, 1H), 4.32 (dd, J=14.8, 6.6 Hz, 1H), 4.11-4.00 (m, 2H), 3.93 (s, 3H), 3.91-3.81 (m, 2H), 3.78 (dd, J=8.8, 3.6 Hz, 1H), 3.69 (d, J=14.3 Hz, 1H), 3.28 (s, 3H), 3.24-3.09 (m, 2H), 2.60-2.34 (m, 3H), 2.31-2.13 (m, 3H), 2.08-1.96 (m, 2H), 1.90-1.60 (m, 4H), 1.29 (d, J=3.4 Hz, 1H), 1.19 (dt, J=8.7, 4.7 Hz, 1H), 1.14 (d, J=6.6 Hz, 3H), 0.58 (d, J=5.0 Hz, 1H). LCMS-ESI+: [M+H]+ calcd for C$_{36}$H$_{44}$ClN$_5$O$_5$S: 718.3; found: 718.0.

Example 168

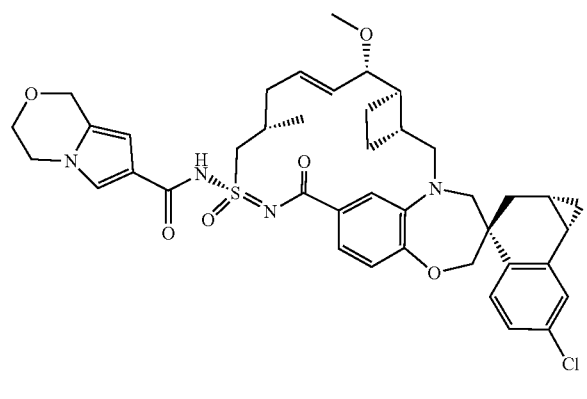 [SMILES: CO[C@H]1/C=C/C[C@H](C)C[S@@](=O)(NC(=O)c2cc3n(c2)CCOC3)=NC(=O)c2ccc3c(c2)N(C[C@@H]2CC[C@H]21)C[C@]1(CO3)C[C@@H]2C[C@@H]2c2cc(Cl)ccc21]

Example 168 was prepared in a similar manner to Intermediate T using Intermediate O and 3,4-dihydro-1H-pyrrolo[2,1-c][1,4]oxazine-7-carboxylic acid. $^1$H NMR (400 MHz, Chloroform-d) δ 7.70 (d, J=8.5 Hz, 1H), 7.42-7.36 (m, 2H), 7.34 (d, J=2.4 Hz, 1H), 7.24-7.14 (m, 2H), 6.93 (d, J=8.2 Hz, 1H), 6.37 (d, J=1.6 Hz, 1H), 5.98 (dt, J=13.9, 6.5 Hz, 1H), 5.62 (dd, J=15.7, 7.5 Hz, 1H), 4.83 (s, 2H), 4.15 (d, J=12.0 Hz, 1H), 4.10-4.02 (m, 5H), 3.93-3.73 (m, 3H), 3.30 (s, 3H), 3.21 (d, J=14.4 Hz, 1H), 3.12 (dd, J=14.9, 9.9 Hz, 1H), 2.58-2.43 (m, 2H), 2.43-2.29 (m, 1H), 2.26 (d, J=14.1 Hz, 1H), 2.18-2.06 (m, 1H), 2.01 (dt, J=8.4, 4.2 Hz, 1H), 1.96-1.87 (m, 1H), 1.85-1.55 (m, 7H), 1.28 (t, J=3.3 Hz, 1H), 1.23-1.14 (m, 1H), 1.12 (d, J=6.8 Hz, 3H), 0.62 (q, J=4.9 Hz, 1H). LCMS-ESI+: [M+H]+ calc'd for C$_{41}$H$_{47}$ClN$_4$O$_6$S: 759.3; found: 759.1.

Example 169

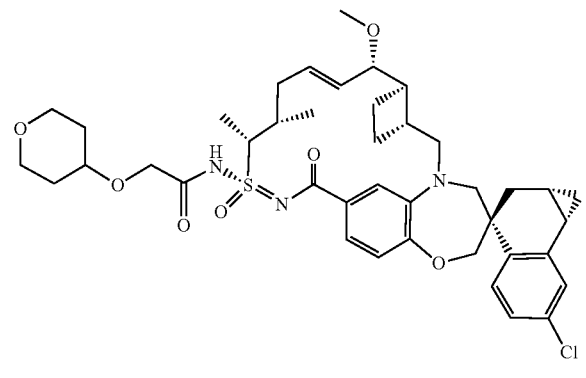

Example 169 was prepared in a similar manner to Example 46 (Steps 7-10) using O-9 in place of I-1-3, and Intermediate A in place of 46-7. $^1$H NMR (400 MHz, Methanol-d$_4$) b 7.70 (d, J=8.5 Hz, 1H), 7.33 (d, J=2.4 Hz, 1H), 7.21-7.10 (m, 2H), 6.99 (s, 1H), 6.90 (d, J=8.2 Hz, 1H), 5.95 (dt, J=14.0, 6.5 Hz, 1H), 5.58 (dd, J=15.3, 8.9 Hz, 1H), 4.33 (d, J=7.4 Hz, 1H), 4.16 (s, 2H), 4.10 (s, 2H), 3.93 (dt, J=11.7, 4.5 Hz, 2H), 3.84 (d, J=15.1 Hz, 1H), 3.78-3.61 (m, 3H), 3.52-3.38 (m, 3H), 3.23 (s, 4H), 3.22-3.06 (m, 1H), 2.53-2.30 (m, 2H), 2.30-2.26 (m, 2H), 2.25 (s, 2H), 2.08-2.01 (m, 1H), 2.01-1.92 (m, 3H), 1.92-1.77 (m, 1H), 1.77-1.56 (m, 5H), 1.52 (d, J=7.0 Hz, 3H), 1.29 (d, J=2.8 Hz, 1H), 1.18 (td, J=8.7, 4.7 Hz, 1H), 1.12 (d, J=6.7 Hz, 3H), 0.60-0.44 (m, 1H). LCMS-ESI+: [M+H]+ calcd for C$_{41}$H$_{52}$ClN$_3$O$_7$S: 766.3; found: 766.7.

Example 170

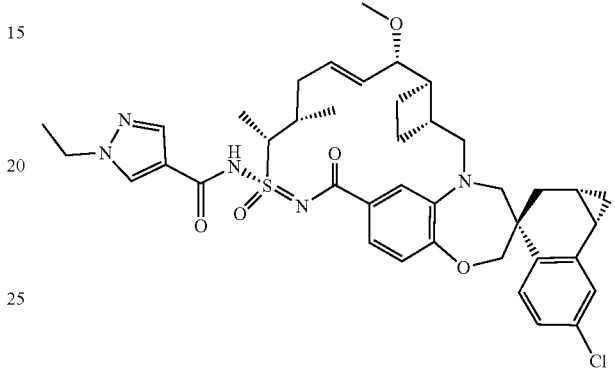

Example 170 was prepared in a similar manner to Example 46 (Steps 7-10) using O-9 in place of I-1-3, Intermediate A in place of 46-7, and using 1-ethyl-1H-pyrazole-4-carboxylic acid in place of 2-tetrahydropyran-4-yloxyacetic acid. $^1$H NMR (400 MHz, Methanol-d$_4$) δ 8.11 (s, 1H), 7.87 (d, J=0.7 Hz, 1H), 7.69 (d, J=8.5 Hz, 1H), 7.33 (d, J=2.3 Hz, 1H), 7.12 (ddd, J=19.1, 8.4, 2.2 Hz, 2H), 6.97-6.82 (m, 2H), 6.02-5.76 (m, 1H), 5.58 (dd, J=15.3, 9.1 Hz, 1H), 4.48-4.37 (m, 1H), 4.21 (q, J=7.3 Hz, 2H), 4.11 (s, 2H), 3.85 (d, J=15.2 Hz, 1H), 3.77-3.58 (m, 2H), 3.23 (s, 3H), 3.21-3.07 (m, 2H), 2.47 (t, J=10.1 Hz, 1H), 2.40-2.17 (m, 4H), 2.15 (d, J=8.5 Hz, 1H), 2.09-2.01 (m, 1H), 2.01-1.90 (m, 1H), 1.90-1.76 (m, 2H), 1.76-1.62 (m, 2H), 1.60 (d, J=7.0 Hz, 3H), 1.47 (t, J=7.3 Hz, 4H), 1.29 (d, J=3.4 Hz, 1H), 1.25-1.10 (m, 4H), 0.55 (q, J=4.8 Hz, 1H). LCMS-ESI+: [M+H]+ calcd for C$_{40}$H$_{48}$ClN$_5$O$_5$S: 746.3; found: 746.0.

Example 171

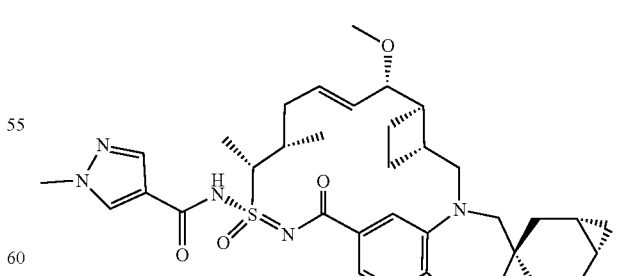

Example 171 was prepared in a similar manner to Example 46 (Steps 7-10) using O-9 in place of I-1-3, Intermediate A in place of 46-7, and using 1-methylpyrazole-4-carboxylic acid in place of 2-tetrahydropyran-4-yloxyacetic acid. $^1$H NMR (400 MHz, Methanol-$d_4$) δ 8.07 (s, 1H), 7.85 (d, J=0.7 Hz, 1H), 7.69 (d, J=8.5 Hz, 1H), 7.33 (d, J=2.3 Hz, 1H), 7.15 (dd, J=8.5, 2.4 Hz, 1H), 7.10 (dd, J=8.2, 2.0 Hz, 1H), 6.94-6.87 (m, 2H), 5.94 (ddd, J=13.7, 8.8, 4.2 Hz, 1H), 5.58 (dd, J=15.2, 9.1 Hz, 1H), 4.43 (q, J=6.8 Hz, 1H), 4.18-4.05 (m, 2H), 3.92 (s, 3H), 3.85 (d, J=15.2 Hz, 1H), 3.73 (dd, J=9.1, 3.3 Hz, 1H), 3.68 (d, J=14.2 Hz, 1H), 3.23 (s, 3H), 3.21-3.12 (m, 2H), 2.55-2.43 (m, 1H), 2.40-2.20 (m, 3H), 2.18-2.08 (m, 1H), 2.04 (td, J=8.4, 3.7 Hz, 1H), 2.00-1.90 (m, 1H), 1.90-1.77 (m, 2H), 1.77-1.62 (m, 4H), 1.60 (d, J=7.0 Hz, 3H), 1.21-1.14 (m, 1H), 1.18 (d, J=6.8 Hz, 3H), 0.55 (q, J=4.9 Hz, 1H). LCMS-ESI+: [M+H]$^+$ calcd for $C_{39}H_{46}ClN_5O_5S$: 732.3; found: 732.0.

Example 172

Example 172 was prepared in a similar manner to Example 46 (Steps 7-10) using O-9 in place of I-1-3, Intermediate A in place of 46-7, and using 3,4-dihydro-1H-pyrrolo[2,1-c][1,4]oxazine-7-carboxylic acid in place of 2-tetrahydropyran-4-yloxyacetic acid. $^1$H NMR (400 MHz, Chloroform-d) δ 7.68 (d, J=8.4 Hz, 1H), 7.31 (dd, J=7.9, 2.0 Hz, 2H), 7.22-7.13 (m, 2H), 7.02 (s, 1H), 6.93 (d, J=8.2 Hz, 1H), 6.32 (d, J=1.6 Hz, 1H), 6.06-5.91 (m, 1H), 5.50 (dd, J=15.2, 8.9 Hz, 1H), 4.79 (s, 2H), 4.55 (s, 1H), 4.14-4.06 (m, 2H), 4.05-3.97 (m, 4H), 3.85 (d, J=15.0 Hz, 1H), 3.73 (d, J=14.2 Hz, 1H), 3.68 (dd, J=8.9, 3.3 Hz, 1H), 3.23 (s, 3H), 3.17-3.04 (m, 2H), 2.52-2.41 (m, 1H), 2.41-2.29 (m, 1H), 2.28-2.08 (m, 4H), 2.04-1.90 (m, 3H), 1.89-1.72 (m, 3H), 1.72-1.60 (m, 3H), 1.58 (d, J=7.1 Hz, 3H), 1.14 (td, J=8.5, 4.7 Hz, 1H), 0.98 (d, J=6.1 Hz, 3H), 0.57 (q, J=4.9 Hz, 1H). LCMS-ESI+: [M+H]$^+$ calcd for $C_{42}H_{49}ClN_4O_6S$: 773.3; found: 773.3.

Example 173

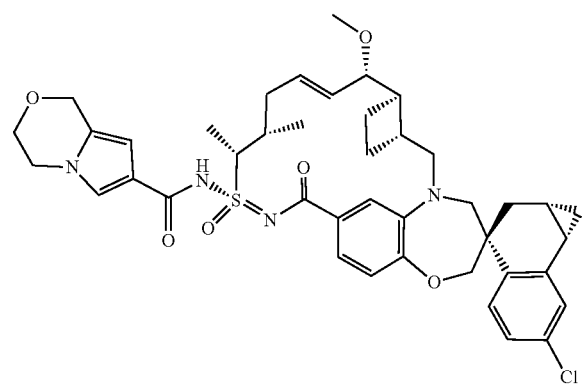

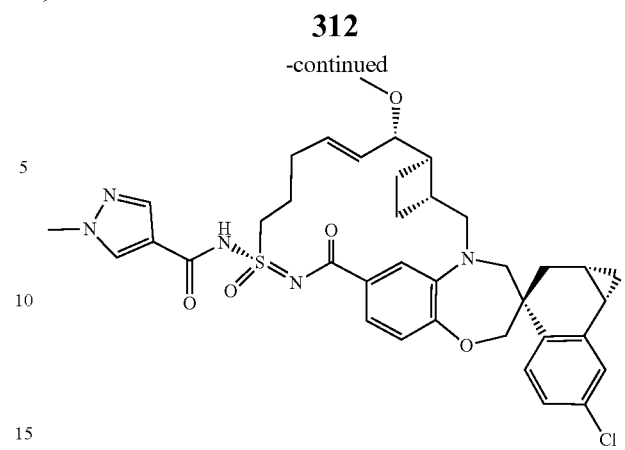

Example 173 was prepared in a similar manner to Intermediate T using Intermediate P and 1-methylpyrazole-4-carboxylic acid. $^1$H NMR (400 MHz, DMSO-$d_6$) δ 8.31 (s, 1H), 7.95 (s, 1H), 7.65 (d, J=8.5 Hz, 1H), 7.43 (d, J=2.4 Hz, 1H), 7.30 (s, 1H), 7.27-7.14 (m, 2H), 6.85 (d, J=8.3 Hz, 1H), 6.52 (s, 1H), 5.87 (d, J=15.6 Hz, 1H), 5.70 (s, 1H), 4.09 (d, J=12.2 Hz, 1H), 3.94 (d, J=12.2 Hz, 1H), 3.87 (s, 3H), 3.80-3.60 (m, 2H), 3.52 (d, J=8.6 Hz, 1H), 3.21 (s, 3H), 3.19-3.04 (m, 1H), 2.74-2.64 (m, 1H), 2.37-2.26 (m, 1H), 2.28-2.14 (m, 2H), 2.07 (dt, J=8.4, 5.1 Hz, 1H), 1.92 (d, J=8.2 Hz, 3H), 1.83-1.46 (m, 5H), 1.32-1.04 (m, 3H), 0.95-0.57 (m, 1H), 0.52 (d, J=4.9 Hz, 1H), 0.07 (s, 1H). LCMS-ESI+: [M+H]$^+$ calcd for $C_{37}H_{42}ClN_5O_5S$: 704.3; found: 704.1.

Example 174

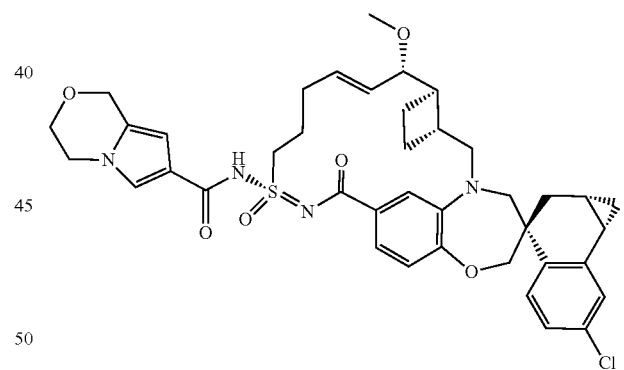

Example 174 was prepared in a similar manner to Intermediate T using Intermediate P and 3,4-dihydro-1H-pyrrolo[2,1-c][1,4]oxazine-7-carboxylic acid. $^1$H NMR (400 MHz, Chloroform-d) δ 7.57 (d, J=8.9 Hz, 1H), 7.42-7.32 (m, 1H), 7.29 (d, J=2.3 Hz, 1H), 7.19 (s, 1H), 6.93 (d, J=8.2 Hz, 1H), 6.29 (d, J=1.6 Hz, 1H), 5.93-5.79 (m, 1H), 5.74 (dd, J=15.8, 7.7 Hz, 1H), 4.83-4.65 (m, 2H), 4.17-3.87 (m, 5H), 3.79 (d, J=14.7 Hz, 1H), 3.70 (d, J=14.5 Hz, 1H), 3.60 (dd, J=7.6, 3.3 Hz, 1H), 3.32 (s, 3H), 3.24 (d, J=14.2 Hz, 1H), 3.12 (dd, J=15.0, 10.9 Hz, 1H), 2.74 (s, 1H), 2.47-2.20 (m, 3H), 2.19-2.03 (m, 1H), 2.01-1.90 (m, 2H), 1.81 (q, J=9.3 Hz, 1H), 1.26 (s, 2H), 1.18-1.02 (m, 1H), 0.93-0.77 (m, 1H), 0.63 (d, J=4.6 Hz, 1H). LCMS-ESI+: [M+H]$^+$ calcd for $C_{40}H_{45}ClN_4O_6S$: 745.3; found: 745.0.

Example 175

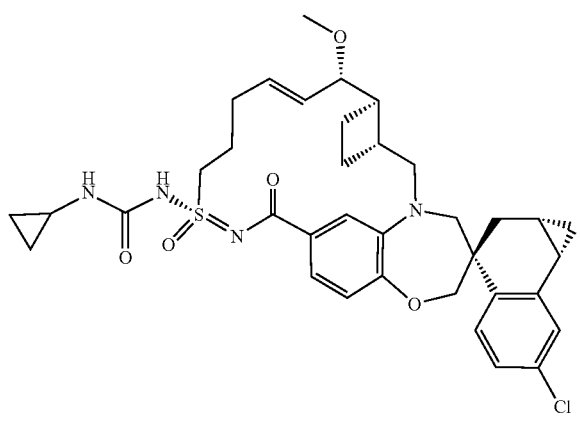

A solution of Intermediate P (0.025 mmol, 15 mg) in CH$_2$Cl$_2$ (0.25 mL) was treated with triethylamine (0.10 mmol, 0.014 mL) and isocyanatocyclopropane (0.075 mmol, 6.3 mg) at room temperature and stirred for 3 hr. The reaction mixture was concentrated, purified by preparative HPLC (60-100 MeCN in water, 0.1% TFA) to afford Example 175. $^1$H NMR (400 MHz, DMSO-d$_6$) δ 7.64 (d, J=8.5 Hz, 1H), 7.43 (d, J=2.4 Hz, 1H), 7.29-7.18 (m, 3H), 6.87 (d, J=8.2 Hz, 1H), 5.87 (dd, J=15.8, 5.5 Hz, 1H), 5.65 (dd, J=15.8, 8.5 Hz, 1H), 4.09 (d, J=12.2 Hz, 1H), 3.94 (d, J=12.2 Hz, 1H), 3.82-3.67 (m, 4H), 3.53 (dd, J=8.6, 3.1 Hz, 1H), 3.19 (s, 3H), 3.17-3.04 (m, 2H), 2.41-2.13 (m, 3H), 2.08 (td, J=8.5, 3.7 Hz, 1H), 1.98-1.79 (m, 2H), 1.68 (qd, J=19.6, 9.1 Hz, 4H), 1.15 (td, J=8.6, 4.4 Hz, 1H), 0.64 (h, J=4.9 Hz, 2H), 0.52 (q, J=4.7 Hz, 1H), 0.43 (d, J=3.1 Hz, 2H). LCMS-ESI+: [M+H]$^+$ calcd for C$_{36}$H$_{43}$ClN$_4$O$_5$S: 679.3; found: 679.5.

Example 176

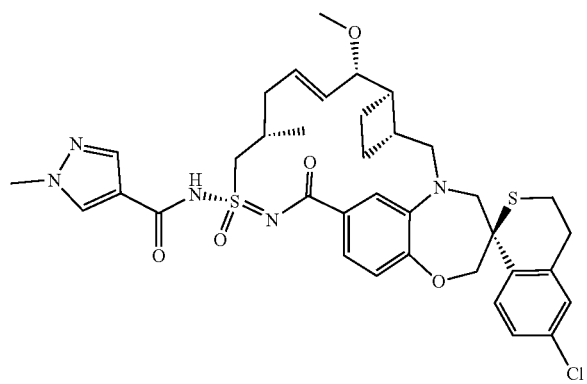 [SMILES: CO[C@H]1/C=C/C[C@H](C)C[S@@](=O)(NC(=O)c2cnn(C)c2)=NC(=O)c2ccc3c(c2)N(C[C@@H]2CC[C@H]21)C[C@]1(CO3)SCCc2cc(Cl)ccc21]

Example 176 was prepared in a similar manner to Intermediate T using Intermediate Q and 1-methyl-1H-pyrazole-4-carboxylic acid. $^1$H NMR (400 MHz, Acetone-d$_6$) b 8.29 (s, 1H), 7.86 (s, 1H), 7.77 (d, J=8.6 Hz, 1H), 7.28 (t, J=8.1 Hz, 2H), 7.22 (d, J=2.3 Hz, 1H), 7.15 (s, 1H), 6.90 (d, J=8.3 Hz, 1H), 6.14 (m, J=14.8 Hz, 1H), 5.65 (dd, J=15.4, 8.2 Hz, 1H), 4.35 (d, J=12.4 Hz, 1H), 4.12 (d, J=12.4 Hz, 1H), 3.95 (s, 3H), 3.76 (d, J=10.8 Hz, 1H), 3.68-3.58 (m, 1H), 3.54 (dd, J=5.6, 4.3 Hz, 1H), 3.31 (s, 2H), 3.25 (s, 3H), 3.22-3.10 (m, 3H), 3.00-2.80 (m, 5H), 2.65-2.55 (m, 1H), 2.52-2.40 (m, 1H), 2.35-2.22 (m, 1H), 2.04-1.92 (m, 1H), 1.89-1.70 (m, 3H), 1.15 (d, J=6.1 Hz, 3H). LCMS-ESI+ (m/z): [M+H]$^+$ calcd for C$_{36}$H$_{43}$ClN$_5$O$_5$S$_2$: 724.2; found: 723.8.

Example 177

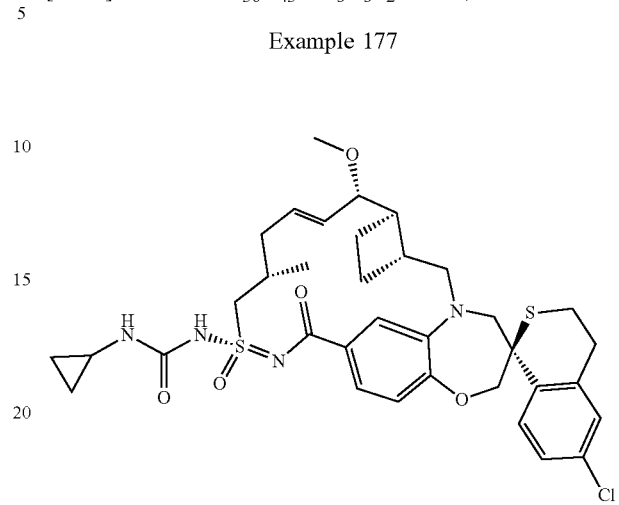

Example 177 was prepared in a similar manner to Example 175 using Intermediate Q in place of Intermediate P. $^1$H NMR (400 MHz, DMSO-d$_6$) δ 7.70 (d, J=8.6 Hz, 1H), 7.38 (dd, J=8.5, 2.5 Hz, 1H), 7.31 (d, J=2.4 Hz, 1H), 7.15 (d, J=8.3 Hz, 1H), 7.00 (s, 1H), 6.89 (d, J=8.2 Hz, 1H), 6.09-5.90 (m, 1H), 5.61-5.40 (m, 1H), 4.36 (d, J=12.4 Hz, 1H), 4.04 (d, J=12.5 Hz, 2H), 3.85 (d, J=14.4 Hz, 2H), 3.75-3.65 (m, 2H), 3.51-3.41 (m, 3H), 3.15 (s, 3H), 3.11-3.03 (m, 3H), 2.87-2.78 (m, 1H), 2.44-2.22 (m, 3H), 2.18-2.04 (m, 1H), 1.98 (s, 1H), 1.86-1.59 (m, 4H), 1.00 (d, J=6.8 Hz, 3H), 0.65 (d, J=7.2 Hz, 2H), 0.51-0.34 (m, 2H). LCMS-ESI+ (m/z): [M+H]$^+$ calcd for C$_{35}$H$_{43}$ClN$_4$O$_5$S$_2$: 699.3, found: 698.8.

Example 178

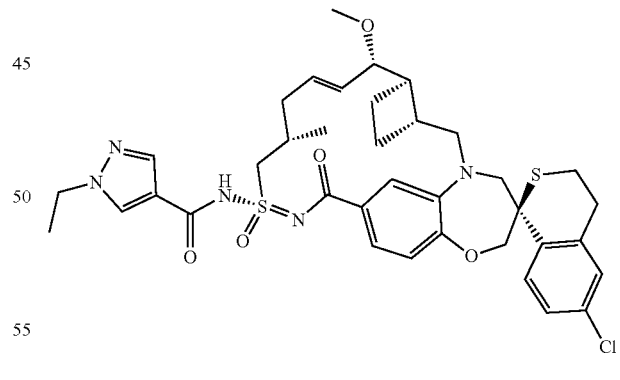

Example 178 was prepared in a similar manner to Intermediate T using Intermediate Q and 1-ethyl-1H-pyrazole-4-carboxylic acid. $^1$H NMR (400 MHz, DMSO-d$_6$) δ 8.35 (s, 1H), 7.94 (s, 1H), 7.71 (d, J=8.6 Hz, 1H), 7.38 (dd, J=8.6, 2.3 Hz, 1H), 7.31 (d, J=2.4 Hz, 1H), 7.16 (dd, J=8.0, 1.8 Hz, 1H), 6.99 (d, J=1.9 Hz, 1H), 6.91 (d, J=8.2 Hz, 1H), 6.10-5.99 (m, 1H), 5.52 (dd, J=15.2, 8.3 Hz, 1H), 4.37 (d, J=12.5 Hz, 1H), 4.19 (t, J=7.2 Hz, 2H), 4.11-4.02 (m, 2H), 3.92-3.83 (m, 2H), 3.73 (d, J=14.9 Hz, 1H), 3.65 (dd, J=8.3, 3.5 Hz, 1H), 3.51-3.47 (m, 1H), 3.45-3.42 (m, 1H), 3.17 (s, 3H), 3.11-3.03 (m, 3H), 2.88-2.79 (m, 1H), 2.42-2.27 (m, 3H), 2.25-2.14 (m, 1H), 2.04-1.95 (m, 1H), 1.85-1.61 (m, 4H), 1.39 (t, J=7.3 Hz, 3H), 1.03 (d, J=6.8 Hz, 3H). LCMS-ESI+ (m/z): [M+H]+ calcd for C₃₇H₄₄ClN₅O₅S₂: 738.4, found: 737.9.

Example 179

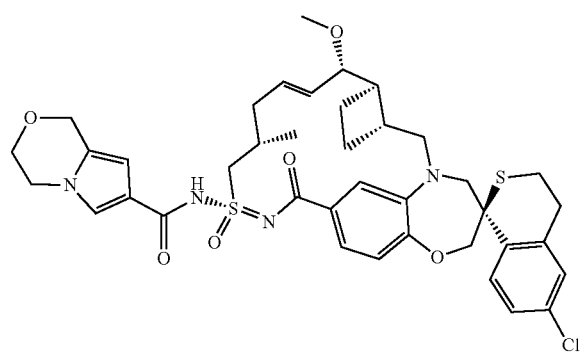

Example 179 was prepared in a similar manner to Intermediate T using Intermediate Q and 3,4-dihydro-1H-pyrrolo[2,1-c][1,4]oxazine-7-carboxylic acid. ¹H NMR (400 MHz, DMSO-d₆) δ 7.71 (d, J=8.6 Hz, 1H), 7.60 (d, J=1.7 Hz, 1H), 7.38 (dd, J=8.6, 2.4 Hz, 1H), 7.31 (d, J=2.4 Hz, 1H), 7.23 (dd, J=8.2, 1.8 Hz, 1H), 7.06 (d, J=1.9 Hz, 1H), 6.91 (d, J=8.2 Hz, 1H), 6.33 (d, J=1.6 Hz, 1H), 6.09-5.99 (m, 1H), 5.53 (dd, J=15.4, 8.1 Hz, 1H), 4.72 (s, 2H), 4.37 (d, J=12.5 Hz, 1H), 4.06-3.96 (m, 6H), 3.94-3.83 (m, 2H), 3.75-3.65 (m, 2H), 3.52-3.45 (m, 2H), 3.17 (s, 3H), 3.11-3.04 (m, 3H), 2.87-2.79 (m, 1H), 2.45-2.29 (m, 3H), 2.26-2.15 (m, 1H), 2.06-1.96 (m, 1H), 1.84-1.62 (m, 4H), 1.02 (d, J=6.9 Hz, 3H). LCMS-ESI+ (m/z): [M+H]+ calcd for C₃₉H₄₅ClN₄O₆S₂: 765.4, found: 764.9.

Example 180

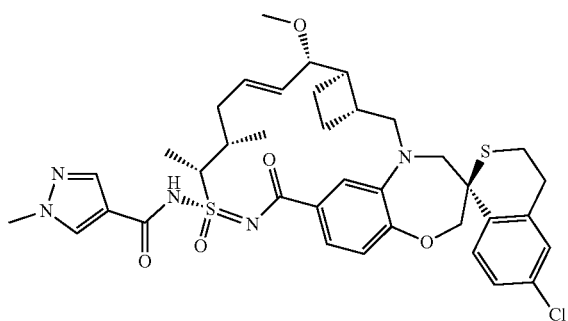 [SMILES: CO[C@H]1/C=C/C[C@H](C)[C@@H](C)[S@@](=O)(NC(=O)c2cnn(C)c2)=NC(=O)c2ccc3c(c2)N(C[C@@H]2CC[C@H]21)C[C@]1(CO3)SCCc2cc(Cl)ccc21]

Example 180 was prepared in a similar manner to Example 46 (Steps 7-10) using Q-15 in place of I-1-3, Intermediate A in place of 46-7, and 1-methyl-1H-pyrazole-4-carboxylic acid in place of 3,4-dihydro-1H-pyrrolo[2,1-c][1,4]oxazine-7-carboxylic acid. ¹H NMR (400 MHz, DMSO-d₆) δ 8.17 (s, 1H), 7.79 (s, 1H), 7.69 (d, J=8.6 Hz, 1H), 7.39 (dd, J=8.6, 2.4 Hz, 1H), 7.32 (d, J=2.4 Hz, 1H), 7.02 (dd, J=8.1, 1.7 Hz, 1H), 6.99-6.94 (m, 1H), 6.88 (s, 1H), 5.86-5.77 (m, 1H), 5.53 (dd, J=15.1, 9.0 Hz, 1H), 4.37 (d, J=12.5 Hz, 1H), 4.23-4.14 (m, 1H), 4.10 (d, J=12.5 Hz, 1H), 3.91-3.82 (m, 4H), 3.73 (d, J=14.7 Hz, 1H), 3.59 (dd, J=9.0, 3.5 Hz, 1H), 3.47-3.44 (m, 2H), 3.14-3.03 (m, 6H), 2.86-2.80 (m, 1H), 2.47-2.37 (m, 1H), 2.28-2.14 (m, 3H), 2.11-2.00 (m, 1H), 1.90-1.64 (m, 4H), 1.48 (d, J=7.0 Hz, 3H), 1.05 (d, J=6.6 Hz, 3H). LCMS-ESI+ (m/z): [M+H]+ calcd for C₃₇H₄₄ClN₅O₅S₂: 738.4, found: 737.9.

Example 181

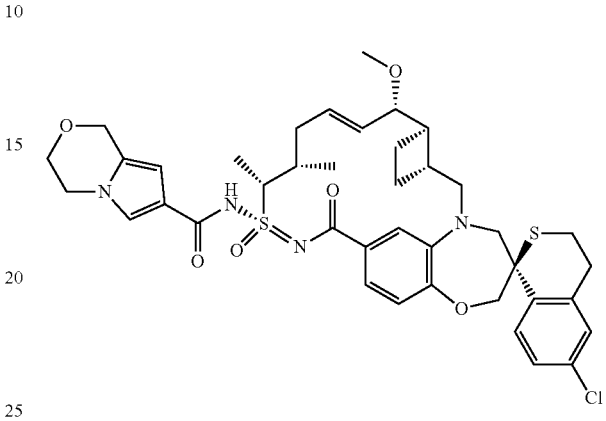

Example 181 was prepared in a similar manner to Example 180 using 3,4-dihydro-1H-pyrrolo[2,1-c][1,4]oxazine-7-carboxylic acid in place of 1-methyl-1H-pyrazole-4-carboxylic acid. ¹H NMR (400 MHz, Methanol-d₄) δ ¹H NMR (400 MHz, DMSO-d₆) δ 7.70 (d, J=8.6 Hz, 1H), 7.42-7.35 (m, 2H), 7.32 (d, J=2.4 Hz, 1H), 7.07 (d, J=8.2 Hz, 1H), 6.98-6.91 (m, 2H), 6.20 (s, 1H), 5.92-5.79 (m, 1H), 5.53 (dd, J=15.2, 8.8 Hz, 1H), 4.71 (s, 2H), 4.38 (d, J=12.5 Hz, 1H), 4.20-4.05 (m, 2H), 4.04-3.91 (m, 4H), 3.86 (d, J=14.5 Hz, 1H), 3.73 (d, J=14.7 Hz, 1H), 3.60 (dd, J=8.8, 3.5 Hz, 1H), 3.50 (s, 2H), 3.17-3.02 (m, 6H), 2.90-2.77 (m, 1H), 2.42 (d, J=11.0 Hz, 1H), 2.24 (d, J=38.4 Hz, 4H), 1.91-1.61 (m, 4H), 1.46 (d, J=7.0 Hz, 3H), 1.01 (d, J=5.7 Hz, 3H). LCMS-ESI+ (m/z): [M+H]+ calcd for C₄₀H₄₇ClN₄O₆S₂: 779.4, found: 779.0.

Example 182

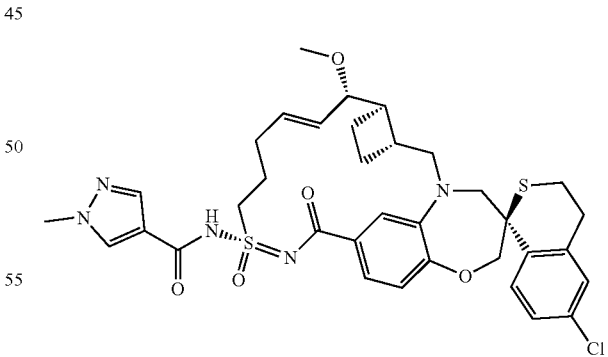

Example 182 was prepared in a similar manner to Intermediate T using Intermediate R and 1-methyl-1H-pyrazole-4-carboxylic acid. ¹H NMR (400 MHz, Acetone-d₆) b 8.47 (s, 1H), 7.83 (s, 1H), 7.72 (d, J=8.7 Hz, 1H), 7.44-7.29 (m, 2H), 7.23-7.08 (m, 2H), 6.98 (d, J=8.3 Hz, 1H), 6.01-5.84 (m, 2H), 4.30 (d, J=12.4 Hz, 1H), 4.06 (d, J=12.4 Hz, 1H), 3.94-3.89 (m, 5H), 3.71 (d, J=14.5 Hz, 2H), 3.67-3.55 (m, 3H), 3.36 (s, 3H), 3.21-3.12 (m, 4H), 2.61-2.51 (m, 2H), 2.40-2.14 (m, 5H), 1.99-1.79 (m, 3H). LCMS-ESI+ (m/z): [M+H]+ calcd for $C_{35}H_{40}ClN_5O_5S_2$: 710.3, found: 708.0.

Example 183

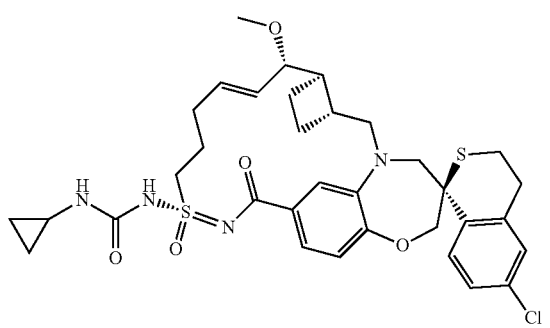 [SMILES: CO[C@H]1/C=C/CCC[S@@](=O)(NC(=O)NC2CC2)=NC(=O)c2ccc3c(c2)N(C[C@@H]2CC[C@H]21)C[C@]1(CO3)SCCc2cc(Cl)ccc21]

Example 183 was prepared in a similar manner to Example 175 using Intermediate R in place of Intermediate P. $^1$H NMR (400 MHz, Acetone-d$_6$) δ 7.74-7.68 (m, 1H), 7.37-7.25 (m, 2H), 7.19 (d, J=2.0 Hz, 1H), 6.96-6.87 (m, 2H), 6.02-5.81 (m, 2H), 4.29 (d, J=12.5 Hz, 1H), 4.05 (d, J=12.4 Hz, 1H), 3.98-3.81 (m, 3H), 3.76-3.65 (m, 2H), 3.63-3.51 (m, 2H), 3.32 (s, 3H), 3.22-3.08 (m, 4H), 2.81-2.21 (m, 8H), 1.96-1.78 (m, 3H), 0.65 (d, J=29.0 Hz, 4H). LCMS-ESI+ (m/z): [M+H]+ calcd for $C_{34}H_{41}ClN_4O_5S_2$: 685.3, found: 684.8.

Example 184

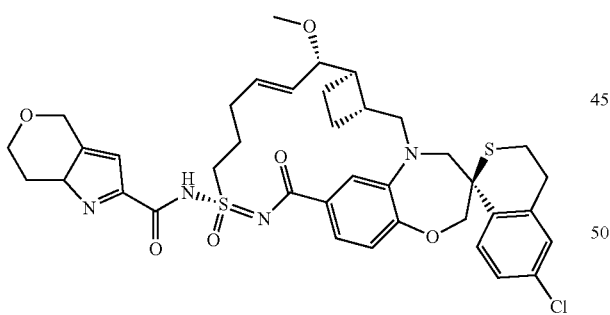

Example 184 was prepared in a similar manner to Intermediate T using Intermediate R and 3,4-dihydro-1H-pyrrolo[2,1-c][1,4]oxazine-7-carboxylic acid. $^1$H NMR (400 MHz, Acetone-d$_6$) δ 7.73-7.66 (m, 2H), 7.42 (dd, J=8.2, 1.9 Hz, 1H), 7.30 (s, 1H), 7.18 (d, J=2.3 Hz, 1H), 7.11-7.03 (m, 1H), 7.00 (d, J=8.2 Hz, 1H), 6.33 (d, J=1.7 Hz, 1H), 6.01-5.83 (m, 2H), 4.80-4.68 (m, 2H), 4.28 (d, J=12.4 Hz, 1H), 4.16-3.97 (m, 7H), 3.91-3.83 (m, 2H), 3.71 (d, J=14.7 Hz, 2H), 3.65-3.58 (m, 2H), 3.31 (s, 3H), 3.22-3.10 (m, 4H), 2.60-2.49 (m, 2H), 2.41-2.13 (m, 6H), 1.91 (dt, J=36.4, 8.9 Hz, 1H). LCMS-ESI+ (m/z): [M+H]+ calcd for $C_{38}H_{43}ClN_4O_6S_2$: 751.4, found: 750.9.

Example 185

Example 185 was prepared in a similar manner to Intermediate T using Intermediate S and 1-methyl-1H-pyrazole-4-carboxylic acid. $^1$H NMR (400 MHz, Acetonitrile-d$_3$) δ 8.06 (s, 1H), 7.89 (s, 1H), 7.71 (d, J=8.5 Hz, 1H), 7.46 (d, J=7.8 Hz, 1H), 7.36 (d, J=7.8 Hz, 1H), 7.27 (dd, J=8.5, 2.4 Hz, 1H), 7.21 (d, J=2.3 Hz, 1H), 5.41 (d, J=3.8 Hz, 2H), 4.28 (d, J=12.4 Hz, 1H), 4.14 (d, J=12.5 Hz, 1H), 4.09-3.94 (m, 2H), 3.91 (s, 4H), 3.70-3.54 (m, 2H), 3.44 (dd, J=14.1, 5.9 Hz, 1H), 3.32 (s, 1H), 3.03 (s, 3H), 2.89-2.67 (m, 3H), 2.58 (q, J=8.0 Hz, 1H), 2.20 (dt, J=15.2, 3.5 Hz, 1H), 2.15-2.00 (m, 2H), 1.92-1.77 (m, 2H), 1.75-1.46 (m, 4H), 1.16 (d, J=6.7 Hz, 3H). LCMS-ESI+ (m/z): [M+H]+ calcd for $C_{36}H_{43}ClN_6O_5S$: 707.3; found: 707.2.

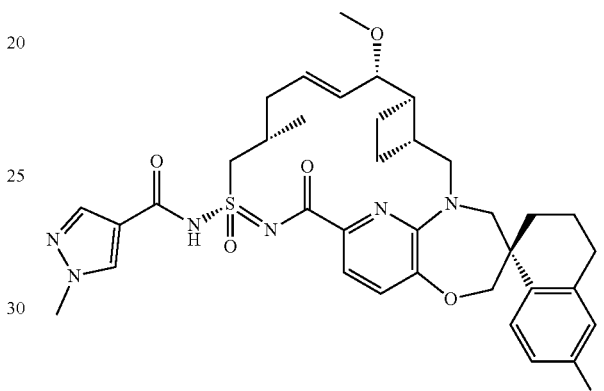

Example 186

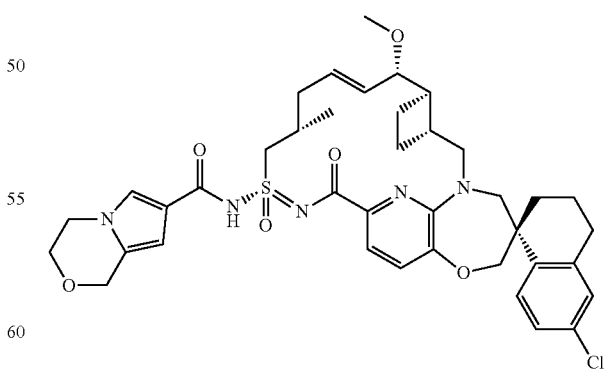

Example 186 was prepared in a similar manner to Intermediate T using Intermediate S and 3,4-dihydro-1H-pyrrolo[2,1-c][1,4]oxazine-7-carboxylic acid. LCMS-ESI+(m/z): [M+H]+ calcd for $C_{39}H_{46}ClN_5O_6S$: 748.3; found: 748.2.

Example 187

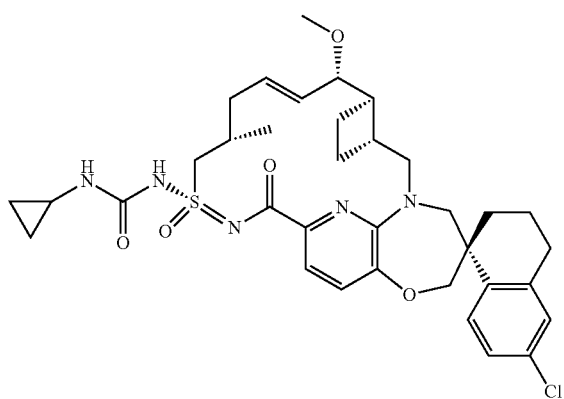 [SMILES: CO[C@H]1/C=C/C[C@H](C)C[S@@](=O)(NC(=O)NC2CC2)=NC(=O)c2ccc3c(n2)N(C[C@@H]2CC[C@H]21)C[C@@]1(CCCc2cc(Cl)ccc21)CO3]

Example 187 was prepared in a similar manner to Example 42 (Step 2) using Intermediate S in place of 42-1. $^1$H NMR (400 MHz, Methanol-$d_4$) δ 7.69 (d, J=8.5 Hz, 1H), 7.31 (d, J=7.8 Hz, 1H), 7.25-7.15 (m, 2H), 7.12 (d, J=2.2 Hz, 1H), 5.72 (s, 1H), 5.45 (dd, J=15.4, 7.4 Hz, 1H), 4.39 (s, 1H), 4.22-3.96 (m, 3H), 3.85 (d, J=14.4 Hz, 1H), 3.55 (s, 1H), 3.46 (d, J=14.5 Hz, 1H), 3.14 (s, 3H), 3.03-2.68 (m, 5H), 2.66-2.27 (m, 5H), 2.08 (t, J=13.6 Hz, 3H), 1.99-1.61 (m, 5H), 1.38 (d, J=80.8 Hz, 2H), 1.13 (d, J=6.4 Hz, 3H), 0.70 (d, J=6.8 Hz, 2H), 0.51 (s, 2H). LCMS-ESI+ (m/z): [M+H]$^+$ calcd for $C_{35}H_{44}ClN_5O_5S$: 682.3; found: 682.1.

Example 188

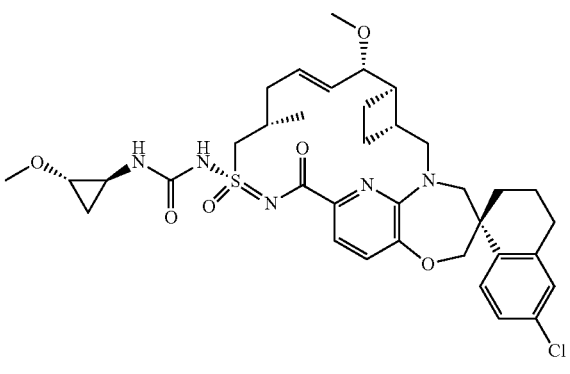 [SMILES: CO[C@H]1/C=C/C[C@H](C)C[S@@](=O)(NC(=O)N[C@H]2C[C@@H]2OC)=NC(=O)c2ccc3c(n2)N(C[C@@H]2CC[C@H]21)C[C@@]1(CCCc2cc(Cl)ccc21)CO3]

To the mixture of rac-(1S*,2S*)-2-methoxycyclopropane-1-carboxylic acid (23.2 mg, 0.2 mmol) in acetonitrile (2 mL) at rt were added triethyl amine (88.38 uL, 0.63 mmol) and diphenyl phosphoryl azide (43 uL, 0.2 mmol). The mixture was heated at 60° C. for 2 h. The reaction mixture was cooled to rt. To this mixture was added Intermediate S, and stirred at 60° C. for 24 h. The reaction was concentrated, re-dissolved in MeOH filtered and purified by Gilson reverse phase prep HPLC, eluted with 60-100% ACN/H$_2$O with 0.1% TFA to give Example 188 (as a mixture of diastereomers). $^1$H NMR (400 MHz, DMSO-$d_6$) δ 7.61 (d, J=8.5 Hz, 1H), 7.30-7.22 (m, 1H), 7.21-7.15 (m, 2H), 7.11 (dd, J=7.8, 2.7 Hz, 1H), 6.96 (d, J=13.0 Hz, 1H), 5.71 (s, 1H), 5.37 (s, 1H), 4.30-3.87 (m, 3H), 3.69 (d, J=14.3 Hz, 2H), 3.28 (s, 6H), 3.18-3.02 (m, 3H), 2.97-2.60 (m, 2H), 2.45-2.15 (m, 3H), 2.11-1.90 (m, 3H), 1.84 (s, 2H), 1.71 (s, 1H), 1.60 (d, J=6.3 Hz, 3H), 1.42 (s, 1H), 1.00 (d, J=6.3 Hz, 3H), 0.88 (d, J=9.5 Hz, 1H), 0.71 (q, J=6.3 Hz, 1H). LCMS-ESI+ (m/z): [M+H]$^+$ calcd for $C_{36}H_{46}ClN_5O_6S$: 712.3; found: 711.9.

Example 189

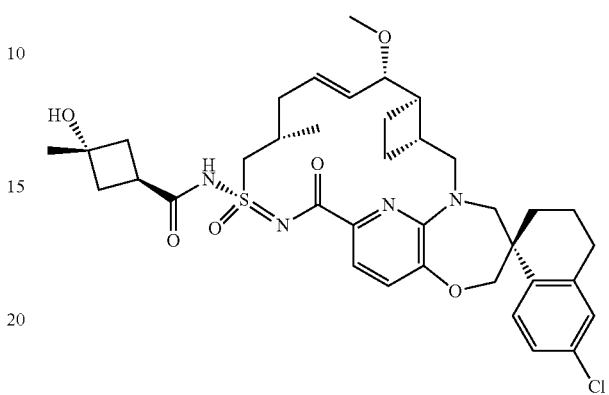

Example 189 was prepared in a similar manner to Intermediate T using Intermediate S and trans-3-hydroxy-3-methylcyclobutane-1-carboxylic acid (stereochemistry tentatively assigned). $^1$H NMR (400 MHz, DMSO-$d_6$) δ 7.61 (d, J=8.5 Hz, 1H), 7.26 (dd, J=8.7, 2.3 Hz, 1H), 7.16 (s, 3H), 5.78 (dt, J=14.8, 6.8 Hz, 1H), 5.45 (dd, J=15.2, 8.5 Hz, 1H), 4.37 (d, J=13.3 Hz, 1H), 4.18 (dd, J=14.7, 6.9 Hz, 1H), 4.06 (d, J=12.4 Hz, 1H), 3.91 (d, J=12.4 Hz, 1H), 3.79 (dd, J=14.8, 5.3 Hz, 1H), 3.68 (d, J=14.5 Hz, 1H), 3.52 (dd, J=8.6, 3.4 Hz, 2H), 3.27 (d, J=14.4 Hz, 1H), 3.09 (s, 3H), 2.87-2.60 (m, 4H), 2.31 (s, 2H), 2.21-1.95 (m, 6H), 1.85 (s, 2H), 1.65 (d, J=35.1 Hz, 4H), 1.49-1.28 (m, 1H), 1.22 (s, 3H), 0.95 (d, J=6.8 Hz, 3H). LCMS-ESI+ (m/z): [M+H]$^+$ calcd for $C_{37}H_{47}ClN_4O_6S$: 711.3; found: 711.2.

Example 190

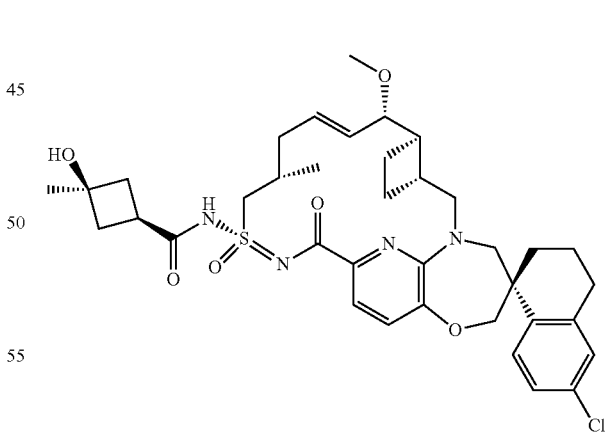

Example 190 was prepared in a similar manner to Intermediate T using Intermediate S and cis-3-hydroxy-3-methylcyclobutane-1-carboxylic acid (stereochemistry tentatively assigned). $^1$H NMR (400 MHz, DMSO-$d_6$) δ 7.61 (d, J=8.6 Hz, 1H), 7.26 (dd, J=8.3, 2.3 Hz, 1H), 7.16 (d, J=2.7 Hz, 3H), 5.85-5.71 (m, 1H), 5.46 (dd, J=15.3, 8.7 Hz, 1H), 4.38 (d, J=13.5 Hz, 1H), 4.18 (dd, J=14.8, 7.0 Hz, 1H), 4.06 (d, J=12.4 Hz, 1H), 3.91 (d, J=12.4 Hz, 1H), 3.80 (dd, J=14.7, 5.1 Hz, 1H), 3.68 (d, J=14.3 Hz, 1H), 3.51 (d, J=9.0 Hz, 3H), 3.27 (d, J=14.4 Hz, 1H), 3.22-3.12 (m, 1H), 3.09 (s, 3H), 2.86-2.59 (m, 3H), 2.29 (d, J=17.6 Hz, 4H), 2.14 (tt, J=13.6, 7.1 Hz, 4H), 1.99 (d, J=13.5 Hz, 1H), 1.85 (s, 2H), 1.65 (d, J=34.7 Hz, 4H), 1.36 (s, 1H), 1.18 (s, 3H), 0.96 (d, J=6.8 Hz, 3H). LCMS-ESI+ (m/z): [M+H]$^+$ calcd for $C_{37}H_{47}ClN_4O_6S$: 711.3; found: 711.2.

Example 191 and Example 192

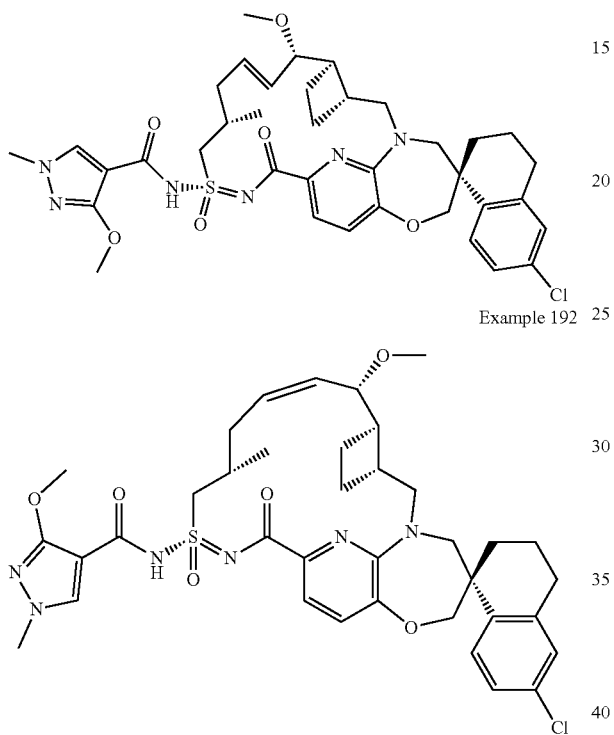

Example 191

Example 192

Example 191 and Example 192 were prepared in a similar manner to Intermediate T using Intermediate S (as a mixture of trans and cis olefins) and 3-methoxy-1-methyl-1H-pyrazole-4-carboxylic acid.

Example 191: $^1$H NMR (400 MHz, Acetonitrile-d$_3$) δ 7.93 (s, 1H), 7.72 (d, J=8.5 Hz, 1H), 7.44 (d, J=7.9 Hz, 1H), 7.35-7.23 (m, 2H), 7.20 (d, J=2.3 Hz, 1H), 5.61-5.43 (m, 2H), 4.30-4.06 (m, 3H), 4.05-3.85 (m, 6H), 3.76 (s, 4H), 3.59-3.37 (m, 2H), 3.18 (q, J=18.2, 16.5 Hz, 1H), 3.08 (s, 3H), 2.96-2.76 (m, 6H), 2.26 (d, J=14.1 Hz, 1H), 2.18-2.01 (m, 1H), 1.94-1.78 (m, 2H), 1.75-1.60 (m, 2H), 1.60-1.45 (m, 1H), 1.30 (s, 1H), 1.11 (d, J=6.7 Hz, 3H). LCMS-ESI+ (m/z): [M+H]$^+$ calcd for $C_{37}H_{45}ClN_6O_6S$: 737.3; found: 737.2.

Example 192: $^1$H NMR (400 MHz, Acetonitrile-d$_3$) δ 7.92 (s, 1H), 7.68 (d, J=8.5 Hz, 1H), 7.49 (d, J=7.9 Hz, 1H), 7.38 (d, J=7.8 Hz, 1H), 7.27 (dd, J=8.5, 2.4 Hz, 1H), 7.20 (d, J=2.4 Hz, 1H), 5.71 (dt, J=11.5, 7.6 Hz, 1H), 5.50-5.38 (m, 1H), 4.29 (d, J=12.5 Hz, 1H), 4.10 (dd, J=29.2, 13.5 Hz, 3H), 4.00 (s, 3H), 3.95-3.82 (m, 2H), 3.76 (s, 5H), 3.63 (d, J=14.5 Hz, 1H), 3.41 (dd, J=15.0, 6.8 Hz, 1H), 3.02 (s, 4H), 2.88-2.71 (m, 3H), 2.63-2.42 (m, 2H), 2.39-2.13 (m, 2H), 2.13-2.00 (m, 1H), 1.94-1.79 (m, 2H), 1.78-1.49 (m, 4H), 1.11 (d, J=7.0 Hz, 3H). LCMS-ESI+ (m/z): [M+H]$^+$ calcd for $C_{37}H_{45}ClN_6O_6S$: 737.3; found: 737.1.

Example 193

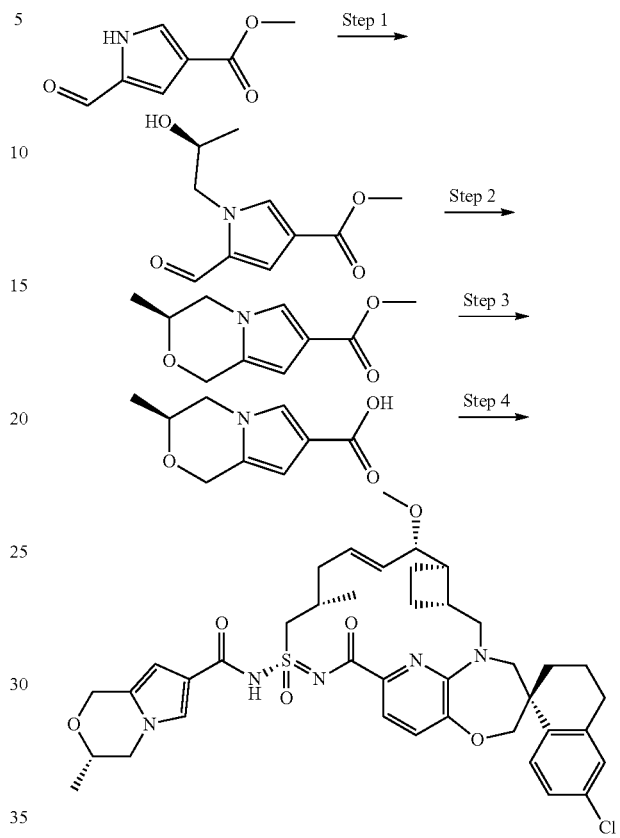

Example 193

Step 1: A vigorously stirred mixture of methyl 5-formyl-1H-pyrrole-3-carboxylate (500 mg, 3.27 mmol), (S)-2-methyloxirane (458 μL, 6.53 mmol), and cesium carbonate (2.13 g, 6.53 mmol) in acetonitrile (6.0 mL) and methanol (2.0 mL) was heated to 60° C. After 45 min, the reaction mixture was allowed to cool to room temperature and ethyl acetate (60 mL) was added. The organic layer was washed with a mixture of water and brine (1:1 v:v, 40 mL), dried over anhydrous sodium sulfate, filtered, and concentrated under reduced pressure. The residue was purified by flash column chromatography on silica gel (0 to 70% ethyl acetate in hexanes) to give 193-1.

Step 2: Trifluoroacetic acid (163 μL, 2.13 mmol) was added via syringe to a stirred solution of 193-1 (150 mg, 0.710 mmol) in dichloromethane (40 mL) at 0° C. After 2 min, triethylsilane (343 μL, 2.15 mmol) was added via syringe, and the resulting mixture was warmed to room temperature. After 45 min, triethylamine (1.0 mL) was added via syringe, and the resulting mixture was concentrated under reduced pressure. The residue was purified by flash column chromatography on silica gel (0 to 40% ethyl acetate in hexanes) to give 193-2.

Step 3: Aqueous sodium hydroxide solution (2.0 M, 800 μL, 1.6 mmol) was added via syringe to a stirred solution of 193-2 (53.6 mg, 0.275 mmol) in tetrahydrofuran (1.0 mL) and methanol (3.0 mL) at room temperature, and the resulting mixture was heated to 60° C. After 3 h, the resulting mixture was allowed to cool to room temperature, and aqueous hydrogen chloride solution (2.0 M, 1.0 mL) and ethyl acetate (30 mL) were added sequentially. The organic layer was washed with brine, dried over anhydrous sodium sulfate, filtered, and concentrated under reduced pressure to give 193-3.

Step 4: Example 193 prepared in a similar manner to Intermediate T using 193-3 and Intermediate S. $^1$H NMR (400 MHz, Acetone-d$_6$) δ 7.80 (d, J=8.5 Hz, 1H), 7.41 (d, J=7.8 Hz, 1H), 7.39-7.35 (m, 1H), 7.33-7.25 (m, 2H), 7.18 (d, J=2.4 Hz, 1H), 6.27 (d, J=1.6 Hz, 1H), 5.71-5.57 (m, 1H), 5.55-5.38 (m, 1H), 4.88 (dd, J=14.3, 0.9 Hz, 1H), 4.72 (d, J=1.3 Hz, 1H), 4.46-3.11 (m, 11H), 3.07 (s, 3H), 2.98-1.43 (m, 16H), 1.32 (d, J=6.2 Hz, 3H), 1.19 (d, J=6.5 Hz, 3H). LCMS-ESI+ (m/z): [M+H]$^+$ calcd for C$_{40}$H$_{48}$ClN$_5$O$_6$S: 762.3; found: 762.2.

Example 194

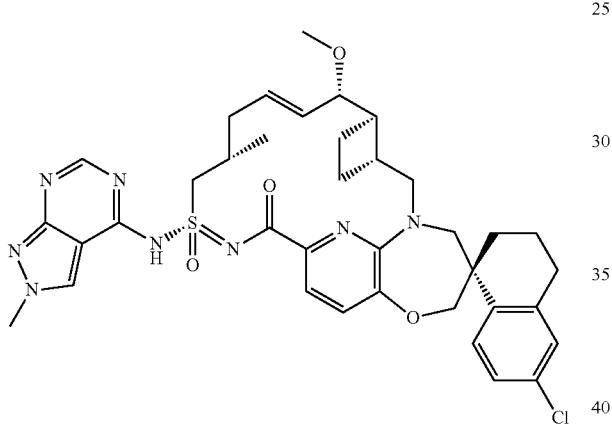

A solution of Intermediate S (20 mg, 0.033 mmol), 4-chloro-2-methyl-2H-pyrazolo[3,4-d]pyrimidine (22.5 mg, 0.13 mmol), and fine powder of C$_{32}$CO$_3$ (54.3 mg, 0.16 mmol) in DMSO was irradiated at 120° C. for 2 h. The reaction was cooled to rt and 4-chloro-2-methyl-2H-pyrazolo[3,4-d]pyrimidine (22.5 mg) was added. This mixture was irradiated at 120° C. for 2 h. The reaction mixture was cooled to rt and added MeOH (2 mL), filtered, and purified by Gilson reverse phase prep HPLC (60-100% ACN/H$_2$O with 0.1% TFA) to afford Example 194. $^1$H NMR (400 MHz, Acetonitrile-d$_3$) δ 8.54 (s, 1H), 8.16 (s, 1H), 7.69 (d, J=8.5 Hz, 1H), 7.26 (dd, J=7.8, 3.0 Hz, 3H), 7.19 (d, J=2.3 Hz, 1H), 5.54 (dt, J=15.5, 8.8 Hz, 2H), 4.41-3.90 (m, 8H), 3.58-3.41 (m, 2H), 3.23 (dd, J=14.6, 6.2 Hz, 1H), 3.12 (s, 3H), 2.94-2.77 (m, 1H), 2.54 (s, 9H), 2.26-2.01 (m, 2H), 1.89-1.63 (m, 2H), 1.55-1.40 (m, 1H), 1.21 (d, J=6.8 Hz, 3H). [M+H]$^+$ calcd for C$_{37}$H$_{43}$ClN$_8$O$_4$S: 731.2; found: 731.3.

Example 195

Example 195 was prepared in a similar manner to Example 42 (Step 2) using Intermediate S and 3-methoxyazetidine. LCMS-ESI+ (m/z): [M+H]$^+$ calcd for C$_{36}$H$_{46}$ClN$_5$O$_6$S: 712.3; found: 711.9.

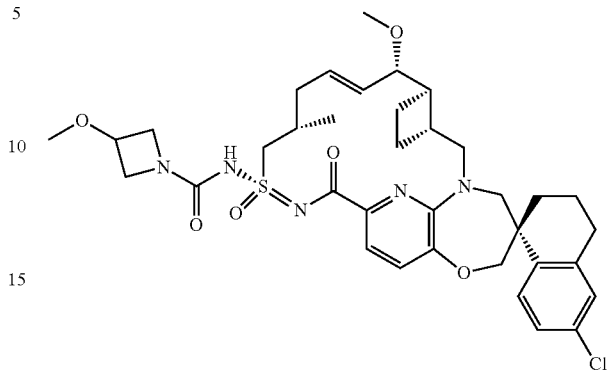

Example 196

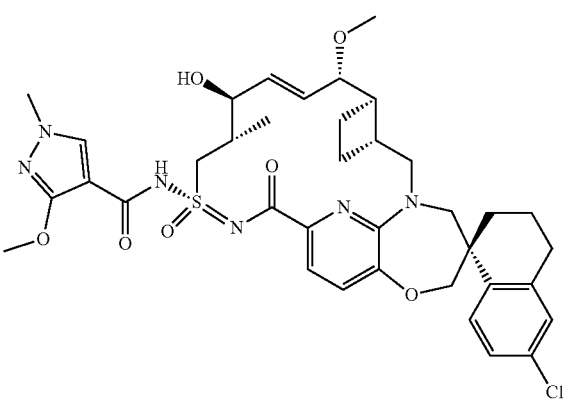 [SMILES: COc1nn(C)cc1C(=O)N[S@@]1(=O)=NC(=O)c2ccc3c(n2)N(C[C@@H]2CC[C@H]2[C@@H](OC)/C=C/[C@H](O)[C@H](C)C1)C[C@@]1(CCCc2cc(Cl)ccc21)CO3]

To a scintillation vial charged with Example 191 (15 mg) and selenium dioxide (9 mg, 4 equiv.), was added 1 mL dioxane. The vial was heated at 100° C. while stirring for 60 min. The vial was allowed to cool to ambient temperature, then it was concentrated, and the residue was redissolved in DMF/DMSO, filtered, and purified by HPLC to give Example 196. $^1$H NMR (400 MHz, Methanol-d$_4$) δ 7.99 (d, J=6.0 Hz, 1H), 7.72 (dd, J=8.5, 3.1 Hz, 1H), 7.42 (dd, J=7.8, 6.1 Hz, 1H), 7.24 (dd, J=21.9, 8.2 Hz, 3H), 7.14 (s, 1H), 5.86-5.41 (m, 2H), 4.39 (s, 1H), 4.27-4.15 (m, 2H), 4.12-4.04 (m, 1H), 3.99 (d, J=3.2 Hz, 4H), 3.96-3.82 (m, 1H), 3.84-3.75 (m, 4H), 3.58-3.44 (m, 2H), 3.09 (s, 3H), 2.85-2.68 (m, 2H), 2.14 (d, J=40.2 Hz, 2H), 1.99-1.75 (m, 5H), 1.78-1.56 (m, 2H), 1.52 (d, J=12.7 Hz, 1H), 1.21 (q, J=8.1, 7.1 Hz, 4H). LCMS-ESI+ (m/z): [M+H]$^+$ calcd for C$_7$H$_{45}$ClN$_6$O$_7$S: 753.3; found: 753.3.

Example 197 and Example 198

Example 197

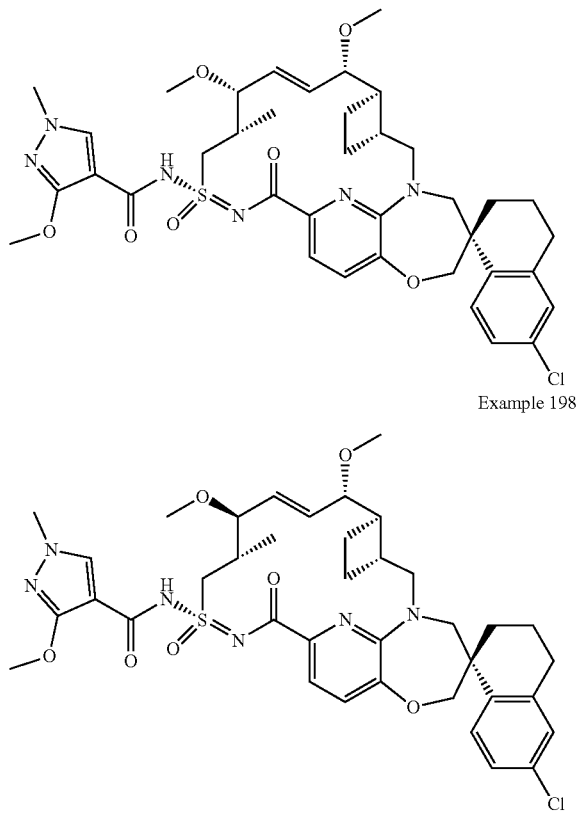

Example 198

To a solution of Example 196 (5.5 mg, as a mixture of diastereomers at OH) in DMF (1 mL) at 0° C. was added 60% sodium hydride dispersion in mineral oil (3 mg, 10 equiv.) followed by iodomethane (2 mg, 2 equiv.). The vial was warmed to ambient temperature while stirring for 60 min. The reaction was filtered and purified by reverse-phase HPLC chromatography to yield Example 197, as the earlier-eluting of two diastereomeric products, and Example 198, as the later eluting.

Example 197: $^1$H NMR (400 MHz, Methanol-d$_4$) δ 7.99 (s, 1H), 7.72 (d, J=8.5 Hz, 1H), 7.45 (d, J=7.8 Hz, 1H), 7.32 (d, J=7.8 Hz, 1H), 7.22 (dd, J=8.5, 2.4 Hz, 1H), 7.14 (d, J=2.3 Hz, 1H), 5.70 (d, J=14.4 Hz, 1H), 5.49 (s, 3H), 5.29-5.14 (m, 1H), 4.39 (d, J=26.7 Hz, 1H), 4.24 (d, J=12.3 Hz, 1H), 4.10 (d, J=12.3 Hz, 1H), 4.00 (s, 3H), 3.91 (d, J=14.6 Hz, 1H), 3.79 (s, 3H), 3.76-3.63 (m, 2H), 3.63-3.48 (m, 2H), 3.38 (t, J=8.5 Hz, 1H), 3.16 (s, 3H), 3.08 (s, 3H), 2.90-2.52 (m, 2H), 2.24-1.98 (m, 2H), 2.02-1.83 (m, 4H), 1.77-1.44 (m, 1H), 1.17 (d, J=6.8 Hz, 3H). LCMS-ESI+ (m/z): [M+H]$^+$ calcd for C$_{38}$H$_{47}$ClN$_6$O$_7$S: 767.3; found: 767.3.

Example 198: $^1$H NMR (400 MHz, Methanol-d$_4$) δ 7.99 (s, 1H), 7.72 (d, J=8.5 Hz, 1H), 7.41 (d, J=7.8 Hz, 1H), 7.24 (d, J=7.8 Hz, 1H), 7.20 (dd, J=8.5, 2.3 Hz, 1H), 7.13 (d, J=2.3 Hz, 1H), 5.70 (dd, J=15.5, 6.9 Hz, 1H), 5.60 (dd, J=15.6, 6.9 Hz, 1H), 4.44-4.13 (m, 2H), 4.08 (d, J=12.3 Hz, 1H), 3.99 (s, 3H), 3.85 (d, J=14.4 Hz, 1H), 3.78 (s, 3H), 3.68 (dd, J=6.7, 1.8 Hz, 1H), 3.63-3.46 (m, 2H), 3.26 (s, 3H), 3.15 (s, 3H), 2.91-2.71 (m, 2H), 2.71-2.57 (m, 3H), 2.22-2.04 (m, 2H), 1.99-1.80 (m, 2H), 1.69 (dq, J=17.4, 9.1 Hz, 2H), 1.54 (dd, J=14.1, 7.3 Hz, 1H), 1.29 (d, J=3.5 Hz, OH), 1.23 (d, J=6.9 Hz, 3H). LCMS-ESI+ (m/z): [M+H]$^+$ calcd for C$_{38}$H$_{47}$ClN$_6$O$_7$S: 767.3; found: 767.4.

Example 199

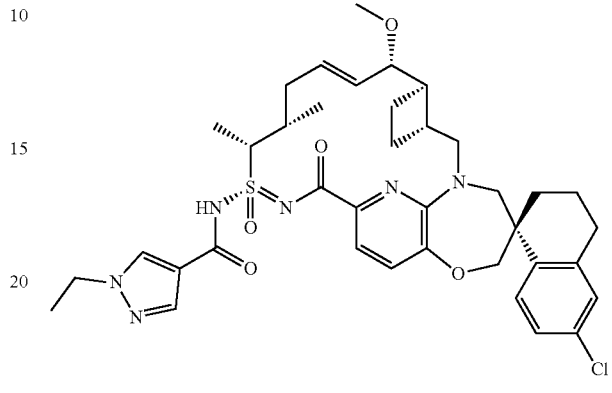

Example 199 was prepared in a manner similar to Example 46, using S-1-6 in place of I-1-3, Intermediate A in place of 46-7, and 1-ethyl-1H-pyrazole-4-carboxylic acid in place of 2-tetrahydropyran-4-yloxyacetic acid. $^1$H NMR (400 MHz, Acetonitrile-d$_3$) δ 8.07 (s, 1H), 7.88 (s, 1H), 7.69 (d, J=8.5 Hz, 1H), 7.46 (d, J=7.8 Hz, 1H), 7.36 (d, J=7.9 Hz, 1H), 7.25 (dd, J=8.6, 2.4 Hz, 1H), 7.18 (d, J=2.3 Hz, 1H), 5.38 (dd, J=15.5, 4.5 Hz, 1H), 5.26-5.14 (m, 1H), 4.27 (d, J=12.5 Hz, 1H), 4.18 (q, J=7.3 Hz, 2H), 4.13 (d, J=12.4 Hz, 1H), 4.03-3.95 (m, 1H), 3.91 (d, J=14.4 Hz, 2H), 3.57 (d, J=14.6 Hz, 2H), 3.43 (d, J=14.9 Hz, 1H), 3.32-3.27 (m, 1H), 2.99 (s, 3H), 2.82-2.70 (m, 2H), 2.58-2.46 (m, 2H), 2.31-2.19 (m, 2H), 2.08-1.99 (m, 2H), 1.92-1.83 (m, 3H), 1.70-1.55 (m, 3H), 1.52 (d, J=7.2 Hz, 3H), 1.44 (t, J=7.3 Hz, 3H), 1.05 (d, J=6.9 Hz, 3H). LCMS-ESI+ (m/z): [M+H]$^+$ calcd for C$_{38}$H$_{47}$ClN$_6$O$_5$S: 735.3; found: 735.1.

Example 200

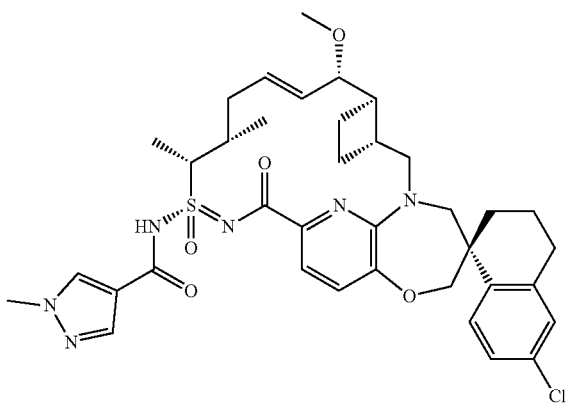 [SMILES: CO[C@H]1/C=C/C[C@H](C)[C@@H](C)[S@@](=O)(NC(=O)c2cnn(C)c2)=NC(=O)c2ccc3c(n2)N(C[C@@H]2CC[C@H]21)C[C@@]1(CCCc2cc(Cl)ccc21)CO3]

Example 200 was prepared in a manner similar to Example 199, using 1-methyl-1H-pyrazole-4-carboxylic acid in place of 1-ethyl-1H-pyrazole-4-carboxylic acid. $^1$H NMR (400 MHz, Acetonitrile-d$_3$) δ 8.10 (s, 1H), 7.92 (s, 1H), 7.66 (d, J=8.5 Hz, 1H), 7.53 (d, J=7.8 Hz, 1H), 7.47 (d, J=7.8 Hz, 1H), 7.26 (dd, J=8.5, 2.4 Hz, 1H), 7.19 (d, J=2.3 Hz, 1H), 5.39 (dd, J=15.2, 3.2 Hz, 1H), 5.10 (tt, J=10.0, 5.1 Hz, 1H), 4.32 (d, J=12.6 Hz, 1H), 4.18-4.07 (m, 2H), 4.05-3.93 (m, 2H), 3.90 (s, 3H), 3.59 (d, J=14.5 Hz, 1H), 3.37 (d, J=15.2 Hz, 1H), 3.31 (d, J=9.2 Hz, 1H), 2.99 (s, 3H), 2.87-2.59 (m, 3H), 2.49 (p, J=8.5 Hz, 1H), 2.28 (ddd, J=10.5, 6.9, 3.4 Hz, 1H), 2.13-1.97 (m, 4H), 1.92-1.83 (m, 4H), 1.78-1.60 (m, 2H), 1.54 (d, J=7.3 Hz, 3H), 1.00 (d, J=6.9 Hz, 3H). LCMS-ESI+ (m/z): [M+H]$^+$ calcd for $C_{37}H_{45}ClN_6O_5S$: 721.3; found: 721.1.

Example 201

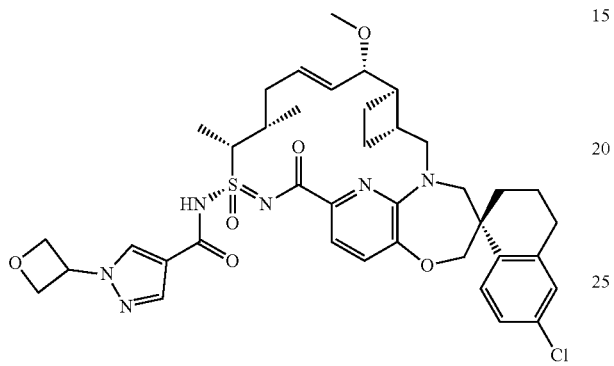

Example 201 was prepared in a manner similar to Example 199, using 1-(oxetan-3-yl)-1H-pyrazole-4-carboxylic acid in place of 1-ethyl-1H-pyrazole-4-carboxylic acid. $^1$H NMR (400 MHz, Acetonitrile-$d_3$) δ 8.20 (d, J=6.0 Hz, 1H), 8.01 (d, J=13.9 Hz, 1H), 7.68 (d, J=8.5 Hz, 1H), 7.48 (dd, J=7.9, 3.1 Hz, 1H), 7.43-7.34 (m, 1H), 7.25 (dd, J=8.5, 2.4 Hz, 1H), 7.19 (d, J=2.3 Hz, 1H), 5.53 (p, J=6.8 Hz, 1H), 5.39 (d, J=15.5 Hz, 1H), 5.24-5.10 (m, 1H), 4.96 (p, J=6.9 Hz, 2H), 4.55 (p, J=6.3 Hz, 1H), 4.29 (d, J=12.5 Hz, 1H), 4.13 (d, J=12.5 Hz, 1H), 3.98 (d, J=6.6 Hz, 1H), 3.95-3.84 (m, 4H), 3.57 (d, J=14.5 Hz, 1H), 3.40 (d, J=15.1 Hz, 1H), 3.30 (dd, J=8.8, 4.0 Hz, 1H), 2.99 (s, 3H), 2.87-2.64 (m, 3H), 2.51 (dt, J=17.8, 9.1 Hz, 1H), 2.35-2.22 (m, 1H), 2.14-1.98 (m, 2H), 1.90-1.79 (m, 5H), 1.63 (dd, J=18.2, 8.7 Hz, 2H), 1.53 (dd, J=7.2, 2.5 Hz, 3H), 1.10-0.97 (m, 3H). LCMS-ESI+ (m/z): [M+H]$^+$ calcd for $C_{39}H_{47}ClN_6O_6S$: 763.3; found: 763.1.

Example 202

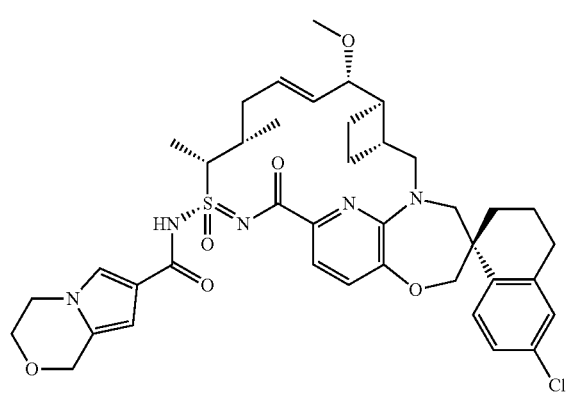 [SMILES: CO[C@H]1/C=C/C[C@H](C)[C@@H](C)[S@@](=O)(NC(=O)c2cc3n(c2)CCOC3)=NC(=O)c2ccc3c(n2)N(C[C@@H]2CC[C@H]21)C[C@@]1(CCCc2cc(Cl)ccc21)CO3]

Example 202 was prepared in a manner similar to Example 199, using 3,4-dihydro-1H-pyrrolo[2,1-c][1,4]oxazine-7-carboxylic acid in place of 1-ethyl-1H-pyrazole-4-carboxylic acid. $^1$H NMR (400 MHz, Acetonitrile-$d_3$) δ 7.65 (d, J=8.5 Hz, 1H), 7.55 (d, J=7.8 Hz, 1H), 7.49 (d, J=7.8 Hz, 1H), 7.43 (d, J=1.8 Hz, 1H), 7.26 (dd, J=8.5, 2.4 Hz, 1H), 7.19 (d, J=2.3 Hz, 1H), 6.30 (d, J=1.6 Hz, 1H), 5.43-5.33 (m, 1H), 5.14-5.00 (m, 1H), 4.74 (s, 2H), 4.33 (d, J=12.6 Hz, 1H), 4.15 (d, J=12.6 Hz, 2H), 4.08-3.90 (m, 5H), 3.60 (d, J=14.5 Hz, 1H), 3.37 (d, J=15.6 Hz, 1H), 3.31 (d, J=9.4 Hz, 1H), 2.99 (s, 3H), 2.88-2.58 (m, 3H), 2.49 (p, J=8.6 Hz, 1H), 2.27 (ddd, J=10.5, 7.0, 3.3 Hz, 1H), 2.14-1.97 (m, 3H), 1.91-1.84 (m, 5H), 1.78-1.56 (m, 3H), 1.54 (d, J=7.2 Hz, 3H), 0.97 (d, J=6.9 Hz, 3H). LCMS-ESI+ (m/z): [M+H]$^+$ calcd for $C_{40}H_{48}ClN_5O_6S$: 762.3; found: 762.0.

Example 203

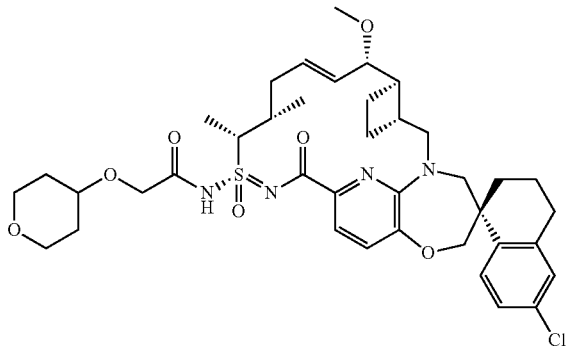 [SMILES: CO[C@H]1/C=C/C[C@H](C)[C@@H](C)[S@@](=O)(NC(=O)COC2CCOCC2)=NC(=O)c2ccc3c(n2)N(C[C@@H]2CC[C@H]21)C[C@@]1(CCCc2cc(Cl)ccc21)CO3]

Example 203 was prepared in a manner similar to Example 46, using S-1-6 in place of I-1-3, and Intermediate A in place of 46-7. $^1$H NMR (400 MHz, Acetonitrile-$d_3$) δ 7.64 (d, J=8.5 Hz, 1H), 7.59-7.51 (m, 2H), 7.27 (dd, J=8.5, 2.4 Hz, 1H), 7.20 (d, J=2.3 Hz, 1H), 5.41 (dt, J=15.2, 2.3 Hz, 1H), 5.09-4.92 (m, 1H), 4.36 (d, J=12.7 Hz, 1H), 4.20 (s, 2H), 4.18-3.95 (m, 4H), 3.89 (dt, J=11.8, 4.3 Hz, 2H), 3.73-3.63 (m, 1H), 3.61 (d, J=14.5 Hz, 1H), 3.40 (tdd, J=10.2, 2.7, 1.0 Hz, 2H), 3.35-3.26 (m, 2H), 2.99 (s, 3H), 2.87-2.70 (m, 2H), 2.61 (p, J=8.5, 8.1 Hz, 1H), 2.44 (p, J=8.7 Hz, 1H), 2.24 (ddd, J=14.2, 6.8, 3.4 Hz, 1H), 2.16-2.06 (m, 1H), 2.05-1.96 (m, 3H), 1.92-1.74 (m, 6H), 1.71-1.54 (m, 4H), 1.52 (d, J=7.3 Hz, 3H), 0.97 (d, J=6.9 Hz, 3H). LCMS-ESI+ (m/z): [M+H]$^+$ calcd for $C_{39}H_{51}ClN_4O_7S$: 755.3; found: 755.4.

Example 204
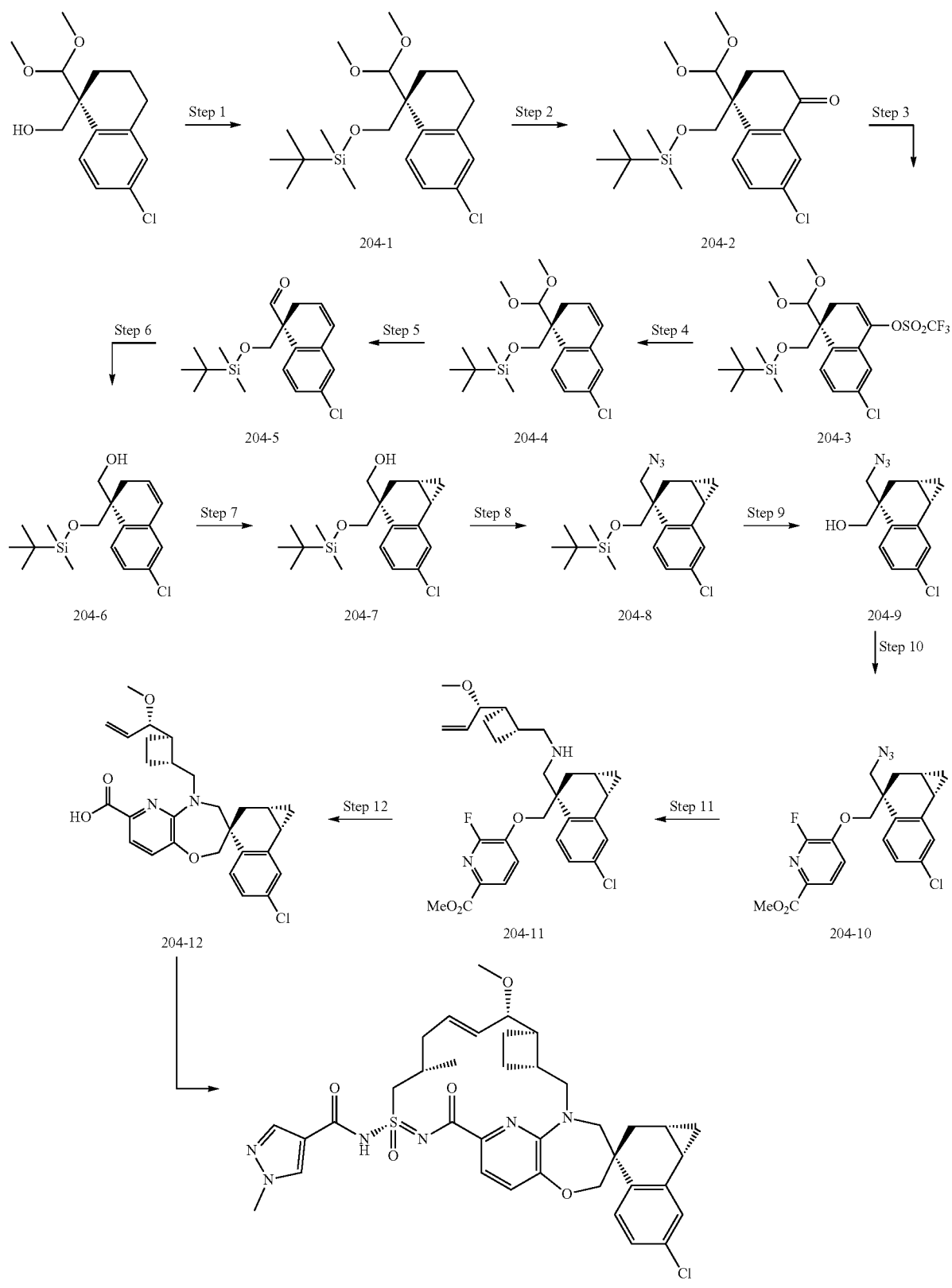
Example 204

Step 1: tert-Butylchlorodimethylsilane (9.26 g, 61.5 mmol) was added to a stirred mixture of (R)-(6-chloro-1-(dimethoxymethyl)-1,2,3,4-tetrahydronaphthalen-1-yl)methanol (15.1 g, 55.9 mmol) and imidazole (4.57 g, 67.1 mmol) in N,N-dimethylformamide (140 mL) at room temperature. After 90 min, ethyl acetate (600 mL) was added, and the organic layer was washed with water (3×200 mL), dried over anhydrous magnesium sulfate, filtered, and concentrated under reduced pressure. The residue was purified by flash column chromatography on silica gel (0 to 20% ethyl acetate in hexanes) to give 204-1.

Step 2: Pyridinium dichromate (76.1 g, 202 mmol) and aqueous tert-butyl hydroperoxide (70% wt, 27.8 mL, 202 mmol) were added sequentially to a stirred biphasic mixture of 204-1 (19.5 g, 50.5 mmol) and celite (19.5 g) in benzene (595 mL) at 0° C., and the resulting mixture was warmed to room temperature. After 2.5 d, the resulting mixture was decanted, and the precipitate was extracted with a mixture of ethyl acetate and hexanes (1:4 v:v, 150 mL). The combined supernatants were washed sequentially with aqueous sodium thiosulfate solution (1.0 M, 2×100 mL) and brine (100 mL), dried over anhydrous magnesium sulfate, filtered, and concentrated under reduced pressure. The residue was purified by flash column chromatography on silica gel (0 to 20% ethyl acetate in hexanes) to give 204-2.

Step 3: Lithium bis(trimethylsilyl)amide solution (1.0 M in tetrahydrofuran, 25.1 mL, 25 mmol) was added via syringe to a stirred solution of 204-2 (10.0 g, 25.1 mmol) in tetrahydrofuran (84 mL) at −78° C. After 45 min, a solution of N-phenyltrifluoromethanesulfonimide (9.04 g, 25.3 mmol) in tetrahydrofuran (12.7 mL) was added via cannula. After 3 h, water (50 mL), diethyl ether (120 mL), and water (100 mL) were added sequentially, and the aqueous layer was extracted with diethyl ether (3×70 mL). The combined organic layers were washed with brine (150 mL), were dried over anhydrous magnesium sulfate, were filtered, and were concentrated under reduced pressure. The residue was purified by flash column chromatography on silica gel (0 to 10% ethyl acetate in hexanes) to give 204-3.

Step 4: A stirred mixture of 204-3 (11.0 g, 20.7 mmol) and [1,1'-bis(diphenylphosphino)ferrocene]dichloropalladium (II) (1.51 g, 2.07 mmol) in N,N-dimethylformamide (100 mL) was sparged with argon for 20 min at room temperature. The resulting mixture was warmed to 60° C., and triethylsilane (16.5 mL, 103 mmol) was added via syringe. After 139 min, the resulting mixture was cooled to room temperature, and diethyl ether was added. The organic layer was washed with water, and the aqueous layer was extracted with diethyl ether. The combined organic layers were washed sequentially with saturated aqueous sodium bicarbonate solution and brine, dried over anhydrous magnesium sulfate, filtered, and concentrated under reduced pressure. The residue was purified by flash column chromatography on silica gel (0 to 10% ethyl acetate in hexanes) to give 204-4.

Step 5: A solution of 204-4 (6.76 g, 17.7 mmol) in acetonitrile (59 mL) was added via cannula to a stirred solution of lithium tetrafluoroborate (1.82 g, 19.4 mmol) in acetonitrile (177 mL) at 0° C., and the resulting mixture was warmed to room temperature. After 2 h, the resulting mixture was poured into saturated aqueous sodium bicarbonate solution, and the aqueous layer was extracted sequentially three times with diethyl ether. The combined organic layers were dried over anhydrous magnesium sulfate, filtered, and concentrated under reduced pressure. The residue was purified by flash column chromatography on silica gel (0 to 10% ethyl acetate in hexanes) to give 204-5.

Step 6: Sodium borohydride (583 mg, 15.4 mmol) was added to a stirred solution of 204-5 (4.72 g, 14.0 mmol) in tetrahydrofuran (11 mL) and methanol (7.0 mL) at 0° C., and the resulting mixture was warmed to room temperature. After 60 min, ethyl acetate was added, and the organic layer was washed sequentially two times with a mixture of water and brine (1:1 v:v), dried over anhydrous magnesium sulfate, filtered, and concentrated under reduced pressure to give 204-6.

Step 7: Diiodomethane (2.99 mL, 37.1 mmol) was added via syringe to a stirred mixture of diethylzinc solution (15% wt in toluene, 12.7 mL, 19 mmol) and dichloromethane (28 mL) at 0° C. After 20 min, a degassed solution of 204-6 (2.93 g, 8.66 mmol) in dichloromethane (18 mL) was added via syringe. After 10 min, the resulting mixture was warmed to room temperature. After 110 min, the resulting mixture was poured into a mixture saturated aqueous sodium bicarbonate solution and saturated aqueous sodium carbonate solution, and ethyl acetate was added. The organic layer was washed sequentially two times with water, dried over anhydrous magnesium sulfate, filtered, and concentrated under reduced pressure. The residue was purified by flash column chromatography on silica gel (0 to 15% ethyl acetate in hexanes) to give 204-7.

Step 8: Diisopropyl azodicarboxylate (145 µL, 737 µmol) and diphenyl phosphorazidate (152 µL, 708 µmol) were added sequentially via syringe to a stirred mixture of 204-7 (100 mg, 283 µmol) and triphenylphosphine (171 mg, 652 µmol) in tetrahydrofuran (2.8 mL) at 0° C. After 1 min, the resulting mixture was warmed to room temperature. After 20 h, the resulting mixture was concentrated under reduced pressure, and the residue was purified by flash column chromatography on silica gel (0 to 20% ethyl acetate in hexanes) to give 204-8.

Step 9: A solution of tetrabutylammonium fluoride (1.0 M in tetrahydrofuran, 328 µL, 328 µmol) was added via syringe to a stirred solution of 204-8 (62.0 mg, 164 µmol) in tetrahydrofuran (1.6 mL) at room temperature. After 135 min, the resulting mixture was poured into saturated aqueous ammonium chloride solution, and the aqueous layer was extracted with ethyl acetate. The combined organic layers were washed sequentially three times with water and once with brine, dried over anhydrous magnesium sulfate, filtered, and concentrated under reduced pressure. The residue was purified by flash column chromatography on silica gel (0 to 50% ethyl acetate in hexanes) to give 204-9.

Step 10: Potassium bis(trimethylsilyl)amide solution (1.0 M in tetrahydrofuran, 2.07 mL, 2.07 mmol) was added via syringe to a stirred mixture of 204-9 (437 mg, 1.66 mmol) and methyl 5,6-difluoropicolinate (373 mg, 2.15 mmol) in N,N-dimethylformamide (10 mL) at −40° C., and the resulting mixture was warmed slowly to 0° C. over 180 min. Water was added, and the aqueous layer was extracted with ethyl acetate. The organic layer was washed sequentially four times with water and one time with brine, dried over anhydrous magnesium sulfate, filtered, and concentrated under reduced pressure. The residue was purified by flash column chromatography on silica gel (0 to 25% ethyl acetate in hexanes) to give 204-10.

Step 11: Trimethylphosphine solution (1.0 M in tetrahydrofuran, 1.75 mL, 1.8 mmol) was added via syringe to a stirred solution of 204-10 (364 mg, 873 µmol) in tetrahydrofuran (3.5 mL) at room temperature. After 60 min, 0-7 (539 mg, 1.75 mmol) was added. After 3 min, the resulting mixture was warmed to 40° C. After 30 min, the resulting mixture was cooled to 0° C., and sodium borohydride (264 mg, 6.99 mmol) and methanol were added sequentially.

After 5 min, the resulting mixture was warmed to room temperature. After 10 min, ethyl acetate (10 mL) was added, and the organic layer was washed with water (2×15 mL), dried over anhydrous magnesium sulfate, filtered, and concentrated under reduced pressure. The residue was purified by flash column chromatography on silica gel (0 to 8% methanol in dichloromethane) to give 204-11.

Step 12: A stirred mixture of 204-11 (208 mg, 393 µmol), N,N-diisopropylethylamine (342 µL, 1.97 mmol) in dimethylsulfoxide (2.2 ml) was warmed to 120° C. After 18 h, the resulting mixture was cooled to room temperature, and aqueous lithium hydroxide solution (2.1 M, 1.85 mL, 3.9 mmol) was added via syringe. After 50 min, methanol (1.0 mL) was added, and the resulting mixture was warmed to 40° C. After 58 min, the resulting mixture was warmed to 45° C. After 17 h, trifluoroacetic acid (100 µL) was added, and the resulting mixture was purified by reverse phase preparative HPLC (0.1% trifluoroacetic acid in acetonitrile/water) to give 204-12.

Preparation of Example 204: Example 204 was prepared in a similar manner to Example 180 using 204-12 in place of Q-15, and Intermediate C in place of Intermediate A. $^1$H NMR (400 MHz, Methanol-d$_4$) δ 8.11 (s, 1H), 7.91 (s, 1H), 7.63 (d, J=8.4 Hz, 1H), 7.38-7.32 (m, 2H), 7.25 (d, J=7.8 Hz, 1H), 7.18 (dd, J=8.4, 2.4 Hz, 1H), 5.77-5.64 (m, 1H), 5.47 (dd, J=15.3, 7.1 Hz, 1H), 4.47-4.39 (m, 1H), 4.21 (d, J=12.4 Hz, 1H), 4.19-4.05 (m, 2H), 3.96 (d, J=14.4 Hz, 1H), 3.92 (s, 3H), 3.73 (dd, J=14.9, 5.3 Hz, 1H), 3.59-3.50 (m, 1H), 3.18-3.06 (m, 1H), 3.14 (s, 3H), 2.70-1.17 (m, 15H), 1.15 (d, J=6.8 Hz, 3H), 0.67-0.57 (m, 1H). LCMS-ESI+ (m/z): [M+H]$^+$ calcd for C$_{37}$H$_{43}$ClN$_6$O$_5$S: 719.3; found: 719.3.

Example 205

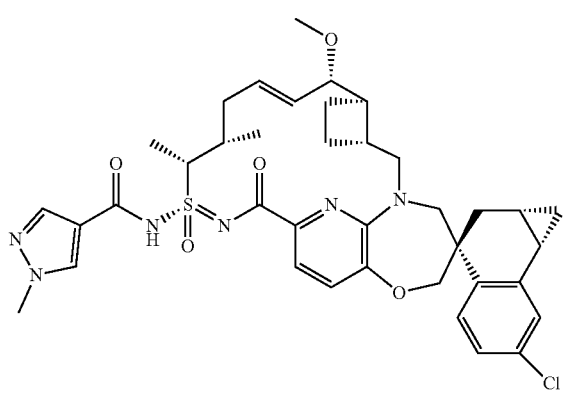 [SMILES: CO[C@H]1/C=C/C[C@H](C)[C@@H](C)[S@@](=O)(NC(=O)c2cnn(C)c2)=NC(=O)c2ccc3c(n2)N(C[C@@H]2CC[C@H]21)C[C@]1(CO3)C[C@@H]2C[C@@H]2c2cc(Cl)ccc21]

Example 205 was synthesized in a manner similar to Example 180 using 204-12 in place of Q-15. $^1$H NMR (400 MHz, Methanol-d$_4$) δ 8.06 (s, 1H), 7.85 (s, 1H), 7.64 (d, J=8.5 Hz, 1H), 7.36 (d, J=2.3 Hz, 1H), 7.33 (d, J=7.8 Hz, 1H), 7.24 (d, J=7.9 Hz, 1H), 7.18 (dd, J=8.5, 2.4 Hz, 1H), 5.53-5.39 (m, 2H), 4.40-4.28 (m, 1H), 4.20 (d, J=12.3 Hz, 1H), 4.13 (d, J=12.3 Hz, 1H), 4.02-3.86 (m, 2H), 3.92 (s, 3H), 3.51-3.44 (m, 2H), 3.23-3.15 (m, 1H), 3.07 (s, 3H), 2.73-1.11 (m, 15H), 1.54 (d, J=7.1 Hz, 3H), 1.20 (d, J=6.9 Hz, 3H), 0.65-0.54 (m, 1H). LCMS-ESI+ (m/z): [M+H]$^+$ calcd for C$_{38}$H$_{45}$ClN$_6$O$_5$S: 733.3; found: 733.3.

Example 206

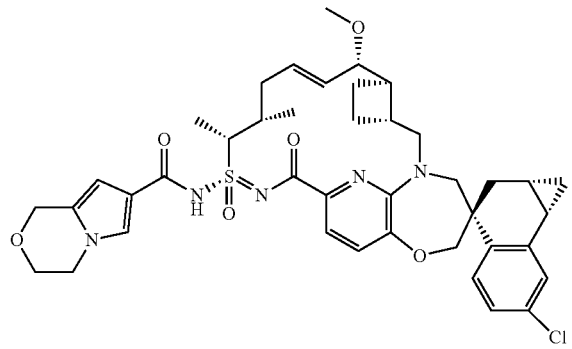 [SMILES: CO[C@H]1/C=C/C[C@H](C)[C@@H](C)[S@@](=O)(NC(=O)c2cc3n(c2)CCOC3)=NC(=O)c2ccc3c(n2)N(C[C@@H]2CC[C@H]21)C[C@]1(CO3)C[C@@H]2C[C@@H]2c2cc(Cl)ccc21]

Example 206 was synthesized in a manner similar to Example 180 using 204-12 in place of Q-15 and using 3,4-dihydro-1H-pyrrolo[2,1-c][1,4]oxazine-7-carboxylic acid in place of 1-methyl-1H-pyrazole-4-carboxylic acid. $^1$H NMR (400 MHz, Methanol-d$_4$) δ 7.63 (d, J=8.5 Hz, 1H), 7.38-7.32 (m, 3H), 7.26 (s, 1H), 7.18 (dd, J=8.5, 2.4 Hz, 1H), 6.27 (s, 1H), 5.51-5.38 (m, 2H), 4.76 (s, 2H), 4.38-4.27 (m, 1H), 4.21 (d, J=12.2 Hz, 1H), 4.14 (d, J=12.2 Hz, 1H), 4.09-3.89 (m, 6H), 3.52-3.10 (m, 3H), 3.07 (s, 3H), 2.80-1.11 (m, 15H), 1.55 (d, J=7.1 Hz, 1H), 1.15 (d, J=7.0 Hz, 1H), 0.61 (d, J=5.0 Hz, 1H). LCMS-ESI+ (m/z): [M+H]$^+$ calcd for C$_{41}$H$_{48}$ClN$_5$O$_6$S: 774.3; found: 774.3.

Example 207

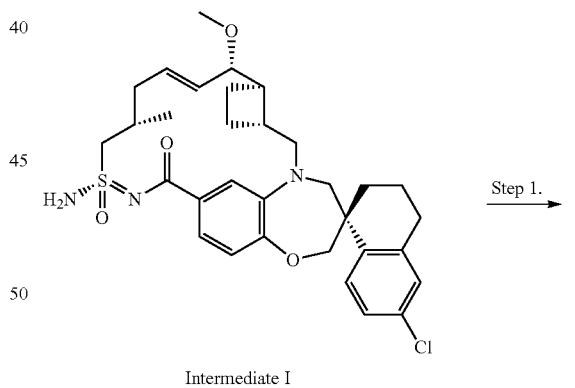

Intermediate I

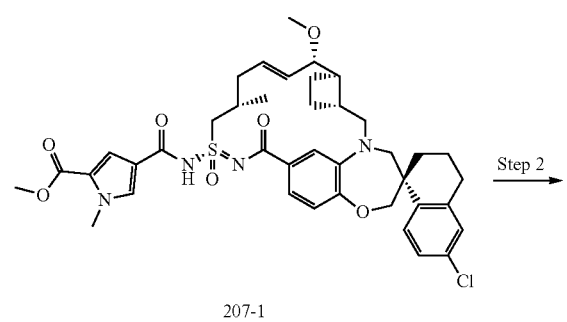

207-1

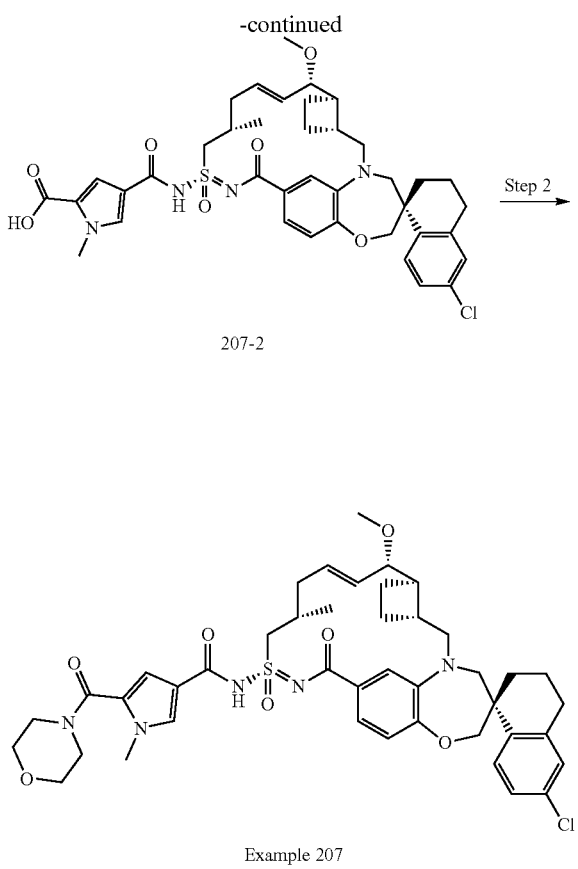

207-2

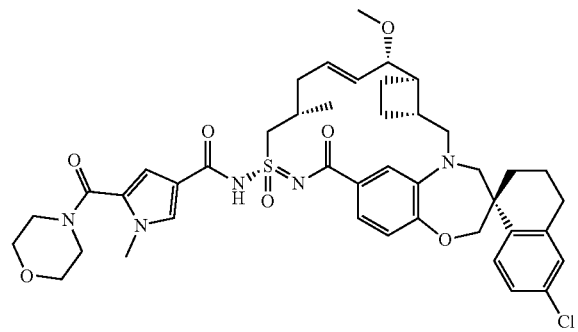

Example 207

Step 1: 207-1 was prepared in a manner similar to Intermediate T using 5-methoxycarbonyl-1-methyl-pyrrole-3-carboxylic acid. LCMS-ESI⁺ (m/z): [M+H]⁺ calcd for C$_{40}$H$_{47}$ClN$_4$O$_7$S: 763.3, found: 763.1.

Step 2: 207-1 (25 mg) in methanol (5 mL) was treated with 1 N aqueous sodium hydroxide and stirred at ambient temperature for 24 hr. The resulting mixture was quenched with 1 N aqueous hydrochloric acid and concentrated in vacuo. The resulting crude product was partitioned between water and dichloromethane, and the organic phase dried over magnesium sulfate, filtered and concentrated. Purification by reverse-phase preparative HPLC yielded 207-2. LCMS-ESI⁺ (m/z): [M+H]⁺ calcd for C$_{39}$H$_{45}$ClN$_4$O$_7$S: 749.3, found: 749.2.

Step 3: To a stirred solution of 207-2 (10 mg) in CH$_2$Cl$_2$ was added EDCl (4.1 mg, 2 equiv.) and DMAP (3.3 mg, 2 equiv.), followed by morpholine (5.8 mg, 5 equiv.). The resulting mixture was stirred at 20° C. for 24 hr, then at 45° C. for 5 hr. The reaction was concentrated, extracted with dichloromethane, and the organic phase concentrated in vacuo. Purification by preparative reverse-phase HPLC (acetonitrile/water, 0.1% TFA) gave Example 207. ¹H NMR (400 MHz, Methanol-d$_4$) δ 7.73 (d, J=8.4 Hz, 1H), 7.67 (s, 1H), 7.27 (d, J=8.2 Hz, 1H), 7.13 (d, J=11.4 Hz, 2H), 7.04 (s, 1H), 6.96-6.84 (m, 2H), 6.10 (dt, J=14.4, 6.8 Hz, 1H), 5.63 (dd, J=15.3, 8.6 Hz, 1H), 4.30 (dd, J=14.7, 6.6 Hz, 1H), 4.17-3.61 (m, 10H), 3.29 (s, 2H), 3.25 (t, J=5.0 Hz, 1H), 3.09 (dd, J=15.2, 9.4 Hz, 1H), 2.91-2.68 (m, 3H), 2.50 (d, J=35.3 Hz, 2H), 2.33-2.06 (m, 3H), 1.96 (s, 2H), 1.79 (d, J=7.0 Hz, 2H), 1.44 (t, J=12.4 Hz, 1H), 1.31 (s, 1H), 1.15 (d, J=6.7 Hz, 3H). LCMS-ESI⁺ (m/z): [M+H]⁺ calcd for C$_{43}$H$_{52}$ClN$_5$O$_7$S: 818.3, found: 818.1.

Example 208

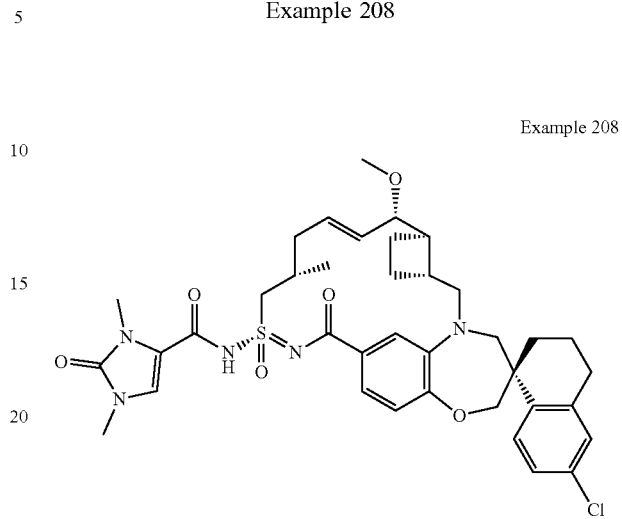

Example 208

Example 208 was prepared in a manner similar to Intermediate T, using 1,3-dimethyl-2-oxo-imidazole-4-carboxylic acid. ¹H NMR (400 MHz, Methanol-d$_4$) δ 7.73 (d, J=8.5 Hz, 1H), 7.46 (s, 1H), 7.20-7.08 (m, 3H), 6.98-6.89 (m, 2H), 6.00 (dt, J=14.3, 6.5 Hz, 1H), 5.61 (dd, J=15.2, 9.1 Hz, 1H), 4.41 (dd, J=14.8, 6.3 Hz, 1H), 4.08 (s, 2H), 3.89-3.61 (m, 5H), 3.54 (s, 3H), 3.35 (s, 3H), 3.27 (s, 3H), 3.09 (dd, J=15.4, 10.3 Hz, 1H), 2.89-2.71 (m, 2H), 2.49 (q, J=11.9 Hz, 2H), 2.37 (q, J=9.0 Hz, 1H), 2.23 (dt, J=12.4, 6.5 Hz, 2H), 2.11 (d, J=13.8 Hz, 1H), 2.02-1.88 (m, 3H), 1.79 (tt, J=17.2, 9.4 Hz, 4H), 1.17 (d, J=6.4 Hz, 3H). LCMS-ESI⁺ (m/z): [M+H]⁺ calcd for C$_{38}$H$_{46}$ClN$_5$O$_6$S: 736.3, found: 736.1.

Example 209

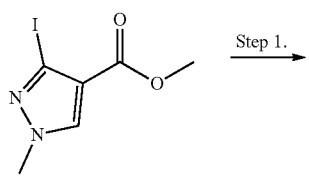

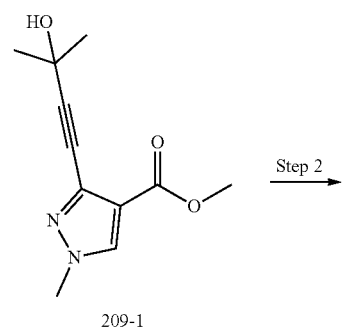

209-1

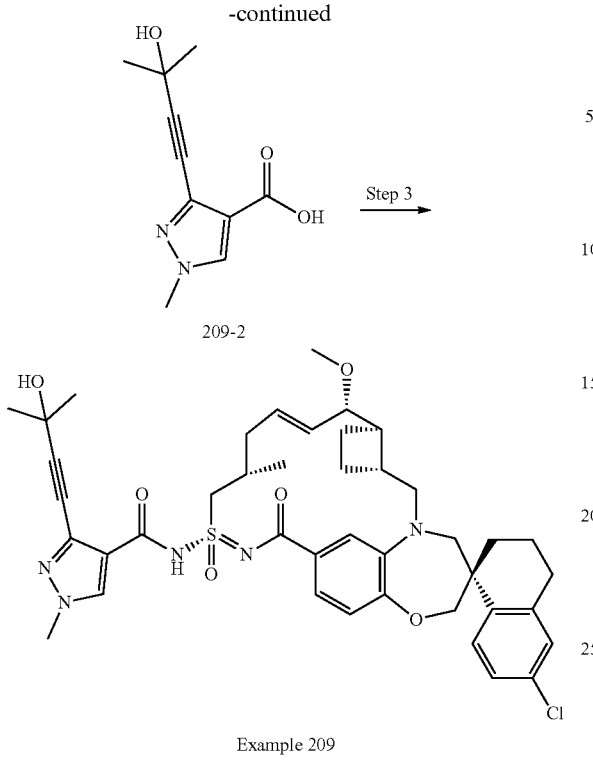

209-2

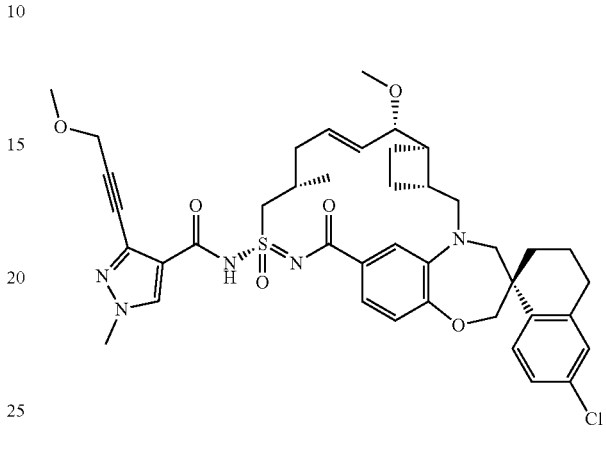

Example 209

Step 1: Methyl 3-iodo-1-methyl-1H-pyrazole-4-carboxylate (150 mg) was combined with 2-methylbut-3-yn-2-ol (95 mg, 2.0 equiv.), bis(triphenylphosphine)palladium dichloride (40 mg, 0.1 equiv.), copper(I) iodide (22 mg, 0.2 equiv.), triethylamine (0.16 mL, 2.0 equiv.), and DMF (5 mL). The mixture was degassed, then stirred for 1 hr. The mixture was concentrated in vacuo, then dissolved in ethyl acetate and washed with water, 5% aqueous LiCl, and brine. The resulting crude was purified by silica gel flash column chromatography (0 to 100% (10% methanol in dichloromethane) in hexanes), then by preparative reverse-phase chromatography (acetonitrile/water, 0.1% TFA) to yield 209-1. $^1$H NMR (400 MHz, Chloroform-d) δ 7.85 (s, 1H), 3.93 (s, 3H), 3.86 (s, 3H), 1.66 (s, 6H).

Step 2: A mixture of 209-1 (125 mg), 1 M lithium hydroxide in water (0.25 mL, 4.5 equiv.) and methanol (6 mL) was heated to 60° C. for 2 hr. The mixture was acidified with 2 N aqueous HCl, then extracted into ethyl acetate. The combined organic phases were washed with brine, dried over sodium sulfate, and concentrated to provide 209-2. $^1$H NMR (400 MHz, DMSO-d$_6$) δ 12.32 (s, 1H), 8.22 (s, 1H), 5.47 (s, 1H), 3.83 (s, 3H), 1.45 (s, 6H).

Step 3: Example 209 was prepared in a manner similar to Intermediate T, using 209-2. $^1$H NMR (400 MHz, Methanol-d$_4$) δ 8.12 (s, 1H), 7.79 (d, J=8.6 Hz, 1H), 7.26 (dd, J=8.1, 1.8 Hz, 1H), 7.19 (dd, J=8.5, 2.3 Hz, 1H), 7.11 (d, J=2.3 Hz, 1H), 6.97 (d, J=1.9 Hz, 1H), 6.83 (d, J=8.1 Hz, 1H), 6.19 (dt, J=13.7, 6.4 Hz, 1H), 5.49 (dd, J=15.2, 9.3 Hz, 1H), 4.48 (dd, J=14.0, 6.5 Hz, 1H), 4.08-4.00 (m, 2H), 3.94 (td, J=11.8, 5.5 Hz, 1H), 3.88 (s, 3H), 3.83 (dd, J=9.3, 3.5 Hz, 1H), 3.66 (d, J=13.8 Hz, 1H), 3.27 (s, 4H), 3.02 (dd, J=15.1, 10.0 Hz, 1H), 2.89-2.71 (m, 2H), 2.58 (dd, J=11.9, 6.4 Hz, 1H), 2.41 (dt, J=26.7, 9.6 Hz, 2H), 2.13 (d, J=13.8 Hz, 1H), 2.09-2.01 (m, 1H), 1.94 (q, J=6.7, 6.1 Hz, 2H), 1.77 (ddt, J=28.3, 18.5, 9.3 Hz, 2H), 1.58 (d, J=5.1 Hz, 6H), 1.51 (s, 1H), 1.42 (t, J=12.5 Hz, 1H), 1.31 (s, 1H), 1.06 (d, J=6.1 Hz, 3H), 0.91 (d, J=7.2 Hz, 1H). LCMS-ESI$^+$ (m/z): [M+H]$^+$ calcd for C$_{42}$H$_{50}$ClN$_5$O$_6$S: 788.3, found: 788.6.

Example 210

Example 210 was prepared in a manner similar to Example 209, using 3-methoxyprop-1-yne. $^1$H NMR (400 MHz, Methanol-d$_4$) δ 8.13 (s, 1H), 7.79 (d, J=8.5 Hz, 1H), 7.25 (dd, J=8.1, 1.8 Hz, 1H), 7.19 (dd, J=8.5, 2.3 Hz, 1H), 7.11 (d, J=2.3 Hz, 1H), 6.96 (d, J=1.9 Hz, 1H), 6.83 (d, J=8.1 Hz, 1H), 6.19 (dt, J=13.9, 6.6 Hz, 1H), 5.48 (dd, J=15.2, 9.3 Hz, 1H), 4.47 (dd, J=14.0, 6.9 Hz, 1H), 4.38 (s, 2H), 4.10-3.99 (m, 2H), 3.97-3.86 (m, 5H), 3.83 (dd, J=9.4, 3.6 Hz, 1H), 3.71-3.60 (m, 1H), 3.47 (s, 3H), 3.26 (s, 4H), 3.01 (dd, J=15.1, 10.0 Hz, 1H), 2.89-2.70 (m, 2H), 2.59 (dd, J=12.7, 6.2 Hz, 1H), 2.42 (dq, J=27.6, 9.2, 8.4 Hz, 2H), 2.17-2.01 (m, 3H), 1.94 (q, J=9.1, 8.2 Hz, 2H), 1.76 (ddt, J=28.5, 18.4, 9.4 Hz, 3H), 1.42 (t, J=12.6 Hz, 1H), 1.36-1.24 (m, 1H), 1.05 (d, J=6.3 Hz, 3H). LCMS-ESI$^+$ (m/z): [M+H]$^+$ calcd for C$_{41}$H$_{48}$ClN$_5$O$_6$S: 774.3, found: 774.8.

Example 211

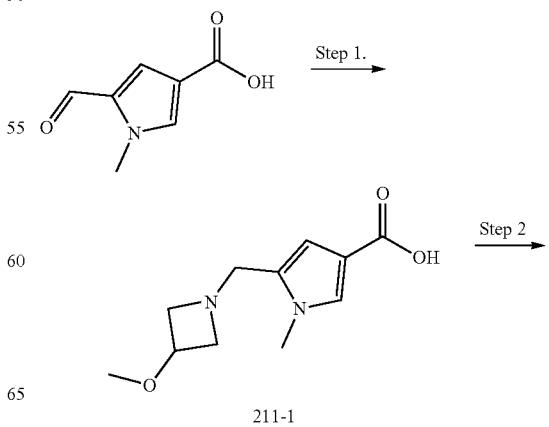

211-1

-continued

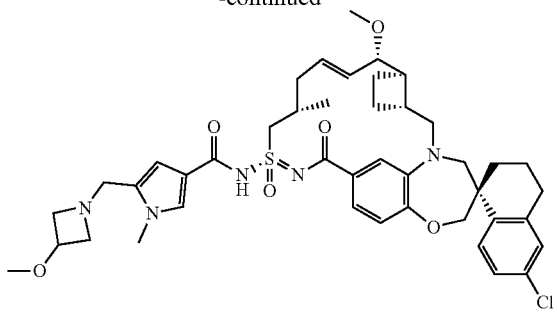

Step 1: A mixture of 5-formyl-1-methyl-1H-pyrrole-3-carboxylic acid (200 mg), 4-methoxyazetidine hydrochloride (242 mg, 1.5 equiv.), and diisopropylethylamine (0.34 mL, 1.5 equiv.) in THF (24 mL) and methanol (20 mL) was stirred at 20° C. for 3 days. Then sodium borohydride (148 mg, 3.0 equiv.) was added, and the reaction was stirred at 20° C. for another 3 hr. The reaction was treated with water and trifluoroacetic acid, then purified by preparative reverse-phase HPLC to give 211-1. $^1$H NMR (400 MHz, DMSO-$d_6$) δ 8.82 (s, 2H), 7.40-7.30 (m, 1H), 6.58 (s, 1H), 6.33 (s, 1H), 6.27 (s, OH), 4.37 (d, J=5.3 Hz, OH), 4.28-4.21 (m, 1H), 4.17-4.09 (m, 2H), 3.85-3.77 (m, 2H), 3.61 (d, J=10.5 Hz, 2H), 3.23 (s, 3H).

Step 2: Example 211 was prepared in a manner similar to Intermediate T, using 211-1. $^1$H NMR (400 MHz, Methanol-$d_4$) δ 7.67 (s, 1H), 7.63 (d, J=8.5 Hz, 1H), 7.30 (dd, J=8.2, 1.9 Hz, 1H), 7.07 (d, J=2.3 Hz, 1H), 7.06-7.02 (m, 2H), 6.93 (d, J=8.4 Hz, 1H), 6.84 (d, J=8.2 Hz, 1H), 6.14 (dd, J=14.9, 7.6 Hz, 1H), 5.67 (dd, J=15.5, 8.3 Hz, 1H), 4.45 (d, J=35.4 Hz, 4H), 4.38-4.28 (m, 1H), 4.21 (dd, J=14.7, 6.6 Hz, 1H), 4.09 (s, 2H), 4.01 (s, 2H), 3.96 (dd, J=14.7, 4.6 Hz, 1H), 3.86-3.78 (m, 2H), 3.76 (s, 3H), 3.64 (dd, J=15.7, 6.2 Hz, 1H), 3.42 (d, J=14.5 Hz, 1H), 3.38 (s, 3H), 3.17-3.06 (m, 1H), 2.86 (d, J=21.6 Hz, 1H), 2.75 (ddd, J=17.1, 11.0, 6.3 Hz, 1H), 2.48 (s, 3H), 2.41-2.20 (m, 2H), 2.20-2.06 (m, 2H), 1.98 (s, 2H), 1.85 (d, J=9.2 Hz, 3H), 1.46-1.29 (m, 1H), 1.17 (d, J=6.3 Hz, 3H). LCMS-ESI$^+$ (m/z): [M+H]$^+$ calcd for $C_{43}H_{54}ClN_5O_6S$: 804.4, found: 804.6.

MCL1/Bim Binding AlphaLISA Assay.

Inhibition of the MCL1 and Bim interaction was measured in the following AlphaLISA assay.

Materials

Recombinant human MCL1 protein (C-terminal 6×His Tagged MCL1 containing residues 171-327) was generated at Gilead Sciences, Inc. (Foster City, CA). A biotinylated peptide derived from human Bim (residues 51-76) was purchased from CPC Scientific (Sunnyvale, CA). (CPC 834113). AlphaLISA anti-6His-acceptor beads (AL128R), AlphaScreen Streptavidin donor beads (6760002B), and Proxiplate-384 Plus (6008289) were purchased from PerkinElmer.

Methods

The AlphaLISA assay was performed in a 384-well Proxiplate in a total volume of 40 μL. The reaction mixture contained 0.0625 nM 6× His-MCL1 (171-327), 0.0625 nM biotinylated-Bim peptide, 10 μg/mL AlphaLISA anti-6×His-AlphaLISA acceptor beads, 40 μg/mL AlphaScreen streptavidin donor beads, and serially diluted test compounds in the binding buffer (20 mM Hepes, pH 7.5 (Teknova $H_{1035}$); 150 mM NaCl (Promega V4221); 0.002% Brij 35 (Thermo Scientific 20150); 1 mM Dithiothreitol (DTT) Solution (Affymetrix 70726); 0.01% BSA (BioLabs B9000S)). 1,000× test compounds were pre-spotted onto 384-well Proxiplate (Labcyte Echo) by Echo 555 Liquid Handler (Labcyte Inc., San Jose, CA) followed by incubation of 5 μL MCL1(171-327) for 1 hour. Then 5 μL Bim (51-76) was added and incubated for 2 hours. Five μL AlphaLISA anti-6His-AlphaLISA acceptor beads were then added for 1 hour followed by addition of 5 μL AlphaScreen streptavidin donor beads for 1 hour. The reaction plates were then read on an Envision multimode reader (PerkinElmer) using AlphaScreen settings. $IC_{50}$ values were calculated and reported in Table 1. Percent inhibition was calculated as shown below:

% Inhibition=100%*(Well−Neg)/(Pos−Neg)

Neg: negative control, DMSO
Pos: positive control, no MCL1 protein, no biotinylated-Bim peptide

TABLE 1

| MCL1/Bim $IC_{50}$ (nM) | |
|---|---|
| Example | $IC_{50}$ (nM) |
| 1 | 0.221 |
| 2 | 1.89 |
| 3 | 0.957 |
| 4 | 0.196 |
| 5 | 0.584 |
| 6 | 0.891 |
| 7 | 1.737 |
| 8 | 0.061 |
| 9 | 0.11 |
| 10 | 0.084 |
| 11 | 0.183 |
| 12 | 0.129 |
| 13 | 2.119 |
| 14 | 0.965 |
| 15 | 1.011 |
| 16 | 3.175 |
| 17 | 2.386 |
| 18 | 0.042 |
| 19 | 0.066 |
| 20 | 0.313 |
| 21 | 0.156 |
| 22 | 0.121 |
| 23 | 0.083 |
| 24 | 0.026 |
| 25 | 0.224 |
| 26 | 0.233 |
| 27 | 0.103 |
| 28 | 0.12 |
| 29 | 0.038 |
| 30 | 0.03 |
| 31 | 0.054 |
| 32 | 0.057 |
| 33 | 0.019 |
| 34 | 0.088 |
| 35 | 0.043 |
| 36 | 0.257 |
| 37 | 0.04 |
| 38 | 0.11 |
| 39 | 0.201 |
| 40 | 0.101 |
| 41 | 0.146 |
| 42 | 0.253 |
| 43 | 1.671 |
| 44 | 0.648 |
| 45 | 0.088 |
| 46 | 0.521 |
| 47 | 0.167 |
| 48 | 0.693 |
| 49 | 0.194 |
| 50 | 0.124 |
| 51 | 0.222 |
| 52 | 0.081 |
| 53 | 0.105 |
| 54 | 0.092 |
| 55 | 0.332 |

TABLE 1-continued

MCL1/Bim IC$_{50}$ (nM)

| Example | IC$_{50}$ (nM) |
|---|---|
| 56 | 0.16 |
| 57 | 0.089 |
| 58 | 0.098 |
| 59 | 0.076 |
| 60 | 0.07 |
| 61 | 0.136 |
| 62 | 0.069 |
| 63 | 0.034 |
| 64 | 0.37 |
| 65 | 0.56 |
| 66 | 0.039 |
| 67 | 0.06 |
| 68 | 0.2 |
| 69 | 2.074 |
| 70 | 0.198 |
| 71 | 0.894 |
| 72 | 0.309 |
| 73 | 0.047 |
| 74 | 0.06 |
| 75 | 0.217 |
| 76 | 0.048 |
| 77 | 0.905 |
| 78 | 0.679 |
| 79 | 0.062 |
| 80 | 0.253 |
| 81 | 0.011 |
| 82 | 0.041 |
| 83 | 0.1 |
| 84 | 0.099 |
| 85 | 0.085 |
| 86 | 0.088 |
| 87 | 0.19 |
| 88 | 0.055 |
| 89 | 0.53 |
| 90 | 2.19 |
| 91 | 0.177 |
| 92 | 2.594 |
| 93 | 0.457 |
| 94 | 0.084 |
| 95 | 4.395 |
| 96 | 0.075 |
| 97 | 0.047 |
| 98 | 0.031 |
| 99 | 0.034 |
| 100 | 0.038 |
| 101 | 0.026 |
| 102 | 0.026 |
| 103 | 0.074 |
| 104 | 0.034 |
| 105 | 0.112 |
| 106 | 0.038 |
| 107 | 0.036 |
| 108 | 0.048 |
| 109 | 0.028 |
| 110 | 0.045 |
| 111 | 0.211 |
| 112 | 0.086 |
| 113 | 0.132 |
| 114 | 0.319 |
| 115 | 0.029 |
| 116 | 0.102 |
| 117 | 0.067 |
| 118 | 0.634 |
| 119 | 0.035 |
| 120 | 0.034 |
| 121 | 0.047 |
| 122 | 0.03 |
| 123 | 0.135 |
| 124 | 0.033 |
| 125 | 0.051 |
| 126 | 0.13 |
| 127 | 0.059 |
| 128 | 0.562 |
| 129 | 0.142 |
| 130 | 0.46 |
| 131 | 0.087 |
| 132 | 0.833 |
| 133 | 0.643 |
| 134 | 0.069 |
| 135 | 0.057 |
| 136 | 0.096 |
| 137 | 1.767 |
| 138 | 1.538 |
| 139 | 0.071 |
| 140 | 0.067 |
| 141 | 0.677 |
| 142 | 0.06 |
| 143 | 0.037 |
| 144 | 0.202 |
| 145 | 0.189 |
| 146 | 0.177 |
| 147 | 0.394 |
| 148 | 0.426 |
| 149 | 0.378 |
| 150 | 0.035 |
| 151 | 0.056 |
| 152 | 0.027 |
| 153 | 0.189 |
| 154 | 0.321 |
| 155 | 0.072 |
| 156 | 0.393 |
| 157 | 0.366 |
| 158 | 3.86 |
| 159 | 0.689 |
| 160 | 0.214 |
| 161 | 0.089 |
| 162 | 0.053 |
| 163 | 0.072 |
| 164 | 0.105 |
| 165 | 0.18 |
| 166 | 0.171 |
| 167 | 0.101 |
| 168 | 0.233 |
| 169 | 0.048 |
| 170 | 0.155 |
| 171 | 0.176 |
| 172 | 0.605 |
| 173 | 0.1 |
| 174 | 0.25 |
| 175 | 0.24 |
| 176 | 0.06 |
| 177 | 0.09 |
| 178 | 0.05 |
| 179 | 0.07 |
| 180 | 0.06 |
| 181 | 0.27 |
| 182 | 0.06 |
| 183 | 0.24 |
| 184 | 0.26 |
| 185 | 0.04 |
| 186 | 0.07 |
| 187 | 0.04 |
| 188 | 0.06 |
| 189 | 0.07 |
| 190 | 0.15 |
| 191 | 0.02 |
| 192 | 0.03 |
| 193 | 0.22 |
| 194 | 0.10 |
| 195 | 0.05 |
| 196 | 0.04 |
| 197 | 0.35 |
| 198 | 0.05 |
| 199 | 0.17 |
| 200 | 0.05 |
| 201 | 0.10 |
| 202 | 0.20 |
| 203 | 0.12 |
| 204 | 0.05 |
| 205 | 0.06 |
| 206 | 0.23 |
| 207 | 0.08 |

TABLE 1-continued

MCL1/Bim IC$_{50}$ (nM)

| Example | IC$_{50}$ (nM) |
|---|---|
| 208 | 0.13 |
| 209 | 0.04 |
| 210 | 0.05 |
| 211 | 0.04 |

SKBR3 Cell Viability Assay
Materials
SKBR3 Cells (ATCC HTB-30) were obtained from ATCC (Manassas, VA) and cultured in McCoy 5A's medium (ATCC 30-2007)+10% fetal bovine serum (SH30071.03, HyClone, Pittsburgh, PA) plus 1× Penicillin-Streptomycin L-glutamine (Corning 30-009-CI, Corning, NY).
Methods
The cell viability assay was conducted in a 384-well tissue culture plate (Grenier 781086, Monroe, NC) in a total volume of 70 μL. Test compounds were prepared in 1,000×, serially diluted, and pre-spotted into 384-well tissue culture plate by Echo 555 Liquid Handler (Labcyte Inc., San Jose, CA). Seventy μL of 6,000 SKBR3 cells were dispensed into each well of the plate and incubated at 37° C. with 5% CO$_2$ for 72 hours. At the end of incubation, 2×CellTiter Glo (CTG) reagents (1 part buffer with 2 parts substrate) (Promega, Madison, WI) were prepared, and the plate and the reagent were equilibrated to room temperature for 30 minutes. CTG reagent was added to each plate by Biomek FX at 20 μL/well with 5 times pipetting and mixing to induce cell lysis. Luminescence was read by Envision multimode reader (PerkinElmer). EC$_{50}$ values were calculated and reported in Table 2. Percent inhibition was calculated as followed:

% Inhibition=100%*(Well−Neg)/(Pos−Neg)

Neg, negative control, DMSO
Pos, positive control, 10 μM Puromycin

TABLE 2

MCL1 CV SKBR3 EC$_{50}$ (nM)

| Example | EC$_{50}$ (nM) |
|---|---|
| 1 | 1393.1 |
| 2 | |
| 3 | 239.6 |
| 4 | |
| 5 | 4181.5 |
| 6 | 4391.1 |
| 7 | |
| 8 | 26.5 |
| 9 | 169.5 |
| 10 | 47.6 |
| 11 | |
| 12 | 38.7 |
| 13 | |
| 14 | |
| 15 | 1402.8 |
| 16 | 8142.6 |
| 17 | 4550.9 |
| 18 | 19.6 |
| 19 | 37.8 |
| 20 | 41.3 |
| 21 | 882.5 |
| 22 | 168.8 |
| 23 | 17.3 |
| 24 | 10.3 |
| 25 | |
| 26 | 118.7 |
| 27 | 40.0 |
| 28 | |
| 29 | 15.3 |
| 30 | 930.3 |
| 31 | 4386.4 |
| 32 | 18.5 |
| 33 | 30.1 |
| 34 | 25.4 |
| 35 | |
| 36 | 1074.8 |
| 37 | 57.7 |
| 38 | |
| 39 | 146.3 |
| 40 | 325.5 |
| 41 | 126.2 |
| 42 | 232.7 |
| 43 | 3572.2 |
| 44 | |
| 45 | |
| 46 | 1602.2 |
| 47 | 81.9 |
| 48 | 173.0 |
| 49 | 524.7 |
| 50 | 361.3 |
| 51 | 432.8 |
| 52 | 9.5 |
| 53 | 21.7 |
| 54 | 103.1 |
| 55 | 426.2 |
| 56 | 93.6 |
| 57 | |
| 58 | 38.3 |
| 59 | |
| 60 | 19.2 |
| 61 | 19.6 |
| 62 | 17.5 |
| 63 | 25.2 |
| 64 | 372.8 |
| 65 | 374.5 |
| 66 | 8.6 |
| 67 | |
| 68 | 93.8 |
| 69 | 999.7 |
| 70 | 92.9 |
| 71 | 192.0 |
| 72 | 293.8 |
| 73 | 13.8 |
| 74 | 187.3 |
| 75 | 170.6 |
| 76 | 24.1 |
| 77 | 477.3 |
| 78 | 1064.1 |
| 79 | 42.9 |
| 80 | 27.5 |
| 81 | 6.3 |
| 82 | 53.6 |
| 83 | 99.1 |
| 84 | 90.0 |
| 85 | 163.6 |
| 86 | 64.6 |
| 87 | 1090.7 |
| 88 | 170.3 |
| 89 | |
| 90 | |
| 91 | 88.4 |
| 92 | 796.5 |
| 93 | 556.2 |
| 94 | |
| 95 | 3631.8 |
| 96 | 1409.8 |
| 97 | 15.8 |
| 98 | 73.3 |
| 99 | 14.2 |
| 100 | 35.4 |
| 101 | 27.0 |

TABLE 2-continued

MCL1 CV SKBR3 EC$_{50}$ (nM)

| Example | EC$_{50}$ (nM) |
|---|---|
| 102 | 16.1 |
| 103 | 34.6 |
| 104 | 54.0 |
| 105 | 162.8 |
| 106 | 133.0 |
| 107 |  |
| 108 | 6.0 |
| 109 | 35.3 |
| 110 | 27.6 |
| 111 | 26.3 |
| 112 | 10.4 |
| 113 | 35.4 |
| 114 | 51.0 |
| 115 | 16.0 |
| 116 | 13.4 |
| 117 | 23.9 |
| 118 | 2519.3 |
| 119 | 243.7 |
| 120 | 35.2 |
| 121 | 67.9 |
| 122 | 17.7 |
| 123 | 69.7 |
| 124 | 10.1 |
| 125 |  |
| 126 |  |
| 127 |  |
| 128 |  |
| 129 | 1207.2 |
| 130 | 2561.0 |
| 131 | 546.1 |
| 132 | 1021.1 |
| 133 | 1370.3 |
| 134 | 100.6 |
| 135 | 92.2 |
| 136 | 67.2 |
| 137 | 560.6 |
| 138 | 1046.5 |
| 139 | 198.5 |
| 140 | 137.9 |
| 141 | 882.0 |
| 142 | 105.6 |
| 143 | 37.5 |
| 144 |  |
| 145 | 178.4 |
| 146 | 293.5 |
| 147 | 531.8 |
| 148 | 1716.1 |
| 149 | 287.2 |
| 150 | 113.8 |
| 151 | 421.6 |
| 152 | 51.4 |
| 153 | 1000.0 |
| 154 | 1465.5 |
| 155 | 88.9 |
| 156 | 368.0 |
| 157 | 229.3 |
| 158 | 1953.2 |
| 159 | 380.6 |
| 160 | 330.7 |
| 161 | 33.8 |
| 162 | 27.7 |
| 163 | 100.1 |
| 164 | 88.1 |
| 165 | 368.7 |
| 166 | 190.4 |
| 167 | 46.3 |
| 168 | 94.0 |
| 169 | 215.0 |
| 170 | 113.3 |
| 171 |  |
| 172 | 159.6 |
| 173 | 309.8 |
| 174 | 353.9 |
| 175 | 637.9 |
| 176 | 72.5 |
| 177 |  |
| 178 | 25.9 |
| 179 | 24.1 |
| 180 | 24.9 |
| 181 | 57.0 |
| 182 |  |
| 183 | 454.3 |
| 184 | 261.5 |
| 185 | 17.2 |
| 186 | 26.6 |
| 187 | 47.8 |
| 188 | 31.9 |
| 189 | 71.8 |
| 190 | 306.0 |
| 191 | 36.6 |
| 192 | 136.2 |
| 193 | 57.3 |
| 194 |  |
| 195 | 23.8 |
| 196 | 81.4 |
| 197 | 516.5 |
| 198 | 22.3 |
| 199 |  |
| 200 | 21.1 |
| 201 | 85.0 |
| 202 |  |
| 203 | 156.5 |
| 204 | 115.0 |
| 205 | 81.3 |
| 206 | 141.5 |
| 207 | 87.7 |
| 208 | 140.0 |
| 209 | 127.3 |
| 210 | 108.8 |
| 211 | 57.1 |

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be considered an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

The invention claimed is:
1. A compound of Formula (II):

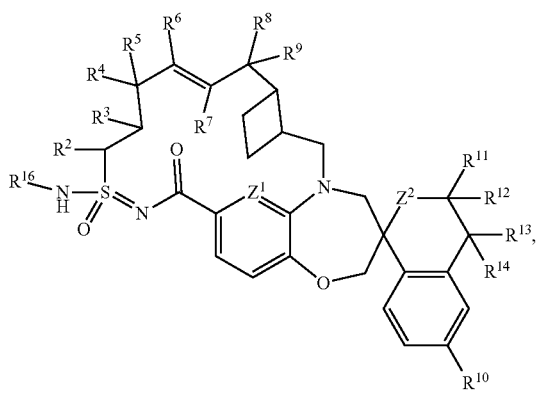

or a pharmaceutically acceptable salt thereof, wherein:
$Z^1$ is selected from $CR^{1a}$, or N;
$Z^2$ is selected from $CR^{2a}R^{2b}$, S, $NR^{2c}$, and O;
  wherein each $R^{1a}$, $R^{2a}$, and $R^{2b}$ is independently selected from hydrogen, halo, $C_{1-6}$alkyl, $C_{1-6}$alkoxyl, $C_{1-6}$haloalkyl, and $C_{1-6}$haloalkoxyl; and
  wherein $R^{2c}$ is independently selected from hydrogen, $C_{1-6}$alkyl, and $C_{1-6}$haloalkyl;
  wherein $R^{16}$ is 3-12 membered heterocyclyl or 5-12 membered heteroaryl; wherein $R^{16}$ is optionally substituted with 1-5 $R^A$;
$R^2$ is selected from hydrogen, halo, $C_{1-6}$alkyl, $C_{1-6}$haloalkyl, $C_{1-6}$alkoxyl, and —$C_{1-4}$alkylene-O—$C_{1-6}$alkyl;
$R^3$ is selected from hydrogen, halo, $C_{1-6}$alkyl, $C_{1-6}$haloalkyl, $C_{1-6}$alkoxyl, $C_{3-10}$cycloalkyl, 3-12 membered heterocyclyl, and —$C_{1-4}$alkylene-O-5-10 membered heteroaryl; wherein each $C_{1-6}$alkyl, $C_{1-6}$haloalkyl, $C_{1-6}$alkoxyl, $C_{3-10}$cycloalkyl, 3-12 membered heterocyclyl, and —$C_{1-4}$alkylene-O-5-10 membered heteroaryl of $R^3$ is optionally substituted with one to four groups independently selected from halo, $C_{1-6}$alkyl, $C_{1-6}$haloalkyl, and $C_{1-6}$alkoxyl;
each $R^4$ and $R^5$ is independently selected from hydrogen, halo, hydroxyl, $C_{1-6}$alkyl, $C_{2-6}$alkenyl, $C_{2-6}$alkynyl, $C_{1-6}$haloalkyl, $C_{1-6}$alkoxyl, $C_{1-6}$haloalkoxyl, —$NR^{aa}R^{bb}$, —NHC(O)—$C_{1-6}$alkyl, —C(O)NH—$C_{1-6}$alkyl, —O—$C_{2-6}$alkynyl, —OC(O)—$C_{1-6}$alkyl, —O—$(CH_2CH_2O)_n$—$C_{1-6}$alkyl, $C_{3-10}$cycloalkyl, 3-12 membered heterocyclyl, —O—$C_{3-10}$cycloalkyl, —O—3-12 membered heterocyclyl, —O—$C_{1-4}$alkylene-$C_{3-10}$cycloalkyl, 5-10 membered heteroaryl, —O—$C_{1-4}$alkylene-3-12 membered heterocyclyl, —O—5-10 membered heteroaryl, and —O—$C_{1-4}$alkylene-5-10 membered heteroaryl;
  wherein each $C_{1-6}$alkyl, $C_{2-6}$alkenyl, $C_{2-6}$alkynyl, $C_{1-6}$haloalkyl, $C_{1-6}$alkoxyl, $C_{1-6}$haloalkoxyl, —NHC(O)—$C_{1-6}$alkyl, —C(O)NH—$C_{1-6}$alkyl, —O—$C_{2-6}$alkynyl, —OC(O)—$C_{1-6}$alkyl, —O—$(CH_2CH_2O)_n$—$C_{1-6}$alkyl, $C_{3-10}$cycloalkyl, 3-12 membered heterocyclyl, —O—$C_{3-10}$cycloalkyl, —O—3-12 membered heterocyclyl, —O—$C_{1-4}$alkylene-$C_{3-10}$cycloalkyl, 5-10 membered heteroaryl, —O—$C_{1-4}$alkylene-3-12 membered heterocyclyl, —O—5-10 membered heteroaryl, and —O—$C_{1-4}$alkylene-5-10 membered heteroaryl of $R^4$ and $R^5$ is optionally substituted with one to four groups independently selected from halo, hydroxyl, oxo, $C_{1-6}$alkyl, $C_{1-6}$alkoxyl, $C_{1-6}$haloalkoxyl, —$NR^{aa}R^{bb}$, $C_{3-10}$cycloalkyl, and 3-12 membered heterocyclyl;
each $R^6$ and $R^7$ is independently selected from hydrogen, halo, hydroxyl, $C_{1-6}$alkyl, $C_{1-6}$alkoxyl, $C_{1-6}$haloalkyl, and $C_{1-6}$haloalkoxyl;
$R^8$ is selected from hydrogen, halo, hydroxyl, oxo, $C_{1-6}$alkyl, $C_{2-6}$alkenyl, $C_{2-6}$alkynyl, $C_{1-6}$alkoxyl, —O—$C_{2-6}$alkenyl, —O—$C_{2-6}$alkynyl, $C_{3-10}$cycloalkyl, 3-12 membered heterocyclyl, $C_{6-10}$aryl, 5-10 membered heteroaryl, —O—$C_{3-10}$cycloalkyl, —O—3-12 membered heterocyclyl, —O—$C_{6-10}$aryl, —O—5-10 membered heteroaryl, —O—$C_{1-4}$alkylene-$C_{3-10}$cycloalkyl, —O—$C_{1-4}$alkylene-3-12 membered heterocyclyl, —O—$C_{1-4}$alkylene-$C_{6-10}$aryl, and —O—$C_{1-4}$alkylene-5-10 membered heteroaryl;
$R^9$ is absent or selected from hydrogen, halo, hydroxyl, $C_{1-6}$alkyl, $C_{2-6}$alkenyl, $C_{2-6}$alkynyl, $C_{1-6}$alkoxyl, —O—$C_{2-6}$alkenyl, —O—$C_{2-6}$alkynyl, $C_{3-10}$cycloalkyl, 3-12 membered heterocyclyl, $C_{6-10}$aryl, 5-10 membered heteroaryl, —O—$C_{3-10}$cycloalkyl, —O—3-12 membered heterocyclyl, —O—$C_{6-10}$aryl, —O—5-10 membered heteroaryl, —O—$C_{1-4}$alkylene-$C_{3-10}$cycloalkyl, —O—$C_{1-4}$alkylene-3-12 membered heterocyclyl, —O—$C_{1-4}$alkylene-$C_{6-10}$aryl, and —O—$C_{1-4}$alkylene-5-10 membered heteroaryl;
  wherein each $C_{1-6}$alkyl, $C_{2-6}$alkenyl, $C_{2-6}$alkynyl, $C_{1-6}$alkoxyl, —O—$C_{2-6}$alkenyl, —O—$C_{2-6}$alkynyl, $C_{3-10}$cycloalkyl, 3-12 membered heterocyclyl, $C_{6-10}$aryl, 5-10 membered heteroaryl, —O—$C_{3-10}$cycloalkyl, —O—3-12 membered heterocyclyl, —O—$C_{6-10}$aryl, —O—5-10 membered heteroaryl, —O—$C_{1-4}$alkylene-$C_{3-10}$cycloalkyl, —O—$C_{1-4}$alkylene-3-12 membered heterocyclyl, —O—$C_{1-4}$alkylene-$C_{6-10}$aryl, and —O—$C_{1-4}$alkylene-5-10 membered heteroaryl of $R^8$ and $R^9$ is independently optionally substituted with 1-5 $R^A$;
$R^{10}$ is selected from hydrogen, halo, hydroxyl, —CN, $C_{1-6}$alkyl, $C_{1-6}$alkoxyl, $C_{1-6}$haloalkyl, and $C_{1-6}$haloalkoxyl;
each $R^{11}$, $R^{12}$, $R^{13}$, and $R^{14}$ is independently selected from hydrogen, halo, hydroxyl, —CN, $C_{1-6}$alkyl, $C_{1-6}$alkoxy, and $C_{1-6}$haloalkyl; or
$R^{11}$ and $R^{13}$ together with the atoms to which they are attached form a $C_{3-6}$ cycloalkyl or 3-6 membered heterocyclyl; wherein the 3-6 membered heterocyclyl has one to three heteroatoms; and wherein each $C_{3-6}$ cycloalkyl and 3-6 membered heterocyclyl is optionally substituted with one to three groups independently selected from halo, hydroxyl, —CN, $C_{1-6}$alkyl, $C_{1-6}$alkoxy, $C_{1-6}$haloalkyl, and $C_{1-6}$haloalkoxyl;
each $R^A$ is independently selected from halo, hydroxyl, oxo, —CN, $C_{1-6}$alkyl, $C_{2-6}$alkenyl, $C_2$-6alkynyl, $C_{1-6}$alkoxyl, $C_{1-6}$haloalkyl, $C_{1-6}$haloalkoxyl, —$C_{1-4}$alkylene-O—$C_{1-4}$alkyl, $C_{3-10}$cycloalkyl, 3-12 membered heterocyclyl, $C_{6-10}$aryl, 5-10 membered heteroaryl, and —$NR^{aa}R^{bb}$;
  wherein each $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, —$C_{1-4}$alkylene-O—$C_{1-4}$alkyl, $C_{3-10}$cycloalkyl, 3-12 membered heterocyclyl, $C_{6-10}$aryl, 5-10 membered heteroaryl of $R^A$ is independently substituted with one to three groups independently selected from halo, hydroxyl, —CN, $C_{1-6}$alkyl, $C_{1-6}$alkoxy, $C_{1-6}$haloalkyl, $C_{1-6}$haloalkoxyl, $C_{3-10}$cycloalkyl, 3-12 membered heterocyclyl, $C_{6-10}$aryl, 5-10 membered heteroaryl, and —NR$^{aa}$R$^{bb}$;

each R$^{aa}$ and R$^{bb}$ is independently selected from hydrogen, $C_{1-6}$alkyl, $C_{3-10}$cycloalkyl, 3-12 membered heterocyclyl, $C_{6-10}$aryl, 5-10 membered heteroaryl, —$C_{1-6}$alkylene-$C_{3-10}$cycloalkyl, —$C_{1-6}$alkylene-3-12 membered heterocyclyl, —$C_{1-6}$alkylene-$C_{6-10}$aryl, and —$C_{1-6}$alkylene-5-10 membered heteroaryl;

wherein each $C_{1-6}$alkyl, $C_{3-10}$cycloalkyl, 3-12 membered heterocyclyl, $C_{6-10}$aryl, 5-10 membered heteroaryl, —$C_{1-6}$alkylene-$C_{3-10}$cycloalkyl, —$C_{1-6}$alkylene-3-12 membered heterocyclyl, —$C_{1-6}$alkylene-$C_{6-10}$aryl, and —$C_{1-6}$alkylene-5-10 membered heteroaryl of R$^{aa}$ and R$^{bb}$ is independently optionally substituted with one to four groups independently selected from halo, $C_{1-6}$alkyl, —CN, $C_{1-6}$alkoxyl, and $C_{1-6}$haloalkyl;

wherein the 3-12 membered heterocyclyl is a single ring or multiple rings having one to four heteroatoms independently selected from nitrogen, sulfur, phosphorus, —N(O)—, —S(O)—, and —S(O)$_2$—; and wherein the multiple rings may be fused, bridged, or spiro; and wherein the 5-10 membered heteroaryl is an aromatic group having a single ring or multiple rings; wherein the 5-10 membered heteroaryl contains one to four heteroatoms independently selected from nitrogen, oxygen, sulfur, —N(O)—, —S(O)—, and —S(O)$_2$.

2. The compound of claim 1, or a pharmaceutically acceptable salt thereof, wherein R$^{16}$ is selected from

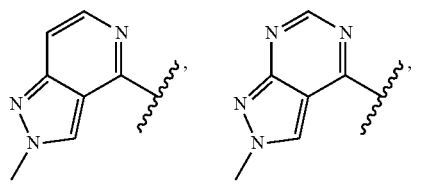

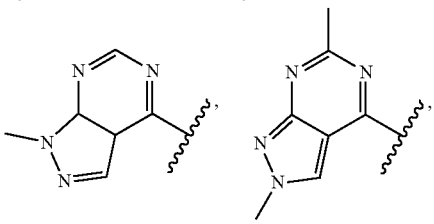

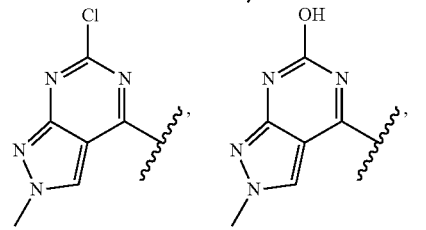

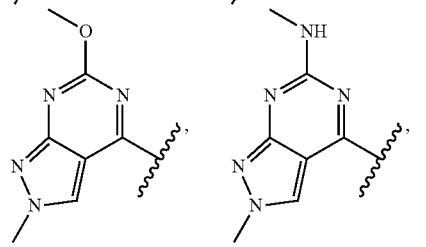

-continued

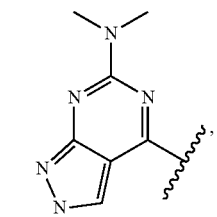

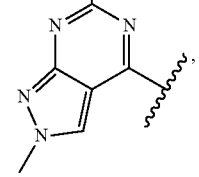

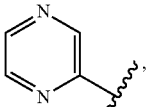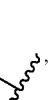, and

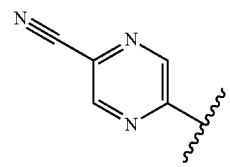

3. The compound of claim 1, or a pharmaceutically acceptable salt thereof, wherein R$^4$ is selected from hydrogen, hydroxyl, F, —CH$_3$, —CH$_2$CH$_3$, —CH$_2$CH$_2$CH$_3$, —OCH$_3$, —OCH$_2$CH$_3$, —OCH$_2$CH$_2$CH$_3$,

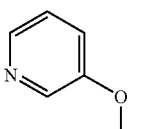

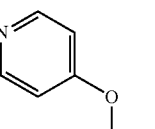

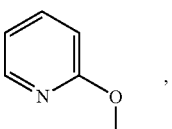

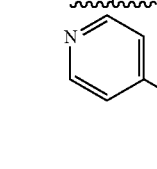

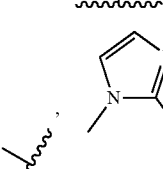

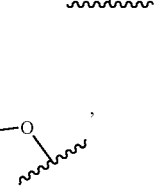

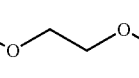

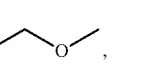

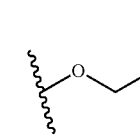

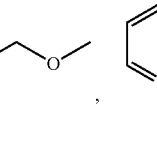

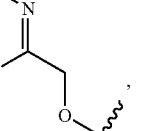

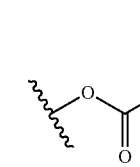

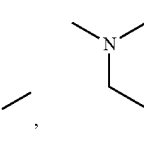

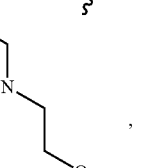

351
-continued
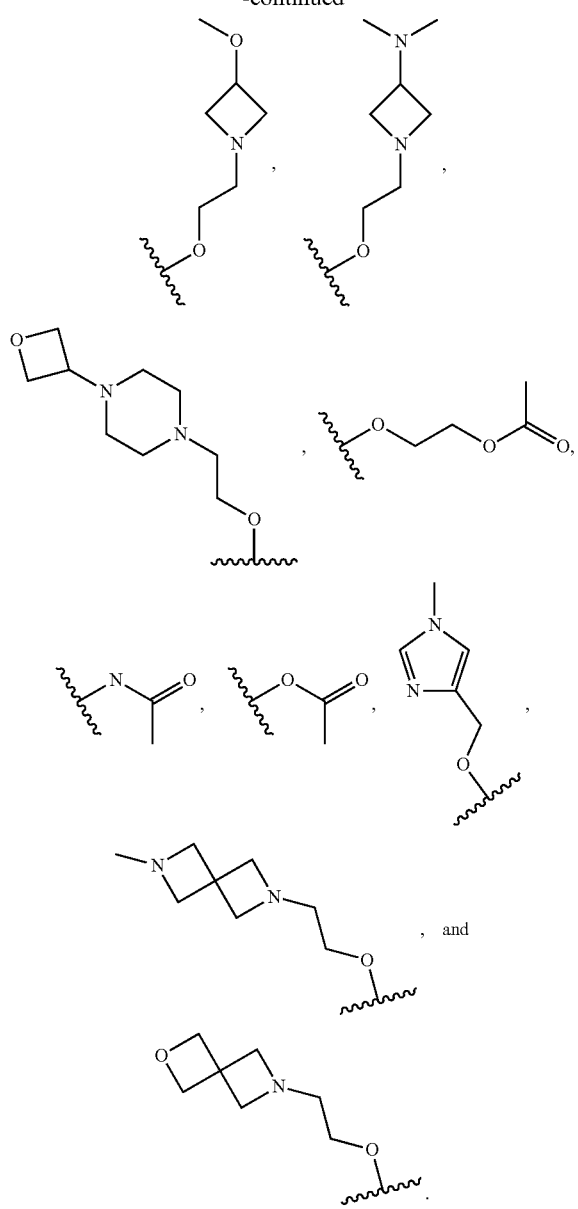
352
-continued
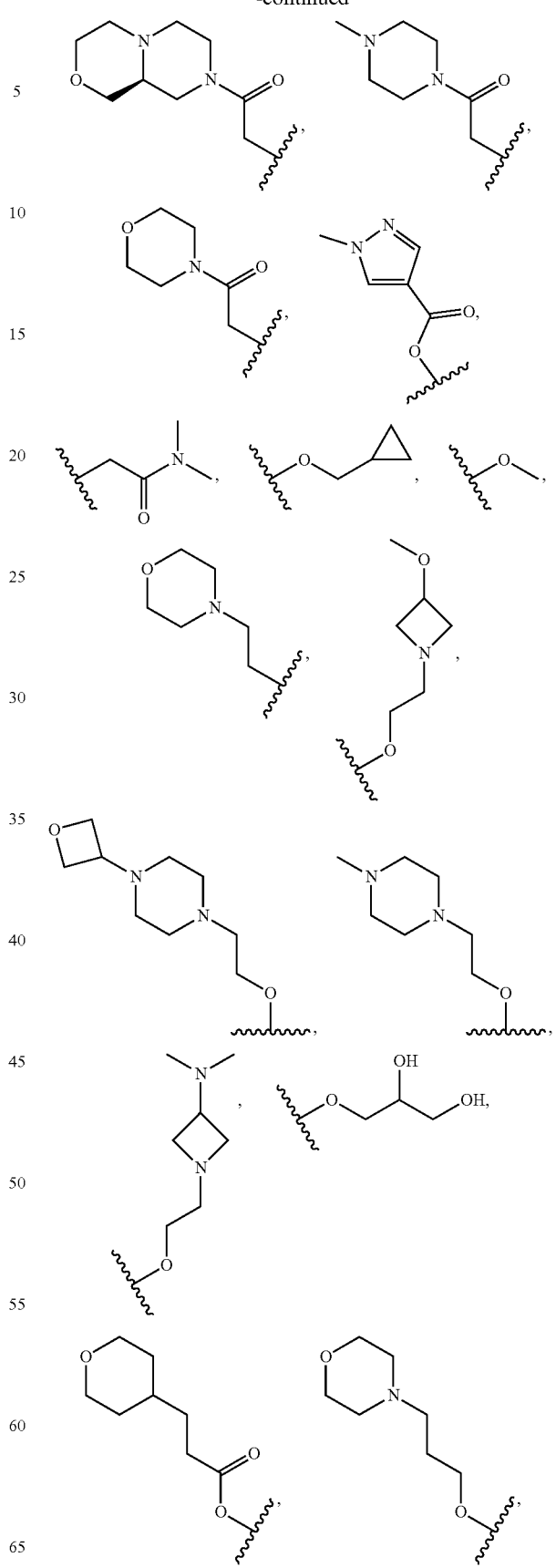
4. The compound of claim 1, or a pharmaceutically acceptable salt thereof, wherein $R^5$ is selected from hydrogen, hydroxyl, and —OCH$_3$.
5. The compound of claim 1, or a pharmaceutically acceptable salt thereof, each $R^8$ and $R^9$ is independently selected from OH, F, —CH$_3$,
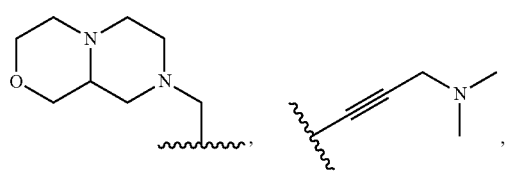

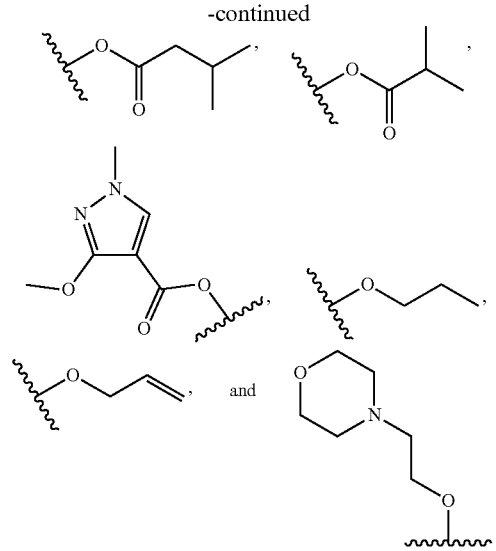
6. The compound of claim 1, or a pharmaceutically acceptable salt thereof, R⁸ is
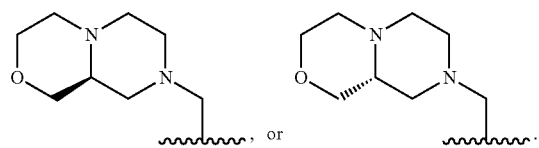 [SMILES: *CN1CCN2CCOC[C@@H]2C1 ; *CN1CCN2CCOC[C@H]2C1]
7. The compound of claim 1, or a pharmaceutically acceptable salt thereof, selected from:
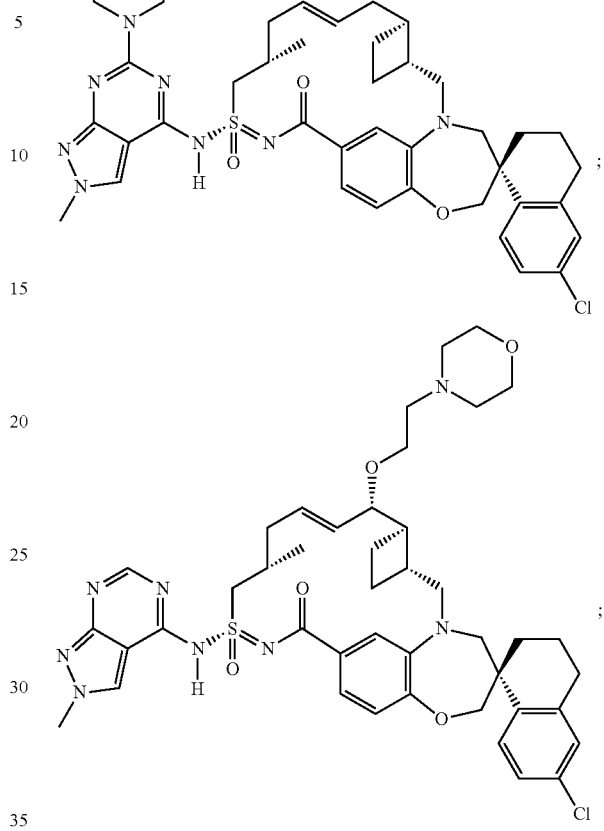
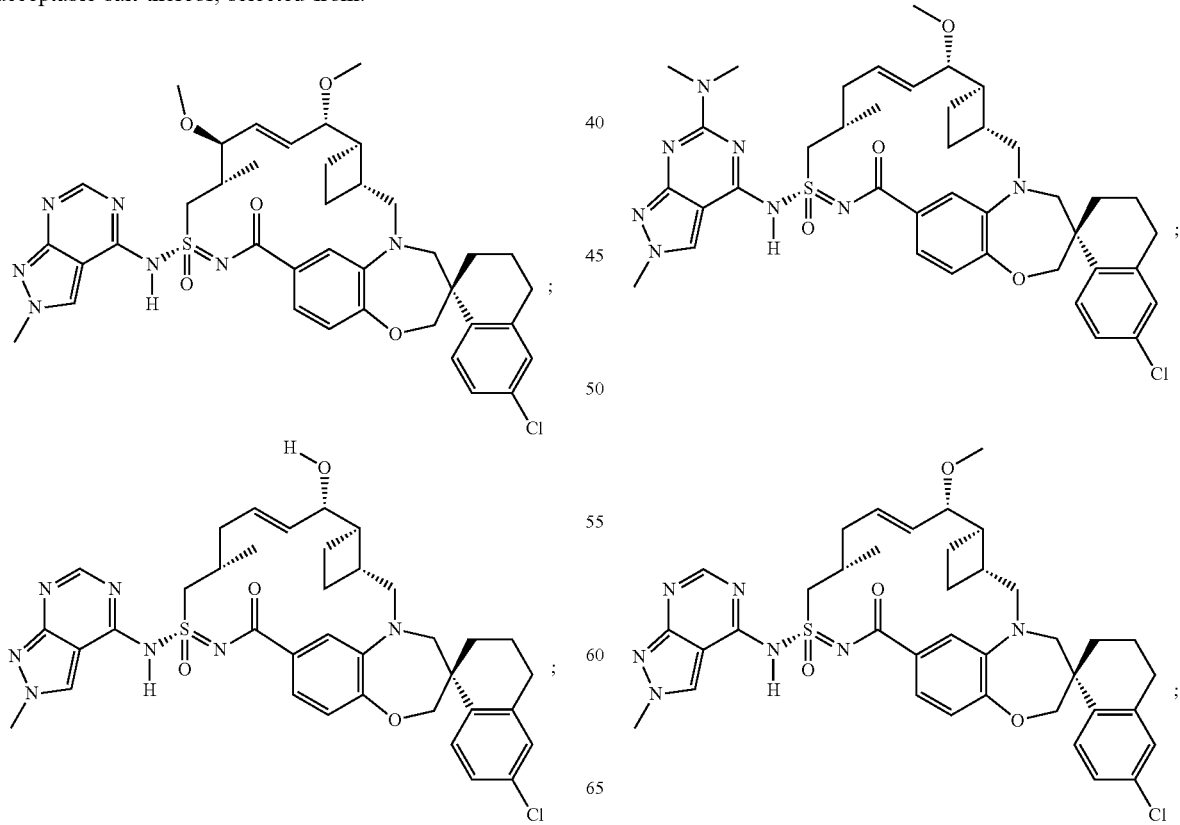

355
-continued
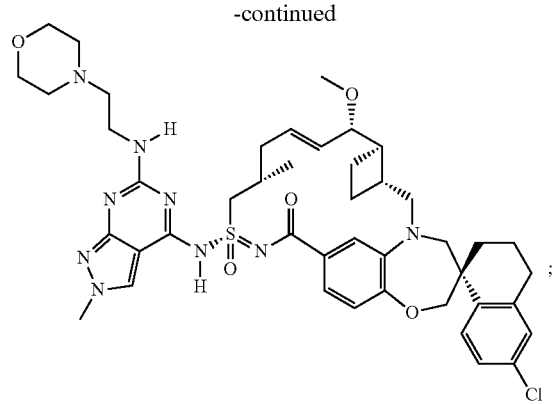
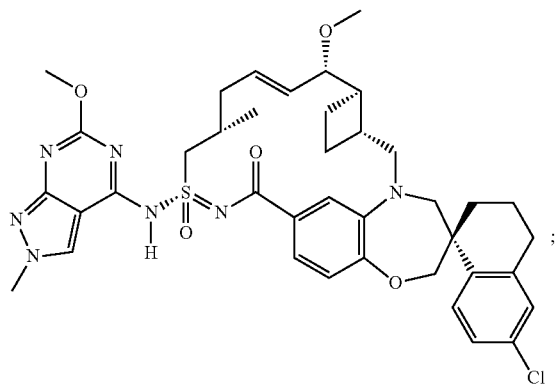
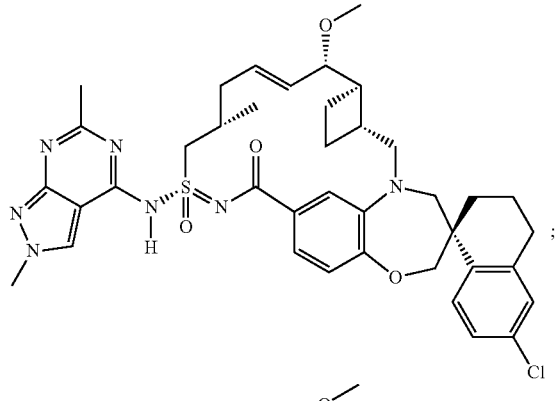
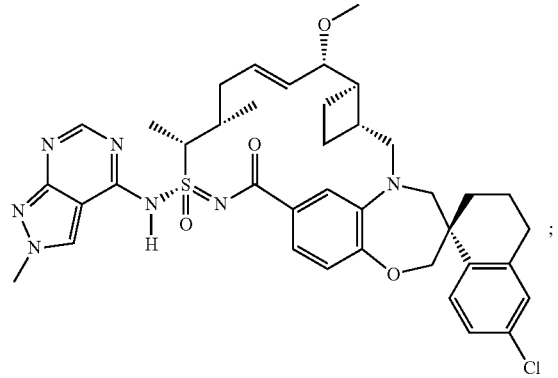
356
-continued
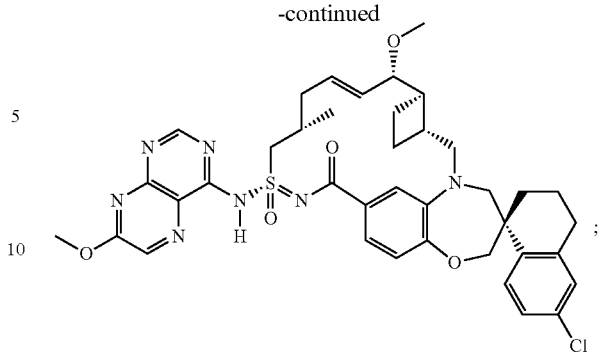
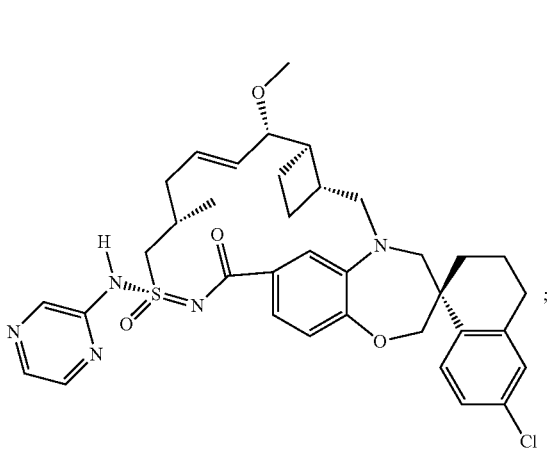
and
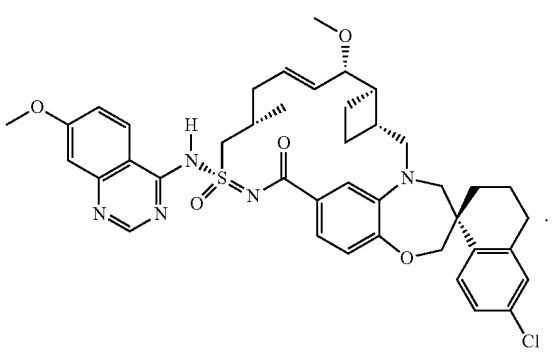
8. A pharmaceutical composition comprising the compound of claim 1, or a pharmaceutically acceptable salt thereof, and a pharmaceutically acceptable excipient.
* * * * *